US010916708B2

(12) United States Patent
Jun et al.

(10) Patent No.: US 10,916,708 B2
(45) Date of Patent: Feb. 9, 2021

(54) CONDENSED CYCLIC COMPOUND AND ORGANIC LIGHT EMITTING DEVICE INCLUDING THE SAME

(71) Applicant: SAMSUNG DISPLAY CO., LTD., Yongin-si (KR)

(72) Inventors: Mieun Jun, Yongin-si (KR); Jongwoo Kim, Yongin-si (KR); Youngkook Kim, Yongin-si (KR); Seokhwan Hwang, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 352 days.

(21) Appl. No.: 15/868,293

(22) Filed: Jan. 11, 2018

(65) Prior Publication Data

US 2018/0366647 A1 Dec. 20, 2018

(30) Foreign Application Priority Data

Jun. 20, 2017 (KR) ........................ 10-2017-0078044

(51) Int. Cl.
*H01L 51/50* (2006.01)
*H01L 51/00* (2006.01)
(Continued)

(52) U.S. Cl.
CPC .......... *H01L 51/006* (2013.01); *C07C 211/54* (2013.01); *C07D 209/82* (2013.01);
(Continued)

(58) Field of Classification Search
None
See application file for complete search history.

(56) References Cited

U.S. PATENT DOCUMENTS 6,465,115 B2 10/2002 Shi et al.
6,596,415 B2 7/2003 Shi et al.
(Continued)

FOREIGN PATENT DOCUMENTS

KR 1020060006760 1/2006
KR 1020100097182 9/2010
(Continued)

OTHER PUBLICATIONS

Invitation pursuant to Rule 61(1) EPC dated Sep. 17, 2018 in corresponding European Patent Application No. 18178737.5 (4 pages).
(Continued)

*Primary Examiner* — Gregory D Clark
(74) *Attorney, Agent, or Firm* — F. Chau & Associates, LLC

(57) ABSTRACT

Provided are a condensed cyclic compound and an organic light-emitting device including the same. The organic light-emitting device may include a first electrode, a second electrode, and an organic layer disposed between the first electrode and the second electrode. The organic layer may include the condensed cyclic compound represented by Formula 1:
(Continued)

<Formula 1>

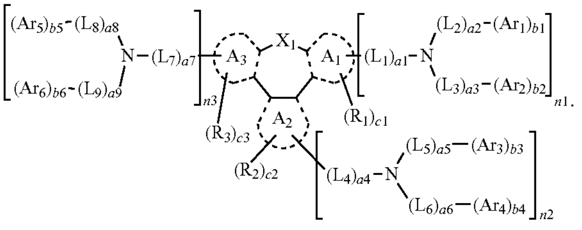

In Formula 1, rings $A_1$, $A_2$, and $A_3$ may each be independently a $C_5$-$C_{60}$ carbocyclic group or a $C_2$-$C_{30}$ heterocyclic group, and n1 to n3 may each be independently 0 or 1, provided that the sum of n1, n2, and n3 is 1. In addition, the descriptions of $X_1$, $L_1$ to $L_9$, a1 to a9, $Ar_1$ to $Ar_6$, b1 to b6, $R_1$ to $R_3$, and c1 to c3 are as defined in the present specification.

22 Claims, 4 Drawing Sheets

(51) Int. Cl.

| | |
|---|---|
| ***C07C 211/54*** | (2006.01) |
| ***C07F 7/08*** | (2006.01) |
| ***C07D 209/82*** | (2006.01) |
| ***C07F 5/02*** | (2006.01) |
| ***C07D 313/06*** | (2006.01) |

(52) U.S. Cl.

CPC ............ *C07D 313/06* (2013.01); *C07F 5/027* (2013.01); *C07F 7/0812* (2013.01); *H01L 51/008* (2013.01); *H01L 51/0052* (2013.01); *H01L 51/0054* (2013.01); *H01L 51/0055* (2013.01); *H01L 51/0057* (2013.01); *H01L 51/0061* (2013.01); *H01L 51/0071* (2013.01); *H01L 51/0072* (2013.01); *H01L 51/0073* (2013.01); *H01L 51/0074* (2013.01); *H01L 51/0094* (2013.01); *H01L 51/50* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | | |
|---|---|---|---|
| 7,053,255 B2 | 5/2006 | Ikeda et al. | |
| 7,233,019 B2 | 6/2007 | Ionkin et al. | |
| 7,571,894 B2 | 8/2009 | Sotoyama | |
| 8,647,754 B2 | 2/2014 | Mizuki et al. | |
| 2001/0023029 A1 | 9/2001 | Shi et al. | |
| 2002/0028346 A1 | 3/2002 | Shi et al. | |
| 2013/0069523 A1 | 3/2013 | Matsuura et al. | |
| 2015/0048324 A1 | 2/2015 | Shin et al. | |
| 2015/0194610 A1 | 7/2015 | Hwang et al. | |
| 2016/0308146 A1 | 10/2016 | Parham et al. | |
| 2017/0117432 A1 | 4/2017 | Kim et al. | |
| 2018/0053899 A1* | 2/2018 | Wu | H01L 51/0073 |

FOREIGN PATENT DOCUMENTS

| | | | |
|---|---|---|---|
| KR | 10-1031463 | 4/2011 | |
| KR | 1020140034709 | 3/2014 | |
| KR | 1020150019724 | 2/2015 | |
| KR | 10-2015-0021861 | 3/2015 | |
| KR | 2015-021861 | * 3/2015 | H01L 51/50 |
| KR | 1020150081736 | 7/2015 | |
| KR | 1020150115227 | 10/2015 | |
| KR | 1020180095081 | 8/2016 | |
| WO | 2015082046 | 6/2015 | |

OTHER PUBLICATIONS

Office Action issued by the Korean Intellectual Property Office dated Apr. 12, 2018 in the examination of the corresponding Korean Patent Application No. 10-2014-0078044 (10 pages).

Partial European Search Report dated Nov. 19, 2018 in corresponding European Patent Application No. 18178737.5 (13 pages).

* cited by examiner

20

30

40

CONDENSED CYCLIC COMPOUND AND ORGANIC LIGHT EMITTING DEVICE INCLUDING THE SAME

CROSS-REFERENCE TO RELATED APPLICATION

This application claims the benefit under 35 U.S.C. § 119 of Korean Patent Application No. 10-2017-0078044, filed on Jun. 20, 2017, in the Korean Intellectual Property Office, the disclosure of which is incorporated by reference herein in its entirety.

TECHNICAL FIELD

Exemplary embodiments relate to a condensed cyclic compound and an organic light-emitting device including the same.

DISCUSSION OF RELATED ART

Organic light-emitting devices are self-emission devices that have wide viewing angles, high contrast ratios, high brightness, low driving voltages, short response times, and many other excellent characteristics in terms of brightness, driving voltage, and response speed, compared to other display devices in the art.

An example of the organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, electrons provided from the second electrode may move toward the emission layer through the electron transport region, and when holes and electrons meet in the emission layer, they may recombine to produce excitons. These excitons transit from an excited state to a ground state, thereby generating light.

SUMMARY

Aspects of the present disclosure provide a condensed cyclic compound and an organic light-emitting device including the same.

An aspect of the present disclosure provides a condensed cyclic compound represented by Formula 1 below:

In Formula 1, $X_1$ may be selected from O, S, Se, $C(R_4)(R_5)$, $Si(R_4)(R_5)$, and $B(R_4)$, rings $A_1$, $A_2$, and $A_3$ may each independently be a $C_5$-$C_{60}$ carbocyclic group or a $C_2$-$C_{30}$ heterocyclic group, $L_1$ to $L_9$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a9 may each independently be an integer from 0 to 5, $Ar_1$ to $Ar_6$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 to b6 may each independently be an integer from 1 to 5, $R_1$ to $R_5$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $—Si(Q_1)(Q_2)$ <Formula 1>

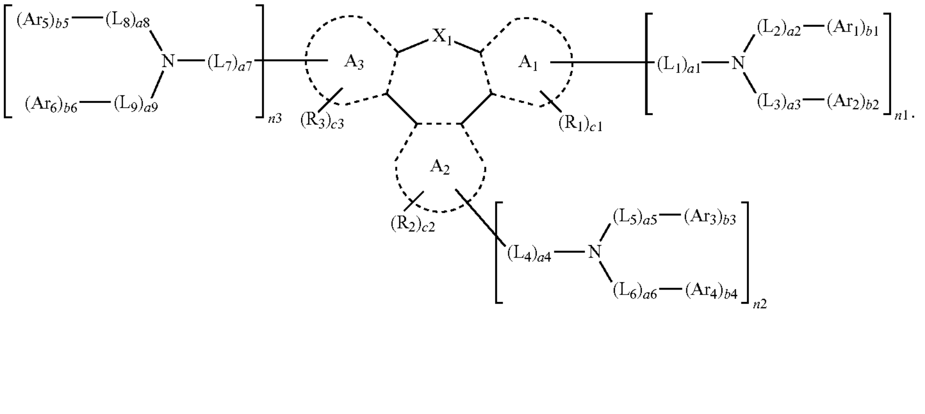

$(Q_3)$, $-N(Q_1)(Q_2)$, $-B(Q_1)(Q_2)$, $-C(=O)(Q_1)$, $-S(=O)_2(Q_1)$, and $-P(=O)(Q_1)(Q_2)$, c1 to c3 may each independently be an integer from 0 to 5, n1 to n3 may each independently be 0 or 1, provided that the sum of n1, n2, and n3 is 1, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{10}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{11})(Q_{12})(Q_{13})$, $-N(Q_{11})(Q_{12})$, $-B(Q_{11})(Q_{12})$, $-C(=O)(Q_{11})$, $-S(=O)_2(Q_{11})$, and $-P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{21})(Q_{22})(Q_{23})$, $-N(Q_{21})(Q_{22})$, $-B(Q_{21})(Q_{22})$, $-C(=O)(Q_{21})$, $-S(=O)_2(Q_{21})$, and $-P(=O)(Q_{21})(Q_{22})$; and $-Si(Q_{31})(Q_{32})(Q_{33})$, $-N(Q_{31})(Q_{32})$, $-B(Q_{31})(Q_{32})$, $-C(=O)_2(Q_{31})$, $-S(=O)_2(Q_{31})$, and $-P(=O)(Q_{31})(Q_{32})$, in which $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group.

Another aspect of the present disclosure provides an organic light-emitting device including: a first electrode; a second electrode facing the first electrode; and an organic layer disposed between the first electrode and the second electrode, in which the organic layer includes an emission layer and at least one condensed cyclic compound represented by Formula 1 described above.

Yet another aspect of the present disclosure provides an organic light-emitting device including: a first electrode; a second electrode facing the first electrode; an emission layer disposed between the first electrode; a hole transport region disposed between the first electrode and the emission layer; and an electron transport region disposed between the emission layer and the second electrode, in which at least one of the hole transport region and the emission layer may include a condensed cyclic compound. The condensed cyclic compound may include a tetracyclic structure including a 7-membered center ring and three fused side rings. The 7-membered center ring may include seven carbon atoms, or 6 carbon atoms and one of O, S, Se, Si and B atoms as ring members. Each of the three fused side rings may share a two carbon border with the 7-membered center ring. The three fused side rings may not share a border with each other. The three fused side rings may each independently be a $C_5$-$C_{60}$ carbocyclic group or a $C_2$-$C_{30}$ heterocyclic group, and one of the three fused side rings may be linked to a tertiary amino group.

BRIEF DESCRIPTION OF THE DRAWINGS

These and/or other aspects of the present disclosure will become apparent and more readily appreciated from the following description of the exemplary embodiments, taken in conjunction with the accompanying drawings in which.

Figure 1:
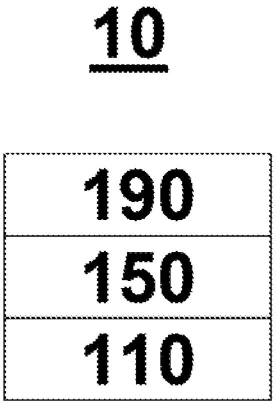
FIG. 1 is a schematic cross-sectional view of an organic light-emitting device according to an exemplary embodiment of the present disclosure.

Since the drawings in FIGS. 1-4 are intended for illustrative purposes, the elements in the drawings are not necessarily drawn to scale. For example, some of the elements may be enlarged or exaggerated for clarity purpose.

DETAILED DESCRIPTION OF THE EMBODIMENTS

Reference will now be made in detail to the embodiments of the present disclosure, examples of which are illustrated in the accompanying drawings, in which like reference numerals refer to like elements throughout. In this regard, the exemplary embodiments of the present disclosure may have different forms and should not be construed as being limited to the specific descriptions set forth herein. Accordingly, the exemplary embodiments are merely described below, by referring to the figures, to explain aspects of the present disclosure. As used herein, the term "and/or" includes any and all combinations of one or more of the associated listed items. Expressions such as "at least one of" when preceding a list of elements, modify the entire list of elements and do not modify the individual elements of the list.

A condensed cyclic compound according to an exemplary embodiment of the present disclosure is represented by Formula 1 below:

imidazole group, a quinoline group, an isoquinoline group, a quinoxaline group, a quinazoline group, a triazine group, an indenopyrazine group, an indenopyridine group, a phenanthroline group, and a phenanthridine group, but the present disclosure is not limited thereto.

In an exemplary embodiment of the present disclosure, rings $A_1$, $A_2$, and $A_3$ in Formula 1 may each independently be selected from a benzene group, a naphthalene group, a pyridine group, a pyrimidine group, a pyrazine group, a quinoline group, an isoquinoline group, a quinoxaline group, and a quinazoline group.

In an exemplary embodiment of the present disclosure, rings $A_1$, $A_2$, and $A_3$ in Formula 1 may each independently be a benzene group or a naphthalene group, but the present disclosure is not limited thereto.

$L_1$ to $L_9$ in Formula 1 may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In an exemplary embodiment of the present disclosure, $L_1$ to $L_9$ in Formula 1 may each independently be selected from:

<Formula 1>

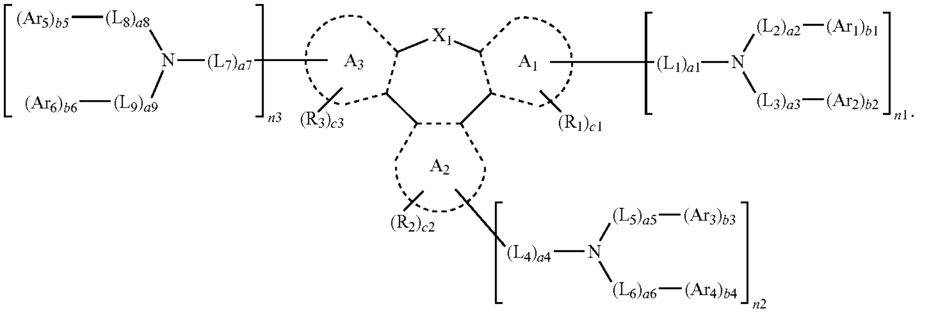

$X_1$ in Formula 1 may be selected from O, S, Se, $C(R_4)(R_5)$, $Si(R_4)(R_5)$, and $B(R_4)$. $R_4$ and $R_5$ are the same as described below.

In an exemplary embodiment of the present disclosure, $X_1$ in Formula 1 may be selected from O, $C(R_4)(R_5)$, $Si(R_4)(R_5)$, and $B(R_4)$, but the present disclosure is not limited thereto.

Rings $A_1$, $A_2$, and $A_3$ in Formula 1 may each be fused with a neighboring 7-membered ring, while sharing two carbon border therewith. Rings $A_1$, $A_2$, and $A_3$ in Formula 1 may each independently be a $C_5$-$C_{60}$ carbocyclic group or a $C_2$-$C_{30}$ heterocyclic group.

In an exemplary embodiment of the present disclosure, rings $A_1$, $A_2$, and $A_3$ in Formula 1 may each independently be selected from a benzene group, a naphthalene group, an anthracene group, a phenanthrene group, a pyrene group, a chrysene group, a triphenylene group, an indene group, a fluorene group, a benzofluorene group, a spiro-bifluorene group, a carbazole group, a dibenzofuran group, a dibenzothiophene group, a pyridine group, a pyrazine group, a pyrimidine group, a pyridazine group, a pyrrole group, an a phenylene group, a pentalenylene group, an indenylene group, a naphthylene group, an azulenylene group, an indacenylene group, an acenaphthylene group, a fluorenylene group, a spiro-bifluorenylene group, a spiro-benzofluorene-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a carbazolylene group, a benzocarbazolylene group, a dibenzocarbazolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azaspiro-bifluorenylene group, an azacarbazolylene group, an azadibenzofuranylene group, an azadibenzothiophenylene group, and an azadibenzosilolylene group; and a phenylene group, a pentalenylene group, an indenylene group, a naphthylene group, an azulenylene group, an indacenylene group, an acenaphthylene group, a fluorenylene group, a spiro-bifluorenylene group, a spiro-benzofluorene-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a carbazolylene group, a benzocarbazolylene group, a dibenzocarbazolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azaspiro-bifluorenylene group, an azacarbazolylene group, an azadibenzofuranylene group, an azadibenzothiophenylene group, and an azadibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, and —$Si(Q_{31})(Q_{32})(Q_{33})$, in which, $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

In an exemplary embodiment of the present disclosure, $L_1$ to $L_9$ in Formula 1 may each independently be selected from groups represented by Formulae 3-1 to 3-102:

Formula 3-1

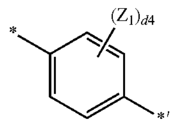

Formula 3-2

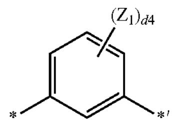

Formula 3-3

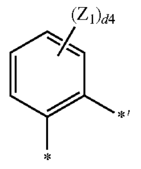

Formula 3-4

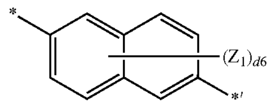

Formula 3-5

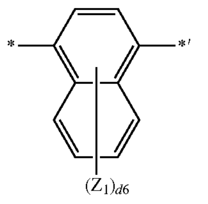

Formula 3-6

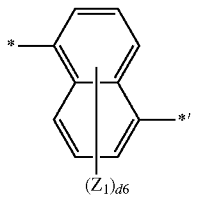

Formula 3-7

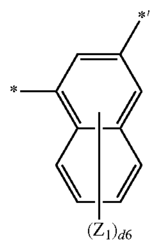

Formula 3-8
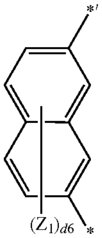
Formula 3-9
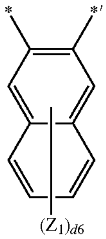
Formula 3-10
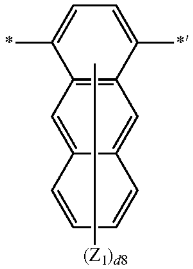
Formula 3-11
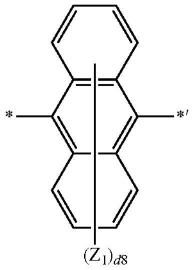
Formula 3-12
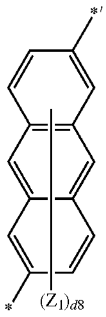
Formula 3-13
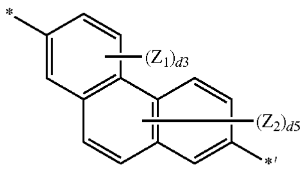
Formula 3-14
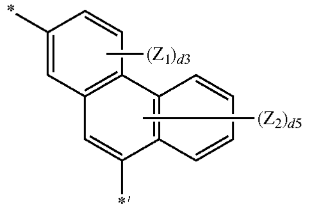
Formula 3-15
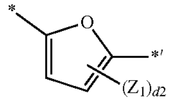
Formula 3-16
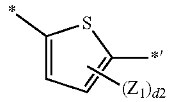
Formula 3-17
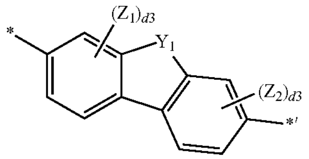
Formula 3-18
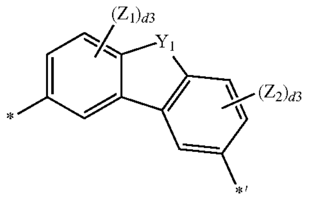
Formula 3-19
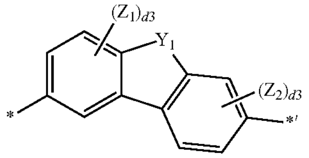
Formula 3-20
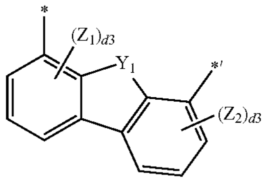
Formula 3-21
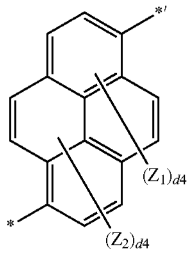

-continued
Formula 3-22
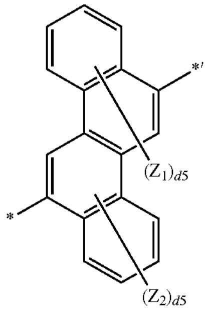
Formula 3-23
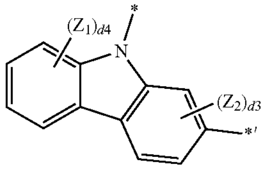
Formula 3-24
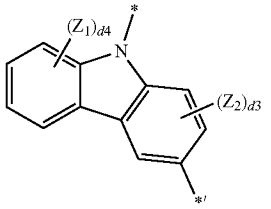
Formula 3-25
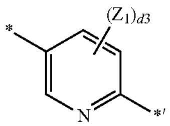
Formula 3-26
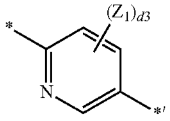
Formula 3-27
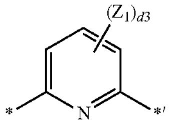
Formula 3-28
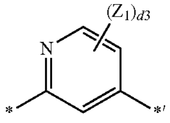
Formula 3-29
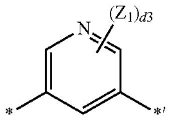
Formula 3-30
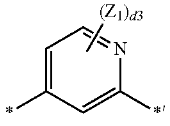
-continued
Formula 3-31
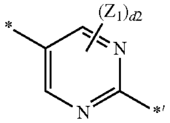
Formula 3-32
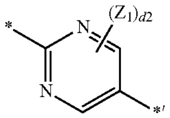
Formula 3-33
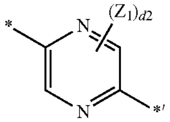
Formula 3-34
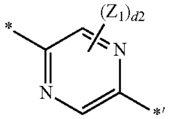
Formula 3-35
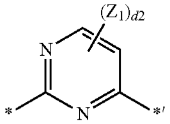
Formula 3-36
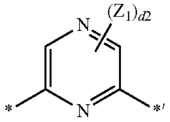
Formula 3-37
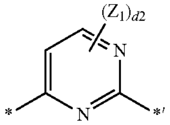
Formula 3-38
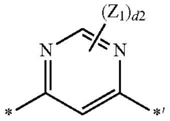
Formula 3-39
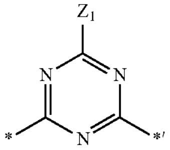
Formula 3-40
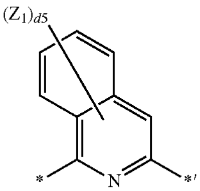
Formula 3-41
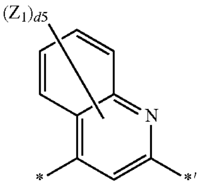

-continued
Formula 3-42
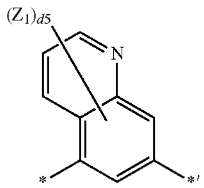
Formula 3-43
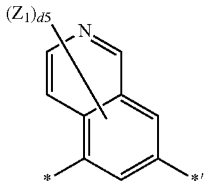
Formula 3-44
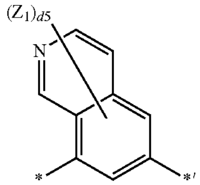
Formula 3-45
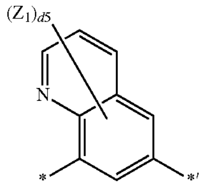
Formula 3-46
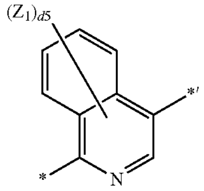
Formula 3-47
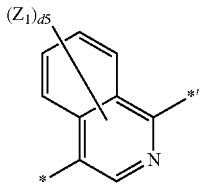
Formula 3-48
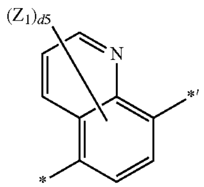
Formula 3-49
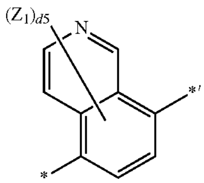
-continued
Formula 3-50
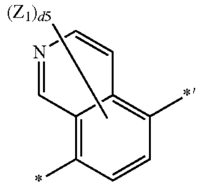
Formula 3-51
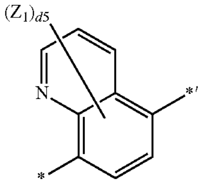
Formula 3-52
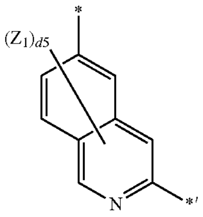
Formula 3-53
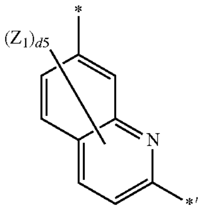
Formula 3-54
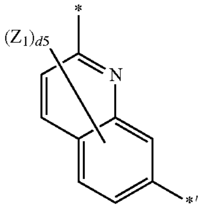
Formula 3-55
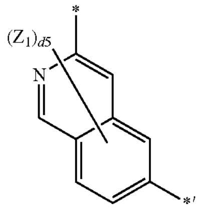
Formula 3-56
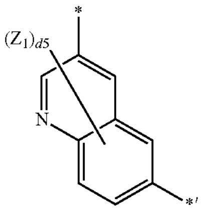

-continued
Formula 3-57
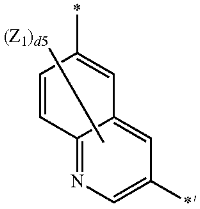
Formula 3-58
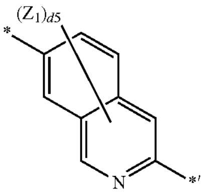
Formula 3-59
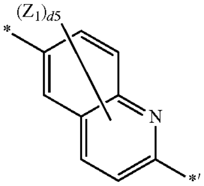
Formula 3-61
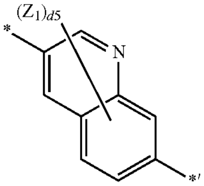
Formula 3-62
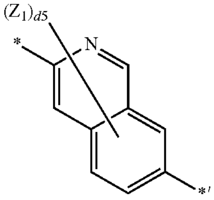
Formula 3-63
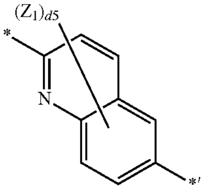
Formula 3-64
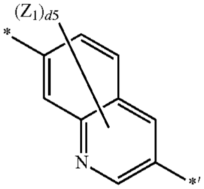
Formula 3-65
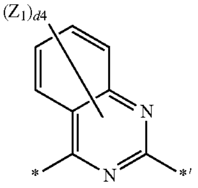
-continued
Formula 3-66
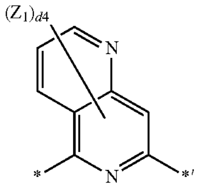
Formula 3-67
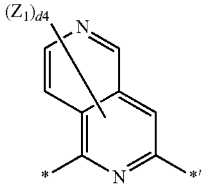
Formula 3-68
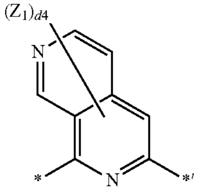
Formula 3-69
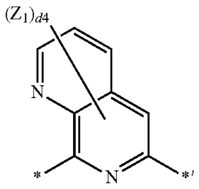
Formula 3-69
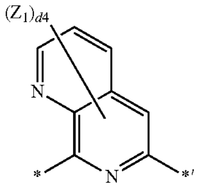
Formula 3-70
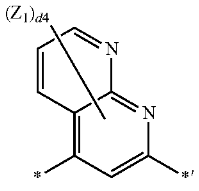
Formula 3-71
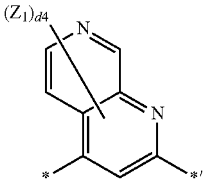
Formula 3-72
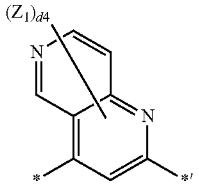

-continued
Formula 3-73
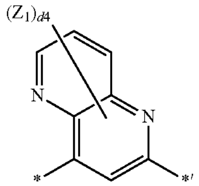
Formula 3-74
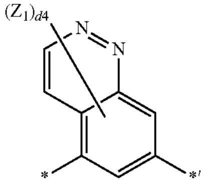
Formula 3-75
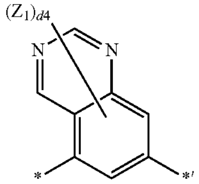
Formula 3-76
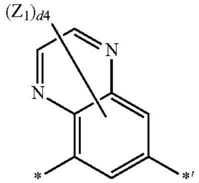
Formula 3-77
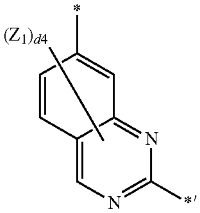
Formula 3-78
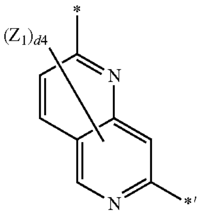
Formula 3-79
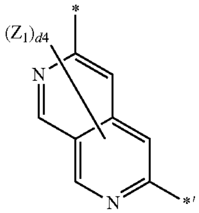
-continued
Formula 3-80
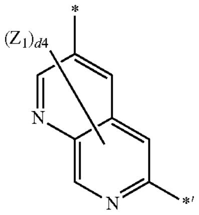
Formula 3-81
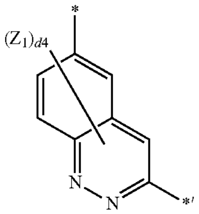
Formula 3-82
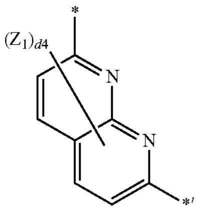
Formula 3-83
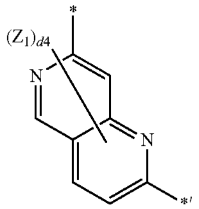
Formula 3-84
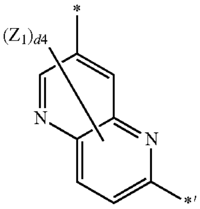
Formula 3-85
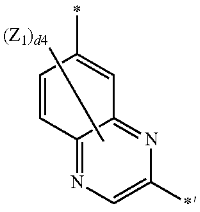
Formula 3-86
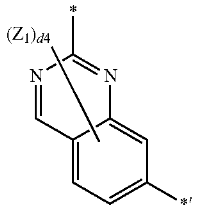

-continued
Formula 3-87
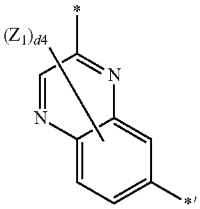
Formula 3-88
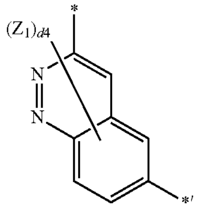
Formula 3-89
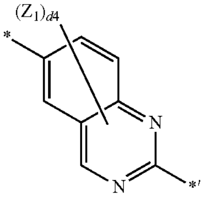
Formula 3-90
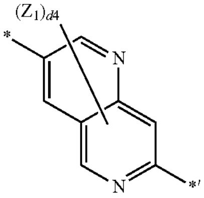
Formula 3-91
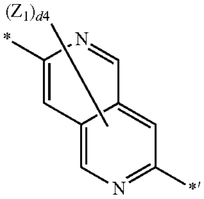
Formula 3-92
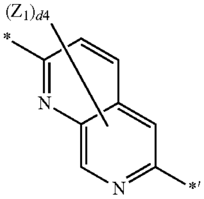
Formula 3-93
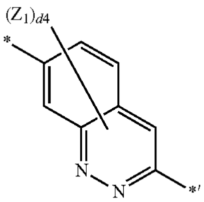
-continued
Formula 3-94
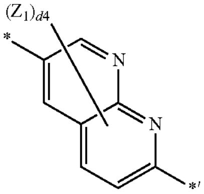
Formula 3-95
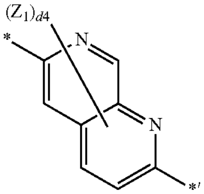
Formula 3-96
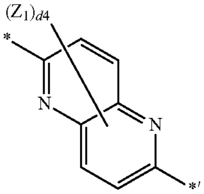
Formula 3-97
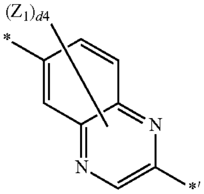
Formula 3-98
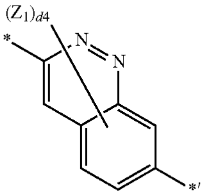
Formula 3-99
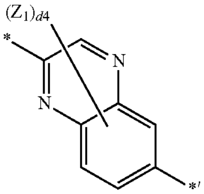
Formula 3-100
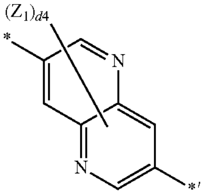
Formula 3-101
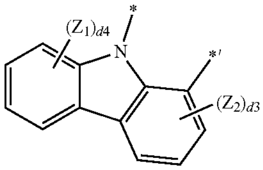

-continued

Formula 3-102

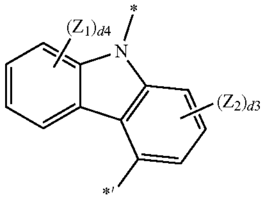

In Formulae 3-1 to 3-102, $Y_1$ may be O, S, $C(Z_3)(Z_4)$, $N(Z_5)$, or $Si(Z_6)(Z_7)$, $Z_1$ to $Z_7$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a siolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, and $—P(=O)(Q_{31})(Q_{32})$, $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, d2 may be an integer from 0 to 2, d3 may be an integer from 0 to 3, d4 may be an integer from 0 to 4, d5 may be an integer from 0 to 5, d6 may be an integer from 0 to 6, d8 may be an integer from 0 to 8, and

* and *' each indicates a binding site to a neighboring atom.

In Formulae 3-1 to 3-102, d2 to d8 indicate the number of sites are substituted. When any d2 to d8 in any of Formulae 3-1 to 3-102 is two or more for any of the corresponding $Z_1$ and $Z_2$, two or more of the corresponding $Z_1$(s) and $Z_2$(s) may be identical to or different from each other. For example, in Formula 3-100, the d4 for $Z_1$ in $(Z_1)_{d4}$ may be 3, then 2 or 3 of these 3 $Z_1$(s) may be identical, or all 3 are different from each other.

In an exemplary embodiment of the present disclosure, $L_1$ to $L_9$ in Formula 1 may each independently be selected from groups represented by Formulae 3-1 to 3-24, and $Z_1$ to $Z_7$ in Formulae 3-1 to 3-24 may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a carbazolyl group, a dibenzofuranyl group, and a dibenzothiophenyl group, but the present disclosure is not limited thereto.

In an exemplary embodiment of the present disclosure, $L_1$ to $L_9$ in Formula 1 may each independently be selected from groups represented by Formulae 4-1 to 4-57:

Formula 4-1

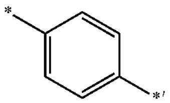

Formula 4-2

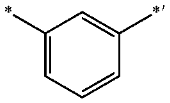

Formula 4-3

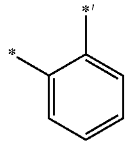

Formula 4-4

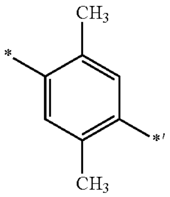

Formula 4-5

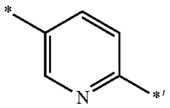

Formula 4-6

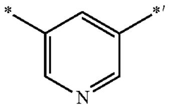

-continued
Formula 4-7
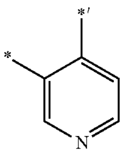
Formula 4-8
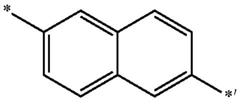
Formula 4-9
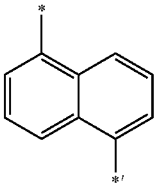
Formula 4-10
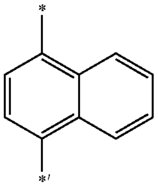
Formula 4-11
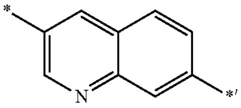
Formula 4-12
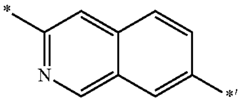
Formula 4-13
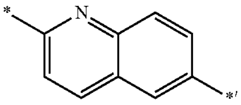
Formula 4-14
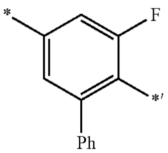
Formula 4-15
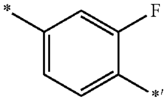
Formula 4-16
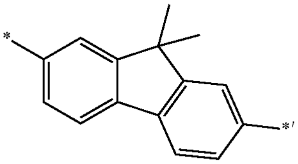
-continued
Formula 4-17
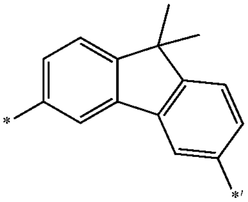
Formula 4-18
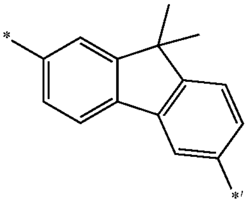
Formula 4-19
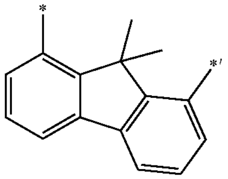
Formula 4-20
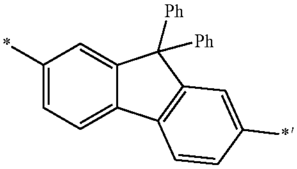
Formula 4-21
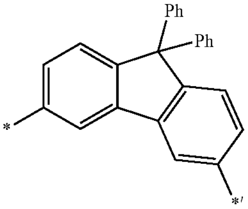
Formula 4-22
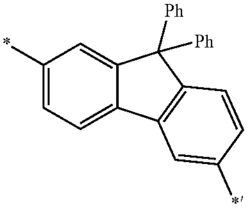
Formula 4-23
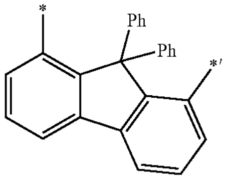
Formula 4-24
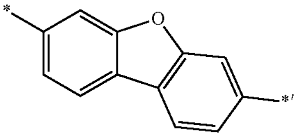

-continued
Formula 4-25
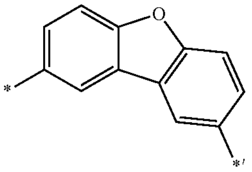
Formula 4-26
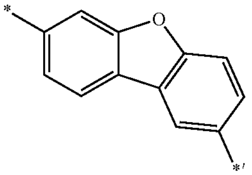
Formula 4-27
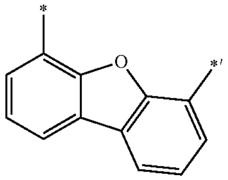
Formula 4-28
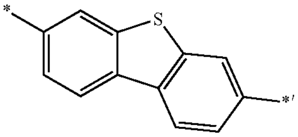
Formula 4-29
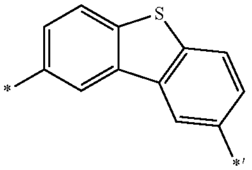
Formula 4-30
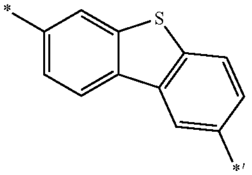
Formula 4-31
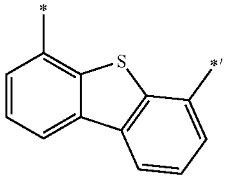
Formula 4-32
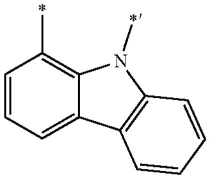
Formula 4-33
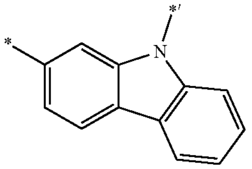
-continued
Formula 4-34
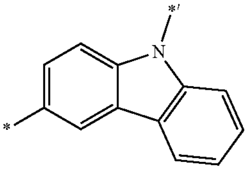
Formula 4-35
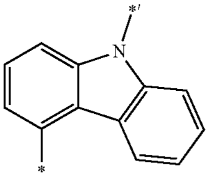
Formula 4-36
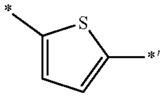
Formula 4-37
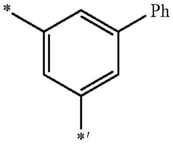
Formula 4-38
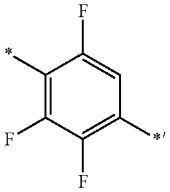
Formula 4-39
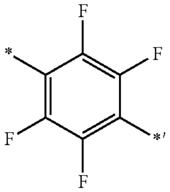
Formula 4-40
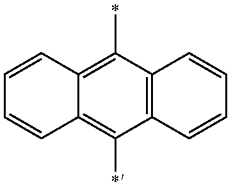
Formula 4-41
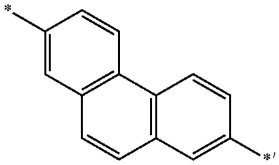
Formula 4-42
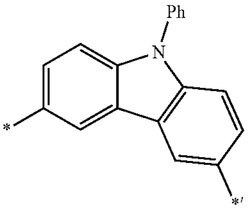

-continued
Formula 4-43
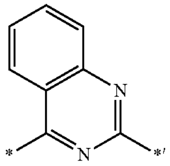
Formula 4-44
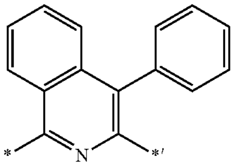
Formula 4-45
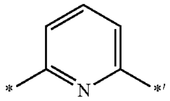
Formula 4-46
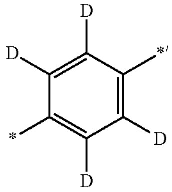
Formula 4-47
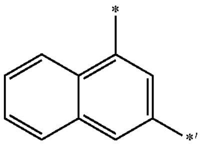
Formula 4-48
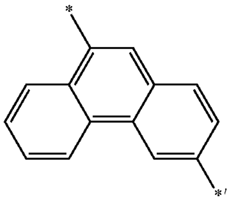
Formula 4-49
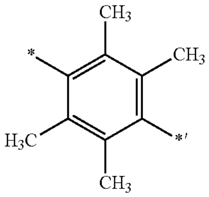
Formula 4-50
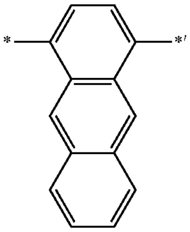
-continued
Formula 4-51
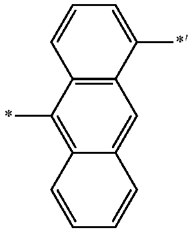
Formula 4-52
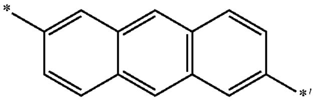
Formula 4-53
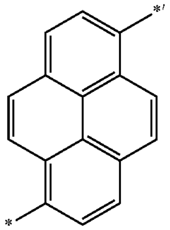
Formula 4-54
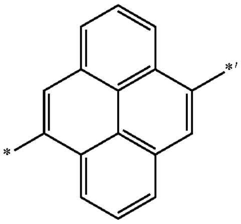
Formula 4-55
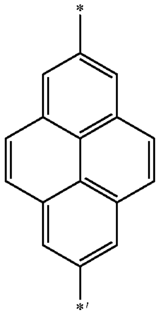
Formula 4-56
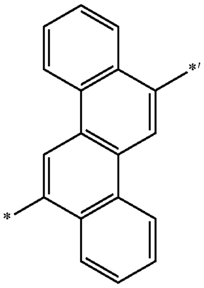
Formula 4-57
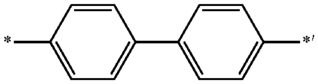
In Formulae 4-1 to 4-57, Ph indicates a phenyl group, and * and *' each indicates a binding site to a neighboring atom.

In an exemplary embodiment of the present disclosure, $L_1$ to $L_9$ in Formula 1 may each independently be selected from groups represented by Formulae 4-1 to 4-35, but the present disclosure is not limited thereto.

In Formula 1, a1 to a9 may each independently be an integer from 0 to 5. As an example, a1 indicates the number of $L_1$(s) in Formula 1, in which, when a1 is 0, *-$(L_1)_{a1}$-*' may be a single bond, and when a1 is two or more, two or more $L_1$(s) may be identical to or different from each other. As such, a2 to a9 may be understood by referring to the description presented in connection with a1 above and the structure of Formula 1.

In an exemplary embodiment of the present disclosure, a1 to a9 in Formula 1 may each independently be 0, 1, or 2. In an exemplary embodiment of the present disclosure, a1 to a9 in Formula 1 may each independently be 0 or 1.

$Ar_1$ to $Ar_6$ in Formula 1 may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In an exemplary embodiment of the present disclosure, $Ar_1$ to $Ar_6$ in Formula 1 may each independently be selected from:

a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group; and a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, in which, $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

In an exemplary embodiment of the present disclosure, $Ar_1$ to $Ar_6$ in Formula 1 may each independently be selected from groups represented by Formulae 5-1 to 5-50 and 6-1 to 6-124:

Formula 5-1

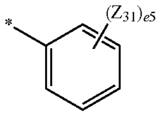

Formula 5-2

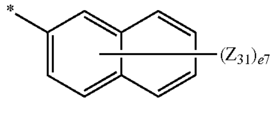

-continued
Formula 5-3
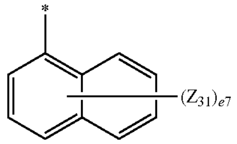
Formula 5-4
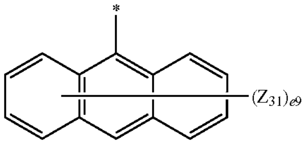
Formula 5-5
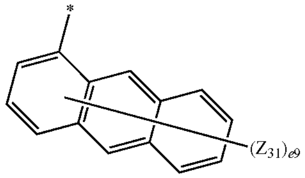
Formula 5-6
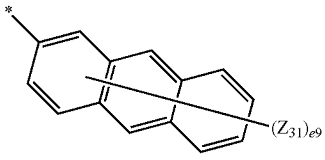
Formula 5-7
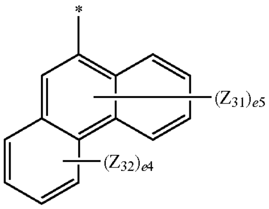
Formula 5-8
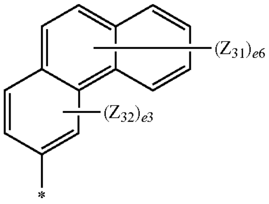
Formula 5-9
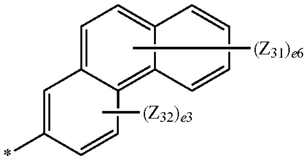
Formula 5-10
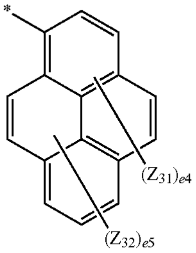
-continued
Formula 5-11
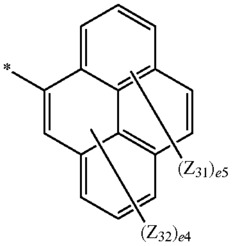
Formula 5-12
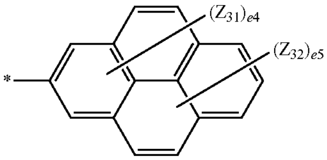
Formula 5-13
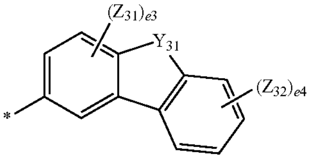
Formula 5-14
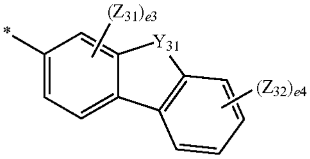
Formula 5-15
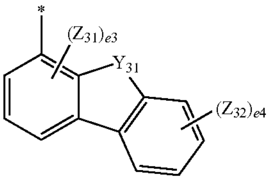
Formula 5-16
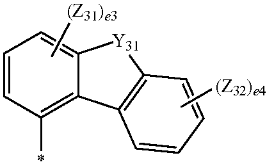
Formula 5-17
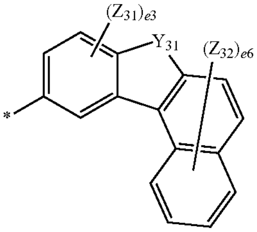
Formula 5-18
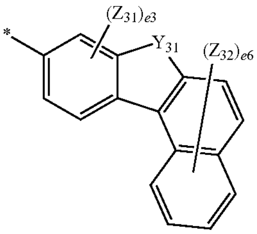

-continued
Formula 5-19
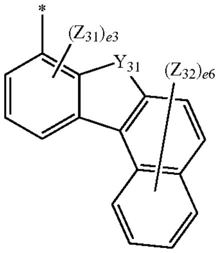
Formula 5-20
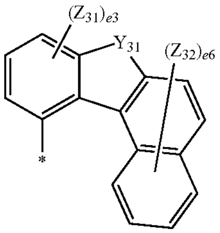
Formula 5-21
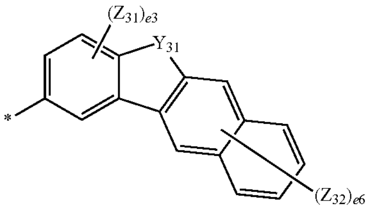
Formula 5-22
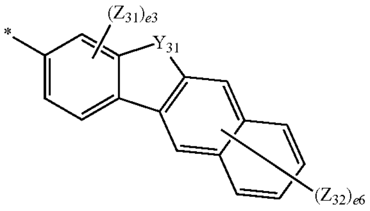
Formula 5-23
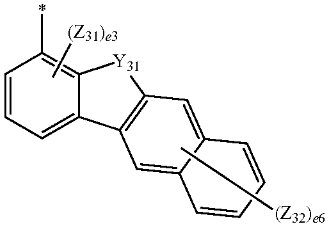
Formula 5-24
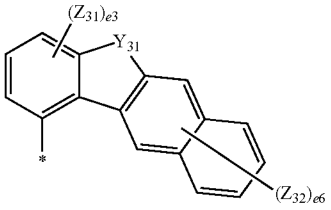
Formula 5-25
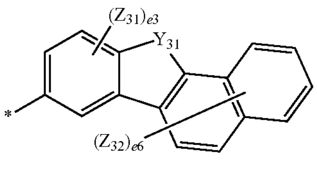
-continued
Formula 5-26
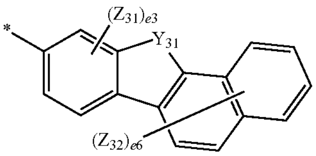
Formula 5-27
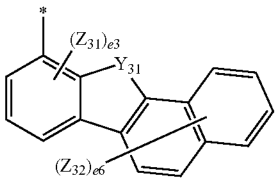
Formula 5-28
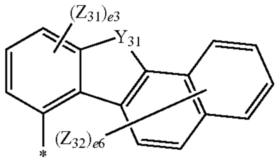
Formula 5-29
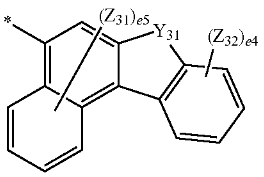
Formula 5-30
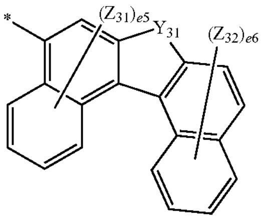
Formula 5-31
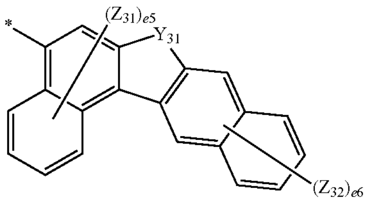
Formula 5-32
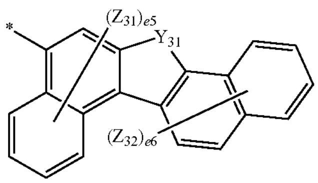
Formula 5-33
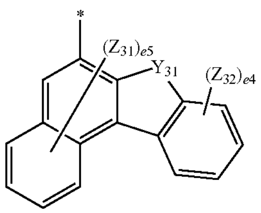

-continued
Formula 5-34
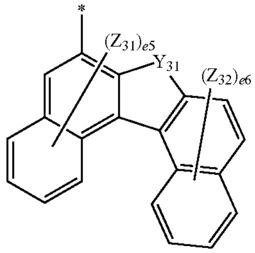
Formula 5-35
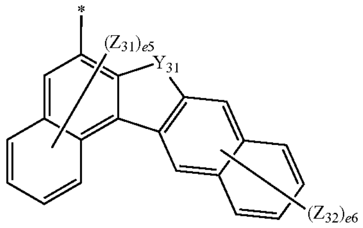
Formula 5-36
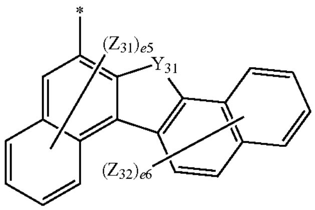
Formula 5-37
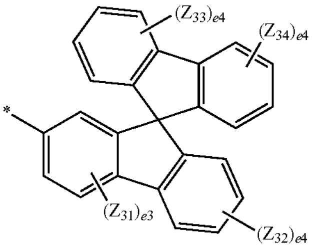
Formula 5-38
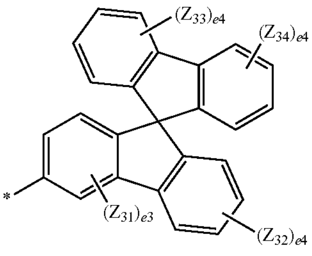
Formula 5-39
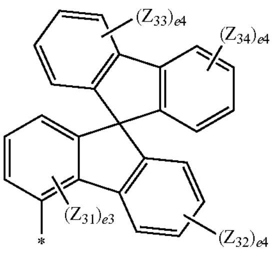
-continued
Formula 5-40
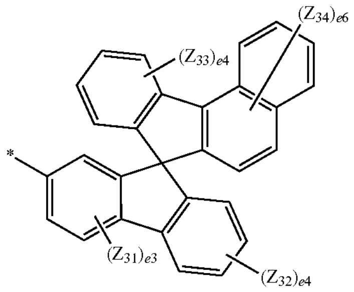
Formula 5-41
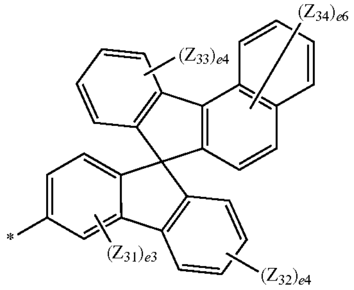
Formula 5-42
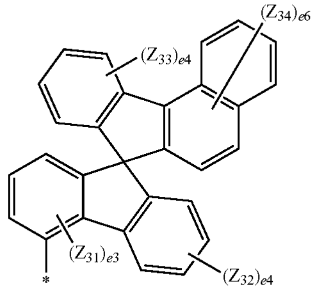
Formula 5-43
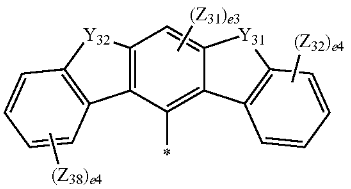
Formula 5-44
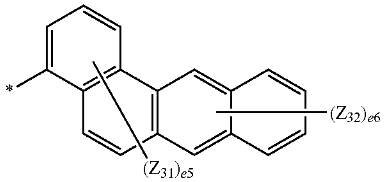
Formula 5-45
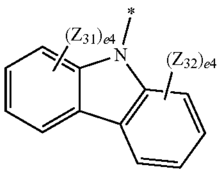

-continued
Formula 5-46
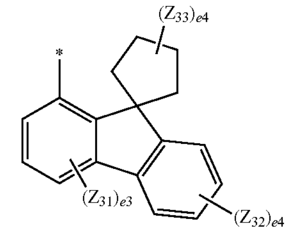
Formula 5-47
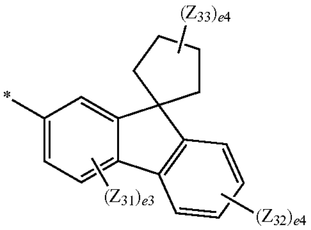
Formula 5-48
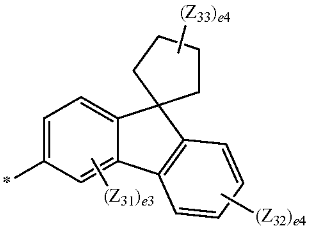
Formula 5-49
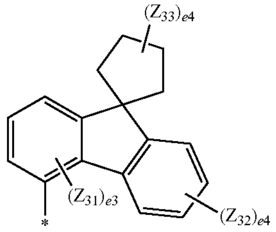
Formula 5-50
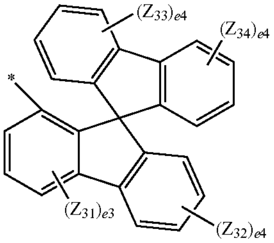
Formula 6-1
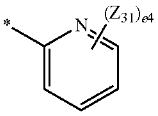
Formula 6-2
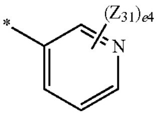
Formula 6-3
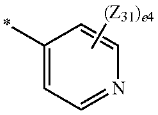
-continued
Formula 6-4
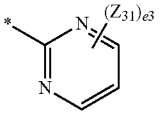
Formula 6-5
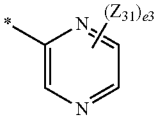
Formula 6-6
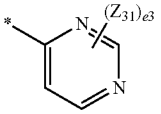
Formula 6-7
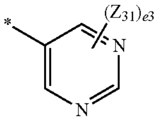
Formula 6-8
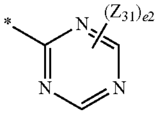
Formula 6-9
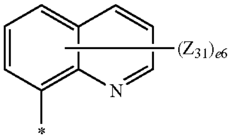
Formula 6-10
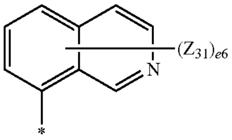
Formula 6-11
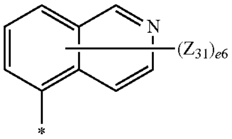
Formula 6-12
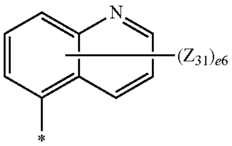
Formula 6-13
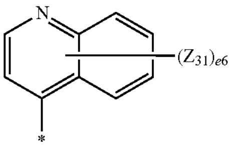
Formula 6-14
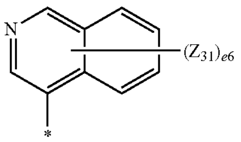

-continued
Formula 6-15
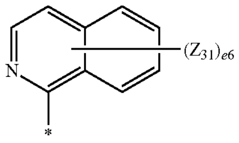
Formula 6-16
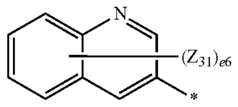
Formula 6-17
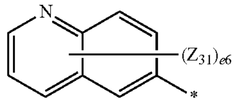
Formula 6-18
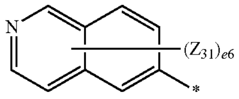
Formula 6-19
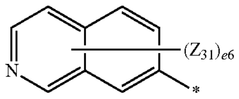
Formula 6-20
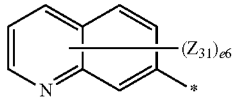
Formula 6-21
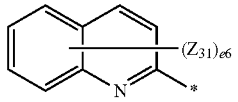
Formula 6-22
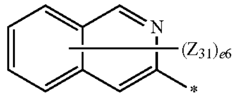
Formula 6-23
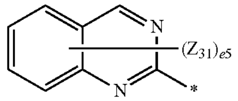
Formula 6-24
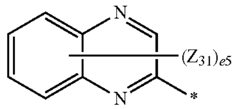
Formula 6-25
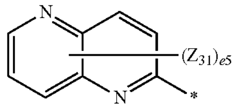
Formula 6-26
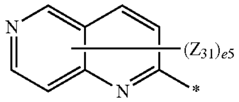
Formula 6-27
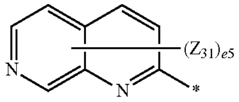
-continued
Formula 6-28
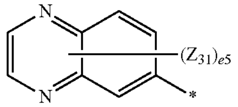
Formula 6-29
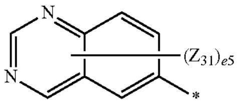
Formula 6-30
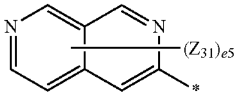
Formula 6-31
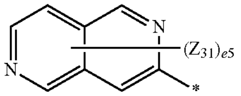
Formula 6-32
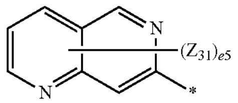
Formula 6-33
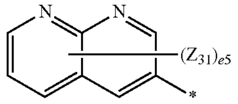
Formula 6-34
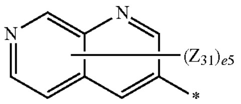
Formula 6-35
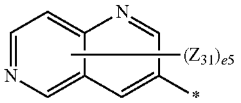
Formula 6-36
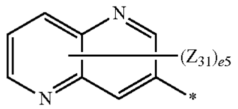
Formula 6-37
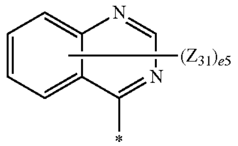
Formula 6-38
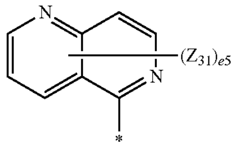
Formula 6-39
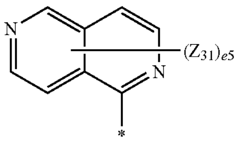

Formula 6-40
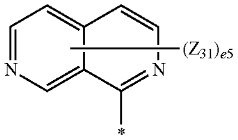
Formula 6-41
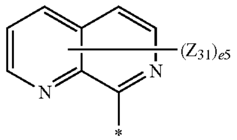
Formula 6-42
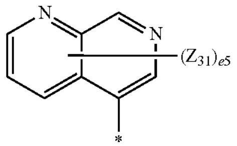
Formula 6-43
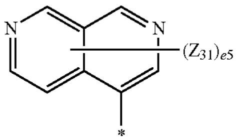
Formula 6-44
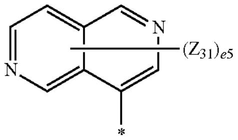
Formula 6-45
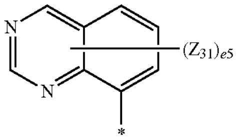
Formula 6-46
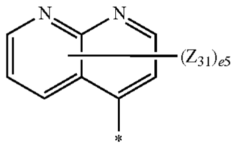
Formula 6-47
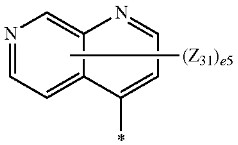
Formula 6-48
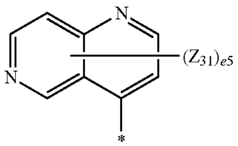
Formula 6-49
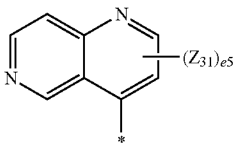
Formula 6-50
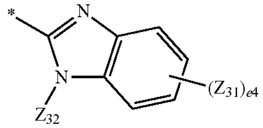
Formula 6-51
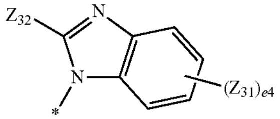
Formula 6-52
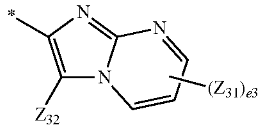
Formula 6-53
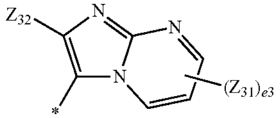
Formula 6-54
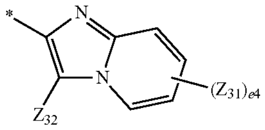
Formula 6-55
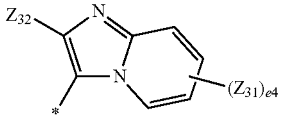
Formula 6-56
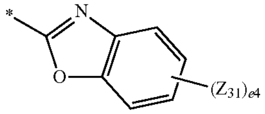
Formula 6-57
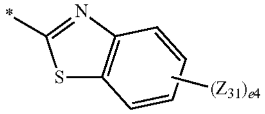
Formula 6-58
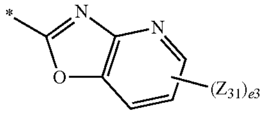
Formula 6-59
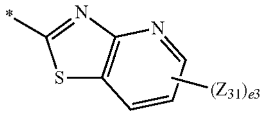
Formula 6-60
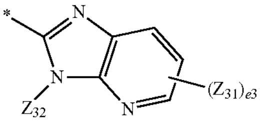
Formula 6-61
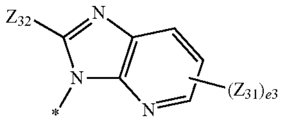

-continued
Formula 6-62
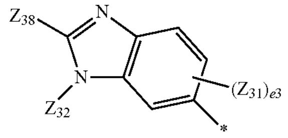
Formula 6-63
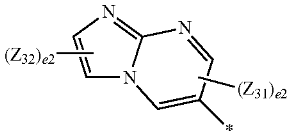
Formula 6-64
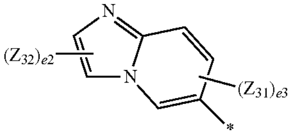
Formula 6-65
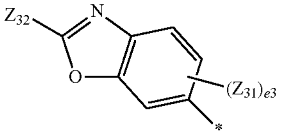
Formula 6-66
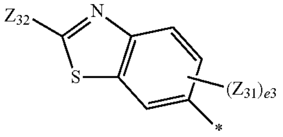
Formula 6-67
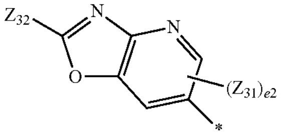
Formula 6-68
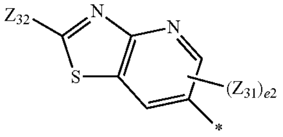
Formula 6-69
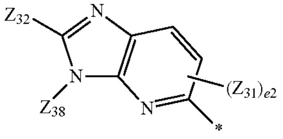
Formula 6-70
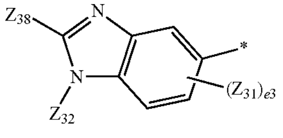
Formula 6-71
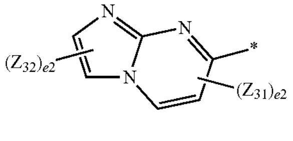
Formula 6-72
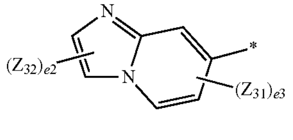
-continued
Formula 6-73
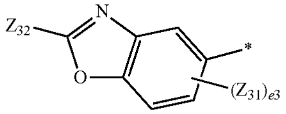
Formula 6-74
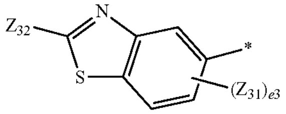
Formula 6-75
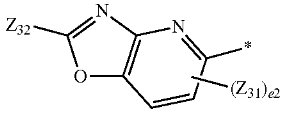
Formula 6-76
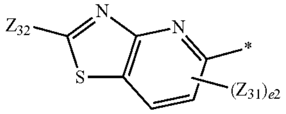
Formula 6-77
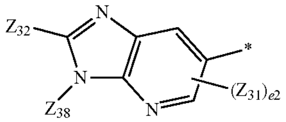
Formula 6-78
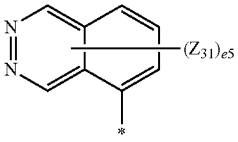
Formula 6-79
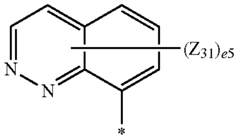
Formula 6-80
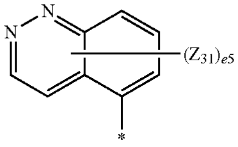
Formula 6-81
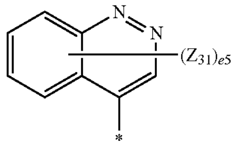
Formula 6-82
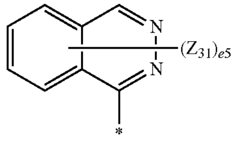
Formula 6-83
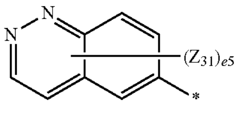

-continued
Formula 6-84
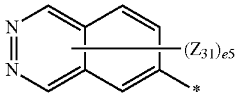
Formula 6-85
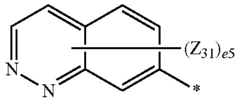
Formula 6-86
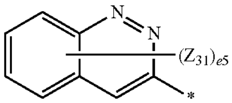
Formula 6-87
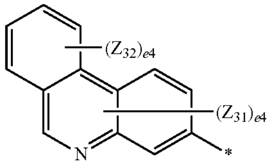
Formula 6-88
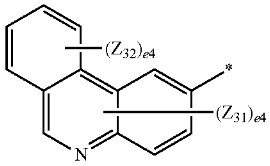
Formula 6-89
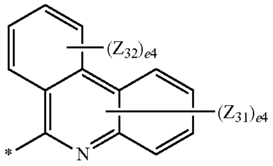
Formula 6-90
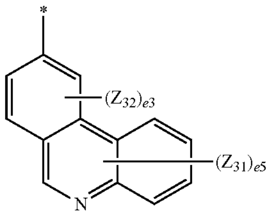
Formula 6-91
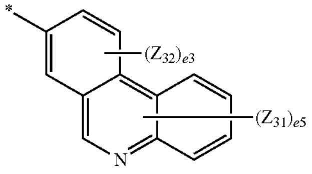
Formula 6-92
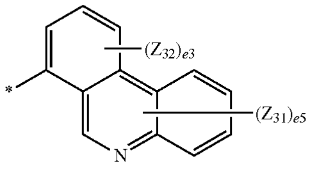
-continued
Formula 6-93
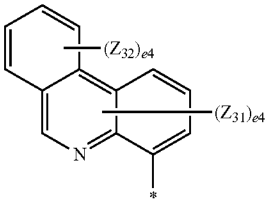
Formula 6-94
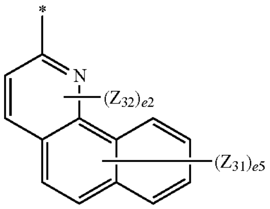
Formula 6-95
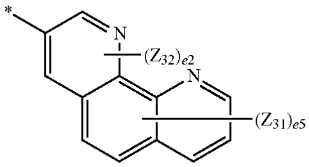
Formula 6-96
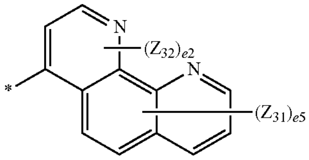
Formula 6-97
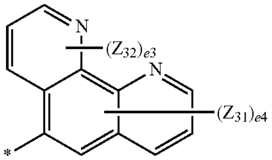
Formula 6-98
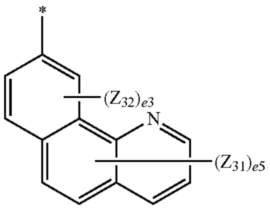
Formula 6-99
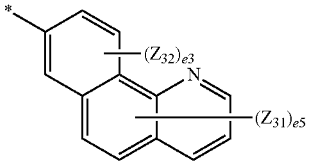
Formula 6-100
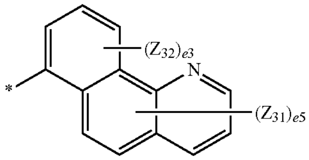

-continued
Formula 6-101
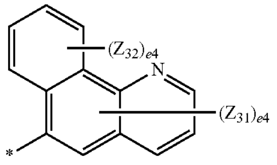
Formula 6-102
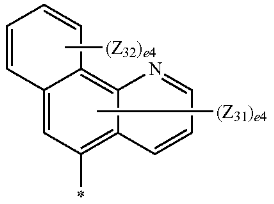
Formula 6-103
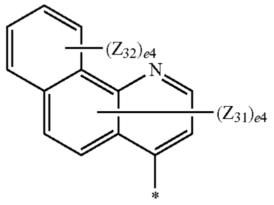
Formula 6-104
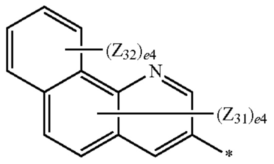
Formula 6-105
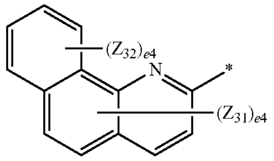
Formula 6-106
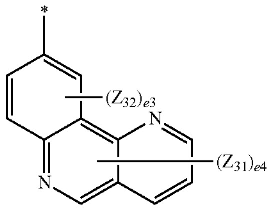
Formula 6-107
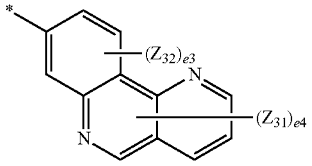
Formula 6-108
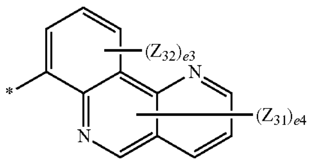
-continued
Formula 6-109
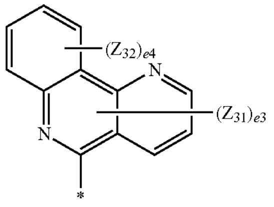
Formula 6-110
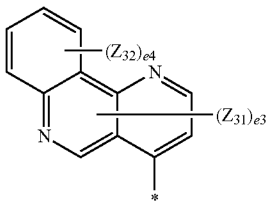
Formula 6-111
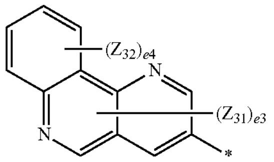
Formula 6-112
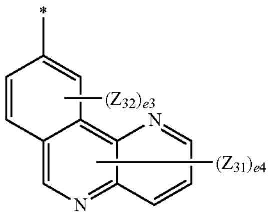
Formula 6-113
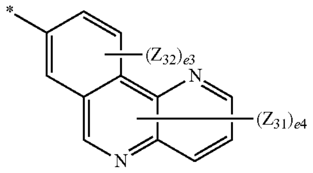
Formula 6-114
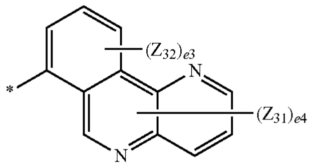
Formula 6-115
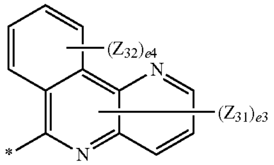
Formula 6-116
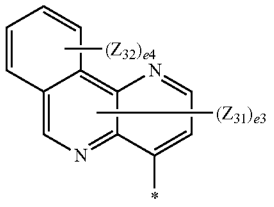

-continued

Formula 6-117

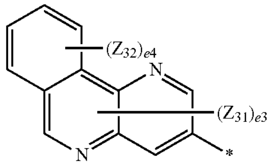

Formula 6-118

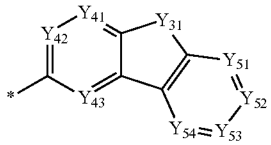

Formula 6-119

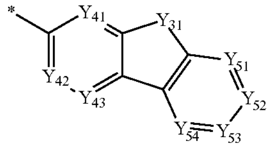

Formula 6-120

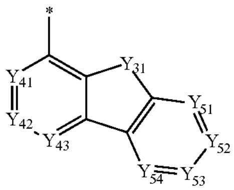

Formula 6-121

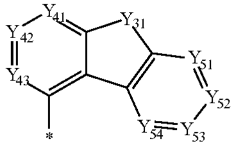

Formula 6-122

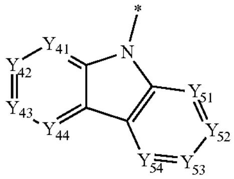

Formula 6-123

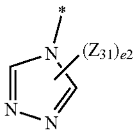

Formula 6-124

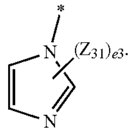

In Formulae 5-1 to 5-50 and 6-1 to 6-124, $Y_{31}$ and $Y_{32}$ may each independently be O, S, $C(Z_{33})(Z_{34})$, $N(Z_{35})$, or $Si(Z_{36})(Z_{37})$, $Y_{41}$ may be N or $C(Z_{41})$, $Y_{42}$ may be N or $C(Z_{42})$, $Y_{43}$ may be N or $C(Z_{43})$, $Y_{44}$ may be N or $C(Z_{44})$, $Y_{51}$ may be N or $C(Z_{51})$, $Y_{52}$ may be N or $C(Z_2)$, $Y_{53}$ may be N or $C(Z_{53})$, $Y_{54}$ may be N or $C(Z_{54})$, at least one of $Y_{41}$ to $Y_{43}$ and $Y_{51}$ to $Y_{54}$ in Formulae 6-118 to 6-121 may be N, and at least one of $Y_{41}$ to $Y_{44}$ and $Y_{51}$ to $Y_{54}$ in Formulae 6-122 may be N, $Z_{31}$ to $Z_{37}$, $Z_{41}$ to $Z_{44}$, and $Z_{51}$ to $Z_{54}$ may each independently be selected from hydrogen, deuterium, —F, —Cl, —Br, —I, —$CF_3$, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, and —$Si(Q_{31})(Q_{32})(Q_{33})$, $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, e2 may be an integer from 0 to 2, e3 may be an integer from 0 to 3, e4 may be an integer from 0 to 4, e5 may be an integer from 0 to 5, e6 may be an integer from 0 to 6, e7 may be an integer from 0 to 7, e9 may be an integer from 0 to 9, and

* indicates a binding site to a neighboring atom.

In Formulae 5-1 to 5-50 and 6-1 to 6-124, e2 to e7 and e9 indicate the number of sites are substituted. When any e2 to e7 and e9 in any of Formulae 5-1 to 5-50 and 6-1 to 6-124 is two or more for any of the corresponding $Z_{31}$ to $Z_{34}$, two or more of the corresponding $Z_{31}$(s) to $Z_{34}$(s) may be identical to or different from each other. For example, in Formula 6-124, the e3 for $Z_{31}$ in $(Z_{31})_{e3}$ may be 3, then 2 or 3 of these 3 $Z_{31}$(s) may be identical, or all 3 are different from each other.

In an exemplary embodiment of the present disclosure, $Ar_1$ to $Ar_6$ in Formula 1 may each independently be selected from groups represented by Formulae 9-1 to 9-116 and 10-1 to 10-121:
Formula 9-1
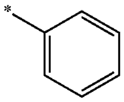
Formula 9-2
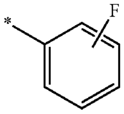
Formula 9-3
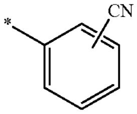
Formula 9-4
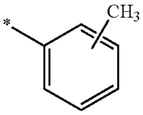
Formula 9-5
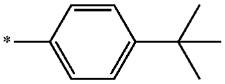
Formula 9-6
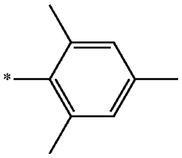
Formula 9-7
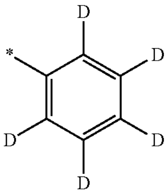
Formula 9-8
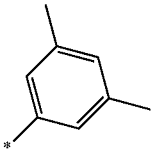
Formula 9-9
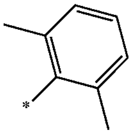
Formula 9-10
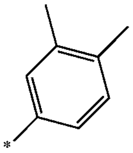
-continued
Formula 9-11
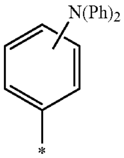
Formula 9-12
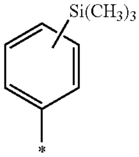
Formula 9-13
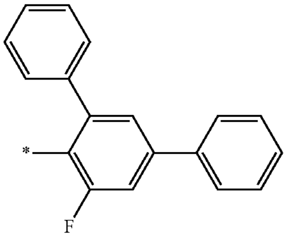
Formula 9-14
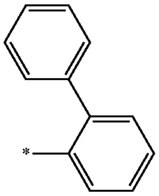
Formula 9-15
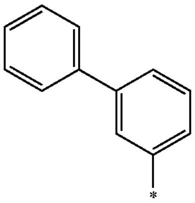
Formula 9-16
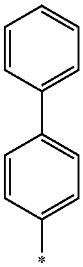
Formula 9-17
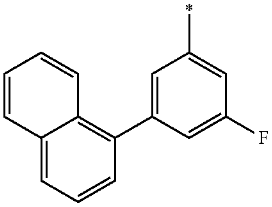

-continued
Formula 9-18
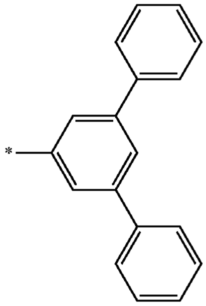
Formula 9-19
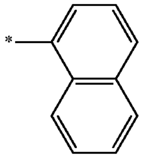
Formula 9-20
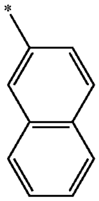
Formula 9-21
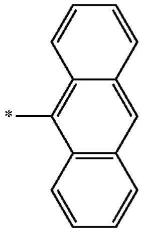
Formula 9-22
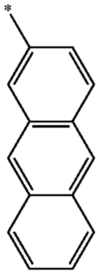
Formula 9-23
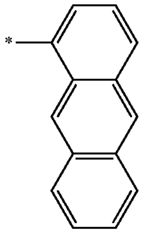
-continued
Formula 9-24
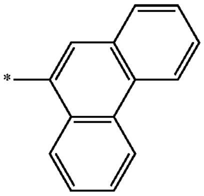
Formula 9-25
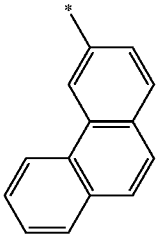
Formula 9-26
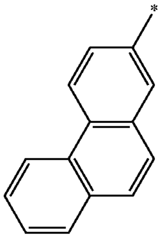
Formula 9-27
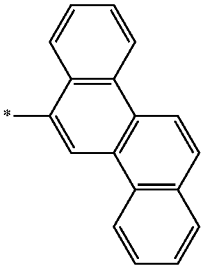
Formula 9-28
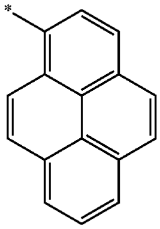
Formula 9-29
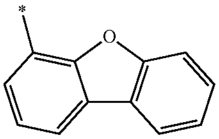
Formula 9-30
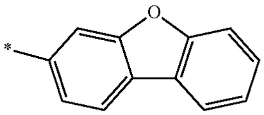
Formula 9-31
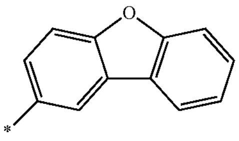

-continued
Formula 9-32
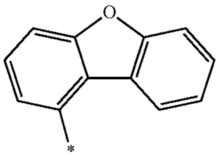
Formula 9-33
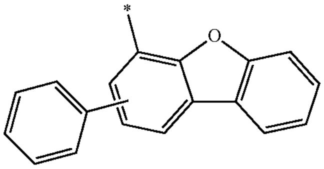
Formula 9-34
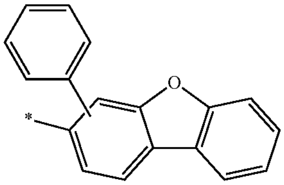
Formula 9-35
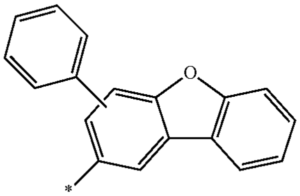
Formula 9-36
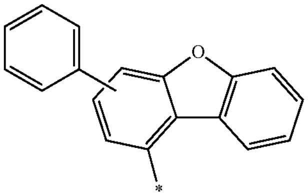
Formula 9-37
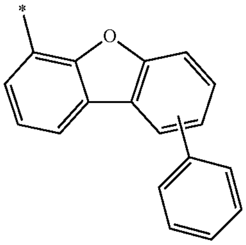
Formula 9-38
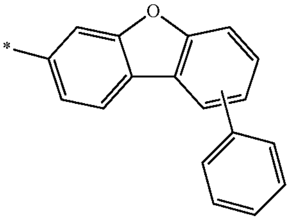
-continued
Formula 9-39
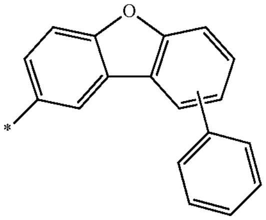
Formula 9-40
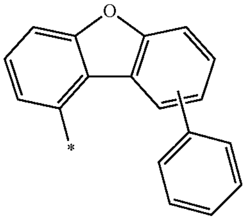
Formula 9-41
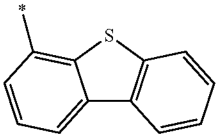
Formula 9-42
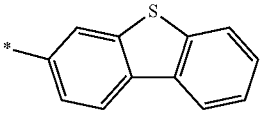
Formula 9-43
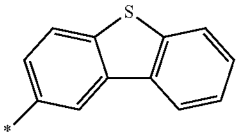
Formula 9-44
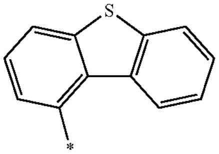
Formula 9-45
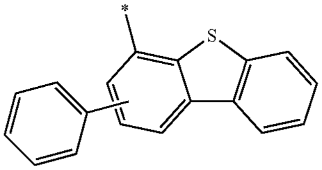
Formula 9-46
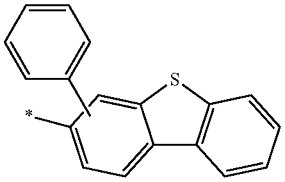
Formula 9-47
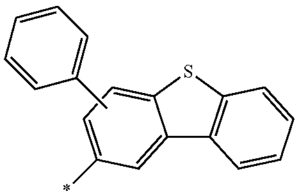

-continued
Formula 9-48
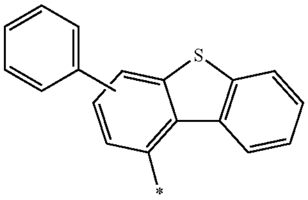
Formula 9-49
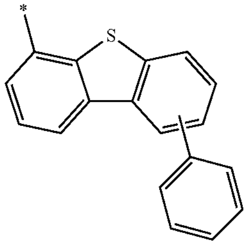
Formula 9-50
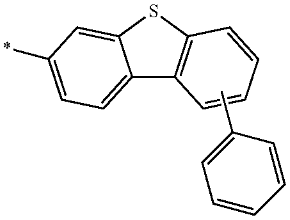
Formula 9-51
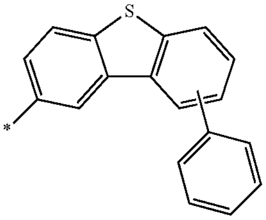
Formula 9-52
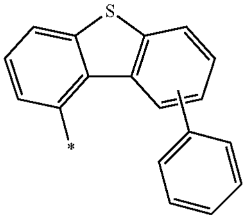
Formula 9-53
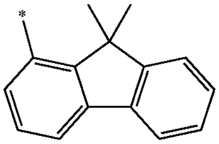
Formula 9-54
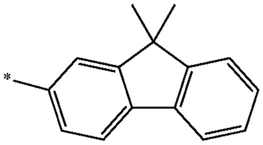
Formula 9-55
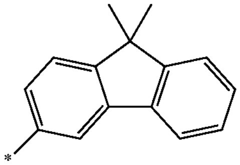
-continued
Formula 9-56
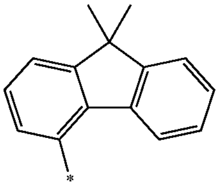
Formula 9-57
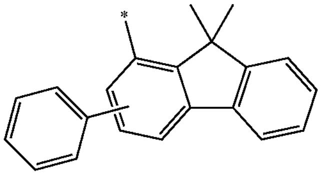
Formula 9-58
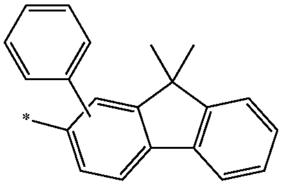
Formula 9-59
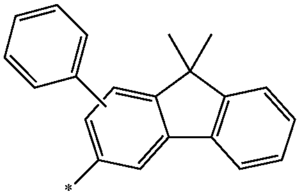
Formula 9-60
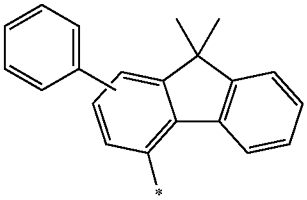
Formula 9-61
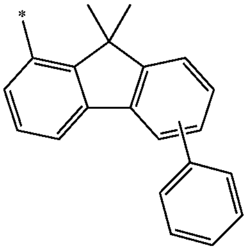
Formula 9-62
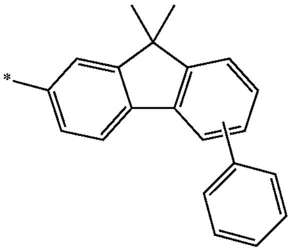

-continued
Formula 9-63
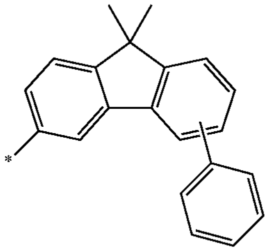
Formula 9-64
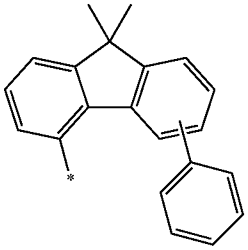
Formula 9-65
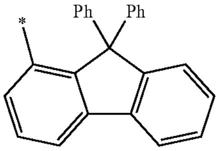
Formula 9-66
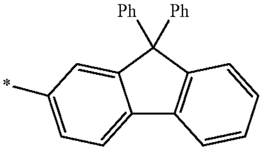
Formula 9-67
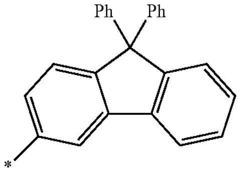
Formula 9-68
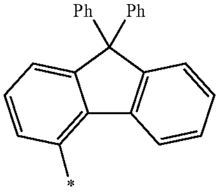
Formula 9-69
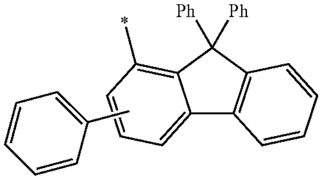
Formula 9-70
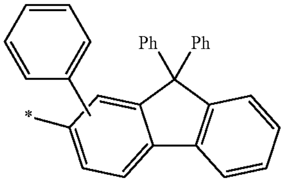
-continued
Formula 9-71
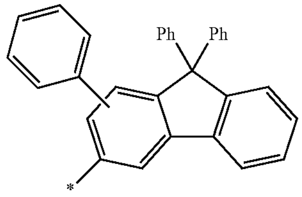
Formula 9-72
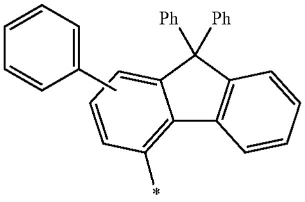
Formula 9-73
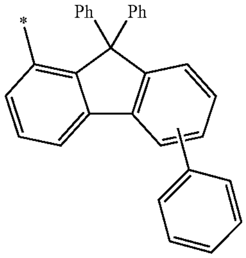
Formula 9-74
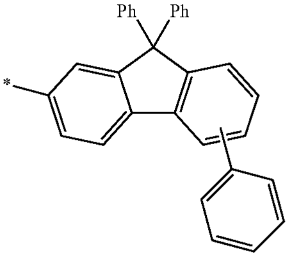
Formula 9-75
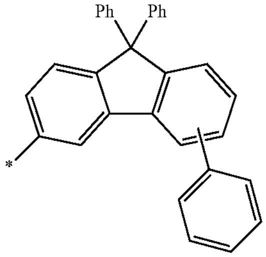
Formula 9-76
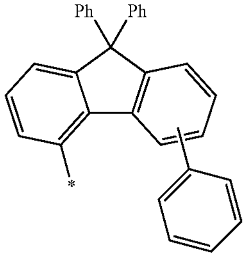

-continued
Formula 9-77
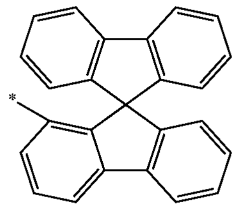
Formula 9-78
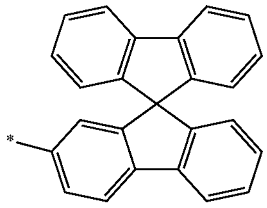
Formula 9-79
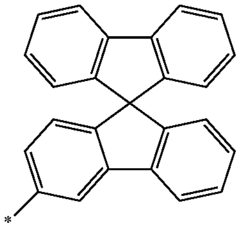
Formula 9-80
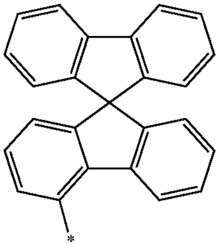
Formula 9-81
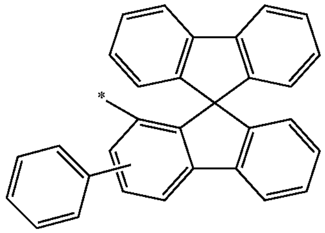
Formula 9-82
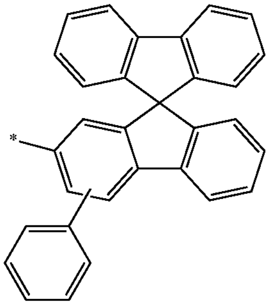
-continued
Formula 9-83
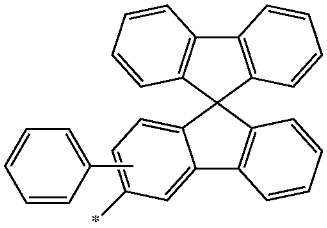
Formula 9-84
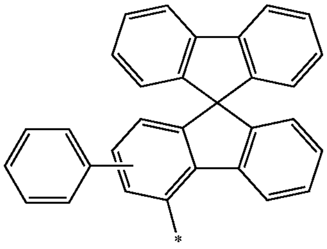
Formula 9-85
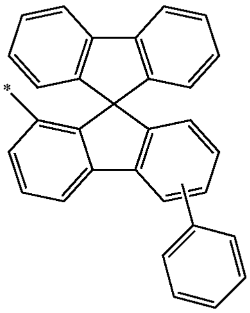
Formula 9-86
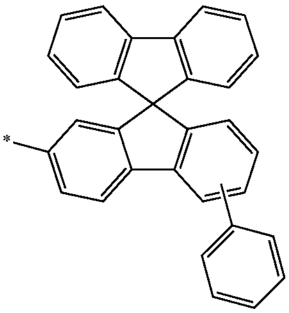
Formula 9-87
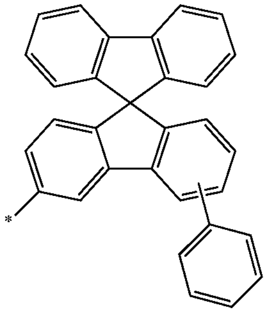

-continued
Formula 9-88
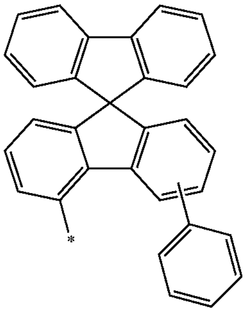
Formula 9-89
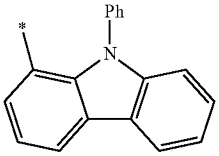
Formula 9-90
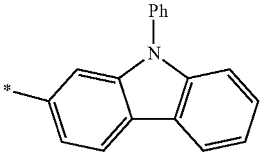
Formula 9-91
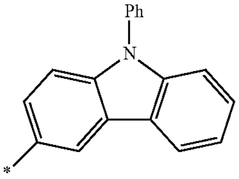
Formula 9-92
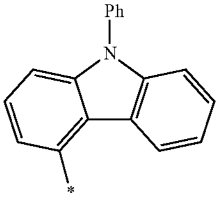
Formula 9-93
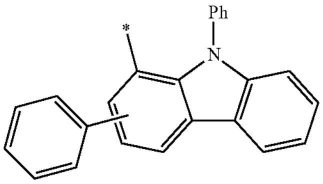
Formula 9-94
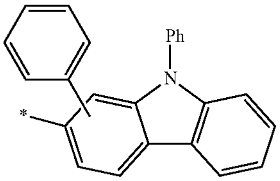
Formula 9-95
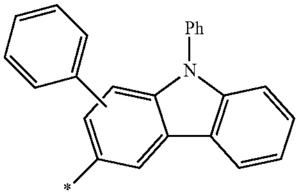
-continued
Formula 9-96
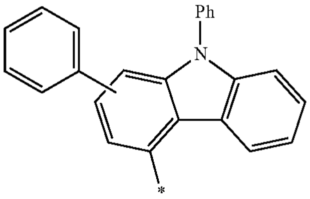
Formula 9-97
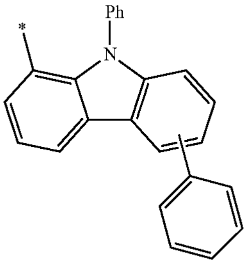
Formula 9-98
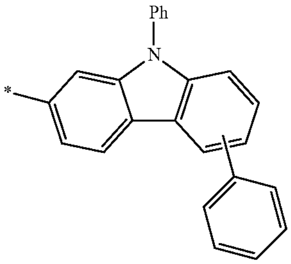
Formula 9-99
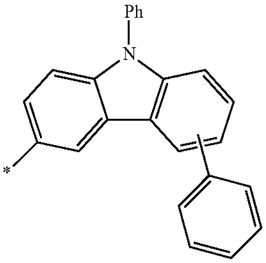
Formula 9-100
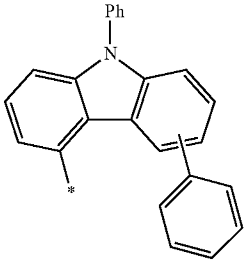
Formula 9-101
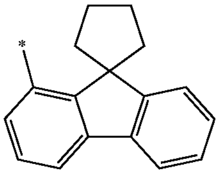

-continued
Formula 9-102
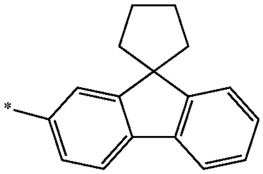
Formula 9-103
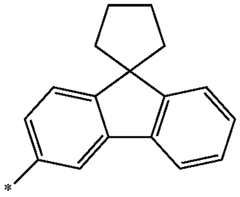
Formula 9-104
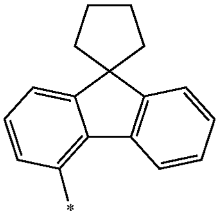
Formula 9-105
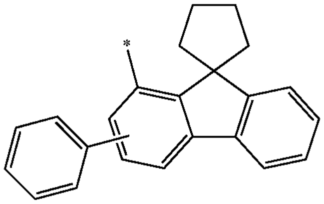
Formula 9-106
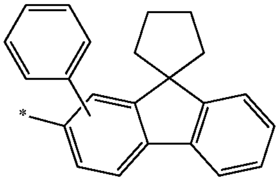
Formula 9-107
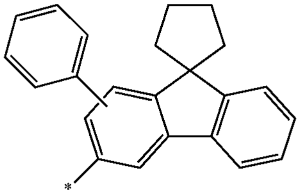
Formula 9-108
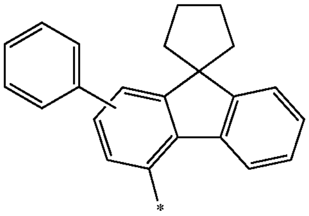
-continued
Formula 9-109
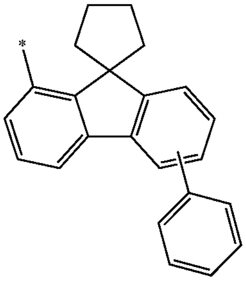
Formula 9-110
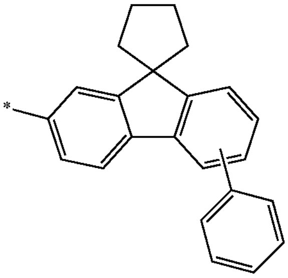
Formula 9-111
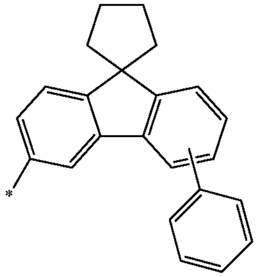
Formula 9-112
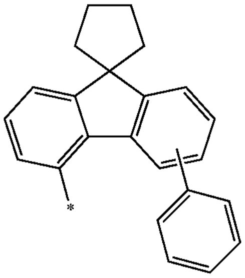
Formula 9-113
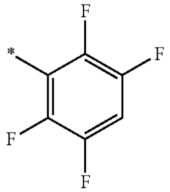
Formula 9-114
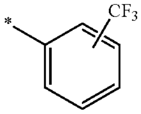

-continued
Formula 9-115
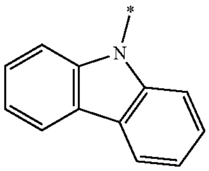
Formula 9-116
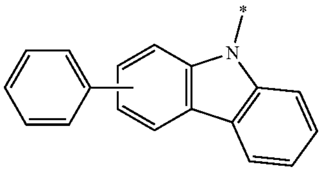
Formula 10-1
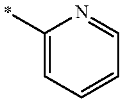
Formula 10-2
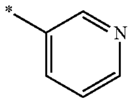
Formula 10-3
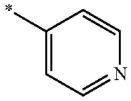
Formula 10-4
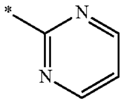
Formula 10-5
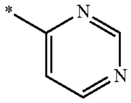
Formula 10-6
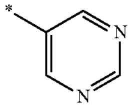
Formula 10-7
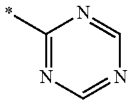
Formula 10-8
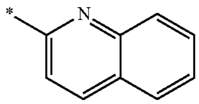
Formula 10-9
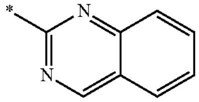
Formula 10-10
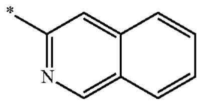
-continued
Formula 10-11
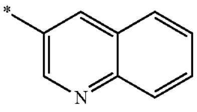
Formula 10-12
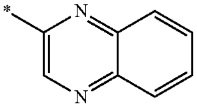
Formula 10-13
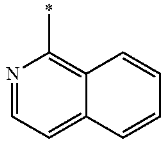
Formula 10-14
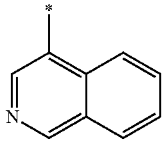
Formula 10-15
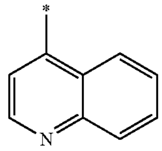
Formula 10-16
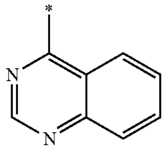
Formula 10-17
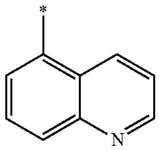
Formula 10-18
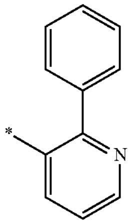
Formula 10-19
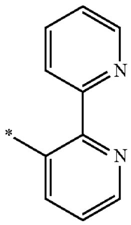

-continued
Formula 10-20
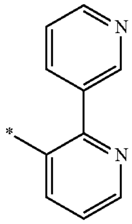
Formula 10-21
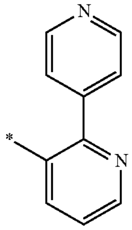
Formula 10-22
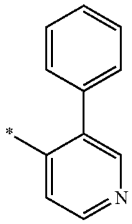
Formula 10-23
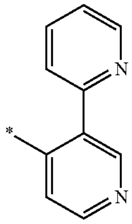
Formula 10-24
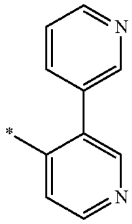
Formula 10-25
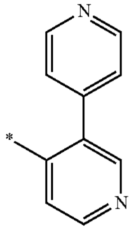
Formula 10-26
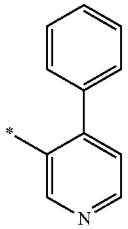
-continued
Formula 10-27
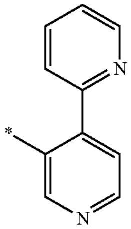
Formula 10-28
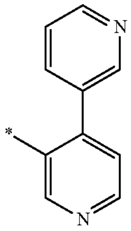
Formula 10-29
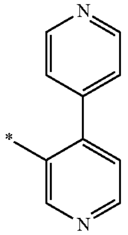
Formula 10-30
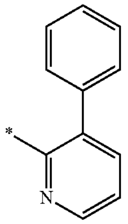
Formula 10-31
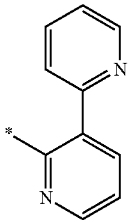
Formula 10-32
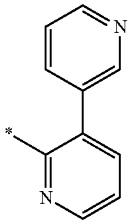

-continued
Formula 10-33
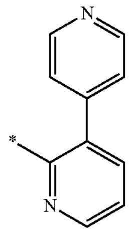
Formula 10-34
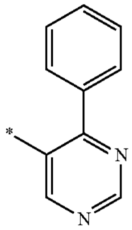
Formula 10-35
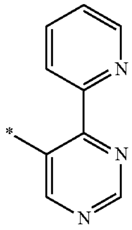
Formula 10-36
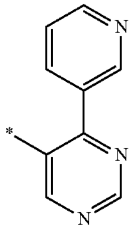
Formula 10-37
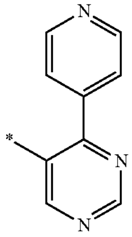
Formula 10-38
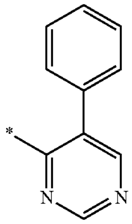
-continued
Formula 10-39
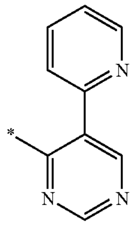
Formula 10-40
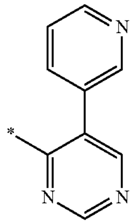
Formula 10-41
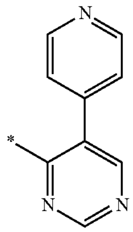
Formula 10-42
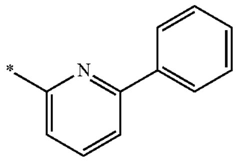
Formula 10-43
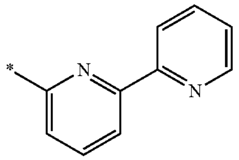
Formula 10-44
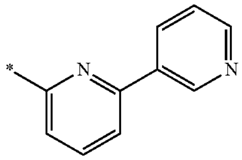
Formula 10-45
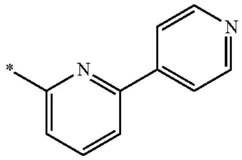
Formula 10-46
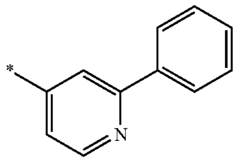

-continued
Formula 10-47
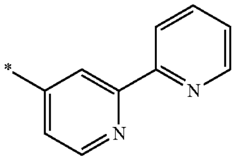
Formula 10-48
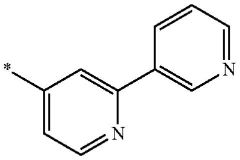
Formula 10-49
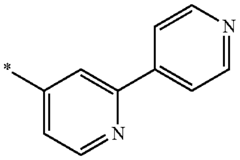
Formula 10-50
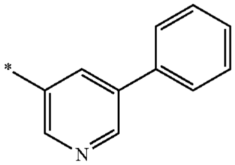
Formula 10-51
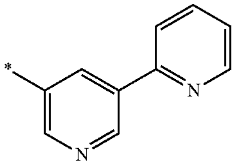
Formula 10-52
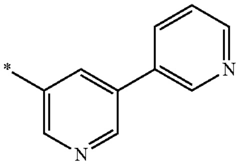
Formula 10-53
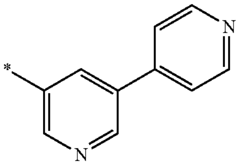
Formula 10-54
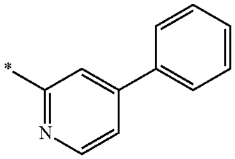
Formula 10-55
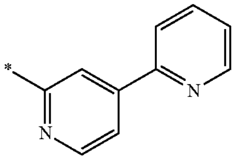
-continued
Formula 10-56
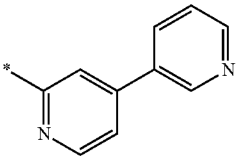
Formula 10-57
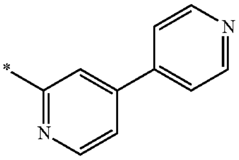
Formula 10-58
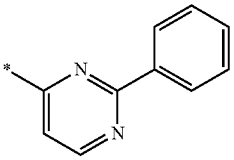
Formula 10-59
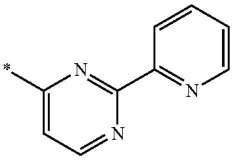
Formula 10-60
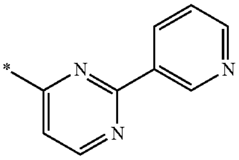
Formula 10-61
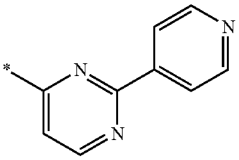
Formula 10-62
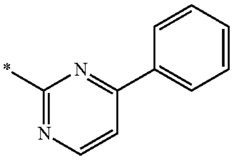
Formula 10-63
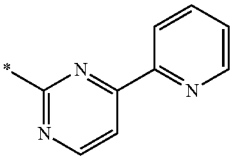
Formula 10-64
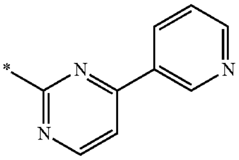

-continued
Formula 10-65
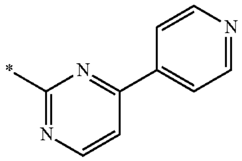
Formula 10-66
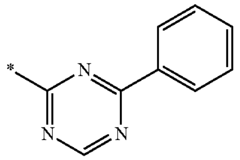
Formula 10-67
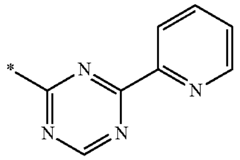
Formula 10-68
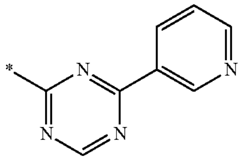
Formula 10-69
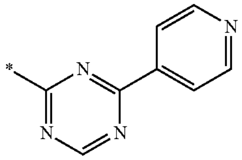
Formula 10-70
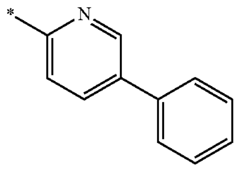
Formula 10-71
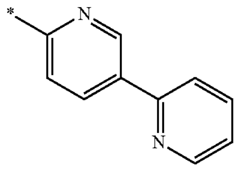
Formula 10-72
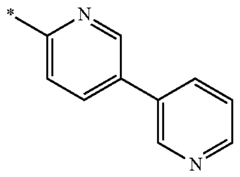
Formula 10-73
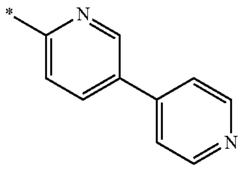
-continued
Formula 10-74
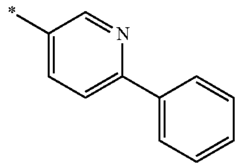
Formula 10-75
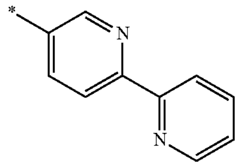
Formula 10-76
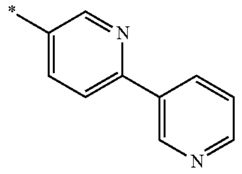
Formula 10-77
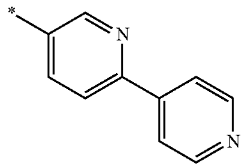
Formula 10-78
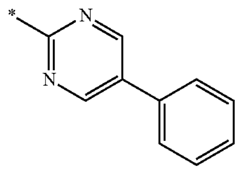
Formula 10-79
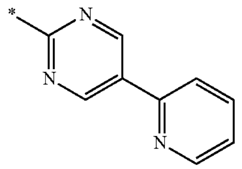
Formula 10-80
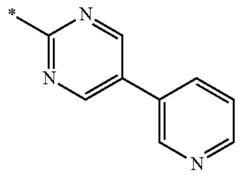
Formula 10-81
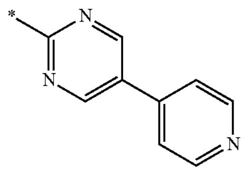
Formula 10-82
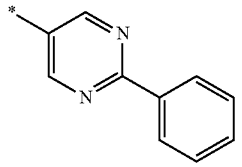

-continued
Formula 10-83
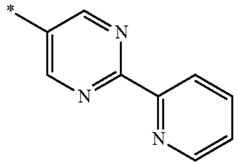
Formula 10-84
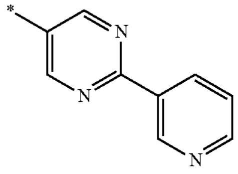
Formula 10-85
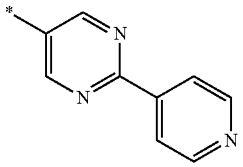
Formula 10-86
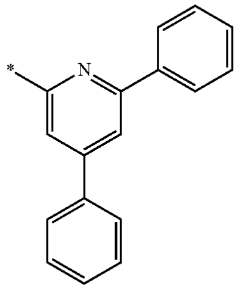
Formula 10-87
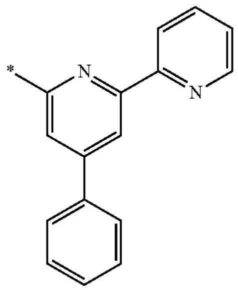
Formula 10-88
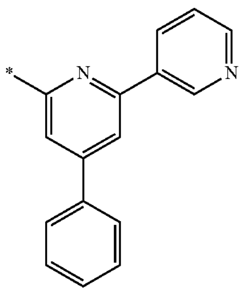
-continued
Formula 10-89
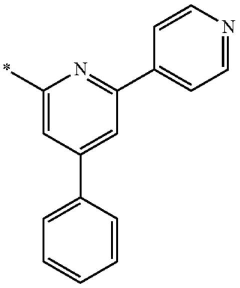
Formula 10-90
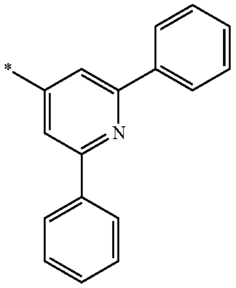
Formula 10-91
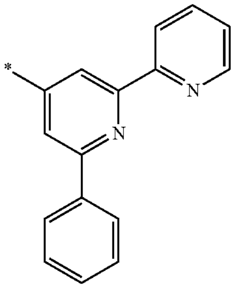
Formula 10-92
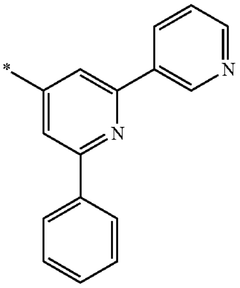
Formula 10-93
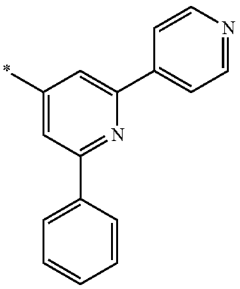

-continued
Formula 10-94
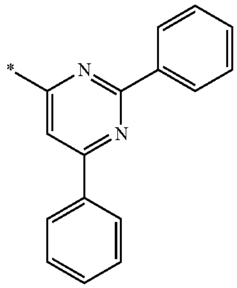
Formula 10-95
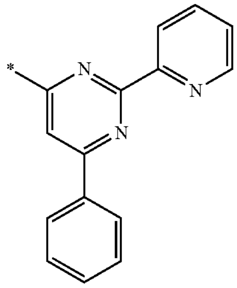
Formula 10-96
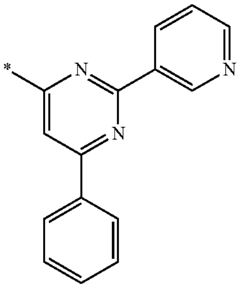
Formula 10-97
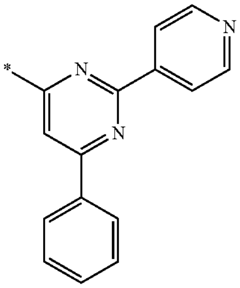
Formula 10-98
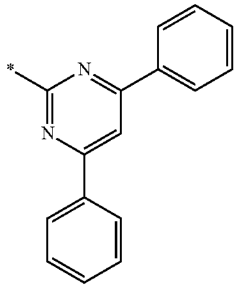
-continued
Formula 10-99
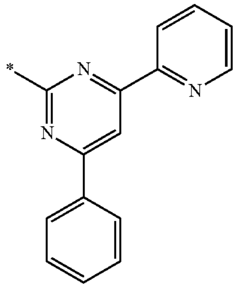
Formula 10-100
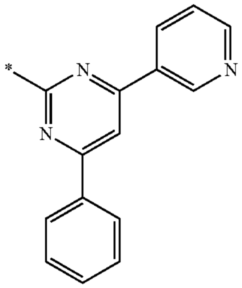
Formula 10-101
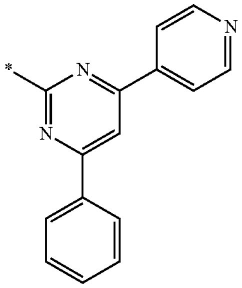
Formula 10-102
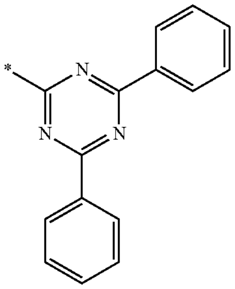
Formula 10-103
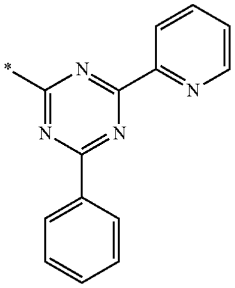

-continued
Formula 10-104
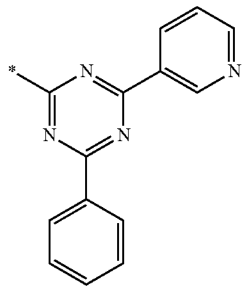
Formula 10-105
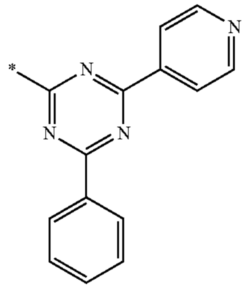
Formula 10-106
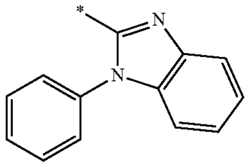
Formula 10-107
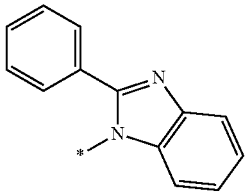
Formula 10-108
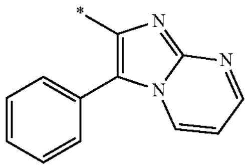
Formula 10-109
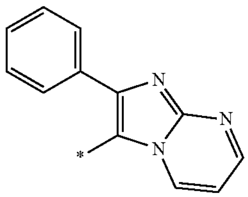
Formula 10-110
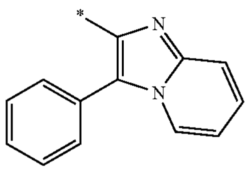
-continued
Formula 10-111
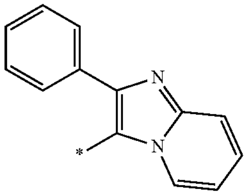
Formula 10-112
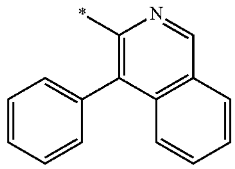
Formula 10-113
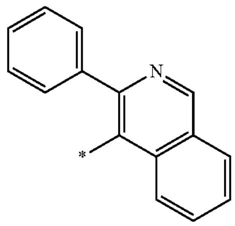
Formula 10-114
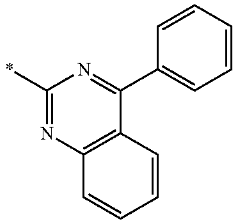
Formula 10-115
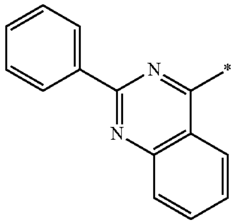
Formula 10-116
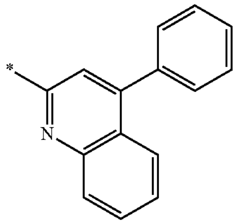
Formula 10-117
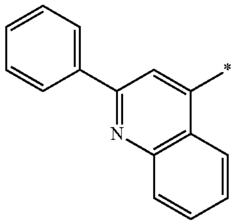

-continued

Formula 10-118

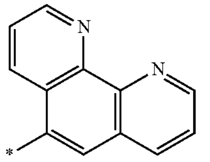

Formula 10-119

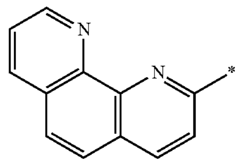

Formula 10-120

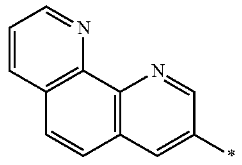

Formula 10-121

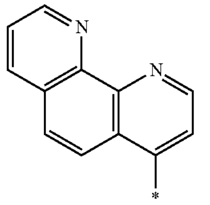

In Formulae 9-1 to 9-116 and 10-1 to 10-121, Ph indicates a phenyl group, and * indicates a binding site to a neighboring atom.

In an exemplary embodiment of the present disclosure, $Ar_1$ to $Ar_6$ in Formula 1 may each independently be selected from groups represented by Formulae 5-1 to 5-50 and 6-1 to 6-3 (for example, groups represented by Formulae 9-1 to 9-116 and 10-1 to 10-3).

In Formula 1, b1 to b6 may each independently be an integer from 1 to 5. In an example, b1 indicates the number of $Ar_1$(s) in Formula 1, in which, when b1 is two or more, two or more $Ar_1$(s) may be identical to or different from each other. As such, b2 to b6 may be understood by referring to the description provided in connection with b1 above and the structure of Formula 1.

In an exemplary embodiment of the present disclosure, b1 to b6 in Formula 1 may each independently be 1 or 2. In an exemplary embodiment of the present disclosure, b1 to b6 in Formula 1 may each be 1.

$R_1$ to $R_5$ in Formula 1 may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $—Si(Q_1)(Q_2)(Q_3)$, $—N(Q_1)(Q_2)$, $—B(Q_1)(Q_2)$, $—C(=O)(Q_1)$, $—S(=O)_2(Q_1)$, and $—P(=O)(Q_1)(Q_2)$.

In an exemplary embodiment of the present disclosure, $R_1$ to $R_5$ in Formula 1 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, and —$Si(Q_{31})(Q_{32})(Q_{33})$, in which, $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

In an exemplary embodiment of the present disclosure, $R_1$ to $R_5$ in Formula 1 may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a mesityl group, and —$Si(Q_1)(Q_2)(Q_3)$, in which $Q_1$ to $Q_3$ may each independently be selected from a $C_1$-$C_{20}$ alkyl group, a $C_1$-$C_{20}$ alkoxy group, a phenyl group, a biphenyl group, a terphenyl group, and a naphthyl group.

In an exemplary embodiment of the present disclosure, in Formula 1, $R_1$ to $R_3$ may each be hydrogen, and $R_4$ and $R_5$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a mesityl group.

In Formula 1, c1 to c3 may each independently be an integer from 0 to 5. In an example, c1 indicates the number of $R_1$(s) in Formula 1, in which, when c1 is two or more, two or more $R_1$(s) may be identical to or different from each other. As such, c2 and c3 may be understood by referring to the description provided in connection with c1 above and the structure of Formula 1.

In an exemplary embodiment of the present disclosure, c1 to c3 in Formula 1 may each independently be 0 or 1. In an exemplary embodiment of the present disclosure, c1 to c3 in Formula 1 may each be 0.

In Formula 1, n1 to n3 may each independently be 0 or 1, provided that the sum of n1, n2, and n3 is 1. Here, n1 indicates the number of groups represented by

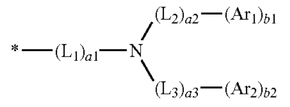

in Formula 1.

In an exemplary embodiment of the present disclosure, in Formula 1, n1 and n2 may each be 0, n3 may be 1, n1 and n3 may each be 0, n2 may be 1, n1 may be 1, and n2 and n3 may each be 0. That is, one amino group is included in the condensed cyclic compound. For example, one of rings $A_1$, $A_2$ and $A_3$ is substituted with a tertiary amino group.

In an exemplary embodiment of the present disclosure, the condensed cyclic compound may include a tetracyclic structure which includes a 7-membered center ring and three fused side rings. The 7-membered center ring may include seven carbon atoms, or 6 carbon atoms and one of O, S, Se, Si and B atoms as ring members. Each of the three fused side rings may share a two carbon border with the 7-membered center ring. The three fused side rings may not share a border with each other. The three fused side rings may each independently be a $C_5$-$C_{60}$ carbocyclic group or a $C_2$-$C_{30}$ heterocyclic group, and one of the three fused side rings may be linked to a tertiary amino group.

In an exemplary embodiment of the present disclosure, the condensed cyclic compound may be represented by one of Formulae 1A to 1C:

Formula 1A

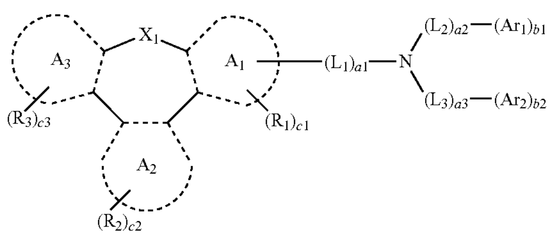

Formula 1B

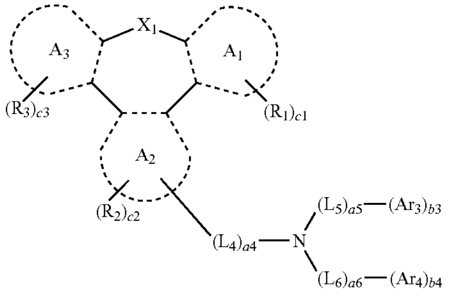

-continued

Formula 1C

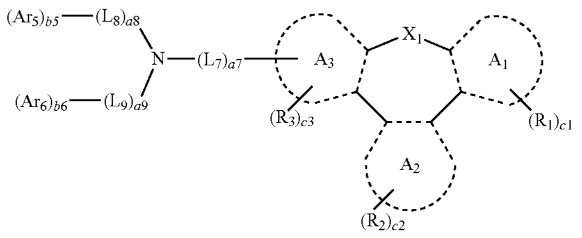

$X_1$, rings $A_1$ to $A_3$, $L_1$ to $L_9$, a1 to a9, $Ar_1$ to $Ar_6$, b1 to b6, $R_1$ to $R_3$, and c1 to c3 in Formulae 1A to 1C are the same as described above with respect to Formula 1.

In an exemplary embodiment of the present disclosure, the condensed cyclic compound may be represented by one of Formulae 1-1 to 1-11:

Formula 1-1

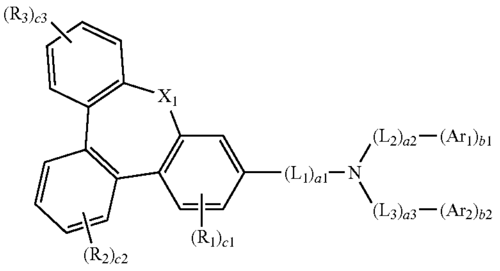

Formula 1-2

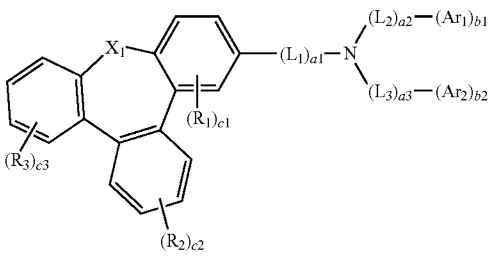

Formula 1-3

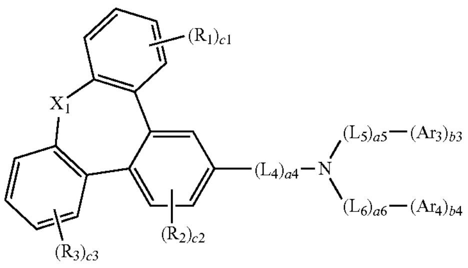

-continued

Formula 1-4

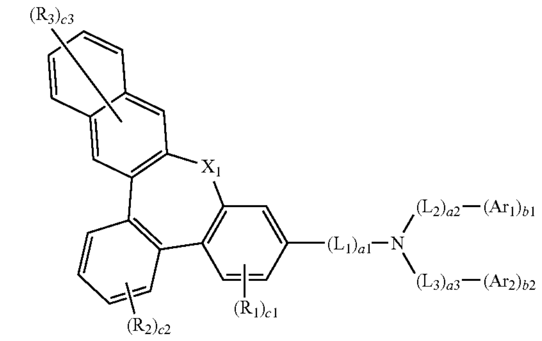

Formula 1-5

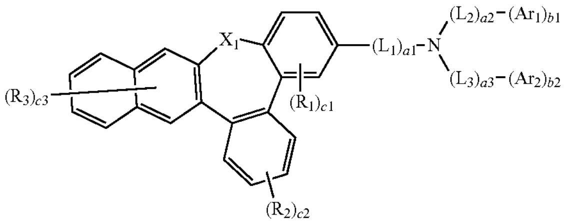

Formula 1-6

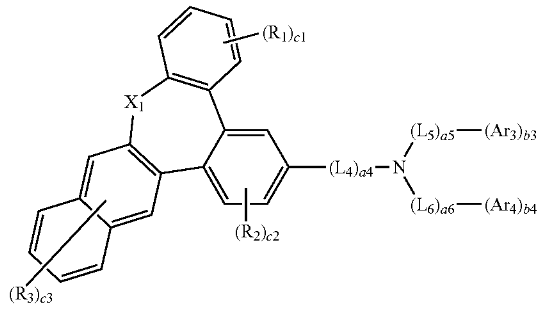

Formula 1-7

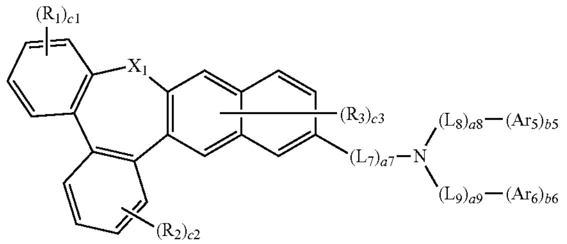

Formula 1-8

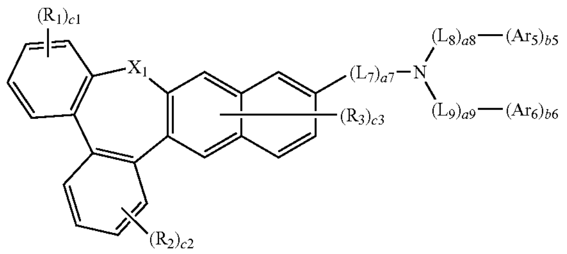

-continued

Formula 1-9

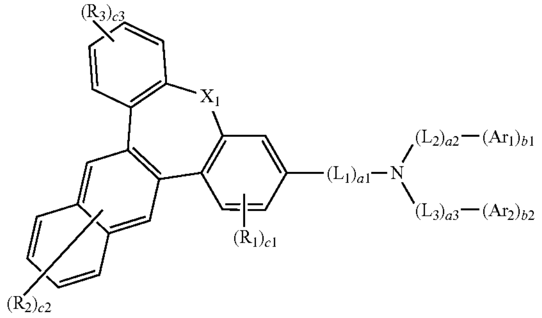

Formula 1-10

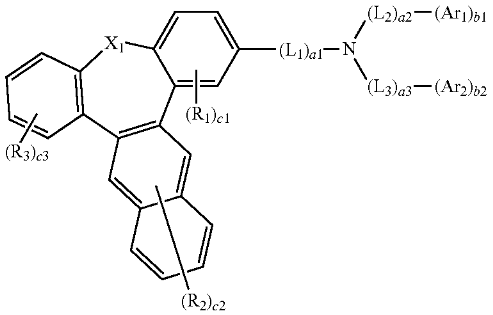

Formula 1-11

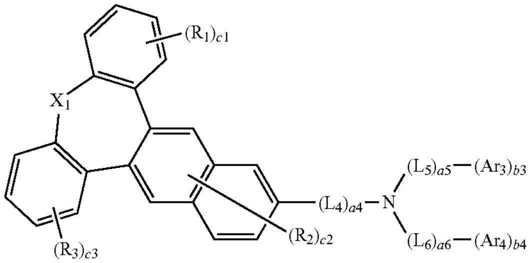

$X_1$, $L_1$ to $L_9$, a1 to a9, $Ar_1$ to $Ar_6$, b1 to b6, R, to $R_3$, and c1 to c3 in Formulae 1-1 to 1-11 are the same as described above with respect to Formula 1.

In an exemplary embodiment of the present disclosure, in Formulae 1-1 to 1-11, $X_1$ may be O, S, $C(R_4)(R_4)$, $Si(R_4)(R_5)$, and $B(R_4)$, $L_1$ to $L_9$ may each independently be selected from groups represented by Formulae 3-1 to 3-102 (for example, groups represented by Formulae 4-1 to 4-57), a1 to a9 may each independently be 0 or 1, $Ar_1$ to $Ar_6$ may each independently be selected from groups represented by Formulae 5-1 to 5-50 and 6-1 to 6-124 (for example, groups represented by Formulae 9-1 to 9-116 and 10-1 to 10-121), b1 to b6 may each be 1, $R_1$ to $R_3$ may each be hydrogen, and $R_4$ and $R_5$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a mesityl group, and c1 to c3 may each independently be 0 or 1.

In an exemplary embodiment of the present disclosure, the condensed cyclic compound may be represented by one of Formulae 1(1) to 1(18):

Formula 1(1)

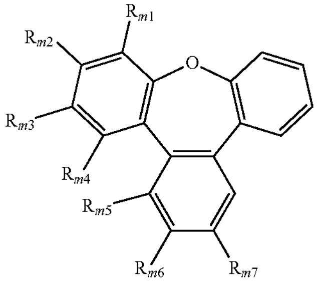

Formula 1(2)

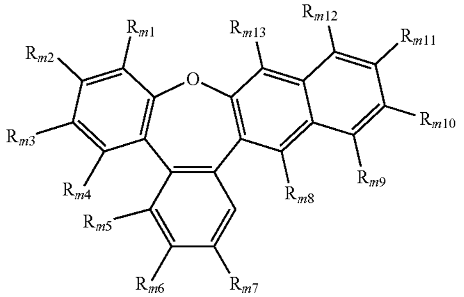

Formula 1(3)

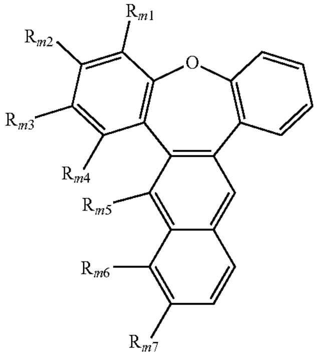

Formula 1(4)

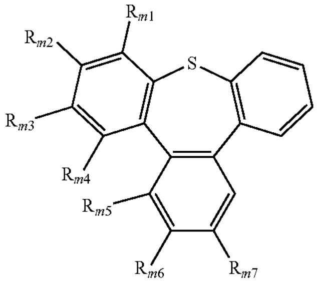

Formula 1(5)

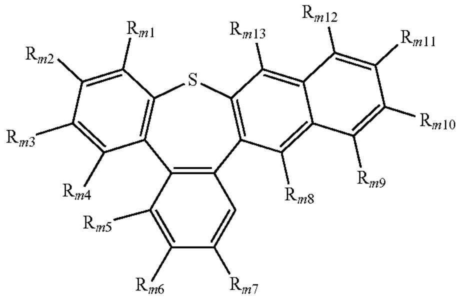

-continued
Formula 1(6)
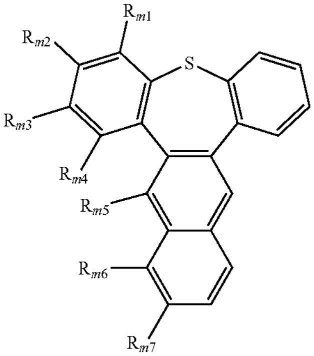
Formula 1(7)
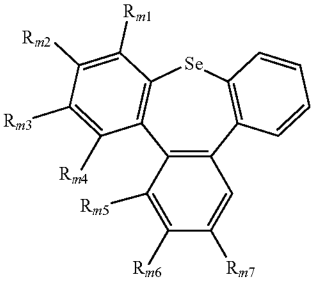
Formula 1(8)
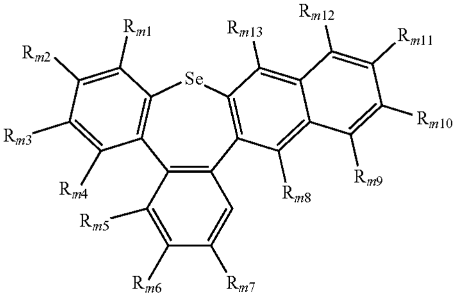
Formula 1(9)
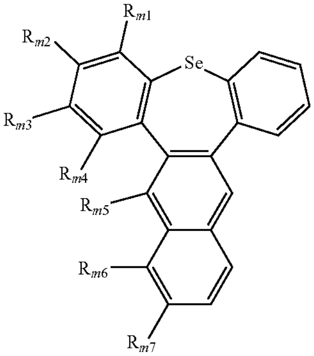
Formula 1(10)
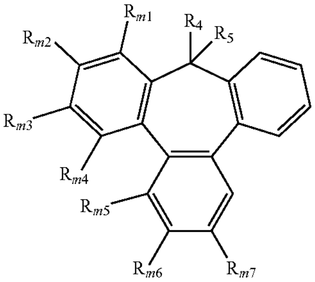
-continued
Formula 1(11)
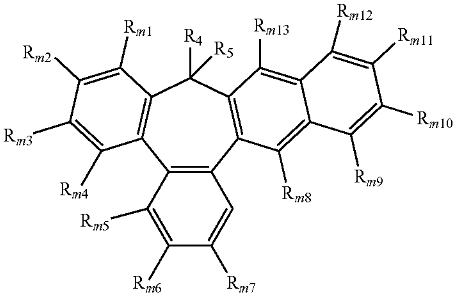
Formula 1(12)
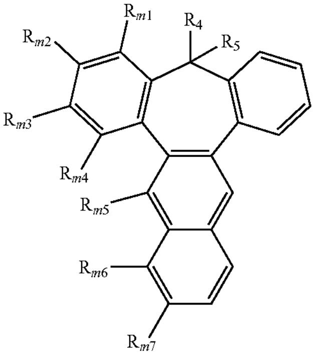
Formula 1(13)
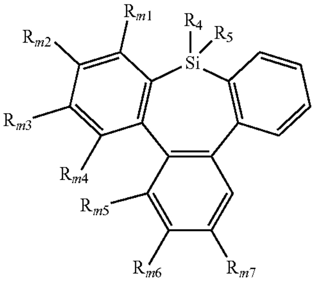
Formula 1(14)
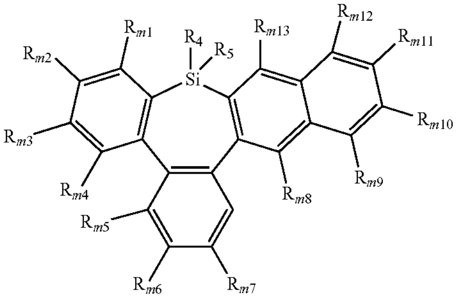

-continued

Formula 1(15)

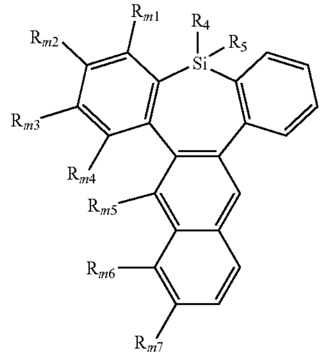

Formula 1(16)

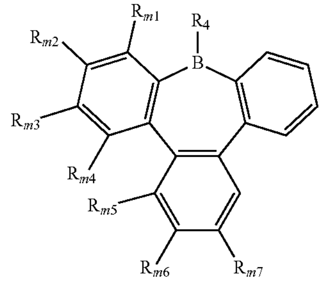

Formula 1(17)

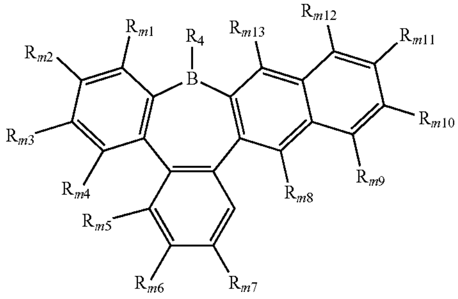

Formula 1(18)

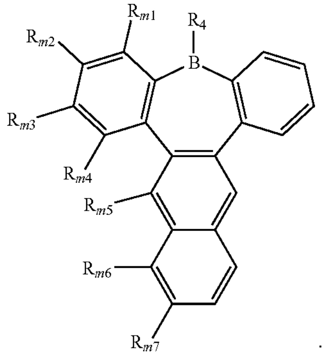

.

In Formulae 1(1) to 1(18), $R_4$ and $R_5$ are the same as described above, $R_{m1}$ to $R_{m4}$ are the same as described in connection with $R_1$, $R_{m5}$ to $R_{m7}$ are the same as described in connection with $R_2$, $R_{m8}$ to $R_{m13}$ are the same as described in connection with $R_3$, one of $R_{m1}$ to $R_{m7}$ in Formulae 1(1), 1(3), 1(4), 1(6), 1(7), 1(9), 1(10), 1(12), 1(13), 1(15), 1(16), and 1(18) may be selected from groups represented by Formulae N-1 to N-41, and one of $R_{m1}$ to $R_{m13}$ in Formulae 1(2), 1(5), 1(8), 1(11), 1(14), and 1(17) may be selected from groups represented by Formulae N-1 to N-41:

Formula N-1

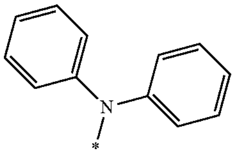

Formula N-2

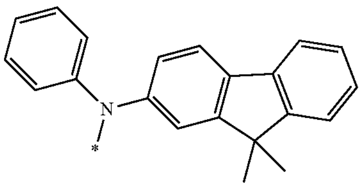

Formula N-3

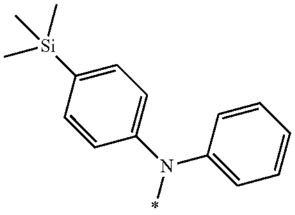

Formula N-4

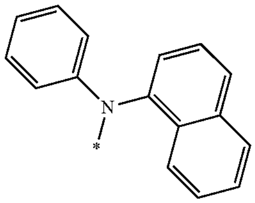

Formula N-5

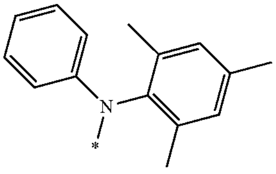

Formula N-6

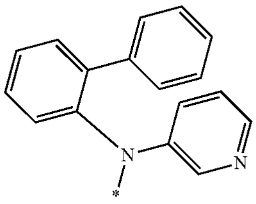

Formula N-7

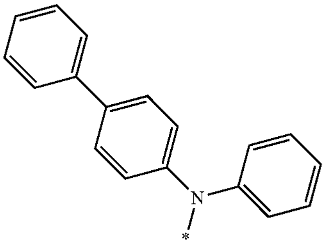

-continued
Formula N-8
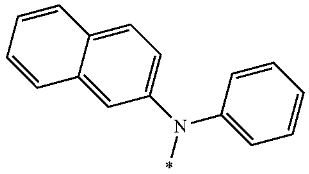
Formula N-9
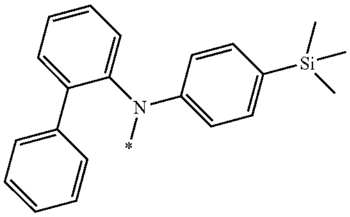
Formula N-10
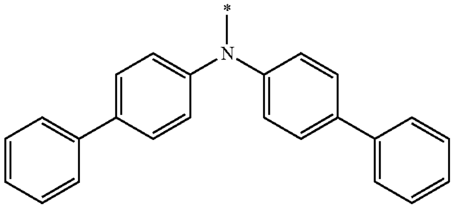
Formula N-11
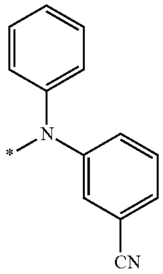
Formula N-12
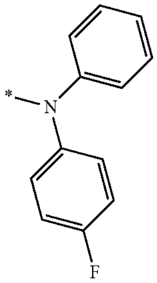
Formula N-13
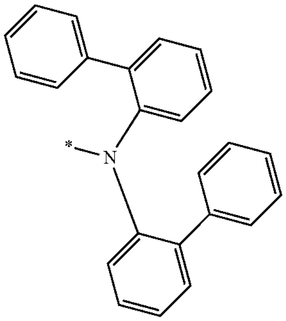
-continued
Formula N-14
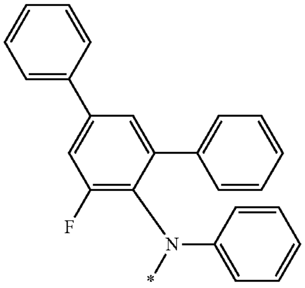
Formula N-15
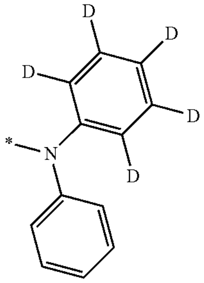
Formula N-16
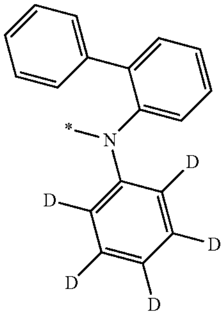
Formula N-17
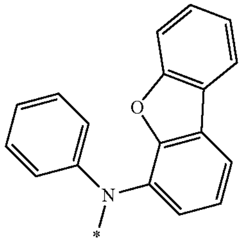
Formula N-18
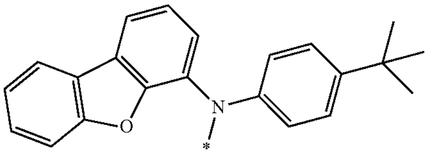
Formula N-19
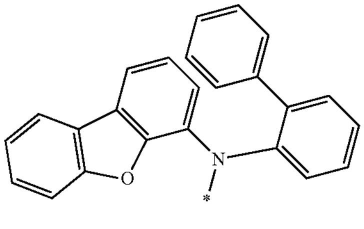

-continued
Formula N-20
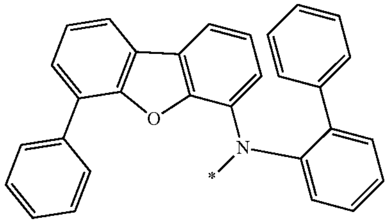
Formula N-21
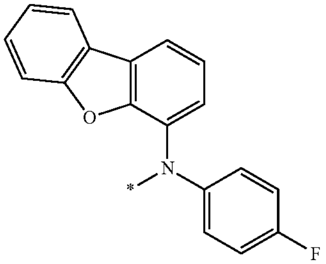
Formula N-22
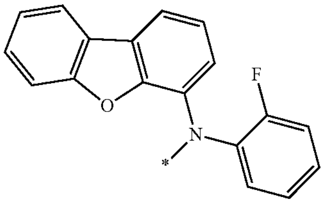
Formula N-23
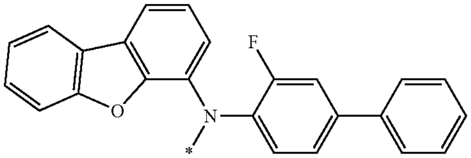
Formula N-24
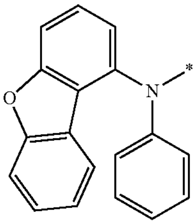
Formula N-25
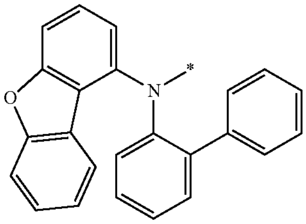
Formula N-26
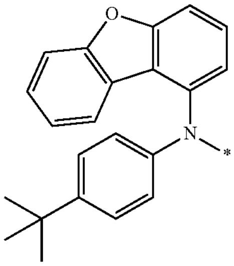
-continued
Formula N-27
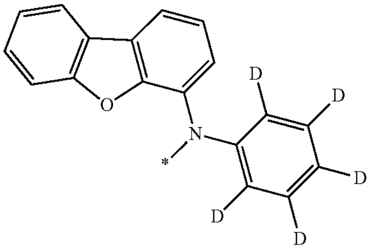
Formula N-28
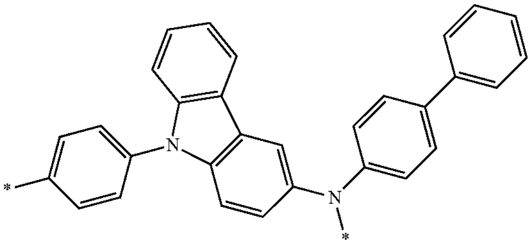
Formula N-29
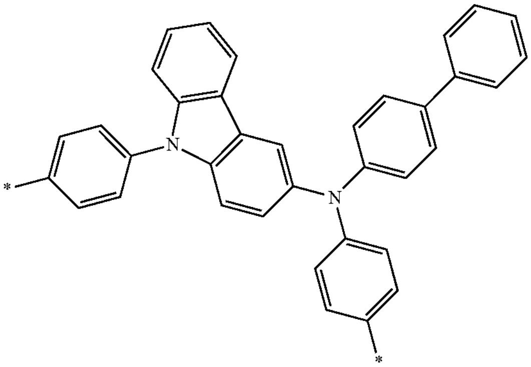
Formula N-30
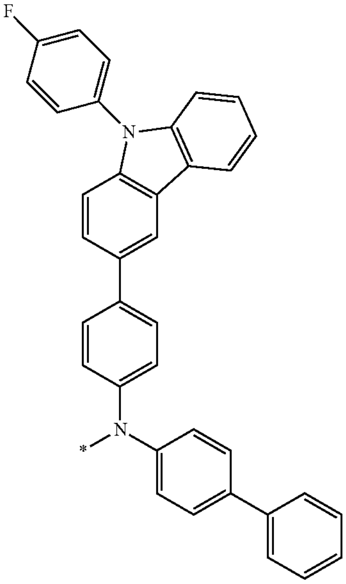

-continued
Formula N-31
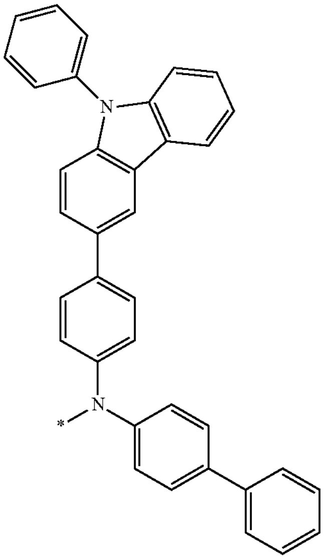
Formula N-32
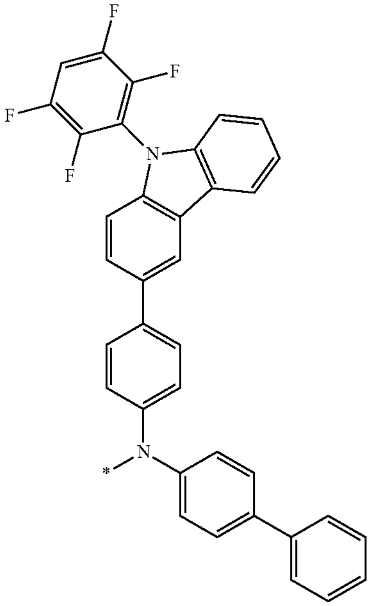
Formula N-33
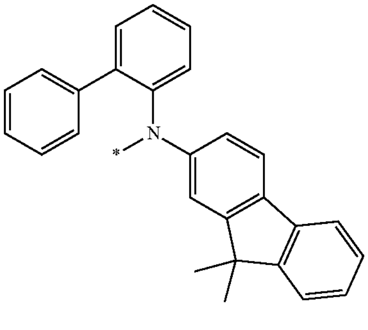
-continued
Formula N-34
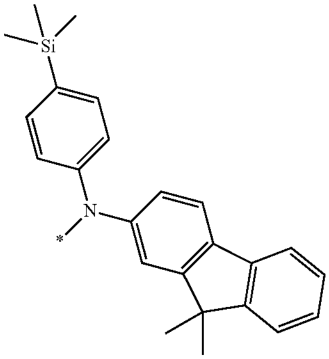
Formula N-35
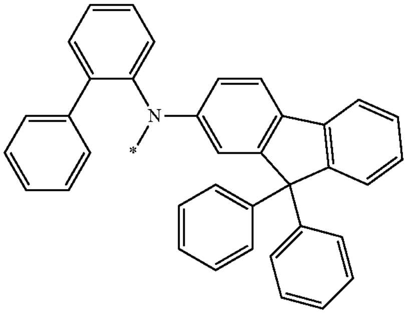
Formula N-36
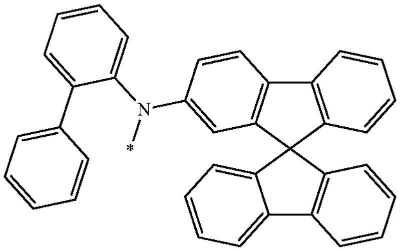
Formula N-37
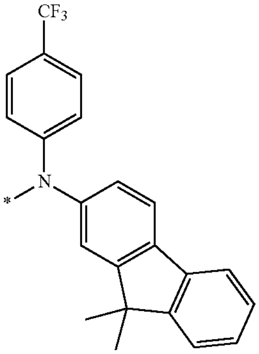
Formula N-38
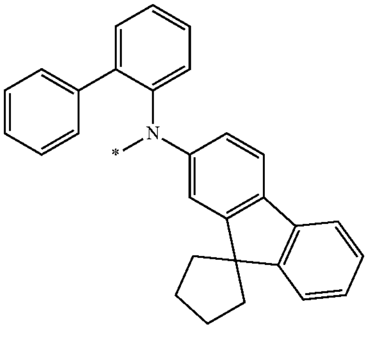

Formula N-39

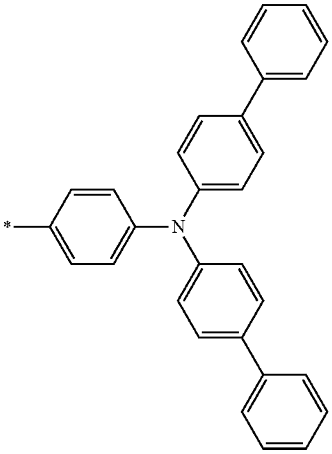

Formula N-40

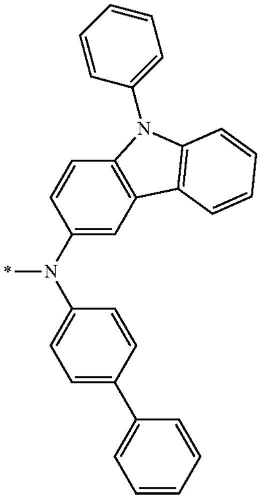

Formula N-41

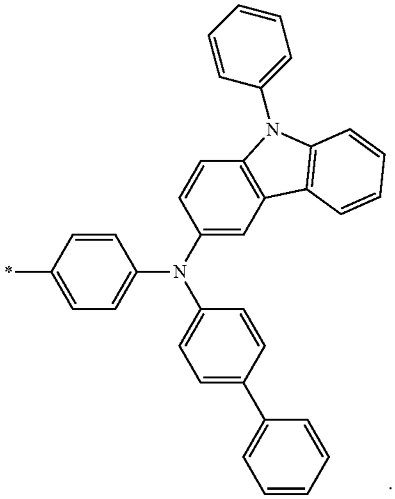

.

Here, * in Formulae N-1 to N-41 indicates a binding site to a neighboring atom.

In an exemplary embodiment of the present disclosure, the condensed cyclic compound may be represented by one of Formulae 1(1) to 1(18), and $R_4$, $R_5$, and $R_{m1}$ to $R_{m13}$ in Formulae 1(1) to 1(18) may each independently be one of Compounds 1 to 3608 as shown in Table 1 below, but the present disclosure is not limited thereto:

TABLE 1

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1 | 1(1) | — | — | H | N-1 | H | H | H | H | H | — | — | — | — | — | — |
| 2 | 1(1) | — | — | H | N-2 | H | H | H | H | H | — | — | — | — | — | — |
| 3 | 1(1) | — | — | H | N-3 | H | H | H | H | H | — | — | — | — | — | — |
| 4 | 1(1) | — | — | H | N-4 | H | H | H | H | H | — | — | — | — | — | — |
| 5 | 1(1) | — | — | H | N-5 | H | H | H | H | H | — | — | — | — | — | — |
| 6 | 1(1) | — | — | H | N-6 | H | H | H | H | H | — | — | — | — | — | — |
| 7 | 1(1) | — | — | H | N-7 | H | H | H | H | H | — | — | — | — | — | — |
| 8 | 1(1) | — | — | H | N-8 | H | H | H | H | H | — | — | — | — | — | — |
| 9 | 1(1) | — | — | H | N-9 | H | H | H | H | H | — | — | — | — | — | — |
| 10 | 1(1) | — | — | H | N-10 | H | H | H | H | H | — | — | — | — | — | — |
| 11 | 1(1) | — | — | H | N-11 | H | H | H | H | H | — | — | — | — | — | — |
| 12 | 1(1) | — | — | H | N-12 | H | H | H | H | H | — | — | — | — | — | — |
| 13 | 1(1) | — | — | H | N-13 | H | H | H | H | H | — | — | — | — | — | — |
| 14 | 1(1) | — | — | H | N-14 | H | H | H | H | H | — | — | — | — | — | — |
| 15 | 1(1) | — | — | H | N-15 | H | H | H | H | H | — | — | — | — | — | — |
| 16 | 1(1) | — | — | H | N-16 | H | H | H | H | H | — | — | — | — | — | — |
| 17 | 1(1) | — | — | H | N-17 | H | H | H | H | H | — | — | — | — | — | — |
| 18 | 1(1) | — | — | H | N-18 | H | H | H | H | H | — | — | — | — | — | — |
| 19 | 1(1) | — | — | H | N-19 | H | H | H | H | H | — | — | — | — | — | — |
| 20 | 1(1) | — | — | H | N-20 | H | H | H | H | H | — | — | — | — | — | — |
| 21 | 1(1) | — | — | H | N-21 | H | H | H | H | H | — | — | — | — | — | — |
| 22 | 1(1) | — | — | H | N-22 | H | H | H | H | H | — | — | — | — | — | — |
| 23 | 1(1) | — | — | H | N-23 | H | H | H | H | H | — | — | — | — | — | — |
| 24 | 1(1) | — | — | H | N-24 | H | H | H | H | H | — | — | — | — | — | — |
| 25 | 1(1) | — | — | H | N-25 | H | H | H | H | H | — | — | — | — | — | — |
| 26 | 1(1) | — | — | H | N-26 | H | H | H | H | H | — | — | — | — | — | — |
| 27 | 1(1) | — | — | H | N-27 | H | H | H | H | H | — | — | — | — | — | — |
| 28 | 1(1) | — | — | H | N-28 | H | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 29 | 1(1) | — | — | H | N-29 | H | H | H | H | H | — | — | — | — | — | — |
| 30 | 1(1) | — | — | H | N-30 | H | H | H | H | H | — | — | — | — | — | — |
| 31 | 1(1) | — | — | H | N-31 | H | H | H | H | H | — | — | — | — | — | — |
| 32 | 1(1) | — | — | H | N-32 | H | H | H | H | H | — | — | — | — | — | — |
| 33 | 1(1) | — | — | H | N-33 | H | H | H | H | H | — | — | — | — | — | — |
| 34 | 1(1) | — | — | H | N-34 | H | H | H | H | H | — | — | — | — | — | — |
| 35 | 1(1) | — | — | H | N-35 | H | H | H | H | H | — | — | — | — | — | — |
| 36 | 1(1) | — | — | H | N-36 | H | H | H | H | H | — | — | — | — | — | — |
| 37 | 1(1) | — | — | H | N-37 | H | H | H | H | H | — | — | — | — | — | — |
| 38 | 1(1) | — | — | H | N-38 | H | H | H | H | H | — | — | — | — | — | — |
| 39 | 1(1) | — | — | H | N-39 | H | H | H | H | H | — | — | — | — | — | — |
| 40 | 1(1) | — | — | H | N-40 | H | H | H | H | H | — | — | — | — | — | — |
| 41 | 1(1) | — | — | H | N-41 | H | H | H | H | H | — | — | — | — | — | — |
| 42 | 1(1) | — | — | H | H | N-1 | H | H | H | H | — | — | — | — | — | — |
| 43 | 1(1) | — | — | H | H | N-2 | H | H | H | H | — | — | — | — | — | — |
| 44 | 1(1) | — | — | H | H | N-3 | H | H | H | H | — | — | — | — | — | — |
| 45 | 1(1) | — | — | H | H | N-4 | H | H | H | H | — | — | — | — | — | — |
| 46 | 1(1) | — | — | H | H | N-5 | H | H | H | H | — | — | — | — | — | — |
| 47 | 1(1) | — | — | H | H | N-6 | H | H | H | H | — | — | — | — | — | — |
| 48 | 1(1) | — | — | H | H | N-7 | H | H | H | H | — | — | — | — | — | — |
| 49 | 1(1) | — | — | H | H | N-8 | H | H | H | H | — | — | — | — | — | — |
| 50 | 1(1) | — | — | H | H | N-9 | H | H | H | H | — | — | — | — | — | — |
| 51 | 1(1) | — | — | H | H | N-10 | H | H | H | H | — | — | — | — | — | — |
| 52 | 1(1) | — | — | H | H | N-11 | H | H | H | H | — | — | — | — | — | — |
| 53 | 1(1) | — | — | H | H | N-12 | H | H | H | H | — | — | — | — | — | — |
| 54 | 1(1) | — | — | H | H | N-13 | H | H | H | H | — | — | — | — | — | — |
| 55 | 1(1) | — | — | H | H | N-14 | H | H | H | H | — | — | — | — | — | — |
| 56 | 1(1) | — | — | H | H | N-15 | H | H | H | H | — | — | — | — | — | — |
| 57 | 1(1) | — | — | H | H | N-16 | H | H | H | H | — | — | — | — | — | — |
| 58 | 1(1) | — | — | H | H | N-17 | H | H | H | H | — | — | — | — | — | — |
| 59 | 1(1) | — | — | H | H | N-18 | H | H | H | H | — | — | — | — | — | — |
| 60 | 1(1) | — | — | H | H | N-19 | H | H | H | H | — | — | — | — | — | — |
| 61 | 1(1) | — | — | H | H | N-20 | H | H | H | H | — | — | — | — | — | — |
| 62 | 1(1) | — | — | H | H | N-21 | H | H | H | H | — | — | — | — | — | — |
| 63 | 1(1) | — | — | H | H | N-22 | H | H | H | H | — | — | — | — | — | — |
| 64 | 1(1) | — | — | H | H | N-23 | H | H | H | H | — | — | — | — | — | — |
| 65 | 1(1) | — | — | H | H | N-24 | H | H | H | H | — | — | — | — | — | — |
| 66 | 1(1) | — | — | H | H | N-25 | H | H | H | H | — | — | — | — | — | — |
| 67 | 1(1) | — | — | H | H | N-26 | H | H | H | H | — | — | — | — | — | — |
| 68 | 1(1) | — | — | H | H | N-27 | H | H | H | H | — | — | — | — | — | — |
| 69 | 1(1) | — | — | H | H | N-28 | H | H | H | H | — | — | — | — | — | — |
| 70 | 1(1) | — | — | H | H | N-29 | H | H | H | H | — | — | — | — | — | — |
| 71 | 1(1) | — | — | H | H | N-30 | H | H | H | H | — | — | — | — | — | — |
| 72 | 1(1) | — | — | H | H | N-31 | H | H | H | H | — | — | — | — | — | — |
| 73 | 1(1) | — | — | H | H | N-32 | H | H | H | H | — | — | — | — | — | — |
| 74 | 1(1) | — | — | H | H | N-33 | H | H | H | H | — | — | — | — | — | — |
| 75 | 1(1) | — | — | H | H | N-34 | H | H | H | H | — | — | — | — | — | — |
| 76 | 1(1) | — | — | H | H | N-35 | H | H | H | H | — | — | — | — | — | — |
| 77 | 1(1) | — | — | H | H | N-36 | H | H | H | H | — | — | — | — | — | — |
| 78 | 1(1) | — | — | H | H | N-37 | H | H | H | H | — | — | — | — | — | — |
| 79 | 1(1) | — | — | H | H | N-38 | H | H | H | H | — | — | — | — | — | — |
| 80 | 1(1) | — | — | H | H | N-39 | H | H | H | H | — | — | — | — | — | — |
| 81 | 1(1) | — | — | H | H | N-40 | H | H | H | H | — | — | — | — | — | — |
| 82 | 1(1) | — | — | H | H | N-41 | H | H | H | H | — | — | — | — | — | — |
| 83 | 1(1) | — | — | H | H | H | H | H | N-1 | H | — | — | — | — | — | — |
| 84 | 1(1) | — | — | H | H | H | H | H | N-2 | H | — | — | — | — | — | — |
| 85 | 1(1) | — | — | H | H | H | H | H | N-3 | H | — | — | — | — | — | — |
| 86 | 1(1) | — | — | H | H | H | H | H | N-4 | H | — | — | — | — | — | — |
| 87 | 1(1) | — | — | H | H | H | H | H | N-5 | H | — | — | — | — | — | — |
| 88 | 1(1) | — | — | H | H | H | H | H | N-6 | H | — | — | — | — | — | — |
| 89 | 1(1) | — | — | H | H | H | H | H | N-7 | H | — | — | — | — | — | — |
| 90 | 1(1) | — | — | H | H | H | H | H | N-8 | H | — | — | — | — | — | — |
| 91 | 1(1) | — | — | H | H | H | H | H | N-9 | H | — | — | — | — | — | — |
| 92 | 1(1) | — | — | H | H | H | H | H | N-10 | H | — | — | — | — | — | — |
| 93 | 1(1) | — | — | H | H | H | H | H | N-11 | H | — | — | — | — | — | — |
| 94 | 1(1) | — | — | H | H | H | H | H | N-12 | H | — | — | — | — | — | — |
| 95 | 1(1) | — | — | H | H | H | H | H | N-13 | H | — | — | — | — | — | — |
| 96 | 1(1) | — | — | H | H | H | H | H | N-14 | H | — | — | — | — | — | — |
| 97 | 1(1) | — | — | H | H | H | H | H | N-15 | H | — | — | — | — | — | — |
| 98 | 1(1) | — | — | H | H | H | H | H | N-16 | H | — | — | — | — | — | — |
| 99 | 1(1) | — | — | H | H | H | H | H | N-17 | H | — | — | — | — | — | — |
| 100 | 1(1) | — | — | H | H | H | H | H | N-18 | H | — | — | — | — | — | — |
| 101 | 1(1) | — | — | H | H | H | H | H | N-19 | H | — | — | — | — | — | — |
| 102 | 1(1) | — | — | H | H | H | H | H | N-20 | H | — | — | — | — | — | — |
| 103 | 1(1) | — | — | H | H | H | H | H | N-21 | H | — | — | — | — | — | — |
| 104 | 1(1) | — | — | H | H | H | H | H | N-22 | H | — | — | — | — | — | — |
| 105 | 1(1) | — | — | H | H | H | H | H | N-23 | H | — | — | — | — | — | — |
| 106 | 1(1) | — | — | H | H | H | H | H | N-24 | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 107 | 1(1) | — | — | H | H | H | H | H | N-25 | H | — | — | — | — | — | — |
| 108 | 1(1) | — | — | H | H | H | H | H | N-26 | H | — | — | — | — | — | — |
| 109 | 1(1) | — | — | H | H | H | H | H | N-27 | H | — | — | — | — | — | — |
| 110 | 1(1) | — | — | H | H | H | H | H | N-28 | H | — | — | — | — | — | — |
| 111 | 1(1) | — | — | H | H | H | H | H | N-29 | H | — | — | — | — | — | — |
| 112 | 1(1) | — | — | H | H | H | H | H | N-30 | H | — | — | — | — | — | — |
| 113 | 1(1) | — | — | H | H | H | H | H | N-31 | H | — | — | — | — | — | — |
| 114 | 1(1) | — | — | H | H | H | H | H | N-32 | H | — | — | — | — | — | — |
| 115 | 1(1) | — | — | H | H | H | H | H | N-33 | H | — | — | — | — | — | — |
| 116 | 1(1) | — | — | H | H | H | H | H | N-34 | H | — | — | — | — | — | — |
| 117 | 1(1) | — | — | H | H | H | H | H | N-35 | H | — | — | — | — | — | — |
| 118 | 1(1) | — | — | H | H | H | H | H | N-36 | H | — | — | — | — | — | — |
| 119 | 1(1) | — | — | H | H | H | H | H | N-37 | H | — | — | — | — | — | — |
| 120 | 1(1) | — | — | H | H | H | H | H | N-38 | H | — | — | — | — | — | — |
| 121 | 1(1) | — | — | H | H | H | H | H | N-39 | H | — | — | — | — | — | — |
| 122 | 1(1) | — | — | H | H | H | H | H | N-40 | H | — | — | — | — | — | — |
| 123 | 1(1) | — | — | H | H | H | H | H | N-41 | H | — | — | — | — | — | — |
| 124 | 1(2) | — | — | H | N-1 | H | H | H | H | H | H | H | H | H | H | H |
| 125 | 1(2) | — | — | H | N-2 | H | H | H | H | H | H | H | H | H | H | H |
| 126 | 1(2) | — | — | H | N-3 | H | H | H | H | H | H | H | H | H | H | H |
| 127 | 1(2) | — | — | H | N-4 | H | H | H | H | H | H | H | H | H | H | H |
| 128 | 1(2) | — | — | H | N-5 | H | H | H | H | H | H | H | H | H | H | H |
| 129 | 1(2) | — | — | H | N-6 | H | H | H | H | H | H | H | H | H | H | H |
| 130 | 1(2) | — | — | H | N-7 | H | H | H | H | H | H | H | H | H | H | H |
| 131 | 1(2) | — | — | H | N-8 | H | H | H | H | H | H | H | H | H | H | H |
| 132 | 1(2) | — | — | H | N-9 | H | H | H | H | H | H | H | H | H | H | H |
| 133 | 1(2) | — | — | H | N-10 | H | H | H | H | H | H | H | H | H | H | H |
| 134 | 1(2) | — | — | H | N-11 | H | H | H | H | H | H | H | H | H | H | H |
| 135 | 1(2) | — | — | H | N-12 | H | H | H | H | H | H | H | H | H | H | H |
| 136 | 1(2) | — | — | H | N-13 | H | H | H | H | H | H | H | H | H | H | H |
| 137 | 1(2) | — | — | H | N-14 | H | H | H | H | H | H | H | H | H | H | H |
| 138 | 1(2) | — | — | H | N-15 | H | H | H | H | H | H | H | H | H | H | H |
| 139 | 1(2) | — | — | H | N-16 | H | H | H | H | H | H | H | H | H | H | H |
| 140 | 1(2) | — | — | H | N-17 | H | H | H | H | H | H | H | H | H | H | H |
| 141 | 1(2) | — | — | H | N-18 | H | H | H | H | H | H | H | H | H | H | H |
| 142 | 1(2) | — | — | H | N-19 | H | H | H | H | H | H | H | H | H | H | H |
| 143 | 1(2) | — | — | H | N-20 | H | H | H | H | H | H | H | H | H | H | H |
| 144 | 1(2) | — | — | H | N-21 | H | H | H | H | H | H | H | H | H | H | H |
| 145 | 1(2) | — | — | H | N-22 | H | H | H | H | H | H | H | H | H | H | H |
| 146 | 1(2) | — | — | H | N-23 | H | H | H | H | H | H | H | H | H | H | H |
| 147 | 1(2) | — | — | H | N-24 | H | H | H | H | H | H | H | H | H | H | H |
| 148 | 1(2) | — | — | H | N-25 | H | H | H | H | H | H | H | H | H | H | H |
| 149 | 1(2) | — | — | H | N-26 | H | H | H | H | H | H | H | H | H | H | H |
| 150 | 1(2) | — | — | H | N-27 | H | H | H | H | H | H | H | H | H | H | H |
| 151 | 1(2) | — | — | H | N-28 | H | H | H | H | H | H | H | H | H | H | H |
| 152 | 1(2) | — | — | H | N-29 | H | H | H | H | H | H | H | H | H | H | H |
| 153 | 1(2) | — | — | H | N-30 | H | H | H | H | H | H | H | H | H | H | H |
| 154 | 1(2) | — | — | H | N-31 | H | H | H | H | H | H | H | H | H | H | H |
| 155 | 1(2) | — | — | H | N-32 | H | H | H | H | H | H | H | H | H | H | H |
| 156 | 1(2) | — | — | H | N-33 | H | H | H | H | H | H | H | H | H | H | H |
| 157 | 1(2) | — | — | H | N-34 | H | H | H | H | H | H | H | H | H | H | H |
| 158 | 1(2) | — | — | H | N-35 | H | H | H | H | H | H | H | H | H | H | H |
| 159 | 1(2) | — | — | H | N-36 | H | H | H | H | H | H | H | H | H | H | H |
| 160 | 1(2) | — | — | H | N-37 | H | H | H | H | H | H | H | H | H | H | H |
| 161 | 1(2) | — | — | H | N-38 | H | H | H | H | H | H | H | H | H | H | H |
| 162 | 1(2) | — | — | H | N-39 | H | H | H | H | H | H | H | H | H | H | H |
| 163 | 1(2) | — | — | H | N-40 | H | H | H | H | H | H | H | H | H | H | H |
| 164 | 1(2) | — | — | H | N-41 | H | H | H | H | H | H | H | H | H | H | H |
| 165 | 1(2) | — | — | H | H | N-1 | H | H | H | H | H | H | H | H | H | H |
| 166 | 1(2) | — | — | H | H | N-2 | H | H | H | H | H | H | H | H | H | H |
| 167 | 1(2) | — | — | H | H | N-3 | H | H | H | H | H | H | H | H | H | H |
| 168 | 1(2) | — | — | H | H | N-4 | H | H | H | H | H | H | H | H | H | H |
| 169 | 1(2) | — | — | H | H | N-5 | H | H | H | H | H | H | H | H | H | H |
| 170 | 1(2) | — | — | H | H | N-6 | H | H | H | H | H | H | H | H | H | H |
| 171 | 1(2) | — | — | H | H | N-7 | H | H | H | H | H | H | H | H | H | H |
| 172 | 1(2) | — | — | H | H | N-8 | H | H | H | H | H | H | H | H | H | H |
| 173 | 1(2) | — | — | H | H | N-9 | H | H | H | H | H | H | H | H | H | H |
| 174 | 1(2) | — | — | H | H | N-10 | H | H | H | H | H | H | H | H | H | H |
| 175 | 1(2) | — | — | H | H | N-11 | H | H | H | H | H | H | H | H | H | H |
| 176 | 1(2) | — | — | H | H | N-12 | H | H | H | H | H | H | H | H | H | H |
| 177 | 1(2) | — | — | H | H | N-13 | H | H | H | H | H | H | H | H | H | H |
| 178 | 1(2) | — | — | H | H | N-14 | H | H | H | H | H | H | H | H | H | H |
| 179 | 1(2) | — | — | H | H | N-15 | H | H | H | H | H | H | H | H | H | H |
| 180 | 1(2) | — | — | H | H | N-16 | H | H | H | H | H | H | H | H | H | H |
| 181 | 1(2) | — | — | H | H | N-17 | H | H | H | H | H | H | H | H | H | H |
| 182 | 1(2) | — | — | H | H | N-18 | H | H | H | H | H | H | H | H | H | H |
| 183 | 1(2) | — | — | H | H | N-19 | H | H | H | H | H | H | H | H | H | H |
| 184 | 1(2) | — | — | H | H | N-20 | H | H | H | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 185 | 1(2) | — | — | H | H | N-21 | H | H | H | H | H | H | H | H | H | H |
| 186 | 1(2) | — | — | H | H | N-22 | H | H | H | H | H | H | H | H | H | H |
| 187 | 1(2) | — | — | H | H | N-23 | H | H | H | H | H | H | H | H | H | H |
| 188 | 1(2) | — | — | H | H | N-24 | H | H | H | H | H | H | H | H | H | H |
| 189 | 1(2) | — | — | H | H | N-25 | H | H | H | H | H | H | H | H | H | H |
| 190 | 1(2) | — | — | H | H | N-26 | H | H | H | H | H | H | H | H | H | H |
| 191 | 1(2) | — | — | H | H | N-27 | H | H | H | H | H | H | H | H | H | H |
| 192 | 1(2) | — | — | H | H | N-28 | H | H | H | H | H | H | H | H | H | H |
| 193 | 1(2) | — | — | H | H | N-29 | H | H | H | H | H | H | H | H | H | H |
| 194 | 1(2) | — | — | H | H | N-30 | H | H | H | H | H | H | H | H | H | H |
| 195 | 1(2) | — | — | H | H | N-31 | H | H | H | H | H | H | H | H | H | H |
| 196 | 1(2) | — | — | H | H | N-32 | H | H | H | H | H | H | H | H | H | H |
| 197 | 1(2) | — | — | H | H | N-33 | H | H | H | H | H | H | H | H | H | H |
| 198 | 1(2) | — | — | H | H | N-34 | H | H | H | H | H | H | H | H | H | H |
| 199 | 1(2) | — | — | H | H | N-35 | H | H | H | H | H | H | H | H | H | H |
| 200 | 1(2) | — | — | H | H | N-36 | H | H | H | H | H | H | H | H | H | H |
| 201 | 1(2) | — | — | H | H | N-37 | H | H | H | H | H | H | H | H | H | H |
| 202 | 1(2) | — | — | H | H | N-38 | H | H | H | H | H | H | H | H | H | H |
| 203 | 1(2) | — | — | H | H | N-39 | H | H | H | H | H | H | H | H | H | H |
| 204 | 1(2) | — | — | H | H | N-40 | H | H | H | H | H | H | H | H | H | H |
| 205 | 1(2) | — | — | H | H | N-41 | H | H | H | H | H | H | H | H | H | H |
| 206 | 1(2) | — | — | H | H | H | H | H | N-1 | H | H | H | H | H | H | H |
| 207 | 1(2) | — | — | H | H | H | H | H | N-2 | H | H | H | H | H | H | H |
| 208 | 1(2) | — | — | H | H | H | H | H | N-3 | H | H | H | H | H | H | H |
| 209 | 1(2) | — | — | H | H | H | H | H | N-4 | H | H | H | H | H | H | H |
| 210 | 1(2) | — | — | H | H | H | H | H | N-5 | H | H | H | H | H | H | H |
| 211 | 1(2) | — | — | H | H | H | H | H | N-6 | H | H | H | H | H | H | H |
| 212 | 1(2) | — | — | H | H | H | H | H | N-7 | H | H | H | H | H | H | H |
| 213 | 1(2) | — | — | H | H | H | H | H | N-8 | H | H | H | H | H | H | H |
| 214 | 1(2) | — | — | H | H | H | H | H | N-9 | H | H | H | H | H | H | H |
| 215 | 1(2) | — | — | H | H | H | H | H | N-10 | H | H | H | H | H | H | H |
| 216 | 1(2) | — | — | H | H | H | H | H | N-11 | H | H | H | H | H | H | H |
| 217 | 1(2) | — | — | H | H | H | H | H | N-12 | H | H | H | H | H | H | H |
| 218 | 1(2) | — | — | H | H | H | H | H | N-13 | H | H | H | H | H | H | H |
| 219 | 1(2) | — | — | H | H | H | H | H | N-14 | H | H | H | H | H | H | H |
| 220 | 1(2) | — | — | H | H | H | H | H | N-15 | H | H | H | H | H | H | H |
| 221 | 1(2) | — | — | H | H | H | H | H | N-16 | H | H | H | H | H | H | H |
| 222 | 1(2) | — | — | H | H | H | H | H | N-17 | H | H | H | H | H | H | H |
| 223 | 1(2) | — | — | H | H | H | H | H | N-18 | H | H | H | H | H | H | H |
| 224 | 1(2) | — | — | H | H | H | H | H | N-19 | H | H | H | H | H | H | H |
| 225 | 1(2) | — | — | H | H | H | H | H | N-20 | H | H | H | H | H | H | H |
| 226 | 1(2) | — | — | H | H | H | H | H | N-21 | H | H | H | H | H | H | H |
| 227 | 1(2) | — | — | H | H | H | H | H | N-22 | H | H | H | H | H | H | H |
| 228 | 1(2) | — | — | H | H | H | H | H | N-23 | H | H | H | H | H | H | H |
| 229 | 1(2) | — | — | H | H | H | H | H | N-24 | H | H | H | H | H | H | H |
| 230 | 1(2) | — | — | H | H | H | H | H | N-25 | H | H | H | H | H | H | H |
| 231 | 1(2) | — | — | H | H | H | H | H | N-26 | H | H | H | H | H | H | H |
| 232 | 1(2) | — | — | H | H | H | H | H | N-27 | H | H | H | H | H | H | H |
| 233 | 1(2) | — | — | H | H | H | H | H | N-28 | H | H | H | H | H | H | H |
| 234 | 1(2) | — | — | H | H | H | H | H | N-29 | H | H | H | H | H | H | H |
| 235 | 1(2) | — | — | H | H | H | H | H | N-30 | H | H | H | H | H | H | H |
| 236 | 1(2) | — | — | H | H | H | H | H | N-31 | H | H | H | H | H | H | H |
| 237 | 1(2) | — | — | H | H | H | H | H | N-32 | H | H | H | H | H | H | H |
| 238 | 1(2) | — | — | H | H | H | H | H | N-33 | H | H | H | H | H | H | H |
| 239 | 1(2) | — | — | H | H | H | H | H | N-34 | H | H | H | H | H | H | H |
| 240 | 1(2) | — | — | H | H | H | H | H | N-35 | H | H | H | H | H | H | H |
| 241 | 1(2) | — | — | H | H | H | H | H | N-36 | H | H | H | H | H | H | H |
| 242 | 1(2) | — | — | H | H | H | H | H | N-37 | H | H | H | H | H | H | H |
| 243 | 1(2) | — | — | H | H | H | H | H | N-38 | H | H | H | H | H | H | H |
| 244 | 1(2) | — | — | H | H | H | H | H | N-39 | H | H | H | H | H | H | H |
| 245 | 1(2) | — | — | H | H | H | H | H | N-40 | H | H | H | H | H | H | H |
| 246 | 1(2) | — | — | H | H | H | H | H | N-41 | H | H | H | H | H | H | H |
| 247 | 1(2) | — | — | H | H | H | H | H | H | H | H | H | N-1 | H | H | H |
| 248 | 1(2) | — | — | H | H | H | H | H | H | H | H | H | N-2 | H | H | H |
| 249 | 1(2) | — | — | H | H | H | H | H | H | H | H | H | N-3 | H | H | H |
| 250 | 1(2) | — | — | H | H | H | H | H | H | H | H | H | N-4 | H | H | H |
| 251 | 1(2) | — | — | H | H | H | H | H | H | H | H | H | N-5 | H | H | H |
| 252 | 1(2) | — | — | H | H | H | H | H | H | H | H | H | N-6 | H | H | H |
| 253 | 1(2) | — | — | H | H | H | H | H | H | H | H | H | N-7 | H | H | H |
| 254 | 1(2) | — | — | H | H | H | H | H | H | H | H | H | N-8 | H | H | H |
| 255 | 1(2) | — | — | H | H | H | H | H | H | H | H | H | N-9 | H | H | H |
| 256 | 1(2) | — | — | H | H | H | H | H | H | H | H | H | N-10 | H | H | H |
| 257 | 1(2) | — | — | H | H | H | H | H | H | H | H | H | N-11 | H | H | H |
| 258 | 1(2) | — | — | H | H | H | H | H | H | H | H | H | N-12 | H | H | H |
| 259 | 1(2) | — | — | H | H | H | H | H | H | H | H | H | N-13 | H | H | H |
| 260 | 1(2) | — | — | H | H | H | H | H | H | H | H | H | N-14 | H | H | H |
| 261 | 1(2) | — | — | H | H | H | H | H | H | H | H | H | N-15 | H | H | H |
| 262 | 1(2) | — | — | H | H | H | H | H | H | H | H | H | N-16 | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 263 | 1(2) | — | — | H | H | H | H | H | H | H | H | H | N-17 | H | H | H |
| 264 | 1(2) | — | — | H | H | H | H | H | H | H | H | H | N-18 | H | H | H |
| 265 | 1(2) | — | — | H | H | H | H | H | H | H | H | H | N-19 | H | H | H |
| 266 | 1(2) | — | — | H | H | H | H | H | H | H | H | H | N-20 | H | H | H |
| 267 | 1(2) | — | — | H | H | H | H | H | H | H | H | H | N-21 | H | H | H |
| 268 | 1(2) | — | — | H | H | H | H | H | H | H | H | H | N-22 | H | H | H |
| 269 | 1(2) | — | — | H | H | H | H | H | H | H | H | H | N-23 | H | H | H |
| 270 | 1(2) | — | — | H | H | H | H | H | H | H | H | H | N-24 | H | H | H |
| 271 | 1(2) | — | — | H | H | H | H | H | H | H | H | H | N-25 | H | H | H |
| 272 | 1(2) | — | — | H | H | H | H | H | H | H | H | H | N-26 | H | H | H |
| 273 | 1(2) | — | — | H | H | H | H | H | H | H | H | H | N-27 | H | H | H |
| 274 | 1(2) | — | — | H | H | H | H | H | H | H | H | H | N-28 | H | H | H |
| 275 | 1(2) | — | — | H | H | H | H | H | H | H | H | H | N-29 | H | H | H |
| 276 | 1(2) | — | — | H | H | H | H | H | H | H | H | H | N-30 | H | H | H |
| 277 | 1(2) | — | — | H | H | H | H | H | H | H | H | H | N-31 | H | H | H |
| 278 | 1(2) | — | — | H | H | H | H | H | H | H | H | H | N-32 | H | H | H |
| 279 | 1(2) | — | — | H | H | H | H | H | H | H | H | H | N-33 | H | H | H |
| 280 | 1(2) | — | — | H | H | H | H | H | H | H | H | H | N-34 | H | H | H |
| 281 | 1(2) | — | — | H | H | H | H | H | H | H | H | H | N-35 | H | H | H |
| 282 | 1(2) | — | — | H | H | H | H | H | H | H | H | H | N-36 | H | H | H |
| 283 | 1(2) | — | — | H | H | H | H | H | H | H | H | H | N-37 | H | H | H |
| 284 | 1(2) | — | — | H | H | H | H | H | H | H | H | H | N-38 | H | H | H |
| 285 | 1(2) | — | — | H | H | H | H | H | H | H | H | H | N-39 | H | H | H |
| 286 | 1(2) | — | — | H | H | H | H | H | H | H | H | H | N-40 | H | H | H |
| 287 | 1(2) | — | — | H | H | H | H | H | H | H | H | H | N-41 | H | H | H |
| 288 | 1(2) | — | — | H | H | H | H | H | H | H | H | H | H | N-1 | H | H |
| 289 | 1(2) | — | — | H | H | H | H | H | H | H | H | H | H | N-2 | H | H |
| 290 | 1(2) | — | — | H | H | H | H | H | H | H | H | H | H | N-3 | H | H |
| 291 | 1(2) | — | — | H | H | H | H | H | H | H | H | H | H | N-4 | H | H |
| 292 | 1(2) | — | — | H | H | H | H | H | H | H | H | H | H | N-5 | H | H |
| 293 | 1(2) | — | — | H | H | H | H | H | H | H | H | H | H | N-6 | H | H |
| 294 | 1(2) | — | — | H | H | H | H | H | H | H | H | H | H | N-7 | H | H |
| 295 | 1(2) | — | — | H | H | H | H | H | H | H | H | H | H | N-8 | H | H |
| 296 | 1(2) | — | — | H | H | H | H | H | H | H | H | H | H | N-9 | H | H |
| 297 | 1(2) | — | — | H | H | H | H | H | H | H | H | H | H | N-10 | H | H |
| 298 | 1(2) | — | — | H | H | H | H | H | H | H | H | H | H | N-11 | H | H |
| 299 | 1(2) | — | — | H | H | H | H | H | H | H | H | H | H | N-12 | H | H |
| 300 | 1(2) | — | — | H | H | H | H | H | H | H | H | H | H | N-13 | H | H |
| 301 | 1(2) | — | — | H | H | H | H | H | H | H | H | H | H | N-14 | H | H |
| 302 | 1(2) | — | — | H | H | H | H | H | H | H | H | H | H | N-15 | H | H |
| 303 | 1(2) | — | — | H | H | H | H | H | H | H | H | H | H | N-16 | H | H |
| 304 | 1(2) | — | — | H | H | H | H | H | H | H | H | H | H | N-17 | H | H |
| 305 | 1(2) | — | — | H | H | H | H | H | H | H | H | H | H | N-18 | H | H |
| 306 | 1(2) | — | — | H | H | H | H | H | H | H | H | H | H | N-19 | H | H |
| 307 | 1(2) | — | — | H | H | H | H | H | H | H | H | H | H | N-20 | H | H |
| 308 | 1(2) | — | — | H | H | H | H | H | H | H | H | H | H | N-21 | H | H |
| 309 | 1(2) | — | — | H | H | H | H | H | H | H | H | H | H | N-22 | H | H |
| 310 | 1(2) | — | — | H | H | H | H | H | H | H | H | H | H | N-23 | H | H |
| 311 | 1(2) | — | — | H | H | H | H | H | H | H | H | H | H | N-24 | H | H |
| 312 | 1(2) | — | — | H | H | H | H | H | H | H | H | H | H | N-25 | H | H |
| 313 | 1(2) | — | — | H | H | H | H | H | H | H | H | H | H | N-26 | H | H |
| 314 | 1(2) | — | — | H | H | H | H | H | H | H | H | H | H | N-27 | H | H |
| 315 | 1(2) | — | — | H | H | H | H | H | H | H | H | H | H | N-28 | H | H |
| 316 | 1(2) | — | — | H | H | H | H | H | H | H | H | H | H | N-29 | H | H |
| 317 | 1(2) | — | — | H | H | H | H | H | H | H | H | H | H | N-30 | H | H |
| 318 | 1(2) | — | — | H | H | H | H | H | H | H | H | H | H | N-31 | H | H |
| 319 | 1(2) | — | — | H | H | H | H | H | H | H | H | H | H | N-32 | H | H |
| 320 | 1(2) | — | — | H | H | H | H | H | H | H | H | H | H | N-33 | H | H |
| 321 | 1(2) | — | — | H | H | H | H | H | H | H | H | H | H | N-34 | H | H |
| 322 | 1(2) | — | — | H | H | H | H | H | H | H | H | H | H | N-35 | H | H |
| 323 | 1(2) | — | — | H | H | H | H | H | H | H | H | H | H | N-36 | H | H |
| 324 | 1(2) | — | — | H | H | H | H | H | H | H | H | H | H | N-37 | H | H |
| 325 | 1(2) | — | — | H | H | H | H | H | H | H | H | H | H | N-38 | H | H |
| 326 | 1(2) | — | — | H | H | H | H | H | H | H | H | H | H | N-39 | H | H |
| 327 | 1(2) | — | — | H | H | H | H | H | H | H | H | H | H | N-40 | H | H |
| 328 | 1(2) | — | — | H | H | H | H | H | H | H | H | H | H | N-41 | H | H |
| 329 | 1(3) | — | — | H | N-1 | H | H | H | H | H | — | — | — | — | — | — |
| 330 | 1(3) | — | — | H | N-2 | H | H | H | H | H | — | — | — | — | — | — |
| 331 | 1(3) | — | — | H | N-3 | H | H | H | H | H | — | — | — | — | — | — |
| 332 | 1(3) | — | — | H | N-4 | H | H | H | H | H | — | — | — | — | — | — |
| 333 | 1(3) | — | — | H | N-5 | H | H | H | H | H | — | — | — | — | — | — |
| 334 | 1(3) | — | — | H | N-6 | H | H | H | H | H | — | — | — | — | — | — |
| 335 | 1(3) | — | — | H | N-7 | H | H | H | H | H | — | — | — | — | — | — |
| 336 | 1(3) | — | — | H | N-8 | H | H | H | H | H | — | — | — | — | — | — |
| 337 | 1(3) | — | — | H | N-9 | H | H | H | H | H | — | — | — | — | — | — |
| 338 | 1(3) | — | — | H | N-10 | H | H | H | H | H | — | — | — | — | — | — |
| 339 | 1(3) | — | — | H | N-11 | H | H | H | H | H | — | — | — | — | — | — |
| 340 | 1(3) | — | — | H | N-12 | H | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 341 | 1(3) | — | — | H | N-13 | H | H | H | H | H | — | — | — | — | — | — |
| 342 | 1(3) | — | — | H | N-14 | H | H | H | H | H | — | — | — | — | — | — |
| 343 | 1(3) | — | — | H | N-15 | H | H | H | H | H | — | — | — | — | — | — |
| 344 | 1(3) | — | — | H | N-16 | H | H | H | H | H | — | — | — | — | — | — |
| 345 | 1(3) | — | — | H | N-17 | H | H | H | H | H | — | — | — | — | — | — |
| 346 | 1(3) | — | — | H | N-18 | H | H | H | H | H | — | — | — | — | — | — |
| 347 | 1(3) | — | — | H | N-19 | H | H | H | H | H | — | — | — | — | — | — |
| 348 | 1(3) | — | — | H | N-20 | H | H | H | H | H | — | — | — | — | — | — |
| 349 | 1(3) | — | — | H | N-21 | H | H | H | H | H | — | — | — | — | — | — |
| 350 | 1(3) | — | — | H | N-22 | H | H | H | H | H | — | — | — | — | — | — |
| 351 | 1(3) | — | — | H | N-23 | H | H | H | H | H | — | — | — | — | — | — |
| 352 | 1(3) | — | — | H | N-24 | H | H | H | H | H | — | — | — | — | — | — |
| 353 | 1(3) | — | — | H | N-25 | H | H | H | H | H | — | — | — | — | — | — |
| 354 | 1(3) | — | — | H | N-26 | H | H | H | H | H | — | — | — | — | — | — |
| 355 | 1(3) | — | — | H | N-27 | H | H | H | H | H | — | — | — | — | — | — |
| 356 | 1(3) | — | — | H | N-28 | H | H | H | H | H | — | — | — | — | — | — |
| 357 | 1(3) | — | — | H | N-29 | H | H | H | H | H | — | — | — | — | — | — |
| 358 | 1(3) | — | — | H | N-30 | H | H | H | H | H | — | — | — | — | — | — |
| 359 | 1(3) | — | — | H | N-31 | H | H | H | H | H | — | — | — | — | — | — |
| 360 | 1(3) | — | — | H | N-32 | H | H | H | H | H | — | — | — | — | — | — |
| 361 | 1(3) | — | — | H | N-33 | H | H | H | H | H | — | — | — | — | — | — |
| 362 | 1(3) | — | — | H | N-34 | H | H | H | H | H | — | — | — | — | — | — |
| 363 | 1(3) | — | — | H | N-35 | H | H | H | H | H | — | — | — | — | — | — |
| 364 | 1(3) | — | — | H | N-36 | H | H | H | H | H | — | — | — | — | — | — |
| 365 | 1(3) | — | — | H | N-37 | H | H | H | H | H | — | — | — | — | — | — |
| 366 | 1(3) | — | — | H | N-38 | H | H | H | H | H | — | — | — | — | — | — |
| 367 | 1(3) | — | — | H | N-39 | H | H | H | H | H | — | — | — | — | — | — |
| 368 | 1(3) | — | — | H | N-40 | H | H | H | H | H | — | — | — | — | — | — |
| 369 | 1(3) | — | — | H | N-41 | H | H | H | H | H | — | — | — | — | — | — |
| 370 | 1(3) | — | — | H | H | N-1 | H | H | H | H | — | — | — | — | — | — |
| 371 | 1(3) | — | — | H | H | N-2 | H | H | H | H | — | — | — | — | — | — |
| 372 | 1(3) | — | — | H | H | N-3 | H | H | H | H | — | — | — | — | — | — |
| 373 | 1(3) | — | — | H | H | N-4 | H | H | H | H | — | — | — | — | — | — |
| 374 | 1(3) | — | — | H | H | N-5 | H | H | H | H | — | — | — | — | — | — |
| 375 | 1(3) | — | — | H | H | N-6 | H | H | H | H | — | — | — | — | — | — |
| 376 | 1(3) | — | — | H | H | N-7 | H | H | H | H | — | — | — | — | — | — |
| 377 | 1(3) | — | — | H | H | N-8 | H | H | H | H | — | — | — | — | — | — |
| 378 | 1(3) | — | — | H | H | N-9 | H | H | H | H | — | — | — | — | — | — |
| 379 | 1(3) | — | — | H | H | N-10 | H | H | H | H | — | — | — | — | — | — |
| 380 | 1(3) | — | — | H | H | N-11 | H | H | H | H | — | — | — | — | — | — |
| 381 | 1(3) | — | — | H | H | N-12 | H | H | H | H | — | — | — | — | — | — |
| 382 | 1(3) | — | — | H | H | N-13 | H | H | H | H | — | — | — | — | — | — |
| 383 | 1(3) | — | — | H | H | N-14 | H | H | H | H | — | — | — | — | — | — |
| 384 | 1(3) | — | — | H | H | N-15 | H | H | H | H | — | — | — | — | — | — |
| 385 | 1(3) | — | — | H | H | N-16 | H | H | H | H | — | — | — | — | — | — |
| 386 | 1(3) | — | — | H | H | N-17 | H | H | H | H | — | — | — | — | — | — |
| 387 | 1(3) | — | — | H | H | N-18 | H | H | H | H | — | — | — | — | — | — |
| 388 | 1(3) | — | — | H | H | N-19 | H | H | H | H | — | — | — | — | — | — |
| 389 | 1(3) | — | — | H | H | N-20 | H | H | H | H | — | — | — | — | — | — |
| 390 | 1(3) | — | — | H | H | N-21 | H | H | H | H | — | — | — | — | — | — |
| 391 | 1(3) | — | — | H | H | N-22 | H | H | H | H | — | — | — | — | — | — |
| 392 | 1(3) | — | — | H | H | N-23 | H | H | H | H | — | — | — | — | — | — |
| 393 | 1(3) | — | — | H | H | N-24 | H | H | H | H | — | — | — | — | — | — |
| 394 | 1(3) | — | — | H | H | N-25 | H | H | H | H | — | — | — | — | — | — |
| 395 | 1(3) | — | — | H | H | N-26 | H | H | H | H | — | — | — | — | — | — |
| 396 | 1(3) | — | — | H | H | N-27 | H | H | H | H | — | — | — | — | — | — |
| 397 | 1(3) | — | — | H | H | N-28 | H | H | H | H | — | — | — | — | — | — |
| 398 | 1(3) | — | — | H | H | N-29 | H | H | H | H | — | — | — | — | — | — |
| 399 | 1(3) | — | — | H | H | N-30 | H | H | H | H | — | — | — | — | — | — |
| 400 | 1(3) | — | — | H | H | N-31 | H | H | H | H | — | — | — | — | — | — |
| 401 | 1(3) | — | — | H | H | N-32 | H | H | H | H | — | — | — | — | — | — |
| 402 | 1(3) | — | — | H | H | N-33 | H | H | H | H | — | — | — | — | — | — |
| 403 | 1(3) | — | — | H | H | N-34 | H | H | H | H | — | — | — | — | — | — |
| 404 | 1(3) | — | — | H | H | N-35 | H | H | H | H | — | — | — | — | — | — |
| 405 | 1(3) | — | — | H | H | N-36 | H | H | H | H | — | — | — | — | — | — |
| 406 | 1(3) | — | — | H | H | N-37 | H | H | H | H | — | — | — | — | — | — |
| 407 | 1(3) | — | — | H | H | N-38 | H | H | H | H | — | — | — | — | — | — |
| 408 | 1(3) | — | — | H | H | N-39 | H | H | H | H | — | — | — | — | — | — |
| 409 | 1(3) | — | — | H | H | N-40 | H | H | H | H | — | — | — | — | — | — |
| 410 | 1(3) | — | — | H | H | N-41 | H | H | H | H | — | — | — | — | — | — |
| 411 | 1(3) | — | — | H | H | H | H | H | H | N-1 | — | — | — | — | — | — |
| 412 | 1(3) | — | — | H | H | H | H | H | H | N-2 | — | — | — | — | — | — |
| 413 | 1(3) | — | — | H | H | H | H | H | H | N-3 | — | — | — | — | — | — |
| 414 | 1(3) | — | — | H | H | H | H | H | H | N-4 | — | — | — | — | — | — |
| 415 | 1(3) | — | — | H | H | H | H | H | H | N-5 | — | — | — | — | — | — |
| 416 | 1(3) | — | — | H | H | H | H | H | H | N-6 | — | — | — | — | — | — |
| 417 | 1(3) | — | — | H | H | H | H | H | H | N-7 | — | — | — | — | — | — |
| 418 | 1(3) | — | — | H | H | H | H | H | H | N-8 | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 419 | 1(3) | — | — | H | H | H | H | H | H | N-9 | — | — | — | — | — | — |
| 420 | 1(3) | — | — | H | H | H | H | H | H | N-10 | — | — | — | — | — | — |
| 421 | 1(3) | — | — | H | H | H | H | H | H | N-11 | — | — | — | — | — | — |
| 422 | 1(3) | — | — | H | H | H | H | H | H | N-12 | — | — | — | — | — | — |
| 423 | 1(3) | — | — | H | H | H | H | H | H | N-13 | — | — | — | — | — | — |
| 424 | 1(3) | — | — | H | H | H | H | H | H | N-14 | — | — | — | — | — | — |
| 425 | 1(3) | — | — | H | H | H | H | H | H | N-15 | — | — | — | — | — | — |
| 426 | 1(3) | — | — | H | H | H | H | H | H | N-16 | — | — | — | — | — | — |
| 427 | 1(3) | — | — | H | H | H | H | H | H | N-17 | — | — | — | — | — | — |
| 428 | 1(3) | — | — | H | H | H | H | H | H | N-18 | — | — | — | — | — | — |
| 429 | 1(3) | — | — | H | H | H | H | H | H | N-19 | — | — | — | — | — | — |
| 430 | 1(3) | — | — | H | H | H | H | H | H | N-20 | — | — | — | — | — | — |
| 431 | 1(3) | — | — | H | H | H | H | H | H | N-21 | — | — | — | — | — | — |
| 432 | 1(3) | — | — | H | H | H | H | H | H | N-22 | — | — | — | — | — | — |
| 433 | 1(3) | — | — | H | H | H | H | H | H | N-23 | — | — | — | — | — | — |
| 434 | 1(3) | — | — | H | H | H | H | H | H | N-24 | — | — | — | — | — | — |
| 435 | 1(3) | — | — | H | H | H | H | H | H | N-25 | — | — | — | — | — | — |
| 436 | 1(3) | — | — | H | H | H | H | H | H | N-26 | — | — | — | — | — | — |
| 437 | 1(3) | — | — | H | H | H | H | H | H | N-27 | — | — | — | — | — | — |
| 438 | 1(3) | — | — | H | H | H | H | H | H | N-28 | — | — | — | — | — | — |
| 439 | 1(3) | — | — | H | H | H | H | H | H | N-29 | — | — | — | — | — | — |
| 440 | 1(3) | — | — | H | H | H | H | H | H | N-30 | — | — | — | — | — | — |
| 441 | 1(3) | — | — | H | H | H | H | H | H | N-31 | — | — | — | — | — | — |
| 442 | 1(3) | — | — | H | H | H | H | H | H | N-32 | — | — | — | — | — | — |
| 443 | 1(3) | — | — | H | H | H | H | H | H | N-33 | — | — | — | — | — | — |
| 444 | 1(3) | — | — | H | H | H | H | H | H | N-34 | — | — | — | — | — | — |
| 445 | 1(3) | — | — | H | H | H | H | H | H | N-35 | — | — | — | — | — | — |
| 446 | 1(3) | — | — | H | H | H | H | H | H | N-36 | — | — | — | — | — | — |
| 447 | 1(3) | — | — | H | H | H | H | H | H | N-37 | — | — | — | — | — | — |
| 448 | 1(3) | — | — | H | H | H | H | H | H | N-38 | — | — | — | — | — | — |
| 449 | 1(3) | — | — | H | H | H | H | H | H | N-39 | — | — | — | — | — | — |
| 450 | 1(3) | — | — | H | H | H | H | H | H | N-40 | — | — | — | — | — | — |
| 451 | 1(3) | — | — | H | H | H | H | H | H | N-41 | — | — | — | — | — | — |
| 452 | 1(4) | — | — | H | N-1 | H | H | H | H | H | — | — | — | — | — | — |
| 453 | 1(4) | — | — | H | N-2 | H | H | H | H | H | — | — | — | — | — | — |
| 454 | 1(4) | — | — | H | N-3 | H | H | H | H | H | — | — | — | — | — | — |
| 455 | 1(4) | — | — | H | N-4 | H | H | H | H | H | — | — | — | — | — | — |
| 456 | 1(4) | — | — | H | N-5 | H | H | H | H | H | — | — | — | — | — | — |
| 457 | 1(4) | — | — | H | N-6 | H | H | H | H | H | — | — | — | — | — | — |
| 458 | 1(4) | — | — | H | N-7 | H | H | H | H | H | — | — | — | — | — | — |
| 459 | 1(4) | — | — | H | N-8 | H | H | H | H | H | — | — | — | — | — | — |
| 460 | 1(4) | — | — | H | N-9 | H | H | H | H | H | — | — | — | — | — | — |
| 461 | 1(4) | — | — | H | N-10 | H | H | H | H | H | — | — | — | — | — | — |
| 462 | 1(4) | — | — | H | N-11 | H | H | H | H | H | — | — | — | — | — | — |
| 463 | 1(4) | — | — | H | N-12 | H | H | H | H | H | — | — | — | — | — | — |
| 464 | 1(4) | — | — | H | N-13 | H | H | H | H | H | — | — | — | — | — | — |
| 465 | 1(4) | — | — | H | N-14 | H | H | H | H | H | — | — | — | — | — | — |
| 466 | 1(4) | — | — | H | N-15 | H | H | H | H | H | — | — | — | — | — | — |
| 467 | 1(4) | — | — | H | N-16 | H | H | H | H | H | — | — | — | — | — | — |
| 468 | 1(4) | — | — | H | N-17 | H | H | H | H | H | — | — | — | — | — | — |
| 469 | 1(4) | — | — | H | N-18 | H | H | H | H | H | — | — | — | — | — | — |
| 470 | 1(4) | — | — | H | N-19 | H | H | H | H | H | — | — | — | — | — | — |
| 471 | 1(4) | — | — | H | N-20 | H | H | H | H | H | — | — | — | — | — | — |
| 472 | 1(4) | — | — | H | N-21 | H | H | H | H | H | — | — | — | — | — | — |
| 473 | 1(4) | — | — | H | N-22 | H | H | H | H | H | — | — | — | — | — | — |
| 474 | 1(4) | — | — | H | N-23 | H | H | H | H | H | — | — | — | — | — | — |
| 475 | 1(4) | — | — | H | N-24 | H | H | H | H | H | — | — | — | — | — | — |
| 476 | 1(4) | — | — | H | N-25 | H | H | H | H | H | — | — | — | — | — | — |
| 477 | 1(4) | — | — | H | N-26 | H | H | H | H | H | — | — | — | — | — | — |
| 478 | 1(4) | — | — | H | N-27 | H | H | H | H | H | — | — | — | — | — | — |
| 479 | 1(4) | — | — | H | N-28 | H | H | H | H | H | — | — | — | — | — | — |
| 480 | 1(4) | — | — | H | N-29 | H | H | H | H | H | — | — | — | — | — | — |
| 481 | 1(4) | — | — | H | N-30 | H | H | H | H | H | — | — | — | — | — | — |
| 482 | 1(4) | — | — | H | N-31 | H | H | H | H | H | — | — | — | — | — | — |
| 483 | 1(4) | — | — | H | N-32 | H | H | H | H | H | — | — | — | — | — | — |
| 484 | 1(4) | — | — | H | N-33 | H | H | H | H | H | — | — | — | — | — | — |
| 485 | 1(4) | — | — | H | N-34 | H | H | H | H | H | — | — | — | — | — | — |
| 486 | 1(4) | — | — | H | N-35 | H | H | H | H | H | — | — | — | — | — | — |
| 487 | 1(4) | — | — | H | N-36 | H | H | H | H | H | — | — | — | — | — | — |
| 488 | 1(4) | — | — | H | N-37 | H | H | H | H | H | — | — | — | — | — | — |
| 489 | 1(4) | — | — | H | N-38 | H | H | H | H | H | — | — | — | — | — | — |
| 490 | 1(4) | — | — | H | N-39 | H | H | H | H | H | — | — | — | — | — | — |
| 491 | 1(4) | — | — | H | N-40 | H | H | H | H | H | — | — | — | — | — | — |
| 492 | 1(4) | — | — | H | N-41 | H | H | H | H | H | — | — | — | — | — | — |
| 493 | 1(4) | — | — | H | H | N-1 | H | H | H | H | — | — | — | — | — | — |
| 494 | 1(4) | — | — | H | H | N-2 | H | H | H | H | — | — | — | — | — | — |
| 495 | 1(4) | — | — | H | H | N-3 | H | H | H | H | — | — | — | — | — | — |
| 496 | 1(4) | — | — | H | H | N-4 | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 497 | 1(4) | — | — | H | H | N-5 | H | H | H | H | — | — | — | — | — | — |
| 498 | 1(4) | — | — | H | H | N-6 | H | H | H | H | — | — | — | — | — | — |
| 499 | 1(4) | — | — | H | H | N-7 | H | H | H | H | — | — | — | — | — | — |
| 500 | 1(4) | — | — | H | H | N-8 | H | H | H | H | — | — | — | — | — | — |
| 501 | 1(4) | — | — | H | H | N-9 | H | H | H | H | — | — | — | — | — | — |
| 502 | 1(4) | — | — | H | H | N-10 | H | H | H | H | — | — | — | — | — | — |
| 503 | 1(4) | — | — | H | H | N-11 | H | H | H | H | — | — | — | — | — | — |
| 504 | 1(4) | — | — | H | H | N-12 | H | H | H | H | — | — | — | — | — | — |
| 505 | 1(4) | — | — | H | H | N-13 | H | H | H | H | — | — | — | — | — | — |
| 506 | 1(4) | — | — | H | H | N-14 | H | H | H | H | — | — | — | — | — | — |
| 507 | 1(4) | — | — | H | H | N-15 | H | H | H | H | — | — | — | — | — | — |
| 508 | 1(4) | — | — | H | H | N-16 | H | H | H | H | — | — | — | — | — | — |
| 509 | 1(4) | — | — | H | H | N-17 | H | H | H | H | — | — | — | — | — | — |
| 510 | 1(4) | — | — | H | H | N-18 | H | H | H | H | — | — | — | — | — | — |
| 511 | 1(4) | — | — | H | H | N-19 | H | H | H | H | — | — | — | — | — | — |
| 512 | 1(4) | — | — | H | H | N-20 | H | H | H | H | — | — | — | — | — | — |
| 513 | 1(4) | — | — | H | H | N-21 | H | H | H | H | — | — | — | — | — | — |
| 514 | 1(4) | — | — | H | H | N-22 | H | H | H | H | — | — | — | — | — | — |
| 515 | 1(4) | — | — | H | H | N-23 | H | H | H | H | — | — | — | — | — | — |
| 516 | 1(4) | — | — | H | H | N-24 | H | H | H | H | — | — | — | — | — | — |
| 517 | 1(4) | — | — | H | H | N-25 | H | H | H | H | — | — | — | — | — | — |
| 518 | 1(4) | — | — | H | H | N-26 | H | H | H | H | — | — | — | — | — | — |
| 519 | 1(4) | — | — | H | H | N-27 | H | H | H | H | — | — | — | — | — | — |
| 520 | 1(4) | — | — | H | H | N-28 | H | H | H | H | — | — | — | — | — | — |
| 521 | 1(4) | — | — | H | H | N-29 | H | H | H | H | — | — | — | — | — | — |
| 522 | 1(4) | — | — | H | H | N-30 | H | H | H | H | — | — | — | — | — | — |
| 523 | 1(4) | — | — | H | H | N-31 | H | H | H | H | — | — | — | — | — | — |
| 524 | 1(4) | — | — | H | H | N-32 | H | H | H | H | — | — | — | — | — | — |
| 525 | 1(4) | — | — | H | H | N-33 | H | H | H | H | — | — | — | — | — | — |
| 526 | 1(4) | — | — | H | H | N-34 | H | H | H | H | — | — | — | — | — | — |
| 527 | 1(4) | — | — | H | H | N-35 | H | H | H | H | — | — | — | — | — | — |
| 528 | 1(4) | — | — | H | H | N-36 | H | H | H | H | — | — | — | — | — | — |
| 529 | 1(4) | — | — | H | H | N-37 | H | H | H | H | — | — | — | — | — | — |
| 530 | 1(4) | — | — | H | H | N-38 | H | H | H | H | — | — | — | — | — | — |
| 531 | 1(4) | — | — | H | H | N-39 | H | H | H | H | — | — | — | — | — | — |
| 532 | 1(4) | — | — | H | H | N-40 | H | H | H | H | — | — | — | — | — | — |
| 533 | 1(4) | — | — | H | H | N-41 | H | H | H | H | — | — | — | — | — | — |
| 534 | 1(4) | — | — | H | H | H | H | H | N-1 | H | — | — | — | — | — | — |
| 535 | 1(4) | — | — | H | H | H | H | H | N-2 | H | — | — | — | — | — | — |
| 536 | 1(4) | — | — | H | H | H | H | H | N-3 | H | — | — | — | — | — | — |
| 537 | 1(4) | — | — | H | H | H | H | H | N-4 | H | — | — | — | — | — | — |
| 538 | 1(4) | — | — | H | H | H | H | H | N-5 | H | — | — | — | — | — | — |
| 539 | 1(4) | — | — | H | H | H | H | H | N-6 | H | — | — | — | — | — | — |
| 540 | 1(4) | — | — | H | H | H | H | H | N-7 | H | — | — | — | — | — | — |
| 541 | 1(4) | — | — | H | H | H | H | H | N-8 | H | — | — | — | — | — | — |
| 542 | 1(4) | — | — | H | H | H | H | H | N-9 | H | — | — | — | — | — | — |
| 543 | 1(4) | — | — | H | H | H | H | H | N-10 | H | — | — | — | — | — | — |
| 544 | 1(4) | — | — | H | H | H | H | H | N-11 | H | — | — | — | — | — | — |
| 545 | 1(4) | — | — | H | H | H | H | H | N-12 | H | — | — | — | — | — | — |
| 546 | 1(4) | — | — | H | H | H | H | H | N-13 | H | — | — | — | — | — | — |
| 547 | 1(4) | — | — | H | H | H | H | H | N-14 | H | — | — | — | — | — | — |
| 548 | 1(4) | — | — | H | H | H | H | H | N-15 | H | — | — | — | — | — | — |
| 549 | 1(4) | — | — | H | H | H | H | H | N-16 | H | — | — | — | — | — | — |
| 550 | 1(4) | — | — | H | H | H | H | H | N-17 | H | — | — | — | — | — | — |
| 551 | 1(4) | — | — | H | H | H | H | H | N-18 | H | — | — | — | — | — | — |
| 552 | 1(4) | — | — | H | H | H | H | H | N-19 | H | — | — | — | — | — | — |
| 553 | 1(4) | — | — | H | H | H | H | H | N-20 | H | — | — | — | — | — | — |
| 554 | 1(4) | — | — | H | H | H | H | H | N-21 | H | — | — | — | — | — | — |
| 555 | 1(4) | — | — | H | H | H | H | H | N-22 | H | — | — | — | — | — | — |
| 556 | 1(4) | — | — | H | H | H | H | H | N-23 | H | — | — | — | — | — | — |
| 557 | 1(4) | — | — | H | H | H | H | H | N-24 | H | — | — | — | — | — | — |
| 558 | 1(4) | — | — | H | H | H | H | H | N-25 | H | — | — | — | — | — | — |
| 559 | 1(4) | — | — | H | H | H | H | H | N-26 | H | — | — | — | — | — | — |
| 560 | 1(4) | — | — | H | H | H | H | H | N-27 | H | — | — | — | — | — | — |
| 561 | 1(4) | — | — | H | H | H | H | H | N-28 | H | — | — | — | — | — | — |
| 562 | 1(4) | — | — | H | H | H | H | H | N-29 | H | — | — | — | — | — | — |
| 563 | 1(4) | — | — | H | H | H | H | H | N-30 | H | — | — | — | — | — | — |
| 564 | 1(4) | — | — | H | H | H | H | H | N-31 | H | — | — | — | — | — | — |
| 565 | 1(4) | — | — | H | H | H | H | H | N-32 | H | — | — | — | — | — | — |
| 566 | 1(4) | — | — | H | H | H | H | H | N-33 | H | — | — | — | — | — | — |
| 567 | 1(4) | — | — | H | H | H | H | H | N-34 | H | — | — | — | — | — | — |
| 568 | 1(4) | — | — | H | H | H | H | H | N-35 | H | — | — | — | — | — | — |
| 569 | 1(4) | — | — | H | H | H | H | H | N-36 | H | — | — | — | — | — | — |
| 570 | 1(4) | — | — | H | H | H | H | H | N-37 | H | — | — | — | — | — | — |
| 571 | 1(4) | — | — | H | H | H | H | H | N-38 | H | — | — | — | — | — | — |
| 572 | 1(4) | — | — | H | H | H | H | H | N-39 | H | — | — | — | — | — | — |
| 573 | 1(4) | — | — | H | H | H | H | H | N-40 | H | — | — | — | — | — | — |
| 574 | 1(4) | — | — | H | H | H | H | H | N-41 | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 575 | 1(5) | — | — | H | N-1 | H | H | H | H | H | H | H | H | H | H | H |
| 576 | 1(5) | — | — | H | N-2 | H | H | H | H | H | H | H | H | H | H | H |
| 577 | 1(5) | — | — | H | N-3 | H | H | H | H | H | H | H | H | H | H | H |
| 578 | 1(5) | — | — | H | N-4 | H | H | H | H | H | H | H | H | H | H | H |
| 579 | 1(5) | — | — | H | N-5 | H | H | H | H | H | H | H | H | H | H | H |
| 580 | 1(5) | — | — | H | N-6 | H | H | H | H | H | H | H | H | H | H | H |
| 581 | 1(5) | — | — | H | N-7 | H | H | H | H | H | H | H | H | H | H | H |
| 582 | 1(5) | — | — | H | N-8 | H | H | H | H | H | H | H | H | H | H | H |
| 583 | 1(5) | — | — | H | N-9 | H | H | H | H | H | H | H | H | H | H | H |
| 584 | 1(5) | — | — | H | N-10 | H | H | H | H | H | H | H | H | H | H | H |
| 585 | 1(5) | — | — | H | N-11 | H | H | H | H | H | H | H | H | H | H | H |
| 586 | 1(5) | — | — | H | N-12 | H | H | H | H | H | H | H | H | H | H | H |
| 587 | 1(5) | — | — | H | N-13 | H | H | H | H | H | H | H | H | H | H | H |
| 588 | 1(5) | — | — | H | N-14 | H | H | H | H | H | H | H | H | H | H | H |
| 589 | 1(5) | — | — | H | N-15 | H | H | H | H | H | H | H | H | H | H | H |
| 590 | 1(5) | — | — | H | N-16 | H | H | H | H | H | H | H | H | H | H | H |
| 591 | 1(5) | — | — | H | N-17 | H | H | H | H | H | H | H | H | H | H | H |
| 592 | 1(5) | — | — | H | N-18 | H | H | H | H | H | H | H | H | H | H | H |
| 593 | 1(5) | — | — | H | N-19 | H | H | H | H | H | H | H | H | H | H | H |
| 594 | 1(5) | — | — | H | N-20 | H | H | H | H | H | H | H | H | H | H | H |
| 595 | 1(5) | — | — | H | N-21 | H | H | H | H | H | H | H | H | H | H | H |
| 596 | 1(5) | — | — | H | N-22 | H | H | H | H | H | H | H | H | H | H | H |
| 597 | 1(5) | — | — | H | N-23 | H | H | H | H | H | H | H | H | H | H | H |
| 598 | 1(5) | — | — | H | N-24 | H | H | H | H | H | H | H | H | H | H | H |
| 599 | 1(5) | — | — | H | N-25 | H | H | H | H | H | H | H | H | H | H | H |
| 600 | 1(5) | — | — | H | N-26 | H | H | H | H | H | H | H | H | H | H | H |
| 601 | 1(5) | — | — | H | N-27 | H | H | H | H | H | H | H | H | H | H | H |
| 602 | 1(5) | — | — | H | N-28 | H | H | H | H | H | H | H | H | H | H | H |
| 603 | 1(5) | — | — | H | N-29 | H | H | H | H | H | H | H | H | H | H | H |
| 604 | 1(5) | — | — | H | N-30 | H | H | H | H | H | H | H | H | H | H | H |
| 605 | 1(5) | — | — | H | N-31 | H | H | H | H | H | H | H | H | H | H | H |
| 606 | 1(5) | — | — | H | N-32 | H | H | H | H | H | H | H | H | H | H | H |
| 607 | 1(5) | — | — | H | N-33 | H | H | H | H | H | H | H | H | H | H | H |
| 608 | 1(5) | — | — | H | N-34 | H | H | H | H | H | H | H | H | H | H | H |
| 609 | 1(5) | — | — | H | N-35 | H | H | H | H | H | H | H | H | H | H | H |
| 610 | 1(5) | — | — | H | N-36 | H | H | H | H | H | H | H | H | H | H | H |
| 611 | 1(5) | — | — | H | N-37 | H | H | H | H | H | H | H | H | H | H | H |
| 612 | 1(5) | — | — | H | N-38 | H | H | H | H | H | H | H | H | H | H | H |
| 613 | 1(5) | — | — | H | N-39 | H | H | H | H | H | H | H | H | H | H | H |
| 614 | 1(5) | — | — | H | N-40 | H | H | H | H | H | H | H | H | H | H | H |
| 615 | 1(5) | — | — | H | N-41 | H | H | H | H | H | H | H | H | H | H | H |
| 616 | 1(5) | — | — | H | H | N-1 | H | H | H | H | H | H | H | H | H | H |
| 617 | 1(5) | — | — | H | H | N-2 | H | H | H | H | H | H | H | H | H | H |
| 618 | 1(5) | — | — | H | H | N-3 | H | H | H | H | H | H | H | H | H | H |
| 619 | 1(5) | — | — | H | H | N-4 | H | H | H | H | H | H | H | H | H | H |
| 620 | 1(5) | — | — | H | H | N-5 | H | H | H | H | H | H | H | H | H | H |
| 621 | 1(5) | — | — | H | H | N-6 | H | H | H | H | H | H | H | H | H | H |
| 622 | 1(5) | — | — | H | H | N-7 | H | H | H | H | H | H | H | H | H | H |
| 623 | 1(5) | — | — | H | H | N-8 | H | H | H | H | H | H | H | H | H | H |
| 624 | 1(5) | — | — | H | H | N-9 | H | H | H | H | H | H | H | H | H | H |
| 625 | 1(5) | — | — | H | H | N-10 | H | H | H | H | H | H | H | H | H | H |
| 626 | 1(5) | — | — | H | H | N-11 | H | H | H | H | H | H | H | H | H | H |
| 627 | 1(5) | — | — | H | H | N-12 | H | H | H | H | H | H | H | H | H | H |
| 628 | 1(5) | — | — | H | H | N-13 | H | H | H | H | H | H | H | H | H | H |
| 629 | 1(5) | — | — | H | H | N-14 | H | H | H | H | H | H | H | H | H | H |
| 630 | 1(5) | — | — | H | H | N-15 | H | H | H | H | H | H | H | H | H | H |
| 631 | 1(5) | — | — | H | H | N-16 | H | H | H | H | H | H | H | H | H | H |
| 632 | 1(5) | — | — | H | H | N-17 | H | H | H | H | H | H | H | H | H | H |
| 633 | 1(5) | — | — | H | H | N-18 | H | H | H | H | H | H | H | H | H | H |
| 634 | 1(5) | — | — | H | H | N-19 | H | H | H | H | H | H | H | H | H | H |
| 635 | 1(5) | — | — | H | H | N-20 | H | H | H | H | H | H | H | H | H | H |
| 636 | 1(5) | — | — | H | H | N-21 | H | H | H | H | H | H | H | H | H | H |
| 637 | 1(5) | — | — | H | H | N-22 | H | H | H | H | H | H | H | H | H | H |
| 638 | 1(5) | — | — | H | H | N-23 | H | H | H | H | H | H | H | H | H | H |
| 639 | 1(5) | — | — | H | H | N-24 | H | H | H | H | H | H | H | H | H | H |
| 640 | 1(5) | — | — | H | H | N-25 | H | H | H | H | H | H | H | H | H | H |
| 641 | 1(5) | — | — | H | H | N-26 | H | H | H | H | H | H | H | H | H | H |
| 642 | 1(5) | — | — | H | H | N-27 | H | H | H | H | H | H | H | H | H | H |
| 643 | 1(5) | — | — | H | H | N-28 | H | H | H | H | H | H | H | H | H | H |
| 644 | 1(5) | — | — | H | H | N-29 | H | H | H | H | H | H | H | H | H | H |
| 645 | 1(5) | — | — | H | H | N-30 | H | H | H | H | H | H | H | H | H | H |
| 646 | 1(5) | — | — | H | H | N-31 | H | H | H | H | H | H | H | H | H | H |
| 647 | 1(5) | — | — | H | H | N-32 | H | H | H | H | H | H | H | H | H | H |
| 648 | 1(5) | — | — | H | H | N-33 | H | H | H | H | H | H | H | H | H | H |
| 649 | 1(5) | — | — | H | H | N-34 | H | H | H | H | H | H | H | H | H | H |
| 650 | 1(5) | — | — | H | H | N-35 | H | H | H | H | H | H | H | H | H | H |
| 651 | 1(5) | — | — | H | H | N-36 | H | H | H | H | H | H | H | H | H | H |
| 652 | 1(5) | — | — | H | H | N-37 | H | H | H | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 653 | 1(5) | — | — | H | H | N-38 | H | H | H | H | H | H | H | H | H | H |
| 654 | 1(5) | — | — | H | H | N-39 | H | H | H | H | H | H | H | H | H | H |
| 655 | 1(5) | — | — | H | H | N-40 | H | H | H | H | H | H | H | H | H | H |
| 656 | 1(5) | — | — | H | H | N-41 | H | H | H | H | H | H | H | H | H | H |
| 657 | 1(5) | — | — | H | H | H | H | H | N-1 | H | H | H | H | H | H | H |
| 658 | 1(5) | — | — | H | H | H | H | H | N-2 | H | H | H | H | H | H | H |
| 659 | 1(5) | — | — | H | H | H | H | H | N-3 | H | H | H | H | H | H | H |
| 660 | 1(5) | — | — | H | H | H | H | H | N-4 | H | H | H | H | H | H | H |
| 661 | 1(5) | — | — | H | H | H | H | H | N-5 | H | H | H | H | H | H | H |
| 662 | 1(5) | — | — | H | H | H | H | H | N-6 | H | H | H | H | H | H | H |
| 663 | 1(5) | — | — | H | H | H | H | H | N-7 | H | H | H | H | H | H | H |
| 664 | 1(5) | — | — | H | H | H | H | H | N-8 | H | H | H | H | H | H | H |
| 665 | 1(5) | — | — | H | H | H | H | H | N-9 | H | H | H | H | H | H | H |
| 666 | 1(5) | — | — | H | H | H | H | H | N-10 | H | H | H | H | H | H | H |
| 667 | 1(5) | — | — | H | H | H | H | H | N-11 | H | H | H | H | H | H | H |
| 668 | 1(5) | — | — | H | H | H | H | H | N-12 | H | H | H | H | H | H | H |
| 669 | 1(5) | — | — | H | H | H | H | H | N-13 | H | H | H | H | H | H | H |
| 670 | 1(5) | — | — | H | H | H | H | H | N-14 | H | H | H | H | H | H | H |
| 671 | 1(5) | — | — | H | H | H | H | H | N-15 | H | H | H | H | H | H | H |
| 672 | 1(5) | — | — | H | H | H | H | H | N-16 | H | H | H | H | H | H | H |
| 673 | 1(5) | — | — | H | H | H | H | H | N-17 | H | H | H | H | H | H | H |
| 674 | 1(5) | — | — | H | H | H | H | H | N-18 | H | H | H | H | H | H | H |
| 675 | 1(5) | — | — | H | H | H | H | H | N-19 | H | H | H | H | H | H | H |
| 676 | 1(5) | — | — | H | H | H | H | H | N-20 | H | H | H | H | H | H | H |
| 677 | 1(5) | — | — | H | H | H | H | H | N-21 | H | H | H | H | H | H | H |
| 678 | 1(5) | — | — | H | H | H | H | H | N-22 | H | H | H | H | H | H | H |
| 679 | 1(5) | — | — | H | H | H | H | H | N-23 | H | H | H | H | H | H | H |
| 680 | 1(5) | — | — | H | H | H | H | H | N-24 | H | H | H | H | H | H | H |
| 681 | 1(5) | — | — | H | H | H | H | H | N-25 | H | H | H | H | H | H | H |
| 682 | 1(5) | — | — | H | H | H | H | H | N-26 | H | H | H | H | H | H | H |
| 683 | 1(5) | — | — | H | H | H | H | H | N-27 | H | H | H | H | H | H | H |
| 684 | 1(5) | — | — | H | H | H | H | H | N-28 | H | H | H | H | H | H | H |
| 685 | 1(5) | — | — | H | H | H | H | H | N-29 | H | H | H | H | H | H | H |
| 686 | 1(5) | — | — | H | H | H | H | H | N-30 | H | H | H | H | H | H | H |
| 687 | 1(5) | — | — | H | H | H | H | H | N-31 | H | H | H | H | H | H | H |
| 688 | 1(5) | — | — | H | H | H | H | H | N-32 | H | H | H | H | H | H | H |
| 689 | 1(5) | — | — | H | H | H | H | H | N-33 | H | H | H | H | H | H | H |
| 690 | 1(5) | — | — | H | H | H | H | H | N-34 | H | H | H | H | H | H | H |
| 691 | 1(5) | — | — | H | H | H | H | H | N-35 | H | H | H | H | H | H | H |
| 692 | 1(5) | — | — | H | H | H | H | H | N-36 | H | H | H | H | H | H | H |
| 693 | 1(5) | — | — | H | H | H | H | H | N-37 | H | H | H | H | H | H | H |
| 694 | 1(5) | — | — | H | H | H | H | H | N-38 | H | H | H | H | H | H | H |
| 695 | 1(5) | — | — | H | H | H | H | H | N-39 | H | H | H | H | H | H | H |
| 696 | 1(5) | — | — | H | H | H | H | H | N-40 | H | H | H | H | H | H | H |
| 697 | 1(5) | — | — | H | H | H | H | H | N-41 | H | H | H | H | H | H | H |
| 698 | 1(5) | — | — | H | H | H | H | H | H | H | H | H | N-1 | H | H | H |
| 699 | 1(5) | — | — | H | H | H | H | H | H | H | H | H | N-2 | H | H | H |
| 700 | 1(5) | — | — | H | H | H | H | H | H | H | H | H | N-3 | H | H | H |
| 701 | 1(5) | — | — | H | H | H | H | H | H | H | H | H | N-4 | H | H | H |
| 702 | 1(5) | — | — | H | H | H | H | H | H | H | H | H | N-5 | H | H | H |
| 703 | 1(5) | — | — | H | H | H | H | H | H | H | H | H | N-6 | H | H | H |
| 704 | 1(5) | — | — | H | H | H | H | H | H | H | H | H | N-7 | H | H | H |
| 705 | 1(5) | — | — | H | H | H | H | H | H | H | H | H | N-8 | H | H | H |
| 706 | 1(5) | — | — | H | H | H | H | H | H | H | H | H | N-9 | H | H | H |
| 707 | 1(5) | — | — | H | H | H | H | H | H | H | H | H | N-10 | H | H | H |
| 708 | 1(5) | — | — | H | H | H | H | H | H | H | H | H | N-11 | H | H | H |
| 709 | 1(5) | — | — | H | H | H | H | H | H | H | H | H | N-12 | H | H | H |
| 710 | 1(5) | — | — | H | H | H | H | H | H | H | H | H | N-13 | H | H | H |
| 711 | 1(5) | — | — | H | H | H | H | H | H | H | H | H | N-14 | H | H | H |
| 712 | 1(5) | — | — | H | H | H | H | H | H | H | H | H | N-15 | H | H | H |
| 713 | 1(5) | — | — | H | H | H | H | H | H | H | H | H | N-16 | H | H | H |
| 714 | 1(5) | — | — | H | H | H | H | H | H | H | H | H | N-17 | H | H | H |
| 715 | 1(5) | — | — | H | H | H | H | H | H | H | H | H | N-18 | H | H | H |
| 716 | 1(5) | — | — | H | H | H | H | H | H | H | H | H | N-19 | H | H | H |
| 717 | 1(5) | — | — | H | H | H | H | H | H | H | H | H | N-20 | H | H | H |
| 718 | 1(5) | — | — | H | H | H | H | H | H | H | H | H | N-21 | H | H | H |
| 719 | 1(5) | — | — | H | H | H | H | H | H | H | H | H | N-22 | H | H | H |
| 720 | 1(5) | — | — | H | H | H | H | H | H | H | H | H | N-23 | H | H | H |
| 721 | 1(5) | — | — | H | H | H | H | H | H | H | H | H | N-24 | H | H | H |
| 722 | 1(5) | — | — | H | H | H | H | H | H | H | H | H | N-25 | H | H | H |
| 723 | 1(5) | — | — | H | H | H | H | H | H | H | H | H | N-26 | H | H | H |
| 724 | 1(5) | — | — | H | H | H | H | H | H | H | H | H | N-27 | H | H | H |
| 725 | 1(5) | — | — | H | H | H | H | H | H | H | H | H | N-28 | H | H | H |
| 726 | 1(5) | — | — | H | H | H | H | H | H | H | H | H | N-29 | H | H | H |
| 727 | 1(5) | — | — | H | H | H | H | H | H | H | H | H | N-30 | H | H | H |
| 728 | 1(5) | — | — | H | H | H | H | H | H | H | H | H | N-31 | H | H | H |
| 729 | 1(5) | — | — | H | H | H | H | H | H | H | H | H | N-32 | H | H | H |
| 730 | 1(5) | — | — | H | H | H | H | H | H | H | H | H | N-33 | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 731 | 1(5) | — | — | H | H | H | H | H | H | H | H | H | N-34 | H | H | H |
| 732 | 1(5) | — | — | H | H | H | H | H | H | H | H | H | N-35 | H | H | H |
| 733 | 1(5) | — | — | H | H | H | H | H | H | H | H | H | N-36 | H | H | H |
| 734 | 1(5) | — | — | H | H | H | H | H | H | H | H | H | N-37 | H | H | H |
| 735 | 1(5) | — | — | H | H | H | H | H | H | H | H | H | N-38 | H | H | H |
| 736 | 1(5) | — | — | H | H | H | H | H | H | H | H | H | N-39 | H | H | H |
| 737 | 1(5) | — | — | H | H | H | H | H | H | H | H | H | N-40 | H | H | H |
| 738 | 1(5) | — | — | H | H | H | H | H | H | H | H | H | N-41 | H | H | H |
| 739 | 1(5) | — | — | H | H | H | H | H | H | H | H | H | H | N-1 | H | H |
| 740 | 1(5) | — | — | H | H | H | H | H | H | H | H | H | H | N-2 | H | H |
| 741 | 1(5) | — | — | H | H | H | H | H | H | H | H | H | H | N-3 | H | H |
| 742 | 1(5) | — | — | H | H | H | H | H | H | H | H | H | H | N-4 | H | H |
| 743 | 1(5) | — | — | H | H | H | H | H | H | H | H | H | H | N-5 | H | H |
| 744 | 1(5) | — | — | H | H | H | H | H | H | H | H | H | H | N-6 | H | H |
| 745 | 1(5) | — | — | H | H | H | H | H | H | H | H | H | H | N-7 | H | H |
| 746 | 1(5) | — | — | H | H | H | H | H | H | H | H | H | H | N-8 | H | H |
| 747 | 1(5) | — | — | H | H | H | H | H | H | H | H | H | H | N-9 | H | H |
| 748 | 1(5) | — | — | H | H | H | H | H | H | H | H | H | H | N-10 | H | H |
| 749 | 1(5) | — | — | H | H | H | H | H | H | H | H | H | H | N-11 | H | H |
| 750 | 1(5) | — | — | H | H | H | H | H | H | H | H | H | H | N-12 | H | H |
| 751 | 1(5) | — | — | H | H | H | H | H | H | H | H | H | H | N-13 | H | H |
| 752 | 1(5) | — | — | H | H | H | H | H | H | H | H | H | H | N-14 | H | H |
| 753 | 1(5) | — | — | H | H | H | H | H | H | H | H | H | H | N-15 | H | H |
| 754 | 1(5) | — | — | H | H | H | H | H | H | H | H | H | H | N-16 | H | H |
| 755 | 1(5) | — | — | H | H | H | H | H | H | H | H | H | H | N-17 | H | H |
| 756 | 1(5) | — | — | H | H | H | H | H | H | H | H | H | H | N-18 | H | H |
| 757 | 1(5) | — | — | H | H | H | H | H | H | H | H | H | H | N-19 | H | H |
| 758 | 1(5) | — | — | H | H | H | H | H | H | H | H | H | H | N-20 | H | H |
| 759 | 1(5) | — | — | H | H | H | H | H | H | H | H | H | H | N-21 | H | H |
| 760 | 1(5) | — | — | H | H | H | H | H | H | H | H | H | H | N-22 | H | H |
| 761 | 1(5) | — | — | H | H | H | H | H | H | H | H | H | H | N-23 | H | H |
| 762 | 1(5) | — | — | H | H | H | H | H | H | H | H | H | H | N-24 | H | H |
| 763 | 1(5) | — | — | H | H | H | H | H | H | H | H | H | H | N-25 | H | H |
| 764 | 1(5) | — | — | H | H | H | H | H | H | H | H | H | H | N-26 | H | H |
| 765 | 1(5) | — | — | H | H | H | H | H | H | H | H | H | H | N-27 | H | H |
| 766 | 1(5) | — | — | H | H | H | H | H | H | H | H | H | H | N-28 | H | H |
| 767 | 1(5) | — | — | H | H | H | H | H | H | H | H | H | H | N-29 | H | H |
| 768 | 1(5) | — | — | H | H | H | H | H | H | H | H | H | H | N-30 | H | H |
| 769 | 1(5) | — | — | H | H | H | H | H | H | H | H | H | H | N-31 | H | H |
| 770 | 1(5) | — | — | H | H | H | H | H | H | H | H | H | H | N-32 | H | H |
| 771 | 1(5) | — | — | H | H | H | H | H | H | H | H | H | H | N-33 | H | H |
| 772 | 1(5) | — | — | H | H | H | H | H | H | H | H | H | H | N-34 | H | H |
| 773 | 1(5) | — | — | H | H | H | H | H | H | H | H | H | H | N-35 | H | H |
| 774 | 1(5) | — | — | H | H | H | H | H | H | H | H | H | H | N-36 | H | H |
| 775 | 1(5) | — | — | H | H | H | H | H | H | H | H | H | H | N-37 | H | H |
| 776 | 1(5) | — | — | H | H | H | H | H | H | H | H | H | H | N-38 | H | H |
| 777 | 1(5) | — | — | H | H | H | H | H | H | H | H | H | H | N-39 | H | H |
| 778 | 1(5) | — | — | H | H | H | H | H | H | H | H | H | H | N-40 | H | H |
| 779 | 1(5) | — | — | H | H | H | H | H | H | H | H | H | H | N-41 | H | H |
| 780 | 1(6) | — | — | H | N-1 | H | H | H | H | H | — | — | — | — | — | — |
| 781 | 1(6) | — | — | H | N-2 | H | H | H | H | H | — | — | — | — | — | — |
| 782 | 1(6) | — | — | H | N-3 | H | H | H | H | H | — | — | — | — | — | — |
| 783 | 1(6) | — | — | H | N-4 | H | H | H | H | H | — | — | — | — | — | — |
| 784 | 1(6) | — | — | H | N-5 | H | H | H | H | H | — | — | — | — | — | — |
| 785 | 1(6) | — | — | H | N-6 | H | H | H | H | H | — | — | — | — | — | — |
| 786 | 1(6) | — | — | H | N-7 | H | H | H | H | H | — | — | — | — | — | — |
| 787 | 1(6) | — | — | H | N-8 | H | H | H | H | H | — | — | — | — | — | — |
| 788 | 1(6) | — | — | H | N-9 | H | H | H | H | H | — | — | — | — | — | — |
| 789 | 1(6) | — | — | H | N-10 | H | H | H | H | H | — | — | — | — | — | — |
| 790 | 1(6) | — | — | H | N-11 | H | H | H | H | H | — | — | — | — | — | — |
| 791 | 1(6) | — | — | H | N-12 | H | H | H | H | H | — | — | — | — | — | — |
| 792 | 1(6) | — | — | H | N-13 | H | H | H | H | H | — | — | — | — | — | — |
| 793 | 1(6) | — | — | H | N-14 | H | H | H | H | H | — | — | — | — | — | — |
| 794 | 1(6) | — | — | H | N-15 | H | H | H | H | H | — | — | — | — | — | — |
| 795 | 1(6) | — | — | H | N-16 | H | H | H | H | H | — | — | — | — | — | — |
| 796 | 1(6) | — | — | H | N-17 | H | H | H | H | H | — | — | — | — | — | — |
| 797 | 1(6) | — | — | H | N-18 | H | H | H | H | H | — | — | — | — | — | — |
| 798 | 1(6) | — | — | H | N-19 | H | H | H | H | H | — | — | — | — | — | — |
| 799 | 1(6) | — | — | H | N-20 | H | H | H | H | H | — | — | — | — | — | — |
| 800 | 1(6) | — | — | H | N-21 | H | H | H | H | H | — | — | — | — | — | — |
| 801 | 1(6) | — | — | H | N-22 | H | H | H | H | H | — | — | — | — | — | — |
| 802 | 1(6) | — | — | H | N-23 | H | H | H | H | H | — | — | — | — | — | — |
| 803 | 1(6) | — | — | H | N-24 | H | H | H | H | H | — | — | — | — | — | — |
| 804 | 1(6) | — | — | H | N-25 | H | H | H | H | H | — | — | — | — | — | — |
| 805 | 1(6) | — | — | H | N-26 | H | H | H | H | H | — | — | — | — | — | — |
| 806 | 1(6) | — | — | H | N-27 | H | H | H | H | H | — | — | — | — | — | — |
| 807 | 1(6) | — | — | H | N-28 | H | H | H | H | H | — | — | — | — | — | — |
| 808 | 1(6) | — | — | H | N-29 | H | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 809 | 1(6) | — | — | H | N-30 | H | H | H | H | H | — | — | — | — | — | — |
| 810 | 1(6) | — | — | H | N-31 | H | H | H | H | H | — | — | — | — | — | — |
| 811 | 1(6) | — | — | H | N-32 | H | H | H | H | H | — | — | — | — | — | — |
| 812 | 1(6) | — | — | H | N-33 | H | H | H | H | H | — | — | — | — | — | — |
| 813 | 1(6) | — | — | H | N-34 | H | H | H | H | H | — | — | — | — | — | — |
| 814 | 1(6) | — | — | H | N-35 | H | H | H | H | H | — | — | — | — | — | — |
| 815 | 1(6) | — | — | H | N-36 | H | H | H | H | H | — | — | — | — | — | — |
| 816 | 1(6) | — | — | H | N-37 | H | H | H | H | H | — | — | — | — | — | — |
| 817 | 1(6) | — | — | H | N-38 | H | H | H | H | H | — | — | — | — | — | — |
| 818 | 1(6) | — | — | H | N-39 | H | H | H | H | H | — | — | — | — | — | — |
| 819 | 1(6) | — | — | H | N-40 | H | H | H | H | H | — | — | — | — | — | — |
| 820 | 1(6) | — | — | H | N-41 | H | H | H | H | H | — | — | — | — | — | — |
| 821 | 1(6) | — | — | H | H | N-1 | H | H | H | H | — | — | — | — | — | — |
| 822 | 1(6) | — | — | H | H | N-2 | H | H | H | H | — | — | — | — | — | — |
| 823 | 1(6) | — | — | H | H | N-3 | H | H | H | H | — | — | — | — | — | — |
| 824 | 1(6) | — | — | H | H | N-4 | H | H | H | H | — | — | — | — | — | — |
| 825 | 1(6) | — | — | H | H | N-5 | H | H | H | H | — | — | — | — | — | — |
| 826 | 1(6) | — | — | H | H | N-6 | H | H | H | H | — | — | — | — | — | — |
| 827 | 1(6) | — | — | H | H | N-7 | H | H | H | H | — | — | — | — | — | — |
| 828 | 1(6) | — | — | H | H | N-8 | H | H | H | H | — | — | — | — | — | — |
| 829 | 1(6) | — | — | H | H | N-9 | H | H | H | H | — | — | — | — | — | — |
| 830 | 1(6) | — | — | H | H | N-10 | H | H | H | H | — | — | — | — | — | — |
| 831 | 1(6) | — | — | H | H | N-11 | H | H | H | H | — | — | — | — | — | — |
| 832 | 1(6) | — | — | H | H | N-12 | H | H | H | H | — | — | — | — | — | — |
| 833 | 1(6) | — | — | H | H | N-13 | H | H | H | H | — | — | — | — | — | — |
| 834 | 1(6) | — | — | H | H | N-14 | H | H | H | H | — | — | — | — | — | — |
| 835 | 1(6) | — | — | H | H | N-15 | H | H | H | H | — | — | — | — | — | — |
| 836 | 1(6) | — | — | H | H | N-16 | H | H | H | H | — | — | — | — | — | — |
| 837 | 1(6) | — | — | H | H | N-17 | H | H | H | H | — | — | — | — | — | — |
| 838 | 1(6) | — | — | H | H | N-18 | H | H | H | H | — | — | — | — | — | — |
| 839 | 1(6) | — | — | H | H | N-19 | H | H | H | H | — | — | — | — | — | — |
| 840 | 1(6) | — | — | H | H | N-20 | H | H | H | H | — | — | — | — | — | — |
| 841 | 1(6) | — | — | H | H | N-21 | H | H | H | H | — | — | — | — | — | — |
| 842 | 1(6) | — | — | H | H | N-22 | H | H | H | H | — | — | — | — | — | — |
| 843 | 1(6) | — | — | H | H | N-23 | H | H | H | H | — | — | — | — | — | — |
| 844 | 1(6) | — | — | H | H | N-24 | H | H | H | H | — | — | — | — | — | — |
| 845 | 1(6) | — | — | H | H | N-25 | H | H | H | H | — | — | — | — | — | — |
| 846 | 1(6) | — | — | H | H | N-26 | H | H | H | H | — | — | — | — | — | — |
| 847 | 1(6) | — | — | H | H | N-27 | H | H | H | H | — | — | — | — | — | — |
| 848 | 1(6) | — | — | H | H | N-28 | H | H | H | H | — | — | — | — | — | — |
| 849 | 1(6) | — | — | H | H | N-29 | H | H | H | H | — | — | — | — | — | — |
| 850 | 1(6) | — | — | H | H | N-30 | H | H | H | H | — | — | — | — | — | — |
| 851 | 1(6) | — | — | H | H | N-31 | H | H | H | H | — | — | — | — | — | — |
| 852 | 1(6) | — | — | H | H | N-32 | H | H | H | H | — | — | — | — | — | — |
| 853 | 1(6) | — | — | H | H | N-33 | H | H | H | H | — | — | — | — | — | — |
| 854 | 1(6) | — | — | H | H | N-34 | H | H | H | H | — | — | — | — | — | — |
| 855 | 1(6) | — | — | H | H | N-35 | H | H | H | H | — | — | — | — | — | — |
| 856 | 1(6) | — | — | H | H | N-36 | H | H | H | H | — | — | — | — | — | — |
| 857 | 1(6) | — | — | H | H | N-37 | H | H | H | H | — | — | — | — | — | — |
| 858 | 1(6) | — | — | H | H | N-38 | H | H | H | H | — | — | — | — | — | — |
| 859 | 1(6) | — | — | H | H | N-39 | H | H | H | H | — | — | — | — | — | — |
| 860 | 1(6) | — | — | H | H | N-40 | H | H | H | H | — | — | — | — | — | — |
| 861 | 1(6) | — | — | H | H | N-41 | H | H | H | H | — | — | — | — | — | — |
| 862 | 1(6) | — | — | H | H | H | H | H | H | N-1 | — | — | — | — | — | — |
| 863 | 1(6) | — | — | H | H | H | H | H | H | N-2 | — | — | — | — | — | — |
| 864 | 1(6) | — | — | H | H | H | H | H | H | N-3 | — | — | — | — | — | — |
| 865 | 1(6) | — | — | H | H | H | H | H | H | N-4 | — | — | — | — | — | — |
| 866 | 1(6) | — | — | H | H | H | H | H | H | N-5 | — | — | — | — | — | — |
| 867 | 1(6) | — | — | H | H | H | H | H | H | N-6 | — | — | — | — | — | — |
| 868 | 1(6) | — | — | H | H | H | H | H | H | N-7 | — | — | — | — | — | — |
| 869 | 1(6) | — | — | H | H | H | H | H | H | N-8 | — | — | — | — | — | — |
| 870 | 1(6) | — | — | H | H | H | H | H | H | N-9 | — | — | — | — | — | — |
| 871 | 1(6) | — | — | H | H | H | H | H | H | N-10 | — | — | — | — | — | — |
| 872 | 1(6) | — | — | H | H | H | H | H | H | N-11 | — | — | — | — | — | — |
| 873 | 1(6) | — | — | H | H | H | H | H | H | N-12 | — | — | — | — | — | — |
| 874 | 1(6) | — | — | H | H | H | H | H | H | N-13 | — | — | — | — | — | — |
| 875 | 1(6) | — | — | H | H | H | H | H | H | N-14 | — | — | — | — | — | — |
| 876 | 1(6) | — | — | H | H | H | H | H | H | N-15 | — | — | — | — | — | — |
| 877 | 1(6) | — | — | H | H | H | H | H | H | N-16 | — | — | — | — | — | — |
| 878 | 1(6) | — | — | H | H | H | H | H | H | N-17 | — | — | — | — | — | — |
| 879 | 1(6) | — | — | H | H | H | H | H | H | N-18 | — | — | — | — | — | — |
| 880 | 1(6) | — | — | H | H | H | H | H | H | N-19 | — | — | — | — | — | — |
| 881 | 1(6) | — | — | H | H | H | H | H | H | N-20 | — | — | — | — | — | — |
| 882 | 1(6) | — | — | H | H | H | H | H | H | N-21 | — | — | — | — | — | — |
| 883 | 1(6) | — | — | H | H | H | H | H | H | N-22 | — | — | — | — | — | — |
| 884 | 1(6) | — | — | H | H | H | H | H | H | N-23 | — | — | — | — | — | — |
| 885 | 1(6) | — | — | H | H | H | H | H | H | N-24 | — | — | — | — | — | — |
| 886 | 1(6) | — | — | H | H | H | H | H | H | N-25 | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 887 | 1(6) | — | — | H | H | H | H | H | H | N-26 | — | — | — | — | — | — |
| 888 | 1(6) | — | — | H | H | H | H | H | H | N-27 | — | — | — | — | — | — |
| 889 | 1(6) | — | — | H | H | H | H | H | H | N-28 | — | — | — | — | — | — |
| 890 | 1(6) | — | — | H | H | H | H | H | H | N-29 | — | — | — | — | — | — |
| 891 | 1(6) | — | — | H | H | H | H | H | H | N-30 | — | — | — | — | — | — |
| 892 | 1(6) | — | — | H | H | H | H | H | H | N-31 | — | — | — | — | — | — |
| 893 | 1(6) | — | — | H | H | H | H | H | H | N-32 | — | — | — | — | — | — |
| 894 | 1(6) | — | — | H | H | H | H | H | H | N-33 | — | — | — | — | — | — |
| 895 | 1(6) | — | — | H | H | H | H | H | H | N-34 | — | — | — | — | — | — |
| 896 | 1(6) | — | — | H | H | H | H | H | H | N-35 | — | — | — | — | — | — |
| 897 | 1(6) | — | — | H | H | H | H | H | H | N-36 | — | — | — | — | — | — |
| 898 | 1(6) | — | — | H | H | H | H | H | H | N-37 | — | — | — | — | — | — |
| 899 | 1(6) | — | — | H | H | H | H | H | H | N-38 | — | — | — | — | — | — |
| 900 | 1(6) | — | — | H | H | H | H | H | H | N-39 | — | — | — | — | — | — |
| 901 | 1(6) | — | — | H | H | H | H | H | H | N-40 | — | — | — | — | — | — |
| 902 | 1(6) | — | — | H | H | H | H | H | H | N-41 | — | — | — | — | — | — |
| 903 | 1(7) | — | — | H | N-1 | H | H | H | H | H | — | — | — | — | — | — |
| 904 | 1(7) | — | — | H | N-2 | H | H | H | H | H | — | — | — | — | — | — |
| 905 | 1(7) | — | — | H | N-3 | H | H | H | H | H | — | — | — | — | — | — |
| 906 | 1(7) | — | — | H | N-4 | H | H | H | H | H | — | — | — | — | — | — |
| 907 | 1(7) | — | — | H | N-5 | H | H | H | H | H | — | — | — | — | — | — |
| 908 | 1(7) | — | — | H | N-6 | H | H | H | H | H | — | — | — | — | — | — |
| 909 | 1(7) | — | — | H | N-7 | H | H | H | H | H | — | — | — | — | — | — |
| 910 | 1(7) | — | — | H | N-8 | H | H | H | H | H | — | — | — | — | — | — |
| 911 | 1(7) | — | — | H | N-9 | H | H | H | H | H | — | — | — | — | — | — |
| 912 | 1(7) | — | — | H | N-10 | H | H | H | H | H | — | — | — | — | — | — |
| 913 | 1(7) | — | — | H | N-11 | H | H | H | H | H | — | — | — | — | — | — |
| 914 | 1(7) | — | — | H | N-12 | H | H | H | H | H | — | — | — | — | — | — |
| 915 | 1(7) | — | — | H | N-13 | H | H | H | H | H | — | — | — | — | — | — |
| 916 | 1(7) | — | — | H | N-14 | H | H | H | H | H | — | — | — | — | — | — |
| 917 | 1(7) | — | — | H | N-15 | H | H | H | H | H | — | — | — | — | — | — |
| 918 | 1(7) | — | — | H | N-16 | H | H | H | H | H | — | — | — | — | — | — |
| 919 | 1(7) | — | — | H | N-17 | H | H | H | H | H | — | — | — | — | — | — |
| 920 | 1(7) | — | — | H | N-18 | H | H | H | H | H | — | — | — | — | — | — |
| 921 | 1(7) | — | — | H | N-19 | H | H | H | H | H | — | — | — | — | — | — |
| 922 | 1(7) | — | — | H | N-20 | H | H | H | H | H | — | — | — | — | — | — |
| 923 | 1(7) | — | — | H | N-21 | H | H | H | H | H | — | — | — | — | — | — |
| 924 | 1(7) | — | — | H | N-22 | H | H | H | H | H | — | — | — | — | — | — |
| 925 | 1(7) | — | — | H | N-23 | H | H | H | H | H | — | — | — | — | — | — |
| 926 | 1(7) | — | — | H | N-24 | H | H | H | H | H | — | — | — | — | — | — |
| 927 | 1(7) | — | — | H | N-25 | H | H | H | H | H | — | — | — | — | — | — |
| 928 | 1(7) | — | — | H | N-26 | H | H | H | H | H | — | — | — | — | — | — |
| 929 | 1(7) | — | — | H | N-27 | H | H | H | H | H | — | — | — | — | — | — |
| 930 | 1(7) | — | — | H | N-28 | H | H | H | H | H | — | — | — | — | — | — |
| 931 | 1(7) | — | — | H | N-29 | H | H | H | H | H | — | — | — | — | — | — |
| 932 | 1(7) | — | — | H | N-30 | H | H | H | H | H | — | — | — | — | — | — |
| 933 | 1(7) | — | — | H | N-31 | H | H | H | H | H | — | — | — | — | — | — |
| 934 | 1(7) | — | — | H | N-32 | H | H | H | H | H | — | — | — | — | — | — |
| 935 | 1(7) | — | — | H | N-33 | H | H | H | H | H | — | — | — | — | — | — |
| 936 | 1(7) | — | — | H | N-34 | H | H | H | H | H | — | — | — | — | — | — |
| 937 | 1(7) | — | — | H | N-35 | H | H | H | H | H | — | — | — | — | — | — |
| 938 | 1(7) | — | — | H | N-36 | H | H | H | H | H | — | — | — | — | — | — |
| 939 | 1(7) | — | — | H | N-37 | H | H | H | H | H | — | — | — | — | — | — |
| 940 | 1(7) | — | — | H | N-38 | H | H | H | H | H | — | — | — | — | — | — |
| 941 | 1(7) | — | — | H | N-39 | H | H | H | H | H | — | — | — | — | — | — |
| 942 | 1(7) | — | — | H | N-40 | H | H | H | H | H | — | — | — | — | — | — |
| 943 | 1(7) | — | — | H | N-41 | H | H | H | H | H | — | — | — | — | — | — |
| 944 | 1(7) | — | — | H | H | N-1 | H | H | H | H | — | — | — | — | — | — |
| 945 | 1(7) | — | — | H | H | N-2 | H | H | H | H | — | — | — | — | — | — |
| 946 | 1(7) | — | — | H | H | N-3 | H | H | H | H | — | — | — | — | — | — |
| 947 | 1(7) | — | — | H | H | N-4 | H | H | H | H | — | — | — | — | — | — |
| 948 | 1(7) | — | — | H | H | N-5 | H | H | H | H | — | — | — | — | — | — |
| 949 | 1(7) | — | — | H | H | N-6 | H | H | H | H | — | — | — | — | — | — |
| 950 | 1(7) | — | — | H | H | N-7 | H | H | H | H | — | — | — | — | — | — |
| 951 | 1(7) | — | — | H | H | N-8 | H | H | H | H | — | — | — | — | — | — |
| 952 | 1(7) | — | — | H | H | N-9 | H | H | H | H | — | — | — | — | — | — |
| 953 | 1(7) | — | — | H | H | N-10 | H | H | H | H | — | — | — | — | — | — |
| 954 | 1(7) | — | — | H | H | N-11 | H | H | H | H | — | — | — | — | — | — |
| 955 | 1(7) | — | — | H | H | N-12 | H | H | H | H | — | — | — | — | — | — |
| 956 | 1(7) | — | — | H | H | N-13 | H | H | H | H | — | — | — | — | — | — |
| 957 | 1(7) | — | — | H | H | N-14 | H | H | H | H | — | — | — | — | — | — |
| 958 | 1(7) | — | — | H | H | N-15 | H | H | H | H | — | — | — | — | — | — |
| 959 | 1(7) | — | — | H | H | N-16 | H | H | H | H | — | — | — | — | — | — |
| 960 | 1(7) | — | — | H | H | N-17 | H | H | H | H | — | — | — | — | — | — |
| 961 | 1(7) | — | — | H | H | N-18 | H | H | H | H | — | — | — | — | — | — |
| 962 | 1(7) | — | — | H | H | N-19 | H | H | H | H | — | — | — | — | — | — |
| 963 | 1(7) | — | — | H | H | N-20 | H | H | H | H | — | — | — | — | — | — |
| 964 | 1(7) | — | — | H | H | N-21 | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 965 | 1(7) | — | — | H | H | N-22 | H | H | H | H | — | — | — | — | — | — |
| 966 | 1(7) | — | — | H | H | N-23 | H | H | H | H | — | — | — | — | — | — |
| 967 | 1(7) | — | — | H | H | N-24 | H | H | H | H | — | — | — | — | — | — |
| 968 | 1(7) | — | — | H | H | N-25 | H | H | H | H | — | — | — | — | — | — |
| 969 | 1(7) | — | — | H | H | N-26 | H | H | H | H | — | — | — | — | — | — |
| 970 | 1(7) | — | — | H | H | N-27 | H | H | H | H | — | — | — | — | — | — |
| 971 | 1(7) | — | — | H | H | N-28 | H | H | H | H | — | — | — | — | — | — |
| 972 | 1(7) | — | — | H | H | N-29 | H | H | H | H | — | — | — | — | — | — |
| 973 | 1(7) | — | — | H | H | N-30 | H | H | H | H | — | — | — | — | — | — |
| 974 | 1(7) | — | — | H | H | N-31 | H | H | H | H | — | — | — | — | — | — |
| 975 | 1(7) | — | — | H | H | N-32 | H | H | H | H | — | — | — | — | — | — |
| 976 | 1(7) | — | — | H | H | N-33 | H | H | H | H | — | — | — | — | — | — |
| 977 | 1(7) | — | — | H | H | N-34 | H | H | H | H | — | — | — | — | — | — |
| 978 | 1(7) | — | — | H | H | N-35 | H | H | H | H | — | — | — | — | — | — |
| 979 | 1(7) | — | — | H | H | N-36 | H | H | H | H | — | — | — | — | — | — |
| 980 | 1(7) | — | — | H | H | N-37 | H | H | H | H | — | — | — | — | — | — |
| 981 | 1(7) | — | — | H | H | N-38 | H | H | H | H | — | — | — | — | — | — |
| 982 | 1(7) | — | — | H | H | N-39 | H | H | H | H | — | — | — | — | — | — |
| 983 | 1(7) | — | — | H | H | N-40 | H | H | H | H | — | — | — | — | — | — |
| 984 | 1(7) | — | — | H | H | N-41 | H | H | H | H | — | — | — | — | — | — |
| 985 | 1(7) | — | — | H | H | H | H | H | N-1 | H | — | — | — | — | — | — |
| 986 | 1(7) | — | — | H | H | H | H | H | N-2 | H | — | — | — | — | — | — |
| 987 | 1(7) | — | — | H | H | H | H | H | N-3 | H | — | — | — | — | — | — |
| 988 | 1(7) | — | — | H | H | H | H | H | N-4 | H | — | — | — | — | — | — |
| 989 | 1(7) | — | — | H | H | H | H | H | N-5 | H | — | — | — | — | — | — |
| 990 | 1(7) | — | — | H | H | H | H | H | N-6 | H | — | — | — | — | — | — |
| 991 | 1(7) | — | — | H | H | H | H | H | N-7 | H | — | — | — | — | — | — |
| 992 | 1(7) | — | — | H | H | H | H | H | N-8 | H | — | — | — | — | — | — |
| 993 | 1(7) | — | — | H | H | H | H | H | N-9 | H | — | — | — | — | — | — |
| 994 | 1(7) | — | — | H | H | H | H | H | N-10 | H | — | — | — | — | — | — |
| 995 | 1(7) | — | — | H | H | H | H | H | N-11 | H | — | — | — | — | — | — |
| 996 | 1(7) | — | — | H | H | H | H | H | N-12 | H | — | — | — | — | — | — |
| 997 | 1(7) | — | — | H | H | H | H | H | N-13 | H | — | — | — | — | — | — |
| 998 | 1(7) | — | — | H | H | H | H | H | N-14 | H | — | — | — | — | — | — |
| 999 | 1(7) | — | — | H | H | H | H | H | N-15 | H | — | — | — | — | — | — |
| 1000 | 1(7) | — | — | H | H | H | H | H | N-16 | H | — | — | — | — | — | — |
| 1001 | 1(7) | — | — | H | H | H | H | H | N-17 | H | — | — | — | — | — | — |
| 1002 | 1(7) | — | — | H | H | H | H | H | N-18 | H | — | — | — | — | — | — |
| 1003 | 1(7) | — | — | H | H | H | H | H | N-19 | H | — | — | — | — | — | — |
| 1004 | 1(7) | — | — | H | H | H | H | H | N-20 | H | — | — | — | — | — | — |
| 1005 | 1(7) | — | — | H | H | H | H | H | N-21 | H | — | — | — | — | — | — |
| 1006 | 1(7) | — | — | H | H | H | H | H | N-22 | H | — | — | — | — | — | — |
| 1007 | 1(7) | — | — | H | H | H | H | H | N-23 | H | — | — | — | — | — | — |
| 1008 | 1(7) | — | — | H | H | H | H | H | N-24 | H | — | — | — | — | — | — |
| 1009 | 1(7) | — | — | H | H | H | H | H | N-25 | H | — | — | — | — | — | — |
| 1010 | 1(7) | — | — | H | H | H | H | H | N-26 | H | — | — | — | — | — | — |
| 1011 | 1(7) | — | — | H | H | H | H | H | N-27 | H | — | — | — | — | — | — |
| 1012 | 1(7) | — | — | H | H | H | H | H | N-28 | H | — | — | — | — | — | — |
| 1013 | 1(7) | — | — | H | H | H | H | H | N-29 | H | — | — | — | — | — | — |
| 1014 | 1(7) | — | — | H | H | H | H | H | N-30 | H | — | — | — | — | — | — |
| 1015 | 1(7) | — | — | H | H | H | H | H | N-31 | H | — | — | — | — | — | — |
| 1016 | 1(7) | — | — | H | H | H | H | H | N-32 | H | — | — | — | — | — | — |
| 1017 | 1(7) | — | — | H | H | H | H | H | N-33 | H | — | — | — | — | — | — |
| 1018 | 1(7) | — | — | H | H | H | H | H | N-34 | H | — | — | — | — | — | — |
| 1019 | 1(7) | — | — | H | H | H | H | H | N-35 | H | — | — | — | — | — | — |
| 1020 | 1(7) | — | — | H | H | H | H | H | N-36 | H | — | — | — | — | — | — |
| 1021 | 1(7) | — | — | H | H | H | H | H | N-37 | H | — | — | — | — | — | — |
| 1022 | 1(7) | — | — | H | H | H | H | H | N-38 | H | — | — | — | — | — | — |
| 1023 | 1(7) | — | — | H | H | H | H | H | N-39 | H | — | — | — | — | — | — |
| 1024 | 1(7) | — | — | H | H | H | H | H | N-40 | H | — | — | — | — | — | — |
| 1025 | 1(7) | — | — | H | H | H | H | H | N-41 | H | — | — | — | — | — | — |
| 1026 | 1(8) | — | — | H | N-1 | H | H | H | H | H | H | H | H | H | H | H |
| 1027 | 1(8) | — | — | H | N-2 | H | H | H | H | H | H | H | H | H | H | H |
| 1028 | 1(8) | — | — | H | N-3 | H | H | H | H | H | H | H | H | H | H | H |
| 1029 | 1(8) | — | — | H | N-4 | H | H | H | H | H | H | H | H | H | H | H |
| 1030 | 1(8) | — | — | H | N-5 | H | H | H | H | H | H | H | H | H | H | H |
| 1031 | 1(8) | — | — | H | N-6 | H | H | H | H | H | H | H | H | H | H | H |
| 1032 | 1(8) | — | — | H | N-7 | H | H | H | H | H | H | H | H | H | H | H |
| 1033 | 1(8) | — | — | H | N-8 | H | H | H | H | H | H | H | H | H | H | H |
| 1034 | 1(8) | — | — | H | N-9 | H | H | H | H | H | H | H | H | H | H | H |
| 1035 | 1(8) | — | — | H | N-10 | H | H | H | H | H | H | H | H | H | H | H |
| 1036 | 1(8) | — | — | H | N-11 | H | H | H | H | H | H | H | H | H | H | H |
| 1037 | 1(8) | — | — | H | N-12 | H | H | H | H | H | H | H | H | H | H | H |
| 1038 | 1(8) | — | — | H | N-13 | H | H | H | H | H | H | H | H | H | H | H |
| 1039 | 1(8) | — | — | H | N-14 | H | H | H | H | H | H | H | H | H | H | H |
| 1040 | 1(8) | — | — | H | N-15 | H | H | H | H | H | H | H | H | H | H | H |
| 1041 | 1(8) | — | — | H | N-16 | H | H | H | H | H | H | H | H | H | H | H |
| 1042 | 1(8) | — | — | H | N-17 | H | H | H | H | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1043 | 1(8) | — | — | H | N-18 | H | H | H | H | H | H | H | H | H | H | H |
| 1044 | 1(8) | — | — | H | N-19 | H | H | H | H | H | H | H | H | H | H | H |
| 1045 | 1(8) | — | — | H | N-20 | H | H | H | H | H | H | H | H | H | H | H |
| 1046 | 1(8) | — | — | H | N-21 | H | H | H | H | H | H | H | H | H | H | H |
| 1047 | 1(8) | — | — | H | N-22 | H | H | H | H | H | H | H | H | H | H | H |
| 1048 | 1(8) | — | — | H | N-23 | H | H | H | H | H | H | H | H | H | H | H |
| 1049 | 1(8) | — | — | H | N-24 | H | H | H | H | H | H | H | H | H | H | H |
| 1050 | 1(8) | — | — | H | N-25 | H | H | H | H | H | H | H | H | H | H | H |
| 1051 | 1(8) | — | — | H | N-26 | H | H | H | H | H | H | H | H | H | H | H |
| 1052 | 1(8) | — | — | H | N-27 | H | H | H | H | H | H | H | H | H | H | H |
| 1053 | 1(8) | — | — | H | N-28 | H | H | H | H | H | H | H | H | H | H | H |
| 1054 | 1(8) | — | — | H | N-29 | H | H | H | H | H | H | H | H | H | H | H |
| 1055 | 1(8) | — | — | H | N-30 | H | H | H | H | H | H | H | H | H | H | H |
| 1056 | 1(8) | — | — | H | N-31 | H | H | H | H | H | H | H | H | H | H | H |
| 1057 | 1(8) | — | — | H | N-32 | H | H | H | H | H | H | H | H | H | H | H |
| 1058 | 1(8) | — | — | H | N-33 | H | H | H | H | H | H | H | H | H | H | H |
| 1059 | 1(8) | — | — | H | N-34 | H | H | H | H | H | H | H | H | H | H | H |
| 1060 | 1(8) | — | — | H | N-35 | H | H | H | H | H | H | H | H | H | H | H |
| 1061 | 1(8) | — | — | H | N-36 | H | H | H | H | H | H | H | H | H | H | H |
| 1062 | 1(8) | — | — | H | N-37 | H | H | H | H | H | H | H | H | H | H | H |
| 1063 | 1(8) | — | — | H | N-38 | H | H | H | H | H | H | H | H | H | H | H |
| 1064 | 1(8) | — | — | H | N-39 | H | H | H | H | H | H | H | H | H | H | H |
| 1065 | 1(8) | — | — | H | N-40 | H | H | H | H | H | H | H | H | H | H | H |
| 1066 | 1(8) | — | — | H | N-41 | H | H | H | H | H | H | H | H | H | H | H |
| 1067 | 1(8) | — | — | H | H | N-1 | H | H | H | H | H | H | H | H | H | H |
| 1068 | 1(8) | — | — | H | H | N-2 | H | H | H | H | H | H | H | H | H | H |
| 1069 | 1(8) | — | — | H | H | N-3 | H | H | H | H | H | H | H | H | H | H |
| 1070 | 1(8) | — | — | H | H | N-4 | H | H | H | H | H | H | H | H | H | H |
| 1071 | 1(8) | — | — | H | H | N-5 | H | H | H | H | H | H | H | H | H | H |
| 1072 | 1(8) | — | — | H | H | N-6 | H | H | H | H | H | H | H | H | H | H |
| 1073 | 1(8) | — | — | H | H | N-7 | H | H | H | H | H | H | H | H | H | H |
| 1074 | 1(8) | — | — | H | H | N-8 | H | H | H | H | H | H | H | H | H | H |
| 1075 | 1(8) | — | — | H | H | N-9 | H | H | H | H | H | H | H | H | H | H |
| 1076 | 1(8) | — | — | H | H | N-10 | H | H | H | H | H | H | H | H | H | H |
| 1077 | 1(8) | — | — | H | H | N-11 | H | H | H | H | H | H | H | H | H | H |
| 1078 | 1(8) | — | — | H | H | N-12 | H | H | H | H | H | H | H | H | H | H |
| 1079 | 1(8) | — | — | H | H | N-13 | H | H | H | H | H | H | H | H | H | H |
| 1080 | 1(8) | — | — | H | H | N-14 | H | H | H | H | H | H | H | H | H | H |
| 1081 | 1(8) | — | — | H | H | N-15 | H | H | H | H | H | H | H | H | H | H |
| 1082 | 1(8) | — | — | H | H | N-16 | H | H | H | H | H | H | H | H | H | H |
| 1083 | 1(8) | — | — | H | H | N-17 | H | H | H | H | H | H | H | H | H | H |
| 1084 | 1(8) | — | — | H | H | N-18 | H | H | H | H | H | H | H | H | H | H |
| 1085 | 1(8) | — | — | H | H | N-19 | H | H | H | H | H | H | H | H | H | H |
| 1086 | 1(8) | — | — | H | H | N-20 | H | H | H | H | H | H | H | H | H | H |
| 1087 | 1(8) | — | — | H | H | N-21 | H | H | H | H | H | H | H | H | H | H |
| 1088 | 1(8) | — | — | H | H | N-22 | H | H | H | H | H | H | H | H | H | H |
| 1089 | 1(8) | — | — | H | H | N-23 | H | H | H | H | H | H | H | H | H | H |
| 1090 | 1(8) | — | — | H | H | N-24 | H | H | H | H | H | H | H | H | H | H |
| 1091 | 1(8) | — | — | H | H | N-25 | H | H | H | H | H | H | H | H | H | H |
| 1092 | 1(8) | — | — | H | H | N-26 | H | H | H | H | H | H | H | H | H | H |
| 1093 | 1(8) | — | — | H | H | N-27 | H | H | H | H | H | H | H | H | H | H |
| 1094 | 1(8) | — | — | H | H | N-28 | H | H | H | H | H | H | H | H | H | H |
| 1095 | 1(8) | — | — | H | H | N-29 | H | H | H | H | H | H | H | H | H | H |
| 1096 | 1(8) | — | — | H | H | N-30 | H | H | H | H | H | H | H | H | H | H |
| 1097 | 1(8) | — | — | H | H | N-31 | H | H | H | H | H | H | H | H | H | H |
| 1098 | 1(8) | — | — | H | H | N-32 | H | H | H | H | H | H | H | H | H | H |
| 1099 | 1(8) | — | — | H | H | N-33 | H | H | H | H | H | H | H | H | H | H |
| 1100 | 1(8) | — | — | H | H | N-34 | H | H | H | H | H | H | H | H | H | H |
| 1101 | 1(8) | — | — | H | H | N-35 | H | H | H | H | H | H | H | H | H | H |
| 1102 | 1(8) | — | — | H | H | N-36 | H | H | H | H | H | H | H | H | H | H |
| 1103 | 1(8) | — | — | H | H | N-37 | H | H | H | H | H | H | H | H | H | H |
| 1104 | 1(8) | — | — | H | H | N-38 | H | H | H | H | H | H | H | H | H | H |
| 1105 | 1(8) | — | — | H | H | N-39 | H | H | H | H | H | H | H | H | H | H |
| 1106 | 1(8) | — | — | H | H | N-40 | H | H | H | H | H | H | H | H | H | H |
| 1107 | 1(8) | — | — | H | H | N-41 | H | H | H | H | H | H | H | H | H | H |
| 1108 | 1(8) | — | — | H | H | H | H | H | N-1 | H | H | H | H | H | H | H |
| 1109 | 1(8) | — | — | H | H | H | H | H | N-2 | H | H | H | H | H | H | H |
| 1110 | 1(8) | — | — | H | H | H | H | H | N-3 | H | H | H | H | H | H | H |
| 1111 | 1(8) | — | — | H | H | H | H | H | N-4 | H | H | H | H | H | H | H |
| 1112 | 1(8) | — | — | H | H | H | H | H | N-5 | H | H | H | H | H | H | H |
| 1113 | 1(8) | — | — | H | H | H | H | H | N-6 | H | H | H | H | H | H | H |
| 1114 | 1(8) | — | — | H | H | H | H | H | N-7 | H | H | H | H | H | H | H |
| 1115 | 1(8) | — | — | H | H | H | H | H | N-8 | H | H | H | H | H | H | H |
| 1116 | 1(8) | — | — | H | H | H | H | H | N-9 | H | H | H | H | H | H | H |
| 1117 | 1(8) | — | — | H | H | H | H | H | N-10 | H | H | H | H | H | H | H |
| 1118 | 1(8) | — | — | H | H | H | H | H | N-11 | H | H | H | H | H | H | H |
| 1119 | 1(8) | — | — | H | H | H | H | H | N-12 | H | H | H | H | H | H | H |
| 1120 | 1(8) | — | — | H | H | H | H | H | N-13 | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1121 | 1(8) | — | — | H | H | H | H | H | N-14 | H | H | H | H | H | H | H |
| 1122 | 1(8) | — | — | H | H | H | H | H | N-15 | H | H | H | H | H | H | H |
| 1123 | 1(8) | — | — | H | H | H | H | H | N-16 | H | H | H | H | H | H | H |
| 1124 | 1(8) | — | — | H | H | H | H | H | N-17 | H | H | H | H | H | H | H |
| 1125 | 1(8) | — | — | H | H | H | H | H | N-18 | H | H | H | H | H | H | H |
| 1126 | 1(8) | — | — | H | H | H | H | H | N-19 | H | H | H | H | H | H | H |
| 1127 | 1(8) | — | — | H | H | H | H | H | N-20 | H | H | H | H | H | H | H |
| 1128 | 1(8) | — | — | H | H | H | H | H | N-21 | H | H | H | H | H | H | H |
| 1129 | 1(8) | — | — | H | H | H | H | H | N-22 | H | H | H | H | H | H | H |
| 1130 | 1(8) | — | — | H | H | H | H | H | N-23 | H | H | H | H | H | H | H |
| 1131 | 1(8) | — | — | H | H | H | H | H | N-24 | H | H | H | H | H | H | H |
| 1132 | 1(8) | — | — | H | H | H | H | H | N-25 | H | H | H | H | H | H | H |
| 1133 | 1(8) | — | — | H | H | H | H | H | N-26 | H | H | H | H | H | H | H |
| 1134 | 1(8) | — | — | H | H | H | H | H | N-27 | H | H | H | H | H | H | H |
| 1135 | 1(8) | — | — | H | H | H | H | H | N-28 | H | H | H | H | H | H | H |
| 1136 | 1(8) | — | — | H | H | H | H | H | N-29 | H | H | H | H | H | H | H |
| 1137 | 1(8) | — | — | H | H | H | H | H | N-30 | H | H | H | H | H | H | H |
| 1138 | 1(8) | — | — | H | H | H | H | H | N-31 | H | H | H | H | H | H | H |
| 1139 | 1(8) | — | — | H | H | H | H | H | N-32 | H | H | H | H | H | H | H |
| 1140 | 1(8) | — | — | H | H | H | H | H | N-33 | H | H | H | H | H | H | H |
| 1141 | 1(8) | — | — | H | H | H | H | H | N-34 | H | H | H | H | H | H | H |
| 1142 | 1(8) | — | — | H | H | H | H | H | N-35 | H | H | H | H | H | H | H |
| 1143 | 1(8) | — | — | H | H | H | H | H | N-36 | H | H | H | H | H | H | H |
| 1144 | 1(8) | — | — | H | H | H | H | H | N-37 | H | H | H | H | H | H | H |
| 1145 | 1(8) | — | — | H | H | H | H | H | N-38 | H | H | H | H | H | H | H |
| 1146 | 1(8) | — | — | H | H | H | H | H | N-39 | H | H | H | H | H | H | H |
| 1147 | 1(8) | — | — | H | H | H | H | H | N-40 | H | H | H | H | H | H | H |
| 1148 | 1(8) | — | — | H | H | H | H | H | N-41 | H | H | H | H | H | H | H |
| 1149 | 1(8) | — | — | H | H | H | H | H | H | H | H | H | N-1 | H | H | H |
| 1150 | 1(8) | — | — | H | H | H | H | H | H | H | H | H | N-2 | H | H | H |
| 1151 | 1(8) | — | — | H | H | H | H | H | H | H | H | H | N-3 | H | H | H |
| 1152 | 1(8) | — | — | H | H | H | H | H | H | H | H | H | N-4 | H | H | H |
| 1153 | 1(8) | — | — | H | H | H | H | H | H | H | H | H | N-5 | H | H | H |
| 1154 | 1(8) | — | — | H | H | H | H | H | H | H | H | H | N-6 | H | H | H |
| 1155 | 1(8) | — | — | H | H | H | H | H | H | H | H | H | N-7 | H | H | H |
| 1156 | 1(8) | — | — | H | H | H | H | H | H | H | H | H | N-8 | H | H | H |
| 1157 | 1(8) | — | — | H | H | H | H | H | H | H | H | H | N-9 | H | H | H |
| 1158 | 1(8) | — | — | H | H | H | H | H | H | H | H | H | N-10 | H | H | H |
| 1159 | 1(8) | — | — | H | H | H | H | H | H | H | H | H | N-11 | H | H | H |
| 1160 | 1(8) | — | — | H | H | H | H | H | H | H | H | H | N-12 | H | H | H |
| 1161 | 1(8) | — | — | H | H | H | H | H | H | H | H | H | N-13 | H | H | H |
| 1162 | 1(8) | — | — | H | H | H | H | H | H | H | H | H | N-14 | H | H | H |
| 1163 | 1(8) | — | — | H | H | H | H | H | H | H | H | H | N-15 | H | H | H |
| 1164 | 1(8) | — | — | H | H | H | H | H | H | H | H | H | N-16 | H | H | H |
| 1165 | 1(8) | — | — | H | H | H | H | H | H | H | H | H | N-17 | H | H | H |
| 1166 | 1(8) | — | — | H | H | H | H | H | H | H | H | H | N-18 | H | H | H |
| 1167 | 1(8) | — | — | H | H | H | H | H | H | H | H | H | N-19 | H | H | H |
| 1168 | 1(8) | — | — | H | H | H | H | H | H | H | H | H | N-20 | H | H | H |
| 1169 | 1(8) | — | — | H | H | H | H | H | H | H | H | H | N-21 | H | H | H |
| 1170 | 1(8) | — | — | H | H | H | H | H | H | H | H | H | N-22 | H | H | H |
| 1171 | 1(8) | — | — | H | H | H | H | H | H | H | H | H | N-23 | H | H | H |
| 1172 | 1(8) | — | — | H | H | H | H | H | H | H | H | H | N-24 | H | H | H |
| 1173 | 1(8) | — | — | H | H | H | H | H | H | H | H | H | N-25 | H | H | H |
| 1174 | 1(8) | — | — | H | H | H | H | H | H | H | H | H | N-26 | H | H | H |
| 1175 | 1(8) | — | — | H | H | H | H | H | H | H | H | H | N-27 | H | H | H |
| 1176 | 1(8) | — | — | H | H | H | H | H | H | H | H | H | N-28 | H | H | H |
| 1177 | 1(8) | — | — | H | H | H | H | H | H | H | H | H | N-29 | H | H | H |
| 1178 | 1(8) | — | — | H | H | H | H | H | H | H | H | H | N-30 | H | H | H |
| 1179 | 1(8) | — | — | H | H | H | H | H | H | H | H | H | N-31 | H | H | H |
| 1180 | 1(8) | — | — | H | H | H | H | H | H | H | H | H | N-32 | H | H | H |
| 1181 | 1(8) | — | — | H | H | H | H | H | H | H | H | H | N-33 | H | H | H |
| 1182 | 1(8) | — | — | H | H | H | H | H | H | H | H | H | N-34 | H | H | H |
| 1183 | 1(8) | — | — | H | H | H | H | H | H | H | H | H | N-35 | H | H | H |
| 1184 | 1(8) | — | — | H | H | H | H | H | H | H | H | H | N-36 | H | H | H |
| 1185 | 1(8) | — | — | H | H | H | H | H | H | H | H | H | N-37 | H | H | H |
| 1186 | 1(8) | — | — | H | H | H | H | H | H | H | H | H | N-38 | H | H | H |
| 1187 | 1(8) | — | — | H | H | H | H | H | H | H | H | H | N-39 | H | H | H |
| 1188 | 1(8) | — | — | H | H | H | H | H | H | H | H | H | N-40 | H | H | H |
| 1189 | 1(8) | — | — | H | H | H | H | H | H | H | H | H | N-41 | H | H | H |
| 1190 | 1(8) | — | — | H | H | H | H | H | H | H | H | H | H | N-1 | H | H |
| 1191 | 1(8) | — | — | H | H | H | H | H | H | H | H | H | H | N-2 | H | H |
| 1192 | 1(8) | — | — | H | H | H | H | H | H | H | H | H | H | N-3 | H | H |
| 1193 | 1(8) | — | — | H | H | H | H | H | H | H | H | H | H | N-4 | H | H |
| 1194 | 1(8) | — | — | H | H | H | H | H | H | H | H | H | H | N-5 | H | H |
| 1195 | 1(8) | — | — | H | H | H | H | H | H | H | H | H | H | N-6 | H | H |
| 1196 | 1(8) | — | — | H | H | H | H | H | H | H | H | H | H | N-7 | H | H |
| 1197 | 1(8) | — | — | H | H | H | H | H | H | H | H | H | H | N-8 | H | H |
| 1198 | 1(8) | — | — | H | H | H | H | H | H | H | H | H | H | N-9 | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1199 | 1(8) | — | — | H | H | H | H | H | H | H | H | H | H | N-10 | H | H |
| 1200 | 1(8) | — | — | H | H | H | H | H | H | H | H | H | H | N-11 | H | H |
| 1201 | 1(8) | — | — | H | H | H | H | H | H | H | H | H | H | N-12 | H | H |
| 1202 | 1(8) | — | — | H | H | H | H | H | H | H | H | H | H | N-13 | H | H |
| 1203 | 1(8) | — | — | H | H | H | H | H | H | H | H | H | H | N-14 | H | H |
| 1204 | 1(8) | — | — | H | H | H | H | H | H | H | H | H | H | N-15 | H | H |
| 1205 | 1(8) | — | — | H | H | H | H | H | H | H | H | H | H | N-16 | H | H |
| 1206 | 1(8) | — | — | H | H | H | H | H | H | H | H | H | H | N-17 | H | H |
| 1207 | 1(8) | — | — | H | H | H | H | H | H | H | H | H | H | N-18 | H | H |
| 1208 | 1(8) | — | — | H | H | H | H | H | H | H | H | H | H | N-19 | H | H |
| 1209 | 1(8) | — | — | H | H | H | H | H | H | H | H | H | H | N-20 | H | H |
| 1210 | 1(8) | — | — | H | H | H | H | H | H | H | H | H | H | N-21 | H | H |
| 1211 | 1(8) | — | — | H | H | H | H | H | H | H | H | H | H | N-22 | H | H |
| 1212 | 1(8) | — | — | H | H | H | H | H | H | H | H | H | H | N-23 | H | H |
| 1213 | 1(8) | — | — | H | H | H | H | H | H | H | H | H | H | N-24 | H | H |
| 1214 | 1(8) | — | — | H | H | H | H | H | H | H | H | H | H | N-25 | H | H |
| 1215 | 1(8) | — | — | H | H | H | H | H | H | H | H | H | H | N-26 | H | H |
| 1216 | 1(8) | — | — | H | H | H | H | H | H | H | H | H | H | N-27 | H | H |
| 1217 | 1(8) | — | — | H | H | H | H | H | H | H | H | H | H | N-28 | H | H |
| 1218 | 1(8) | — | — | H | H | H | H | H | H | H | H | H | H | N-29 | H | H |
| 1219 | 1(8) | — | — | H | H | H | H | H | H | H | H | H | H | N-30 | H | H |
| 1220 | 1(8) | — | — | H | H | H | H | H | H | H | H | H | H | N-31 | H | H |
| 1221 | 1(8) | — | — | H | H | H | H | H | H | H | H | H | H | N-32 | H | H |
| 1222 | 1(8) | — | — | H | H | H | H | H | H | H | H | H | H | N-33 | H | H |
| 1223 | 1(8) | — | — | H | H | H | H | H | H | H | H | H | H | N-34 | H | H |
| 1224 | 1(8) | — | — | H | H | H | H | H | H | H | H | H | H | N-35 | H | H |
| 1225 | 1(8) | — | — | H | H | H | H | H | H | H | H | H | H | N-36 | H | H |
| 1226 | 1(8) | — | — | H | H | H | H | H | H | H | H | H | H | N-37 | H | H |
| 1227 | 1(8) | — | — | H | H | H | H | H | H | H | H | H | H | N-38 | H | H |
| 1228 | 1(8) | — | — | H | H | H | H | H | H | H | H | H | H | N-39 | H | H |
| 1229 | 1(8) | — | — | H | H | H | H | H | H | H | H | H | H | N-40 | H | H |
| 1230 | 1(8) | — | — | H | H | H | H | H | H | H | H | H | H | N-41 | H | H |
| 1231 | 1(9) | — | — | H | N-1 | H | H | H | H | H | — | — | — | — | — | — |
| 1232 | 1(9) | — | — | H | N-2 | H | H | H | H | H | — | — | — | — | — | — |
| 1233 | 1(9) | — | — | H | N-3 | H | H | H | H | H | — | — | — | — | — | — |
| 1234 | 1(9) | — | — | H | N-4 | H | H | H | H | H | — | — | — | — | — | — |
| 1235 | 1(9) | — | — | H | N-5 | H | H | H | H | H | — | — | — | — | — | — |
| 1236 | 1(9) | — | — | H | N-6 | H | H | H | H | H | — | — | — | — | — | — |
| 1237 | 1(9) | — | — | H | N-7 | H | H | H | H | H | — | — | — | — | — | — |
| 1238 | 1(9) | — | — | H | N-8 | H | H | H | H | H | — | — | — | — | — | — |
| 1239 | 1(9) | — | — | H | N-9 | H | H | H | H | H | — | — | — | — | — | — |
| 1240 | 1(9) | — | — | H | N-10 | H | H | H | H | H | — | — | — | — | — | — |
| 1241 | 1(9) | — | — | H | N-11 | H | H | H | H | H | — | — | — | — | — | — |
| 1242 | 1(9) | — | — | H | N-12 | H | H | H | H | H | — | — | — | — | — | — |
| 1243 | 1(9) | — | — | H | N-13 | H | H | H | H | H | — | — | — | — | — | — |
| 1244 | 1(9) | — | — | H | N-14 | H | H | H | H | H | — | — | — | — | — | — |
| 1245 | 1(9) | — | — | H | N-15 | H | H | H | H | H | — | — | — | — | — | — |
| 1246 | 1(9) | — | — | H | N-16 | H | H | H | H | H | — | — | — | — | — | — |
| 1247 | 1(9) | — | — | H | N-17 | H | H | H | H | H | — | — | — | — | — | — |
| 1248 | 1(9) | — | — | H | N-18 | H | H | H | H | H | — | — | — | — | — | — |
| 1249 | 1(9) | — | — | H | N-19 | H | H | H | H | H | — | — | — | — | — | — |
| 1250 | 1(9) | — | — | H | N-20 | H | H | H | H | H | — | — | — | — | — | — |
| 1251 | 1(9) | — | — | H | N-21 | H | H | H | H | H | — | — | — | — | — | — |
| 1252 | 1(9) | — | — | H | N-22 | H | H | H | H | H | — | — | — | — | — | — |
| 1253 | 1(9) | — | — | H | N-23 | H | H | H | H | H | — | — | — | — | — | — |
| 1254 | 1(9) | — | — | H | N-24 | H | H | H | H | H | — | — | — | — | — | — |
| 1255 | 1(9) | — | — | H | N-25 | H | H | H | H | H | — | — | — | — | — | — |
| 1256 | 1(9) | — | — | H | N-26 | H | H | H | H | H | — | — | — | — | — | — |
| 1257 | 1(9) | — | — | H | N-27 | H | H | H | H | H | — | — | — | — | — | — |
| 1258 | 1(9) | — | — | H | N-28 | H | H | H | H | H | — | — | — | — | — | — |
| 1259 | 1(9) | — | — | H | N-29 | H | H | H | H | H | — | — | — | — | — | — |
| 1260 | 1(9) | — | — | H | N-30 | H | H | H | H | H | — | — | — | — | — | — |
| 1261 | 1(9) | — | — | H | N-31 | H | H | H | H | H | — | — | — | — | — | — |
| 1262 | 1(9) | — | — | H | N-32 | H | H | H | H | H | — | — | — | — | — | — |
| 1263 | 1(9) | — | — | H | N-33 | H | H | H | H | H | — | — | — | — | — | — |
| 1264 | 1(9) | — | — | H | N-34 | H | H | H | H | H | — | — | — | — | — | — |
| 1265 | 1(9) | — | — | H | N-35 | H | H | H | H | H | — | — | — | — | — | — |
| 1266 | 1(9) | — | — | H | N-36 | H | H | H | H | H | — | — | — | — | — | — |
| 1267 | 1(9) | — | — | H | N-37 | H | H | H | H | H | — | — | — | — | — | — |
| 1268 | 1(9) | — | — | H | N-38 | H | H | H | H | H | — | — | — | — | — | — |
| 1269 | 1(9) | — | — | H | N-39 | H | H | H | H | H | — | — | — | — | — | — |
| 1270 | 1(9) | — | — | H | N-40 | H | H | H | H | H | — | — | — | — | — | — |
| 1271 | 1(9) | — | — | H | N-41 | H | H | H | H | H | — | — | — | — | — | — |
| 1272 | 1(9) | — | — | H | H | N-1 | H | H | H | H | — | — | — | — | — | — |
| 1273 | 1(9) | — | — | H | H | N-2 | H | H | H | H | — | — | — | — | — | — |
| 1274 | 1(9) | — | — | H | H | N-3 | H | H | H | H | — | — | — | — | — | — |
| 1275 | 1(9) | — | — | H | H | N-4 | H | H | H | H | — | — | — | — | — | — |
| 1276 | 1(9) | — | — | H | H | N-5 | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1277 | 1(9) | — | — | H | H | N-6 | H | H | H | H | — | — | — | — | — | — |
| 1278 | 1(9) | — | — | H | H | N-7 | H | H | H | H | — | — | — | — | — | — |
| 1279 | 1(9) | — | — | H | H | N-8 | H | H | H | H | — | — | — | — | — | — |
| 1280 | 1(9) | — | — | H | H | N-9 | H | H | H | H | — | — | — | — | — | — |
| 1281 | 1(9) | — | — | H | H | N-10 | H | H | H | H | — | — | — | — | — | — |
| 1282 | 1(9) | — | — | H | H | N-11 | H | H | H | H | — | — | — | — | — | — |
| 1283 | 1(9) | — | — | H | H | N-12 | H | H | H | H | — | — | — | — | — | — |
| 1284 | 1(9) | — | — | H | H | N-13 | H | H | H | H | — | — | — | — | — | — |
| 1285 | 1(9) | — | — | H | H | N-14 | H | H | H | H | — | — | — | — | — | — |
| 1286 | 1(9) | — | — | H | H | N-15 | H | H | H | H | — | — | — | — | — | — |
| 1287 | 1(9) | — | — | H | H | N-16 | H | H | H | H | — | — | — | — | — | — |
| 1288 | 1(9) | — | — | H | H | N-17 | H | H | H | H | — | — | — | — | — | — |
| 1289 | 1(9) | — | — | H | H | N-18 | H | H | H | H | — | — | — | — | — | — |
| 1290 | 1(9) | — | — | H | H | N-19 | H | H | H | H | — | — | — | — | — | — |
| 1291 | 1(9) | — | — | H | H | N-20 | H | H | H | H | — | — | — | — | — | — |
| 1292 | 1(9) | — | — | H | H | N-21 | H | H | H | H | — | — | — | — | — | — |
| 1293 | 1(9) | — | — | H | H | N-22 | H | H | H | H | — | — | — | — | — | — |
| 1294 | 1(9) | — | — | H | H | N-23 | H | H | H | H | — | — | — | — | — | — |
| 1295 | 1(9) | — | — | H | H | N-24 | H | H | H | H | — | — | — | — | — | — |
| 1296 | 1(9) | — | — | H | H | N-25 | H | H | H | H | — | — | — | — | — | — |
| 1297 | 1(9) | — | — | H | H | N-26 | H | H | H | H | — | — | — | — | — | — |
| 1298 | 1(9) | — | — | H | H | N-27 | H | H | H | H | — | — | — | — | — | — |
| 1299 | 1(9) | — | — | H | H | N-28 | H | H | H | H | — | — | — | — | — | — |
| 1300 | 1(9) | — | — | H | H | N-29 | H | H | H | H | — | — | — | — | — | — |
| 1301 | 1(9) | — | — | H | H | N-30 | H | H | H | H | — | — | — | — | — | — |
| 1302 | 1(9) | — | — | H | H | N-31 | H | H | H | H | — | — | — | — | — | — |
| 1303 | 1(9) | — | — | H | H | N-32 | H | H | H | H | — | — | — | — | — | — |
| 1304 | 1(9) | — | — | H | H | N-33 | H | H | H | H | — | — | — | — | — | — |
| 1305 | 1(9) | — | — | H | H | N-34 | H | H | H | H | — | — | — | — | — | — |
| 1306 | 1(9) | — | — | H | H | N-35 | H | H | H | H | — | — | — | — | — | — |
| 1307 | 1(9) | — | — | H | H | N-36 | H | H | H | H | — | — | — | — | — | — |
| 1308 | 1(9) | — | — | H | H | N-37 | H | H | H | H | — | — | — | — | — | — |
| 1309 | 1(9) | — | — | H | H | N-38 | H | H | H | H | — | — | — | — | — | — |
| 1310 | 1(9) | — | — | H | H | N-39 | H | H | H | H | — | — | — | — | — | — |
| 1311 | 1(9) | — | — | H | H | N-40 | H | H | H | H | — | — | — | — | — | — |
| 1312 | 1(9) | — | — | H | H | N-41 | H | H | H | H | — | — | — | — | — | — |
| 1313 | 1(9) | — | — | H | H | H | H | H | H | N-1 | — | — | — | — | — | — |
| 1314 | 1(9) | — | — | H | H | H | H | H | H | N-2 | — | — | — | — | — | — |
| 1315 | 1(9) | — | — | H | H | H | H | H | H | N-3 | — | — | — | — | — | — |
| 1316 | 1(9) | — | — | H | H | H | H | H | H | N-4 | — | — | — | — | — | — |
| 1317 | 1(9) | — | — | H | H | H | H | H | H | N-5 | — | — | — | — | — | — |
| 1318 | 1(9) | — | — | H | H | H | H | H | H | N-6 | — | — | — | — | — | — |
| 1319 | 1(9) | — | — | H | H | H | H | H | H | N-7 | — | — | — | — | — | — |
| 1320 | 1(9) | — | — | H | H | H | H | H | H | N-8 | — | — | — | — | — | — |
| 1321 | 1(9) | — | — | H | H | H | H | H | H | N-9 | — | — | — | — | — | — |
| 1322 | 1(9) | — | — | H | H | H | H | H | H | N-10 | — | — | — | — | — | — |
| 1323 | 1(9) | — | — | H | H | H | H | H | H | N-11 | — | — | — | — | — | — |
| 1324 | 1(9) | — | — | H | H | H | H | H | H | N-12 | — | — | — | — | — | — |
| 1325 | 1(9) | — | — | H | H | H | H | H | H | N-13 | — | — | — | — | — | — |
| 1326 | 1(9) | — | — | H | H | H | H | H | H | N-14 | — | — | — | — | — | — |
| 1327 | 1(9) | — | — | H | H | H | H | H | H | N-15 | — | — | — | — | — | — |
| 1328 | 1(9) | — | — | H | H | H | H | H | H | N-16 | — | — | — | — | — | — |
| 1329 | 1(9) | — | — | H | H | H | H | H | H | N-17 | — | — | — | — | — | — |
| 1330 | 1(9) | — | — | H | H | H | H | H | H | N-18 | — | — | — | — | — | — |
| 1331 | 1(9) | — | — | H | H | H | H | H | H | N-19 | — | — | — | — | — | — |
| 1332 | 1(9) | — | — | H | H | H | H | H | H | N-20 | — | — | — | — | — | — |
| 1333 | 1(9) | — | — | H | H | H | H | H | H | N-21 | — | — | — | — | — | — |
| 1334 | 1(9) | — | — | H | H | H | H | H | H | N-22 | — | — | — | — | — | — |
| 1335 | 1(9) | — | — | H | H | H | H | H | H | N-23 | — | — | — | — | — | — |
| 1336 | 1(9) | — | — | H | H | H | H | H | H | N-24 | — | — | — | — | — | — |
| 1337 | 1(9) | — | — | H | H | H | H | H | H | N-25 | — | — | — | — | — | — |
| 1338 | 1(9) | — | — | H | H | H | H | H | H | N-26 | — | — | — | — | — | — |
| 1339 | 1(9) | — | — | H | H | H | H | H | H | N-27 | — | — | — | — | — | — |
| 1340 | 1(9) | — | — | H | H | H | H | H | H | N-28 | — | — | — | — | — | — |
| 1341 | 1(9) | — | — | H | H | H | H | H | H | N-29 | — | — | — | — | — | — |
| 1342 | 1(9) | — | — | H | H | H | H | H | H | N-30 | — | — | — | — | — | — |
| 1343 | 1(9) | — | — | H | H | H | H | H | H | N-31 | — | — | — | — | — | — |
| 1344 | 1(9) | — | — | H | H | H | H | H | H | N-32 | — | — | — | — | — | — |
| 1345 | 1(9) | — | — | H | H | H | H | H | H | N-33 | — | — | — | — | — | — |
| 1346 | 1(9) | — | — | H | H | H | H | H | H | N-34 | — | — | — | — | — | — |
| 1347 | 1(9) | — | — | H | H | H | H | H | H | N-35 | — | — | — | — | — | — |
| 1348 | 1(9) | — | — | H | H | H | H | H | H | N-36 | — | — | — | — | — | — |
| 1349 | 1(9) | — | — | H | H | H | H | H | H | N-37 | — | — | — | — | — | — |
| 1350 | 1(9) | — | — | H | H | H | H | H | H | N-38 | — | — | — | — | — | — |
| 1351 | 1(9) | — | — | H | H | H | H | H | H | N-39 | — | — | — | — | — | — |
| 1352 | 1(9) | — | — | H | H | H | H | H | H | N-40 | — | — | — | — | — | — |
| 1353 | 1(9) | — | — | H | H | H | H | H | H | N-41 | — | — | — | — | — | — |
| 1354 | 1(10) | Me | Me | H | N-1 | H | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1355 | 1(10) | Me | Me | H | N-2 | H | H | H | H | H | — | — | — | — | — | — |
| 1356 | 1(10) | Me | Me | H | N-3 | H | H | H | H | H | — | — | — | — | — | — |
| 1357 | 1(10) | Me | Me | H | N-4 | H | H | H | H | H | — | — | — | — | — | — |
| 1358 | 1(10) | Me | Me | H | N-5 | H | H | H | H | H | — | — | — | — | — | — |
| 1359 | 1(10) | Me | Me | H | N-6 | H | H | H | H | H | — | — | — | — | — | — |
| 1360 | 1(10) | Me | Me | H | N-7 | H | H | H | H | H | — | — | — | — | — | — |
| 1361 | 1(10) | Me | Me | H | N-8 | H | H | H | H | H | — | — | — | — | — | — |
| 1362 | 1(10) | Me | Me | H | N-9 | H | H | H | H | H | — | — | — | — | — | — |
| 1363 | 1(10) | Me | Me | H | N-10 | H | H | H | H | H | — | — | — | — | — | — |
| 1364 | 1(10) | Me | Me | H | N-11 | H | H | H | H | H | — | — | — | — | — | — |
| 1365 | 1(10) | Me | Me | H | N-12 | H | H | H | H | H | — | — | — | — | — | — |
| 1366 | 1(10) | Me | Me | H | N-13 | H | H | H | H | H | — | — | — | — | — | — |
| 1367 | 1(10) | Me | Me | H | N-14 | H | H | H | H | H | — | — | — | — | — | — |
| 1368 | 1(10) | Me | Me | H | N-15 | H | H | H | H | H | — | — | — | — | — | — |
| 1369 | 1(10) | Me | Me | H | N-16 | H | H | H | H | H | — | — | — | — | — | — |
| 1370 | 1(10) | Me | Me | H | N-17 | H | H | H | H | H | — | — | — | — | — | — |
| 1371 | 1(10) | Me | Me | H | N-18 | H | H | H | H | H | — | — | — | — | — | — |
| 1372 | 1(10) | Me | Me | H | N-19 | H | H | H | H | H | — | — | — | — | — | — |
| 1373 | 1(10) | Me | Me | H | N-20 | H | H | H | H | H | — | — | — | — | — | — |
| 1374 | 1(10) | Me | Me | H | N-21 | H | H | H | H | H | — | — | — | — | — | — |
| 1375 | 1(10) | Me | Me | H | N-22 | H | H | H | H | H | — | — | — | — | — | — |
| 1376 | 1(10) | Me | Me | H | N-23 | H | H | H | H | H | — | — | — | — | — | — |
| 1377 | 1(10) | Me | Me | H | N-24 | H | H | H | H | H | — | — | — | — | — | — |
| 1378 | 1(10) | Me | Me | H | N-25 | H | H | H | H | H | — | — | — | — | — | — |
| 1379 | 1(10) | Me | Me | H | N-26 | H | H | H | H | H | — | — | — | — | — | — |
| 1380 | 1(10) | Me | Me | H | N-27 | H | H | H | H | H | — | — | — | — | — | — |
| 1381 | 1(10) | Me | Me | H | N-28 | H | H | H | H | H | — | — | — | — | — | — |
| 1382 | 1(10) | Me | Me | H | N-29 | H | H | H | H | H | — | — | — | — | — | — |
| 1383 | 1(10) | Me | Me | H | N-30 | H | H | H | H | H | — | — | — | — | — | — |
| 1384 | 1(10) | Me | Me | H | N-31 | H | H | H | H | H | — | — | — | — | — | — |
| 1385 | 1(10) | Me | Me | H | N-32 | H | H | H | H | H | — | — | — | — | — | — |
| 1386 | 1(10) | Me | Me | H | N-33 | H | H | H | H | H | — | — | — | — | — | — |
| 1387 | 1(10) | Me | Me | H | N-34 | H | H | H | H | H | — | — | — | — | — | — |
| 1388 | 1(10) | Me | Me | H | N-35 | H | H | H | H | H | — | — | — | — | — | — |
| 1389 | 1(10) | Me | Me | H | N-36 | H | H | H | H | H | — | — | — | — | — | — |
| 1390 | 1(10) | Me | Me | H | N-37 | H | H | H | H | H | — | — | — | — | — | — |
| 1391 | 1(10) | Me | Me | H | N-38 | H | H | H | H | H | — | — | — | — | — | — |
| 1392 | 1(10) | Me | Me | H | N-39 | H | H | H | H | H | — | — | — | — | — | — |
| 1393 | 1(10) | Me | Me | H | N-40 | H | H | H | H | H | — | — | — | — | — | — |
| 1394 | 1(10) | Me | Me | H | N-41 | H | H | H | H | H | — | — | — | — | — | — |
| 1395 | 1(10) | Me | Me | H | H | N-1 | H | H | H | H | — | — | — | — | — | — |
| 1396 | 1(10) | Me | Me | H | H | N-2 | H | H | H | H | — | — | — | — | — | — |
| 1397 | 1(10) | Me | Me | H | H | N-3 | H | H | H | H | — | — | — | — | — | — |
| 1398 | 1(10) | Me | Me | H | H | N-4 | H | H | H | H | — | — | — | — | — | — |
| 1399 | 1(10) | Me | Me | H | H | N-5 | H | H | H | H | — | — | — | — | — | — |
| 1400 | 1(10) | Me | Me | H | H | N-6 | H | H | H | H | — | — | — | — | — | — |
| 1401 | 1(10) | Me | Me | H | H | N-7 | H | H | H | H | — | — | — | — | — | — |
| 1402 | 1(10) | Me | Me | H | H | N-8 | H | H | H | H | — | — | — | — | — | — |
| 1403 | 1(10) | Me | Me | H | H | N-9 | H | H | H | H | — | — | — | — | — | — |
| 1404 | 1(10) | Me | Me | H | H | N-10 | H | H | H | H | — | — | — | — | — | — |
| 1405 | 1(10) | Me | Me | H | H | N-11 | H | H | H | H | — | — | — | — | — | — |
| 1406 | 1(10) | Me | Me | H | H | N-12 | H | H | H | H | — | — | — | — | — | — |
| 1407 | 1(10) | Me | Me | H | H | N-13 | H | H | H | H | — | — | — | — | — | — |
| 1408 | 1(10) | Me | Me | H | H | N-14 | H | H | H | H | — | — | — | — | — | — |
| 1409 | 1(10) | Me | Me | H | H | N-15 | H | H | H | H | — | — | — | — | — | — |
| 1410 | 1(10) | Me | Me | H | H | N-16 | H | H | H | H | — | — | — | — | — | — |
| 1411 | 1(10) | Me | Me | H | H | N-17 | H | H | H | H | — | — | — | — | — | — |
| 1412 | 1(10) | Me | Me | H | H | N-18 | H | H | H | H | — | — | — | — | — | — |
| 1413 | 1(10) | Me | Me | H | H | N-19 | H | H | H | H | — | — | — | — | — | — |
| 1414 | 1(10) | Me | Me | H | H | N-20 | H | H | H | H | — | — | — | — | — | — |
| 1415 | 1(10) | Me | Me | H | H | N-21 | H | H | H | H | — | — | — | — | — | — |
| 1416 | 1(10) | Me | Me | H | H | N-22 | H | H | H | H | — | — | — | — | — | — |
| 1417 | 1(10) | Me | Me | H | H | N-23 | H | H | H | H | — | — | — | — | — | — |
| 1418 | 1(10) | Me | Me | H | H | N-24 | H | H | H | H | — | — | — | — | — | — |
| 1419 | 1(10) | Me | Me | H | H | N-25 | H | H | H | H | — | — | — | — | — | — |
| 1420 | 1(10) | Me | Me | H | H | N-26 | H | H | H | H | — | — | — | — | — | — |
| 1421 | 1(10) | Me | Me | H | H | N-27 | H | H | H | H | — | — | — | — | — | — |
| 1422 | 1(10) | Me | Me | H | H | N-28 | H | H | H | H | — | — | — | — | — | — |
| 1423 | 1(10) | Me | Me | H | H | N-29 | H | H | H | H | — | — | — | — | — | — |
| 1424 | 1(10) | Me | Me | H | H | N-30 | H | H | H | H | — | — | — | — | — | — |
| 1425 | 1(10) | Me | Me | H | H | N-31 | H | H | H | H | — | — | — | — | — | — |
| 1426 | 1(10) | Me | Me | H | H | N-32 | H | H | H | H | — | — | — | — | — | — |
| 1427 | 1(10) | Me | Me | H | H | N-33 | H | H | H | H | — | — | — | — | — | — |
| 1428 | 1(10) | Me | Me | H | H | N-34 | H | H | H | H | — | — | — | — | — | — |
| 1429 | 1(10) | Me | Me | H | H | N-35 | H | H | H | H | — | — | — | — | — | — |
| 1430 | 1(10) | Me | Me | H | H | N-36 | H | H | H | H | — | — | — | — | — | — |
| 1431 | 1(10) | Me | Me | H | H | N-37 | H | H | H | H | — | — | — | — | — | — |
| 1432 | 1(10) | Me | Me | H | H | N-38 | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1433 | 1(10) | Me | Me | H | H | N-39 | H | H | H | H | — | — | — | — | — | — |
| 1434 | 1(10) | Me | Me | H | H | N-40 | H | H | H | H | — | — | — | — | — | — |
| 1435 | 1(10) | Me | Me | H | H | N-41 | H | H | H | H | — | — | — | — | — | — |
| 1436 | 1(10) | Me | Me | H | H | H | H | H | N-1 | H | — | — | — | — | — | — |
| 1437 | 1(10) | Me | Me | H | H | H | H | H | N-2 | H | — | — | — | — | — | — |
| 1438 | 1(10) | Me | Me | H | H | H | H | H | N-3 | H | — | — | — | — | — | — |
| 1439 | 1(10) | Me | Me | H | H | H | H | H | N-4 | H | — | — | — | — | — | — |
| 1440 | 1(10) | Me | Me | H | H | H | H | H | N-5 | H | — | — | — | — | — | — |
| 1441 | 1(10) | Me | Me | H | H | H | H | H | N-6 | H | — | — | — | — | — | — |
| 1442 | 1(10) | Me | Me | H | H | H | H | H | N-7 | H | — | — | — | — | — | — |
| 1443 | 1(10) | Me | Me | H | H | H | H | H | N-8 | H | — | — | — | — | — | — |
| 1444 | 1(10) | Me | Me | H | H | H | H | H | N-9 | H | — | — | — | — | — | — |
| 1445 | 1(10) | Me | Me | H | H | H | H | H | N-10 | H | — | — | — | — | — | — |
| 1446 | 1(10) | Me | Me | H | H | H | H | H | N-11 | H | — | — | — | — | — | — |
| 1447 | 1(10) | Me | Me | H | H | H | H | H | N-12 | H | — | — | — | — | — | — |
| 1448 | 1(10) | Me | Me | H | H | H | H | H | N-13 | H | — | — | — | — | — | — |
| 1449 | 1(10) | Me | Me | H | H | H | H | H | N-14 | H | — | — | — | — | — | — |
| 1450 | 1(10) | Me | Me | H | H | H | H | H | N-15 | H | — | — | — | — | — | — |
| 1451 | 1(10) | Me | Me | H | H | H | H | H | N-16 | H | — | — | — | — | — | — |
| 1452 | 1(10) | Me | Me | H | H | H | H | H | N-17 | H | — | — | — | — | — | — |
| 1453 | 1(10) | Me | Me | H | H | H | H | H | N-18 | H | — | — | — | — | — | — |
| 1454 | 1(10) | Me | Me | H | H | H | H | H | N-19 | H | — | — | — | — | — | — |
| 1455 | 1(10) | Me | Me | H | H | H | H | H | N-20 | H | — | — | — | — | — | — |
| 1456 | 1(10) | Me | Me | H | H | H | H | H | N-21 | H | — | — | — | — | — | — |
| 1457 | 1(10) | Me | Me | H | H | H | H | H | N-22 | H | — | — | — | — | — | — |
| 1458 | 1(10) | Me | Me | H | H | H | H | H | N-23 | H | — | — | — | — | — | — |
| 1459 | 1(10) | Me | Me | H | H | H | H | H | N-24 | H | — | — | — | — | — | — |
| 1460 | 1(10) | Me | Me | H | H | H | H | H | N-25 | H | — | — | — | — | — | — |
| 1461 | 1(10) | Me | Me | H | H | H | H | H | N-26 | H | — | — | — | — | — | — |
| 1462 | 1(10) | Me | Me | H | H | H | H | H | N-27 | H | — | — | — | — | — | — |
| 1463 | 1(10) | Me | Me | H | H | H | H | H | N-28 | H | — | — | — | — | — | — |
| 1464 | 1(10) | Me | Me | H | H | H | H | H | N-29 | H | — | — | — | — | — | — |
| 1465 | 1(10) | Me | Me | H | H | H | H | H | N-30 | H | — | — | — | — | — | — |
| 1466 | 1(10) | Me | Me | H | H | H | H | H | N-31 | H | — | — | — | — | — | — |
| 1467 | 1(10) | Me | Me | H | H | H | H | H | N-32 | H | — | — | — | — | — | — |
| 1468 | 1(10) | Me | Me | H | H | H | H | H | N-33 | H | — | — | — | — | — | — |
| 1469 | 1(10) | Me | Me | H | H | H | H | H | N-34 | H | — | — | — | — | — | — |
| 1470 | 1(10) | Me | Me | H | H | H | H | H | N-35 | H | — | — | — | — | — | — |
| 1471 | 1(10) | Me | Me | H | H | H | H | H | N-36 | H | — | — | — | — | — | — |
| 1472 | 1(10) | Me | Me | H | H | H | H | H | N-37 | H | — | — | — | — | — | — |
| 1473 | 1(10) | Me | Me | H | H | H | H | H | N-38 | H | — | — | — | — | — | — |
| 1474 | 1(10) | Me | Me | H | H | H | H | H | N-39 | H | — | — | — | — | — | — |
| 1475 | 1(10) | Me | Me | H | H | H | H | H | N-40 | H | — | — | — | — | — | — |
| 1476 | 1(10) | Me | Me | H | H | H | H | H | N-41 | H | — | — | — | — | — | — |
| 1477 | 1(11) | Me | Me | H | N-1 | H | H | H | H | H | H | H | H | H | H | H |
| 1478 | 1(11) | Me | Me | H | N-2 | H | H | H | H | H | H | H | H | H | H | H |
| 1479 | 1(11) | Me | Me | H | N-3 | H | H | H | H | H | H | H | H | H | H | H |
| 1480 | 1(11) | Me | Me | H | N-4 | H | H | H | H | H | H | H | H | H | H | H |
| 1481 | 1(11) | Me | Me | H | N-5 | H | H | H | H | H | H | H | H | H | H | H |
| 1482 | 1(11) | Me | Me | H | N-6 | H | H | H | H | H | H | H | H | H | H | H |
| 1483 | 1(11) | Me | Me | H | N-7 | H | H | H | H | H | H | H | H | H | H | H |
| 1484 | 1(11) | Me | Me | H | N-8 | H | H | H | H | H | H | H | H | H | H | H |
| 1485 | 1(11) | Me | Me | H | N-9 | H | H | H | H | H | H | H | H | H | H | H |
| 1486 | 1(11) | Me | Me | H | N-10 | H | H | H | H | H | H | H | H | H | H | H |
| 1487 | 1(11) | Me | Me | H | N-11 | H | H | H | H | H | H | H | H | H | H | H |
| 1488 | 1(11) | Me | Me | H | N-12 | H | H | H | H | H | H | H | H | H | H | H |
| 1489 | 1(11) | Me | Me | H | N-13 | H | H | H | H | H | H | H | H | H | H | H |
| 1490 | 1(11) | Me | Me | H | N-14 | H | H | H | H | H | H | H | H | H | H | H |
| 1491 | 1(11) | Me | Me | H | N-15 | H | H | H | H | H | H | H | H | H | H | H |
| 1492 | 1(11) | Me | Me | H | N-16 | H | H | H | H | H | H | H | H | H | H | H |
| 1493 | 1(11) | Me | Me | H | N-17 | H | H | H | H | H | H | H | H | H | H | H |
| 1494 | 1(11) | Me | Me | H | N-18 | H | H | H | H | H | H | H | H | H | H | H |
| 1495 | 1(11) | Me | Me | H | N-19 | H | H | H | H | H | H | H | H | H | H | H |
| 1496 | 1(11) | Me | Me | H | N-20 | H | H | H | H | H | H | H | H | H | H | H |
| 1497 | 1(11) | Me | Me | H | N-21 | H | H | H | H | H | H | H | H | H | H | H |
| 1498 | 1(11) | Me | Me | H | N-22 | H | H | H | H | H | H | H | H | H | H | H |
| 1499 | 1(11) | Me | Me | H | N-23 | H | H | H | H | H | H | H | H | H | H | H |
| 1500 | 1(11) | Me | Me | H | N-24 | H | H | H | H | H | H | H | H | H | H | H |
| 1501 | 1(11) | Me | Me | H | N-25 | H | H | H | H | H | H | H | H | H | H | H |
| 1502 | 1(11) | Me | Me | H | N-26 | H | H | H | H | H | H | H | H | H | H | H |
| 1503 | 1(11) | Me | Me | H | N-27 | H | H | H | H | H | H | H | H | H | H | H |
| 1504 | 1(11) | Me | Me | H | N-28 | H | H | H | H | H | H | H | H | H | H | H |
| 1505 | 1(11) | Me | Me | H | N-29 | H | H | H | H | H | H | H | H | H | H | H |
| 1506 | 1(11) | Me | Me | H | N-30 | H | H | H | H | H | H | H | H | H | H | H |
| 1507 | 1(11) | Me | Me | H | N-31 | H | H | H | H | H | H | H | H | H | H | H |
| 1508 | 1(11) | Me | Me | H | N-32 | H | H | H | H | H | H | H | H | H | H | H |
| 1509 | 1(11) | Me | Me | H | N-33 | H | H | H | H | H | H | H | H | H | H | H |
| 1510 | 1(11) | Me | Me | H | N-34 | H | H | H | H | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1511 | 1(11) | Me | Me | H | N-35 | H | H | H | H | H | H | H | H | H | H | H |
| 1512 | 1(11) | Me | Me | H | N-36 | H | H | H | H | H | H | H | H | H | H | H |
| 1513 | 1(11) | Me | Me | H | N-37 | H | H | H | H | H | H | H | H | H | H | H |
| 1514 | 1(11) | Me | Me | H | N-38 | H | H | H | H | H | H | H | H | H | H | H |
| 1515 | 1(11) | Me | Me | H | N-39 | H | H | H | H | H | H | H | H | H | H | H |
| 1516 | 1(11) | Me | Me | H | N-40 | H | H | H | H | H | H | H | H | H | H | H |
| 1517 | 1(11) | Me | Me | H | N-41 | H | H | H | H | H | H | H | H | H | H | H |
| 1518 | 1(11) | Me | Me | H | H | N-1 | H | H | H | H | H | H | H | H | H | H |
| 1519 | 1(11) | Me | Me | H | H | N-2 | H | H | H | H | H | H | H | H | H | H |
| 1520 | 1(11) | Me | Me | H | H | N-3 | H | H | H | H | H | H | H | H | H | H |
| 1521 | 1(11) | Me | Me | H | H | N-4 | H | H | H | H | H | H | H | H | H | H |
| 1522 | 1(11) | Me | Me | H | H | N-5 | H | H | H | H | H | H | H | H | H | H |
| 1523 | 1(11) | Me | Me | H | H | N-6 | H | H | H | H | H | H | H | H | H | H |
| 1524 | 1(11) | Me | Me | H | H | N-7 | H | H | H | H | H | H | H | H | H | H |
| 1525 | 1(11) | Me | Me | H | H | N-8 | H | H | H | H | H | H | H | H | H | H |
| 1526 | 1(11) | Me | Me | H | H | N-9 | H | H | H | H | H | H | H | H | H | H |
| 1527 | 1(11) | Me | Me | H | H | N-10 | H | H | H | H | H | H | H | H | H | H |
| 1528 | 1(11) | Me | Me | H | H | N-11 | H | H | H | H | H | H | H | H | H | H |
| 1529 | 1(11) | Me | Me | H | H | N-12 | H | H | H | H | H | H | H | H | H | H |
| 1530 | 1(11) | Me | Me | H | H | N-13 | H | H | H | H | H | H | H | H | H | H |
| 1531 | 1(11) | Me | Me | H | H | N-14 | H | H | H | H | H | H | H | H | H | H |
| 1532 | 1(11) | Me | Me | H | H | N-15 | H | H | H | H | H | H | H | H | H | H |
| 1533 | 1(11) | Me | Me | H | H | N-16 | H | H | H | H | H | H | H | H | H | H |
| 1534 | 1(11) | Me | Me | H | H | N-17 | H | H | H | H | H | H | H | H | H | H |
| 1535 | 1(11) | Me | Me | H | H | N-18 | H | H | H | H | H | H | H | H | H | H |
| 1536 | 1(11) | Me | Me | H | H | N-19 | H | H | H | H | H | H | H | H | H | H |
| 1537 | 1(11) | Me | Me | H | H | N-20 | H | H | H | H | H | H | H | H | H | H |
| 1538 | 1(11) | Me | Me | H | H | N-21 | H | H | H | H | H | H | H | H | H | H |
| 1539 | 1(11) | Me | Me | H | H | N-22 | H | H | H | H | H | H | H | H | H | H |
| 1540 | 1(11) | Me | Me | H | H | N-23 | H | H | H | H | H | H | H | H | H | H |
| 1541 | 1(11) | Me | Me | H | H | N-24 | H | H | H | H | H | H | H | H | H | H |
| 1542 | 1(11) | Me | Me | H | H | N-25 | H | H | H | H | H | H | H | H | H | H |
| 1543 | 1(11) | Me | Me | H | H | N-26 | H | H | H | H | H | H | H | H | H | H |
| 1544 | 1(11) | Me | Me | H | H | N-27 | H | H | H | H | H | H | H | H | H | H |
| 1545 | 1(11) | Me | Me | H | H | N-28 | H | H | H | H | H | H | H | H | H | H |
| 1546 | 1(11) | Me | Me | H | H | N-29 | H | H | H | H | H | H | H | H | H | H |
| 1547 | 1(11) | Me | Me | H | H | N-30 | H | H | H | H | H | H | H | H | H | H |
| 1548 | 1(11) | Me | Me | H | H | N-31 | H | H | H | H | H | H | H | H | H | H |
| 1549 | 1(11) | Me | Me | H | H | N-32 | H | H | H | H | H | H | H | H | H | H |
| 1550 | 1(11) | Me | Me | H | H | N-33 | H | H | H | H | H | H | H | H | H | H |
| 1551 | 1(11) | Me | Me | H | H | N-34 | H | H | H | H | H | H | H | H | H | H |
| 1552 | 1(11) | Me | Me | H | H | N-35 | H | H | H | H | H | H | H | H | H | H |
| 1553 | 1(11) | Me | Me | H | H | N-36 | H | H | H | H | H | H | H | H | H | H |
| 1554 | 1(11) | Me | Me | H | H | N-37 | H | H | H | H | H | H | H | H | H | H |
| 1555 | 1(11) | Me | Me | H | H | N-38 | H | H | H | H | H | H | H | H | H | H |
| 1556 | 1(11) | Me | Me | H | H | N-39 | H | H | H | H | H | H | H | H | H | H |
| 1557 | 1(11) | Me | Me | H | H | N-40 | H | H | H | H | H | H | H | H | H | H |
| 1558 | 1(11) | Me | Me | H | H | N-41 | H | H | H | H | H | H | H | H | H | H |
| 1559 | 1(11) | Me | Me | H | H | H | H | H | N-1 | H | H | H | H | H | H | H |
| 1560 | 1(11) | Me | Me | H | H | H | H | H | N-2 | H | H | H | H | H | H | H |
| 1561 | 1(11) | Me | Me | H | H | H | H | H | N-3 | H | H | H | H | H | H | H |
| 1562 | 1(11) | Me | Me | H | H | H | H | H | N-4 | H | H | H | H | H | H | H |
| 1563 | 1(11) | Me | Me | H | H | H | H | H | N-5 | H | H | H | H | H | H | H |
| 1564 | 1(11) | Me | Me | H | H | H | H | H | N-6 | H | H | H | H | H | H | H |
| 1565 | 1(11) | Me | Me | H | H | H | H | H | N-7 | H | H | H | H | H | H | H |
| 1566 | 1(11) | Me | Me | H | H | H | H | H | N-8 | H | H | H | H | H | H | H |
| 1567 | 1(11) | Me | Me | H | H | H | H | H | N-9 | H | H | H | H | H | H | H |
| 1568 | 1(11) | Me | Me | H | H | H | H | H | N-10 | H | H | H | H | H | H | H |
| 1569 | 1(11) | Me | Me | H | H | H | H | H | N-11 | H | H | H | H | H | H | H |
| 1570 | 1(11) | Me | Me | H | H | H | H | H | N-12 | H | H | H | H | H | H | H |
| 1571 | 1(11) | Me | Me | H | H | H | H | H | N-13 | H | H | H | H | H | H | H |
| 1572 | 1(11) | Me | Me | H | H | H | H | H | N-14 | H | H | H | H | H | H | H |
| 1573 | 1(11) | Me | Me | H | H | H | H | H | N-15 | H | H | H | H | H | H | H |
| 1574 | 1(11) | Me | Me | H | H | H | H | H | N-16 | H | H | H | H | H | H | H |
| 1575 | 1(11) | Me | Me | H | H | H | H | H | N-17 | H | H | H | H | H | H | H |
| 1576 | 1(11) | Me | Me | H | H | H | H | H | N-18 | H | H | H | H | H | H | H |
| 1577 | 1(11) | Me | Me | H | H | H | H | H | N-19 | H | H | H | H | H | H | H |
| 1578 | 1(11) | Me | Me | H | H | H | H | H | N-20 | H | H | H | H | H | H | H |
| 1579 | 1(11) | Me | Me | H | H | H | H | H | N-21 | H | H | H | H | H | H | H |
| 1580 | 1(11) | Me | Me | H | H | H | H | H | N-22 | H | H | H | H | H | H | H |
| 1581 | 1(11) | Me | Me | H | H | H | H | H | N-23 | H | H | H | H | H | H | H |
| 1582 | 1(11) | Me | Me | H | H | H | H | H | N-24 | H | H | H | H | H | H | H |
| 1583 | 1(11) | Me | Me | H | H | H | H | H | N-25 | H | H | H | H | H | H | H |
| 1584 | 1(11) | Me | Me | H | H | H | H | H | N-26 | H | H | H | H | H | H | H |
| 1585 | 1(11) | Me | Me | H | H | H | H | H | N-27 | H | H | H | H | H | H | H |
| 1586 | 1(11) | Me | Me | H | H | H | H | H | N-28 | H | H | H | H | H | H | H |
| 1587 | 1(11) | Me | Me | H | H | H | H | H | N-29 | H | H | H | H | H | H | H |
| 1588 | 1(11) | Me | Me | H | H | H | H | H | N-30 | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1589 | 1(11) | Me | Me | H | H | H | H | H | N-31 | H | H | H | H | H | H | H |
| 1590 | 1(11) | Me | Me | H | H | H | H | H | N-32 | H | H | H | H | H | H | H |
| 1591 | 1(11) | Me | Me | H | H | H | H | H | N-33 | H | H | H | H | H | H | H |
| 1592 | 1(11) | Me | Me | H | H | H | H | H | N-34 | H | H | H | H | H | H | H |
| 1593 | 1(11) | Me | Me | H | H | H | H | H | N-35 | H | H | H | H | H | H | H |
| 1594 | 1(11) | Me | Me | H | H | H | H | H | N-36 | H | H | H | H | H | H | H |
| 1595 | 1(11) | Me | Me | H | H | H | H | H | N-37 | H | H | H | H | H | H | H |
| 1596 | 1(11) | Me | Me | H | H | H | H | H | N-38 | H | H | H | H | H | H | H |
| 1597 | 1(11) | Me | Me | H | H | H | H | H | N-39 | H | H | H | H | H | H | H |
| 1598 | 1(11) | Me | Me | H | H | H | H | H | N-40 | H | H | H | H | H | H | H |
| 1599 | 1(11) | Me | Me | H | H | H | H | H | N-41 | H | H | H | H | H | H | H |
| 1600 | 1(11) | Me | Me | H | H | H | H | H | H | H | H | H | N-1 | H | H | H |
| 1601 | 1(11) | Me | Me | H | H | H | H | H | H | H | H | H | N-2 | H | H | H |
| 1602 | 1(11) | Me | Me | H | H | H | H | H | H | H | H | H | N-3 | H | H | H |
| 1603 | 1(11) | Me | Me | H | H | H | H | H | H | H | H | H | N-4 | H | H | H |
| 1604 | 1(11) | Me | Me | H | H | H | H | H | H | H | H | H | N-5 | H | H | H |
| 1605 | 1(11) | Me | Me | H | H | H | H | H | H | H | H | H | N-6 | H | H | H |
| 1606 | 1(11) | Me | Me | H | H | H | H | H | H | H | H | H | N-7 | H | H | H |
| 1607 | 1(11) | Me | Me | H | H | H | H | H | H | H | H | H | N-8 | H | H | H |
| 1608 | 1(11) | Me | Me | H | H | H | H | H | H | H | H | H | N-9 | H | H | H |
| 1609 | 1(11) | Me | Me | H | H | H | H | H | H | H | H | H | N-10 | H | H | H |
| 1610 | 1(11) | Me | Me | H | H | H | H | H | H | H | H | H | N-11 | H | H | H |
| 1611 | 1(11) | Me | Me | H | H | H | H | H | H | H | H | H | N-12 | H | H | H |
| 1612 | 1(11) | Me | Me | H | H | H | H | H | H | H | H | H | N-13 | H | H | H |
| 1613 | 1(11) | Me | Me | H | H | H | H | H | H | H | H | H | N-14 | H | H | H |
| 1614 | 1(11) | Me | Me | H | H | H | H | H | H | H | H | H | N-15 | H | H | H |
| 1615 | 1(11) | Me | Me | H | H | H | H | H | H | H | H | H | N-16 | H | H | H |
| 1616 | 1(11) | Me | Me | H | H | H | H | H | H | H | H | H | N-17 | H | H | H |
| 1617 | 1(11) | Me | Me | H | H | H | H | H | H | H | H | H | N-18 | H | H | H |
| 1618 | 1(11) | Me | Me | H | H | H | H | H | H | H | H | H | N-19 | H | H | H |
| 1619 | 1(11) | Me | Me | H | H | H | H | H | H | H | H | H | N-20 | H | H | H |
| 1620 | 1(11) | Me | Me | H | H | H | H | H | H | H | H | H | N-21 | H | H | H |
| 1621 | 1(11) | Me | Me | H | H | H | H | H | H | H | H | H | N-22 | H | H | H |
| 1622 | 1(11) | Me | Me | H | H | H | H | H | H | H | H | H | N-23 | H | H | H |
| 1623 | 1(11) | Me | Me | H | H | H | H | H | H | H | H | H | N-24 | H | H | H |
| 1624 | 1(11) | Me | Me | H | H | H | H | H | H | H | H | H | N-25 | H | H | H |
| 1625 | 1(11) | Me | Me | H | H | H | H | H | H | H | H | H | N-26 | H | H | H |
| 1626 | 1(11) | Me | Me | H | H | H | H | H | H | H | H | H | N-27 | H | H | H |
| 1627 | 1(11) | Me | Me | H | H | H | H | H | H | H | H | H | N-28 | H | H | H |
| 1628 | 1(11) | Me | Me | H | H | H | H | H | H | H | H | H | N-29 | H | H | H |
| 1629 | 1(11) | Me | Me | H | H | H | H | H | H | H | H | H | N-30 | H | H | H |
| 1630 | 1(11) | Me | Me | H | H | H | H | H | H | H | H | H | N-31 | H | H | H |
| 1631 | 1(11) | Me | Me | H | H | H | H | H | H | H | H | H | N-32 | H | H | H |
| 1632 | 1(11) | Me | Me | H | H | H | H | H | H | H | H | H | N-33 | H | H | H |
| 1633 | 1(11) | Me | Me | H | H | H | H | H | H | H | H | H | N-34 | H | H | H |
| 1634 | 1(11) | Me | Me | H | H | H | H | H | H | H | H | H | N-35 | H | H | H |
| 1635 | 1(11) | Me | Me | H | H | H | H | H | H | H | H | H | N-36 | H | H | H |
| 1636 | 1(11) | Me | Me | H | H | H | H | H | H | H | H | H | N-37 | H | H | H |
| 1637 | 1(11) | Me | Me | H | H | H | H | H | H | H | H | H | N-38 | H | H | H |
| 1638 | 1(11) | Me | Me | H | H | H | H | H | H | H | H | H | N-39 | H | H | H |
| 1639 | 1(11) | Me | Me | H | H | H | H | H | H | H | H | H | N-40 | H | H | H |
| 1640 | 1(11) | Me | Me | H | H | H | H | H | H | H | H | H | N-41 | H | H | H |
| 1641 | 1(11) | Me | Me | H | H | H | H | H | H | H | H | H | H | N-1 | H | H |
| 1642 | 1(11) | Me | Me | H | H | H | H | H | H | H | H | H | H | N-2 | H | H |
| 1643 | 1(11) | Me | Me | H | H | H | H | H | H | H | H | H | H | N-3 | H | H |
| 1644 | 1(11) | Me | Me | H | H | H | H | H | H | H | H | H | H | N-4 | H | H |
| 1645 | 1(11) | Me | Me | H | H | H | H | H | H | H | H | H | H | N-5 | H | H |
| 1646 | 1(11) | Me | Me | H | H | H | H | H | H | H | H | H | H | N-6 | H | H |
| 1647 | 1(11) | Me | Me | H | H | H | H | H | H | H | H | H | H | N-7 | H | H |
| 1648 | 1(11) | Me | Me | H | H | H | H | H | H | H | H | H | H | N-8 | H | H |
| 1649 | 1(11) | Me | Me | H | H | H | H | H | H | H | H | H | H | N-9 | H | H |
| 1650 | 1(11) | Me | Me | H | H | H | H | H | H | H | H | H | H | N-10 | H | H |
| 1651 | 1(11) | Me | Me | H | H | H | H | H | H | H | H | H | H | N-11 | H | H |
| 1652 | 1(11) | Me | Me | H | H | H | H | H | H | H | H | H | H | N-12 | H | H |
| 1653 | 1(11) | Me | Me | H | H | H | H | H | H | H | H | H | H | N-13 | H | H |
| 1654 | 1(11) | Me | Me | H | H | H | H | H | H | H | H | H | H | N-14 | H | H |
| 1655 | 1(11) | Me | Me | H | H | H | H | H | H | H | H | H | H | N-15 | H | H |
| 1656 | 1(11) | Me | Me | H | H | H | H | H | H | H | H | H | H | N-16 | H | H |
| 1657 | 1(11) | Me | Me | H | H | H | H | H | H | H | H | H | H | N-17 | H | H |
| 1658 | 1(11) | Me | Me | H | H | H | H | H | H | H | H | H | H | N-18 | H | H |
| 1659 | 1(11) | Me | Me | H | H | H | H | H | H | H | H | H | H | N-19 | H | H |
| 1660 | 1(11) | Me | Me | H | H | H | H | H | H | H | H | H | H | N-20 | H | H |
| 1661 | 1(11) | Me | Me | H | H | H | H | H | H | H | H | H | H | N-21 | H | H |
| 1662 | 1(11) | Me | Me | H | H | H | H | H | H | H | H | H | H | N-22 | H | H |
| 1663 | 1(11) | Me | Me | H | H | H | H | H | H | H | H | H | H | N-23 | H | H |
| 1664 | 1(11) | Me | Me | H | H | H | H | H | H | H | H | H | H | N-24 | H | H |
| 1665 | 1(11) | Me | Me | H | H | H | H | H | H | H | H | H | H | N-25 | H | H |
| 1666 | 1(11) | Me | Me | H | H | H | H | H | H | H | H | H | H | N-26 | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1667 | 1(11) | Me | Me | H | H | H | H | H | H | H | H | H | H | N-27 | H | H |
| 1668 | 1(11) | Me | Me | H | H | H | H | H | H | H | H | H | H | N-28 | H | H |
| 1669 | 1(11) | Me | Me | H | H | H | H | H | H | H | H | H | H | N-29 | H | H |
| 1670 | 1(11) | Me | Me | H | H | H | H | H | H | H | H | H | H | N-30 | H | H |
| 1671 | 1(11) | Me | Me | H | H | H | H | H | H | H | H | H | H | N-31 | H | H |
| 1672 | 1(11) | Me | Me | H | H | H | H | H | H | H | H | H | H | N-32 | H | H |
| 1673 | 1(11) | Me | Me | H | H | H | H | H | H | H | H | H | H | N-33 | H | H |
| 1674 | 1(11) | Me | Me | H | H | H | H | H | H | H | H | H | H | N-34 | H | H |
| 1675 | 1(11) | Me | Me | H | H | H | H | H | H | H | H | H | H | N-35 | H | H |
| 1676 | 1(11) | Me | Me | H | H | H | H | H | H | H | H | H | H | N-36 | H | H |
| 1677 | 1(11) | Me | Me | H | H | H | H | H | H | H | H | H | H | N-37 | H | H |
| 1678 | 1(11) | Me | Me | H | H | H | H | H | H | H | H | H | H | N-38 | H | H |
| 1679 | 1(11) | Me | Me | H | H | H | H | H | H | H | H | H | H | N-39 | H | H |
| 1680 | 1(11) | Me | Me | H | H | H | H | H | H | H | H | H | H | N-40 | H | H |
| 1681 | 1(11) | Me | Me | H | H | H | H | H | H | H | H | H | H | N-41 | H | H |
| 1682 | 1(12) | Me | Me | H | N-1 | H | H | H | H | H | — | — | — | — | — | — |
| 1683 | 1(12) | Me | Me | H | N-2 | H | H | H | H | H | — | — | — | — | — | — |
| 1684 | 1(12) | Me | Me | H | N-3 | H | H | H | H | H | — | — | — | — | — | — |
| 1685 | 1(12) | Me | Me | H | N-4 | H | H | H | H | H | — | — | — | — | — | — |
| 1686 | 1(12) | Me | Me | H | N-5 | H | H | H | H | H | — | — | — | — | — | — |
| 1687 | 1(12) | Me | Me | H | N-6 | H | H | H | H | H | — | — | — | — | — | — |
| 1688 | 1(12) | Me | Me | H | N-7 | H | H | H | H | H | — | — | — | — | — | — |
| 1689 | 1(12) | Me | Me | H | N-8 | H | H | H | H | H | — | — | — | — | — | — |
| 1690 | 1(12) | Me | Me | H | N-9 | H | H | H | H | H | — | — | — | — | — | — |
| 1691 | 1(12) | Me | Me | H | N-10 | H | H | H | H | H | — | — | — | — | — | — |
| 1692 | 1(12) | Me | Me | H | N-11 | H | H | H | H | H | — | — | — | — | — | — |
| 1693 | 1(12) | Me | Me | H | N-12 | H | H | H | H | H | — | — | — | — | — | — |
| 1694 | 1(12) | Me | Me | H | N-13 | H | H | H | H | H | — | — | — | — | — | — |
| 1695 | 1(12) | Me | Me | H | N-14 | H | H | H | H | H | — | — | — | — | — | — |
| 1696 | 1(12) | Me | Me | H | N-15 | H | H | H | H | H | — | — | — | — | — | — |
| 1697 | 1(12) | Me | Me | H | N-16 | H | H | H | H | H | — | — | — | — | — | — |
| 1698 | 1(12) | Me | Me | H | N-17 | H | H | H | H | H | — | — | — | — | — | — |
| 1699 | 1(12) | Me | Me | H | N-18 | H | H | H | H | H | — | — | — | — | — | — |
| 1700 | 1(12) | Me | Me | H | N-19 | H | H | H | H | H | — | — | — | — | — | — |
| 1701 | 1(12) | Me | Me | H | N-20 | H | H | H | H | H | — | — | — | — | — | — |
| 1702 | 1(12) | Me | Me | H | N-21 | H | H | H | H | H | — | — | — | — | — | — |
| 1703 | 1(12) | Me | Me | H | N-22 | H | H | H | H | H | — | — | — | — | — | — |
| 1704 | 1(12) | Me | Me | H | N-23 | H | H | H | H | H | — | — | — | — | — | — |
| 1705 | 1(12) | Me | Me | H | N-24 | H | H | H | H | H | — | — | — | — | — | — |
| 1706 | 1(12) | Me | Me | H | N-25 | H | H | H | H | H | — | — | — | — | — | — |
| 1707 | 1(12) | Me | Me | H | N-26 | H | H | H | H | H | — | — | — | — | — | — |
| 1708 | 1(12) | Me | Me | H | N-27 | H | H | H | H | H | — | — | — | — | — | — |
| 1709 | 1(12) | Me | Me | H | N-28 | H | H | H | H | H | — | — | — | — | — | — |
| 1710 | 1(12) | Me | Me | H | N-29 | H | H | H | H | H | — | — | — | — | — | — |
| 1711 | 1(12) | Me | Me | H | N-30 | H | H | H | H | H | — | — | — | — | — | — |
| 1712 | 1(12) | Me | Me | H | N-31 | H | H | H | H | H | — | — | — | — | — | — |
| 1713 | 1(12) | Me | Me | H | N-32 | H | H | H | H | H | — | — | — | — | — | — |
| 1714 | 1(12) | Me | Me | H | N-33 | H | H | H | H | H | — | — | — | — | — | — |
| 1715 | 1(12) | Me | Me | H | N-34 | H | H | H | H | H | — | — | — | — | — | — |
| 1716 | 1(12) | Me | Me | H | N-35 | H | H | H | H | H | — | — | — | — | — | — |
| 1717 | 1(12) | Me | Me | H | N-36 | H | H | H | H | H | — | — | — | — | — | — |
| 1718 | 1(12) | Me | Me | H | N-37 | H | H | H | H | H | — | — | — | — | — | — |
| 1719 | 1(12) | Me | Me | H | N-38 | H | H | H | H | H | — | — | — | — | — | — |
| 1720 | 1(12) | Me | Me | H | N-39 | H | H | H | H | H | — | — | — | — | — | — |
| 1721 | 1(12) | Me | Me | H | N-40 | H | H | H | H | H | — | — | — | — | — | — |
| 1722 | 1(12) | Me | Me | H | N-41 | H | H | H | H | H | — | — | — | — | — | — |
| 1723 | 1(12) | Me | Me | H | H | N-1 | H | H | H | H | — | — | — | — | — | — |
| 1724 | 1(12) | Me | Me | H | H | N-2 | H | H | H | H | — | — | — | — | — | — |
| 1725 | 1(12) | Me | Me | H | H | N-3 | H | H | H | H | — | — | — | — | — | — |
| 1726 | 1(12) | Me | Me | H | H | N-4 | H | H | H | H | — | — | — | — | — | — |
| 1727 | 1(12) | Me | Me | H | H | N-5 | H | H | H | H | — | — | — | — | — | — |
| 1728 | 1(12) | Me | Me | H | H | N-6 | H | H | H | H | — | — | — | — | — | — |
| 1729 | 1(12) | Me | Me | H | H | N-7 | H | H | H | H | — | — | — | — | — | — |
| 1730 | 1(12) | Me | Me | H | H | N-8 | H | H | H | H | — | — | — | — | — | — |
| 1731 | 1(12) | Me | Me | H | H | N-9 | H | H | H | H | — | — | — | — | — | — |
| 1732 | 1(12) | Me | Me | H | H | N-10 | H | H | H | H | — | — | — | — | — | — |
| 1733 | 1(12) | Me | Me | H | H | N-11 | H | H | H | H | — | — | — | — | — | — |
| 1734 | 1(12) | Me | Me | H | H | N-12 | H | H | H | H | — | — | — | — | — | — |
| 1735 | 1(12) | Me | Me | H | H | N-13 | H | H | H | H | — | — | — | — | — | — |
| 1736 | 1(12) | Me | Me | H | H | N-14 | H | H | H | H | — | — | — | — | — | — |
| 1737 | 1(12) | Me | Me | H | H | N-15 | H | H | H | H | — | — | — | — | — | — |
| 1738 | 1(12) | Me | Me | H | H | N-16 | H | H | H | H | — | — | — | — | — | — |
| 1739 | 1(12) | Me | Me | H | H | N-17 | H | H | H | H | — | — | — | — | — | — |
| 1740 | 1(12) | Me | Me | H | H | N-18 | H | H | H | H | — | — | — | — | — | — |
| 1741 | 1(12) | Me | Me | H | H | N-19 | H | H | H | H | — | — | — | — | — | — |
| 1742 | 1(12) | Me | Me | H | H | N-20 | H | H | H | H | — | — | — | — | — | — |
| 1743 | 1(12) | Me | Me | H | H | N-21 | H | H | H | H | — | — | — | — | — | — |
| 1744 | 1(12) | Me | Me | H | H | N-22 | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1745 | 1(12) | Me | Me | H | H | N-23 | H | H | H | H | — | — | — | — | — | — |
| 1746 | 1(12) | Me | Me | H | H | N-24 | H | H | H | H | — | — | — | — | — | — |
| 1747 | 1(12) | Me | Me | H | H | N-25 | H | H | H | H | — | — | — | — | — | — |
| 1748 | 1(12) | Me | Me | H | H | N-26 | H | H | H | H | — | — | — | — | — | — |
| 1749 | 1(12) | Me | Me | H | H | N-27 | H | H | H | H | — | — | — | — | — | — |
| 1750 | 1(12) | Me | Me | H | H | N-28 | H | H | H | H | — | — | — | — | — | — |
| 1751 | 1(12) | Me | Me | H | H | N-29 | H | H | H | H | — | — | — | — | — | — |
| 1752 | 1(12) | Me | Me | H | H | N-30 | H | H | H | H | — | — | — | — | — | — |
| 1753 | 1(12) | Me | Me | H | H | N-31 | H | H | H | H | — | — | — | — | — | — |
| 1754 | 1(12) | Me | Me | H | H | N-32 | H | H | H | H | — | — | — | — | — | — |
| 1755 | 1(12) | Me | Me | H | H | N-33 | H | H | H | H | — | — | — | — | — | — |
| 1756 | 1(12) | Me | Me | H | H | N-34 | H | H | H | H | — | — | — | — | — | — |
| 1757 | 1(12) | Me | Me | H | H | N-35 | H | H | H | H | — | — | — | — | — | — |
| 1758 | 1(12) | Me | Me | H | H | N-36 | H | H | H | H | — | — | — | — | — | — |
| 1759 | 1(12) | Me | Me | H | H | N-37 | H | H | H | H | — | — | — | — | — | — |
| 1760 | 1(12) | Me | Me | H | H | N-38 | H | H | H | H | — | — | — | — | — | — |
| 1761 | 1(12) | Me | Me | H | H | N-39 | H | H | H | H | — | — | — | — | — | — |
| 1762 | 1(12) | Me | Me | H | H | N-40 | H | H | H | H | — | — | — | — | — | — |
| 1763 | 1(12) | Me | Me | H | H | N-41 | H | H | H | H | — | — | — | — | — | — |
| 1764 | 1(12) | Me | Me | H | H | H | H | H | H | N-1 | — | — | — | — | — | — |
| 1765 | 1(12) | Me | Me | H | H | H | H | H | H | N-2 | — | — | — | — | — | — |
| 1766 | 1(12) | Me | Me | H | H | H | H | H | H | N-3 | — | — | — | — | — | — |
| 1767 | 1(12) | Me | Me | H | H | H | H | H | H | N-4 | — | — | — | — | — | — |
| 1768 | 1(12) | Me | Me | H | H | H | H | H | H | N-5 | — | — | — | — | — | — |
| 1769 | 1(12) | Me | Me | H | H | H | H | H | H | N-6 | — | — | — | — | — | — |
| 1770 | 1(12) | Me | Me | H | H | H | H | H | H | N-7 | — | — | — | — | — | — |
| 1771 | 1(12) | Me | Me | H | H | H | H | H | H | N-8 | — | — | — | — | — | — |
| 1772 | 1(12) | Me | Me | H | H | H | H | H | H | N-9 | — | — | — | — | — | — |
| 1773 | 1(12) | Me | Me | H | H | H | H | H | H | N-10 | — | — | — | — | — | — |
| 1774 | 1(12) | Me | Me | H | H | H | H | H | H | N-11 | — | — | — | — | — | — |
| 1775 | 1(12) | Me | Me | H | H | H | H | H | H | N-12 | — | — | — | — | — | — |
| 1776 | 1(12) | Me | Me | H | H | H | H | H | H | N-13 | — | — | — | — | — | — |
| 1777 | 1(12) | Me | Me | H | H | H | H | H | H | N-14 | — | — | — | — | — | — |
| 1778 | 1(12) | Me | Me | H | H | H | H | H | H | N-15 | — | — | — | — | — | — |
| 1779 | 1(12) | Me | Me | H | H | H | H | H | H | N-16 | — | — | — | — | — | — |
| 1780 | 1(12) | Me | Me | H | H | H | H | H | H | N-17 | — | — | — | — | — | — |
| 1781 | 1(12) | Me | Me | H | H | H | H | H | H | N-18 | — | — | — | — | — | — |
| 1782 | 1(12) | Me | Me | H | H | H | H | H | H | N-19 | — | — | — | — | — | — |
| 1783 | 1(12) | Me | Me | H | H | H | H | H | H | N-20 | — | — | — | — | — | — |
| 1784 | 1(12) | Me | Me | H | H | H | H | H | H | N-21 | — | — | — | — | — | — |
| 1785 | 1(12) | Me | Me | H | H | H | H | H | H | N-22 | — | — | — | — | — | — |
| 1786 | 1(12) | Me | Me | H | H | H | H | H | H | N-23 | — | — | — | — | — | — |
| 1787 | 1(12) | Me | Me | H | H | H | H | H | H | N-24 | — | — | — | — | — | — |
| 1788 | 1(12) | Me | Me | H | H | H | H | H | H | N-25 | — | — | — | — | — | — |
| 1789 | 1(12) | Me | Me | H | H | H | H | H | H | N-26 | — | — | — | — | — | — |
| 1790 | 1(12) | Me | Me | H | H | H | H | H | H | N-27 | — | — | — | — | — | — |
| 1791 | 1(12) | Me | Me | H | H | H | H | H | H | N-28 | — | — | — | — | — | — |
| 1792 | 1(12) | Me | Me | H | H | H | H | H | H | N-29 | — | — | — | — | — | — |
| 1793 | 1(12) | Me | Me | H | H | H | H | H | H | N-30 | — | — | — | — | — | — |
| 1794 | 1(12) | Me | Me | H | H | H | H | H | H | N-31 | — | — | — | — | — | — |
| 1795 | 1(12) | Me | Me | H | H | H | H | H | H | N-32 | — | — | — | — | — | — |
| 1796 | 1(12) | Me | Me | H | H | H | H | H | H | N-33 | — | — | — | — | — | — |
| 1797 | 1(12) | Me | Me | H | H | H | H | H | H | N-34 | — | — | — | — | — | — |
| 1798 | 1(12) | Me | Me | H | H | H | H | H | H | N-35 | — | — | — | — | — | — |
| 1799 | 1(12) | Me | Me | H | H | H | H | H | H | N-36 | — | — | — | — | — | — |
| 1800 | 1(12) | Me | Me | H | H | H | H | H | H | N-37 | — | — | — | — | — | — |
| 1801 | 1(12) | Me | Me | H | H | H | H | H | H | N-38 | — | — | — | — | — | — |
| 1802 | 1(12) | Me | Me | H | H | H | H | H | H | N-39 | — | — | — | — | — | — |
| 1803 | 1(12) | Me | Me | H | H | H | H | H | H | N-40 | — | — | — | — | — | — |
| 1804 | 1(12) | Me | Me | H | H | H | H | H | H | N-41 | — | — | — | — | — | — |
| 1805 | 1(10) | Ph | Ph | H | N-1 | H | H | H | H | H | — | — | — | — | — | — |
| 1806 | 1(10) | Ph | Ph | H | N-2 | H | H | H | H | H | — | — | — | — | — | — |
| 1807 | 1(10) | Ph | Ph | H | N-3 | H | H | H | H | H | — | — | — | — | — | — |
| 1808 | 1(10) | Ph | Ph | H | N-4 | H | H | H | H | H | — | — | — | — | — | — |
| 1809 | 1(10) | Ph | Ph | H | N-5 | H | H | H | H | H | — | — | — | — | — | — |
| 1810 | 1(10) | Ph | Ph | H | N-6 | H | H | H | H | H | — | — | — | — | — | — |
| 1811 | 1(10) | Ph | Ph | H | N-7 | H | H | H | H | H | — | — | — | — | — | — |
| 1812 | 1(10) | Ph | Ph | H | N-8 | H | H | H | H | H | — | — | — | — | — | — |
| 1813 | 1(10) | Ph | Ph | H | N-9 | H | H | H | H | H | — | — | — | — | — | — |
| 1814 | 1(10) | Ph | Ph | H | N-10 | H | H | H | H | H | — | — | — | — | — | — |
| 1815 | 1(10) | Ph | Ph | H | N-11 | H | H | H | H | H | — | — | — | — | — | — |
| 1816 | 1(10) | Ph | Ph | H | N-12 | H | H | H | H | H | — | — | — | — | — | — |
| 1817 | 1(10) | Ph | Ph | H | N-13 | H | H | H | H | H | — | — | — | — | — | — |
| 1818 | 1(10) | Ph | Ph | H | N-14 | H | H | H | H | H | — | — | — | — | — | — |
| 1819 | 1(10) | Ph | Ph | H | N-15 | H | H | H | H | H | — | — | — | — | — | — |
| 1820 | 1(10) | Ph | Ph | H | N-16 | H | H | H | H | H | — | — | — | — | — | — |
| 1821 | 1(10) | Ph | Ph | H | N-17 | H | H | H | H | H | — | — | — | — | — | — |
| 1822 | 1(10) | Ph | Ph | H | N-18 | H | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1823 | 1(10) | Ph | Ph | H | N-19 | H | H | H | H | H | — | — | — | — | — | — |
| 1824 | 1(10) | Ph | Ph | H | N-20 | H | H | H | H | H | — | — | — | — | — | — |
| 1825 | 1(10) | Ph | Ph | H | N-21 | H | H | H | H | H | — | — | — | — | — | — |
| 1826 | 1(10) | Ph | Ph | H | N-22 | H | H | H | H | H | — | — | — | — | — | — |
| 1827 | 1(10) | Ph | Ph | H | N-23 | H | H | H | H | H | — | — | — | — | — | — |
| 1828 | 1(10) | Ph | Ph | H | N-24 | H | H | H | H | H | — | — | — | — | — | — |
| 1829 | 1(10) | Ph | Ph | H | N-25 | H | H | H | H | H | — | — | — | — | — | — |
| 1830 | 1(10) | Ph | Ph | H | N-26 | H | H | H | H | H | — | — | — | — | — | — |
| 1831 | 1(10) | Ph | Ph | H | N-27 | H | H | H | H | H | — | — | — | — | — | — |
| 1832 | 1(10) | Ph | Ph | H | N-28 | H | H | H | H | H | — | — | — | — | — | — |
| 1833 | 1(10) | Ph | Ph | H | N-29 | H | H | H | H | H | — | — | — | — | — | — |
| 1834 | 1(10) | Ph | Ph | H | N-30 | H | H | H | H | H | — | — | — | — | — | — |
| 1835 | 1(10) | Ph | Ph | H | N-31 | H | H | H | H | H | — | — | — | — | — | — |
| 1836 | 1(10) | Ph | Ph | H | N-32 | H | H | H | H | H | — | — | — | — | — | — |
| 1837 | 1(10) | Ph | Ph | H | N-33 | H | H | H | H | H | — | — | — | — | — | — |
| 1838 | 1(10) | Ph | Ph | H | N-34 | H | H | H | H | H | — | — | — | — | — | — |
| 1839 | 1(10) | Ph | Ph | H | N-35 | H | H | H | H | H | — | — | — | — | — | — |
| 1840 | 1(10) | Ph | Ph | H | N-36 | H | H | H | H | H | — | — | — | — | — | — |
| 1841 | 1(10) | Ph | Ph | H | N-37 | H | H | H | H | H | — | — | — | — | — | — |
| 1842 | 1(10) | Ph | Ph | H | N-38 | H | H | H | H | H | — | — | — | — | — | — |
| 1843 | 1(10) | Ph | Ph | H | N-39 | H | H | H | H | H | — | — | — | — | — | — |
| 1844 | 1(10) | Ph | Ph | H | N-40 | H | H | H | H | H | — | — | — | — | — | — |
| 1845 | 1(10) | Ph | Ph | H | N-41 | H | H | H | H | H | — | — | — | — | — | — |
| 1846 | 1(10) | Ph | Ph | H | H | N-1 | H | H | H | H | — | — | — | — | — | — |
| 1847 | 1(10) | Ph | Ph | H | H | N-2 | H | H | H | H | — | — | — | — | — | — |
| 1848 | 1(10) | Ph | Ph | H | H | N-3 | H | H | H | H | — | — | — | — | — | — |
| 1849 | 1(10) | Ph | Ph | H | H | N-4 | H | H | H | H | — | — | — | — | — | — |
| 1850 | 1(10) | Ph | Ph | H | H | N-5 | H | H | H | H | — | — | — | — | — | — |
| 1851 | 1(10) | Ph | Ph | H | H | N-6 | H | H | H | H | — | — | — | — | — | — |
| 1852 | 1(10) | Ph | Ph | H | H | N-7 | H | H | H | H | — | — | — | — | — | — |
| 1853 | 1(10) | Ph | Ph | H | H | N-8 | H | H | H | H | — | — | — | — | — | — |
| 1854 | 1(10) | Ph | Ph | H | H | N-9 | H | H | H | H | — | — | — | — | — | — |
| 1855 | 1(10) | Ph | Ph | H | H | N-10 | H | H | H | H | — | — | — | — | — | — |
| 1856 | 1(10) | Ph | Ph | H | H | N-11 | H | H | H | H | — | — | — | — | — | — |
| 1857 | 1(10) | Ph | Ph | H | H | N-12 | H | H | H | H | — | — | — | — | — | — |
| 1858 | 1(10) | Ph | Ph | H | H | N-13 | H | H | H | H | — | — | — | — | — | — |
| 1859 | 1(10) | Ph | Ph | H | H | N-14 | H | H | H | H | — | — | — | — | — | — |
| 1860 | 1(10) | Ph | Ph | H | H | N-15 | H | H | H | H | — | — | — | — | — | — |
| 1861 | 1(10) | Ph | Ph | H | H | N-16 | H | H | H | H | — | — | — | — | — | — |
| 1862 | 1(10) | Ph | Ph | H | H | N-17 | H | H | H | H | — | — | — | — | — | — |
| 1863 | 1(10) | Ph | Ph | H | H | N-18 | H | H | H | H | — | — | — | — | — | — |
| 1864 | 1(10) | Ph | Ph | H | H | N-19 | H | H | H | H | — | — | — | — | — | — |
| 1865 | 1(10) | Ph | Ph | H | H | N-20 | H | H | H | H | — | — | — | — | — | — |
| 1866 | 1(10) | Ph | Ph | H | H | N-21 | H | H | H | H | — | — | — | — | — | — |
| 1867 | 1(10) | Ph | Ph | H | H | N-22 | H | H | H | H | — | — | — | — | — | — |
| 1868 | 1(10) | Ph | Ph | H | H | N-23 | H | H | H | H | — | — | — | — | — | — |
| 1869 | 1(10) | Ph | Ph | H | H | N-24 | H | H | H | H | — | — | — | — | — | — |
| 1870 | 1(10) | Ph | Ph | H | H | N-25 | H | H | H | H | — | — | — | — | — | — |
| 1871 | 1(10) | Ph | Ph | H | H | N-26 | H | H | H | H | — | — | — | — | — | — |
| 1872 | 1(10) | Ph | Ph | H | H | N-27 | H | H | H | H | — | — | — | — | — | — |
| 1873 | 1(10) | Ph | Ph | H | H | N-28 | H | H | H | H | — | — | — | — | — | — |
| 1874 | 1(10) | Ph | Ph | H | H | N-29 | H | H | H | H | — | — | — | — | — | — |
| 1875 | 1(10) | Ph | Ph | H | H | N-30 | H | H | H | H | — | — | — | — | — | — |
| 1876 | 1(10) | Ph | Ph | H | H | N-31 | H | H | H | H | — | — | — | — | — | — |
| 1877 | 1(10) | Ph | Ph | H | H | N-32 | H | H | H | H | — | — | — | — | — | — |
| 1878 | 1(10) | Ph | Ph | H | H | N-33 | H | H | H | H | — | — | — | — | — | — |
| 1879 | 1(10) | Ph | Ph | H | H | N-34 | H | H | H | H | — | — | — | — | — | — |
| 1880 | 1(10) | Ph | Ph | H | H | N-35 | H | H | H | H | — | — | — | — | — | — |
| 1881 | 1(10) | Ph | Ph | H | H | N-36 | H | H | H | H | — | — | — | — | — | — |
| 1882 | 1(10) | Ph | Ph | H | H | N-37 | H | H | H | H | — | — | — | — | — | — |
| 1883 | 1(10) | Ph | Ph | H | H | N-38 | H | H | H | H | — | — | — | — | — | — |
| 1884 | 1(10) | Ph | Ph | H | H | N-39 | H | H | H | H | — | — | — | — | — | — |
| 1885 | 1(10) | Ph | Ph | H | H | N-40 | H | H | H | H | — | — | — | — | — | — |
| 1886 | 1(10) | Ph | Ph | H | H | N-41 | H | H | H | H | — | — | — | — | — | — |
| 1887 | 1(10) | Ph | Ph | H | H | H | H | H | N-1 | H | — | — | — | — | — | — |
| 1888 | 1(10) | Ph | Ph | H | H | H | H | H | N-2 | H | — | — | — | — | — | — |
| 1889 | 1(10) | Ph | Ph | H | H | H | H | H | N-3 | H | — | — | — | — | — | — |
| 1890 | 1(10) | Ph | Ph | H | H | H | H | H | N-4 | H | — | — | — | — | — | — |
| 1891 | 1(10) | Ph | Ph | H | H | H | H | H | N-5 | H | — | — | — | — | — | — |
| 1892 | 1(10) | Ph | Ph | H | H | H | H | H | N-6 | H | — | — | — | — | — | — |
| 1893 | 1(10) | Ph | Ph | H | H | H | H | H | N-7 | H | — | — | — | — | — | — |
| 1894 | 1(10) | Ph | Ph | H | H | H | H | H | N-8 | H | — | — | — | — | — | — |
| 1895 | 1(10) | Ph | Ph | H | H | H | H | H | N-9 | H | — | — | — | — | — | — |
| 1896 | 1(10) | Ph | Ph | H | H | H | H | H | N-10 | H | — | — | — | — | — | — |
| 1897 | 1(10) | Ph | Ph | H | H | H | H | H | N-11 | H | — | — | — | — | — | — |
| 1898 | 1(10) | Ph | Ph | H | H | H | H | H | N-12 | H | — | — | — | — | — | — |
| 1899 | 1(10) | Ph | Ph | H | H | H | H | H | N-13 | H | — | — | — | — | — | — |
| 1900 | 1(10) | Ph | Ph | H | H | H | H | H | N-14 | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1901 | 1(10) | Ph | Ph | H | H | H | H | H | N-15 | H | — | — | — | — | — | — |
| 1902 | 1(10) | Ph | Ph | H | H | H | H | H | N-16 | H | — | — | — | — | — | — |
| 1903 | 1(10) | Ph | Ph | H | H | H | H | H | N-17 | H | — | — | — | — | — | — |
| 1904 | 1(10) | Ph | Ph | H | H | H | H | H | N-18 | H | — | — | — | — | — | — |
| 1905 | 1(10) | Ph | Ph | H | H | H | H | H | N-19 | H | — | — | — | — | — | — |
| 1906 | 1(10) | Ph | Ph | H | H | H | H | H | N-20 | H | — | — | — | — | — | — |
| 1907 | 1(10) | Ph | Ph | H | H | H | H | H | N-21 | H | — | — | — | — | — | — |
| 1908 | 1(10) | Ph | Ph | H | H | H | H | H | N-22 | H | — | — | — | — | — | — |
| 1909 | 1(10) | Ph | Ph | H | H | H | H | H | N-23 | H | — | — | — | — | — | — |
| 1910 | 1(10) | Ph | Ph | H | H | H | H | H | N-24 | H | — | — | — | — | — | — |
| 1911 | 1(10) | Ph | Ph | H | H | H | H | H | N-25 | H | — | — | — | — | — | — |
| 1912 | 1(10) | Ph | Ph | H | H | H | H | H | N-26 | H | — | — | — | — | — | — |
| 1913 | 1(10) | Ph | Ph | H | H | H | H | H | N-27 | H | — | — | — | — | — | — |
| 1914 | 1(10) | Ph | Ph | H | H | H | H | H | N-28 | H | — | — | — | — | — | — |
| 1915 | 1(10) | Ph | Ph | H | H | H | H | H | N-29 | H | — | — | — | — | — | — |
| 1916 | 1(10) | Ph | Ph | H | H | H | H | H | N-30 | H | — | — | — | — | — | — |
| 1917 | 1(10) | Ph | Ph | H | H | H | H | H | N-31 | H | — | — | — | — | — | — |
| 1918 | 1(10) | Ph | Ph | H | H | H | H | H | N-32 | H | — | — | — | — | — | — |
| 1919 | 1(10) | Ph | Ph | H | H | H | H | H | N-33 | H | — | — | — | — | — | — |
| 1920 | 1(10) | Ph | Ph | H | H | H | H | H | N-34 | H | — | — | — | — | — | — |
| 1921 | 1(10) | Ph | Ph | H | H | H | H | H | N-35 | H | — | — | — | — | — | — |
| 1922 | 1(10) | Ph | Ph | H | H | H | H | H | N-36 | H | — | — | — | — | — | — |
| 1923 | 1(10) | Ph | Ph | H | H | H | H | H | N-37 | H | — | — | — | — | — | — |
| 1924 | 1(10) | Ph | Ph | H | H | H | H | H | N-38 | H | — | — | — | — | — | — |
| 1925 | 1(10) | Ph | Ph | H | H | H | H | H | N-39 | H | — | — | — | — | — | — |
| 1926 | 1(10) | Ph | Ph | H | H | H | H | H | N-40 | H | — | — | — | — | — | — |
| 1927 | 1(10) | Ph | Ph | H | H | H | H | H | N-41 | H | — | — | — | — | — | — |
| 1928 | 1(11) | Ph | Ph | H | N-1 | H | H | H | H | H | H | H | H | H | H | H |
| 1929 | 1(11) | Ph | Ph | H | N-2 | H | H | H | H | H | H | H | H | H | H | H |
| 1930 | 1(11) | Ph | Ph | H | N-3 | H | H | H | H | H | H | H | H | H | H | H |
| 1931 | 1(11) | Ph | Ph | H | N-4 | H | H | H | H | H | H | H | H | H | H | H |
| 1932 | 1(11) | Ph | Ph | H | N-5 | H | H | H | H | H | H | H | H | H | H | H |
| 1933 | 1(11) | Ph | Ph | H | N-6 | H | H | H | H | H | H | H | H | H | H | H |
| 1934 | 1(11) | Ph | Ph | H | N-7 | H | H | H | H | H | H | H | H | H | H | H |
| 1935 | 1(11) | Ph | Ph | H | N-8 | H | H | H | H | H | H | H | H | H | H | H |
| 1936 | 1(11) | Ph | Ph | H | N-9 | H | H | H | H | H | H | H | H | H | H | H |
| 1937 | 1(11) | Ph | Ph | H | N-10 | H | H | H | H | H | H | H | H | H | H | H |
| 1938 | 1(11) | Ph | Ph | H | N-11 | H | H | H | H | H | H | H | H | H | H | H |
| 1939 | 1(11) | Ph | Ph | H | N-12 | H | H | H | H | H | H | H | H | H | H | H |
| 1940 | 1(11) | Ph | Ph | H | N-13 | H | H | H | H | H | H | H | H | H | H | H |
| 1941 | 1(11) | Ph | Ph | H | N-14 | H | H | H | H | H | H | H | H | H | H | H |
| 1942 | 1(11) | Ph | Ph | H | N-15 | H | H | H | H | H | H | H | H | H | H | H |
| 1943 | 1(11) | Ph | Ph | H | N-16 | H | H | H | H | H | H | H | H | H | H | H |
| 1944 | 1(11) | Ph | Ph | H | N-17 | H | H | H | H | H | H | H | H | H | H | H |
| 1945 | 1(11) | Ph | Ph | H | N-18 | H | H | H | H | H | H | H | H | H | H | H |
| 1946 | 1(11) | Ph | Ph | H | N-19 | H | H | H | H | H | H | H | H | H | H | H |
| 1947 | 1(11) | Ph | Ph | H | N-20 | H | H | H | H | H | H | H | H | H | H | H |
| 1948 | 1(11) | Ph | Ph | H | N-21 | H | H | H | H | H | H | H | H | H | H | H |
| 1949 | 1(11) | Ph | Ph | H | N-22 | H | H | H | H | H | H | H | H | H | H | H |
| 1950 | 1(11) | Ph | Ph | H | N-23 | H | H | H | H | H | H | H | H | H | H | H |
| 1951 | 1(11) | Ph | Ph | H | N-24 | H | H | H | H | H | H | H | H | H | H | H |
| 1952 | 1(11) | Ph | Ph | H | N-25 | H | H | H | H | H | H | H | H | H | H | H |
| 1953 | 1(11) | Ph | Ph | H | N-26 | H | H | H | H | H | H | H | H | H | H | H |
| 1954 | 1(11) | Ph | Ph | H | N-27 | H | H | H | H | H | H | H | H | H | H | H |
| 1955 | 1(11) | Ph | Ph | H | N-28 | H | H | H | H | H | H | H | H | H | H | H |
| 1956 | 1(11) | Ph | Ph | H | N-29 | H | H | H | H | H | H | H | H | H | H | H |
| 1957 | 1(11) | Ph | Ph | H | N-30 | H | H | H | H | H | H | H | H | H | H | H |
| 1958 | 1(11) | Ph | Ph | H | N-31 | H | H | H | H | H | H | H | H | H | H | H |
| 1959 | 1(11) | Ph | Ph | H | N-32 | H | H | H | H | H | H | H | H | H | H | H |
| 1960 | 1(11) | Ph | Ph | H | N-33 | H | H | H | H | H | H | H | H | H | H | H |
| 1961 | 1(11) | Ph | Ph | H | N-34 | H | H | H | H | H | H | H | H | H | H | H |
| 1962 | 1(11) | Ph | Ph | H | N-35 | H | H | H | H | H | H | H | H | H | H | H |
| 1963 | 1(11) | Ph | Ph | H | N-36 | H | H | H | H | H | H | H | H | H | H | H |
| 1964 | 1(11) | Ph | Ph | H | N-37 | H | H | H | H | H | H | H | H | H | H | H |
| 1965 | 1(11) | Ph | Ph | H | N-38 | H | H | H | H | H | H | H | H | H | H | H |
| 1966 | 1(11) | Ph | Ph | H | N-39 | H | H | H | H | H | H | H | H | H | H | H |
| 1967 | 1(11) | Ph | Ph | H | N-40 | H | H | H | H | H | H | H | H | H | H | H |
| 1968 | 1(11) | Ph | Ph | H | N-41 | H | H | H | H | H | H | H | H | H | H | H |
| 1969 | 1(11) | Ph | Ph | H | H | N-1 | H | H | H | H | H | H | H | H | H | H |
| 1970 | 1(11) | Ph | Ph | H | H | N-2 | H | H | H | H | H | H | H | H | H | H |
| 1971 | 1(11) | Ph | Ph | H | H | N-3 | H | H | H | H | H | H | H | H | H | H |
| 1972 | 1(11) | Ph | Ph | H | H | N-4 | H | H | H | H | H | H | H | H | H | H |
| 1973 | 1(11) | Ph | Ph | H | H | N-5 | H | H | H | H | H | H | H | H | H | H |
| 1974 | 1(11) | Ph | Ph | H | H | N-6 | H | H | H | H | H | H | H | H | H | H |
| 1975 | 1(11) | Ph | Ph | H | H | N-7 | H | H | H | H | H | H | H | H | H | H |
| 1976 | 1(11) | Ph | Ph | H | H | N-8 | H | H | H | H | H | H | H | H | H | H |
| 1977 | 1(11) | Ph | Ph | H | H | N-9 | H | H | H | H | H | H | H | H | H | H |
| 1978 | 1(11) | Ph | Ph | H | H | N-10 | H | H | H | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 1979 | 1(11) | Ph | Ph | H | H | N-11 | H | H | H | H | H | H | H | H | H | H |
| 1980 | 1(11) | Ph | Ph | H | H | N-12 | H | H | H | H | H | H | H | H | H | H |
| 1981 | 1(11) | Ph | Ph | H | H | N-13 | H | H | H | H | H | H | H | H | H | H |
| 1982 | 1(11) | Ph | Ph | H | H | N-14 | H | H | H | H | H | H | H | H | H | H |
| 1983 | 1(11) | Ph | Ph | H | H | N-15 | H | H | H | H | H | H | H | H | H | H |
| 1984 | 1(11) | Ph | Ph | H | H | N-16 | H | H | H | H | H | H | H | H | H | H |
| 1985 | 1(11) | Ph | Ph | H | H | N-17 | H | H | H | H | H | H | H | H | H | H |
| 1986 | 1(11) | Ph | Ph | H | H | N-18 | H | H | H | H | H | H | H | H | H | H |
| 1987 | 1(11) | Ph | Ph | H | H | N-19 | H | H | H | H | H | H | H | H | H | H |
| 1988 | 1(11) | Ph | Ph | H | H | N-20 | H | H | H | H | H | H | H | H | H | H |
| 1989 | 1(11) | Ph | Ph | H | H | N-21 | H | H | H | H | H | H | H | H | H | H |
| 1990 | 1(11) | Ph | Ph | H | H | N-22 | H | H | H | H | H | H | H | H | H | H |
| 1991 | 1(11) | Ph | Ph | H | H | N-23 | H | H | H | H | H | H | H | H | H | H |
| 1992 | 1(11) | Ph | Ph | H | H | N-24 | H | H | H | H | H | H | H | H | H | H |
| 1993 | 1(11) | Ph | Ph | H | H | N-25 | H | H | H | H | H | H | H | H | H | H |
| 1994 | 1(11) | Ph | Ph | H | H | N-26 | H | H | H | H | H | H | H | H | H | H |
| 1995 | 1(11) | Ph | Ph | H | H | N-27 | H | H | H | H | H | H | H | H | H | H |
| 1996 | 1(11) | Ph | Ph | H | H | N-28 | H | H | H | H | H | H | H | H | H | H |
| 1997 | 1(11) | Ph | Ph | H | H | N-29 | H | H | H | H | H | H | H | H | H | H |
| 1998 | 1(11) | Ph | Ph | H | H | N-30 | H | H | H | H | H | H | H | H | H | H |
| 1999 | 1(11) | Ph | Ph | H | H | N-31 | H | H | H | H | H | H | H | H | H | H |
| 2000 | 1(11) | Ph | Ph | H | H | N-32 | H | H | H | H | H | H | H | H | H | H |
| 2001 | 1(11) | Ph | Ph | H | H | N-33 | H | H | H | H | H | H | H | H | H | H |
| 2002 | 1(11) | Ph | Ph | H | H | N-34 | H | H | H | H | H | H | H | H | H | H |
| 2003 | 1(11) | Ph | Ph | H | H | N-35 | H | H | H | H | H | H | H | H | H | H |
| 2004 | 1(11) | Ph | Ph | H | H | N-36 | H | H | H | H | H | H | H | H | H | H |
| 2005 | 1(11) | Ph | Ph | H | H | N-37 | H | H | H | H | H | H | H | H | H | H |
| 2006 | 1(11) | Ph | Ph | H | H | N-38 | H | H | H | H | H | H | H | H | H | H |
| 2007 | 1(11) | Ph | Ph | H | H | N-39 | H | H | H | H | H | H | H | H | H | H |
| 2008 | 1(11) | Ph | Ph | H | H | N-40 | H | H | H | H | H | H | H | H | H | H |
| 2009 | 1(11) | Ph | Ph | H | H | N-41 | H | H | H | H | H | H | H | H | H | H |
| 2010 | 1(11) | Ph | Ph | H | H | H | H | H | N-1 | H | H | H | H | H | H | H |
| 2011 | 1(11) | Ph | Ph | H | H | H | H | H | N-2 | H | H | H | H | H | H | H |
| 2012 | 1(11) | Ph | Ph | H | H | H | H | H | N-3 | H | H | H | H | H | H | H |
| 2013 | 1(11) | Ph | Ph | H | H | H | H | H | N-4 | H | H | H | H | H | H | H |
| 2014 | 1(11) | Ph | Ph | H | H | H | H | H | N-5 | H | H | H | H | H | H | H |
| 2015 | 1(11) | Ph | Ph | H | H | H | H | H | N-6 | H | H | H | H | H | H | H |
| 2016 | 1(11) | Ph | Ph | H | H | H | H | H | N-7 | H | H | H | H | H | H | H |
| 2017 | 1(11) | Ph | Ph | H | H | H | H | H | N-8 | H | H | H | H | H | H | H |
| 2018 | 1(11) | Ph | Ph | H | H | H | H | H | N-9 | H | H | H | H | H | H | H |
| 2019 | 1(11) | Ph | Ph | H | H | H | H | H | N-10 | H | H | H | H | H | H | H |
| 2020 | 1(11) | Ph | Ph | H | H | H | H | H | N-11 | H | H | H | H | H | H | H |
| 2021 | 1(11) | Ph | Ph | H | H | H | H | H | N-12 | H | H | H | H | H | H | H |
| 2022 | 1(11) | Ph | Ph | H | H | H | H | H | N-13 | H | H | H | H | H | H | H |
| 2023 | 1(11) | Ph | Ph | H | H | H | H | H | N-14 | H | H | H | H | H | H | H |
| 2024 | 1(11) | Ph | Ph | H | H | H | H | H | N-15 | H | H | H | H | H | H | H |
| 2025 | 1(11) | Ph | Ph | H | H | H | H | H | N-16 | H | H | H | H | H | H | H |
| 2026 | 1(11) | Ph | Ph | H | H | H | H | H | N-17 | H | H | H | H | H | H | H |
| 2027 | 1(11) | Ph | Ph | H | H | H | H | H | N-18 | H | H | H | H | H | H | H |
| 2028 | 1(11) | Ph | Ph | H | H | H | H | H | N-19 | H | H | H | H | H | H | H |
| 2029 | 1(11) | Ph | Ph | H | H | H | H | H | N-20 | H | H | H | H | H | H | H |
| 2030 | 1(11) | Ph | Ph | H | H | H | H | H | N-21 | H | H | H | H | H | H | H |
| 2031 | 1(11) | Ph | Ph | H | H | H | H | H | N-22 | H | H | H | H | H | H | H |
| 2032 | 1(11) | Ph | Ph | H | H | H | H | H | N-23 | H | H | H | H | H | H | H |
| 2033 | 1(11) | Ph | Ph | H | H | H | H | H | N-24 | H | H | H | H | H | H | H |
| 2034 | 1(11) | Ph | Ph | H | H | H | H | H | N-25 | H | H | H | H | H | H | H |
| 2035 | 1(11) | Ph | Ph | H | H | H | H | H | N-26 | H | H | H | H | H | H | H |
| 2036 | 1(11) | Ph | Ph | H | H | H | H | H | N-27 | H | H | H | H | H | H | H |
| 2037 | 1(11) | Ph | Ph | H | H | H | H | H | N-28 | H | H | H | H | H | H | H |
| 2038 | 1(11) | Ph | Ph | H | H | H | H | H | N-29 | H | H | H | H | H | H | H |
| 2039 | 1(11) | Ph | Ph | H | H | H | H | H | N-30 | H | H | H | H | H | H | H |
| 2040 | 1(11) | Ph | Ph | H | H | H | H | H | N-31 | H | H | H | H | H | H | H |
| 2041 | 1(11) | Ph | Ph | H | H | H | H | H | N-32 | H | H | H | H | H | H | H |
| 2042 | 1(11) | Ph | Ph | H | H | H | H | H | N-33 | H | H | H | H | H | H | H |
| 2043 | 1(11) | Ph | Ph | H | H | H | H | H | N-34 | H | H | H | H | H | H | H |
| 2044 | 1(11) | Ph | Ph | H | H | H | H | H | N-35 | H | H | H | H | H | H | H |
| 2045 | 1(11) | Ph | Ph | H | H | H | H | H | N-36 | H | H | H | H | H | H | H |
| 2046 | 1(11) | Ph | Ph | H | H | H | H | H | N-37 | H | H | H | H | H | H | H |
| 2047 | 1(11) | Ph | Ph | H | H | H | H | H | N-38 | H | H | H | H | H | H | H |
| 2048 | 1(11) | Ph | Ph | H | H | H | H | H | N-39 | H | H | H | H | H | H | H |
| 2049 | 1(11) | Ph | Ph | H | H | H | H | H | N-40 | H | H | H | H | H | H | H |
| 2050 | 1(11) | Ph | Ph | H | H | H | H | H | N-41 | H | H | H | H | H | H | H |
| 2051 | 1(11) | Ph | Ph | H | H | H | H | H | H | H | H | H | N-1 | H | H | H |
| 2052 | 1(11) | Ph | Ph | H | H | H | H | H | H | H | H | H | N-2 | H | H | H |
| 2053 | 1(11) | Ph | Ph | H | H | H | H | H | H | H | H | H | N-3 | H | H | H |
| 2054 | 1(11) | Ph | Ph | H | H | H | H | H | H | H | H | H | N-4 | H | H | H |
| 2055 | 1(11) | Ph | Ph | H | H | H | H | H | H | H | H | H | N-5 | H | H | H |
| 2056 | 1(11) | Ph | Ph | H | H | H | H | H | H | H | H | H | N-6 | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2057 | 1(11) | Ph | Ph | H | H | H | H | H | H | H | H | H | N-7 | H | H | H |
| 2058 | 1(11) | Ph | Ph | H | H | H | H | H | H | H | H | H | N-8 | H | H | H |
| 2059 | 1(11) | Ph | Ph | H | H | H | H | H | H | H | H | H | N-9 | H | H | H |
| 2060 | 1(11) | Ph | Ph | H | H | H | H | H | H | H | H | H | N-10 | H | H | H |
| 2061 | 1(11) | Ph | Ph | H | H | H | H | H | H | H | H | H | N-11 | H | H | H |
| 2062 | 1(11) | Ph | Ph | H | H | H | H | H | H | H | H | H | N-12 | H | H | H |
| 2063 | 1(11) | Ph | Ph | H | H | H | H | H | H | H | H | H | N-13 | H | H | H |
| 2064 | 1(11) | Ph | Ph | H | H | H | H | H | H | H | H | H | N-14 | H | H | H |
| 2065 | 1(11) | Ph | Ph | H | H | H | H | H | H | H | H | H | N-15 | H | H | H |
| 2066 | 1(11) | Ph | Ph | H | H | H | H | H | H | H | H | H | N-16 | H | H | H |
| 2067 | 1(11) | Ph | Ph | H | H | H | H | H | H | H | H | H | N-17 | H | H | H |
| 2068 | 1(11) | Ph | Ph | H | H | H | H | H | H | H | H | H | N-18 | H | H | H |
| 2069 | 1(11) | Ph | Ph | H | H | H | H | H | H | H | H | H | N-19 | H | H | H |
| 2070 | 1(11) | Ph | Ph | H | H | H | H | H | H | H | H | H | N-20 | H | H | H |
| 2071 | 1(11) | Ph | Ph | H | H | H | H | H | H | H | H | H | N-21 | H | H | H |
| 2072 | 1(11) | Ph | Ph | H | H | H | H | H | H | H | H | H | N-22 | H | H | H |
| 2073 | 1(11) | Ph | Ph | H | H | H | H | H | H | H | H | H | N-23 | H | H | H |
| 2074 | 1(11) | Ph | Ph | H | H | H | H | H | H | H | H | H | N-24 | H | H | H |
| 2075 | 1(11) | Ph | Ph | H | H | H | H | H | H | H | H | H | N-25 | H | H | H |
| 2076 | 1(11) | Ph | Ph | H | H | H | H | H | H | H | H | H | N-26 | H | H | H |
| 2077 | 1(11) | Ph | Ph | H | H | H | H | H | H | H | H | H | N-27 | H | H | H |
| 2078 | 1(11) | Ph | Ph | H | H | H | H | H | H | H | H | H | N-28 | H | H | H |
| 2079 | 1(11) | Ph | Ph | H | H | H | H | H | H | H | H | H | N-29 | H | H | H |
| 2080 | 1(11) | Ph | Ph | H | H | H | H | H | H | H | H | H | N-30 | H | H | H |
| 2081 | 1(11) | Ph | Ph | H | H | H | H | H | H | H | H | H | N-31 | H | H | H |
| 2082 | 1(11) | Ph | Ph | H | H | H | H | H | H | H | H | H | N-32 | H | H | H |
| 2083 | 1(11) | Ph | Ph | H | H | H | H | H | H | H | H | H | N-33 | H | H | H |
| 2084 | 1(11) | Ph | Ph | H | H | H | H | H | H | H | H | H | N-34 | H | H | H |
| 2085 | 1(11) | Ph | Ph | H | H | H | H | H | H | H | H | H | N-35 | H | H | H |
| 2086 | 1(11) | Ph | Ph | H | H | H | H | H | H | H | H | H | N-36 | H | H | H |
| 2087 | 1(11) | Ph | Ph | H | H | H | H | H | H | H | H | H | N-37 | H | H | H |
| 2088 | 1(11) | Ph | Ph | H | H | H | H | H | H | H | H | H | N-38 | H | H | H |
| 2089 | 1(11) | Ph | Ph | H | H | H | H | H | H | H | H | H | N-39 | H | H | H |
| 2090 | 1(11) | Ph | Ph | H | H | H | H | H | H | H | H | H | N-40 | H | H | H |
| 2091 | 1(11) | Ph | Ph | H | H | H | H | H | H | H | H | H | N-41 | H | H | H |
| 2092 | 1(11) | Ph | Ph | H | H | H | H | H | H | H | H | H | H | N-1 | H | H |
| 2093 | 1(11) | Ph | Ph | H | H | H | H | H | H | H | H | H | H | N-2 | H | H |
| 2094 | 1(11) | Ph | Ph | H | H | H | H | H | H | H | H | H | H | N-3 | H | H |
| 2095 | 1(11) | Ph | Ph | H | H | H | H | H | H | H | H | H | H | N-4 | H | H |
| 2096 | 1(11) | Ph | Ph | H | H | H | H | H | H | H | H | H | H | N-5 | H | H |
| 2097 | 1(11) | Ph | Ph | H | H | H | H | H | H | H | H | H | H | N-6 | H | H |
| 2098 | 1(11) | Ph | Ph | H | H | H | H | H | H | H | H | H | H | N-7 | H | H |
| 2099 | 1(11) | Ph | Ph | H | H | H | H | H | H | H | H | H | H | N-8 | H | H |
| 2100 | 1(11) | Ph | Ph | H | H | H | H | H | H | H | H | H | H | N-9 | H | H |
| 2101 | 1(11) | Ph | Ph | H | H | H | H | H | H | H | H | H | H | N-10 | H | H |
| 2102 | 1(11) | Ph | Ph | H | H | H | H | H | H | H | H | H | H | N-11 | H | H |
| 2103 | 1(11) | Ph | Ph | H | H | H | H | H | H | H | H | H | H | N-12 | H | H |
| 2104 | 1(11) | Ph | Ph | H | H | H | H | H | H | H | H | H | H | N-13 | H | H |
| 2105 | 1(11) | Ph | Ph | H | H | H | H | H | H | H | H | H | H | N-14 | H | H |
| 2106 | 1(11) | Ph | Ph | H | H | H | H | H | H | H | H | H | H | N-15 | H | H |
| 2107 | 1(11) | Ph | Ph | H | H | H | H | H | H | H | H | H | H | N-16 | H | H |
| 2108 | 1(11) | Ph | Ph | H | H | H | H | H | H | H | H | H | H | N-17 | H | H |
| 2109 | 1(11) | Ph | Ph | H | H | H | H | H | H | H | H | H | H | N-18 | H | H |
| 2110 | 1(11) | Ph | Ph | H | H | H | H | H | H | H | H | H | H | N-19 | H | H |
| 2111 | 1(11) | Ph | Ph | H | H | H | H | H | H | H | H | H | H | N-20 | H | H |
| 2112 | 1(11) | Ph | Ph | H | H | H | H | H | H | H | H | H | H | N-21 | H | H |
| 2113 | 1(11) | Ph | Ph | H | H | H | H | H | H | H | H | H | H | N-22 | H | H |
| 2114 | 1(11) | Ph | Ph | H | H | H | H | H | H | H | H | H | H | N-23 | H | H |
| 2115 | 1(11) | Ph | Ph | H | H | H | H | H | H | H | H | H | H | N-24 | H | H |
| 2116 | 1(11) | Ph | Ph | H | H | H | H | H | H | H | H | H | H | N-25 | H | H |
| 2117 | 1(11) | Ph | Ph | H | H | H | H | H | H | H | H | H | H | N-26 | H | H |
| 2118 | 1(11) | Ph | Ph | H | H | H | H | H | H | H | H | H | H | N-27 | H | H |
| 2119 | 1(11) | Ph | Ph | H | H | H | H | H | H | H | H | H | H | N-28 | H | H |
| 2120 | 1(11) | Ph | Ph | H | H | H | H | H | H | H | H | H | H | N-29 | H | H |
| 2121 | 1(11) | Ph | Ph | H | H | H | H | H | H | H | H | H | H | N-30 | H | H |
| 2122 | 1(11) | Ph | Ph | H | H | H | H | H | H | H | H | H | H | N-31 | H | H |
| 2123 | 1(11) | Ph | Ph | H | H | H | H | H | H | H | H | H | H | N-32 | H | H |
| 2124 | 1(11) | Ph | Ph | H | H | H | H | H | H | H | H | H | H | N-33 | H | H |
| 2125 | 1(11) | Ph | Ph | H | H | H | H | H | H | H | H | H | H | N-34 | H | H |
| 2126 | 1(11) | Ph | Ph | H | H | H | H | H | H | H | H | H | H | N-35 | H | H |
| 2127 | 1(11) | Ph | Ph | H | H | H | H | H | H | H | H | H | H | N-36 | H | H |
| 2128 | 1(11) | Ph | Ph | H | H | H | H | H | H | H | H | H | H | N-37 | H | H |
| 2129 | 1(11) | Ph | Ph | H | H | H | H | H | H | H | H | H | H | N-38 | H | H |
| 2130 | 1(11) | Ph | Ph | H | H | H | H | H | H | H | H | H | H | N-39 | H | H |
| 2131 | 1(11) | Ph | Ph | H | H | H | H | H | H | H | H | H | H | N-40 | H | H |
| 2132 | 1(11) | Ph | Ph | H | H | H | H | H | H | H | H | H | H | N-41 | H | H |
| 2133 | 1(12) | Ph | Ph | H | N-1 | H | H | H | H | H | — | — | — | — | — | — |
| 2134 | 1(12) | Ph | Ph | H | N-2 | H | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2135 | 1(12) | Ph | Ph | H | N-3 | H | H | H | H | H | — | — | — | — | — | — |
| 2136 | 1(12) | Ph | Ph | H | N-4 | H | H | H | H | H | — | — | — | — | — | — |
| 2137 | 1(12) | Ph | Ph | H | N-5 | H | H | H | H | H | — | — | — | — | — | — |
| 2138 | 1(12) | Ph | Ph | H | N-6 | H | H | H | H | H | — | — | — | — | — | — |
| 2139 | 1(12) | Ph | Ph | H | N-7 | H | H | H | H | H | — | — | — | — | — | — |
| 2140 | 1(12) | Ph | Ph | H | N-8 | H | H | H | H | H | — | — | — | — | — | — |
| 2141 | 1(12) | Ph | Ph | H | N-9 | H | H | H | H | H | — | — | — | — | — | — |
| 2142 | 1(12) | Ph | Ph | H | N-10 | H | H | H | H | H | — | — | — | — | — | — |
| 2143 | 1(12) | Ph | Ph | H | N-11 | H | H | H | H | H | — | — | — | — | — | — |
| 2144 | 1(12) | Ph | Ph | H | N-12 | H | H | H | H | H | — | — | — | — | — | — |
| 2145 | 1(12) | Ph | Ph | H | N-13 | H | H | H | H | H | — | — | — | — | — | — |
| 2146 | 1(12) | Ph | Ph | H | N-14 | H | H | H | H | H | — | — | — | — | — | — |
| 2147 | 1(12) | Ph | Ph | H | N-15 | H | H | H | H | H | — | — | — | — | — | — |
| 2148 | 1(12) | Ph | Ph | H | N-16 | H | H | H | H | H | — | — | — | — | — | — |
| 2149 | 1(12) | Ph | Ph | H | N-17 | H | H | H | H | H | — | — | — | — | — | — |
| 2150 | 1(12) | Ph | Ph | H | N-18 | H | H | H | H | H | — | — | — | — | — | — |
| 2151 | 1(12) | Ph | Ph | H | N-19 | H | H | H | H | H | — | — | — | — | — | — |
| 2152 | 1(12) | Ph | Ph | H | N-20 | H | H | H | H | H | — | — | — | — | — | — |
| 2153 | 1(12) | Ph | Ph | H | N-21 | H | H | H | H | H | — | — | — | — | — | — |
| 2154 | 1(12) | Ph | Ph | H | N-22 | H | H | H | H | H | — | — | — | — | — | — |
| 2155 | 1(12) | Ph | Ph | H | N-23 | H | H | H | H | H | — | — | — | — | — | — |
| 2156 | 1(12) | Ph | Ph | H | N-24 | H | H | H | H | H | — | — | — | — | — | — |
| 2157 | 1(12) | Ph | Ph | H | N-25 | H | H | H | H | H | — | — | — | — | — | — |
| 2158 | 1(12) | Ph | Ph | H | N-26 | H | H | H | H | H | — | — | — | — | — | — |
| 2159 | 1(12) | Ph | Ph | H | N-27 | H | H | H | H | H | — | — | — | — | — | — |
| 2160 | 1(12) | Ph | Ph | H | N-28 | H | H | H | H | H | — | — | — | — | — | — |
| 2161 | 1(12) | Ph | Ph | H | N-29 | H | H | H | H | H | — | — | — | — | — | — |
| 2162 | 1(12) | Ph | Ph | H | N-30 | H | H | H | H | H | — | — | — | — | — | — |
| 2163 | 1(12) | Ph | Ph | H | N-31 | H | H | H | H | H | — | — | — | — | — | — |
| 2164 | 1(12) | Ph | Ph | H | N-32 | H | H | H | H | H | — | — | — | — | — | — |
| 2165 | 1(12) | Ph | Ph | H | N-33 | H | H | H | H | H | — | — | — | — | — | — |
| 2166 | 1(12) | Ph | Ph | H | N-34 | H | H | H | H | H | — | — | — | — | — | — |
| 2167 | 1(12) | Ph | Ph | H | N-35 | H | H | H | H | H | — | — | — | — | — | — |
| 2168 | 1(12) | Ph | Ph | H | N-36 | H | H | H | H | H | — | — | — | — | — | — |
| 2169 | 1(12) | Ph | Ph | H | N-37 | H | H | H | H | H | — | — | — | — | — | — |
| 2170 | 1(12) | Ph | Ph | H | N-38 | H | H | H | H | H | — | — | — | — | — | — |
| 2171 | 1(12) | Ph | Ph | H | N-39 | H | H | H | H | H | — | — | — | — | — | — |
| 2172 | 1(12) | Ph | Ph | H | N-40 | H | H | H | H | H | — | — | — | — | — | — |
| 2173 | 1(12) | Ph | Ph | H | N-41 | H | H | H | H | H | — | — | — | — | — | — |
| 2174 | 1(12) | Ph | Ph | H | H | N-1 | H | H | H | H | — | — | — | — | — | — |
| 2175 | 1(12) | Ph | Ph | H | H | N-2 | H | H | H | H | — | — | — | — | — | — |
| 2176 | 1(12) | Ph | Ph | H | H | N-3 | H | H | H | H | — | — | — | — | — | — |
| 2177 | 1(12) | Ph | Ph | H | H | N-4 | H | H | H | H | — | — | — | — | — | — |
| 2178 | 1(12) | Ph | Ph | H | H | N-5 | H | H | H | H | — | — | — | — | — | — |
| 2179 | 1(12) | Ph | Ph | H | H | N-6 | H | H | H | H | — | — | — | — | — | — |
| 2180 | 1(12) | Ph | Ph | H | H | N-7 | H | H | H | H | — | — | — | — | — | — |
| 2181 | 1(12) | Ph | Ph | H | H | N-8 | H | H | H | H | — | — | — | — | — | — |
| 2182 | 1(12) | Ph | Ph | H | H | N-9 | H | H | H | H | — | — | — | — | — | — |
| 2183 | 1(12) | Ph | Ph | H | H | N-10 | H | H | H | H | — | — | — | — | — | — |
| 2184 | 1(12) | Ph | Ph | H | H | N-11 | H | H | H | H | — | — | — | — | — | — |
| 2185 | 1(12) | Ph | Ph | H | H | N-12 | H | H | H | H | — | — | — | — | — | — |
| 2186 | 1(12) | Ph | Ph | H | H | N-13 | H | H | H | H | — | — | — | — | — | — |
| 2187 | 1(12) | Ph | Ph | H | H | N-14 | H | H | H | H | — | — | — | — | — | — |
| 2188 | 1(12) | Ph | Ph | H | H | N-15 | H | H | H | H | — | — | — | — | — | — |
| 2189 | 1(12) | Ph | Ph | H | H | N-16 | H | H | H | H | — | — | — | — | — | — |
| 2190 | 1(12) | Ph | Ph | H | H | N-17 | H | H | H | H | — | — | — | — | — | — |
| 2191 | 1(12) | Ph | Ph | H | H | N-18 | H | H | H | H | — | — | — | — | — | — |
| 2192 | 1(12) | Ph | Ph | H | H | N-19 | H | H | H | H | — | — | — | — | — | — |
| 2193 | 1(12) | Ph | Ph | H | H | N-20 | H | H | H | H | — | — | — | — | — | — |
| 2194 | 1(12) | Ph | Ph | H | H | N-21 | H | H | H | H | — | — | — | — | — | — |
| 2195 | 1(12) | Ph | Ph | H | H | N-22 | H | H | H | H | — | — | — | — | — | — |
| 2196 | 1(12) | Ph | Ph | H | H | N-23 | H | H | H | H | — | — | — | — | — | — |
| 2197 | 1(12) | Ph | Ph | H | H | N-24 | H | H | H | H | — | — | — | — | — | — |
| 2198 | 1(12) | Ph | Ph | H | H | N-25 | H | H | H | H | — | — | — | — | — | — |
| 2199 | 1(12) | Ph | Ph | H | H | N-26 | H | H | H | H | — | — | — | — | — | — |
| 2200 | 1(12) | Ph | Ph | H | H | N-27 | H | H | H | H | — | — | — | — | — | — |
| 2201 | 1(12) | Ph | Ph | H | H | N-28 | H | H | H | H | — | — | — | — | — | — |
| 2202 | 1(12) | Ph | Ph | H | H | N-29 | H | H | H | H | — | — | — | — | — | — |
| 2203 | 1(12) | Ph | Ph | H | H | N-30 | H | H | H | H | — | — | — | — | — | — |
| 2204 | 1(12) | Ph | Ph | H | H | N-31 | H | H | H | H | — | — | — | — | — | — |
| 2205 | 1(12) | Ph | Ph | H | H | N-32 | H | H | H | H | — | — | — | — | — | — |
| 2206 | 1(12) | Ph | Ph | H | H | N-33 | H | H | H | H | — | — | — | — | — | — |
| 2207 | 1(12) | Ph | Ph | H | H | N-34 | H | H | H | H | — | — | — | — | — | — |
| 2208 | 1(12) | Ph | Ph | H | H | N-35 | H | H | H | H | — | — | — | — | — | — |
| 2209 | 1(12) | Ph | Ph | H | H | N-36 | H | H | H | H | — | — | — | — | — | — |
| 2210 | 1(12) | Ph | Ph | H | H | N-37 | H | H | H | H | — | — | — | — | — | — |
| 2211 | 1(12) | Ph | Ph | H | H | N-38 | H | H | H | H | — | — | — | — | — | — |
| 2212 | 1(12) | Ph | Ph | H | H | N-39 | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2213 | 1(12) | Ph | Ph | H | H | N-40 | H | H | H | H | — | — | — | — | — | — |
| 2214 | 1(12) | Ph | Ph | H | H | N-41 | H | H | H | H | — | — | — | — | — | — |
| 2215 | 1(12) | Ph | Ph | H | H | H | H | H | H | N-1 | — | — | — | — | — | — |
| 2216 | 1(12) | Ph | Ph | H | H | H | H | H | H | N-2 | — | — | — | — | — | — |
| 2217 | 1(12) | Ph | Ph | H | H | H | H | H | H | N-3 | — | — | — | — | — | — |
| 2218 | 1(12) | Ph | Ph | H | H | H | H | H | H | N-4 | — | — | — | — | — | — |
| 2219 | 1(12) | Ph | Ph | H | H | H | H | H | H | N-5 | — | — | — | — | — | — |
| 2220 | 1(12) | Ph | Ph | H | H | H | H | H | H | N-6 | — | — | — | — | — | — |
| 2221 | 1(12) | Ph | Ph | H | H | H | H | H | H | N-7 | — | — | — | — | — | — |
| 2222 | 1(12) | Ph | Ph | H | H | H | H | H | H | N-8 | — | — | — | — | — | — |
| 2223 | 1(12) | Ph | Ph | H | H | H | H | H | H | N-9 | — | — | — | — | — | — |
| 2224 | 1(12) | Ph | Ph | H | H | H | H | H | H | N-10 | — | — | — | — | — | — |
| 2225 | 1(12) | Ph | Ph | H | H | H | H | H | H | N-11 | — | — | — | — | — | — |
| 2226 | 1(12) | Ph | Ph | H | H | H | H | H | H | N-12 | — | — | — | — | — | — |
| 2227 | 1(12) | Ph | Ph | H | H | H | H | H | H | N-13 | — | — | — | — | — | — |
| 2228 | 1(12) | Ph | Ph | H | H | H | H | H | H | N-14 | — | — | — | — | — | — |
| 2229 | 1(12) | Ph | Ph | H | H | H | H | H | H | N-15 | — | — | — | — | — | — |
| 2230 | 1(12) | Ph | Ph | H | H | H | H | H | H | N-16 | — | — | — | — | — | — |
| 2231 | 1(12) | Ph | Ph | H | H | H | H | H | H | N-17 | — | — | — | — | — | — |
| 2232 | 1(12) | Ph | Ph | H | H | H | H | H | H | N-18 | — | — | — | — | — | — |
| 2233 | 1(12) | Ph | Ph | H | H | H | H | H | H | N-19 | — | — | — | — | — | — |
| 2234 | 1(12) | Ph | Ph | H | H | H | H | H | H | N-20 | — | — | — | — | — | — |
| 2235 | 1(12) | Ph | Ph | H | H | H | H | H | H | N-21 | — | — | — | — | — | — |
| 2236 | 1(12) | Ph | Ph | H | H | H | H | H | H | N-22 | — | — | — | — | — | — |
| 2237 | 1(12) | Ph | Ph | H | H | H | H | H | H | N-23 | — | — | — | — | — | — |
| 2238 | 1(12) | Ph | Ph | H | H | H | H | H | H | N-24 | — | — | — | — | — | — |
| 2239 | 1(12) | Ph | Ph | H | H | H | H | H | H | N-25 | — | — | — | — | — | — |
| 2240 | 1(12) | Ph | Ph | H | H | H | H | H | H | N-26 | — | — | — | — | — | — |
| 2241 | 1(12) | Ph | Ph | H | H | H | H | H | H | N-27 | — | — | — | — | — | — |
| 2242 | 1(12) | Ph | Ph | H | H | H | H | H | H | N-28 | — | — | — | — | — | — |
| 2243 | 1(12) | Ph | Ph | H | H | H | H | H | H | N-29 | — | — | — | — | — | — |
| 2244 | 1(12) | Ph | Ph | H | H | H | H | H | H | N-30 | — | — | — | — | — | — |
| 2245 | 1(12) | Ph | Ph | H | H | H | H | H | H | N-31 | — | — | — | — | — | — |
| 2246 | 1(12) | Ph | Ph | H | H | H | H | H | H | N-32 | — | — | — | — | — | — |
| 2247 | 1(12) | Ph | Ph | H | H | H | H | H | H | N-33 | — | — | — | — | — | — |
| 2248 | 1(12) | Ph | Ph | H | H | H | H | H | H | N-34 | — | — | — | — | — | — |
| 2249 | 1(12) | Ph | Ph | H | H | H | H | H | H | N-35 | — | — | — | — | — | — |
| 2250 | 1(12) | Ph | Ph | H | H | H | H | H | H | N-36 | — | — | — | — | — | — |
| 2251 | 1(12) | Ph | Ph | H | H | H | H | H | H | N-37 | — | — | — | — | — | — |
| 2252 | 1(12) | Ph | Ph | H | H | H | H | H | H | N-38 | — | — | — | — | — | — |
| 2253 | 1(12) | Ph | Ph | H | H | H | H | H | H | N-39 | — | — | — | — | — | — |
| 2254 | 1(12) | Ph | Ph | H | H | H | H | H | H | N-40 | — | — | — | — | — | — |
| 2255 | 1(12) | Ph | Ph | H | H | H | H | H | H | N-41 | — | — | — | — | — | — |
| 2256 | 1(13) | Me | Me | H | N-1 | H | H | H | H | H | — | — | — | — | — | — |
| 2257 | 1(13) | Me | Me | H | N-2 | H | H | H | H | H | — | — | — | — | — | — |
| 2258 | 1(13) | Me | Me | H | N-3 | H | H | H | H | H | — | — | — | — | — | — |
| 2259 | 1(13) | Me | Me | H | N-4 | H | H | H | H | H | — | — | — | — | — | — |
| 2260 | 1(13) | Me | Me | H | N-5 | H | H | H | H | H | — | — | — | — | — | — |
| 2261 | 1(13) | Me | Me | H | N-6 | H | H | H | H | H | — | — | — | — | — | — |
| 2262 | 1(13) | Me | Me | H | N-7 | H | H | H | H | H | — | — | — | — | — | — |
| 2263 | 1(13) | Me | Me | H | N-8 | H | H | H | H | H | — | — | — | — | — | — |
| 2264 | 1(13) | Me | Me | H | N-9 | H | H | H | H | H | — | — | — | — | — | — |
| 2265 | 1(13) | Me | Me | H | N-10 | H | H | H | H | H | — | — | — | — | — | — |
| 2266 | 1(13) | Me | Me | H | N-11 | H | H | H | H | H | — | — | — | — | — | — |
| 2267 | 1(13) | Me | Me | H | N-12 | H | H | H | H | H | — | — | — | — | — | — |
| 2268 | 1(13) | Me | Me | H | N-13 | H | H | H | H | H | — | — | — | — | — | — |
| 2269 | 1(13) | Me | Me | H | N-14 | H | H | H | H | H | — | — | — | — | — | — |
| 2270 | 1(13) | Me | Me | H | N-15 | H | H | H | H | H | — | — | — | — | — | — |
| 2271 | 1(13) | Me | Me | H | N-16 | H | H | H | H | H | — | — | — | — | — | — |
| 2272 | 1(13) | Me | Me | H | N-17 | H | H | H | H | H | — | — | — | — | — | — |
| 2273 | 1(13) | Me | Me | H | N-18 | H | H | H | H | H | — | — | — | — | — | — |
| 2274 | 1(13) | Me | Me | H | N-19 | H | H | H | H | H | — | — | — | — | — | — |
| 2275 | 1(13) | Me | Me | H | N-20 | H | H | H | H | H | — | — | — | — | — | — |
| 2276 | 1(13) | Me | Me | H | N-21 | H | H | H | H | H | — | — | — | — | — | — |
| 2277 | 1(13) | Me | Me | H | N-22 | H | H | H | H | H | — | — | — | — | — | — |
| 2278 | 1(13) | Me | Me | H | N-23 | H | H | H | H | H | — | — | — | — | — | — |
| 2279 | 1(13) | Me | Me | H | N-24 | H | H | H | H | H | — | — | — | — | — | — |
| 2280 | 1(13) | Me | Me | H | N-25 | H | H | H | H | H | — | — | — | — | — | — |
| 2281 | 1(13) | Me | Me | H | N-26 | H | H | H | H | H | — | — | — | — | — | — |
| 2282 | 1(13) | Me | Me | H | N-27 | H | H | H | H | H | — | — | — | — | — | — |
| 2283 | 1(13) | Me | Me | H | N-28 | H | H | H | H | H | — | — | — | — | — | — |
| 2284 | 1(13) | Me | Me | H | N-29 | H | H | H | H | H | — | — | — | — | — | — |
| 2285 | 1(13) | Me | Me | H | N-30 | H | H | H | H | H | — | — | — | — | — | — |
| 2286 | 1(13) | Me | Me | H | N-31 | H | H | H | H | H | — | — | — | — | — | — |
| 2287 | 1(13) | Me | Me | H | N-32 | H | H | H | H | H | — | — | — | — | — | — |
| 2288 | 1(13) | Me | Me | H | N-33 | H | H | H | H | H | — | — | — | — | — | — |
| 2289 | 1(13) | Me | Me | H | N-34 | H | H | H | H | H | — | — | — | — | — | — |
| 2290 | 1(13) | Me | Me | H | N-35 | H | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2291 | 1(13) | Me | Me | H | N-36 | H | H | H | H | H | — | — | — | — | — | — |
| 2292 | 1(13) | Me | Me | H | N-37 | H | H | H | H | H | — | — | — | — | — | — |
| 2293 | 1(13) | Me | Me | H | N-38 | H | H | H | H | H | — | — | — | — | — | — |
| 2294 | 1(13) | Me | Me | H | N-39 | H | H | H | H | H | — | — | — | — | — | — |
| 2295 | 1(13) | Me | Me | H | N-40 | H | H | H | H | H | — | — | — | — | — | — |
| 2296 | 1(13) | Me | Me | H | N-41 | H | H | H | H | H | — | — | — | — | — | — |
| 2297 | 1(13) | Me | Me | H | H | N-1 | H | H | H | H | — | — | — | — | — | — |
| 2298 | 1(13) | Me | Me | H | H | N-2 | H | H | H | H | — | — | — | — | — | — |
| 2299 | 1(13) | Me | Me | H | H | N-3 | H | H | H | H | — | — | — | — | — | — |
| 2300 | 1(13) | Me | Me | H | H | N-4 | H | H | H | H | — | — | — | — | — | — |
| 2301 | 1(13) | Me | Me | H | H | N-5 | H | H | H | H | — | — | — | — | — | — |
| 2302 | 1(13) | Me | Me | H | H | N-6 | H | H | H | H | — | — | — | — | — | — |
| 2303 | 1(13) | Me | Me | H | H | N-7 | H | H | H | H | — | — | — | — | — | — |
| 2304 | 1(13) | Me | Me | H | H | N-8 | H | H | H | H | — | — | — | — | — | — |
| 2305 | 1(13) | Me | Me | H | H | N-9 | H | H | H | H | — | — | — | — | — | — |
| 2306 | 1(13) | Me | Me | H | H | N-10 | H | H | H | H | — | — | — | — | — | — |
| 2307 | 1(13) | Me | Me | H | H | N-11 | H | H | H | H | — | — | — | — | — | — |
| 2308 | 1(13) | Me | Me | H | H | N-12 | H | H | H | H | — | — | — | — | — | — |
| 2309 | 1(13) | Me | Me | H | H | N-13 | H | H | H | H | — | — | — | — | — | — |
| 2310 | 1(13) | Me | Me | H | H | N-14 | H | H | H | H | — | — | — | — | — | — |
| 2311 | 1(13) | Me | Me | H | H | N-15 | H | H | H | H | — | — | — | — | — | — |
| 2312 | 1(13) | Me | Me | H | H | N-16 | H | H | H | H | — | — | — | — | — | — |
| 2313 | 1(13) | Me | Me | H | H | N-17 | H | H | H | H | — | — | — | — | — | — |
| 2314 | 1(13) | Me | Me | H | H | N-18 | H | H | H | H | — | — | — | — | — | — |
| 2315 | 1(13) | Me | Me | H | H | N-19 | H | H | H | H | — | — | — | — | — | — |
| 2316 | 1(13) | Me | Me | H | H | N-20 | H | H | H | H | — | — | — | — | — | — |
| 2317 | 1(13) | Me | Me | H | H | N-21 | H | H | H | H | — | — | — | — | — | — |
| 2318 | 1(13) | Me | Me | H | H | N-22 | H | H | H | H | — | — | — | — | — | — |
| 2319 | 1(13) | Me | Me | H | H | N-23 | H | H | H | H | — | — | — | — | — | — |
| 2320 | 1(13) | Me | Me | H | H | N-24 | H | H | H | H | — | — | — | — | — | — |
| 2321 | 1(13) | Me | Me | H | H | N-25 | H | H | H | H | — | — | — | — | — | — |
| 2322 | 1(13) | Me | Me | H | H | N-26 | H | H | H | H | — | — | — | — | — | — |
| 2323 | 1(13) | Me | Me | H | H | N-27 | H | H | H | H | — | — | — | — | — | — |
| 2324 | 1(13) | Me | Me | H | H | N-28 | H | H | H | H | — | — | — | — | — | — |
| 2325 | 1(13) | Me | Me | H | H | N-29 | H | H | H | H | — | — | — | — | — | — |
| 2326 | 1(13) | Me | Me | H | H | N-30 | H | H | H | H | — | — | — | — | — | — |
| 2327 | 1(13) | Me | Me | H | H | N-31 | H | H | H | H | — | — | — | — | — | — |
| 2328 | 1(13) | Me | Me | H | H | N-32 | H | H | H | H | — | — | — | — | — | — |
| 2329 | 1(13) | Me | Me | H | H | N-33 | H | H | H | H | — | — | — | — | — | — |
| 2330 | 1(13) | Me | Me | H | H | N-34 | H | H | H | H | — | — | — | — | — | — |
| 2331 | 1(13) | Me | Me | H | H | N-35 | H | H | H | H | — | — | — | — | — | — |
| 2332 | 1(13) | Me | Me | H | H | N-36 | H | H | H | H | — | — | — | — | — | — |
| 2333 | 1(13) | Me | Me | H | H | N-37 | H | H | H | H | — | — | — | — | — | — |
| 2334 | 1(13) | Me | Me | H | H | N-38 | H | H | H | H | — | — | — | — | — | — |
| 2335 | 1(13) | Me | Me | H | H | N-39 | H | H | H | H | — | — | — | — | — | — |
| 2336 | 1(13) | Me | Me | H | H | N-40 | H | H | H | H | — | — | — | — | — | — |
| 2337 | 1(13) | Me | Me | H | H | N-41 | H | H | H | H | — | — | — | — | — | — |
| 2338 | 1(13) | Me | Me | H | H | H | H | H | N-1 | H | — | — | — | — | — | — |
| 2339 | 1(13) | Me | Me | H | H | H | H | H | N-2 | H | — | — | — | — | — | — |
| 2340 | 1(13) | Me | Me | H | H | H | H | H | N-3 | H | — | — | — | — | — | — |
| 2341 | 1(13) | Me | Me | H | H | H | H | H | N-4 | H | — | — | — | — | — | — |
| 2342 | 1(13) | Me | Me | H | H | H | H | H | N-5 | H | — | — | — | — | — | — |
| 2343 | 1(13) | Me | Me | H | H | H | H | H | N-6 | H | — | — | — | — | — | — |
| 2344 | 1(13) | Me | Me | H | H | H | H | H | N-7 | H | — | — | — | — | — | — |
| 2345 | 1(13) | Me | Me | H | H | H | H | H | N-8 | H | — | — | — | — | — | — |
| 2346 | 1(13) | Me | Me | H | H | H | H | H | N-9 | H | — | — | — | — | — | — |
| 2347 | 1(13) | Me | Me | H | H | H | H | H | N-10 | H | — | — | — | — | — | — |
| 2348 | 1(13) | Me | Me | H | H | H | H | H | N-11 | H | — | — | — | — | — | — |
| 2349 | 1(13) | Me | Me | H | H | H | H | H | N-12 | H | — | — | — | — | — | — |
| 2350 | 1(13) | Me | Me | H | H | H | H | H | N-13 | H | — | — | — | — | — | — |
| 2351 | 1(13) | Me | Me | H | H | H | H | H | N-14 | H | — | — | — | — | — | — |
| 2352 | 1(13) | Me | Me | H | H | H | H | H | N-15 | H | — | — | — | — | — | — |
| 2353 | 1(13) | Me | Me | H | H | H | H | H | N-16 | H | — | — | — | — | — | — |
| 2354 | 1(13) | Me | Me | H | H | H | H | H | N-17 | H | — | — | — | — | — | — |
| 2355 | 1(13) | Me | Me | H | H | H | H | H | N-18 | H | — | — | — | — | — | — |
| 2356 | 1(13) | Me | Me | H | H | H | H | H | N-19 | H | — | — | — | — | — | — |
| 2357 | 1(13) | Me | Me | H | H | H | H | H | N-20 | H | — | — | — | — | — | — |
| 2358 | 1(13) | Me | Me | H | H | H | H | H | N-21 | H | — | — | — | — | — | — |
| 2359 | 1(13) | Me | Me | H | H | H | H | H | N-22 | H | — | — | — | — | — | — |
| 2360 | 1(13) | Me | Me | H | H | H | H | H | N-23 | H | — | — | — | — | — | — |
| 2361 | 1(13) | Me | Me | H | H | H | H | H | N-24 | H | — | — | — | — | — | — |
| 2362 | 1(13) | Me | Me | H | H | H | H | H | N-25 | H | — | — | — | — | — | — |
| 2363 | 1(13) | Me | Me | H | H | H | H | H | N-26 | H | — | — | — | — | — | — |
| 2364 | 1(13) | Me | Me | H | H | H | H | H | N-27 | H | — | — | — | — | — | — |
| 2365 | 1(13) | Me | Me | H | H | H | H | H | N-28 | H | — | — | — | — | — | — |
| 2366 | 1(13) | Me | Me | H | H | H | H | H | N-29 | H | — | — | — | — | — | — |
| 2367 | 1(13) | Me | Me | H | H | H | H | H | N-30 | H | — | — | — | — | — | — |
| 2368 | 1(13) | Me | Me | H | H | H | H | H | N-31 | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2369 | 1(13) | Me | Me | H | H | H | H | H | N-32 | H | — | — | — | — | — | — |
| 2370 | 1(13) | Me | Me | H | H | H | H | H | N-33 | H | — | — | — | — | — | — |
| 2371 | 1(13) | Me | Me | H | H | H | H | H | N-34 | H | — | — | — | — | — | — |
| 2372 | 1(13) | Me | Me | H | H | H | H | H | N-35 | H | — | — | — | — | — | — |
| 2373 | 1(13) | Me | Me | H | H | H | H | H | N-36 | H | — | — | — | — | — | — |
| 2374 | 1(13) | Me | Me | H | H | H | H | H | N-37 | H | — | — | — | — | — | — |
| 2375 | 1(13) | Me | Me | H | H | H | H | H | N-38 | H | — | — | — | — | — | — |
| 2376 | 1(13) | Me | Me | H | H | H | H | H | N-39 | H | — | — | — | — | — | — |
| 2377 | 1(13) | Me | Me | H | H | H | H | H | N-40 | H | — | — | — | — | — | — |
| 2378 | 1(13) | Me | Me | H | H | H | H | H | N-41 | H | — | — | — | — | — | — |
| 2379 | 1(14) | Me | Me | H | N-1 | H | H | H | H | H | H | H | H | H | H | H |
| 2380 | 1(14) | Me | Me | H | N-2 | H | H | H | H | H | H | H | H | H | H | H |
| 2381 | 1(14) | Me | Me | H | N-3 | H | H | H | H | H | H | H | H | H | H | H |
| 2382 | 1(14) | Me | Me | H | N-4 | H | H | H | H | H | H | H | H | H | H | H |
| 2383 | 1(14) | Me | Me | H | N-5 | H | H | H | H | H | H | H | H | H | H | H |
| 2384 | 1(14) | Me | Me | H | N-6 | H | H | H | H | H | H | H | H | H | H | H |
| 2385 | 1(14) | Me | Me | H | N-7 | H | H | H | H | H | H | H | H | H | H | H |
| 2386 | 1(14) | Me | Me | H | N-8 | H | H | H | H | H | H | H | H | H | H | H |
| 2387 | 1(14) | Me | Me | H | N-9 | H | H | H | H | H | H | H | H | H | H | H |
| 2388 | 1(14) | Me | Me | H | N-10 | H | H | H | H | H | H | H | H | H | H | H |
| 2389 | 1(14) | Me | Me | H | N-11 | H | H | H | H | H | H | H | H | H | H | H |
| 2390 | 1(14) | Me | Me | H | N-12 | H | H | H | H | H | H | H | H | H | H | H |
| 2391 | 1(14) | Me | Me | H | N-13 | H | H | H | H | H | H | H | H | H | H | H |
| 2392 | 1(14) | Me | Me | H | N-14 | H | H | H | H | H | H | H | H | H | H | H |
| 2393 | 1(14) | Me | Me | H | N-15 | H | H | H | H | H | H | H | H | H | H | H |
| 2394 | 1(14) | Me | Me | H | N-16 | H | H | H | H | H | H | H | H | H | H | H |
| 2395 | 1(14) | Me | Me | H | N-17 | H | H | H | H | H | H | H | H | H | H | H |
| 2396 | 1(14) | Me | Me | H | N-18 | H | H | H | H | H | H | H | H | H | H | H |
| 2397 | 1(14) | Me | Me | H | N-19 | H | H | H | H | H | H | H | H | H | H | H |
| 2398 | 1(14) | Me | Me | H | N-20 | H | H | H | H | H | H | H | H | H | H | H |
| 2399 | 1(14) | Me | Me | H | N-21 | H | H | H | H | H | H | H | H | H | H | H |
| 2400 | 1(14) | Me | Me | H | N-22 | H | H | H | H | H | H | H | H | H | H | H |
| 2401 | 1(14) | Me | Me | H | N-23 | H | H | H | H | H | H | H | H | H | H | H |
| 2402 | 1(14) | Me | Me | H | N-24 | H | H | H | H | H | H | H | H | H | H | H |
| 2403 | 1(14) | Me | Me | H | N-25 | H | H | H | H | H | H | H | H | H | H | H |
| 2404 | 1(14) | Me | Me | H | N-26 | H | H | H | H | H | H | H | H | H | H | H |
| 2405 | 1(14) | Me | Me | H | N-27 | H | H | H | H | H | H | H | H | H | H | H |
| 2406 | 1(14) | Me | Me | H | N-28 | H | H | H | H | H | H | H | H | H | H | H |
| 2407 | 1(14) | Me | Me | H | N-29 | H | H | H | H | H | H | H | H | H | H | H |
| 2408 | 1(14) | Me | Me | H | N-30 | H | H | H | H | H | H | H | H | H | H | H |
| 2409 | 1(14) | Me | Me | H | N-31 | H | H | H | H | H | H | H | H | H | H | H |
| 2410 | 1(14) | Me | Me | H | N-32 | H | H | H | H | H | H | H | H | H | H | H |
| 2411 | 1(14) | Me | Me | H | N-33 | H | H | H | H | H | H | H | H | H | H | H |
| 2412 | 1(14) | Me | Me | H | N-34 | H | H | H | H | H | H | H | H | H | H | H |
| 2413 | 1(14) | Me | Me | H | N-35 | H | H | H | H | H | H | H | H | H | H | H |
| 2414 | 1(14) | Me | Me | H | N-36 | H | H | H | H | H | H | H | H | H | H | H |
| 2415 | 1(14) | Me | Me | H | N-37 | H | H | H | H | H | H | H | H | H | H | H |
| 2416 | 1(14) | Me | Me | H | N-38 | H | H | H | H | H | H | H | H | H | H | H |
| 2417 | 1(14) | Me | Me | H | N-39 | H | H | H | H | H | H | H | H | H | H | H |
| 2418 | 1(14) | Me | Me | H | N-40 | H | H | H | H | H | H | H | H | H | H | H |
| 2419 | 1(14) | Me | Me | H | N-41 | H | H | H | H | H | H | H | H | H | H | H |
| 2420 | 1(14) | Me | Me | H | H | N-1 | H | H | H | H | H | H | H | H | H | H |
| 2421 | 1(14) | Me | Me | H | H | N-2 | H | H | H | H | H | H | H | H | H | H |
| 2422 | 1(14) | Me | Me | H | H | N-3 | H | H | H | H | H | H | H | H | H | H |
| 2423 | 1(14) | Me | Me | H | H | N-4 | H | H | H | H | H | H | H | H | H | H |
| 2424 | 1(14) | Me | Me | H | H | N-5 | H | H | H | H | H | H | H | H | H | H |
| 2425 | 1(14) | Me | Me | H | H | N-6 | H | H | H | H | H | H | H | H | H | H |
| 2426 | 1(14) | Me | Me | H | H | N-7 | H | H | H | H | H | H | H | H | H | H |
| 2427 | 1(14) | Me | Me | H | H | N-8 | H | H | H | H | H | H | H | H | H | H |
| 2428 | 1(14) | Me | Me | H | H | N-9 | H | H | H | H | H | H | H | H | H | H |
| 2429 | 1(14) | Me | Me | H | H | N-10 | H | H | H | H | H | H | H | H | H | H |
| 2430 | 1(14) | Me | Me | H | H | N-11 | H | H | H | H | H | H | H | H | H | H |
| 2431 | 1(14) | Me | Me | H | H | N-12 | H | H | H | H | H | H | H | H | H | H |
| 2432 | 1(14) | Me | Me | H | H | N-13 | H | H | H | H | H | H | H | H | H | H |
| 2433 | 1(14) | Me | Me | H | H | N-14 | H | H | H | H | H | H | H | H | H | H |
| 2434 | 1(14) | Me | Me | H | H | N-15 | H | H | H | H | H | H | H | H | H | H |
| 2435 | 1(14) | Me | Me | H | H | N-16 | H | H | H | H | H | H | H | H | H | H |
| 2436 | 1(14) | Me | Me | H | H | N-17 | H | H | H | H | H | H | H | H | H | H |
| 2437 | 1(14) | Me | Me | H | H | N-18 | H | H | H | H | H | H | H | H | H | H |
| 2438 | 1(14) | Me | Me | H | H | N-19 | H | H | H | H | H | H | H | H | H | H |
| 2439 | 1(14) | Me | Me | H | H | N-20 | H | H | H | H | H | H | H | H | H | H |
| 2440 | 1(14) | Me | Me | H | H | N-21 | H | H | H | H | H | H | H | H | H | H |
| 2441 | 1(14) | Me | Me | H | H | N-22 | H | H | H | H | H | H | H | H | H | H |
| 2442 | 1(14) | Me | Me | H | H | N-23 | H | H | H | H | H | H | H | H | H | H |
| 2443 | 1(14) | Me | Me | H | H | N-24 | H | H | H | H | H | H | H | H | H | H |
| 2444 | 1(14) | Me | Me | H | H | N-25 | H | H | H | H | H | H | H | H | H | H |
| 2445 | 1(14) | Me | Me | H | H | N-26 | H | H | H | H | H | H | H | H | H | H |
| 2446 | 1(14) | Me | Me | H | H | N-27 | H | H | H | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2447 | 1(14) | Me | Me | H | H | N-28 | H | H | H | H | H | H | H | H | H | H |
| 2448 | 1(14) | Me | Me | H | H | N-29 | H | H | H | H | H | H | H | H | H | H |
| 2449 | 1(14) | Me | Me | H | H | N-30 | H | H | H | H | H | H | H | H | H | H |
| 2450 | 1(14) | Me | Me | H | H | N-31 | H | H | H | H | H | H | H | H | H | H |
| 2451 | 1(14) | Me | Me | H | H | N-32 | H | H | H | H | H | H | H | H | H | H |
| 2452 | 1(14) | Me | Me | H | H | N-33 | H | H | H | H | H | H | H | H | H | H |
| 2453 | 1(14) | Me | Me | H | H | N-34 | H | H | H | H | H | H | H | H | H | H |
| 2454 | 1(14) | Me | Me | H | H | N-35 | H | H | H | H | H | H | H | H | H | H |
| 2455 | 1(14) | Me | Me | H | H | N-36 | H | H | H | H | H | H | H | H | H | H |
| 2456 | 1(14) | Me | Me | H | H | N-37 | H | H | H | H | H | H | H | H | H | H |
| 2457 | 1(14) | Me | Me | H | H | N-38 | H | H | H | H | H | H | H | H | H | H |
| 2458 | 1(14) | Me | Me | H | H | N-39 | H | H | H | H | H | H | H | H | H | H |
| 2459 | 1(14) | Me | Me | H | H | N-40 | H | H | H | H | H | H | H | H | H | H |
| 2460 | 1(14) | Me | Me | H | H | N-41 | H | H | H | H | H | H | H | H | H | H |
| 2461 | 1(14) | Me | Me | H | H | H | H | H | N-1 | H | H | H | H | H | H | H |
| 2462 | 1(14) | Me | Me | H | H | H | H | H | N-2 | H | H | H | H | H | H | H |
| 2463 | 1(14) | Me | Me | H | H | H | H | H | N-3 | H | H | H | H | H | H | H |
| 2464 | 1(14) | Me | Me | H | H | H | H | H | N-4 | H | H | H | H | H | H | H |
| 2465 | 1(14) | Me | Me | H | H | H | H | H | N-5 | H | H | H | H | H | H | H |
| 2466 | 1(14) | Me | Me | H | H | H | H | H | N-6 | H | H | H | H | H | H | H |
| 2467 | 1(14) | Me | Me | H | H | H | H | H | N-7 | H | H | H | H | H | H | H |
| 2468 | 1(14) | Me | Me | H | H | H | H | H | N-8 | H | H | H | H | H | H | H |
| 2469 | 1(14) | Me | Me | H | H | H | H | H | N-9 | H | H | H | H | H | H | H |
| 2470 | 1(14) | Me | Me | H | H | H | H | H | N-10 | H | H | H | H | H | H | H |
| 2471 | 1(14) | Me | Me | H | H | H | H | H | N-11 | H | H | H | H | H | H | H |
| 2472 | 1(14) | Me | Me | H | H | H | H | H | N-12 | H | H | H | H | H | H | H |
| 2473 | 1(14) | Me | Me | H | H | H | H | H | N-13 | H | H | H | H | H | H | H |
| 2474 | 1(14) | Me | Me | H | H | H | H | H | N-14 | H | H | H | H | H | H | H |
| 2475 | 1(14) | Me | Me | H | H | H | H | H | N-15 | H | H | H | H | H | H | H |
| 2476 | 1(14) | Me | Me | H | H | H | H | H | N-16 | H | H | H | H | H | H | H |
| 2477 | 1(14) | Me | Me | H | H | H | H | H | N-17 | H | H | H | H | H | H | H |
| 2478 | 1(14) | Me | Me | H | H | H | H | H | N-18 | H | H | H | H | H | H | H |
| 2479 | 1(14) | Me | Me | H | H | H | H | H | N-19 | H | H | H | H | H | H | H |
| 2480 | 1(14) | Me | Me | H | H | H | H | H | N-20 | H | H | H | H | H | H | H |
| 2481 | 1(14) | Me | Me | H | H | H | H | H | N-21 | H | H | H | H | H | H | H |
| 2482 | 1(14) | Me | Me | H | H | H | H | H | N-22 | H | H | H | H | H | H | H |
| 2483 | 1(14) | Me | Me | H | H | H | H | H | N-23 | H | H | H | H | H | H | H |
| 2484 | 1(14) | Me | Me | H | H | H | H | H | N-24 | H | H | H | H | H | H | H |
| 2485 | 1(14) | Me | Me | H | H | H | H | H | N-25 | H | H | H | H | H | H | H |
| 2486 | 1(14) | Me | Me | H | H | H | H | H | N-26 | H | H | H | H | H | H | H |
| 2487 | 1(14) | Me | Me | H | H | H | H | H | N-27 | H | H | H | H | H | H | H |
| 2488 | 1(14) | Me | Me | H | H | H | H | H | N-28 | H | H | H | H | H | H | H |
| 2489 | 1(14) | Me | Me | H | H | H | H | H | N-29 | H | H | H | H | H | H | H |
| 2490 | 1(14) | Me | Me | H | H | H | H | H | N-30 | H | H | H | H | H | H | H |
| 2491 | 1(14) | Me | Me | H | H | H | H | H | N-31 | H | H | H | H | H | H | H |
| 2492 | 1(14) | Me | Me | H | H | H | H | H | N-32 | H | H | H | H | H | H | H |
| 2493 | 1(14) | Me | Me | H | H | H | H | H | N-33 | H | H | H | H | H | H | H |
| 2494 | 1(14) | Me | Me | H | H | H | H | H | N-34 | H | H | H | H | H | H | H |
| 2495 | 1(14) | Me | Me | H | H | H | H | H | N-35 | H | H | H | H | H | H | H |
| 2496 | 1(14) | Me | Me | H | H | H | H | H | N-36 | H | H | H | H | H | H | H |
| 2497 | 1(14) | Me | Me | H | H | H | H | H | N-37 | H | H | H | H | H | H | H |
| 2498 | 1(14) | Me | Me | H | H | H | H | H | N-38 | H | H | H | H | H | H | H |
| 2499 | 1(14) | Me | Me | H | H | H | H | H | N-39 | H | H | H | H | H | H | H |
| 2500 | 1(14) | Me | Me | H | H | H | H | H | N-40 | H | H | H | H | H | H | H |
| 2501 | 1(14) | Me | Me | H | H | H | H | H | N-41 | H | H | H | H | H | H | H |
| 2502 | 1(14) | Me | Me | H | H | H | H | H | H | H | H | H | N-1 | H | H | H |
| 2503 | 1(14) | Me | Me | H | H | H | H | H | H | H | H | H | N-2 | H | H | H |
| 2504 | 1(14) | Me | Me | H | H | H | H | H | H | H | H | H | N-3 | H | H | H |
| 2505 | 1(14) | Me | Me | H | H | H | H | H | H | H | H | H | N-4 | H | H | H |
| 2506 | 1(14) | Me | Me | H | H | H | H | H | H | H | H | H | N-5 | H | H | H |
| 2507 | 1(14) | Me | Me | H | H | H | H | H | H | H | H | H | N-6 | H | H | H |
| 2508 | 1(14) | Me | Me | H | H | H | H | H | H | H | H | H | N-7 | H | H | H |
| 2509 | 1(14) | Me | Me | H | H | H | H | H | H | H | H | H | N-8 | H | H | H |
| 2510 | 1(14) | Me | Me | H | H | H | H | H | H | H | H | H | N-9 | H | H | H |
| 2511 | 1(14) | Me | Me | H | H | H | H | H | H | H | H | H | N-10 | H | H | H |
| 2512 | 1(14) | Me | Me | H | H | H | H | H | H | H | H | H | N-11 | H | H | H |
| 2513 | 1(14) | Me | Me | H | H | H | H | H | H | H | H | H | N-12 | H | H | H |
| 2514 | 1(14) | Me | Me | H | H | H | H | H | H | H | H | H | N-13 | H | H | H |
| 2515 | 1(14) | Me | Me | H | H | H | H | H | H | H | H | H | N-14 | H | H | H |
| 2516 | 1(14) | Me | Me | H | H | H | H | H | H | H | H | H | N-15 | H | H | H |
| 2517 | 1(14) | Me | Me | H | H | H | H | H | H | H | H | H | N-16 | H | H | H |
| 2518 | 1(14) | Me | Me | H | H | H | H | H | H | H | H | H | N-17 | H | H | H |
| 2519 | 1(14) | Me | Me | H | H | H | H | H | H | H | H | H | N-18 | H | H | H |
| 2520 | 1(14) | Me | Me | H | H | H | H | H | H | H | H | H | N-19 | H | H | H |
| 2521 | 1(14) | Me | Me | H | H | H | H | H | H | H | H | H | N-20 | H | H | H |
| 2522 | 1(14) | Me | Me | H | H | H | H | H | H | H | H | H | N-21 | H | H | H |
| 2523 | 1(14) | Me | Me | H | H | H | H | H | H | H | H | H | N-22 | H | H | H |
| 2524 | 1(14) | Me | Me | H | H | H | H | H | H | H | H | H | N-23 | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2525 | 1(14) | Me | Me | H | H | H | H | H | H | H | H | H | N-24 | H | H | H |
| 2526 | 1(14) | Me | Me | H | H | H | H | H | H | H | H | H | N-25 | H | H | H |
| 2527 | 1(14) | Me | Me | H | H | H | H | H | H | H | H | H | N-26 | H | H | H |
| 2528 | 1(14) | Me | Me | H | H | H | H | H | H | H | H | H | N-27 | H | H | H |
| 2529 | 1(14) | Me | Me | H | H | H | H | H | H | H | H | H | N-28 | H | H | H |
| 2530 | 1(14) | Me | Me | H | H | H | H | H | H | H | H | H | N-29 | H | H | H |
| 2531 | 1(14) | Me | Me | H | H | H | H | H | H | H | H | H | N-30 | H | H | H |
| 2532 | 1(14) | Me | Me | H | H | H | H | H | H | H | H | H | N-31 | H | H | H |
| 2533 | 1(14) | Me | Me | H | H | H | H | H | H | H | H | H | N-32 | H | H | H |
| 2534 | 1(14) | Me | Me | H | H | H | H | H | H | H | H | H | N-33 | H | H | H |
| 2535 | 1(14) | Me | Me | H | H | H | H | H | H | H | H | H | N-34 | H | H | H |
| 2536 | 1(14) | Me | Me | H | H | H | H | H | H | H | H | H | N-35 | H | H | H |
| 2537 | 1(14) | Me | Me | H | H | H | H | H | H | H | H | H | N-36 | H | H | H |
| 2538 | 1(14) | Me | Me | H | H | H | H | H | H | H | H | H | N-37 | H | H | H |
| 2539 | 1(14) | Me | Me | H | H | H | H | H | H | H | H | H | N-38 | H | H | H |
| 2540 | 1(14) | Me | Me | H | H | H | H | H | H | H | H | H | N-39 | H | H | H |
| 2541 | 1(14) | Me | Me | H | H | H | H | H | H | H | H | H | N-40 | H | H | H |
| 2542 | 1(14) | Me | Me | H | H | H | H | H | H | H | H | H | N-41 | H | H | H |
| 2543 | 1(14) | Me | Me | H | H | H | H | H | H | H | H | H | H | N-1 | H | H |
| 2544 | 1(14) | Me | Me | H | H | H | H | H | H | H | H | H | H | N-2 | H | H |
| 2545 | 1(14) | Me | Me | H | H | H | H | H | H | H | H | H | H | N-3 | H | H |
| 2546 | 1(14) | Me | Me | H | H | H | H | H | H | H | H | H | H | N-4 | H | H |
| 2547 | 1(14) | Me | Me | H | H | H | H | H | H | H | H | H | H | N-5 | H | H |
| 2548 | 1(14) | Me | Me | H | H | H | H | H | H | H | H | H | H | N-6 | H | H |
| 2549 | 1(14) | Me | Me | H | H | H | H | H | H | H | H | H | H | N-7 | H | H |
| 2550 | 1(14) | Me | Me | H | H | H | H | H | H | H | H | H | H | N-8 | H | H |
| 2551 | 1(14) | Me | Me | H | H | H | H | H | H | H | H | H | H | N-9 | H | H |
| 2552 | 1(14) | Me | Me | H | H | H | H | H | H | H | H | H | H | N-10 | H | H |
| 2553 | 1(14) | Me | Me | H | H | H | H | H | H | H | H | H | H | N-11 | H | H |
| 2554 | 1(14) | Me | Me | H | H | H | H | H | H | H | H | H | H | N-12 | H | H |
| 2555 | 1(14) | Me | Me | H | H | H | H | H | H | H | H | H | H | N-13 | H | H |
| 2556 | 1(14) | Me | Me | H | H | H | H | H | H | H | H | H | H | N-14 | H | H |
| 2557 | 1(14) | Me | Me | H | H | H | H | H | H | H | H | H | H | N-15 | H | H |
| 2558 | 1(14) | Me | Me | H | H | H | H | H | H | H | H | H | H | N-16 | H | H |
| 2559 | 1(14) | Me | Me | H | H | H | H | H | H | H | H | H | H | N-17 | H | H |
| 2560 | 1(14) | Me | Me | H | H | H | H | H | H | H | H | H | H | N-18 | H | H |
| 2561 | 1(14) | Me | Me | H | H | H | H | H | H | H | H | H | H | N-19 | H | H |
| 2562 | 1(14) | Me | Me | H | H | H | H | H | H | H | H | H | H | N-20 | H | H |
| 2563 | 1(14) | Me | Me | H | H | H | H | H | H | H | H | H | H | N-21 | H | H |
| 2564 | 1(14) | Me | Me | H | H | H | H | H | H | H | H | H | H | N-22 | H | H |
| 2565 | 1(14) | Me | Me | H | H | H | H | H | H | H | H | H | H | N-23 | H | H |
| 2566 | 1(14) | Me | Me | H | H | H | H | H | H | H | H | H | H | N-24 | H | H |
| 2567 | 1(14) | Me | Me | H | H | H | H | H | H | H | H | H | H | N-25 | H | H |
| 3568 | 1(14) | Me | Me | H | H | H | H | H | H | H | H | H | H | N-26 | H | H |
| 2569 | 1(14) | Me | Me | H | H | H | H | H | H | H | H | H | H | N-27 | H | H |
| 2570 | 1(14) | Me | Me | H | H | H | H | H | H | H | H | H | H | N-28 | H | H |
| 2571 | 1(14) | Me | Me | H | H | H | H | H | H | H | H | H | H | N-29 | H | H |
| 2572 | 1(14) | Me | Me | H | H | H | H | H | H | H | H | H | H | N-30 | H | H |
| 2573 | 1(14) | Me | Me | H | H | H | H | H | H | H | H | H | H | N-31 | H | H |
| 2574 | 1(14) | Me | Me | H | H | H | H | H | H | H | H | H | H | N-32 | H | H |
| 2575 | 1(14) | Me | Me | H | H | H | H | H | H | H | H | H | H | N-33 | H | H |
| 2576 | 1(14) | Me | Me | H | H | H | H | H | H | H | H | H | H | N-34 | H | H |
| 2577 | 1(14) | Me | Me | H | H | H | H | H | H | H | H | H | H | N-35 | H | H |
| 2578 | 1(14) | Me | Me | H | H | H | H | H | H | H | H | H | H | N-36 | H | H |
| 2579 | 1(14) | Me | Me | H | H | H | H | H | H | H | H | H | H | N-37 | H | H |
| 2580 | 1(14) | Me | Me | H | H | H | H | H | H | H | H | H | H | N-38 | H | H |
| 2581 | 1(14) | Me | Me | H | H | H | H | H | H | H | H | H | H | N-39 | H | H |
| 2582 | 1(14) | Me | Me | H | H | H | H | H | H | H | H | H | H | N-40 | H | H |
| 2583 | 1(14) | Me | Me | H | H | H | H | H | H | H | H | H | H | N-41 | H | H |
| 2584 | 1(15) | Me | Me | H | N-1 | H | H | H | H | H | — | — | — | — | — | — |
| 2585 | 1(15) | Me | Me | H | N-2 | H | H | H | H | H | — | — | — | — | — | — |
| 2586 | 1(15) | Me | Me | H | N-3 | H | H | H | H | H | — | — | — | — | — | — |
| 2587 | 1(15) | Me | Me | H | N-4 | H | H | H | H | H | — | — | — | — | — | — |
| 2588 | 1(15) | Me | Me | H | N-5 | H | H | H | H | H | — | — | — | — | — | — |
| 2589 | 1(15) | Me | Me | H | N-6 | H | H | H | H | H | — | — | — | — | — | — |
| 2590 | 1(15) | Me | Me | H | N-7 | H | H | H | H | H | — | — | — | — | — | — |
| 2591 | 1(15) | Me | Me | H | N-8 | H | H | H | H | H | — | — | — | — | — | — |
| 2592 | 1(15) | Me | Me | H | N-9 | H | H | H | H | H | — | — | — | — | — | — |
| 2593 | 1(15) | Me | Me | H | N-10 | H | H | H | H | H | — | — | — | — | — | — |
| 2594 | 1(15) | Me | Me | H | N-11 | H | H | H | H | H | — | — | — | — | — | — |
| 2595 | 1(15) | Me | Me | H | N-12 | H | H | H | H | H | — | — | — | — | — | — |
| 2596 | 1(15) | Me | Me | H | N-13 | H | H | H | H | H | — | — | — | — | — | — |
| 2597 | 1(15) | Me | Me | H | N-14 | H | H | H | H | H | — | — | — | — | — | — |
| 2598 | 1(15) | Me | Me | H | N-15 | H | H | H | H | H | — | — | — | — | — | — |
| 2599 | 1(15) | Me | Me | H | N-16 | H | H | H | H | H | — | — | — | — | — | — |
| 2600 | 1(15) | Me | Me | H | N-17 | H | H | H | H | H | — | — | — | — | — | — |
| 2601 | 1(15) | Me | Me | H | N-18 | H | H | H | H | H | — | — | — | — | — | — |
| 2602 | 1(15) | Me | Me | H | N-19 | H | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2603 | 1(15) | Me | Me | H | N-20 | H | H | H | H | H | — | — | — | — | — | — |
| 2604 | 1(15) | Me | Me | H | N-21 | H | H | H | H | H | — | — | — | — | — | — |
| 2605 | 1(15) | Me | Me | H | N-22 | H | H | H | H | H | — | — | — | — | — | — |
| 2606 | 1(15) | Me | Me | H | N-23 | H | H | H | H | H | — | — | — | — | — | — |
| 2607 | 1(15) | Me | Me | H | N-24 | H | H | H | H | H | — | — | — | — | — | — |
| 2608 | 1(15) | Me | Me | H | N-25 | H | H | H | H | H | — | — | — | — | — | — |
| 2609 | 1(15) | Me | Me | H | N-26 | H | H | H | H | H | — | — | — | — | — | — |
| 2610 | 1(15) | Me | Me | H | N-27 | H | H | H | H | H | — | — | — | — | — | — |
| 2611 | 1(15) | Me | Me | H | N-28 | H | H | H | H | H | — | — | — | — | — | — |
| 2612 | 1(15) | Me | Me | H | N-29 | H | H | H | H | H | — | — | — | — | — | — |
| 2613 | 1(15) | Me | Me | H | N-30 | H | H | H | H | H | — | — | — | — | — | — |
| 2614 | 1(15) | Me | Me | H | N-31 | H | H | H | H | H | — | — | — | — | — | — |
| 2615 | 1(15) | Me | Me | H | N-32 | H | H | H | H | H | — | — | — | — | — | — |
| 2616 | 1(15) | Me | Me | H | N-33 | H | H | H | H | H | — | — | — | — | — | — |
| 2617 | 1(15) | Me | Me | H | N-34 | H | H | H | H | H | — | — | — | — | — | — |
| 2618 | 1(15) | Me | Me | H | N-35 | H | H | H | H | H | — | — | — | — | — | — |
| 2619 | 1(15) | Me | Me | H | N-36 | H | H | H | H | H | — | — | — | — | — | — |
| 2620 | 1(15) | Me | Me | H | N-37 | H | H | H | H | H | — | — | — | — | — | — |
| 2621 | 1(15) | Me | Me | H | N-38 | H | H | H | H | H | — | — | — | — | — | — |
| 2622 | 1(15) | Me | Me | H | N-39 | H | H | H | H | H | — | — | — | — | — | — |
| 2623 | 1(15) | Me | Me | H | N-40 | H | H | H | H | H | — | — | — | — | — | — |
| 2624 | 1(15) | Me | Me | H | N-41 | H | H | H | H | H | — | — | — | — | — | — |
| 2625 | 1(15) | Me | Me | H | H | N-1 | H | H | H | H | — | — | — | — | — | — |
| 2626 | 1(15) | Me | Me | H | H | N-2 | H | H | H | H | — | — | — | — | — | — |
| 2627 | 1(15) | Me | Me | H | H | N-3 | H | H | H | H | — | — | — | — | — | — |
| 2628 | 1(15) | Me | Me | H | H | N-4 | H | H | H | H | — | — | — | — | — | — |
| 2629 | 1(15) | Me | Me | H | H | N-5 | H | H | H | H | — | — | — | — | — | — |
| 2630 | 1(15) | Me | Me | H | H | N-6 | H | H | H | H | — | — | — | — | — | — |
| 2631 | 1(15) | Me | Me | H | H | N-7 | H | H | H | H | — | — | — | — | — | — |
| 2632 | 1(15) | Me | Me | H | H | N-8 | H | H | H | H | — | — | — | — | — | — |
| 2633 | 1(15) | Me | Me | H | H | N-9 | H | H | H | H | — | — | — | — | — | — |
| 2634 | 1(15) | Me | Me | H | H | N-10 | H | H | H | H | — | — | — | — | — | — |
| 2635 | 1(15) | Me | Me | H | H | N-11 | H | H | H | H | — | — | — | — | — | — |
| 2636 | 1(15) | Me | Me | H | H | N-12 | H | H | H | H | — | — | — | — | — | — |
| 2637 | 1(15) | Me | Me | H | H | N-13 | H | H | H | H | — | — | — | — | — | — |
| 2638 | 1(15) | Me | Me | H | H | N-14 | H | H | H | H | — | — | — | — | — | — |
| 2639 | 1(15) | Me | Me | H | H | N-15 | H | H | H | H | — | — | — | — | — | — |
| 2640 | 1(15) | Me | Me | H | H | N-16 | H | H | H | H | — | — | — | — | — | — |
| 2641 | 1(15) | Me | Me | H | H | N-17 | H | H | H | H | — | — | — | — | — | — |
| 2642 | 1(15) | Me | Me | H | H | N-18 | H | H | H | H | — | — | — | — | — | — |
| 2643 | 1(15) | Me | Me | H | H | N-19 | H | H | H | H | — | — | — | — | — | — |
| 2644 | 1(15) | Me | Me | H | H | N-20 | H | H | H | H | — | — | — | — | — | — |
| 2645 | 1(15) | Me | Me | H | H | N-21 | H | H | H | H | — | — | — | — | — | — |
| 2646 | 1(15) | Me | Me | H | H | N-22 | H | H | H | H | — | — | — | — | — | — |
| 2647 | 1(15) | Me | Me | H | H | N-23 | H | H | H | H | — | — | — | — | — | — |
| 2648 | 1(15) | Me | Me | H | H | N-24 | H | H | H | H | — | — | — | — | — | — |
| 2649 | 1(15) | Me | Me | H | H | N-25 | H | H | H | H | — | — | — | — | — | — |
| 2650 | 1(15) | Me | Me | H | H | N-26 | H | H | H | H | — | — | — | — | — | — |
| 2651 | 1(15) | Me | Me | H | H | N-27 | H | H | H | H | — | — | — | — | — | — |
| 2652 | 1(15) | Me | Me | H | H | N-28 | H | H | H | H | — | — | — | — | — | — |
| 2653 | 1(15) | Me | Me | H | H | N-29 | H | H | H | H | — | — | — | — | — | — |
| 2654 | 1(15) | Me | Me | H | H | N-30 | H | H | H | H | — | — | — | — | — | — |
| 2655 | 1(15) | Me | Me | H | H | N-31 | H | H | H | H | — | — | — | — | — | — |
| 2656 | 1(15) | Me | Me | H | H | N-32 | H | H | H | H | — | — | — | — | — | — |
| 2657 | 1(15) | Me | Me | H | H | N-33 | H | H | H | H | — | — | — | — | — | — |
| 2658 | 1(15) | Me | Me | H | H | N-34 | H | H | H | H | — | — | — | — | — | — |
| 3659 | 1(15) | Me | Me | H | H | N-35 | H | H | H | H | — | — | — | — | — | — |
| 2660 | 1(15) | Me | Me | H | H | N-36 | H | H | H | H | — | — | — | — | — | — |
| 3661 | 1(15) | Me | Me | H | H | N-37 | H | H | H | H | — | — | — | — | — | — |
| 3662 | 1(15) | Me | Me | H | H | N-38 | H | H | H | H | — | — | — | — | — | — |
| 2663 | 1(15) | Me | Me | H | H | N-39 | H | H | H | H | — | — | — | — | — | — |
| 2664 | 1(15) | Me | Me | H | H | N-40 | H | H | H | H | — | — | — | — | — | — |
| 2665 | 1(15) | Me | Me | H | H | N-41 | H | H | H | H | — | — | — | — | — | — |
| 2666 | 1(15) | Me | Me | H | H | H | H | H | H | N-1 | — | — | — | — | — | — |
| 2667 | 1(15) | Me | Me | H | H | H | H | H | H | N-2 | — | — | — | — | — | — |
| 2668 | 1(15) | Me | Me | H | H | H | H | H | H | N-3 | — | — | — | — | — | — |
| 2669 | 1(15) | Me | Me | H | H | H | H | H | H | N-4 | — | — | — | — | — | — |
| 2670 | 1(15) | Me | Me | H | H | H | H | H | H | N-5 | — | — | — | — | — | — |
| 2671 | 1(15) | Me | Me | H | H | H | H | H | H | N-6 | — | — | — | — | — | — |
| 2672 | 1(15) | Me | Me | H | H | H | H | H | H | N-7 | — | — | — | — | — | — |
| 2673 | 1(15) | Me | Me | H | H | H | H | H | H | N-8 | — | — | — | — | — | — |
| 2674 | 1(15) | Me | Me | H | H | H | H | H | H | N-9 | — | — | — | — | — | — |
| 2675 | 1(15) | Me | Me | H | H | H | H | H | H | N-10 | — | — | — | — | — | — |
| 2676 | 1(15) | Me | Me | H | H | H | H | H | H | N-11 | — | — | — | — | — | — |
| 2677 | 1(15) | Me | Me | H | H | H | H | H | H | N-12 | — | — | — | — | — | — |
| 2678 | 1(15) | Me | Me | H | H | H | H | H | H | N-13 | — | — | — | — | — | — |
| 2679 | 1(15) | Me | Me | H | H | H | H | H | H | N-14 | — | — | — | — | — | — |
| 2680 | 1(15) | Me | Me | H | H | H | H | H | H | N-15 | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2681 | 1(15) | Me | Me | H | H | H | H | H | H | N-16 | — | — | — | — | — | — |
| 2682 | 1(15) | Me | Me | H | H | H | H | H | H | N-17 | — | — | — | — | — | — |
| 2683 | 1(15) | Me | Me | H | H | H | H | H | H | N-18 | — | — | — | — | — | — |
| 2684 | 1(15) | Me | Me | H | H | H | H | H | H | N-19 | — | — | — | — | — | — |
| 2685 | 1(15) | Me | Me | H | H | H | H | H | H | N-20 | — | — | — | — | — | — |
| 2686 | 1(15) | Me | Me | H | H | H | H | H | H | N-21 | — | — | — | — | — | — |
| 2687 | 1(15) | Me | Me | H | H | H | H | H | H | N-22 | — | — | — | — | — | — |
| 2688 | 1(15) | Me | Me | H | H | H | H | H | H | N-23 | — | — | — | — | — | — |
| 2689 | 1(15) | Me | Me | H | H | H | H | H | H | N-24 | — | — | — | — | — | — |
| 2690 | 1(15) | Me | Me | H | H | H | H | H | H | N-25 | — | — | — | — | — | — |
| 2691 | 1(15) | Me | Me | H | H | H | H | H | H | N-26 | — | — | — | — | — | — |
| 2692 | 1(15) | Me | Me | H | H | H | H | H | H | N-27 | — | — | — | — | — | — |
| 2693 | 1(15) | Me | Me | H | H | H | H | H | H | N-28 | — | — | — | — | — | — |
| 2694 | 1(15) | Me | Me | H | H | H | H | H | H | N-29 | — | — | — | — | — | — |
| 2695 | 1(15) | Me | Me | H | H | H | H | H | H | N-30 | — | — | — | — | — | — |
| 2696 | 1(15) | Me | Me | H | H | H | H | H | H | N-31 | — | — | — | — | — | — |
| 2697 | 1(15) | Me | Me | H | H | H | H | H | H | N-32 | — | — | — | — | — | — |
| 2698 | 1(15) | Me | Me | H | H | H | H | H | H | N-33 | — | — | — | — | — | — |
| 2699 | 1(15) | Me | Me | H | H | H | H | H | H | N-34 | — | — | — | — | — | — |
| 2700 | 1(15) | Me | Me | H | H | H | H | H | H | N-35 | — | — | — | — | — | — |
| 2701 | 1(15) | Me | Me | H | H | H | H | H | H | N-36 | — | — | — | — | — | — |
| 2702 | 1(15) | Me | Me | H | H | H | H | H | H | N-37 | — | — | — | — | — | — |
| 2703 | 1(15) | Me | Me | H | H | H | H | H | H | N-38 | — | — | — | — | — | — |
| 2704 | 1(15) | Me | Me | H | H | H | H | H | H | N-39 | — | — | — | — | — | — |
| 2705 | 1(15) | Me | Me | H | H | H | H | H | H | N-40 | — | — | — | — | — | — |
| 2706 | 1(15) | Me | Me | H | H | H | H | H | H | N-41 | — | — | — | — | — | — |
| 2707 | 1(13) | Ph | Ph | H | N-1 | H | H | H | H | H | — | — | — | — | — | — |
| 2708 | 1(13) | Ph | Ph | H | N-2 | H | H | H | H | H | — | — | — | — | — | — |
| 2709 | 1(13) | Ph | Ph | H | N-3 | H | H | H | H | H | — | — | — | — | — | — |
| 2710 | 1(13) | Ph | Ph | H | N-4 | H | H | H | H | H | — | — | — | — | — | — |
| 2711 | 1(13) | Ph | Ph | H | N-5 | H | H | H | H | H | — | — | — | — | — | — |
| 2712 | 1(13) | Ph | Ph | H | N-6 | H | H | H | H | H | — | — | — | — | — | — |
| 2713 | 1(13) | Ph | Ph | H | N-7 | H | H | H | H | H | — | — | — | — | — | — |
| 2714 | 1(13) | Ph | Ph | H | N-8 | H | H | H | H | H | — | — | — | — | — | — |
| 2715 | 1(13) | Ph | Ph | H | N-9 | H | H | H | H | H | — | — | — | — | — | — |
| 2716 | 1(13) | Ph | Ph | H | N-10 | H | H | H | H | H | — | — | — | — | — | — |
| 2717 | 1(13) | Ph | Ph | H | N-11 | H | H | H | H | H | — | — | — | — | — | — |
| 2718 | 1(13) | Ph | Ph | H | N-12 | H | H | H | H | H | — | — | — | — | — | — |
| 2719 | 1(13) | Ph | Ph | H | N-13 | H | H | H | H | H | — | — | — | — | — | — |
| 2720 | 1(13) | Ph | Ph | H | N-14 | H | H | H | H | H | — | — | — | — | — | — |
| 2721 | 1(13) | Ph | Ph | H | N-15 | H | H | H | H | H | — | — | — | — | — | — |
| 2722 | 1(13) | Ph | Ph | H | N-16 | H | H | H | H | H | — | — | — | — | — | — |
| 2723 | 1(13) | Ph | Ph | H | N-17 | H | H | H | H | H | — | — | — | — | — | — |
| 2724 | 1(13) | Ph | Ph | H | N-18 | H | H | H | H | H | — | — | — | — | — | — |
| 2725 | 1(13) | Ph | Ph | H | N-19 | H | H | H | H | H | — | — | — | — | — | — |
| 2726 | 1(13) | Ph | Ph | H | N-20 | H | H | H | H | H | — | — | — | — | — | — |
| 2727 | 1(13) | Ph | Ph | H | N-21 | H | H | H | H | H | — | — | — | — | — | — |
| 2728 | 1(13) | Ph | Ph | H | N-22 | H | H | H | H | H | — | — | — | — | — | — |
| 2729 | 1(13) | Ph | Ph | H | N-23 | H | H | H | H | H | — | — | — | — | — | — |
| 2730 | 1(13) | Ph | Ph | H | N-24 | H | H | H | H | H | — | — | — | — | — | — |
| 2731 | 1(13) | Ph | Ph | H | N-25 | H | H | H | H | H | — | — | — | — | — | — |
| 2732 | 1(13) | Ph | Ph | H | N-26 | H | H | H | H | H | — | — | — | — | — | — |
| 2733 | 1(13) | Ph | Ph | H | N-27 | H | H | H | H | H | — | — | — | — | — | — |
| 2734 | 1(13) | Ph | Ph | H | N-28 | H | H | H | H | H | — | — | — | — | — | — |
| 2735 | 1(13) | Ph | Ph | H | N-29 | H | H | H | H | H | — | — | — | — | — | — |
| 2736 | 1(13) | Ph | Ph | H | N-30 | H | H | H | H | H | — | — | — | — | — | — |
| 2737 | 1(13) | Ph | Ph | H | N-31 | H | H | H | H | H | — | — | — | — | — | — |
| 2738 | 1(13) | Ph | Ph | H | N-32 | H | H | H | H | H | — | — | — | — | — | — |
| 2739 | 1(13) | Ph | Ph | H | N-33 | H | H | H | H | H | — | — | — | — | — | — |
| 2740 | 1(13) | Ph | Ph | H | N-34 | H | H | H | H | H | — | — | — | — | — | — |
| 2741 | 1(13) | Ph | Ph | H | N-35 | H | H | H | H | H | — | — | — | — | — | — |
| 2742 | 1(13) | Ph | Ph | H | N-36 | H | H | H | H | H | — | — | — | — | — | — |
| 2743 | 1(13) | Ph | Ph | H | N-37 | H | H | H | H | H | — | — | — | — | — | — |
| 2744 | 1(13) | Ph | Ph | H | N-38 | H | H | H | H | H | — | — | — | — | — | — |
| 2745 | 1(13) | Ph | Ph | H | N-39 | H | H | H | H | H | — | — | — | — | — | — |
| 2746 | 1(13) | Ph | Ph | H | N-40 | H | H | H | H | H | — | — | — | — | — | — |
| 2747 | 1(13) | Ph | Ph | H | N-41 | H | H | H | H | H | — | — | — | — | — | — |
| 2748 | 1(13) | Ph | Ph | H | H | N-1 | H | H | H | H | — | — | — | — | — | — |
| 2749 | 1(13) | Ph | Ph | H | H | N-2 | H | H | H | H | — | — | — | — | — | — |
| 2750 | 1(13) | Ph | Ph | H | H | N-3 | H | H | H | H | — | — | — | — | — | — |
| 2751 | 1(13) | Ph | Ph | H | H | N-4 | H | H | H | H | — | — | — | — | — | — |
| 2752 | 1(13) | Ph | Ph | H | H | N-5 | H | H | H | H | — | — | — | — | — | — |
| 2753 | 1(13) | Ph | Ph | H | H | N-6 | H | H | H | H | — | — | — | — | — | — |
| 2754 | 1(13) | Ph | Ph | H | H | N-7 | H | H | H | H | — | — | — | — | — | — |
| 2755 | 1(13) | Ph | Ph | H | H | N-8 | H | H | H | H | — | — | — | — | — | — |
| 2756 | 1(13) | Ph | Ph | H | H | N-9 | H | H | H | H | — | — | — | — | — | — |
| 2757 | 1(13) | Ph | Ph | H | H | N-10 | H | H | H | H | — | — | — | — | — | — |
| 2758 | 1(13) | Ph | Ph | H | H | N-11 | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2759 | 1(13) | Ph | Ph | H | H | N-12 | H | H | H | H | — | — | — | — | — | — |
| 2760 | 1(13) | Ph | Ph | H | H | N-13 | H | H | H | H | — | — | — | — | — | — |
| 2761 | 1(13) | Ph | Ph | H | H | N-14 | H | H | H | H | — | — | — | — | — | — |
| 2762 | 1(13) | Ph | Ph | H | H | N-15 | H | H | H | H | — | — | — | — | — | — |
| 2763 | 1(13) | Ph | Ph | H | H | N-16 | H | H | H | H | — | — | — | — | — | — |
| 2764 | 1(13) | Ph | Ph | H | H | N-17 | H | H | H | H | — | — | — | — | — | — |
| 2765 | 1(13) | Ph | Ph | H | H | N-18 | H | H | H | H | — | — | — | — | — | — |
| 2766 | 1(13) | Ph | Ph | H | H | N-19 | H | H | H | H | — | — | — | — | — | — |
| 2767 | 1(13) | Ph | Ph | H | H | N-20 | H | H | H | H | — | — | — | — | — | — |
| 2768 | 1(13) | Ph | Ph | H | H | N-21 | H | H | H | H | — | — | — | — | — | — |
| 2769 | 1(13) | Ph | Ph | H | H | N-22 | H | H | H | H | — | — | — | — | — | — |
| 2770 | 1(13) | Ph | Ph | H | H | N-23 | H | H | H | H | — | — | — | — | — | — |
| 2771 | 1(13) | Ph | Ph | H | H | N-24 | H | H | H | H | — | — | — | — | — | — |
| 2772 | 1(13) | Ph | Ph | H | H | N-25 | H | H | H | H | — | — | — | — | — | — |
| 2773 | 1(13) | Ph | Ph | H | H | N-26 | H | H | H | H | — | — | — | — | — | — |
| 2774 | 1(13) | Ph | Ph | H | H | N-27 | H | H | H | H | — | — | — | — | — | — |
| 2775 | 1(13) | Ph | Ph | H | H | N-28 | H | H | H | H | — | — | — | — | — | — |
| 2776 | 1(13) | Ph | Ph | H | H | N-29 | H | H | H | H | — | — | — | — | — | — |
| 2777 | 1(13) | Ph | Ph | H | H | N-30 | H | H | H | H | — | — | — | — | — | — |
| 2778 | 1(13) | Ph | Ph | H | H | N-31 | H | H | H | H | — | — | — | — | — | — |
| 2779 | 1(13) | Ph | Ph | H | H | N-32 | H | H | H | H | — | — | — | — | — | — |
| 2780 | 1(13) | Ph | Ph | H | H | N-33 | H | H | H | H | — | — | — | — | — | — |
| 2781 | 1(13) | Ph | Ph | H | H | N-34 | H | H | H | H | — | — | — | — | — | — |
| 2782 | 1(13) | Ph | Ph | H | H | N-35 | H | H | H | H | — | — | — | — | — | — |
| 2783 | 1(13) | Ph | Ph | H | H | N-36 | H | H | H | H | — | — | — | — | — | — |
| 2784 | 1(13) | Ph | Ph | H | H | N-37 | H | H | H | H | — | — | — | — | — | — |
| 2785 | 1(13) | Ph | Ph | H | H | N-38 | H | H | H | H | — | — | — | — | — | — |
| 2786 | 1(13) | Ph | Ph | H | H | N-39 | H | H | H | H | — | — | — | — | — | — |
| 2787 | 1(13) | Ph | Ph | H | H | N-40 | H | H | H | H | — | — | — | — | — | — |
| 2788 | 1(13) | Ph | Ph | H | H | N-41 | H | H | H | H | — | — | — | — | — | — |
| 2789 | 1(13) | Ph | Ph | H | H | H | H | H | N-1 | H | — | — | — | — | — | — |
| 2790 | 1(13) | Ph | Ph | H | H | H | H | H | N-2 | H | — | — | — | — | — | — |
| 2791 | 1(13) | Ph | Ph | H | H | H | H | H | N-3 | H | — | — | — | — | — | — |
| 2792 | 1(13) | Ph | Ph | H | H | H | H | H | N-4 | H | — | — | — | — | — | — |
| 2793 | 1(13) | Ph | Ph | H | H | H | H | H | N-5 | H | — | — | — | — | — | — |
| 2794 | 1(13) | Ph | Ph | H | H | H | H | H | N-6 | H | — | — | — | — | — | — |
| 2795 | 1(13) | Ph | Ph | H | H | H | H | H | N-7 | H | — | — | — | — | — | — |
| 2796 | 1(13) | Ph | Ph | H | H | H | H | H | N-8 | H | — | — | — | — | — | — |
| 2797 | 1(13) | Ph | Ph | H | H | H | H | H | N-9 | H | — | — | — | — | — | — |
| 2798 | 1(13) | Ph | Ph | H | H | H | H | H | N-10 | H | — | — | — | — | — | — |
| 2799 | 1(13) | Ph | Ph | H | H | H | H | H | N-11 | H | — | — | — | — | — | — |
| 2800 | 1(13) | Ph | Ph | H | H | H | H | H | N-12 | H | — | — | — | — | — | — |
| 2801 | 1(13) | Ph | Ph | H | H | H | H | H | N-13 | H | — | — | — | — | — | — |
| 2802 | 1(13) | Ph | Ph | H | H | H | H | H | N-14 | H | — | — | — | — | — | — |
| 2803 | 1(13) | Ph | Ph | H | H | H | H | H | N-15 | H | — | — | — | — | — | — |
| 2804 | 1(13) | Ph | Ph | H | H | H | H | H | N-16 | H | — | — | — | — | — | — |
| 2805 | 1(13) | Ph | Ph | H | H | H | H | H | N-17 | H | — | — | — | — | — | — |
| 2806 | 1(13) | Ph | Ph | H | H | H | H | H | N-18 | H | — | — | — | — | — | — |
| 2807 | 1(13) | Ph | Ph | H | H | H | H | H | N-19 | H | — | — | — | — | — | — |
| 2808 | 1(13) | Ph | Ph | H | H | H | H | H | N-20 | H | — | — | — | — | — | — |
| 2809 | 1(13) | Ph | Ph | H | H | H | H | H | N-21 | H | — | — | — | — | — | — |
| 2810 | 1(13) | Ph | Ph | H | H | H | H | H | N-22 | H | — | — | — | — | — | — |
| 2811 | 1(13) | Ph | Ph | H | H | H | H | H | N-23 | H | — | — | — | — | — | — |
| 2812 | 1(13) | Ph | Ph | H | H | H | H | H | N-24 | H | — | — | — | — | — | — |
| 2813 | 1(13) | Ph | Ph | H | H | H | H | H | N-25 | H | — | — | — | — | — | — |
| 2814 | 1(13) | Ph | Ph | H | H | H | H | H | N-26 | H | — | — | — | — | — | — |
| 2815 | 1(13) | Ph | Ph | H | H | H | H | H | N-27 | H | — | — | — | — | — | — |
| 2816 | 1(13) | Ph | Ph | H | H | H | H | H | N-28 | H | — | — | — | — | — | — |
| 2817 | 1(13) | Ph | Ph | H | H | H | H | H | N-29 | H | — | — | — | — | — | — |
| 2818 | 1(13) | Ph | Ph | H | H | H | H | H | N-30 | H | — | — | — | — | — | — |
| 2819 | 1(13) | Ph | Ph | H | H | H | H | H | N-31 | H | — | — | — | — | — | — |
| 2820 | 1(13) | Ph | Ph | H | H | H | H | H | N-32 | H | — | — | — | — | — | — |
| 2821 | 1(13) | Ph | Ph | H | H | H | H | H | N-33 | H | — | — | — | — | — | — |
| 2822 | 1(13) | Ph | Ph | H | H | H | H | H | N-34 | H | — | — | — | — | — | — |
| 2823 | 1(13) | Ph | Ph | H | H | H | H | H | N-35 | H | — | — | — | — | — | — |
| 2824 | 1(13) | Ph | Ph | H | H | H | H | H | N-36 | H | — | — | — | — | — | — |
| 2825 | 1(13) | Ph | Ph | H | H | H | H | H | N-37 | H | — | — | — | — | — | — |
| 2826 | 1(13) | Ph | Ph | H | H | H | H | H | N-38 | H | — | — | — | — | — | — |
| 2827 | 1(13) | Ph | Ph | H | H | H | H | H | N-39 | H | — | — | — | — | — | — |
| 2828 | 1(13) | Ph | Ph | H | H | H | H | H | N-40 | H | — | — | — | — | — | — |
| 2829 | 1(13) | Ph | Ph | H | H | H | H | H | N-41 | H | — | — | — | — | — | — |
| 2830 | 1(14) | Ph | Ph | H | N-1 | H | H | H | H | H | H | H | H | H | H | H |
| 2831 | 1(14) | Ph | Ph | H | N-2 | H | H | H | H | H | H | H | H | H | H | H |
| 2832 | 1(14) | Ph | Ph | H | N-3 | H | H | H | H | H | H | H | H | H | H | H |
| 2833 | 1(14) | Ph | Ph | H | N-4 | H | H | H | H | H | H | H | H | H | H | H |
| 2834 | 1(14) | Ph | Ph | H | N-5 | H | H | H | H | H | H | H | H | H | H | H |
| 2835 | 1(14) | Ph | Ph | H | N-6 | H | H | H | H | H | H | H | H | H | H | H |
| 2836 | 1(14) | Ph | Ph | H | N-7 | H | H | H | H | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2837 | 1(14) | Ph | Ph | H | N-8 | H | H | H | H | H | H | H | H | H | H | H |
| 2838 | 1(14) | Ph | Ph | H | N-9 | H | H | H | H | H | H | H | H | H | H | H |
| 2839 | 1(14) | Ph | Ph | H | N-10 | H | H | H | H | H | H | H | H | H | H | H |
| 2840 | 1(14) | Ph | Ph | H | N-11 | H | H | H | H | H | H | H | H | H | H | H |
| 2841 | 1(14) | Ph | Ph | H | N-12 | H | H | H | H | H | H | H | H | H | H | H |
| 2842 | 1(14) | Ph | Ph | H | N-13 | H | H | H | H | H | H | H | H | H | H | H |
| 2843 | 1(14) | Ph | Ph | H | N-14 | H | H | H | H | H | H | H | H | H | H | H |
| 2844 | 1(14) | Ph | Ph | H | N-15 | H | H | H | H | H | H | H | H | H | H | H |
| 2845 | 1(14) | Ph | Ph | H | N-16 | H | H | H | H | H | H | H | H | H | H | H |
| 2846 | 1(14) | Ph | Ph | H | N-17 | H | H | H | H | H | H | H | H | H | H | H |
| 2847 | 1(14) | Ph | Ph | H | N-18 | H | H | H | H | H | H | H | H | H | H | H |
| 2848 | 1(14) | Ph | Ph | H | N-19 | H | H | H | H | H | H | H | H | H | H | H |
| 2849 | 1(14) | Ph | Ph | H | N-20 | H | H | H | H | H | H | H | H | H | H | H |
| 2850 | 1(14) | Ph | Ph | H | N-21 | H | H | H | H | H | H | H | H | H | H | H |
| 2851 | 1(14) | Ph | Ph | H | N-22 | H | H | H | H | H | H | H | H | H | H | H |
| 2852 | 1(14) | Ph | Ph | H | N-23 | H | H | H | H | H | H | H | H | H | H | H |
| 2853 | 1(14) | Ph | Ph | H | N-24 | H | H | H | H | H | H | H | H | H | H | H |
| 2854 | 1(14) | Ph | Ph | H | N-25 | H | H | H | H | H | H | H | H | H | H | H |
| 2855 | 1(14) | Ph | Ph | H | N-26 | H | H | H | H | H | H | H | H | H | H | H |
| 2856 | 1(14) | Ph | Ph | H | N-27 | H | H | H | H | H | H | H | H | H | H | H |
| 2857 | 1(14) | Ph | Ph | H | N-28 | H | H | H | H | H | H | H | H | H | H | H |
| 2858 | 1(14) | Ph | Ph | H | N-29 | H | H | H | H | H | H | H | H | H | H | H |
| 2859 | 1(14) | Ph | Ph | H | N-30 | H | H | H | H | H | H | H | H | H | H | H |
| 2860 | 1(14) | Ph | Ph | H | N-31 | H | H | H | H | H | H | H | H | H | H | H |
| 2861 | 1(14) | Ph | Ph | H | N-32 | H | H | H | H | H | H | H | H | H | H | H |
| 2862 | 1(14) | Ph | Ph | H | N-33 | H | H | H | H | H | H | H | H | H | H | H |
| 2863 | 1(14) | Ph | Ph | H | N-34 | H | H | H | H | H | H | H | H | H | H | H |
| 2864 | 1(14) | Ph | Ph | H | N-35 | H | H | H | H | H | H | H | H | H | H | H |
| 2865 | 1(14) | Ph | Ph | H | N-36 | H | H | H | H | H | H | H | H | H | H | H |
| 2866 | 1(14) | Ph | Ph | H | N-37 | H | H | H | H | H | H | H | H | H | H | H |
| 2867 | 1(14) | Ph | Ph | H | N-38 | H | H | H | H | H | H | H | H | H | H | H |
| 2868 | 1(14) | Ph | Ph | H | N-39 | H | H | H | H | H | H | H | H | H | H | H |
| 2869 | 1(14) | Ph | Ph | H | N-40 | H | H | H | H | H | H | H | H | H | H | H |
| 2870 | 1(14) | Ph | Ph | H | N-41 | H | H | H | H | H | H | H | H | H | H | H |
| 2871 | 1(14) | Ph | Ph | H | H | N-1 | H | H | H | H | H | H | H | H | H | H |
| 2872 | 1(14) | Ph | Ph | H | H | N-2 | H | H | H | H | H | H | H | H | H | H |
| 2873 | 1(14) | Ph | Ph | H | H | N-3 | H | H | H | H | H | H | H | H | H | H |
| 2874 | 1(14) | Ph | Ph | H | H | N-4 | H | H | H | H | H | H | H | H | H | H |
| 2875 | 1(14) | Ph | Ph | H | H | N-5 | H | H | H | H | H | H | H | H | H | H |
| 2876 | 1(14) | Ph | Ph | H | H | N-6 | H | H | H | H | H | H | H | H | H | H |
| 2877 | 1(14) | Ph | Ph | H | H | N-7 | H | H | H | H | H | H | H | H | H | H |
| 2878 | 1(14) | Ph | Ph | H | H | N-8 | H | H | H | H | H | H | H | H | H | H |
| 2879 | 1(14) | Ph | Ph | H | H | N-9 | H | H | H | H | H | H | H | H | H | H |
| 2880 | 1(14) | Ph | Ph | H | H | N-10 | H | H | H | H | H | H | H | H | H | H |
| 2881 | 1(14) | Ph | Ph | H | H | N-11 | H | H | H | H | H | H | H | H | H | H |
| 2882 | 1(14) | Ph | Ph | H | H | N-12 | H | H | H | H | H | H | H | H | H | H |
| 2883 | 1(14) | Ph | Ph | H | H | N-13 | H | H | H | H | H | H | H | H | H | H |
| 2884 | 1(14) | Ph | Ph | H | H | N-14 | H | H | H | H | H | H | H | H | H | H |
| 2885 | 1(14) | Ph | Ph | H | H | N-15 | H | H | H | H | H | H | H | H | H | H |
| 2886 | 1(14) | Ph | Ph | H | H | N-16 | H | H | H | H | H | H | H | H | H | H |
| 2887 | 1(14) | Ph | Ph | H | H | N-17 | H | H | H | H | H | H | H | H | H | H |
| 2888 | 1(14) | Ph | Ph | H | H | N-18 | H | H | H | H | H | H | H | H | H | H |
| 2889 | 1(14) | Ph | Ph | H | H | N-19 | H | H | H | H | H | H | H | H | H | H |
| 2890 | 1(14) | Ph | Ph | H | H | N-20 | H | H | H | H | H | H | H | H | H | H |
| 2891 | 1(14) | Ph | Ph | H | H | N-21 | H | H | H | H | H | H | H | H | H | H |
| 2892 | 1(14) | Ph | Ph | H | H | N-22 | H | H | H | H | H | H | H | H | H | H |
| 2893 | 1(14) | Ph | Ph | H | H | N-23 | H | H | H | H | H | H | H | H | H | H |
| 2894 | 1(14) | Ph | Ph | H | H | N-24 | H | H | H | H | H | H | H | H | H | H |
| 2895 | 1(14) | Ph | Ph | H | H | N-25 | H | H | H | H | H | H | H | H | H | H |
| 2896 | 1(14) | Ph | Ph | H | H | N-26 | H | H | H | H | H | H | H | H | H | H |
| 2897 | 1(14) | Ph | Ph | H | H | N-27 | H | H | H | H | H | H | H | H | H | H |
| 2898 | 1(14) | Ph | Ph | H | H | N-28 | H | H | H | H | H | H | H | H | H | H |
| 2899 | 1(14) | Ph | Ph | H | H | N-29 | H | H | H | H | H | H | H | H | H | H |
| 2900 | 1(14) | Ph | Ph | H | H | N-30 | H | H | H | H | H | H | H | H | H | H |
| 2901 | 1(14) | Ph | Ph | H | H | N-31 | H | H | H | H | H | H | H | H | H | H |
| 2902 | 1(14) | Ph | Ph | H | H | N-32 | H | H | H | H | H | H | H | H | H | H |
| 2903 | 1(14) | Ph | Ph | H | H | N-33 | H | H | H | H | H | H | H | H | H | H |
| 2904 | 1(14) | Ph | Ph | H | H | N-34 | H | H | H | H | H | H | H | H | H | H |
| 2905 | 1(14) | Ph | Ph | H | H | N-35 | H | H | H | H | H | H | H | H | H | H |
| 2906 | 1(14) | Ph | Ph | H | H | N-36 | H | H | H | H | H | H | H | H | H | H |
| 2907 | 1(14) | Ph | Ph | H | H | N-37 | H | H | H | H | H | H | H | H | H | H |
| 2908 | 1(14) | Ph | Ph | H | H | N-38 | H | H | H | H | H | H | H | H | H | H |
| 2909 | 1(14) | Ph | Ph | H | H | N-39 | H | H | H | H | H | H | H | H | H | H |
| 2910 | 1(14) | Ph | Ph | H | H | N-40 | H | H | H | H | H | H | H | H | H | H |
| 2911 | 1(14) | Ph | Ph | H | H | N-41 | H | H | H | H | H | H | H | H | H | H |
| 2912 | 1(14) | Ph | Ph | H | H | H | H | H | N-1 | H | H | H | H | H | H | H |
| 2913 | 1(14) | Ph | Ph | H | H | H | H | H | N-2 | H | H | H | H | H | H | H |
| 2914 | 1(14) | Ph | Ph | H | H | H | H | H | N-3 | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2915 | 1(14) | Ph | Ph | H | H | H | H | H | N-4 | H | H | H | H | H | H | H |
| 2916 | 1(14) | Ph | Ph | H | H | H | H | H | N-5 | H | H | H | H | H | H | H |
| 2917 | 1(14) | Ph | Ph | H | H | H | H | H | N-6 | H | H | H | H | H | H | H |
| 2918 | 1(14) | Ph | Ph | H | H | H | H | H | N-7 | H | H | H | H | H | H | H |
| 2919 | 1(14) | Ph | Ph | H | H | H | H | H | N-8 | H | H | H | H | H | H | H |
| 2920 | 1(14) | Ph | Ph | H | H | H | H | H | N-9 | H | H | H | H | H | H | H |
| 2921 | 1(14) | Ph | Ph | H | H | H | H | H | N-10 | H | H | H | H | H | H | H |
| 2922 | 1(14) | Ph | Ph | H | H | H | H | H | N-11 | H | H | H | H | H | H | H |
| 2923 | 1(14) | Ph | Ph | H | H | H | H | H | N-12 | H | H | H | H | H | H | H |
| 2924 | 1(14) | Ph | Ph | H | H | H | H | H | N-13 | H | H | H | H | H | H | H |
| 2925 | 1(14) | Ph | Ph | H | H | H | H | H | N-14 | H | H | H | H | H | H | H |
| 2926 | 1(14) | Ph | Ph | H | H | H | H | H | N-15 | H | H | H | H | H | H | H |
| 2927 | 1(14) | Ph | Ph | H | H | H | H | H | N-16 | H | H | H | H | H | H | H |
| 2928 | 1(14) | Ph | Ph | H | H | H | H | H | N-17 | H | H | H | H | H | H | H |
| 2929 | 1(14) | Ph | Ph | H | H | H | H | H | N-18 | H | H | H | H | H | H | H |
| 2930 | 1(14) | Ph | Ph | H | H | H | H | H | N-19 | H | H | H | H | H | H | H |
| 2931 | 1(14) | Ph | Ph | H | H | H | H | H | N-20 | H | H | H | H | H | H | H |
| 2932 | 1(14) | Ph | Ph | H | H | H | H | H | N-21 | H | H | H | H | H | H | H |
| 2933 | 1(14) | Ph | Ph | H | H | H | H | H | N-22 | H | H | H | H | H | H | H |
| 2934 | 1(14) | Ph | Ph | H | H | H | H | H | N-23 | H | H | H | H | H | H | H |
| 2935 | 1(14) | Ph | Ph | H | H | H | H | H | N-24 | H | H | H | H | H | H | H |
| 2936 | 1(14) | Ph | Ph | H | H | H | H | H | N-25 | H | H | H | H | H | H | H |
| 2937 | 1(14) | Ph | Ph | H | H | H | H | H | N-26 | H | H | H | H | H | H | H |
| 2938 | 1(14) | Ph | Ph | H | H | H | H | H | N-27 | H | H | H | H | H | H | H |
| 2939 | 1(14) | Ph | Ph | H | H | H | H | H | N-28 | H | H | H | H | H | H | H |
| 2940 | 1(14) | Ph | Ph | H | H | H | H | H | N-29 | H | H | H | H | H | H | H |
| 2941 | 1(14) | Ph | Ph | H | H | H | H | H | N-30 | H | H | H | H | H | H | H |
| 2942 | 1(14) | Ph | Ph | H | H | H | H | H | N-31 | H | H | H | H | H | H | H |
| 2943 | 1(14) | Ph | Ph | H | H | H | H | H | N-32 | H | H | H | H | H | H | H |
| 2944 | 1(14) | Ph | Ph | H | H | H | H | H | N-33 | H | H | H | H | H | H | H |
| 2945 | 1(14) | Ph | Ph | H | H | H | H | H | N-34 | H | H | H | H | H | H | H |
| 2946 | 1(14) | Ph | Ph | H | H | H | H | H | N-35 | H | H | H | H | H | H | H |
| 2947 | 1(14) | Ph | Ph | H | H | H | H | H | N-36 | H | H | H | H | H | H | H |
| 2948 | 1(14) | Ph | Ph | H | H | H | H | H | N-37 | H | H | H | H | H | H | H |
| 2949 | 1(14) | Ph | Ph | H | H | H | H | H | N-38 | H | H | H | H | H | H | H |
| 2950 | 1(14) | Ph | Ph | H | H | H | H | H | N-39 | H | H | H | H | H | H | H |
| 2951 | 1(14) | Ph | Ph | H | H | H | H | H | N-40 | H | H | H | H | H | H | H |
| 2952 | 1(14) | Ph | Ph | H | H | H | H | H | N-41 | H | H | H | H | H | H | H |
| 2953 | 1(14) | Ph | Ph | H | H | H | H | H | H | H | H | H | N-1 | H | H | H |
| 2954 | 1(14) | Ph | Ph | H | H | H | H | H | H | H | H | H | N-2 | H | H | H |
| 2955 | 1(14) | Ph | Ph | H | H | H | H | H | H | H | H | H | N-3 | H | H | H |
| 2956 | 1(14) | Ph | Ph | H | H | H | H | H | H | H | H | H | N-4 | H | H | H |
| 2957 | 1(14) | Ph | Ph | H | H | H | H | H | H | H | H | H | N-5 | H | H | H |
| 2958 | 1(14) | Ph | Ph | H | H | H | H | H | H | H | H | H | N-6 | H | H | H |
| 2959 | 1(14) | Ph | Ph | H | H | H | H | H | H | H | H | H | N-7 | H | H | H |
| 2960 | 1(14) | Ph | Ph | H | H | H | H | H | H | H | H | H | N-8 | H | H | H |
| 2961 | 1(14) | Ph | Ph | H | H | H | H | H | H | H | H | H | N-9 | H | H | H |
| 2962 | 1(14) | Ph | Ph | H | H | H | H | H | H | H | H | H | N-10 | H | H | H |
| 2963 | 1(14) | Ph | Ph | H | H | H | H | H | H | H | H | H | N-11 | H | H | H |
| 2964 | 1(14) | Ph | Ph | H | H | H | H | H | H | H | H | H | N-12 | H | H | H |
| 2965 | 1(14) | Ph | Ph | H | H | H | H | H | H | H | H | H | N-13 | H | H | H |
| 2966 | 1(14) | Ph | Ph | H | H | H | H | H | H | H | H | H | N-14 | H | H | H |
| 2967 | 1(14) | Ph | Ph | H | H | H | H | H | H | H | H | H | N-15 | H | H | H |
| 2968 | 1(14) | Ph | Ph | H | H | H | H | H | H | H | H | H | N-16 | H | H | H |
| 2969 | 1(14) | Ph | Ph | H | H | H | H | H | H | H | H | H | N-17 | H | H | H |
| 2970 | 1(14) | Ph | Ph | H | H | H | H | H | H | H | H | H | N-18 | H | H | H |
| 2971 | 1(14) | Ph | Ph | H | H | H | H | H | H | H | H | H | N-19 | H | H | H |
| 2972 | 1(14) | Ph | Ph | H | H | H | H | H | H | H | H | H | N-20 | H | H | H |
| 2973 | 1(14) | Ph | Ph | H | H | H | H | H | H | H | H | H | N-21 | H | H | H |
| 2974 | 1(14) | Ph | Ph | H | H | H | H | H | H | H | H | H | N-22 | H | H | H |
| 2975 | 1(14) | Ph | Ph | H | H | H | H | H | H | H | H | H | N-23 | H | H | H |
| 2976 | 1(14) | Ph | Ph | H | H | H | H | H | H | H | H | H | N-24 | H | H | H |
| 2977 | 1(14) | Ph | Ph | H | H | H | H | H | H | H | H | H | N-25 | H | H | H |
| 2978 | 1(14) | Ph | Ph | H | H | H | H | H | H | H | H | H | N-26 | H | H | H |
| 2979 | 1(14) | Ph | Ph | H | H | H | H | H | H | H | H | H | N-27 | H | H | H |
| 2980 | 1(14) | Ph | Ph | H | H | H | H | H | H | H | H | H | N-28 | H | H | H |
| 2981 | 1(14) | Ph | Ph | H | H | H | H | H | H | H | H | H | N-29 | H | H | H |
| 2982 | 1(14) | Ph | Ph | H | H | H | H | H | H | H | H | H | N-30 | H | H | H |
| 2983 | 1(14) | Ph | Ph | H | H | H | H | H | H | H | H | H | N-31 | H | H | H |
| 2984 | 1(14) | Ph | Ph | H | H | H | H | H | H | H | H | H | N-32 | H | H | H |
| 2985 | 1(14) | Ph | Ph | H | H | H | H | H | H | H | H | H | N-33 | H | H | H |
| 2986 | 1(14) | Ph | Ph | H | H | H | H | H | H | H | H | H | N-34 | H | H | H |
| 2987 | 1(14) | Ph | Ph | H | H | H | H | H | H | H | H | H | N-35 | H | H | H |
| 2988 | 1(14) | Ph | Ph | H | H | H | H | H | H | H | H | H | N-36 | H | H | H |
| 2989 | 1(14) | Ph | Ph | H | H | H | H | H | H | H | H | H | N-37 | H | H | H |
| 2990 | 1(14) | Ph | Ph | H | H | H | H | H | H | H | H | H | N-38 | H | H | H |
| 2991 | 1(14) | Ph | Ph | H | H | H | H | H | H | H | H | H | N-39 | H | H | H |
| 2992 | 1(14) | Ph | Ph | H | H | H | H | H | H | H | H | H | N-40 | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 2993 | 1(14) | Ph | Ph | H | H | H | H | H | H | H | H | H | N-41 | H | H | H |
| 2994 | 1(14) | Ph | Ph | H | H | H | H | H | H | H | H | H | H | N-1 | H | H |
| 2995 | 1(14) | Ph | Ph | H | H | H | H | H | H | H | H | H | H | N-2 | H | H |
| 2996 | 1(14) | Ph | Ph | H | H | H | H | H | H | H | H | H | H | N-3 | H | H |
| 2997 | 1(14) | Ph | Ph | H | H | H | H | H | H | H | H | H | H | N-4 | H | H |
| 2998 | 1(14) | Ph | Ph | H | H | H | H | H | H | H | H | H | H | N-5 | H | H |
| 2999 | 1(14) | Ph | Ph | H | H | H | H | H | H | H | H | H | H | N-6 | H | H |
| 3000 | 1(14) | Ph | Ph | H | H | H | H | H | H | H | H | H | H | N-7 | H | H |
| 3001 | 1(14) | Ph | Ph | H | H | H | H | H | H | H | H | H | H | N-8 | H | H |
| 3002 | 1(14) | Ph | Ph | H | H | H | H | H | H | H | H | H | H | N-9 | H | H |
| 3003 | 1(14) | Ph | Ph | H | H | H | H | H | H | H | H | H | H | N-10 | H | H |
| 3004 | 1(14) | Ph | Ph | H | H | H | H | H | H | H | H | H | H | N-11 | H | H |
| 3005 | 1(14) | Ph | Ph | H | H | H | H | H | H | H | H | H | H | N-12 | H | H |
| 3006 | 1(14) | Ph | Ph | H | H | H | H | H | H | H | H | H | H | N-13 | H | H |
| 3007 | 1(14) | Ph | Ph | H | H | H | H | H | H | H | H | H | H | N-14 | H | H |
| 3008 | 1(14) | Ph | Ph | H | H | H | H | H | H | H | H | H | H | N-15 | H | H |
| 3009 | 1(14) | Ph | Ph | H | H | H | H | H | H | H | H | H | H | N-16 | H | H |
| 3010 | 1(14) | Ph | Ph | H | H | H | H | H | H | H | H | H | H | N-17 | H | H |
| 3011 | 1(14) | Ph | Ph | H | H | H | H | H | H | H | H | H | H | N-18 | H | H |
| 3012 | 1(14) | Ph | Ph | H | H | H | H | H | H | H | H | H | H | N-19 | H | H |
| 3013 | 1(14) | Ph | Ph | H | H | H | H | H | H | H | H | H | H | N-20 | H | H |
| 3014 | 1(14) | Ph | Ph | H | H | H | H | H | H | H | H | H | H | N-21 | H | H |
| 3015 | 1(14) | Ph | Ph | H | H | H | H | H | H | H | H | H | H | N-22 | H | H |
| 3016 | 1(14) | Ph | Ph | H | H | H | H | H | H | H | H | H | H | N-23 | H | H |
| 3017 | 1(14) | Ph | Ph | H | H | H | H | H | H | H | H | H | H | N-24 | H | H |
| 3018 | 1(14) | Ph | Ph | H | H | H | H | H | H | H | H | H | H | N-25 | H | H |
| 3019 | 1(14) | Ph | Ph | H | H | H | H | H | H | H | H | H | H | N-26 | H | H |
| 3020 | 1(14) | Ph | Ph | H | H | H | H | H | H | H | H | H | H | N-27 | H | H |
| 3021 | 1(14) | Ph | Ph | H | H | H | H | H | H | H | H | H | H | N-28 | H | H |
| 3022 | 1(14) | Ph | Ph | H | H | H | H | H | H | H | H | H | H | N-29 | H | H |
| 3023 | 1(14) | Ph | Ph | H | H | H | H | H | H | H | H | H | H | N-30 | H | H |
| 3024 | 1(14) | Ph | Ph | H | H | H | H | H | H | H | H | H | H | N-31 | H | H |
| 3025 | 1(14) | Ph | Ph | H | H | H | H | H | H | H | H | H | H | N-32 | H | H |
| 3026 | 1(14) | Ph | Ph | H | H | H | H | H | H | H | H | H | H | N-33 | H | H |
| 3027 | 1(14) | Ph | Ph | H | H | H | H | H | H | H | H | H | H | N-34 | H | H |
| 3028 | 1(14) | Ph | Ph | H | H | H | H | H | H | H | H | H | H | N-35 | H | H |
| 3029 | 1(14) | Ph | Ph | H | H | H | H | H | H | H | H | H | H | N-36 | H | H |
| 3030 | 1(14) | Ph | Ph | H | H | H | H | H | H | H | H | H | H | N-37 | H | H |
| 3031 | 1(14) | Ph | Ph | H | H | H | H | H | H | H | H | H | H | N-38 | H | H |
| 3032 | 1(14) | Ph | Ph | H | H | H | H | H | H | H | H | H | H | N-39 | H | H |
| 3033 | 1(14) | Ph | Ph | H | H | H | H | H | H | H | H | H | H | N-40 | H | H |
| 3034 | 1(14) | Ph | Ph | H | H | H | H | H | H | H | H | H | H | N-41 | H | H |
| 3035 | 1(15) | Ph | Ph | H | N-1 | H | H | H | H | H | — | — | — | — | — | — |
| 3036 | 1(15) | Ph | Ph | H | N-2 | H | H | H | H | H | — | — | — | — | — | — |
| 3037 | 1(15) | Ph | Ph | H | N-3 | H | H | H | H | H | — | — | — | — | — | — |
| 3038 | 1(15) | Ph | Ph | H | N-4 | H | H | H | H | H | — | — | — | — | — | — |
| 3039 | 1(15) | Ph | Ph | H | N-5 | H | H | H | H | H | — | — | — | — | — | — |
| 3040 | 1(15) | Ph | Ph | H | N-6 | H | H | H | H | H | — | — | — | — | — | — |
| 3041 | 1(15) | Ph | Ph | H | N-7 | H | H | H | H | H | — | — | — | — | — | — |
| 3042 | 1(15) | Ph | Ph | H | N-8 | H | H | H | H | H | — | — | — | — | — | — |
| 3043 | 1(15) | Ph | Ph | H | N-9 | H | H | H | H | H | — | — | — | — | — | — |
| 3044 | 1(15) | Ph | Ph | H | N-10 | H | H | H | H | H | — | — | — | — | — | — |
| 3045 | 1(15) | Ph | Ph | H | N-11 | H | H | H | H | H | — | — | — | — | — | — |
| 3046 | 1(15) | Ph | Ph | H | N-12 | H | H | H | H | H | — | — | — | — | — | — |
| 3047 | 1(15) | Ph | Ph | H | N-13 | H | H | H | H | H | — | — | — | — | — | — |
| 3048 | 1(15) | Ph | Ph | H | N-14 | H | H | H | H | H | — | — | — | — | — | — |
| 3049 | 1(15) | Ph | Ph | H | N-15 | H | H | H | H | H | — | — | — | — | — | — |
| 3050 | 1(15) | Ph | Ph | H | N-16 | H | H | H | H | H | — | — | — | — | — | — |
| 3051 | 1(15) | Ph | Ph | H | N-17 | H | H | H | H | H | — | — | — | — | — | — |
| 3052 | 1(15) | Ph | Ph | H | N-18 | H | H | H | H | H | — | — | — | — | — | — |
| 3053 | 1(15) | Ph | Ph | H | N-19 | H | H | H | H | H | — | — | — | — | — | — |
| 3054 | 1(15) | Ph | Ph | H | N-20 | H | H | H | H | H | — | — | — | — | — | — |
| 3055 | 1(15) | Ph | Ph | H | N-21 | H | H | H | H | H | — | — | — | — | — | — |
| 3056 | 1(15) | Ph | Ph | H | N-22 | H | H | H | H | H | — | — | — | — | — | — |
| 3057 | 1(15) | Ph | Ph | H | N-23 | H | H | H | H | H | — | — | — | — | — | — |
| 3058 | 1(15) | Ph | Ph | H | N-24 | H | H | H | H | H | — | — | — | — | — | — |
| 3059 | 1(15) | Ph | Ph | H | N-25 | H | H | H | H | H | — | — | — | — | — | — |
| 3060 | 1(15) | Ph | Ph | H | N-26 | H | H | H | H | H | — | — | — | — | — | — |
| 3061 | 1(15) | Ph | Ph | H | N-27 | H | H | H | H | H | — | — | — | — | — | — |
| 3062 | 1(15) | Ph | Ph | H | N-28 | H | H | H | H | H | — | — | — | — | — | — |
| 3063 | 1(15) | Ph | Ph | H | N-29 | H | H | H | H | H | — | — | — | — | — | — |
| 3064 | 1(15) | Ph | Ph | H | N-30 | H | H | H | H | H | — | — | — | — | — | — |
| 3065 | 1(15) | Ph | Ph | H | N-31 | H | H | H | H | H | — | — | — | — | — | — |
| 3066 | 1(15) | Ph | Ph | H | N-32 | H | H | H | H | H | — | — | — | — | — | — |
| 3067 | 1(15) | Ph | Ph | H | N-33 | H | H | H | H | H | — | — | — | — | — | — |
| 3068 | 1(15) | Ph | Ph | H | N-34 | H | H | H | H | H | — | — | — | — | — | — |
| 3069 | 1(15) | Ph | Ph | H | N-35 | H | H | H | H | H | — | — | — | — | — | — |
| 3070 | 1(15) | Ph | Ph | H | N-36 | H | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 3071 | 1(15) | Ph | Ph | H | N-37 | H | H | H | H | H | — | — | — | — | — | — |
| 3072 | 1(15) | Ph | Ph | H | N-38 | H | H | H | H | H | — | — | — | — | — | — |
| 3073 | 1(15) | Ph | Ph | H | N-39 | H | H | H | H | H | — | — | — | — | — | — |
| 3074 | 1(15) | Ph | Ph | H | N-40 | H | H | H | H | H | — | — | — | — | — | — |
| 3075 | 1(15) | Ph | Ph | H | N-41 | H | H | H | H | H | — | — | — | — | — | — |
| 3076 | 1(15) | Ph | Ph | H | H | N-1 | H | H | H | H | — | — | — | — | — | — |
| 3077 | 1(15) | Ph | Ph | H | H | N-2 | H | H | H | H | — | — | — | — | — | — |
| 3078 | 1(15) | Ph | Ph | H | H | N-3 | H | H | H | H | — | — | — | — | — | — |
| 3079 | 1(15) | Ph | Ph | H | H | N-4 | H | H | H | H | — | — | — | — | — | — |
| 3080 | 1(15) | Ph | Ph | H | H | N-5 | H | H | H | H | — | — | — | — | — | — |
| 3081 | 1(15) | Ph | Ph | H | H | N-6 | H | H | H | H | — | — | — | — | — | — |
| 3082 | 1(15) | Ph | Ph | H | H | N-7 | H | H | H | H | — | — | — | — | — | — |
| 3083 | 1(15) | Ph | Ph | H | H | N-8 | H | H | H | H | — | — | — | — | — | — |
| 3084 | 1(15) | Ph | Ph | H | H | N-9 | H | H | H | H | — | — | — | — | — | — |
| 3085 | 1(15) | Ph | Ph | H | H | N-10 | H | H | H | H | — | — | — | — | — | — |
| 3086 | 1(15) | Ph | Ph | H | H | N-11 | H | H | H | H | — | — | — | — | — | — |
| 3087 | 1(15) | Ph | Ph | H | H | N-12 | H | H | H | H | — | — | — | — | — | — |
| 3088 | 1(15) | Ph | Ph | H | H | N-13 | H | H | H | H | — | — | — | — | — | — |
| 3089 | 1(15) | Ph | Ph | H | H | N-14 | H | H | H | H | — | — | — | — | — | — |
| 3090 | 1(15) | Ph | Ph | H | H | N-15 | H | H | H | H | — | — | — | — | — | — |
| 3091 | 1(15) | Ph | Ph | H | H | N-16 | H | H | H | H | — | — | — | — | — | — |
| 3092 | 1(15) | Ph | Ph | H | H | N-17 | H | H | H | H | — | — | — | — | — | — |
| 3093 | 1(15) | Ph | Ph | H | H | N-18 | H | H | H | H | — | — | — | — | — | — |
| 3094 | 1(15) | Ph | Ph | H | H | N-19 | H | H | H | H | — | — | — | — | — | — |
| 3095 | 1(15) | Ph | Ph | H | H | N-20 | H | H | H | H | — | — | — | — | — | — |
| 3096 | 1(15) | Ph | Ph | H | H | N-21 | H | H | H | H | — | — | — | — | — | — |
| 3097 | 1(15) | Ph | Ph | H | H | N-22 | H | H | H | H | — | — | — | — | — | — |
| 3098 | 1(15) | Ph | Ph | H | H | N-23 | H | H | H | H | — | — | — | — | — | — |
| 3099 | 1(15) | Ph | Ph | H | H | N-24 | H | H | H | H | — | — | — | — | — | — |
| 3100 | 1(15) | Ph | Ph | H | H | N-25 | H | H | H | H | — | — | — | — | — | — |
| 3101 | 1(15) | Ph | Ph | H | H | N-26 | H | H | H | H | — | — | — | — | — | — |
| 3102 | 1(15) | Ph | Ph | H | H | N-27 | H | H | H | H | — | — | — | — | — | — |
| 3103 | 1(15) | Ph | Ph | H | H | N-28 | H | H | H | H | — | — | — | — | — | — |
| 3104 | 1(15) | Ph | Ph | H | H | N-29 | H | H | H | H | — | — | — | — | — | — |
| 3105 | 1(15) | Ph | Ph | H | H | N-30 | H | H | H | H | — | — | — | — | — | — |
| 3106 | 1(15) | Ph | Ph | H | H | N-31 | H | H | H | H | — | — | — | — | — | — |
| 3107 | 1(15) | Ph | Ph | H | H | N-32 | H | H | H | H | — | — | — | — | — | — |
| 3108 | 1(15) | Ph | Ph | H | H | N-33 | H | H | H | H | — | — | — | — | — | — |
| 3109 | 1(15) | Ph | Ph | H | H | N-34 | H | H | H | H | — | — | — | — | — | — |
| 3110 | 1(15) | Ph | Ph | H | H | N-35 | H | H | H | H | — | — | — | — | — | — |
| 3111 | 1(15) | Ph | Ph | H | H | N-36 | H | H | H | H | — | — | — | — | — | — |
| 3112 | 1(15) | Ph | Ph | H | H | N-37 | H | H | H | H | — | — | — | — | — | — |
| 3113 | 1(15) | Ph | Ph | H | H | N-38 | H | H | H | H | — | — | — | — | — | — |
| 3114 | 1(15) | Ph | Ph | H | H | N-39 | H | H | H | H | — | — | — | — | — | — |
| 3115 | 1(15) | Ph | Ph | H | H | N-40 | H | H | H | H | — | — | — | — | — | — |
| 3116 | 1(15) | Ph | Ph | H | H | N-41 | H | H | H | H | — | — | — | — | — | — |
| 3117 | 1(15) | Ph | Ph | H | H | H | H | H | H | N-1 | — | — | — | — | — | — |
| 3118 | 1(15) | Ph | Ph | H | H | H | H | H | H | N-2 | — | — | — | — | — | — |
| 3119 | 1(15) | Ph | Ph | H | H | H | H | H | H | N-3 | — | — | — | — | — | — |
| 3120 | 1(15) | Ph | Ph | H | H | H | H | H | H | N-4 | — | — | — | — | — | — |
| 3121 | 1(15) | Ph | Ph | H | H | H | H | H | H | N-5 | — | — | — | — | — | — |
| 3122 | 1(15) | Ph | Ph | H | H | H | H | H | H | N-6 | — | — | — | — | — | — |
| 3123 | 1(15) | Ph | Ph | H | H | H | H | H | H | N-7 | — | — | — | — | — | — |
| 3124 | 1(15) | Ph | Ph | H | H | H | H | H | H | N-8 | — | — | — | — | — | — |
| 3125 | 1(15) | Ph | Ph | H | H | H | H | H | H | N-9 | — | — | — | — | — | — |
| 3126 | 1(15) | Ph | Ph | H | H | H | H | H | H | N-10 | — | — | — | — | — | — |
| 3127 | 1(15) | Ph | Ph | H | H | H | H | H | H | N-11 | — | — | — | — | — | — |
| 3128 | 1(15) | Ph | Ph | H | H | H | H | H | H | N-12 | — | — | — | — | — | — |
| 3129 | 1(15) | Ph | Ph | H | H | H | H | H | H | N-13 | — | — | — | — | — | — |
| 3130 | 1(15) | Ph | Ph | H | H | H | H | H | H | N-14 | — | — | — | — | — | — |
| 3131 | 1(15) | Ph | Ph | H | H | H | H | H | H | N-15 | — | — | — | — | — | — |
| 3132 | 1(15) | Ph | Ph | H | H | H | H | H | H | N-16 | — | — | — | — | — | — |
| 3133 | 1(15) | Ph | Ph | H | H | H | H | H | H | N-17 | — | — | — | — | — | — |
| 3134 | 1(15) | Ph | Ph | H | H | H | H | H | H | N-18 | — | — | — | — | — | — |
| 3135 | 1(15) | Ph | Ph | H | H | H | H | H | H | N-19 | — | — | — | — | — | — |
| 3136 | 1(15) | Ph | Ph | H | H | H | H | H | H | N-20 | — | — | — | — | — | — |
| 3137 | 1(15) | Ph | Ph | H | H | H | H | H | H | N-21 | — | — | — | — | — | — |
| 3138 | 1(15) | Ph | Ph | H | H | H | H | H | H | N-22 | — | — | — | — | — | — |
| 3139 | 1(15) | Ph | Ph | H | H | H | H | H | H | N-23 | — | — | — | — | — | — |
| 3140 | 1(15) | Ph | Ph | H | H | H | H | H | H | N-24 | — | — | — | — | — | — |
| 3141 | 1(15) | Ph | Ph | H | H | H | H | H | H | N-25 | — | — | — | — | — | — |
| 3142 | 1(15) | Ph | Ph | H | H | H | H | H | H | N-26 | — | — | — | — | — | — |
| 3143 | 1(15) | Ph | Ph | H | H | H | H | H | H | N-27 | — | — | — | — | — | — |
| 3144 | 1(15) | Ph | Ph | H | H | H | H | H | H | N-28 | — | — | — | — | — | — |
| 3145 | 1(15) | Ph | Ph | H | H | H | H | H | H | N-29 | — | — | — | — | — | — |
| 3146 | 1(15) | Ph | Ph | H | H | H | H | H | H | N-30 | — | — | — | — | — | — |
| 3147 | 1(15) | Ph | Ph | H | H | H | H | H | H | N-31 | — | — | — | — | — | — |
| 3148 | 1(15) | Ph | Ph | H | H | H | H | H | H | N-32 | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 3149 | 1(15) | Ph | Ph | H | H | H | H | H | H | N-33 | — | — | — | — | — | — |
| 3150 | 1(15) | Ph | Ph | H | H | H | H | H | H | N-34 | — | — | — | — | — | — |
| 3151 | 1(15) | Ph | Ph | H | H | H | H | H | H | N-35 | — | — | — | — | — | — |
| 3152 | 1(15) | Ph | Ph | H | H | H | H | H | H | N-36 | — | — | — | — | — | — |
| 3153 | 1(15) | Ph | Ph | H | H | H | H | H | H | N-37 | — | — | — | — | — | — |
| 3154 | 1(15) | Ph | Ph | H | H | H | H | H | H | N-38 | — | — | — | — | — | — |
| 3155 | 1(15) | Ph | Ph | H | H | H | H | H | H | N-39 | — | — | — | — | — | — |
| 3156 | 1(15) | Ph | Ph | H | H | H | H | H | H | N-40 | — | — | — | — | — | — |
| 3157 | 1(15) | Ph | Ph | H | H | H | H | H | H | N-41 | — | — | — | — | — | — |
| 3158 | 1(16) | Mes | — | H | N-1 | H | H | H | H | H | — | — | — | — | — | — |
| 3159 | 1(16) | Mes | — | H | N-2 | H | H | H | H | H | — | — | — | — | — | — |
| 3160 | 1(16) | Mes | — | H | N-3 | H | H | H | H | H | — | — | — | — | — | — |
| 3161 | 1(16) | Mes | — | H | N-4 | H | H | H | H | H | — | — | — | — | — | — |
| 3162 | 1(16) | Mes | — | H | N-5 | H | H | H | H | H | — | — | — | — | — | — |
| 3163 | 1(16) | Mes | — | H | N-6 | H | H | H | H | H | — | — | — | — | — | — |
| 3164 | 1(16) | Mes | — | H | N-7 | H | H | H | H | H | — | — | — | — | — | — |
| 3165 | 1(16) | Mes | — | H | N-8 | H | H | H | H | H | — | — | — | — | — | — |
| 3166 | 1(16) | Mes | — | H | N-9 | H | H | H | H | H | — | — | — | — | — | — |
| 3167 | 1(16) | Mes | — | H | N-10 | H | H | H | H | H | — | — | — | — | — | — |
| 3168 | 1(16) | Mes | — | H | N-11 | H | H | H | H | H | — | — | — | — | — | — |
| 3169 | 1(16) | Mes | — | H | N-12 | H | H | H | H | H | — | — | — | — | — | — |
| 3170 | 1(16) | Mes | — | H | N-13 | H | H | H | H | H | — | — | — | — | — | — |
| 3171 | 1(16) | Mes | — | H | N-14 | H | H | H | H | H | — | — | — | — | — | — |
| 3172 | 1(16) | Mes | — | H | N-15 | H | H | H | H | H | — | — | — | — | — | — |
| 3173 | 1(16) | Mes | — | H | N-16 | H | H | H | H | H | — | — | — | — | — | — |
| 3174 | 1(16) | Mes | — | H | N-17 | H | H | H | H | H | — | — | — | — | — | — |
| 3175 | 1(16) | Mes | — | H | N-18 | H | H | H | H | H | — | — | — | — | — | — |
| 3176 | 1(16) | Mes | — | H | N-19 | H | H | H | H | H | — | — | — | — | — | — |
| 3177 | 1(16) | Mes | — | H | N-20 | H | H | H | H | H | — | — | — | — | — | — |
| 3178 | 1(16) | Mes | — | H | N-21 | H | H | H | H | H | — | — | — | — | — | — |
| 3179 | 1(16) | Mes | — | H | N-22 | H | H | H | H | H | — | — | — | — | — | — |
| 3180 | 1(16) | Mes | — | H | N-23 | H | H | H | H | H | — | — | — | — | — | — |
| 3181 | 1(16) | Mes | — | H | N-24 | H | H | H | H | H | — | — | — | — | — | — |
| 3182 | 1(16) | Mes | — | H | N-25 | H | H | H | H | H | — | — | — | — | — | — |
| 3183 | 1(16) | Mes | — | H | N-26 | H | H | H | H | H | — | — | — | — | — | — |
| 3184 | 1(16) | Mes | — | H | N-27 | H | H | H | H | H | — | — | — | — | — | — |
| 3185 | 1(16) | Mes | — | H | N-28 | H | H | H | H | H | — | — | — | — | — | — |
| 3186 | 1(16) | Mes | — | H | N-29 | H | H | H | H | H | — | — | — | — | — | — |
| 3187 | 1(16) | Mes | — | H | N-30 | H | H | H | H | H | — | — | — | — | — | — |
| 3188 | 1(16) | Mes | — | H | N-31 | H | H | H | H | H | — | — | — | — | — | — |
| 3189 | 1(16) | Mes | — | H | N-32 | H | H | H | H | H | — | — | — | — | — | — |
| 3190 | 1(16) | Mes | — | H | N-33 | H | H | H | H | H | — | — | — | — | — | — |
| 3191 | 1(16) | Mes | — | H | N-34 | H | H | H | H | H | — | — | — | — | — | — |
| 3192 | 1(16) | Mes | — | H | N-35 | H | H | H | H | H | — | — | — | — | — | — |
| 3193 | 1(16) | Mes | — | H | N-36 | H | H | H | H | H | — | — | — | — | — | — |
| 3194 | 1(16) | Mes | — | H | N-37 | H | H | H | H | H | — | — | — | — | — | — |
| 3195 | 1(16) | Mes | — | H | N-38 | H | H | H | H | H | — | — | — | — | — | — |
| 3196 | 1(16) | Mes | — | H | N-39 | H | H | H | H | H | — | — | — | — | — | — |
| 3197 | 1(16) | Mes | — | H | N-40 | H | H | H | H | H | — | — | — | — | — | — |
| 3198 | 1(16) | Mes | — | H | N-41 | H | H | H | H | H | — | — | — | — | — | — |
| 3199 | 1(16) | Mes | — | H | H | N-1 | H | H | H | H | — | — | — | — | — | — |
| 3200 | 1(16) | Mes | — | H | H | N-2 | H | H | H | H | — | — | — | — | — | — |
| 3201 | 1(16) | Mes | — | H | H | N-3 | H | H | H | H | — | — | — | — | — | — |
| 3202 | 1(16) | Mes | — | H | H | N-4 | H | H | H | H | — | — | — | — | — | — |
| 3203 | 1(16) | Mes | — | H | H | N-5 | H | H | H | H | — | — | — | — | — | — |
| 3204 | 1(16) | Mes | — | H | H | N-6 | H | H | H | H | — | — | — | — | — | — |
| 3205 | 1(16) | Mes | — | H | H | N-7 | H | H | H | H | — | — | — | — | — | — |
| 3206 | 1(16) | Mes | — | H | H | N-8 | H | H | H | H | — | — | — | — | — | — |
| 3207 | 1(16) | Mes | — | H | H | N-9 | H | H | H | H | — | — | — | — | — | — |
| 3208 | 1(16) | Mes | — | H | H | N-10 | H | H | H | H | — | — | — | — | — | — |
| 3209 | 1(16) | Mes | — | H | H | N-11 | H | H | H | H | — | — | — | — | — | — |
| 3210 | 1(16) | Mes | — | H | H | N-12 | H | H | H | H | — | — | — | — | — | — |
| 3211 | 1(16) | Mes | — | H | H | N-13 | H | H | H | H | — | — | — | — | — | — |
| 3212 | 1(16) | Mes | — | H | H | N-14 | H | H | H | H | — | — | — | — | — | — |
| 3213 | 1(16) | Mes | — | H | H | N-15 | H | H | H | H | — | — | — | — | — | — |
| 3214 | 1(16) | Mes | — | H | H | N-16 | H | H | H | H | — | — | — | — | — | — |
| 3215 | 1(16) | Mes | — | H | H | N-17 | H | H | H | H | — | — | — | — | — | — |
| 3216 | 1(16) | Mes | — | H | H | N-18 | H | H | H | H | — | — | — | — | — | — |
| 3217 | 1(16) | Mes | — | H | H | N-19 | H | H | H | H | — | — | — | — | — | — |
| 3218 | 1(16) | Mes | — | H | H | N-20 | H | H | H | H | — | — | — | — | — | — |
| 3219 | 1(16) | Mes | — | H | H | N-21 | H | H | H | H | — | — | — | — | — | — |
| 3220 | 1(16) | Mes | — | H | H | N-22 | H | H | H | H | — | — | — | — | — | — |
| 3221 | 1(16) | Mes | — | H | H | N-23 | H | H | H | H | — | — | — | — | — | — |
| 3222 | 1(16) | Mes | — | H | H | N-24 | H | H | H | H | — | — | — | — | — | — |
| 3223 | 1(16) | Mes | — | H | H | N-25 | H | H | H | H | — | — | — | — | — | — |
| 3224 | 1(16) | Mes | — | H | H | N-26 | H | H | H | H | — | — | — | — | — | — |
| 3225 | 1(16) | Mes | — | H | H | N-27 | H | H | H | H | — | — | — | — | — | — |
| 3226 | 1(16) | Mes | — | H | H | N-28 | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 3227 | 1(16) | Mes | — | H | H | N-29 | H | H | H | H | — | — | — | — | — | — |
| 3228 | 1(16) | Mes | — | H | H | N-30 | H | H | H | H | — | — | — | — | — | — |
| 3229 | 1(16) | Mes | — | H | H | N-31 | H | H | H | H | — | — | — | — | — | — |
| 3230 | 1(16) | Mes | — | H | H | N-32 | H | H | H | H | — | — | — | — | — | — |
| 3231 | 1(16) | Mes | — | H | H | N-33 | H | H | H | H | — | — | — | — | — | — |
| 3232 | 1(16) | Mes | — | H | H | N-34 | H | H | H | H | — | — | — | — | — | — |
| 3233 | 1(16) | Mes | — | H | H | N-35 | H | H | H | H | — | — | — | — | — | — |
| 3234 | 1(16) | Mes | — | H | H | N-36 | H | H | H | H | — | — | — | — | — | — |
| 3235 | 1(16) | Mes | — | H | H | N-37 | H | H | H | H | — | — | — | — | — | — |
| 3236 | 1(16) | Mes | — | H | H | N-38 | H | H | H | H | — | — | — | — | — | — |
| 3237 | 1(16) | Mes | — | H | H | N-39 | H | H | H | H | — | — | — | — | — | — |
| 3238 | 1(16) | Mes | — | H | H | N-40 | H | H | H | H | — | — | — | — | — | — |
| 3239 | 1(16) | Mes | — | H | H | N-41 | H | H | H | H | — | — | — | — | — | — |
| 3240 | 1(16) | Mes | — | H | H | H | H | H | N-1 | H | — | — | — | — | — | — |
| 3241 | 1(16) | Mes | — | H | H | H | H | H | N-2 | H | — | — | — | — | — | — |
| 3242 | 1(16) | Mes | — | H | H | H | H | H | N-3 | H | — | — | — | — | — | — |
| 3243 | 1(16) | Mes | — | H | H | H | H | H | N-4 | H | — | — | — | — | — | — |
| 3244 | 1(16) | Mes | — | H | H | H | H | H | N-5 | H | — | — | — | — | — | — |
| 3245 | 1(16) | Mes | — | H | H | H | H | H | N-6 | H | — | — | — | — | — | — |
| 3246 | 1(16) | Mes | — | H | H | H | H | H | N-7 | H | — | — | — | — | — | — |
| 3247 | 1(16) | Mes | — | H | H | H | H | H | N-8 | H | — | — | — | — | — | — |
| 3248 | 1(16) | Mes | — | H | H | H | H | H | N-9 | H | — | — | — | — | — | — |
| 3249 | 1(16) | Mes | — | H | H | H | H | H | N-10 | H | — | — | — | — | — | — |
| 3250 | 1(16) | Mes | — | H | H | H | H | H | N-11 | H | — | — | — | — | — | — |
| 3251 | 1(16) | Mes | — | H | H | H | H | H | N-12 | H | — | — | — | — | — | — |
| 3252 | 1(16) | Mes | — | H | H | H | H | H | N-13 | H | — | — | — | — | — | — |
| 3253 | 1(16) | Mes | — | H | H | H | H | H | N-14 | H | — | — | — | — | — | — |
| 3254 | 1(16) | Mes | — | H | H | H | H | H | N-15 | H | — | — | — | — | — | — |
| 3255 | 1(16) | Mes | — | H | H | H | H | H | N-16 | H | — | — | — | — | — | — |
| 3256 | 1(16) | Mes | — | H | H | H | H | H | N-17 | H | — | — | — | — | — | — |
| 3257 | 1(16) | Mes | — | H | H | H | H | H | N-18 | H | — | — | — | — | — | — |
| 3258 | 1(16) | Mes | — | H | H | H | H | H | N-19 | H | — | — | — | — | — | — |
| 3259 | 1(16) | Mes | — | H | H | H | H | H | N-20 | H | — | — | — | — | — | — |
| 3260 | 1(16) | Mes | — | H | H | H | H | H | N-21 | H | — | — | — | — | — | — |
| 3261 | 1(16) | Mes | — | H | H | H | H | H | N-22 | H | — | — | — | — | — | — |
| 3262 | 1(16) | Mes | — | H | H | H | H | H | N-23 | H | — | — | — | — | — | — |
| 3263 | 1(16) | Mes | — | H | H | H | H | H | N-24 | H | — | — | — | — | — | — |
| 3264 | 1(16) | Mes | — | H | H | H | H | H | N-25 | H | — | — | — | — | — | — |
| 3265 | 1(16) | Mes | — | H | H | H | H | H | N-26 | H | — | — | — | — | — | — |
| 3266 | 1(16) | Mes | — | H | H | H | H | H | N-27 | H | — | — | — | — | — | — |
| 3267 | 1(16) | Mes | — | H | H | H | H | H | N-28 | H | — | — | — | — | — | — |
| 3268 | 1(16) | Mes | — | H | H | H | H | H | N-29 | H | — | — | — | — | — | — |
| 3269 | 1(16) | Mes | — | H | H | H | H | H | N-30 | H | — | — | — | — | — | — |
| 3270 | 1(16) | Mes | — | H | H | H | H | H | N-31 | H | — | — | — | — | — | — |
| 3271 | 1(16) | Mes | — | H | H | H | H | H | N-32 | H | — | — | — | — | — | — |
| 3272 | 1(16) | Mes | — | H | H | H | H | H | N-33 | H | — | — | — | — | — | — |
| 3273 | 1(16) | Mes | — | H | H | H | H | H | N-34 | H | — | — | — | — | — | — |
| 3274 | 1(16) | Mes | — | H | H | H | H | H | N-35 | H | — | — | — | — | — | — |
| 3275 | 1(16) | Mes | — | H | H | H | H | H | N-36 | H | — | — | — | — | — | — |
| 3276 | 1(16) | Mes | — | H | H | H | H | H | N-37 | H | — | — | — | — | — | — |
| 3277 | 1(16) | Mes | — | H | H | H | H | H | N-38 | H | — | — | — | — | — | — |
| 3278 | 1(16) | Mes | — | H | H | H | H | H | N-39 | H | — | — | — | — | — | — |
| 3279 | 1(16) | Mes | — | H | H | H | H | H | N-40 | H | — | — | — | — | — | — |
| 3280 | 1(16) | Mes | — | H | H | H | H | H | N-41 | H | — | — | — | — | — | — |
| 3281 | 1(17) | Mes | — | H | N-1 | H | H | H | H | H | H | H | H | H | H | H |
| 3282 | 1(17) | Mes | — | H | N-2 | H | H | H | H | H | H | H | H | H | H | H |
| 3283 | 1(17) | Mes | — | H | N-3 | H | H | H | H | H | H | H | H | H | H | H |
| 3284 | 1(17) | Mes | — | H | N-4 | H | H | H | H | H | H | H | H | H | H | H |
| 3285 | 1(17) | Mes | — | H | N-5 | H | H | H | H | H | H | H | H | H | H | H |
| 3286 | 1(17) | Mes | — | H | N-6 | H | H | H | H | H | H | H | H | H | H | H |
| 3287 | 1(17) | Mes | — | H | N-7 | H | H | H | H | H | H | H | H | H | H | H |
| 3288 | 1(17) | Mes | — | H | N-8 | H | H | H | H | H | H | H | H | H | H | H |
| 3289 | 1(17) | Mes | — | H | N-9 | H | H | H | H | H | H | H | H | H | H | H |
| 3290 | 1(17) | Mes | — | H | N-10 | H | H | H | H | H | H | H | H | H | H | H |
| 3291 | 1(17) | Mes | — | H | N-11 | H | H | H | H | H | H | H | H | H | H | H |
| 3292 | 1(17) | Mes | — | H | N-12 | H | H | H | H | H | H | H | H | H | H | H |
| 3293 | 1(17) | Mes | — | H | N-13 | H | H | H | H | H | H | H | H | H | H | H |
| 3294 | 1(17) | Mes | — | H | N-14 | H | H | H | H | H | H | H | H | H | H | H |
| 3295 | 1(17) | Mes | — | H | N-15 | H | H | H | H | H | H | H | H | H | H | H |
| 3296 | 1(17) | Mes | — | H | N-16 | H | H | H | H | H | H | H | H | H | H | H |
| 3297 | 1(17) | Mes | — | H | N-17 | H | H | H | H | H | H | H | H | H | H | H |
| 3298 | 1(17) | Mes | — | H | N-18 | H | H | H | H | H | H | H | H | H | H | H |
| 3299 | 1(17) | Mes | — | H | N-19 | H | H | H | H | H | H | H | H | H | H | H |
| 3300 | 1(17) | Mes | — | H | N-20 | H | H | H | H | H | H | H | H | H | H | H |
| 3301 | 1(17) | Mes | — | H | N-21 | H | H | H | H | H | H | H | H | H | H | H |
| 3302 | 1(17) | Mes | — | H | N-22 | H | H | H | H | H | H | H | H | H | H | H |
| 3303 | 1(17) | Mes | — | H | N-23 | H | H | H | H | H | H | H | H | H | H | H |
| 3304 | 1(17) | Mes | — | H | N-24 | H | H | H | H | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 3305 | 1(17) | Mes | — | H | N-25 | H | H | H | H | H | H | H | H | H | H | H |
| 3306 | 1(17) | Mes | — | H | N-26 | H | H | H | H | H | H | H | H | H | H | H |
| 3307 | 1(17) | Mes | — | H | N-27 | H | H | H | H | H | H | H | H | H | H | H |
| 3308 | 1(17) | Mes | — | H | N-28 | H | H | H | H | H | H | H | H | H | H | H |
| 3309 | 1(17) | Mes | — | H | N-29 | H | H | H | H | H | H | H | H | H | H | H |
| 3310 | 1(17) | Mes | — | H | N-30 | H | H | H | H | H | H | H | H | H | H | H |
| 3311 | 1(17) | Mes | — | H | N-31 | H | H | H | H | H | H | H | H | H | H | H |
| 3312 | 1(17) | Mes | — | H | N-32 | H | H | H | H | H | H | H | H | H | H | H |
| 3313 | 1(17) | Mes | — | H | N-33 | H | H | H | H | H | H | H | H | H | H | H |
| 3314 | 1(17) | Mes | — | H | N-34 | H | H | H | H | H | H | H | H | H | H | H |
| 3315 | 1(17) | Mes | — | H | N-35 | H | H | H | H | H | H | H | H | H | H | H |
| 3316 | 1(17) | Mes | — | H | N-36 | H | H | H | H | H | H | H | H | H | H | H |
| 3317 | 1(17) | Mes | — | H | N-37 | H | H | H | H | H | H | H | H | H | H | H |
| 3318 | 1(17) | Mes | — | H | N-38 | H | H | H | H | H | H | H | H | H | H | H |
| 3319 | 1(17) | Mes | — | H | N-39 | H | H | H | H | H | H | H | H | H | H | H |
| 3320 | 1(17) | Mes | — | H | N-40 | H | H | H | H | H | H | H | H | H | H | H |
| 3321 | 1(17) | Mes | — | H | N-41 | H | H | H | H | H | H | H | H | H | H | H |
| 3322 | 1(17) | Mes | — | H | H | N-1 | H | H | H | H | H | H | H | H | H | H |
| 3323 | 1(17) | Mes | — | H | H | N-2 | H | H | H | H | H | H | H | H | H | H |
| 3324 | 1(17) | Mes | — | H | H | N-3 | H | H | H | H | H | H | H | H | H | H |
| 3325 | 1(17) | Mes | — | H | H | N-4 | H | H | H | H | H | H | H | H | H | H |
| 3326 | 1(17) | Mes | — | H | H | N-5 | H | H | H | H | H | H | H | H | H | H |
| 3327 | 1(17) | Mes | — | H | H | N-6 | H | H | H | H | H | H | H | H | H | H |
| 3328 | 1(17) | Mes | — | H | H | N-7 | H | H | H | H | H | H | H | H | H | H |
| 3329 | 1(17) | Mes | — | H | H | N-8 | H | H | H | H | H | H | H | H | H | H |
| 3330 | 1(17) | Mes | — | H | H | N-9 | H | H | H | H | H | H | H | H | H | H |
| 3331 | 1(17) | Mes | — | H | H | N-10 | H | H | H | H | H | H | H | H | H | H |
| 3332 | 1(17) | Mes | — | H | H | N-11 | H | H | H | H | H | H | H | H | H | H |
| 3333 | 1(17) | Mes | — | H | H | N-12 | H | H | H | H | H | H | H | H | H | H |
| 3334 | 1(17) | Mes | — | H | H | N-13 | H | H | H | H | H | H | H | H | H | H |
| 3335 | 1(17) | Mes | — | H | H | N-14 | H | H | H | H | H | H | H | H | H | H |
| 3336 | 1(17) | Mes | — | H | H | N-15 | H | H | H | H | H | H | H | H | H | H |
| 3337 | 1(17) | Mes | — | H | H | N-16 | H | H | H | H | H | H | H | H | H | H |
| 3338 | 1(17) | Mes | — | H | H | N-17 | H | H | H | H | H | H | H | H | H | H |
| 3339 | 1(17) | Mes | — | H | H | N-18 | H | H | H | H | H | H | H | H | H | H |
| 3340 | 1(17) | Mes | — | H | H | N-19 | H | H | H | H | H | H | H | H | H | H |
| 3341 | 1(17) | Mes | — | H | H | N-20 | H | H | H | H | H | H | H | H | H | H |
| 3342 | 1(17) | Mes | — | H | H | N-21 | H | H | H | H | H | H | H | H | H | H |
| 3343 | 1(17) | Mes | — | H | H | N-22 | H | H | H | H | H | H | H | H | H | H |
| 3344 | 1(17) | Mes | — | H | H | N-23 | H | H | H | H | H | H | H | H | H | H |
| 3345 | 1(17) | Mes | — | H | H | N-24 | H | H | H | H | H | H | H | H | H | H |
| 3346 | 1(17) | Mes | — | H | H | N-25 | H | H | H | H | H | H | H | H | H | H |
| 3347 | 1(17) | Mes | — | H | H | N-26 | H | H | H | H | H | H | H | H | H | H |
| 3348 | 1(17) | Mes | — | H | H | N-27 | H | H | H | H | H | H | H | H | H | H |
| 3349 | 1(17) | Mes | — | H | H | N-28 | H | H | H | H | H | H | H | H | H | H |
| 3350 | 1(17) | Mes | — | H | H | N-29 | H | H | H | H | H | H | H | H | H | H |
| 3351 | 1(17) | Mes | — | H | H | N-30 | H | H | H | H | H | H | H | H | H | H |
| 3352 | 1(17) | Mes | — | H | H | N-31 | H | H | H | H | H | H | H | H | H | H |
| 3353 | 1(17) | Mes | — | H | H | N-32 | H | H | H | H | H | H | H | H | H | H |
| 3354 | 1(17) | Mes | — | H | H | N-33 | H | H | H | H | H | H | H | H | H | H |
| 3355 | 1(17) | Mes | — | H | H | N-34 | H | H | H | H | H | H | H | H | H | H |
| 3356 | 1(17) | Mes | — | H | H | N-35 | H | H | H | H | H | H | H | H | H | H |
| 3357 | 1(17) | Mes | — | H | H | N-36 | H | H | H | H | H | H | H | H | H | H |
| 3358 | 1(17) | Mes | — | H | H | N-37 | H | H | H | H | H | H | H | H | H | H |
| 3359 | 1(17) | Mes | — | H | H | N-38 | H | H | H | H | H | H | H | H | H | H |
| 3360 | 1(17) | Mes | — | H | H | N-39 | H | H | H | H | H | H | H | H | H | H |
| 3361 | 1(17) | Mes | — | H | H | N-40 | H | H | H | H | H | H | H | H | H | H |
| 3362 | 1(17) | Mes | — | H | H | N-41 | H | H | H | H | H | H | H | H | H | H |
| 3363 | 1(17) | Mes | — | H | H | H | H | H | N-1 | H | H | H | H | H | H | H |
| 3364 | 1(17) | Mes | — | H | H | H | H | H | N-2 | H | H | H | H | H | H | H |
| 3365 | 1(17) | Mes | — | H | H | H | H | H | N-3 | H | H | H | H | H | H | H |
| 3366 | 1(17) | Mes | — | H | H | H | H | H | N-4 | H | H | H | H | H | H | H |
| 3367 | 1(17) | Mes | — | H | H | H | H | H | N-5 | H | H | H | H | H | H | H |
| 3368 | 1(17) | Mes | — | H | H | H | H | H | N-6 | H | H | H | H | H | H | H |
| 3369 | 1(17) | Mes | — | H | H | H | H | H | N-7 | H | H | H | H | H | H | H |
| 3370 | 1(17) | Mes | — | H | H | H | H | H | N-8 | H | H | H | H | H | H | H |
| 3371 | 1(17) | Mes | — | H | H | H | H | H | N-9 | H | H | H | H | H | H | H |
| 3372 | 1(17) | Mes | — | H | H | H | H | H | N-10 | H | H | H | H | H | H | H |
| 3373 | 1(17) | Mes | — | H | H | H | H | H | N-11 | H | H | H | H | H | H | H |
| 3374 | 1(17) | Mes | — | H | H | H | H | H | N-12 | H | H | H | H | H | H | H |
| 3375 | 1(17) | Mes | — | H | H | H | H | H | N-13 | H | H | H | H | H | H | H |
| 3376 | 1(17) | Mes | — | H | H | H | H | H | N-14 | H | H | H | H | H | H | H |
| 3377 | 1(17) | Mes | — | H | H | H | H | H | N-15 | H | H | H | H | H | H | H |
| 3378 | 1(17) | Mes | — | H | H | H | H | H | N-16 | H | H | H | H | H | H | H |
| 3379 | 1(17) | Mes | — | H | H | H | H | H | N-17 | H | H | H | H | H | H | H |
| 3380 | 1(17) | Mes | — | H | H | H | H | H | N-18 | H | H | H | H | H | H | H |
| 3381 | 1(17) | Mes | — | H | H | H | H | H | N-19 | H | H | H | H | H | H | H |
| 3382 | 1(17) | Mes | — | H | H | H | H | H | N-20 | H | H | H | H | H | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 3383 | 1(17) | Mes | — | H | H | H | H | H | N-21 | H | H | H | H | H | H | H |
| 3384 | 1(17) | Mes | — | H | H | H | H | H | N-22 | H | H | H | H | H | H | H |
| 3385 | 1(17) | Mes | — | H | H | H | H | H | N-23 | H | H | H | H | H | H | H |
| 3386 | 1(17) | Mes | — | H | H | H | H | H | N-24 | H | H | H | H | H | H | H |
| 3387 | 1(17) | Mes | — | H | H | H | H | H | N-25 | H | H | H | H | H | H | H |
| 3388 | 1(17) | Mes | — | H | H | H | H | H | N-26 | H | H | H | H | H | H | H |
| 3389 | 1(17) | Mes | — | H | H | H | H | H | N-27 | H | H | H | H | H | H | H |
| 3390 | 1(17) | Mes | — | H | H | H | H | H | N-28 | H | H | H | H | H | H | H |
| 3391 | 1(17) | Mes | — | H | H | H | H | H | N-29 | H | H | H | H | H | H | H |
| 3392 | 1(17) | Mes | — | H | H | H | H | H | N-30 | H | H | H | H | H | H | H |
| 3393 | 1(17) | Mes | — | H | H | H | H | H | N-31 | H | H | H | H | H | H | H |
| 3394 | 1(17) | Mes | — | H | H | H | H | H | N-32 | H | H | H | H | H | H | H |
| 3395 | 1(17) | Mes | — | H | H | H | H | H | N-33 | H | H | H | H | H | H | H |
| 3396 | 1(17) | Mes | — | H | H | H | H | H | N-34 | H | H | H | H | H | H | H |
| 3397 | 1(17) | Mes | — | H | H | H | H | H | N-35 | H | H | H | H | H | H | H |
| 3398 | 1(17) | Mes | — | H | H | H | H | H | N-36 | H | H | H | H | H | H | H |
| 3399 | 1(17) | Mes | — | H | H | H | H | H | N-37 | H | H | H | H | H | H | H |
| 3400 | 1(17) | Mes | — | H | H | H | H | H | N-38 | H | H | H | H | H | H | H |
| 3401 | 1(17) | Mes | — | H | H | H | H | H | N-39 | H | H | H | H | H | H | H |
| 3402 | 1(17) | Mes | — | H | H | H | H | H | N-40 | H | H | H | H | H | H | H |
| 3403 | 1(17) | Mes | — | H | H | H | H | H | N-41 | H | H | H | H | H | H | H |
| 3404 | 1(17) | Mes | — | H | H | H | H | H | H | H | H | H | N-1 | H | H | H |
| 3405 | 1(17) | Mes | — | H | H | H | H | H | H | H | H | H | N-2 | H | H | H |
| 3406 | 1(17) | Mes | — | H | H | H | H | H | H | H | H | H | N-3 | H | H | H |
| 3407 | 1(17) | Mes | — | H | H | H | H | H | H | H | H | H | N-4 | H | H | H |
| 3408 | 1(17) | Mes | — | H | H | H | H | H | H | H | H | H | N-5 | H | H | H |
| 3409 | 1(17) | Mes | — | H | H | H | H | H | H | H | H | H | N-6 | H | H | H |
| 3410 | 1(17) | Mes | — | H | H | H | H | H | H | H | H | H | N-7 | H | H | H |
| 3411 | 1(17) | Mes | — | H | H | H | H | H | H | H | H | H | N-8 | H | H | H |
| 3412 | 1(17) | Mes | — | H | H | H | H | H | H | H | H | H | N-9 | H | H | H |
| 3413 | 1(17) | Mes | — | H | H | H | H | H | H | H | H | H | N-10 | H | H | H |
| 3414 | 1(17) | Mes | — | H | H | H | H | H | H | H | H | H | N-11 | H | H | H |
| 3415 | 1(17) | Mes | — | H | H | H | H | H | H | H | H | H | N-12 | H | H | H |
| 3416 | 1(17) | Mes | — | H | H | H | H | H | H | H | H | H | N-13 | H | H | H |
| 3417 | 1(17) | Mes | — | H | H | H | H | H | H | H | H | H | N-14 | H | H | H |
| 3418 | 1(17) | Mes | — | H | H | H | H | H | H | H | H | H | N-15 | H | H | H |
| 3419 | 1(17) | Mes | — | H | H | H | H | H | H | H | H | H | N-16 | H | H | H |
| 3420 | 1(17) | Mes | — | H | H | H | H | H | H | H | H | H | N-17 | H | H | H |
| 3421 | 1(17) | Mes | — | H | H | H | H | H | H | H | H | H | N-18 | H | H | H |
| 3422 | 1(17) | Mes | — | H | H | H | H | H | H | H | H | H | N-19 | H | H | H |
| 3423 | 1(17) | Mes | — | H | H | H | H | H | H | H | H | H | N-20 | H | H | H |
| 3424 | 1(17) | Mes | — | H | H | H | H | H | H | H | H | H | N-21 | H | H | H |
| 3425 | 1(17) | Mes | — | H | H | H | H | H | H | H | H | H | N-22 | H | H | H |
| 3426 | 1(17) | Mes | — | H | H | H | H | H | H | H | H | H | N-23 | H | H | H |
| 3427 | 1(17) | Mes | — | H | H | H | H | H | H | H | H | H | N-24 | H | H | H |
| 3428 | 1(17) | Mes | — | H | H | H | H | H | H | H | H | H | N-25 | H | H | H |
| 3429 | 1(17) | Mes | — | H | H | H | H | H | H | H | H | H | N-26 | H | H | H |
| 3430 | 1(17) | Mes | — | H | H | H | H | H | H | H | H | H | N-27 | H | H | H |
| 3431 | 1(17) | Mes | — | H | H | H | H | H | H | H | H | H | N-28 | H | H | H |
| 3432 | 1(17) | Mes | — | H | H | H | H | H | H | H | H | H | N-29 | H | H | H |
| 3433 | 1(17) | Mes | — | H | H | H | H | H | H | H | H | H | N-30 | H | H | H |
| 3434 | 1(17) | Mes | — | H | H | H | H | H | H | H | H | H | N-31 | H | H | H |
| 3435 | 1(17) | Mes | — | H | H | H | H | H | H | H | H | H | N-32 | H | H | H |
| 3436 | 1(17) | Mes | — | H | H | H | H | H | H | H | H | H | N-33 | H | H | H |
| 3437 | 1(17) | Mes | — | H | H | H | H | H | H | H | H | H | N-34 | H | H | H |
| 3438 | 1(17) | Mes | — | H | H | H | H | H | H | H | H | H | N-35 | H | H | H |
| 3439 | 1(17) | Mes | — | H | H | H | H | H | H | H | H | H | N-36 | H | H | H |
| 3440 | 1(17) | Mes | — | H | H | H | H | H | H | H | H | H | N-37 | H | H | H |
| 3441 | 1(17) | Mes | — | H | H | H | H | H | H | H | H | H | N-38 | H | H | H |
| 3442 | 1(17) | Mes | — | H | H | H | H | H | H | H | H | H | N-39 | H | H | H |
| 3443 | 1(17) | Mes | — | H | H | H | H | H | H | H | H | H | N-40 | H | H | H |
| 3444 | 1(17) | Mes | — | H | H | H | H | H | H | H | H | H | N-41 | H | H | H |
| 3445 | 1(17) | Mes | — | H | H | H | H | H | H | H | H | H | H | N-1 | H | H |
| 3446 | 1(17) | Mes | — | H | H | H | H | H | H | H | H | H | H | N-2 | H | H |
| 3447 | 1(17) | Mes | — | H | H | H | H | H | H | H | H | H | H | N-3 | H | H |
| 3448 | 1(17) | Mes | — | H | H | H | H | H | H | H | H | H | H | N-4 | H | H |
| 3449 | 1(17) | Mes | — | H | H | H | H | H | H | H | H | H | H | N-5 | H | H |
| 3450 | 1(17) | Mes | — | H | H | H | H | H | H | H | H | H | H | N-6 | H | H |
| 3451 | 1(17) | Mes | — | H | H | H | H | H | H | H | H | H | H | N-7 | H | H |
| 3452 | 1(17) | Mes | — | H | H | H | H | H | H | H | H | H | H | N-8 | H | H |
| 3453 | 1(17) | Mes | — | H | H | H | H | H | H | H | H | H | H | N-9 | H | H |
| 3454 | 1(17) | Mes | — | H | H | H | H | H | H | H | H | H | H | N-10 | H | H |
| 3455 | 1(17) | Mes | — | H | H | H | H | H | H | H | H | H | H | N-11 | H | H |
| 3456 | 1(17) | Mes | — | H | H | H | H | H | H | H | H | H | H | N-12 | H | H |
| 3457 | 1(17) | Mes | — | H | H | H | H | H | H | H | H | H | H | N-13 | H | H |
| 3458 | 1(17) | Mes | — | H | H | H | H | H | H | H | H | H | H | N-14 | H | H |
| 3459 | 1(17) | Mes | — | H | H | H | H | H | H | H | H | H | H | N-15 | H | H |
| 3460 | 1(17) | Mes | — | H | H | H | H | H | H | H | H | H | H | N-16 | H | H |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 3461 | 1(17) | Mes | — | H | H | H | H | H | H | H | H | H | H | N-17 | H | H |
| 3462 | 1(17) | Mes | — | H | H | H | H | H | H | H | H | H | H | N-18 | H | H |
| 3463 | 1(17) | Mes | — | H | H | H | H | H | H | H | H | H | H | N-19 | H | H |
| 3464 | 1(17) | Mes | — | H | H | H | H | H | H | H | H | H | H | N-20 | H | H |
| 3465 | 1(17) | Mes | — | H | H | H | H | H | H | H | H | H | H | N-21 | H | H |
| 3466 | 1(17) | Mes | — | H | H | H | H | H | H | H | H | H | H | N-22 | H | H |
| 3467 | 1(17) | Mes | — | H | H | H | H | H | H | H | H | H | H | N-23 | H | H |
| 3468 | 1(17) | Mes | — | H | H | H | H | H | H | H | H | H | H | N-24 | H | H |
| 3469 | 1(17) | Mes | — | H | H | H | H | H | H | H | H | H | H | N-25 | H | H |
| 3470 | 1(17) | Mes | — | H | H | H | H | H | H | H | H | H | H | N-26 | H | H |
| 3471 | 1(17) | Mes | — | H | H | H | H | H | H | H | H | H | H | N-27 | H | H |
| 3472 | 1(17) | Mes | — | H | H | H | H | H | H | H | H | H | H | N-28 | H | H |
| 3473 | 1(17) | Mes | — | H | H | H | H | H | H | H | H | H | H | N-29 | H | H |
| 3474 | 1(17) | Mes | — | H | H | H | H | H | H | H | H | H | H | N-30 | H | H |
| 3475 | 1(17) | Mes | — | H | H | H | H | H | H | H | H | H | H | N-31 | H | H |
| 3476 | 1(17) | Mes | — | H | H | H | H | H | H | H | H | H | H | N-32 | H | H |
| 3477 | 1(17) | Mes | — | H | H | H | H | H | H | H | H | H | H | N-33 | H | H |
| 3478 | 1(17) | Mes | — | H | H | H | H | H | H | H | H | H | H | N-34 | H | H |
| 3479 | 1(17) | Mes | — | H | H | H | H | H | H | H | H | H | H | N-35 | H | H |
| 3480 | 1(17) | Mes | — | H | H | H | H | H | H | H | H | H | H | N-36 | H | H |
| 3481 | 1(17) | Mes | — | H | H | H | H | H | H | H | H | H | H | N-37 | H | H |
| 3482 | 1(17) | Mes | — | H | H | H | H | H | H | H | H | H | H | N-38 | H | H |
| 3483 | 1(17) | Mes | — | H | H | H | H | H | H | H | H | H | H | N-39 | H | H |
| 3484 | 1(17) | Mes | — | H | H | H | H | H | H | H | H | H | H | N-40 | H | H |
| 3485 | 1(17) | Mes | — | H | H | H | H | H | H | H | H | H | H | N-41 | H | H |
| 3486 | 1(18) | Mes | — | H | N-1 | H | H | H | H | H | — | — | — | — | — | — |
| 3487 | 1(18) | Mes | — | H | N-2 | H | H | H | H | H | — | — | — | — | — | — |
| 3488 | 1(18) | Mes | — | H | N-3 | H | H | H | H | H | — | — | — | — | — | — |
| 3489 | 1(18) | Mes | — | H | N-4 | H | H | H | H | H | — | — | — | — | — | — |
| 3490 | 1(18) | Mes | — | H | N-5 | H | H | H | H | H | — | — | — | — | — | — |
| 3491 | 1(18) | Mes | — | H | N-6 | H | H | H | H | H | — | — | — | — | — | — |
| 3492 | 1(18) | Mes | — | H | N-7 | H | H | H | H | H | — | — | — | — | — | — |
| 3493 | 1(18) | Mes | — | H | N-8 | H | H | H | H | H | — | — | — | — | — | — |
| 3494 | 1(18) | Mes | — | H | N-9 | H | H | H | H | H | — | — | — | — | — | — |
| 3495 | 1(18) | Mes | — | H | N-10 | H | H | H | H | H | — | — | — | — | — | — |
| 3496 | 1(18) | Mes | — | H | N-11 | H | H | H | H | H | — | — | — | — | — | — |
| 3497 | 1(18) | Mes | — | H | N-12 | H | H | H | H | H | — | — | — | — | — | — |
| 3498 | 1(18) | Mes | — | H | N-13 | H | H | H | H | H | — | — | — | — | — | — |
| 3499 | 1(18) | Mes | — | H | N-14 | H | H | H | H | H | — | — | — | — | — | — |
| 3500 | 1(18) | Mes | — | H | N-15 | H | H | H | H | H | — | — | — | — | — | — |
| 3501 | 1(18) | Mes | — | H | N-16 | H | H | H | H | H | — | — | — | — | — | — |
| 3502 | 1(18) | Mes | — | H | N-17 | H | H | H | H | H | — | — | — | — | — | — |
| 3503 | 1(18) | Mes | — | H | N-18 | H | H | H | H | H | — | — | — | — | — | — |
| 3504 | 1(18) | Mes | — | H | N-19 | H | H | H | H | H | — | — | — | — | — | — |
| 3505 | 1(18) | Mes | — | H | N-20 | H | H | H | H | H | — | — | — | — | — | — |
| 3506 | 1(18) | Mes | — | H | N-21 | H | H | H | H | H | — | — | — | — | — | — |
| 3507 | 1(18) | Mes | — | H | N-22 | H | H | H | H | H | — | — | — | — | — | — |
| 3508 | 1(18) | Mes | — | H | N-23 | H | H | H | H | H | — | — | — | — | — | — |
| 3509 | 1(18) | Mes | — | H | N-24 | H | H | H | H | H | — | — | — | — | — | — |
| 3510 | 1(18) | Mes | — | H | N-25 | H | H | H | H | H | — | — | — | — | — | — |
| 3511 | 1(18) | Mes | — | H | N-26 | H | H | H | H | H | — | — | — | — | — | — |
| 3512 | 1(18) | Mes | — | H | N-27 | H | H | H | H | H | — | — | — | — | — | — |
| 3513 | 1(18) | Mes | — | H | N-28 | H | H | H | H | H | — | — | — | — | — | — |
| 3514 | 1(18) | Mes | — | H | N-29 | H | H | H | H | H | — | — | — | — | — | — |
| 3515 | 1(18) | Mes | — | H | N-30 | H | H | H | H | H | — | — | — | — | — | — |
| 3516 | 1(18) | Mes | — | H | N-31 | H | H | H | H | H | — | — | — | — | — | — |
| 3517 | 1(18) | Mes | — | H | N-32 | H | H | H | H | H | — | — | — | — | — | — |
| 3518 | 1(18) | Mes | — | H | N-33 | H | H | H | H | H | — | — | — | — | — | — |
| 3519 | 1(18) | Mes | — | H | N-34 | H | H | H | H | H | — | — | — | — | — | — |
| 3520 | 1(18) | Mes | — | H | N-35 | H | H | H | H | H | — | — | — | — | — | — |
| 3521 | 1(18) | Mes | — | H | N-36 | H | H | H | H | H | — | — | — | — | — | — |
| 3522 | 1(18) | Mes | — | H | N-37 | H | H | H | H | H | — | — | — | — | — | — |
| 3523 | 1(18) | Mes | — | H | N-38 | H | H | H | H | H | — | — | — | — | — | — |
| 3524 | 1(18) | Mes | — | H | N-39 | H | H | H | H | H | — | — | — | — | — | — |
| 3525 | 1(18) | Mes | — | H | N-40 | H | H | H | H | H | — | — | — | — | — | — |
| 3526 | 1(18) | Mes | — | H | N-41 | H | H | H | H | H | — | — | — | — | — | — |
| 3527 | 1(18) | Mes | — | H | H | N-1 | H | H | H | H | — | — | — | — | — | — |
| 3528 | 1(18) | Mes | — | H | H | N-2 | H | H | H | H | — | — | — | — | — | — |
| 3529 | 1(18) | Mes | — | H | H | N-3 | H | H | H | H | — | — | — | — | — | — |
| 3530 | 1(18) | Mes | — | H | H | N-4 | H | H | H | H | — | — | — | — | — | — |
| 3531 | 1(18) | Mes | — | H | H | N-5 | H | H | H | H | — | — | — | — | — | — |
| 3532 | 1(18) | Mes | — | H | H | N-6 | H | H | H | H | — | — | — | — | — | — |
| 3533 | 1(18) | Mes | — | H | H | N-7 | H | H | H | H | — | — | — | — | — | — |
| 3534 | 1(18) | Mes | — | H | H | N-8 | H | H | H | H | — | — | — | — | — | — |
| 3535 | 1(18) | Mes | — | H | H | N-9 | H | H | H | H | — | — | — | — | — | — |
| 3536 | 1(18) | Mes | — | H | H | N-10 | H | H | H | H | — | — | — | — | — | — |
| 3537 | 1(18) | Mes | — | H | H | N-11 | H | H | H | H | — | — | — | — | — | — |
| 3538 | 1(18) | Mes | — | H | H | N-12 | H | H | H | H | — | — | — | — | — | — |

TABLE 1-continued

| 화합물 | 화학식 | $R_4$ | $R_5$ | $R_{s1}$ | $R_{s2}$ | $R_{s3}$ | $R_{s4}$ | $R_{s5}$ | $R_{s6}$ | $R_{s7}$ | $R_{s8}$ | $R_{s9}$ | $R_{s10}$ | $R_{s11}$ | $R_{s12}$ | $R_{s13}$ |
|---|---|---|---|---|---|---|---|---|---|---|---|---|---|---|---|---|
| 3539 | 1(18) | Mes | — | H | H | N-13 | H | H | H | H | — | — | — | — | — | — |
| 3540 | 1(18) | Mes | — | H | H | N-14 | H | H | H | H | — | — | — | — | — | — |
| 3541 | 1(18) | Mes | — | H | H | N-15 | H | H | H | H | — | — | — | — | — | — |
| 3542 | 1(18) | Mes | — | H | H | N-16 | H | H | H | H | — | — | — | — | — | — |
| 3543 | 1(18) | Mes | — | H | H | N-17 | H | H | H | H | — | — | — | — | — | — |
| 3544 | 1(18) | Mes | — | H | H | N-18 | H | H | H | H | — | — | — | — | — | — |
| 3545 | 1(18) | Mes | — | H | H | N-19 | H | H | H | H | — | — | — | — | — | — |
| 3546 | 1(18) | Mes | — | H | H | N-20 | H | H | H | H | — | — | — | — | — | — |
| 3547 | 1(18) | Mes | — | H | H | N-21 | H | H | H | H | — | — | — | — | — | — |
| 3548 | 1(18) | Mes | — | H | H | N-22 | H | H | H | H | — | — | — | — | — | — |
| 3549 | 1(18) | Mes | — | H | H | N-23 | H | H | H | H | — | — | — | — | — | — |
| 3550 | 1(18) | Mes | — | H | H | N-24 | H | H | H | H | — | — | — | — | — | — |
| 3551 | 1(18) | Mes | — | H | H | N-25 | H | H | H | H | — | — | — | — | — | — |
| 3552 | 1(18) | Mes | — | H | H | N-26 | H | H | H | H | — | — | — | — | — | — |
| 3553 | 1(18) | Mes | — | H | H | N-27 | H | H | H | H | — | — | — | — | — | — |
| 3554 | 1(18) | Mes | — | H | H | N-28 | H | H | H | H | — | — | — | — | — | — |
| 3555 | 1(18) | Mes | — | H | H | N-29 | H | H | H | H | — | — | — | — | — | — |
| 3556 | 1(18) | Mes | — | H | H | N-30 | H | H | H | H | — | — | — | — | — | — |
| 3557 | 1(18) | Mes | — | H | H | N-31 | H | H | H | H | — | — | — | — | — | — |
| 3558 | 1(18) | Mes | — | H | H | N-32 | H | H | H | H | — | — | — | — | — | — |
| 3559 | 1(18) | Mes | — | H | H | N-33 | H | H | H | H | — | — | — | — | — | — |
| 3560 | 1(18) | Mes | — | H | H | N-34 | H | H | H | H | — | — | — | — | — | — |
| 3561 | 1(18) | Mes | — | H | H | N-35 | H | H | H | H | — | — | — | — | — | — |
| 5562 | 1(18) | Mes | — | H | H | N-36 | H | H | H | H | — | — | — | — | — | — |
| 3563 | 1(18) | Mes | — | H | H | N-37 | H | H | H | H | — | — | — | — | — | — |
| 3564 | 1(18) | Mes | — | H | H | N-38 | H | H | H | H | — | — | — | — | — | — |
| 3565 | 1(18) | Mes | — | H | H | N-39 | H | H | H | H | — | — | — | — | — | — |
| 3566 | 1(18) | Mes | — | H | H | N-40 | H | H | H | H | — | — | — | — | — | — |
| 3567 | 1(18) | Mes | — | H | H | N-41 | H | H | H | H | — | — | — | — | — | — |
| 3568 | 1(18) | Mes | — | H | H | H | H | H | H | N-1 | — | — | — | — | — | — |
| 3569 | 1(18) | Mes | — | H | H | H | H | H | H | N-2 | — | — | — | — | — | — |
| 3570 | 1(18) | Mes | — | H | H | H | H | H | H | N-3 | — | — | — | — | — | — |
| 3571 | 1(18) | Mes | — | H | H | H | H | H | H | N-4 | — | — | — | — | — | — |
| 3572 | 1(18) | Mes | — | H | H | H | H | H | H | N-5 | — | — | — | — | — | — |
| 3573 | 1(18) | Mes | — | H | H | H | H | H | H | N-6 | — | — | — | — | — | — |
| 3574 | 1(18) | Mes | — | H | H | H | H | H | H | N-7 | — | — | — | — | — | — |
| 3575 | 1(18) | Mes | — | H | H | H | H | H | H | N-8 | — | — | — | — | — | — |
| 3576 | 1(18) | Mes | — | H | H | H | H | H | H | N-9 | — | — | — | — | — | — |
| 3577 | 1(18) | Mes | — | H | H | H | H | H | H | N-10 | — | — | — | — | — | — |
| 3578 | 1(18) | Mes | — | H | H | H | H | H | H | N-11 | — | — | — | — | — | — |
| 3579 | 1(18) | Mes | — | H | H | H | H | H | H | N-12 | — | — | — | — | — | — |
| 3580 | 1(18) | Mes | — | H | H | H | H | H | H | N-13 | — | — | — | — | — | — |
| 3581 | 1(18) | Mes | — | H | H | H | H | H | H | N-14 | — | — | — | — | — | — |
| 3582 | 1(18) | Mes | — | H | H | H | H | H | H | N-15 | — | — | — | — | — | — |
| 3583 | 1(18) | Mes | — | H | H | H | H | H | H | N-16 | — | — | — | — | — | — |
| 3584 | 1(18) | Mes | — | H | H | H | H | H | H | N-17 | — | — | — | — | — | — |
| 3585 | 1(18) | Mes | — | H | H | H | H | H | H | N-18 | — | — | — | — | — | — |
| 3586 | 1(18) | Mes | — | H | H | H | H | H | H | N-19 | — | — | — | — | — | — |
| 3587 | 1(18) | Mes | — | H | H | H | H | H | H | N-20 | — | — | — | — | — | — |
| 3588 | 1(18) | Mes | — | H | H | H | H | H | H | N-21 | — | — | — | — | — | — |
| 3589 | 1(18) | Mes | — | H | H | H | H | H | H | N-22 | — | — | — | — | — | — |
| 3590 | 1(18) | Mes | — | H | H | H | H | H | H | N-23 | — | — | — | — | — | — |
| 3591 | 1(18) | Mes | — | H | H | H | H | H | H | N-24 | — | — | — | — | — | — |
| 3592 | 1(18) | Mes | — | H | H | H | H | H | H | N-25 | — | — | — | — | — | — |
| 3593 | 1(18) | Mes | — | H | H | H | H | H | H | N-26 | — | — | — | — | — | — |
| 3594 | 1(18) | Mes | — | H | H | H | H | H | H | N-27 | — | — | — | — | — | — |
| 3595 | 1(18) | Mes | — | H | H | H | H | H | H | N-28 | — | — | — | — | — | — |
| 3596 | 1(18) | Mes | — | H | H | H | H | H | H | N-29 | — | — | — | — | — | — |
| 3597 | 1(18) | Mes | — | H | H | H | H | H | H | N-30 | — | — | — | — | — | — |
| 3598 | 1(18) | Mes | — | H | H | H | H | H | H | N-31 | — | — | — | — | — | — |
| 3599 | 1(18) | Mes | — | H | H | H | H | H | H | N-32 | — | — | — | — | — | — |
| 3600 | 1(18) | Mes | — | H | H | H | H | H | H | N-33 | — | — | — | — | — | — |
| 3601 | 1(18) | Mes | — | H | H | H | H | H | H | N-34 | — | — | — | — | — | — |
| 3602 | 1(18) | Mes | — | H | H | H | H | H | H | N-35 | — | — | — | — | — | — |
| 3603 | 1(18) | Mes | — | H | H | H | H | H | H | N-36 | — | — | — | — | — | — |
| 3604 | 1(18) | Mes | — | H | H | H | H | H | H | N-37 | — | — | — | — | — | — |
| 3605 | 1(18) | Mes | — | H | H | H | H | H | H | N-38 | — | — | — | — | — | — |
| 3606 | 1(18) | Mes | — | H | H | H | H | H | H | N-39 | — | — | — | — | — | — |
| 3507 | 1(18) | Mes | — | H | H | H | H | H | H | N-40 | — | — | — | — | — | — |
| 3608 | 1(18) | Mes | — | H | H | H | H | H | H | N-41 | — | — | — | — | — | — |

In Table 1, H indicates hydrogen, Me indicates a methyl group, Ph indicates a phenyl group, and Mes indicates a mesityl group.

The condensed cyclic compound represented by Formula 1 has a core A (see Formula 1' below). The core A has a structure in which three ring groups are condensed with a 7-membered ring, and thus, structural stability may be enhanced. Also, hole transport and injection capability may be facilitated by changing the type of the ring group.

<Formula 1'>

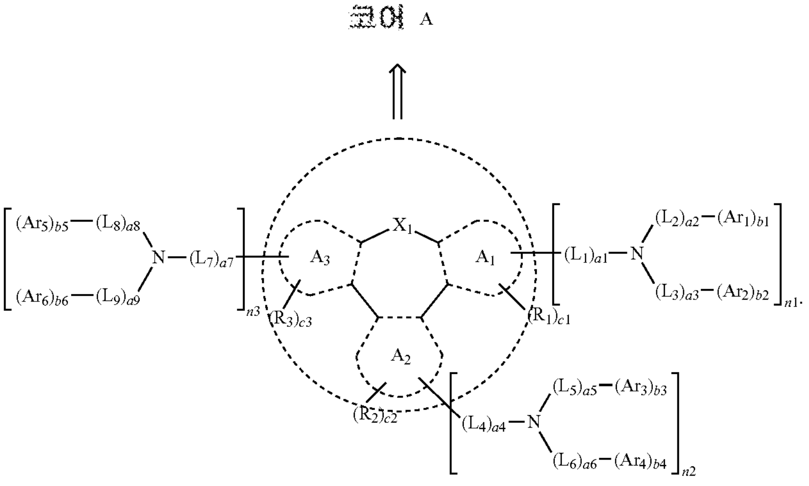

In the condensed cyclic compound represented by Formula 1, n1 to n3 may each independently be 0 or 1, provided that the sum of n1, n2, and n3 is 1. That is, the condensed cyclic compound represented by Formula 1 is a monoamine-based compound having one amino group. Accordingly, the condensed cyclic compound may have fast hole transport and injection capability. Therefore, an electronic device, for example, an organic light-emitting device, which includes the condensed cyclic compound represented by Formula 1, may have a low driving voltage, high luminance, high efficiency, and a long lifespan.

A synthesis method for the condensed cyclic compound represented by Formula 1 would be apparent to those of ordinary skill in the art by referring to the following examples.

At least one condensed cyclic compound represented by Formula 1 may be used between a pair of electrodes constituting an organic light-emitting device. For example, the condensed cyclic compound may be included in at least one layer selected from a hole transport region and an emission layer. In an exemplary embodiment of the present disclosure, the condensed cyclic compound represented by Formula 1 may be used as a material for forming a capping layer positioned outside the pair of electrodes of the organic light-emitting device.

According to an exemplary embodiment of the present disclosure, there is provided an organic light-emitting device including: a first electrode; a second electrode facing the first electrode; and an organic layer between the first electrode and the second electrode, the organic layer including an emission layer, wherein the organic layer includes at least one condensed cyclic compound represented by Formula 1.

The expression "(an organic layer) includes at least one condensed cyclic compound represented by Formula 1" used herein may include a case in which "(an organic layer) includes identical compounds represented by Formula 1", and a case in which "(an organic layer) includes two or more different condensed cyclic compounds represented by Formula 1."

In an exemplary embodiment of the present disclosure, the organic layer may include, as the condensed cyclic compound, only Compound 1. In this regard, Compound 1 may exist in an emission layer of the organic light-emitting device. In an exemplary embodiment of the present disclosure, the organic layer may include, as the condensed cyclic compound, Compound 1 and Compound 2. In this regard, Compound 1 and Compound 2 may exist in an identical layer (for example, Compound 1 and Compound 2 may all exist in an emission layer), or in different layers (for example, Compound 1 may exist in an emission layer and Compound 2 may exist in a hole transport layer or a hole injection layer).

According to an exemplary embodiment of the present disclosure, the first electrode of the organic light-emitting device may be an anode, and the second electrode of the organic light-emitting device may be a cathode. The organic layer of the organic light-emitting device may further include a hole transport region between the first electrode and the emission layer, and an electron transport region between the emission layer and the second electrode. The hole transport region may include a hole injection layer, a hole transport layer, an emission auxiliary layer, an electron blocking layer, or any combination thereof, and the electron transport region may include a hole blocking layer, a buffer layer, an electron transport layer, an electron injection layer, or any combination thereof.

In an exemplary embodiment of the present disclosure, the hole transport region may include the condensed cyclic compound represented by Formula 1. In an exemplary embodiment of the present disclosure, the hole transport region may include a hole transport layer, which includes the condensed cyclic compound represented by Formula 1. In an exemplary embodiment of the present disclosure, the hole transport region may include a hole injection layer, which includes the condensed cyclic compound represented by Formula 1. However, the present disclosure is not limited thereto.

In an exemplary embodiment of the present disclosure, the emission layer may include the condensed cyclic compound represented by Formula 1. The emission layer may further include, in addition to the condensed cyclic compound represented by Formula 1, a host. In an exemplary embodiment of the present disclosure, the emission layer of the organic light-emitting device may include a host and a dopant, wherein the host may include a fluorescent host and the dopant may include the condensed cyclic compound represented by Formula 1. However, the present disclosure is not limited thereto.

The organic light-emitting device may further include at least one selected from a first capping layer disposed in a pathway along which light generated in an emission layer proceeds toward the outside through the first electrode and a second capping layer disposed in a pathway along which light generated in an emission layer proceeds toward the outside through the second electrode, and the at least one selected from the first capping layer and the second capping layer may include at least one of the condensed cyclic compounds represented by Formula 1.

In an exemplary of the present disclosure, the organic light-emitting device may have i) a stacked structure including a first electrode, an organic layer, a second electrode, and a second capping layer which are sequentially stacked in this stated order, ii) a stacked structure including a first capping layer, a first electrode, an organic layer, and a second electrode which are sequentially stacked in this stated order, or iii) a stacked structure including a first capping layer, a first electrode, an organic layer, a second electrode, and a second capping layer which are sequentially stacked in this stated order, and at least one selected from the first capping layer and the second capping layer may include the condensed cyclic compound represented by Formula 1.

The term "organic layer" used herein refers to a single layer and/or a plurality of layers disposed between the first electrode and the second electrode of the organic light-emitting device. A material included in the "organic layer" is not limited to an organic material.

[Description of FIG. 1]

FIG. 1 is a schematic view of an organic light-emitting device 10 according to an exemplary embodiment of the present disclosure. The organic light-emitting device 10 includes a first electrode 110, an organic layer 150, and a second electrode 190.

Hereinafter, the structure of the organic light-emitting device 10 according to an exemplary embodiment of the present disclosure and a method of manufacturing the organic light-emitting device 10 will be described in connection with FIG. 1.

[First Electrode 110]

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for the first electrode 110 may be selected from materials with high work function to facilitate hole injection.

The first electrode 110 may be a reflective electrode, a semi-transmissive electrode, or a transmissive electrode. When the first electrode 110 is a transmissive electrode, a material for forming the first electrode 110 may be selected from indium tin oxide (ITO), indium zinc oxide (IZO), tin oxide ($SnO_2$), zinc oxide (ZnO), and any combinations thereof, but the present disclosure is not limited thereto. In an exemplary embodiment of the present disclosure, when the first electrode 110 is a semi-transmissive electrode or a reflectable electrode, a material for forming the first electrode 110 may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but the present disclosure is not limited thereto.

The first electrode 110 may have a single-layered structure, or a multi-layered structure including two or more layers. For example, the first electrode 110 may have a three-layered structure of ITO/Ag/ITO, but the present disclosure is not limited thereto.

[Organic Layer 150]

The organic layer 150 is disposed on the first electrode 110. The organic layer 150 may include an emission layer.

The organic layer 150 may further include a hole transport region disposed between the first electrode 110 and the emission layer, and an electron transport region disposed between the emission layer and the second electrode 190.

[Hole Transport Region in Organic Layer 150]

The hole transport region may have i) a single-layered structure including a single layer which includes a single material, ii) a single-layered structure including a single layer which includes a plurality of different materials, or iii) a multi-layered structure having a plurality of layers which include a plurality of different materials.

The hole transport region may include at least one layer selected from a hole injection layer, a hole transport layer, an emission auxiliary layer, and an electron blocking layer.

In an exemplary embodiment of the present disclosure, the hole transport region may have a single-layered structure including a single layer which includes a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, in which for each structure, constituting layers are sequentially stacked on and from the first electrode 110 in this stated order, but the present disclosure is not limited thereto.

In an exemplary embodiment of the present disclosure, the hole transport region may include the condensed cyclic compound represented by Formula 1. For example, the hole transport region may include a hole transport layer, which includes the condensed cyclic compound represented by Formula 1.

In an exemplary embodiment of the present disclosure, the hole transport region may include at least one selected from 4,4',4"-tris(3-methylphenylphenylamino)triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), N,N'-di (naphthalene-1-yl)-N,N'-diphenylbenzidine (NPB, NPD), β-NPB, N,N'-bis(3-methylphenyl)-N,N'-diphenyl-[1,1'-biphenyl]-4,4'-diamine (TPD), Spiro-TPD, Spiro-NPB, methylated-NPB, 4,4'-cyclohexylidenebis[N,N-bis(4-methylphenyl)benzenamine] (TAPC), 4,4'-bis[N,N'-(3-tolyl)amino]-3,3'-dimethylbiphenyl (HMTPD), 4,4',4"-tris(N-carbazolyl) triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202:

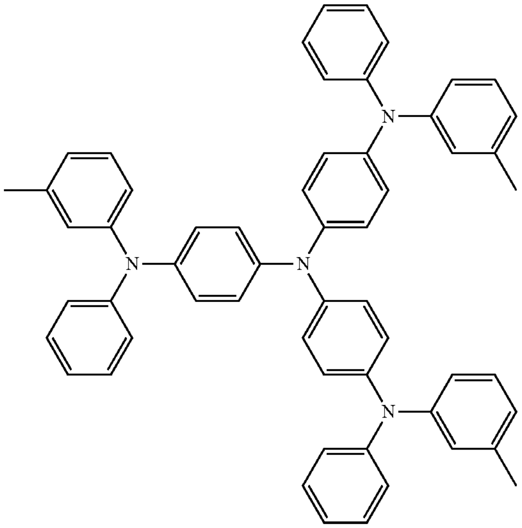

m-MTDATA

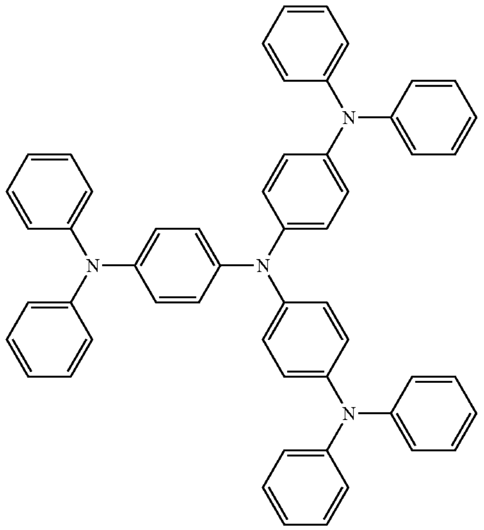

TDATA

-continued

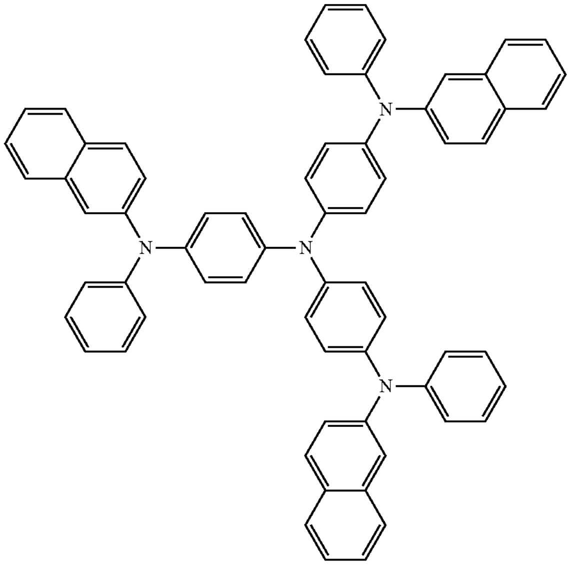

2-TNATA

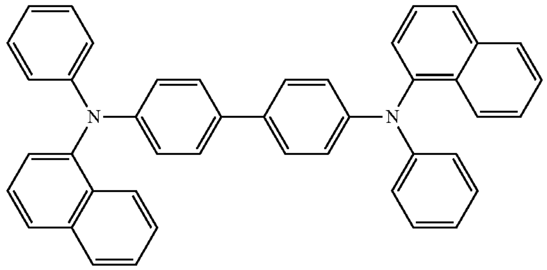

NPB

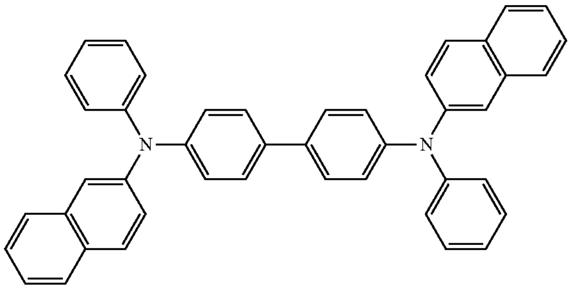

β-NPB

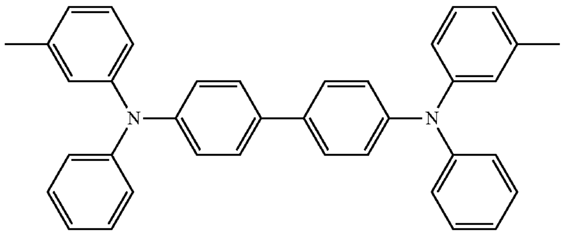

TPD

-continued

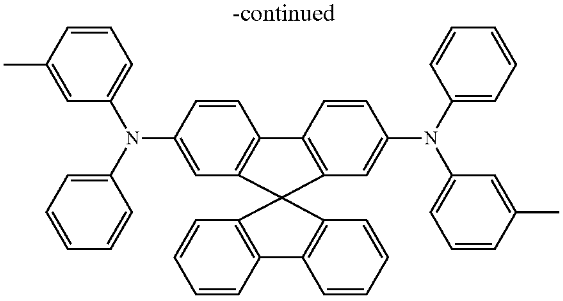

Spiro-TPD

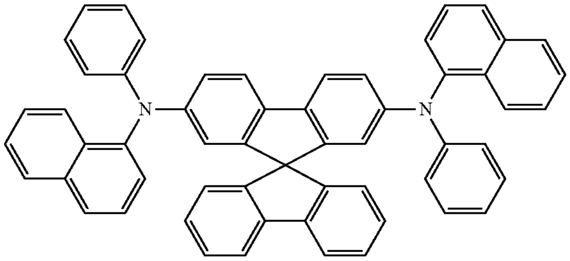

Spiro-NPB

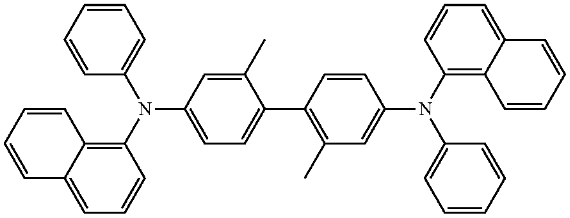

methylated NPB

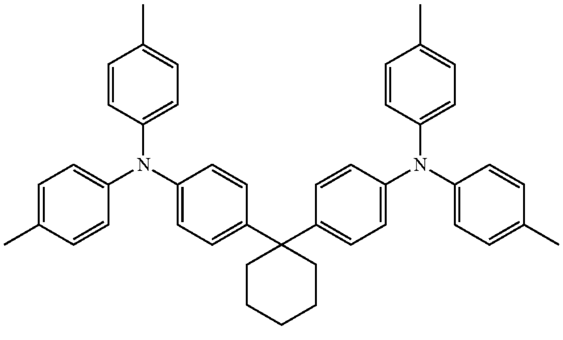

TAPC

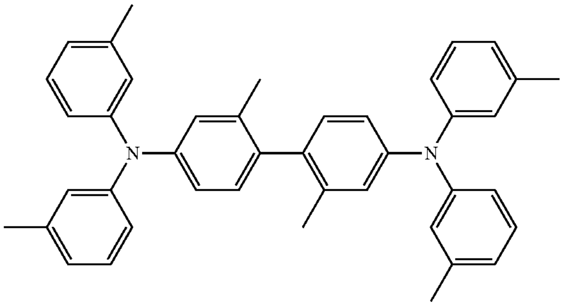

HMTPD

<Formula 201>

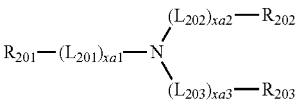

-continued

<Formula 202>

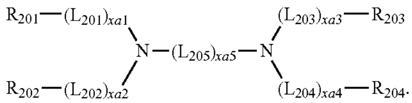

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{10}$ heteroarylene group, a substituted or unsubstituted divalent non-aromatic condensed polycyclic group, and a substituted or unsubstituted divalent non-aromatic condensed heteropolycydic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{10}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In an exemplary embodiment of the present disclosure, in Formula 202, $R_{20}$, and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In an exemplary embodiment of the present disclosure, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —$Si(Q_{31})(Q_{32})(Q_{33})$, and —$N(Q_{31})(Q_{32})$, in which $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In an exemplary embodiment of the present disclosure, xa1 to xa4 may each independently be 0, 1, or 2.

In an exemplary embodiment of the present disclosure, xa5 may be 1, 2, 3, or 4.

In an exemplary embodiment of the present disclosure, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosiloyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —$Si(Q_{31})(Q_{32})(Q_{33})$ and —$N(Q_{31})(Q_{32})$, in which $Q_{31}$ to $Q_{33}$ are the same as described above.

In an exemplary embodiment of the present disclosure, at least one of $R_{201}$ to $R_{203}$ in Formula 201 may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but the present disclosure is not limited thereto.

In an exemplary embodiment of the present disclosure, in Formula 202, i) $R_{201}$ and $R_{202}$ may be linked via a single bond, and/or ii) $R_{203}$ and $R_{204}$ may be linked via a single bond.

In an exemplary embodiment of the present disclosure, at least one of $R_{201}$ to $R_{204}$ in Formula 202 may be selected from:

a carbazolyl group; and a carbazolyl group, substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but the present disclosure is not limited thereto.

The compound represented by Formula 201 may be represented by Formula 201A:

<Formula 201A>

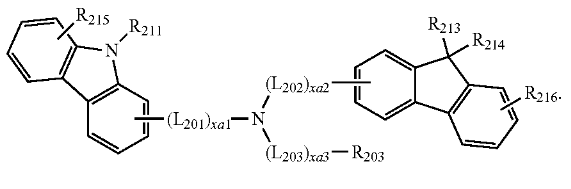

In an exemplary embodiment of the present disclosure, the compound represented by Formula 201 may be represented by Formula 201A(1) below, but the present disclosure is not limited thereto:

<Formula 201A(1)>

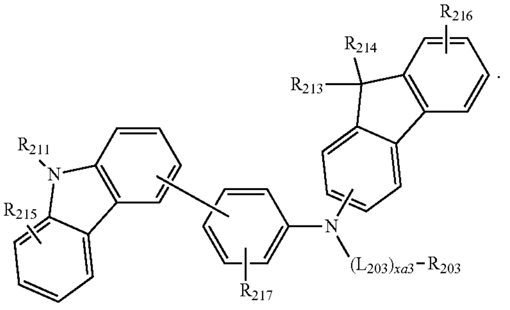

In an exemplary embodiment of the present disclosure, the compound represented by Formula 201 may be represented by Formula 201A(1) below, but the present disclosure is not limited thereto:

<Formula 201A-1>

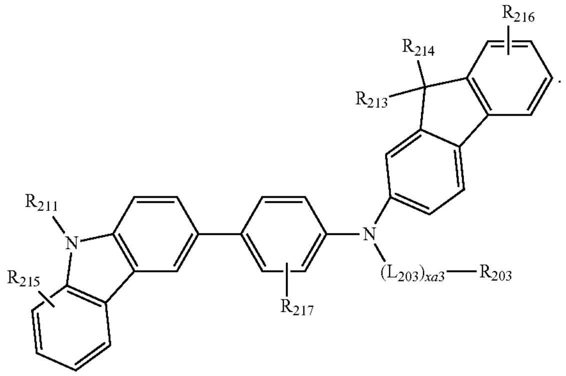

In an exemplary embodiment of the present disclosure, the compound represented by Formula 202 may be represented by Formula 202A:

<Formula 202A>

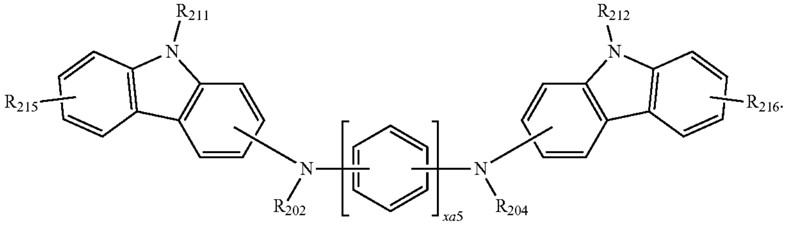

In an exemplary embodiment of the present disclosure, the compound represented by Formula 202 may be represented by Formula 202A-1:

<Formula 202A-1>

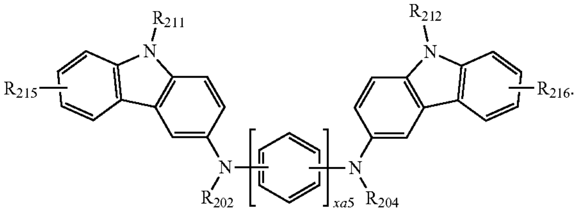

In Formulae 201A, 201A(1), 201A-1, 202A, and 202A-1, $L_{201}$ to $L_{203}$, xa1 to xa3, xa5, and $R_{202}$ to $R_{204}$ are the same as described above, $R_{211}$ and $R_{212}$ are the same as described in connection with $R_{203}$, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but the present disclosure is not limited thereto:

HT1

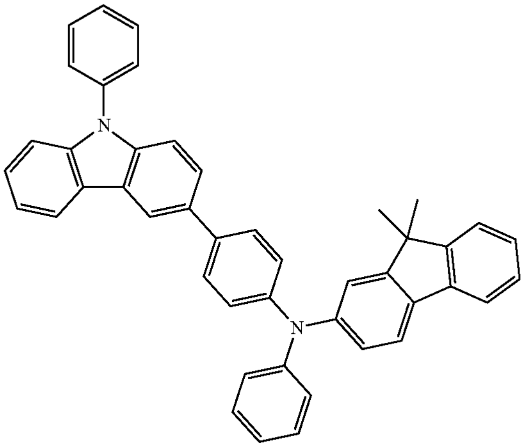

HT2

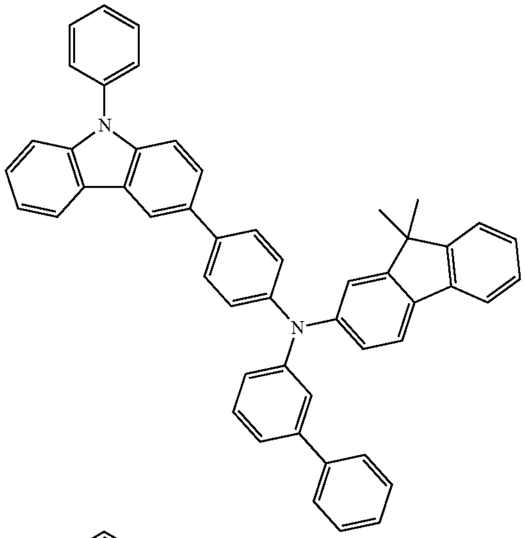

HT3

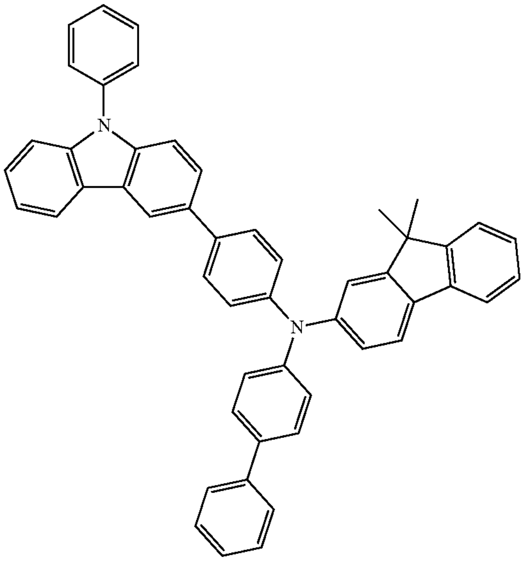

HT4

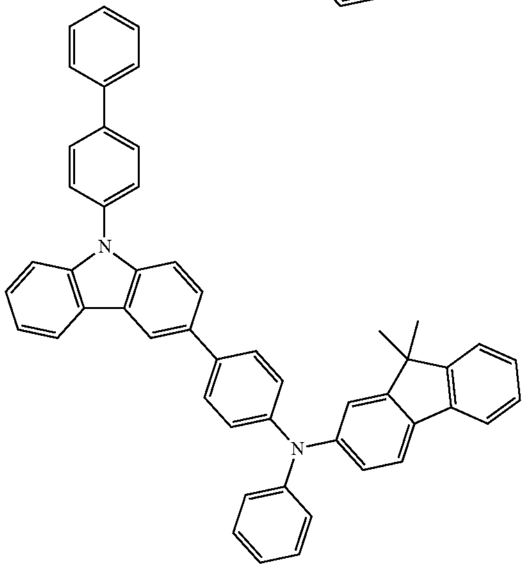

-continued
HT5
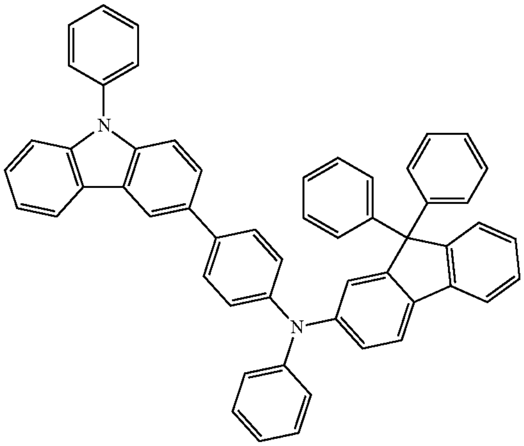
HT6
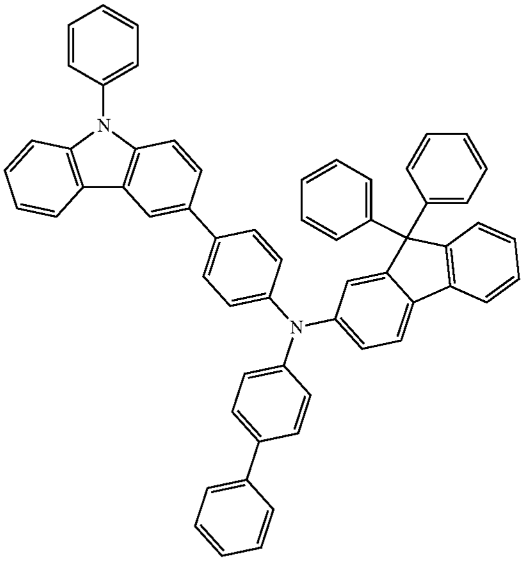
HT7
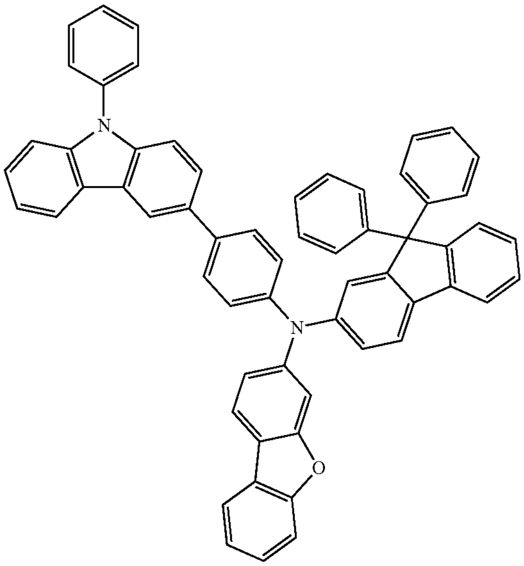
HT8
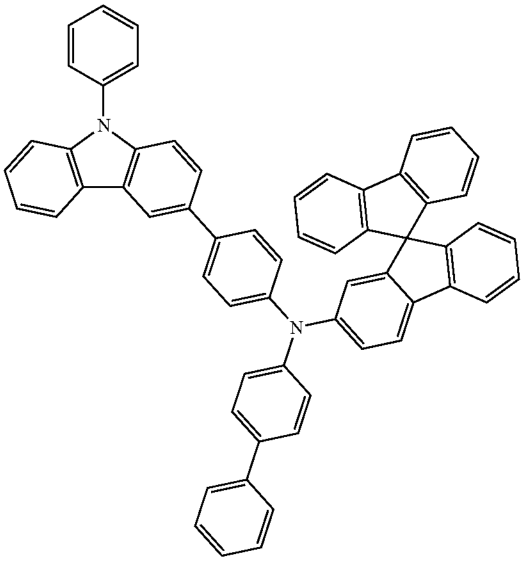

-continued
HT9
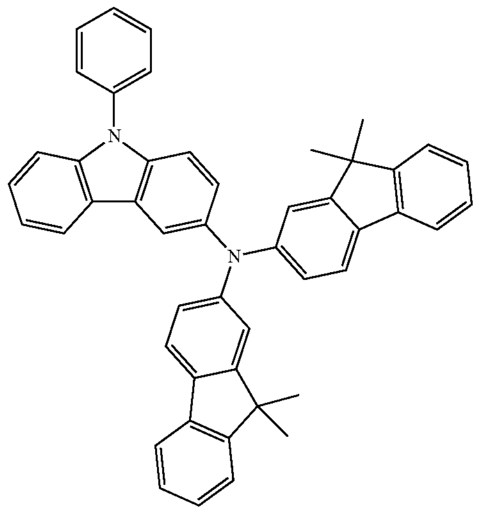
HT10
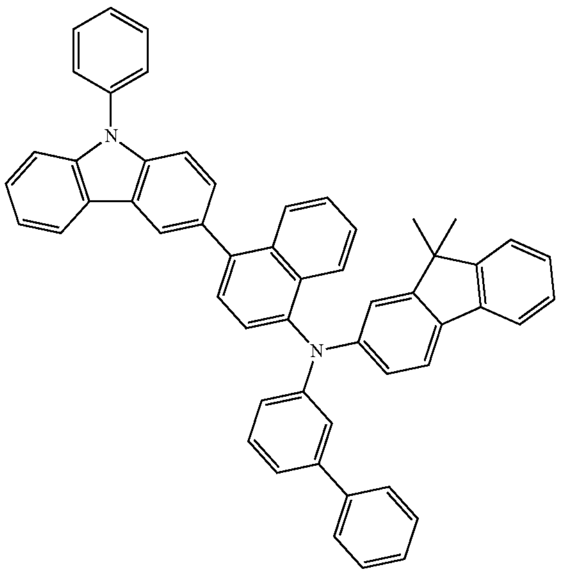
HT11
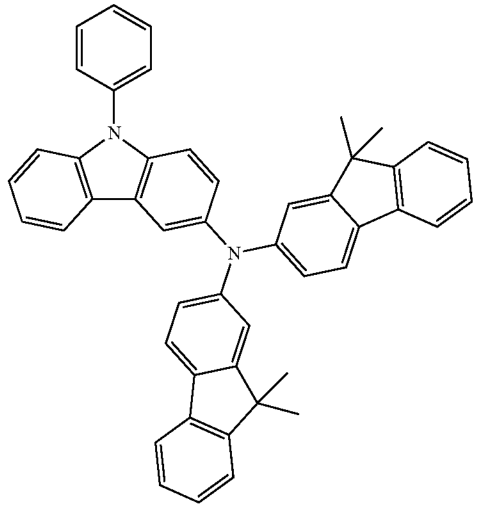
HT12
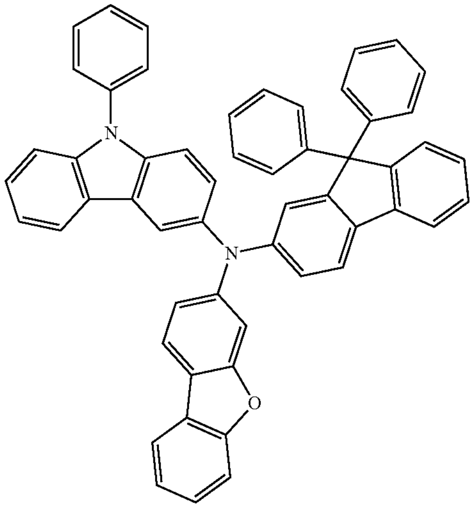
HT13
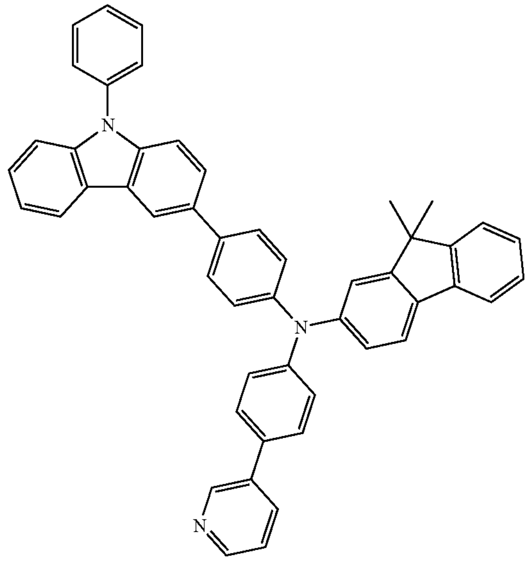
HT14
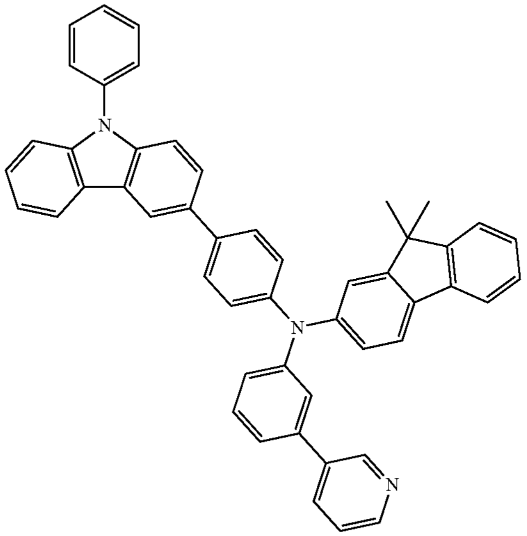

-continued
HT15
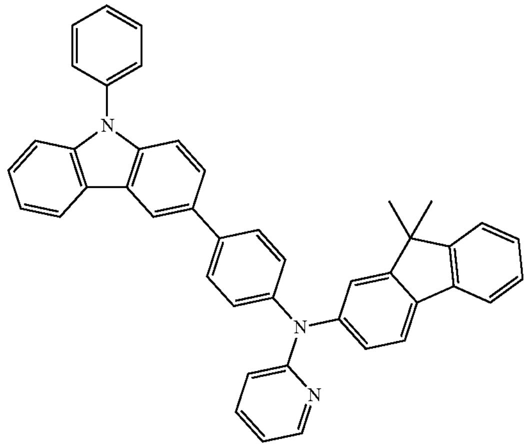
HT16
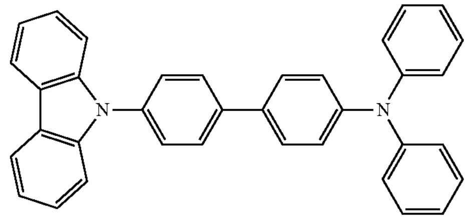
HT17
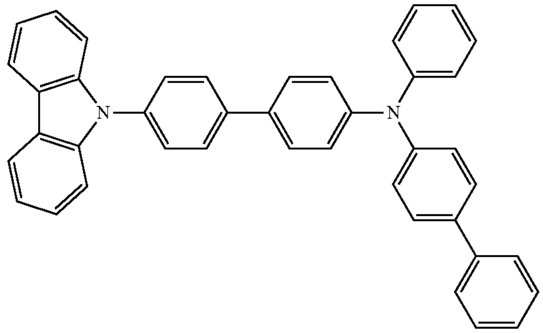
HT18
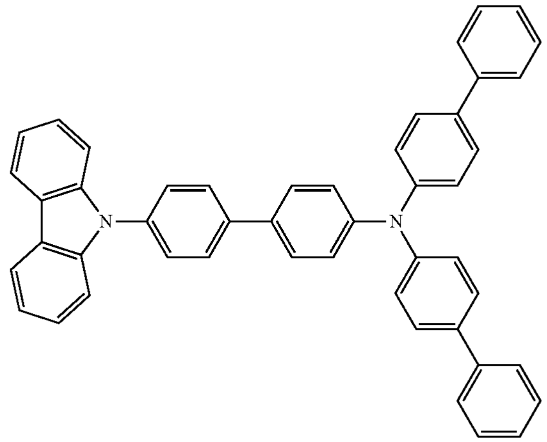
HT19
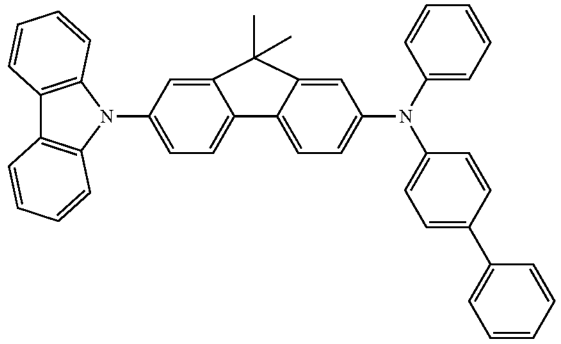
HT20
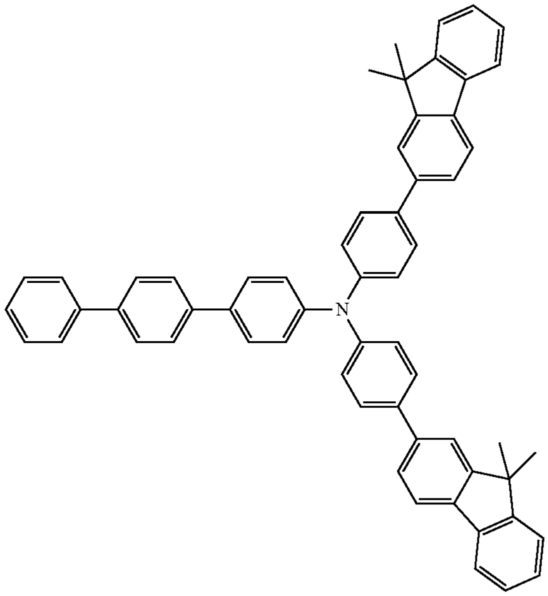

-continued
HT21
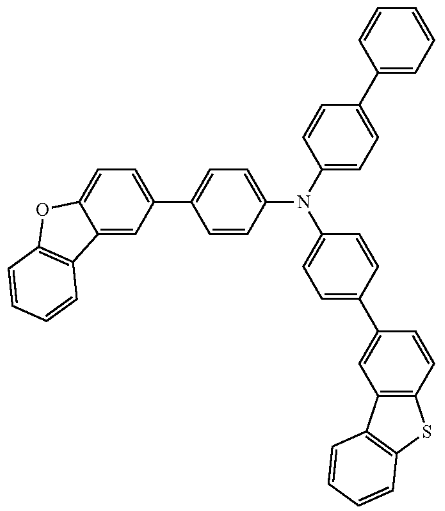
HT22
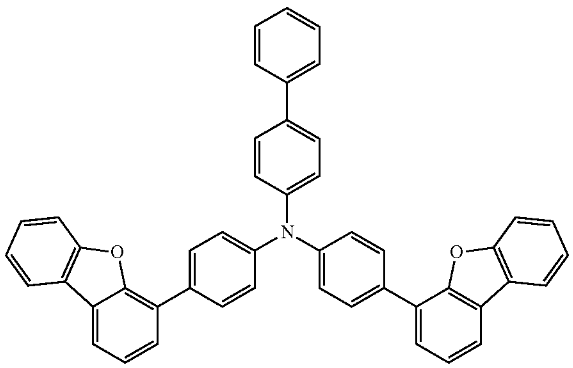
HT23
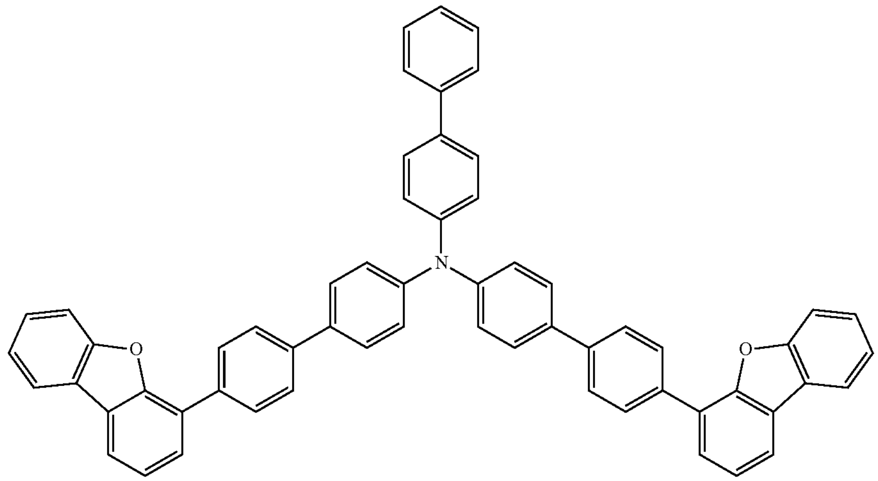
HT24
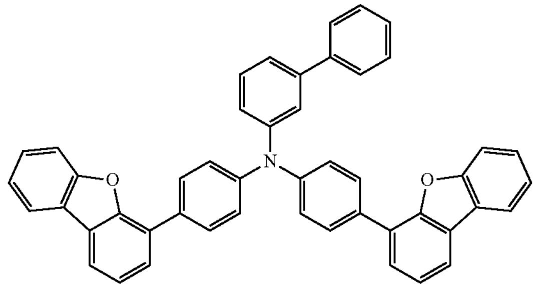
HT25
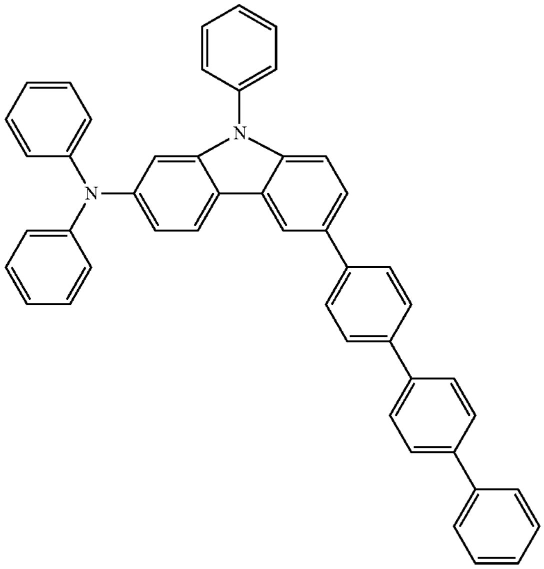

-continued
HT26
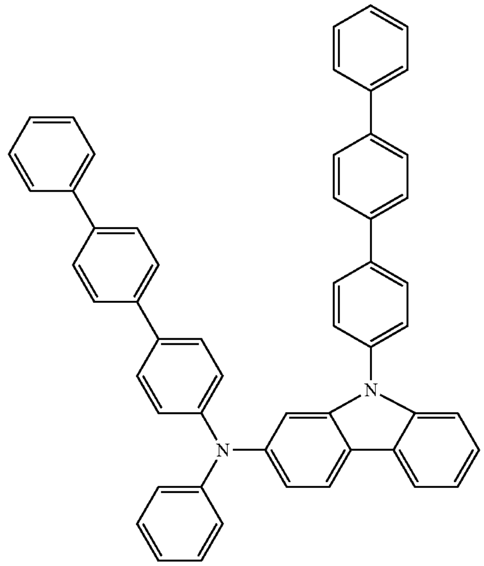
HT27
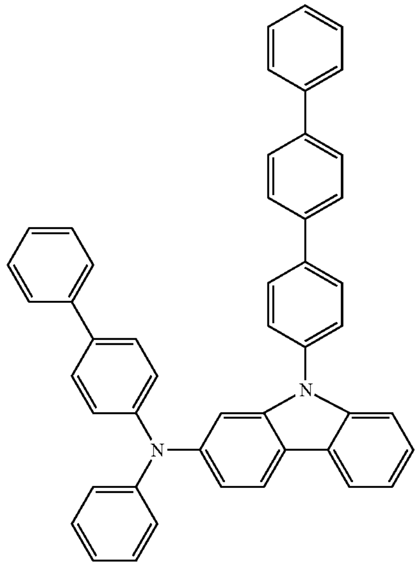
HT28
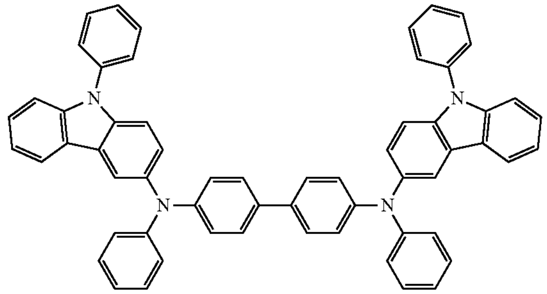
HT29
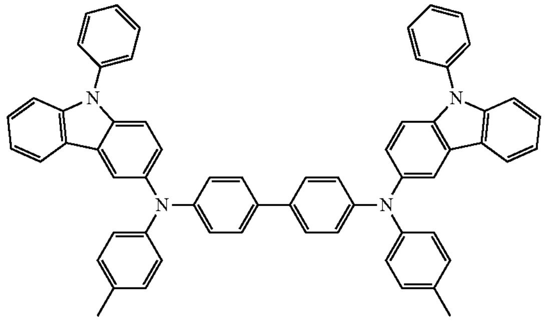
HT30
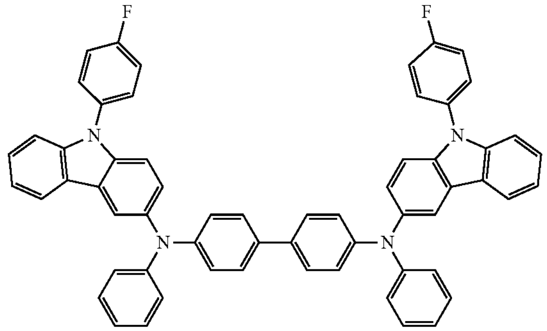
HT31
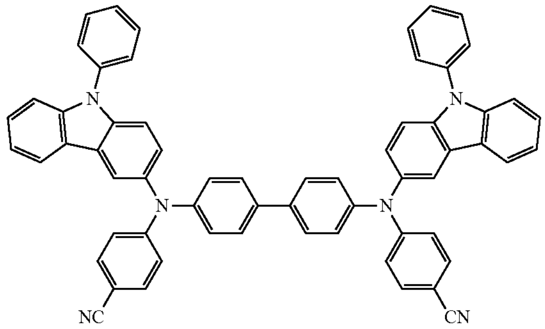

-continued
HT32
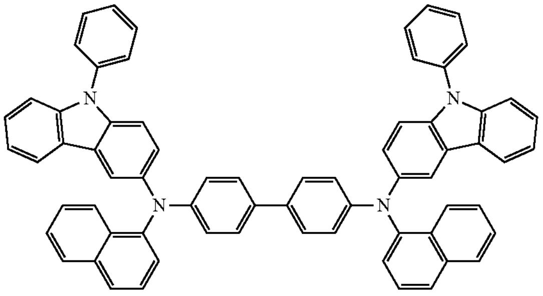
HT33
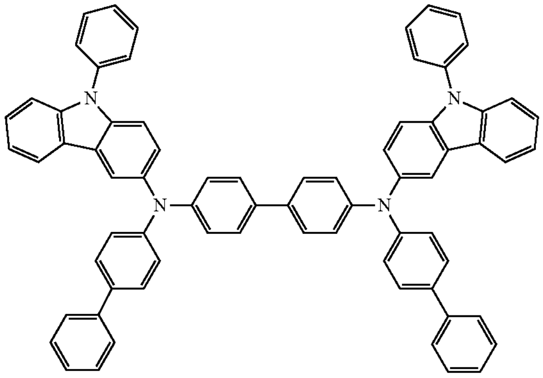
HT34
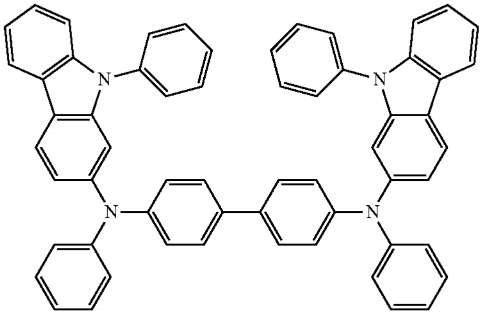
HT35
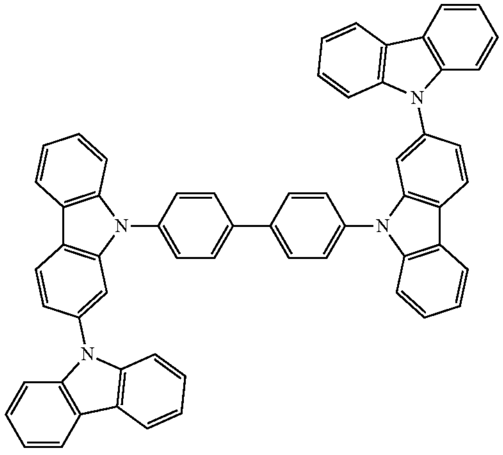
HT36
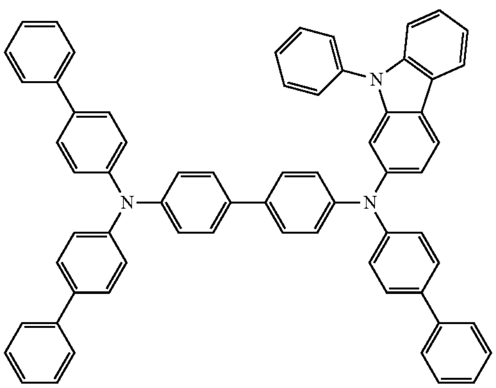
HT37
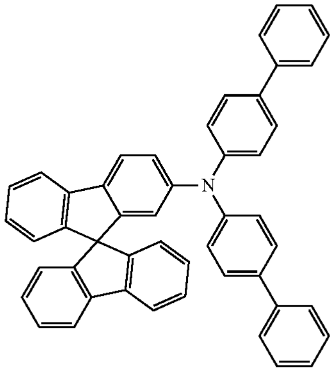

-continued

HT38

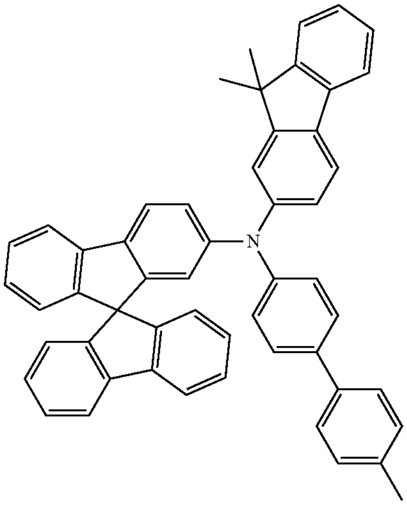

HT39

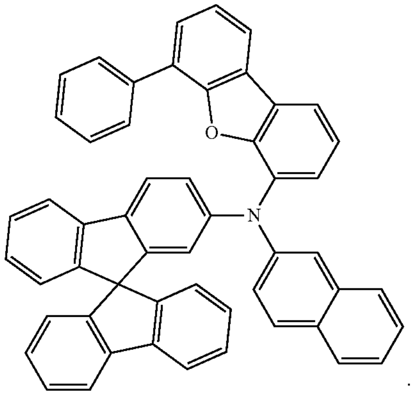

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 9,000 Å for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

[P-Dopant]

The hole transport region may further include, in addition to these materials, a charge-generation material for the enhancement of conductive properties. The charge-generation material may be homogeneously or non-homogeneously dispersed in the hole transport region.

The charge-generation material may be, for example, a p-dopant.

In an exemplary embodiment of the present disclosure, the p-dopant may have a lowest unoccupied molecular orbital of about −3.5 eV or less.

The p-dopant may include at least one selected from a quinone derivative, a metal oxide, and a cyano group-containing compound, but the present disclosure is not limited thereto.

In an exemplary embodiment of the present disclosure, the p-dopant may include at least one selected from:

a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,11-hexaazatriphenylene-hexacarbonitrile (HAT-CN); and a compound represented by Formula 221 below, but the present disclosure is not limited thereto:

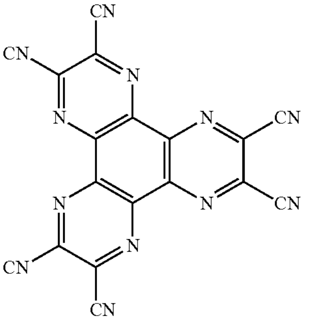

<HAT-CN>

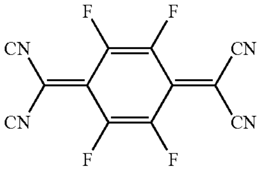

<F4-TCNQ>

<Formula 221>

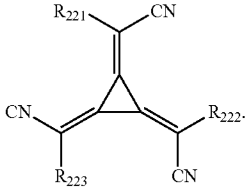

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, in which at least one selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

[Emission Layer in Organic Layer 150]

When the organic light-emitting device 10 is a full-color organic light-emitting device, the emission layer may be patterned into a red emission layer, a green emission layer, or a blue emission layer, according to a sub-pixel. In an exemplary embodiment of the present disclosure, the emission layer may have a stacked structure of two or more layers selected from a red emission layer, a green emission layer, and a blue emission layer, in which the two or more layers contact each other or are separated from each other. In an exemplary embodiment of the present disclosure, the emission layer may include two or more materials selected from a red light-emitting material, a green light-emitting material, and a blue light-emitting material, in which the two or more materials are mixed with each other in a single layer to emit white light.

The emission layer may include the condensed cyclic compound represented by Formula 1.

The emission layer may include a host and a dopant. The dopant may include at least one selected from a phosphorescent dopant and a fluorescent dopant.

In the emission layer, an amount of the dopant may be in a range of about 0.01 parts by weight to about 15 parts based on 100 parts by weight of the host, but the present disclosure is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

[Host in Emission Layer]

In an exemplary embodiment of the present disclosure, the host may include a compound represented by Formula 301 below:

$$[Ar_{301}]_{xb11}\text{-}[(L_{301})_{xb1}\text{-}R_{301}]_{xb21}. \quad \text{<Formula 301>}$$

In Formula 301, $Ar_{301}$ may be a substituted or unsubstituted $C_5$-$C_{60}$ carbocyclic group or a substituted or unsubstituted $C_1$-$C_{10}$ heterocyclic group, xb11 may be 1, 2, or 3, $L_{30}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$, arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $—Si(Q_{301})(Q_{302})(Q_{303})$, $—N(Q_{301})(Q_{302})$, $—B(Q_{301})(Q_{302})$, $—C(=O)(Q_{301})$, $—S(=O)_2(Q_{301})$, and $—P(=O)(Q_{301})(Q_{302})$, xb21 may be an integer from 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but the present disclosure is not limited thereto.

In an exemplary embodiment of the present disclosure, $Ar_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, and $—P(=O)(Q_{31})(Q_{32})$, in which $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but the present disclosure is not limited thereto.

When xb11 in Formula 301 is two or more, two or more $Ar_{301}$(s) may be linked via a single bond.

In an exemplary embodiment of the present disclosure, the compound represented by Formula 301 may be represented by Formula 301-1 or 301-2:

<Formula 301-1>

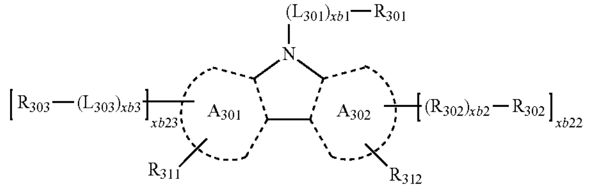

-continued

<Formula 301-2>

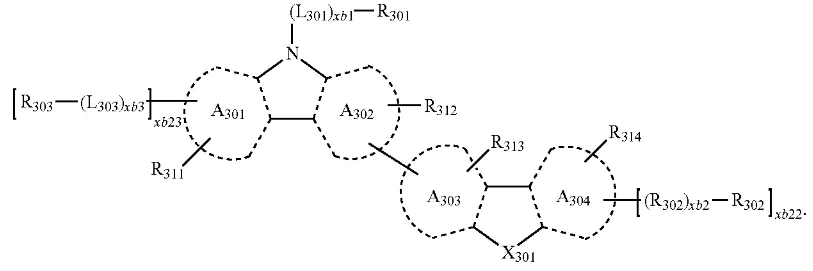

In Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-[$(L_{304})_{xb4}$-$R_{304}$].

$R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_3$)($Q_{32}$), —C(═O)($Q_{31}$), —S(═O)$_2$($Q_{31}$), and —P(═O)($Q_{31}$)($Q_{32}$), xb22 and xb23 may each independently be 0, 1, or 2, $L_{301}$, xb1, $R_{301}$, and $Q_{31}$ to $Q_{33}$ may be the same as described above, $L_{302}$ to $L_{304}$ may each independently be the same as described in connection with $L_{301}$, xb2 to xb4 may each independently be the same as described in connection with xb1, and $R_{302}$ to $R_{304}$ may each independently be the same as described in connection with $R_{301}$.

In an exemplary embodiment of the present disclosure, $L_{301}$ to $L_{304}$ in Formulae 301, 301-1, and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, in which $Q_{31}$ to $Q_{33}$ are the same as described above.

In an exemplary embodiment of the present disclosure, $R_{301}$ to $R_{304}$ in Formulae 301, 301-1, and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosiiolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, in which $Q_{31}$ to $Q_{33}$ are the same as described above.

In an exemplary embodiment of the present disclosure, the host may include an alkaline earth metal complex. For example, the host may be selected from a Be complex (for example, Compound H55 as shown below), a Mg complex, and a Zn complex.

The host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but the present disclosure is not limited thereto:

H1

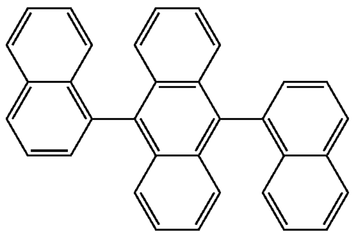

H2

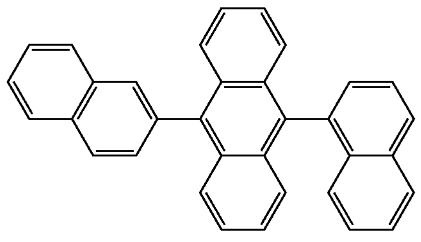

-continued
H3
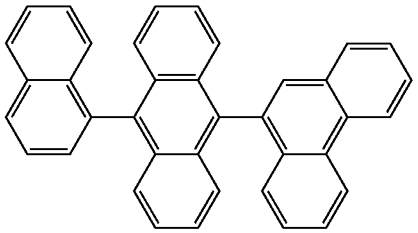
H4
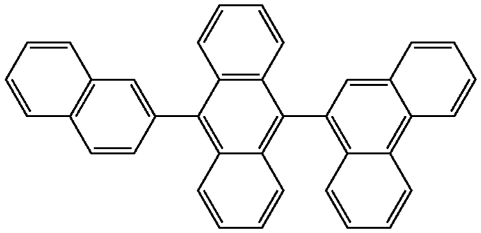
H5
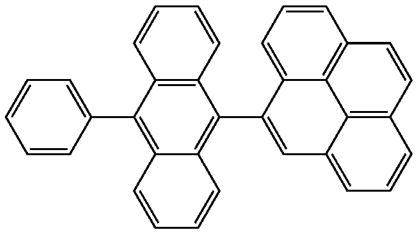
H6
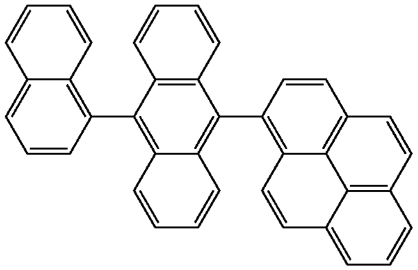
H7
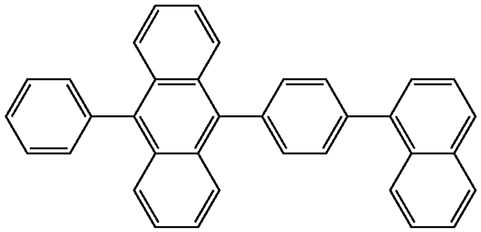
H8
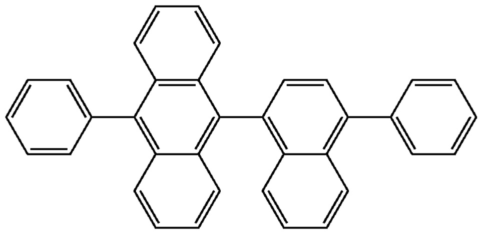
-continued
H9
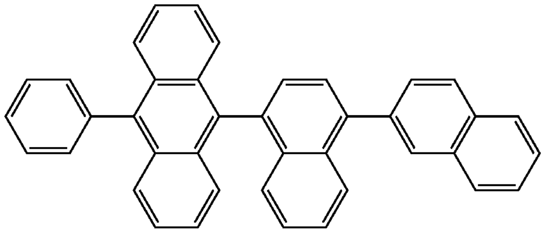
H10
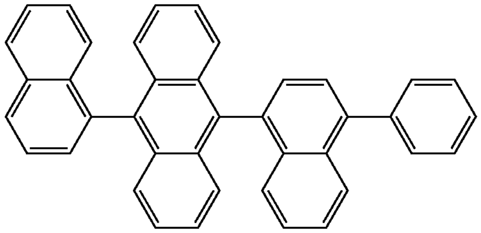
H11
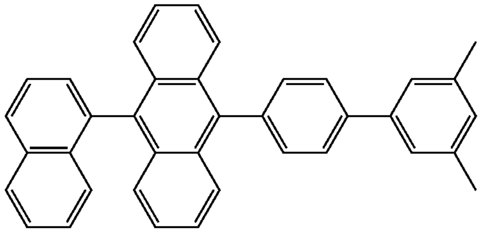
H12
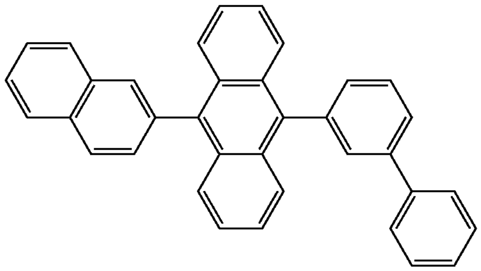
H13
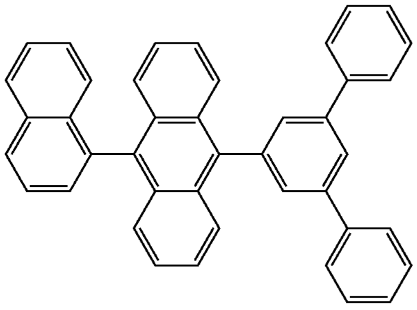

-continued
H14
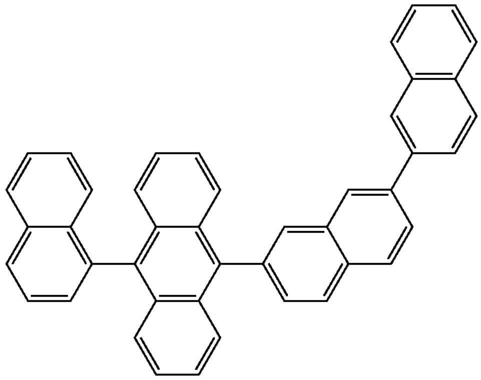
H15
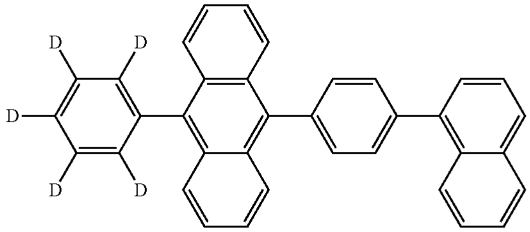
H16
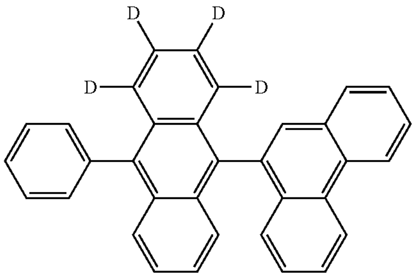
H17
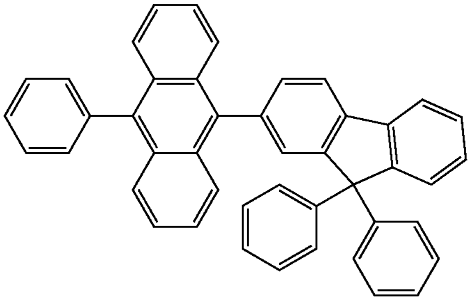
H18
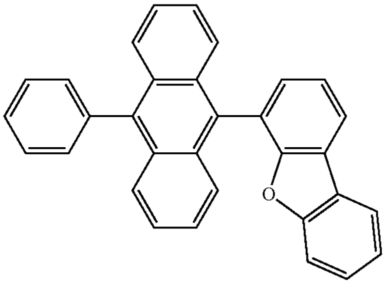
-continued
H19
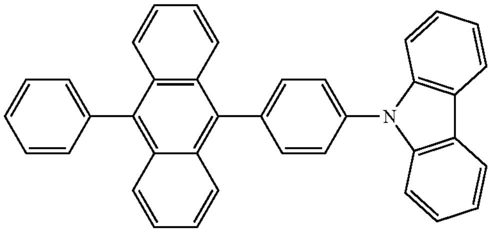
H20
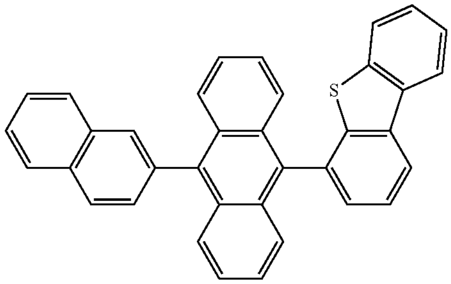
H21
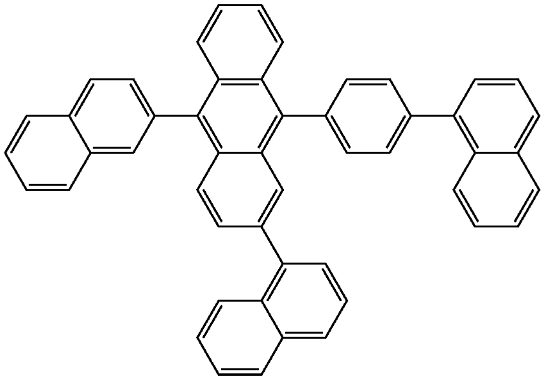
H22
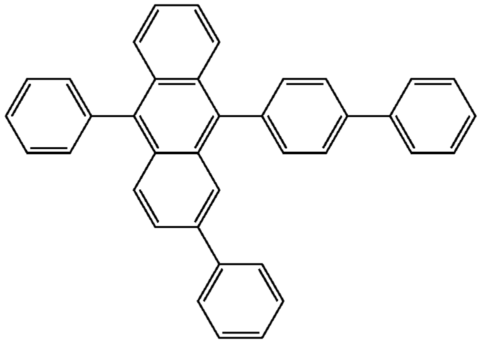

-continued
H23
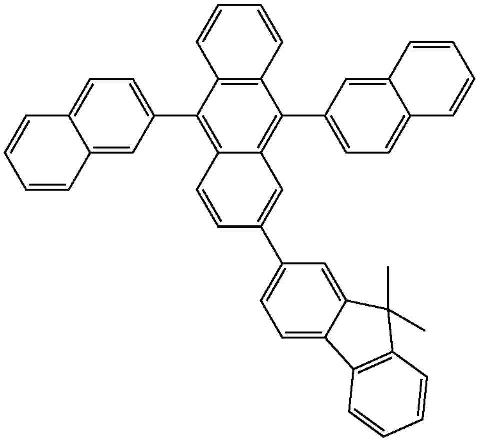
H24
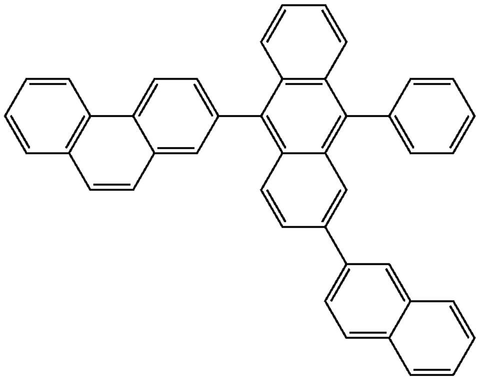
H25
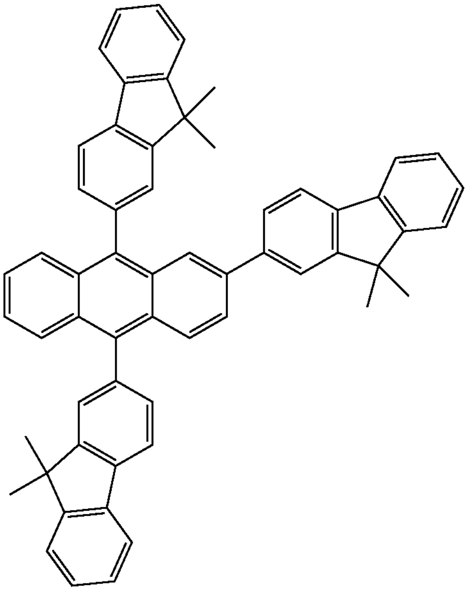
-continued
H26
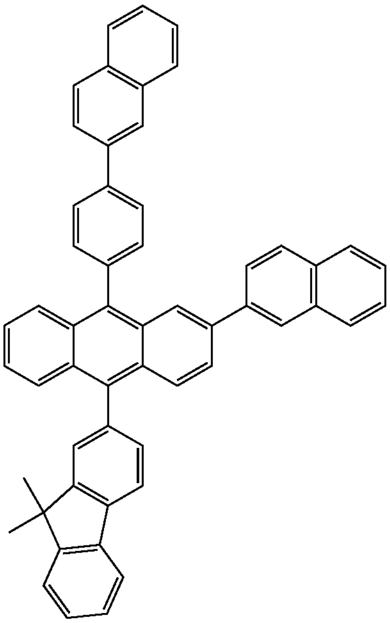
H27
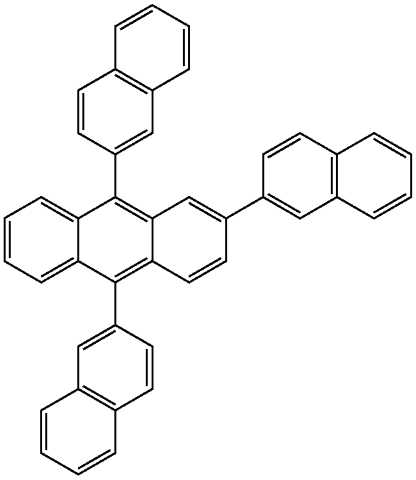
H28
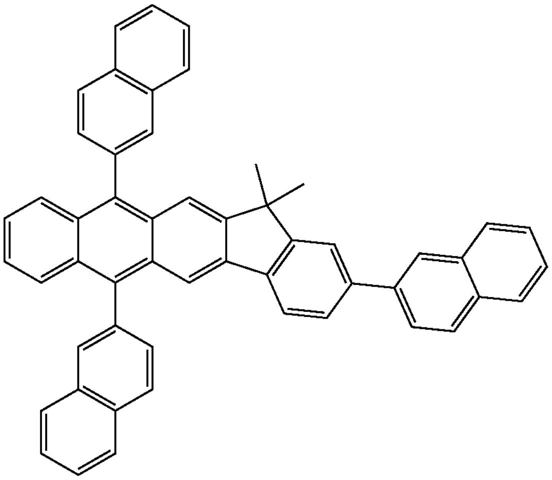

-continued
H29
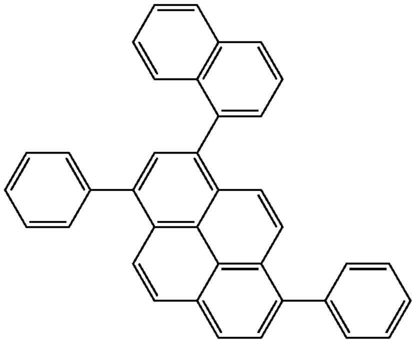
H30
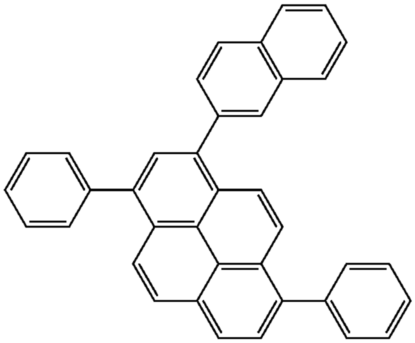
H31
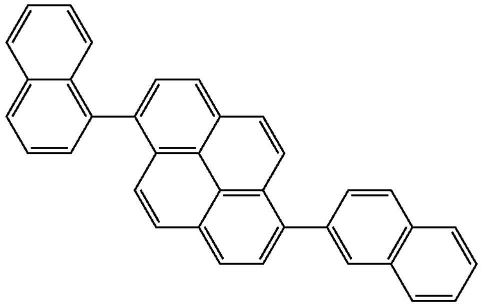
H32
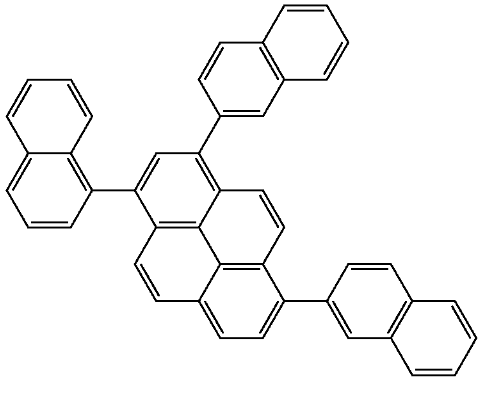
H33
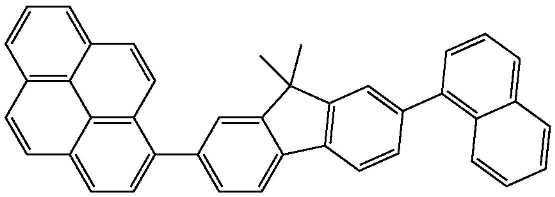
-continued
H34
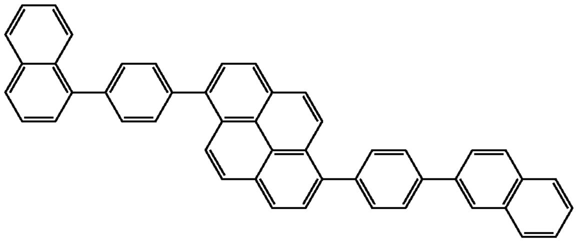
H35
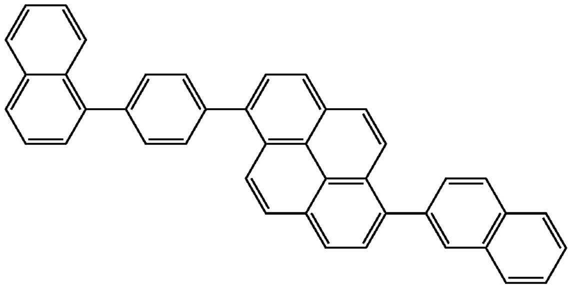
H36
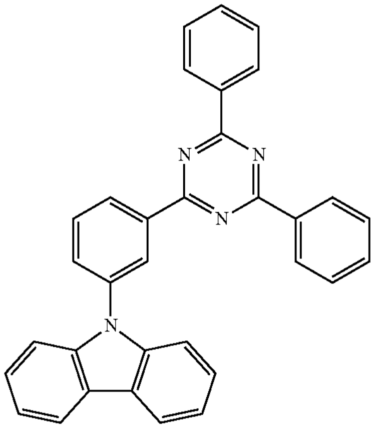
H37
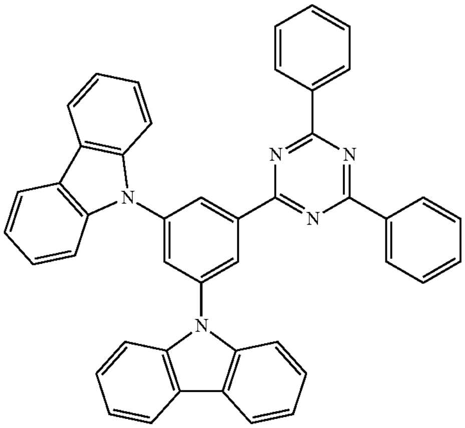

-continued
H38
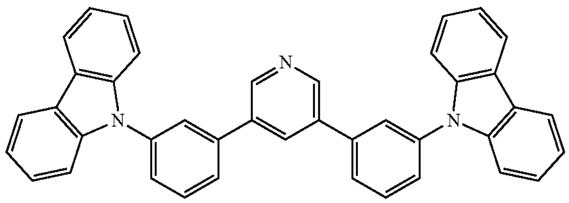
H39
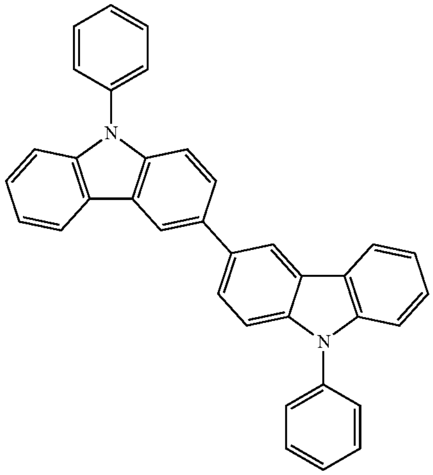
H40
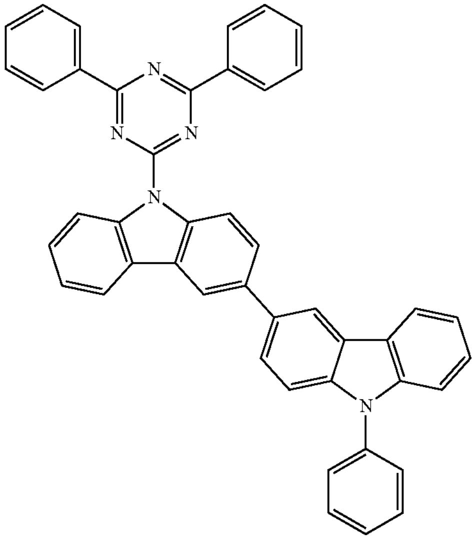
-continued
H41
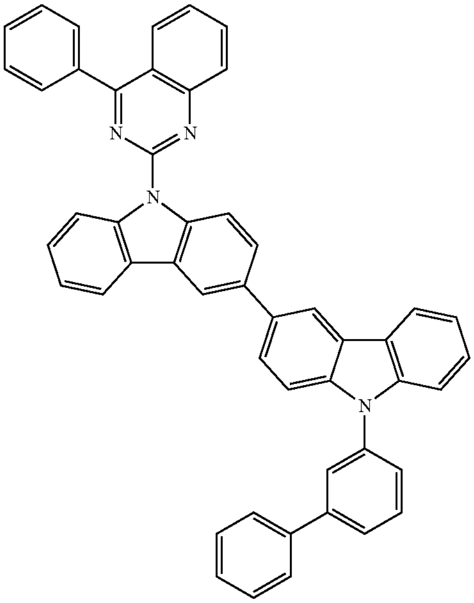
H42
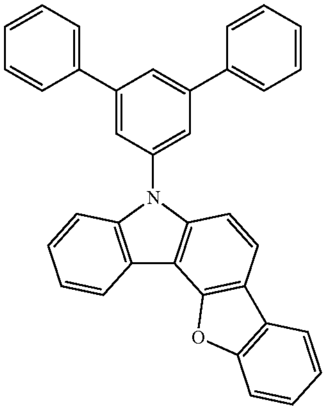
H43
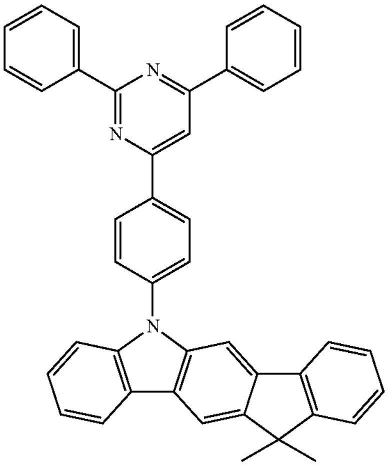

-continued
H44
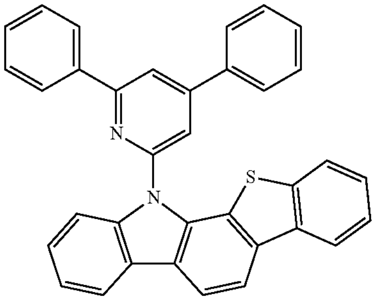
H45
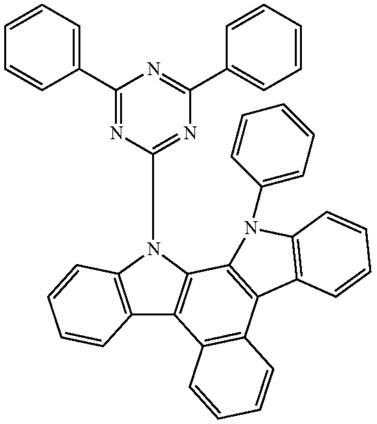
H46
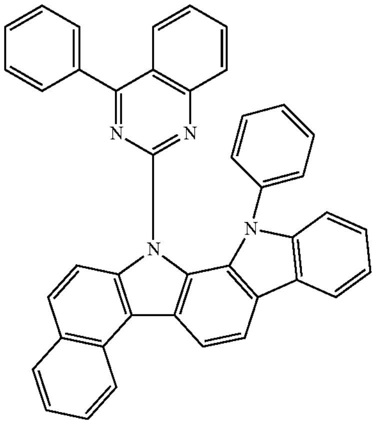
H47
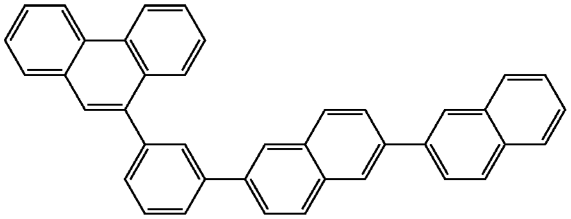
H48
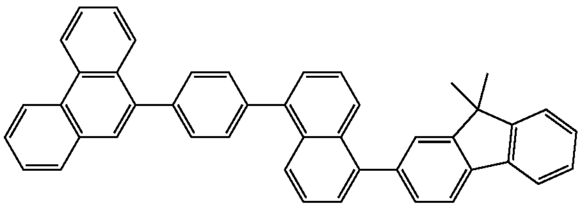
-continued
H49
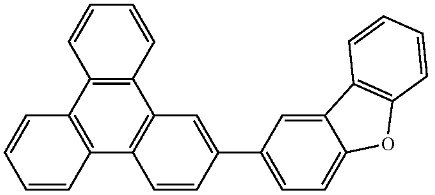
H50
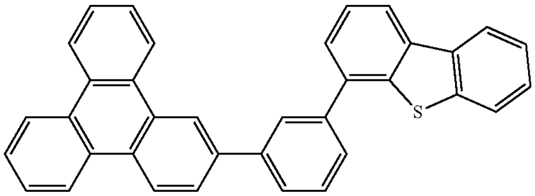
H51
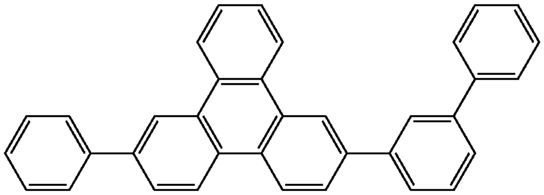
H52
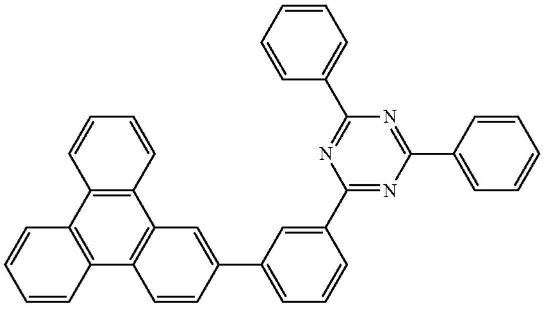
H53
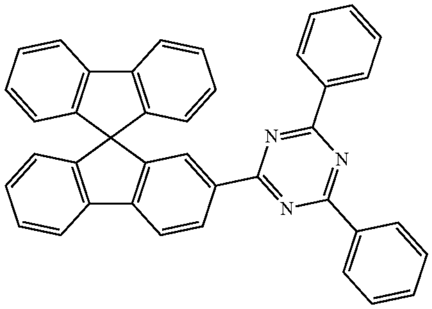

-continued

H54

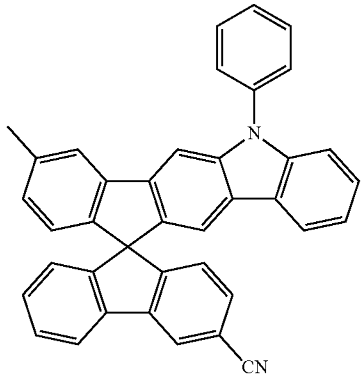

H55

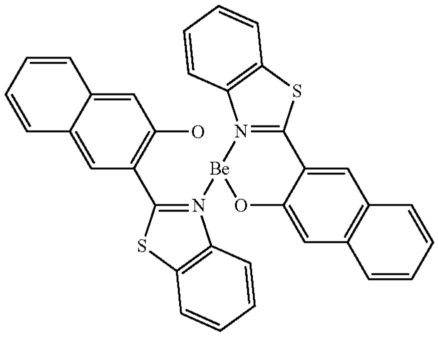

.

[Phosphorescent Dopant Included in Emission Layer in Organic Layer 150]

The phosphorescent dopant may include an organometallic complex represented by Formula 401 and a ligand represented by Formula 402 below:

<Formula 401>

$M(L_{401})_{xc1}(L_{402})_{xc2}$

<Formula 402>

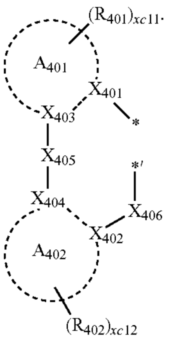

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$(s) may be identical to or different from each other, $L_{402}$ may be an organic ligand, and xc2 may be an integer from 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be a $C_5$-$C_{60}$ cyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)($Q_{412}$)-*', *—C($Q_{411}$)=*', or *=C($Q_{411}$)=*', and $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{401}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=OX)($Q_{401}$)($Q_{402}$), in which $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

* and *' in Formula 402 each indicates a binding site to M in Formula 401.

In an exemplary embodiment of the present disclosure, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In an exemplary embodiment of the present disclosure, in Formula 402, i) $X_{401}$ may be nitrogen, and $X_{402}$ may be carbon, or ii) both $X_{401}$ and $X_{402}$ may each be nitrogen at the same time.

In an exemplary embodiment of the present disclosure, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbomanyl group, a norbomenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbomanyl group, a norbomenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbomanyl group, a norbomenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(═O)($Q_{401}$), —S(═O)$_2$($Q_{401}$), and —P(═O)($Q_{401}$)($Q_{402}$), in which $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but the present disclosure is not limited thereto.

In an exemplary embodiment of the present disclosure, when xc1 in Formula 401 is two or more, two $A_{401}$(s) in two or more $L_{401}$(s) may optionally be linked via $X_{407}$, which is a linking group, or two $A_{402}$(s) may optionally be linked via $X_{406}$, which is a linking group (see Compounds PD1 to PD4 and PD7 as shown below). $X_{401}$ and $X_{406}$ may each independently be a single bond, *—O—*', *—S—*', *—C(═O)—*, *—N($Q_{413}$)-*', *—C($Q_{413}$)($Q_{414}$)-*', or *—C($Q_{413}$)═C($Q_{414}$)-*' (in which $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but the present disclosure is not limited thereto.

$L_{402}$ in Formula 401 may be a monovalent, divalent, or trivalent organic ligand. For example, $L_{402}$ may be selected from a halogen, a diketone (for example, acetylacetonate), a carboxylic acid (for example, picolinate), —C(═O), an isonitrile, —CN, and a phosphorus-containing compound (for example, phosphine or phosphite), but the present disclosure is not limited thereto.

In an exemplary embodiment of the present disclosure, the phosphorescent dopant may be selected from, for example, Compounds PD1 to PD25, but the present disclosure is not limited thereto:

PD1

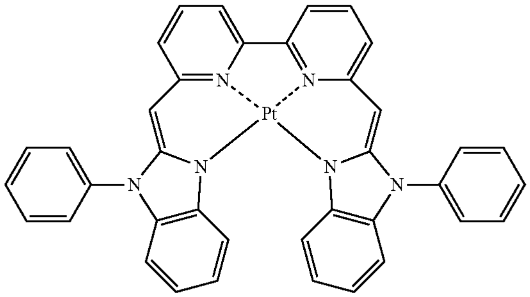

PD2

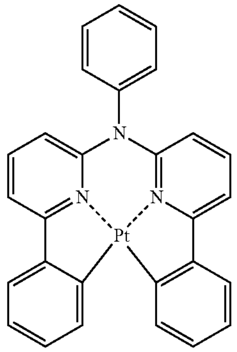

PD3

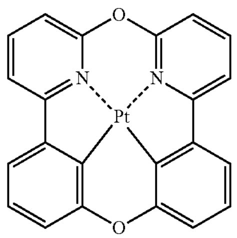

PD4

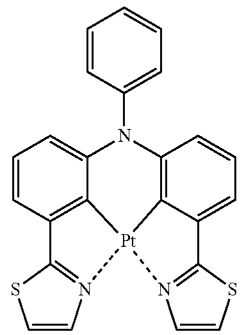

-continued
PD5
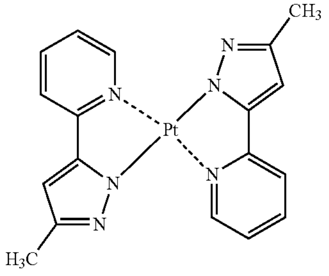
PD6
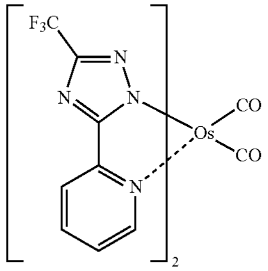
PD7
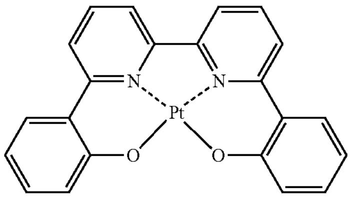
PD8
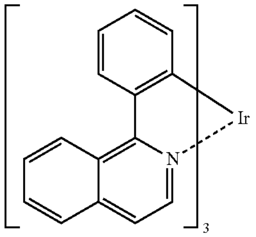
PD9
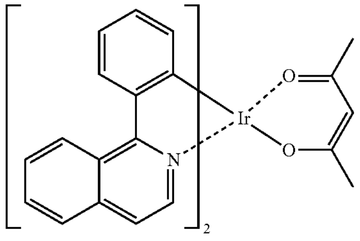
PD10
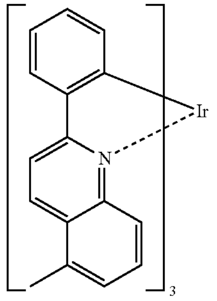
-continued
PD11
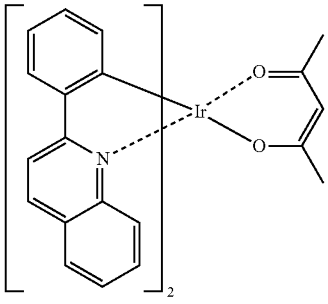
PD12
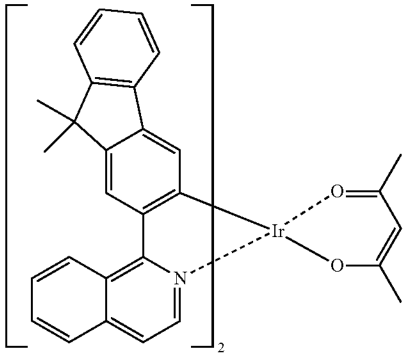
PD13
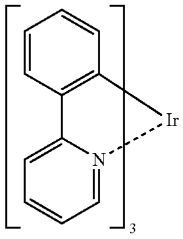
PD14
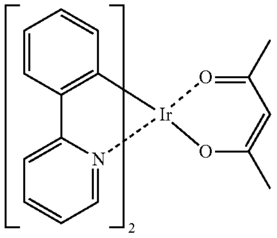
PD15
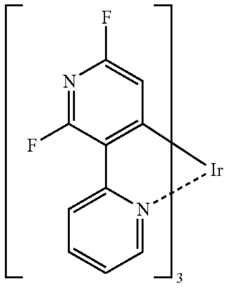

-continued
PD16
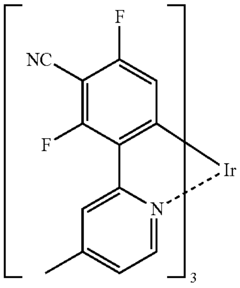
PD17
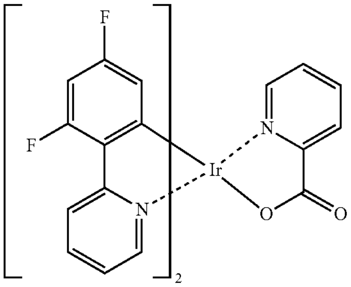
PD18
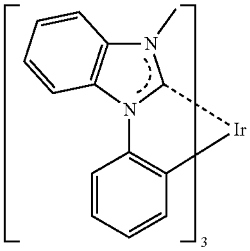
PD19
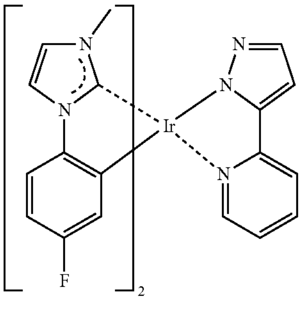
PD20
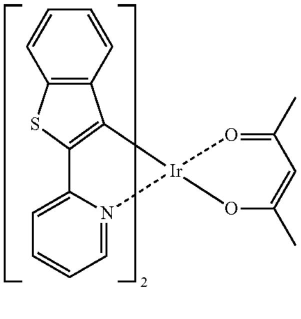
-continued
PD21
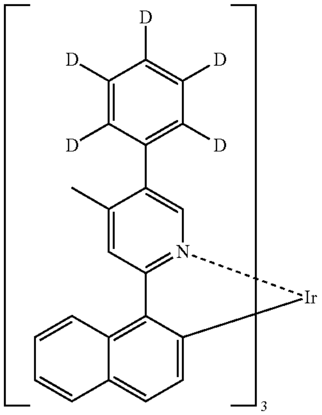
PD22
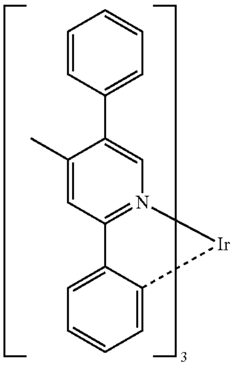
PD23
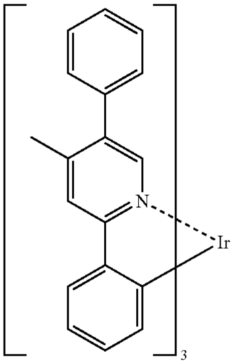
PD24
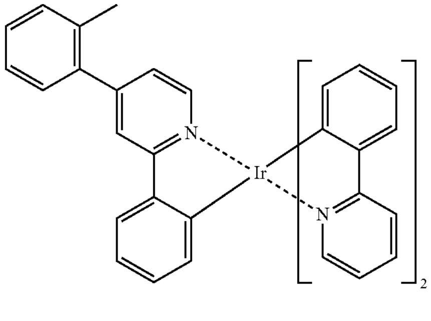

-continued

PD25

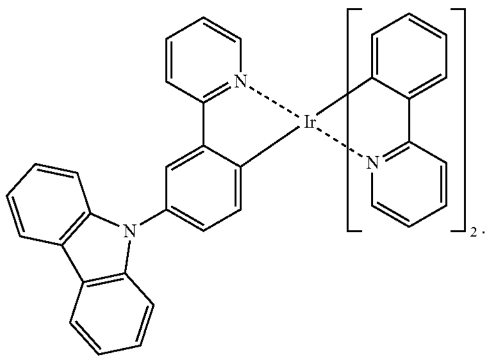

[Fluorescent Dopant in Emission Layer]

The fluorescent dopant may include the condensed cyclic compound represented by Formula 1.

In an exemplary embodiment of the present disclosure, the fluorescent dopant may include an arylamine compound or a styrylamine compound.

The fluorescent dopant may include a compound represented by Formula 501 below:

<Formula 501>

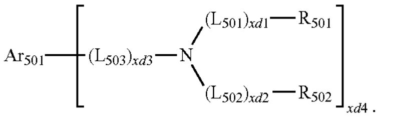

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In an exemplary embodiment of the present disclosure, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In an exemplary embodiment of the present disclosure, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In an exemplary embodiment of the present disclosure, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —$Si(Q_{31})(Q_{32})(Q_{33})$, in which $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In an exemplary embodiment of the present disclosure, xd4 in Formula 501 may be 2, but the present disclosure is not limited thereto.

In an exemplary embodiment of the present disclosure, the fluorescent dopant may be selected from, for example, Compounds FD1 to FD22:

FD1

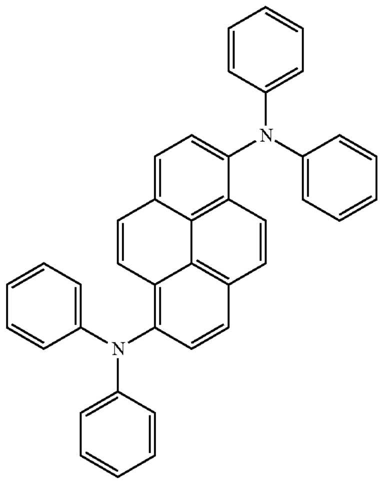

FD2

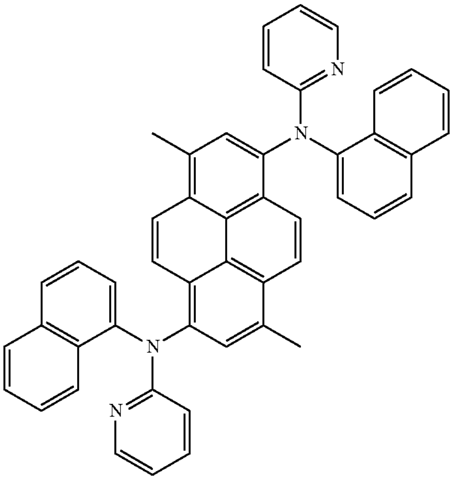

FD3

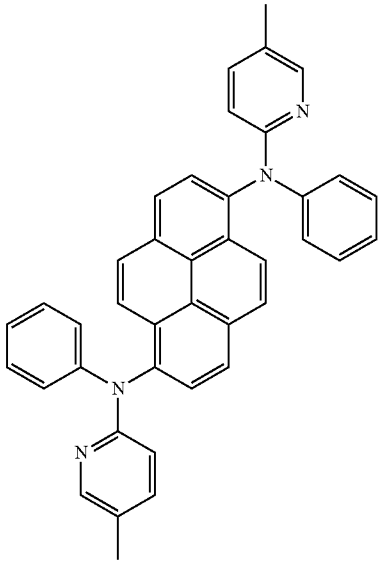

-continued
FD4
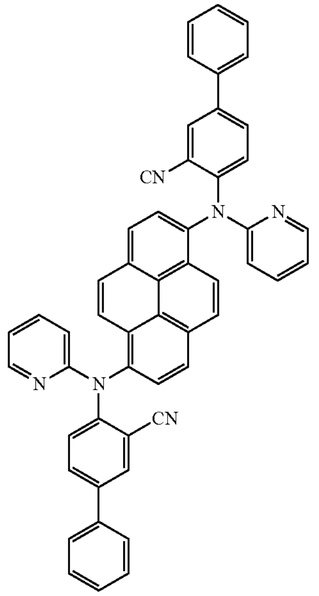
FD5
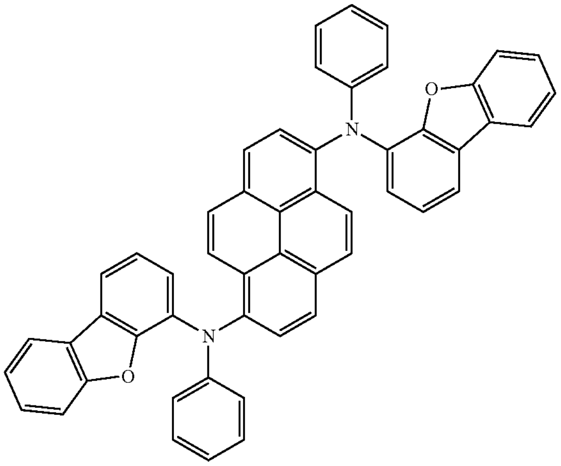
FD6
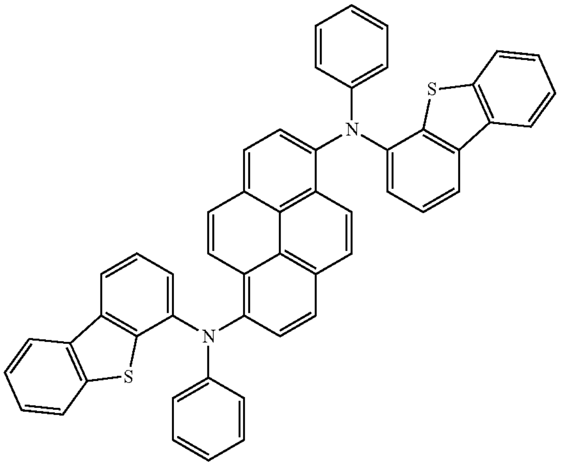
-continued
FD7
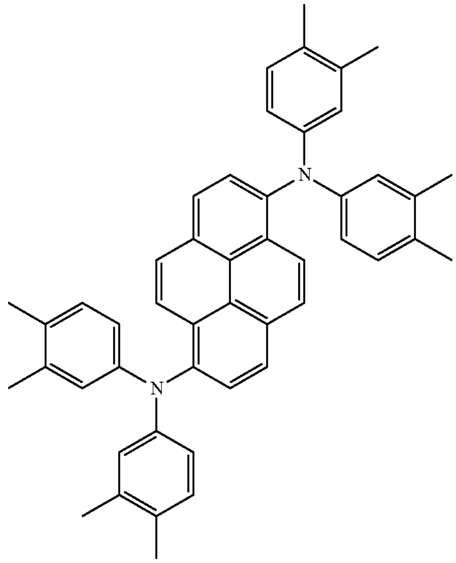
FD8
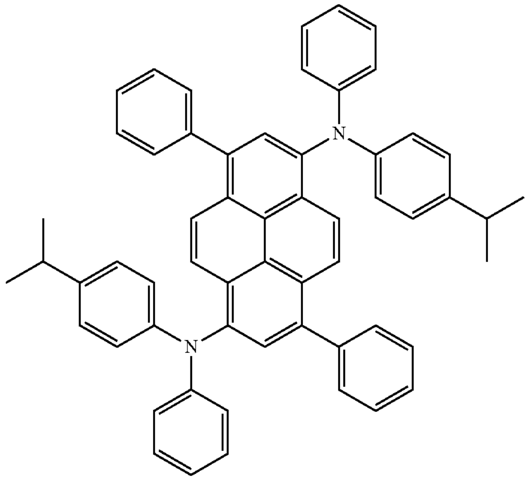
FD9
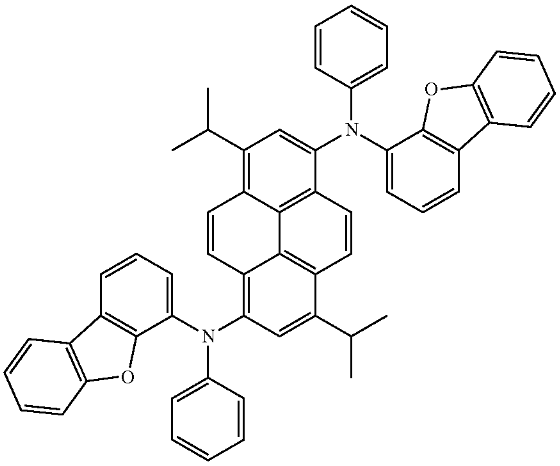

-continued
FD10
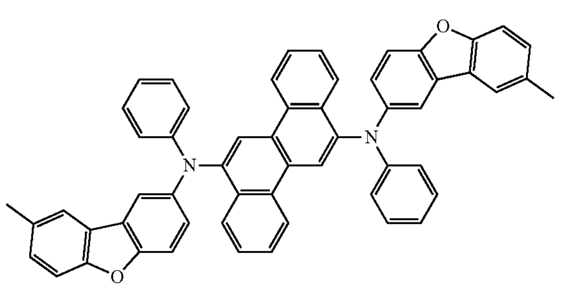
FD11
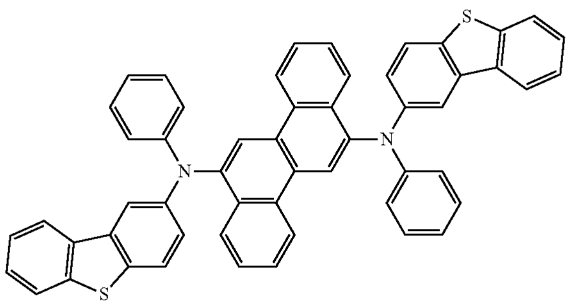
FD12
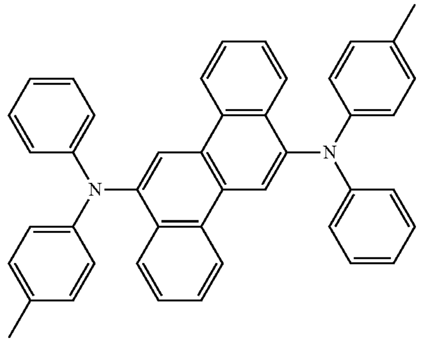
FD13
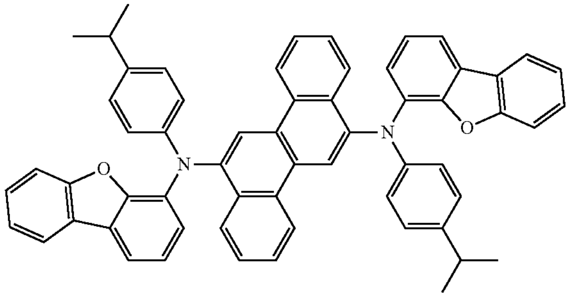
FD14
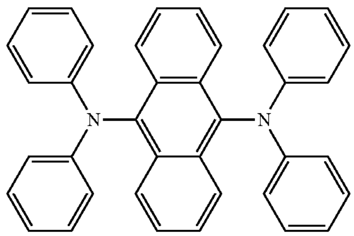
-continued
FD15
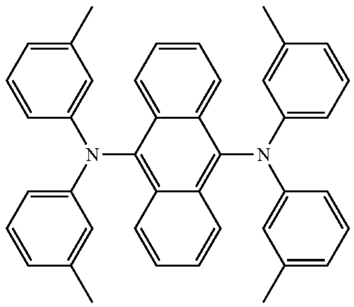
FD16
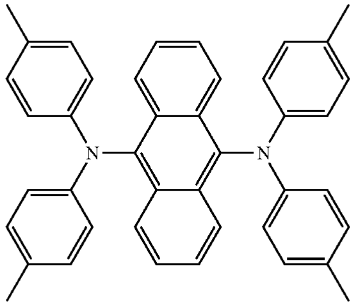
FD17
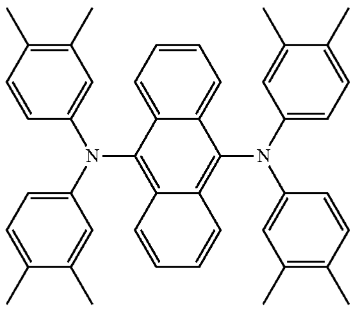
FD18
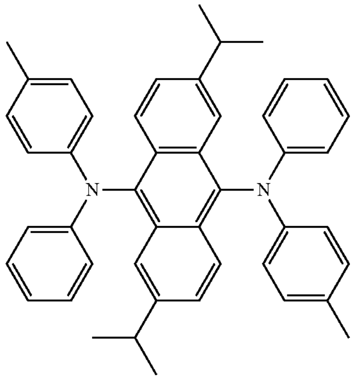

-continued
FD19
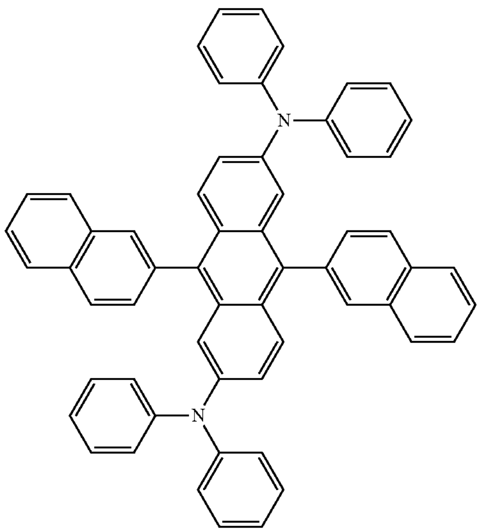
FD20
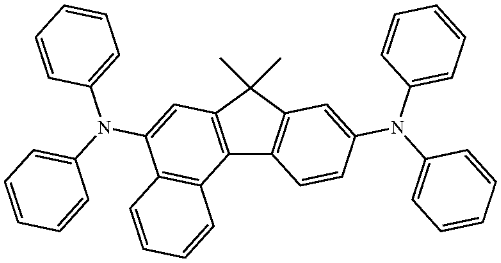
-continued
FD21
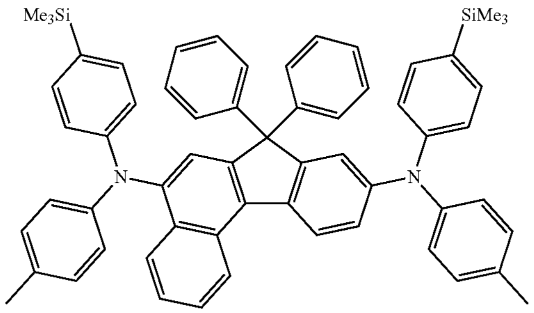
FD22
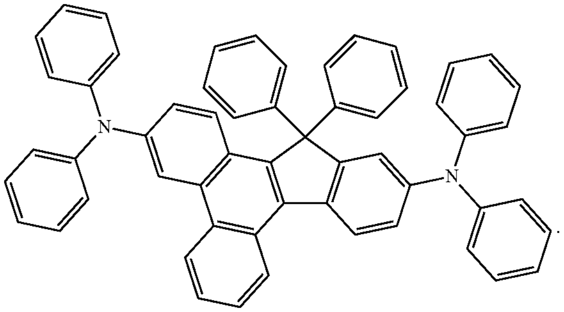
In an exemplary embodiment of the present disclosure, the fluorescent dopant may be selected from the following compounds, but the present disclosure is not limited thereto:
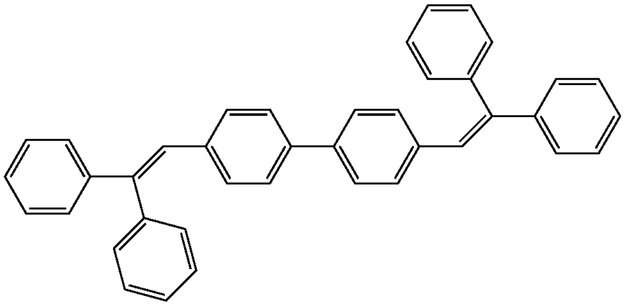
DPVBi
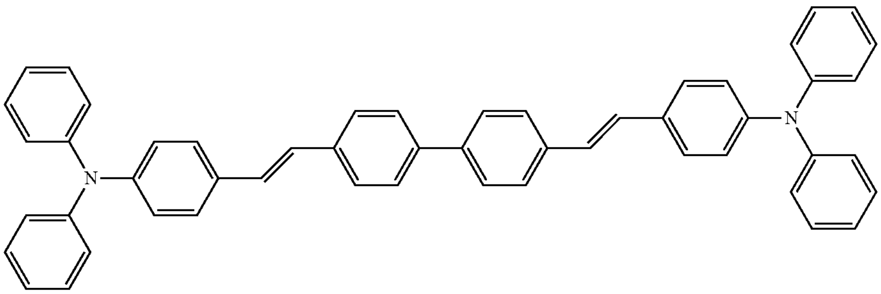
DPAVBi -continued

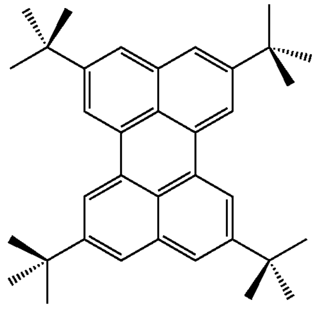

TBPe

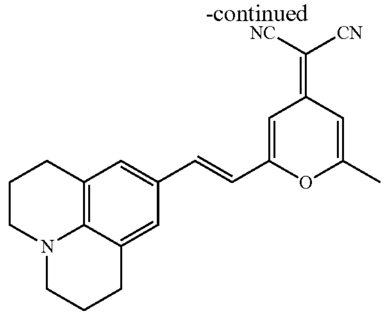

DCM

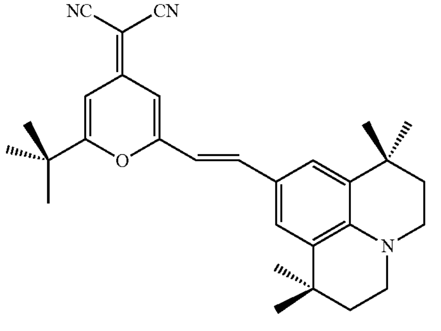

DCJTB

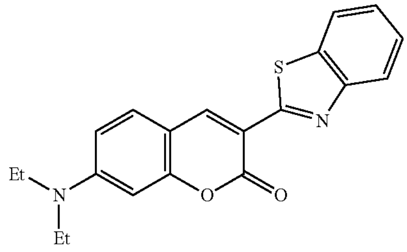

Coumarin 6

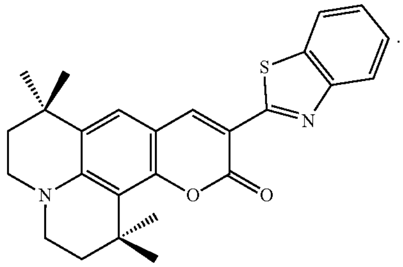

C545T

[Electron Transport Region in Organic Layer 150]

The electron transport region may have i) a single-layered structure including a single layer which includes a single material, ii) a single-layered structure including a single layer which includes a plurality of different materials, or iii) a multi-layered structure having a plurality of layers which include a plurality of different materials.

The electron transport region may include at least one selected from a buffer layer, a hole blocking layer, an electron control layer, an electron transport layer, and an electron injection layer, but the present disclosure is not limited thereto.

In an exemplary embodiment of the present disclosure, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, in which for each structure, constituting layers are sequentially stacked on and from an emission layer. However, the present disclosure is not limited thereto.

The electron transport region (for example, a buffer layer, a hole blocking layer, an electron control layer, and/or an electron transport layer in the electron transport region) may include a metal-free compound containing at least one w electron-depleted nitrogen-containing ring.

The "π electron-depleted nitrogen-containing ring" may indicate a $C_1$-$C_{60}$ heterocyclic group having at least one *—N=*' moiety as a ring-forming moiety.

In an exemplary embodiment of the present disclosure, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one of 5-membered to 7-membered heteromonocyclic groups, each having at least one *—N=*' moiety, is condensed with at least one $C_6$-$C_{60}$ carbocyclic group.

Examples of the π electron-depleted nitrogen-containing ring include an imidazole group, a pyrazole group, a thiazole group, an isothiazole group, an oxazole group, an isoxazole group, a pyridine group, a pyrazine group, a pyrimidine group, a pyridazine group, indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, but the present disclosure is not limited thereto.

In an exemplary embodiment of the present disclosure, the electron transport region may include a compound represented by Formula 601:

$$[Ar_{601}]_{xe11}\text{-}[(L_{601})_{xe1}\text{-}R_{601}]_{xe21}. \qquad \text{<Formula 601>}$$

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(═O)($Q_{601}$), —S(═O)$_2$($Q_{601}$), and —P(═O)($Q_{601}$)($Q_{602}$), in which $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer of 1 to 5.

In an exemplary embodiment of the present disclosure, at least one selected from $Ar_{601}$ in the number of xe1 and $R_{601}$ in the number of xe21 may include the π electron-depleted nitrogen-containing ring.

In an exemplary embodiment of the present disclosure, in Formula 601, ring $Ar_{601}$ may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(═O)$_2$($Q_{31}$), and —P(═O)($Q_{31}$)($Q_{32}$), in which $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more Ar601(s) may be linked via a single bond.

In an exemplary embodiment of the present disclosure, $Ar_{601}$ in Formula 601 may be an anthracene group.

In an exemplary embodiment of the present disclosure, a compound represented by Formula 601 may be represented by Formula 601-1:

<Formula 601-1>

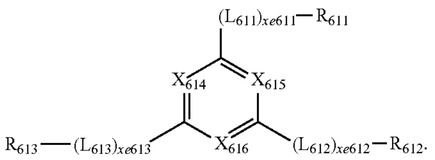

In Formula 601-1, $X_{614}$ may be N or C($R_{614}$), $X_{615}$ may be N or C($R_{615}$), $X_{616}$ may be N or C($R_{616}$), and at least one selected from $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In an exemplary embodiment of the present disclosure, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a thiophenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but the present disclosure is not limited thereto.

In an exemplary embodiment of the present disclosure, in Formulae 601 and 601-1, xe1 and xe611 to xe613 may each independently be 0, 1, or 2.

In an exemplary embodiment of the present disclosure, in Formulae 601 and 601-1, $R_{601}$ and $R_{611}$ to $R_{613}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosiolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazotyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazoyl group, a dibenzocarbazolyl group, a dibenzosilolyl group, a pyridinyl group, an imidazoyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), in which Q$_{601}$ and Q$_{602}$ are the same as described above.

The electron transport region may include at least one compound selected from, for example, Compounds ET1 to ET36, but the present disclosure is not limited thereto:

ET1

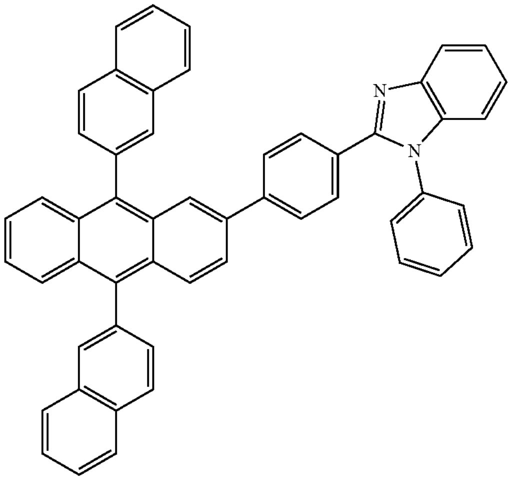

ET2

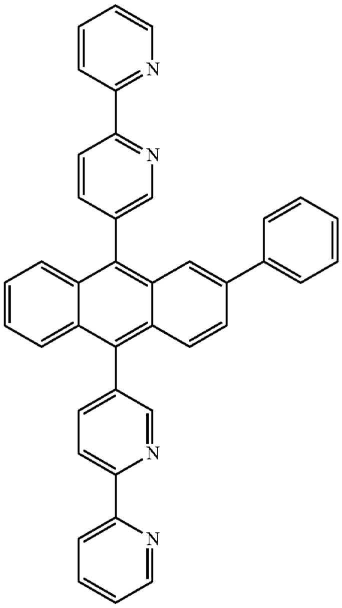

-continued

ET3

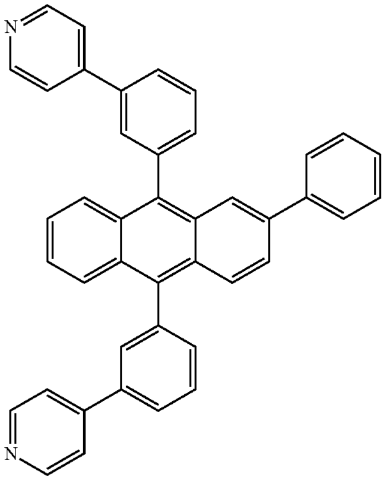

ET4

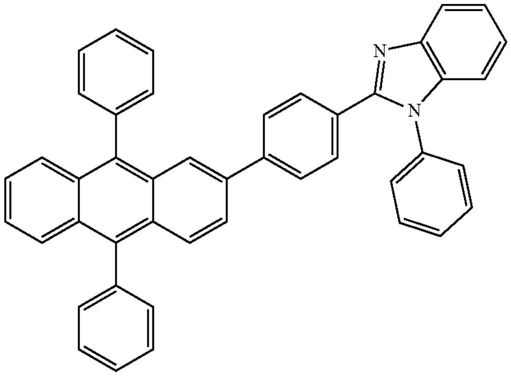

ET5

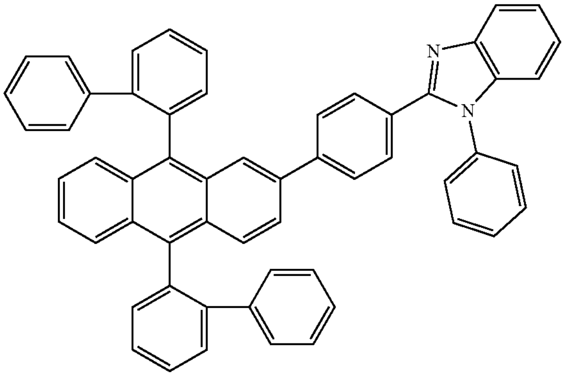

-continued
ET6
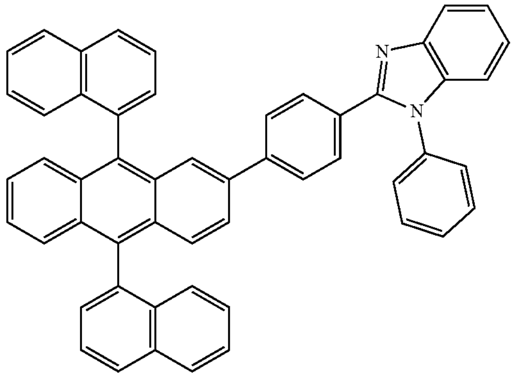
ET7
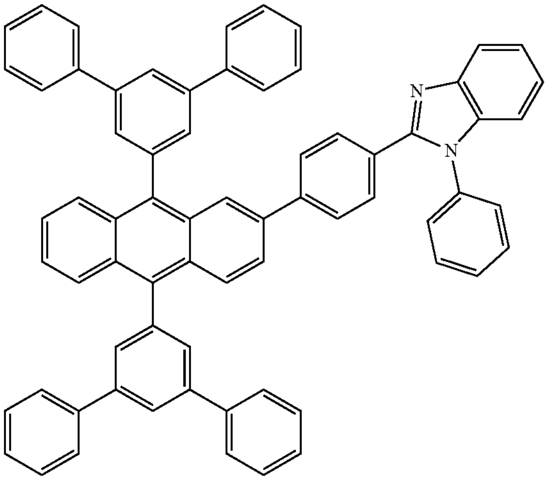
ET8
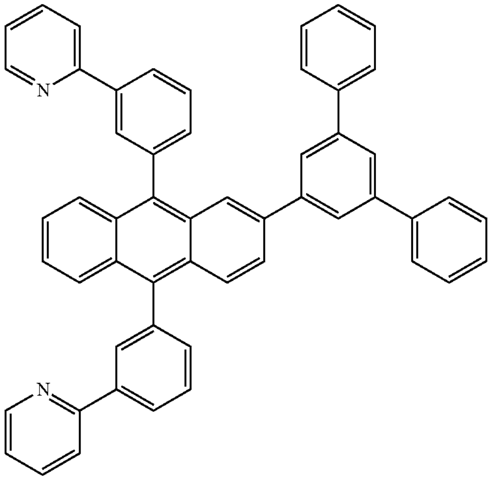
-continued
ET9
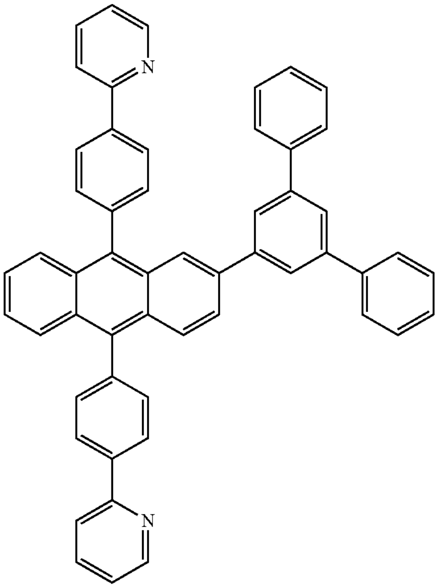
ET10
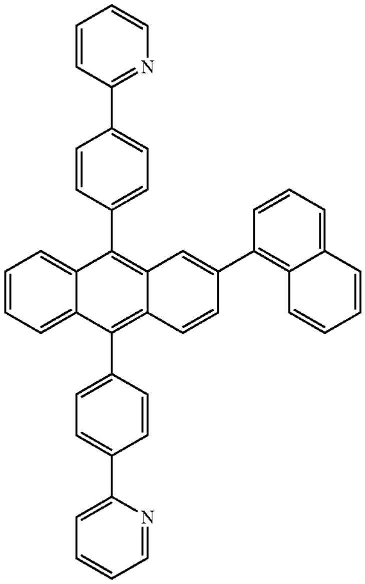

-continued
ET11
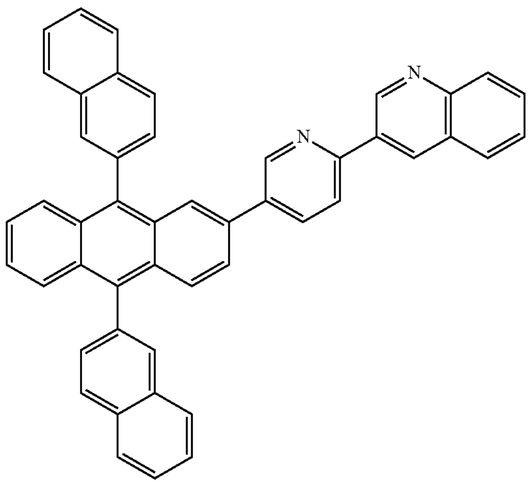
ET12
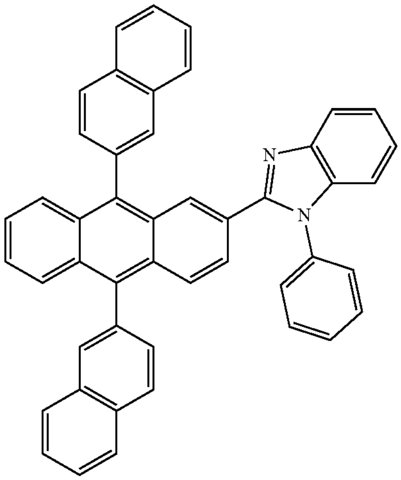
ET13
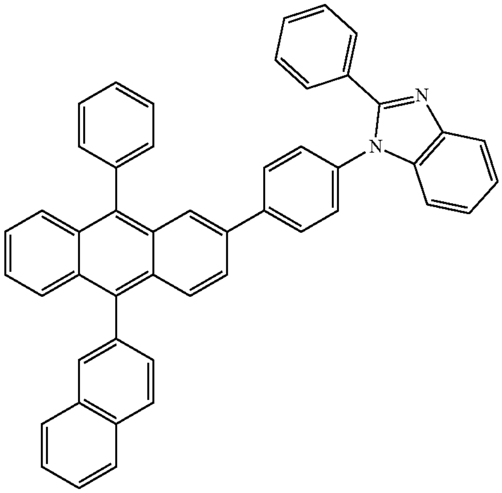
-continued
ET14
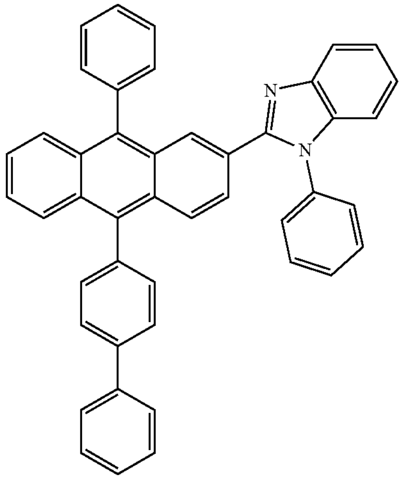
ET15
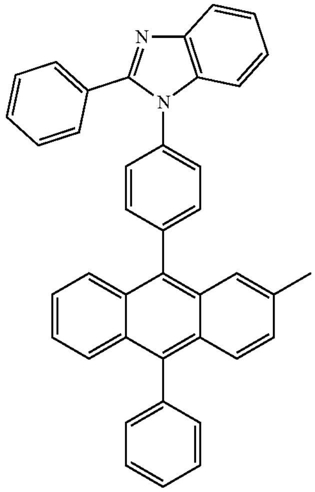
ET16
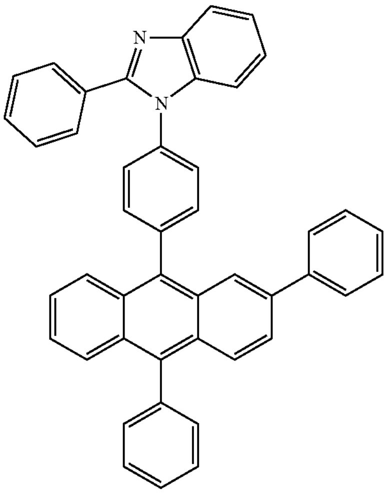

-continued
ET17
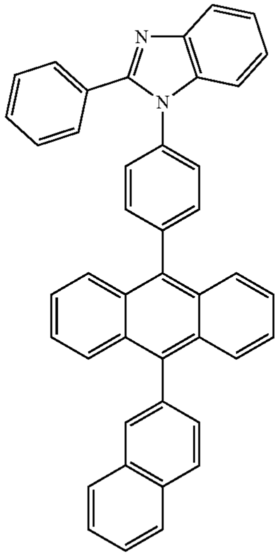
ET18
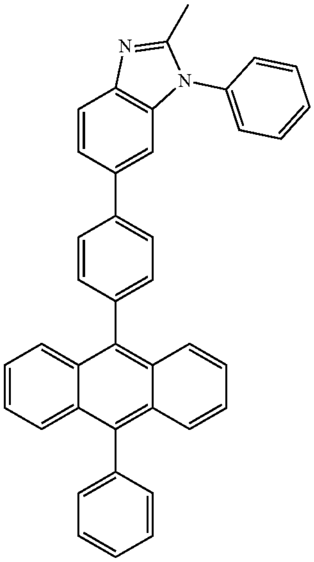
ET19
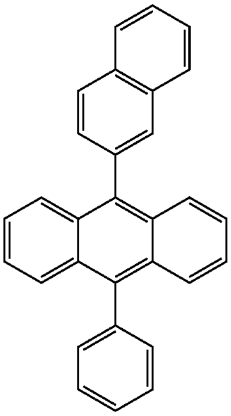
-continued
ET20
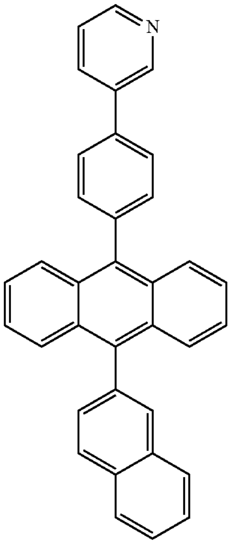
ET21
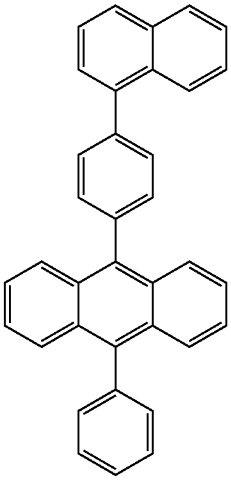
ET22
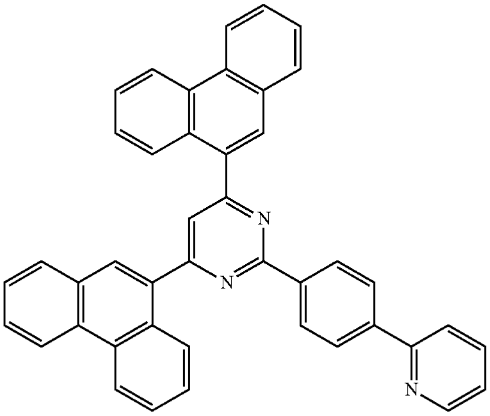

ET23
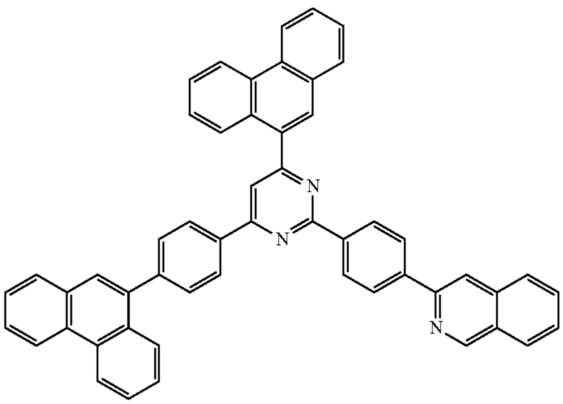
ET24
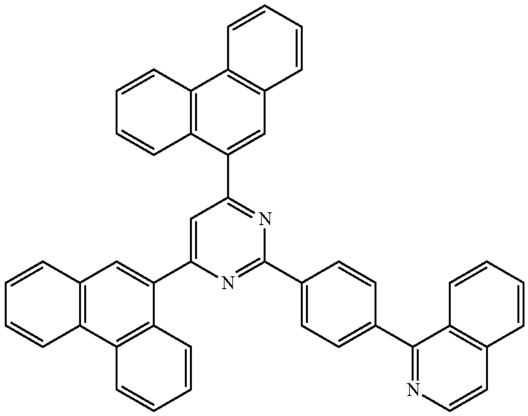
ET25
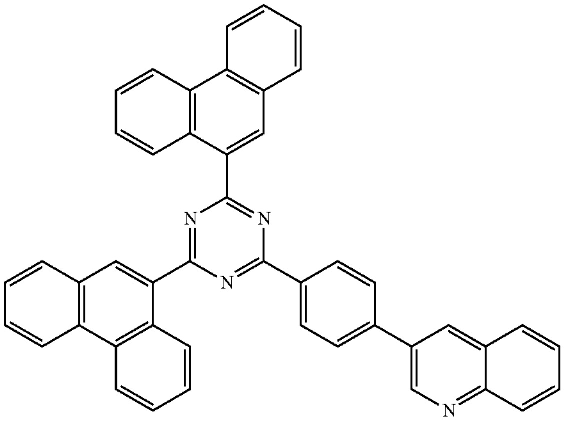
ET26
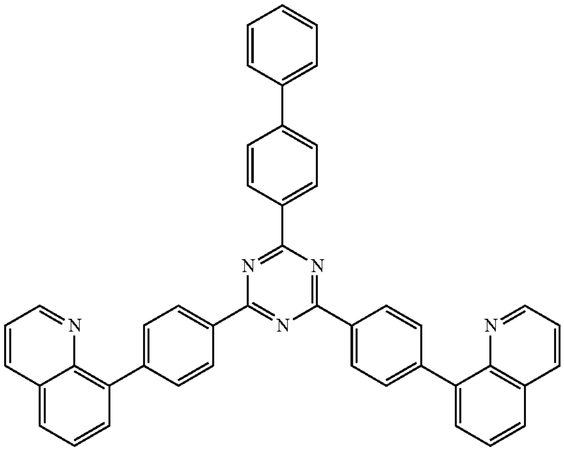
ET27
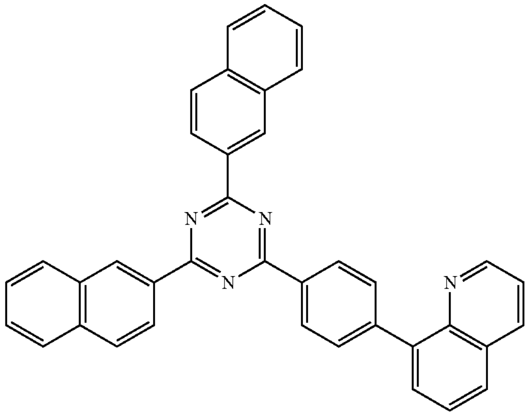
ET28
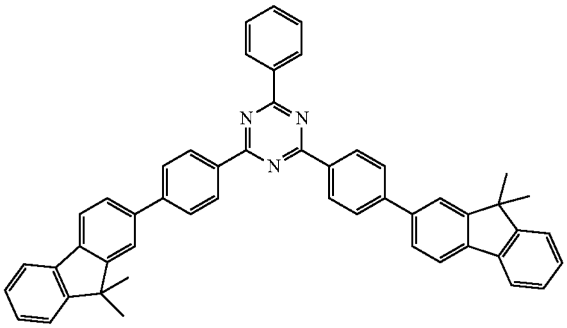

-continued
ET29
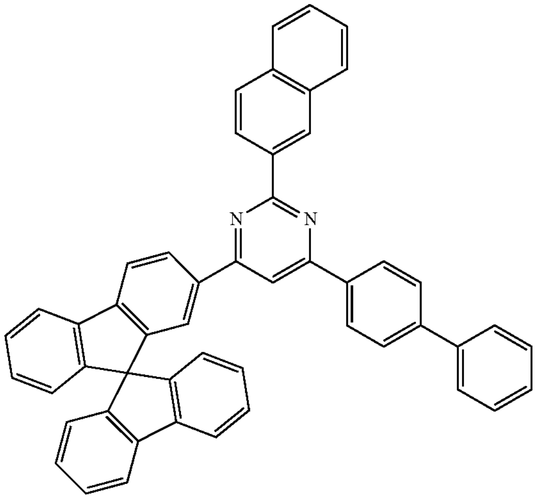
ET30
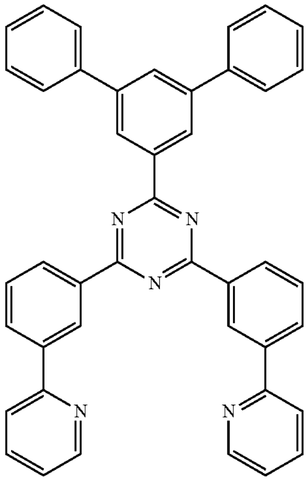
ET31
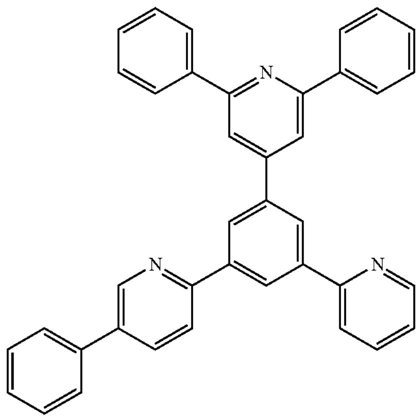
-continued
ET32
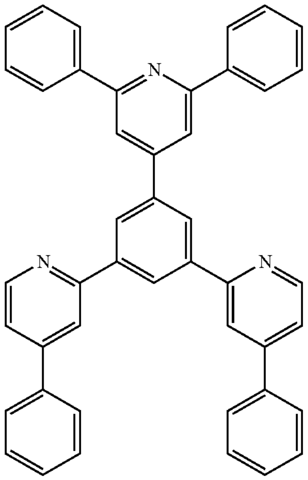
ET33
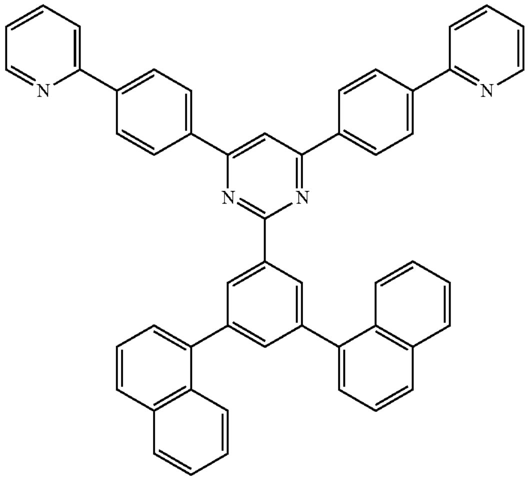
ET34
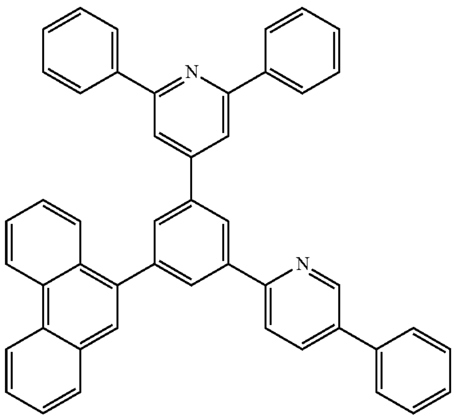

-continued

ET35

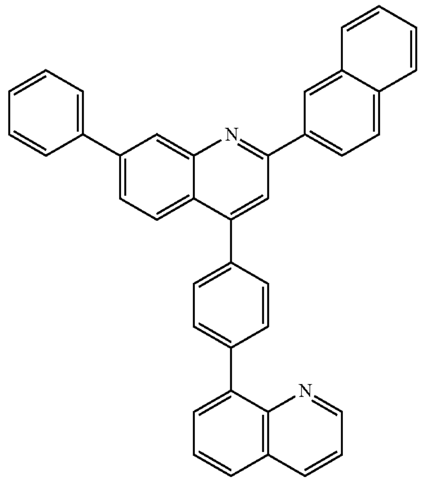

ET36

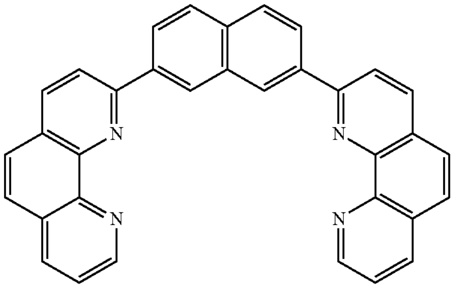

In an exemplary embodiment of the present disclosure, the electron transport region may include at least one compound selected from 2,9-dimethyl-4,7-diphenyl-1,10-phenanthroline (BCP), 4,7-diphenyl-1,10-phenanthroline (Bphen), tris(8-hydroxyquinolino)aluminum (Alq3), bis(2-methyl-8-quinolinolato-N1,O8)-(1,1'-biphenyl-4-olato)aluminum (BAlq), 3-(biphenyl-4-yl)-5-(4-tert-butylphenyl)-4-phenyl-4H-1,2,4-triazole (TAZ), and 4-(naphthalen-1-yl)-3,5-diphenyl-4H-1,2,4-triazole (NTAZ):

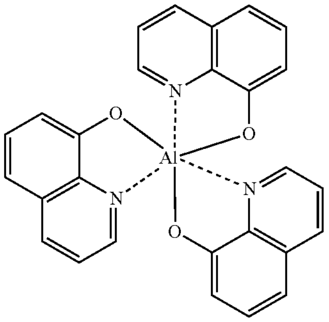

$Alq_3$

-continued

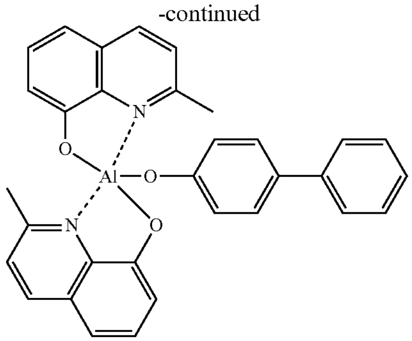

BAlq

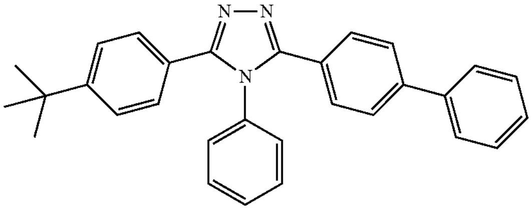

TAZ

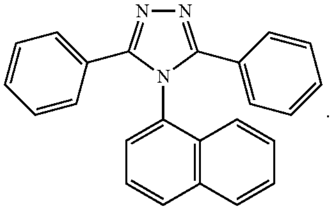

NTAZ

A thickness of the buffer layer, the hole blocking layer, or the electron control layer may be in a range of about 20 Å to about 1,000 Å, for example, about 30 Å to about 300 Å. When the thicknesses of the buffer layer, the hole blocking layer, and the electron control layer are within these ranges, the electron blocking layer may have excellent electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, and a cyclopentadiene, but the present disclosure is not limited thereto.

In an exemplary embodiment of the present disclosure, the metal-containing material may include a Li complex. The Li complex may include, for example, Compound ET-D1 (lithium quinolate, LiQ) or ET-D2:

ET-D1

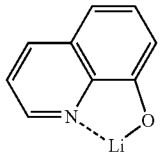

ET-D2

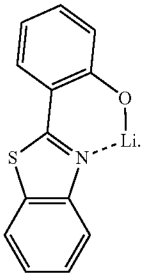

The electron transport region may include an electron injection layer that facilitates injection of electrons from the second electrode 190. The electron injection layer may directly contact the second electrode 190.

The electron injection layer may have i) a single-layered structure including a single layer which includes a single material, ii) a single-layered structure including a single layer which includes a plurality of different materials, or iii) a multi-layered structure having a plurality of layers which include a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from, for example, Li, Na, K, Rb, and Cs. In an exemplary embodiment of the present disclosure, the alkali metal may be Li, Na, or Cs. In an exemplary embodiment of the present disclosure, the alkali metal may be Li or Cs, but the present disclosure is not limited thereto.

The alkaline earth metal may be selected from, for example, Mg, Ca, Sr, and Ba.

The rare earth metal may be selected from, for example, Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides such as, for example, $Li_2O$, $Cs_2O$, and $K_2O$, and alkali metal halides such as, for example, LiF, NaF, CsF, KF, LiI, NaI, CsI, and KI. In an exemplary embodiment of the present disclosure, the alkali metal compound may be selected from, for example, LiF, $Li_2O$, NaF, LiI, NaI, CsI, and KI, but the present disclosure is not limited thereto.

The alkaline earth-metal compound may be selected from alkaline earth-metal oxides such as, for example, BaO, SrO, CaO, $Ba_xSr_{1-x}O$ (0<x<1), and $Ba_xCa_{1-x}O$ (0<x<1). In an exemplary embodiment of the present disclosure, the alkaline earth-metal compound may be selected from, for example, BaO, SrO, and CaO, but the present disclosure is not limited thereto.

The rare earth metal compound may be selected from, for example, $YbF_3$, $ScF_3$, $ScO_3$, $Y_2O_3$, $Ce_2O_3$, $GdF_3$, and $TbF_3$. In an exemplary embodiment of the present disclosure, the rare earth metal compound may be selected from, for example, $YbF_3$, $ScF_3$, $TbF_3$, $YbI_3$, $ScI_3$, and $TbI_3$, but the present disclosure is not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazole, hydroxy phenylpyridine, hydroxy phenylbenzimidazole, hydroxy phenylbenzothiazole, bipyridine, phenanthroline, and cyclopentadiene, but the present disclosure is not limited thereto.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In an exemplary embodiment of the present disclosure, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

[Second Electrode 190]

The second electrode 190 may be disposed on the organic layer 150 having above described structure. The second electrode 190 may be a cathode which is an electron injection electrode, and in this regard, a material for forming the second electrode 190 may be selected from a metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but the present disclosure is not limited thereto. The second electrode 190 may be a transmissive electrode, a semi-transmissive electrode, or a reflective electrode.

The second electrode 190 may have a single-layered structure, or a multi-layered structure including two or more layers.

Figure 2:
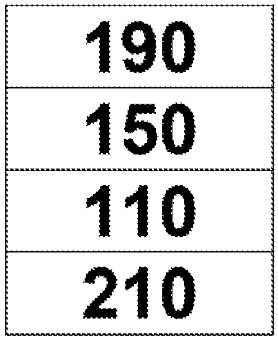
FIG. 2 is a schematic cross-sectional view of an organic light-emitting device according to an exemplary embodiment of the present disclosure.
Figure 3:
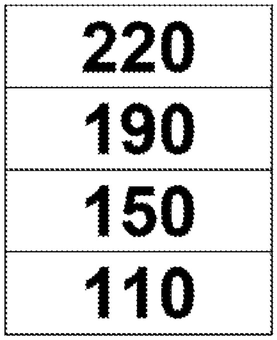
FIG. 3 is a schematic cross-sectional view of an organic light-emitting device according to an exemplary embodiment of the present disclosure.
Figure 4:
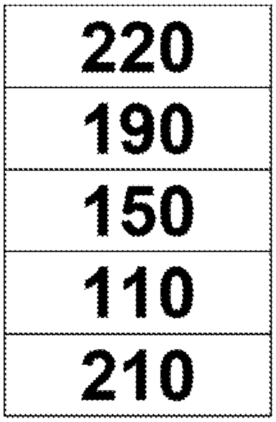
FIG. 4 is a schematic cross-sectional view of an organic light-emitting device according to an exemplary embodiment of the present disclosure.

[Description of FIGS. 2 to 4]

FIGS. 2-4 each represents a schematic cross-sectional view of an organic light-emitting device, in which: an organic light-emitting device 20 of FIG. 2 includes a first capping layer 210, a first electrode 110, an organic layer 150, and a second electrode 190, which are sequentially stacked in this stated order; an organic light-emitting device 30 of FIG. 3 includes a first electrode 110, an organic layer 150, a second electrode 190, and a second capping layer 220, which are sequentially stacked in this stated order; and an organic light-emitting device 40 of FIG. 4 includes a first capping layer 210, a first electrode 110, an organic layer 150, a second electrode 190, and a second capping layer 220, which are sequentially stacked in this stated order.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

The first capping layer 210 and the second capping layer 220 may each independently include at least one material selected from carbocyclic compounds, heterocyclic compounds, amine-based compounds, porphyrine derivatives, phthalocyanine derivatives, a naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I.

In an exemplary embodiment of the present disclosure, the first capping layer 210 and the second capping layer 220 may each independently include an amine-based compound.

In an exemplary embodiment of the present disclosure, at least one selected from the first capping layer 210 and the second capping layer 220 illustrated in FIG. 4 may include the condensed cyclic compound represented by Formula 1.

In an exemplary embodiment of the present disclosure, the first capping layer 210 and the second capping layer 220 may each independently include the compound represented by Formula 201 or the compound represented by Formula 202.

In an exemplary embodiment of the present disclosure, the first capping layer 210 and the second capping layer 220 may each independently include a compound selected from, for example, Compounds HT28 to HT33 and Compounds CP1 to CP5, but the present disclosure is not limited thereto:

CP1

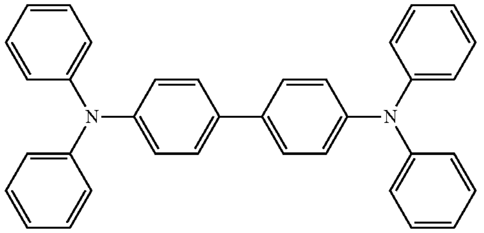

CP2

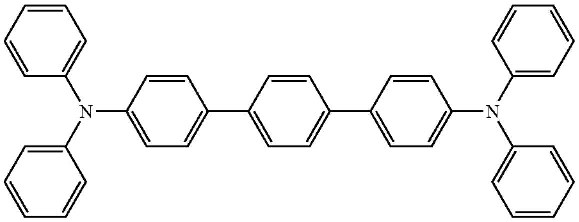

CP3

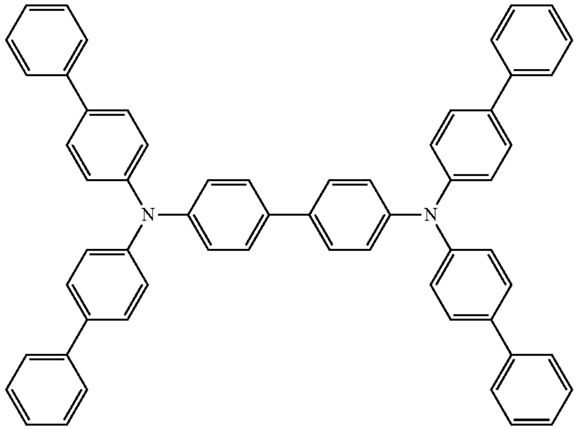

CP4

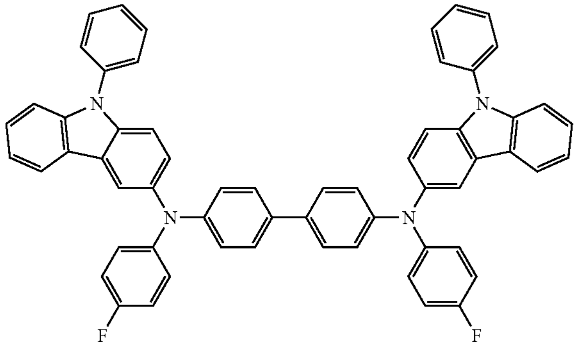

CP5

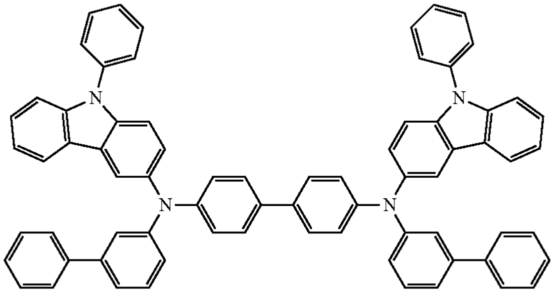

.

Hereinbefore, the organic light-emitting device according to an exemplary embodiment of the present disclosure has been described in connection with FIGS. 1-4, However, the present disclosure is not limited thereto.

Layers constituting the hole transport region, an emission layer, and layers constituting the electron transport region may be formed in a certain region by using one or more suitable methods selected from, for example, vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, for example, the vacuum deposition may be performed at a deposition temperature of about 100° C. to about 500° C., at a vacuum degree of about $10^{-8}$ torr to about $10^{-3}$ torr, and at a deposition rate of about 0.01 Å/sec to about 100 Å/sec by taking into account the material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to about 200° C. by taking into account the material to be included in a layer to be formed, and the structure of a layer to be formed.

[General Definition of Substituents]

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{10}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_2$-$C_{10}$ heterocycloalkenyl group" as used herein refers to a monovalent monocyclic group that has at least one heteroatom selected from N, O, Si, P, and S as a ring-forming atom, 2 to 10 carbon atoms, and at least one carbon-carbon double bond in its ring. No n-limiting examples of the $C_2$-$C_{10}$ heterocycloalkenyl group include a 2,3-dihydrofuranyl group, and a 2,3-dihydrothiophenyl group. The term "$C_2$-$C_{10}$ heterocycloalkenylene group," used herein, refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a carbocyclic aromatic system that has at least one heteroatom selected from N, O, Si, P, and S as a ring-forming atom, in addition to 1 to 1 carbon atoms. The term "$C_1$-$C_{60}$ heteroarylene group" as used herein refers to a divalent group having a carbocyclic aromatic system that has at least one heteroatom selected from N, O, Si, P, and S as a ring-forming atom, in addition to 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each includes two or more rings, the rings may be fused to each other.

The term "$C_6$-$C_{60}$ aryloxy group" as used herein indicates —$OA_{102}$ (wherein $A_{102}$ is the $C_6$-$C_{60}$ aryl group), and a $C_6$-$C_{60}$ arylthio group indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed with each other, only carbon atoms as ring-forming atoms, and no aromaticity in its entire molecular structure. A detailed example of the monovalent non-aromatic condensed polycyclic group is a fluorenyl group. The term "divalent non-aromatic condensed polycyclic group," used herein, refers to a divalent group having the same structure as the monovalent non-aromatic condensed polycyclic group.

The term "monovalent non-aromatic condensed heteropolycyclic group" as used herein refers to a monovalent group (for example, having 1 to 60 carbon atoms) having two or more rings condensed to each other, at least one heteroatom selected from N, O, Si, P, and S, other than carbon atoms, as a ring-forming atom, and no aromaticity in its entire molecular structure. An example of the monovalent non-aromatic condensed heteropolycyclic group is a carbazolyl group. The term "divalent non-aromatic condensed heteropolycyclic group" as used herein refers to a divalent group having the same structure as the monovalent non-aromatic condensed heteropolycyclic group.

The term "$C_6$-$C_{60}$ carbocyclic group" as used herein refers to a monocyclic or polycyclic group having 5 to 60 carbon atoms in which a ring-forming atom is a carbon atom only. The $C_5$-$C_{10}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In an exemplary embodiment of the present disclosure, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_5$-$C_{60}$ carbocyclic group, except that as a ring-forming atom, at least one heteroatom selected from N, O, Si, P, and S is used in addition to carbon (the number of carbon atoms may be in a range of 1 to 60). Heterocyclic group includes one or more heterocyclic rings.

At least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{10}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{10}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{10}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, and $Q_{11}$, to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{10}$ heteroaryl group, a monovalent non-aromatic condensed polycyclic group, a monovalent non-aromatic condensed heteropolycyclic group, a biphenyl group, and a terphenyl group.

The term "Ph" as used herein represents a phenyl group, the term "Me" as used herein represents a methyl group, the term "Et" as used herein represents an ethyl group, the term "ter-Bu" or "$Bu^t$," as used herein, represents a tert-butyl group, and the term "OMe" as used herein represents a methoxy group.

The term "biphenyl group" used herein refers to a "phenyl group substituted with a phenyl group. The "biphenyl group" is one of a "substituted phenyl group" having a "$C_6$-$C_{60}$ aryl group" as a substituent.

The term "terphenyl group" used herein refers to a "phenyl group substituted with a biphenyl group. That is, the "terphenyl group" is one of a "phenyl group" having, as a substituent, a "$C_6$-$C_6$ aryl group substituted with a $C_6$-$C_6$ aryl group."

* and *' used herein, unless defined otherwise, each refer to a binding site to a neighboring atom in a corresponding formula.

The condensed cyclic compound represented by Formula 1 may be synthesized by using a known organic synthesis method. A synthesis method of the condensed cyclic compound may be recognizable by one of ordinary skill in the art in view of the following exemplary embodiments.

Hereinafter, a compound according to an exemplary embodiment of the present disclosure and an organic light-emitting device according to an exemplary embodiment of the present disclosure will be described in detail with reference to Synthesis Examples and Examples. The expression "B was used instead of A" used in describing Synthesis Examples means that an identical number of molar equivalents of B was used in place of molar equivalents of A.

SYNTHESIS EXAMPLES

Synthesis Example 1: Synthesis of Compound 1363

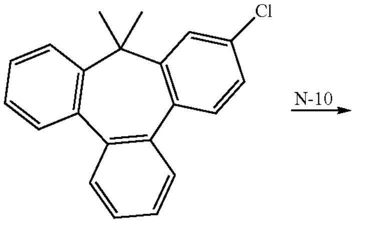

1(10)-A

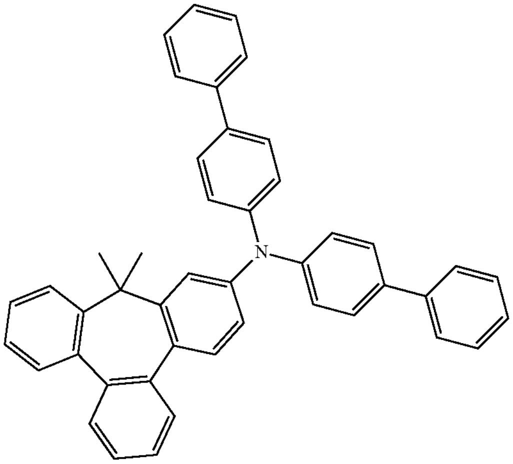

1363

1.52 g (5.00 mmol) of Compound 1(10)-A, 3.37 g (10.5 mmol) of amine Compound N-10, 69.6 mg (0.076 mmol) of tris(dibenzylideneacetone)dipalladium(0) ($Pd_2(dba)_3$), 30.8 mg (0.152 mmol) of tri-tert-butylphosphine (PtBus), and 1.92 g (20.0 mmol) of sodium tert-butoxide (NaOtBu) were dissolved in 100 mL of toluene and stirred at a temperature of 120° C. for 8 hours. The reaction solution was cooled to room temperature, and an organic layer was extracted therefrom three times by using salt water, water, and diethylether. The extracted organic layer was dried by using magnesium sulfate, and a solvent was evaporated therefrom. Then, the residue obtained therefrom was separated and purified by silica gel column chromatography to obtain 2.39 g (yield: 81%) of Compound 1363. The obtained compound was identified by liquid chromatography/mass spectrometry (LC-MS) and $^1$H nuclear magnetic resonance (NMR).

$C_{45}H_{35}N$: M+1 589.28

$^1$H NMR (500 MHz, $CDCl_3$) δ=7.96 (2H, d), 7.76-7.74 (6H, m), 7.60-7.37 (20H, m), 7.27 (1H, d), 1.58 (6H, s).

Synthesis Example 2: Synthesis of Compound 1404

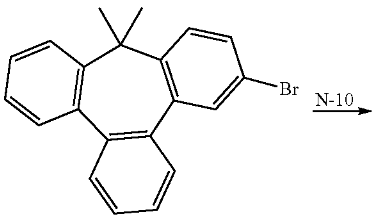

1(10)-B

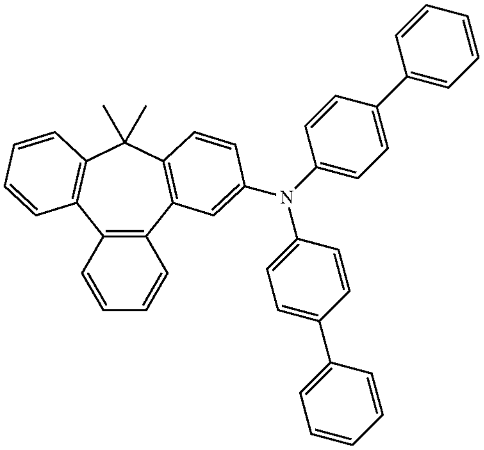

1404

2.60 g (yield: 88%) of Compound 1404 was synthesized in the same manner as in Synthesis Example 1, except that Compound 1(10)-B was used instead of Compound 1(10)-A. The obtained compound was identified by LC-MS and $^1$H NMR.

$C_{45}H_{35}N$: M+1 589.28

$^1$H NMR (500 MHz, $CDCl_3$) δ=7.96 (2H, d), 7.76-7.75 (6H, m), 7.60-7.26 (21H, m), 1.69 (6H, s).

Synthesis Example 3: Synthesis of Compound 2284

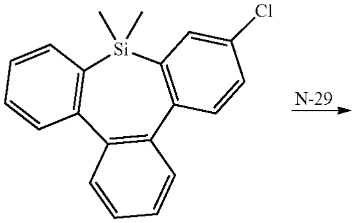

1(13)-A

-continued

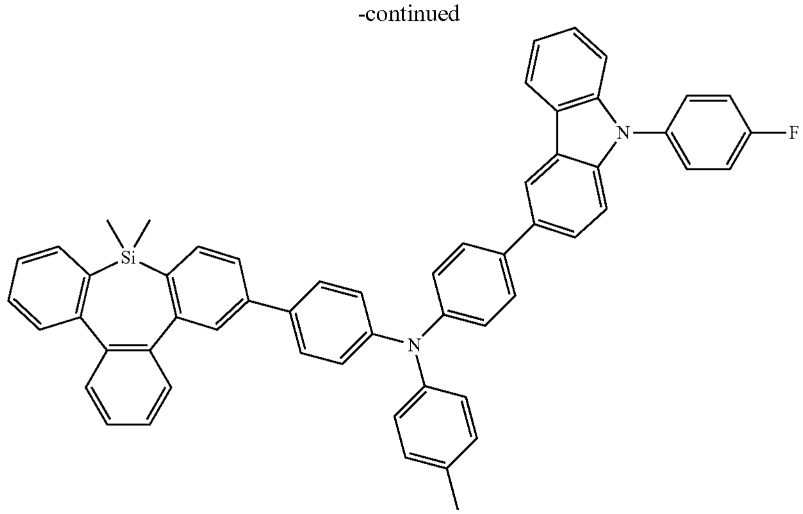

2284

Compound 1(13)-A, a boronic acid of amine Compound N-29, tetrakis(triphenylphosphine)palladium(0) (Pd $(PPh_3)_4$), and potassium carbonate ($K_2CO_3$) were added to a mixture of tetrahydrofuran (THF) and water and stirred at a temperature of 100° C. for 4 hours. The reaction solution was cooled to room temperature and washed by using salt water. An organic layer was extracted therefrom three times by using diethylether. The extracted organic layer was dried by using magnesium sulfate, and a solvent was evaporated therefrom. Then, the residue obtained therefrom was separated and purified by silica gel column chromatography to obtain 2.84 g (yield: 78%) of Compound 2284. The obtained compound was identified by LC-MS and $^1$H NMR.

$C_{51}H_{39}FN_2Si$: M+1 726.29

$^1$H NMR (500 MHz, $CDCl_3$) δ=8.19 (1H, d), 8.04-7.87 (8H, m), 7.37-7.34 (4H, m), 7.20-7.13 (5H, m), 2.32 (3H, s), 0.66 (6H, s).

Synthesis Example 4: Synthesis of Compound 2766

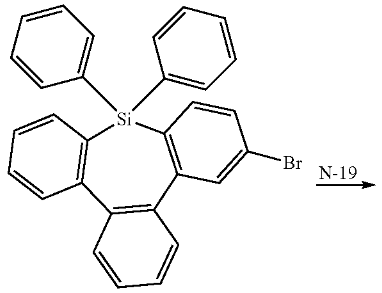

1(13)-B

-continued

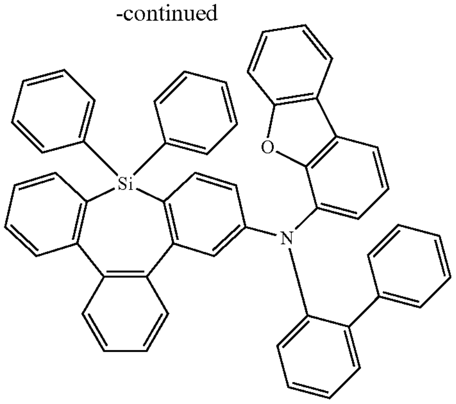

2766

2.90 g (yield: 78%) of Compound 2766 was synthesized in the same manner as in Synthesis Example 1, except that Compound 1(13)-B was used instead of Compound 1(10)-A, and amine Compound N-19 was used instead of amine Compound N-10. The obtained compound was identified by LC-MS and $^1$H NMR.

$C_{54}H_{37}NOSi$: M+1 743.26

$^1$H NMR (500 MHz, $CDCl_3$) δ=8.10 (1H, d), 7.98-7.96 (3H, m), 7.60-7.31 (30H, m), 7.14-7.08 (2H, m), 6.97 (1H, d).

Synthesis Example 5: Synthesis of Compound 126

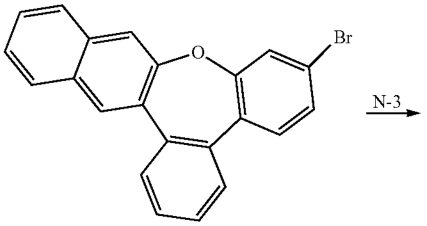

1(2)-A

-continued

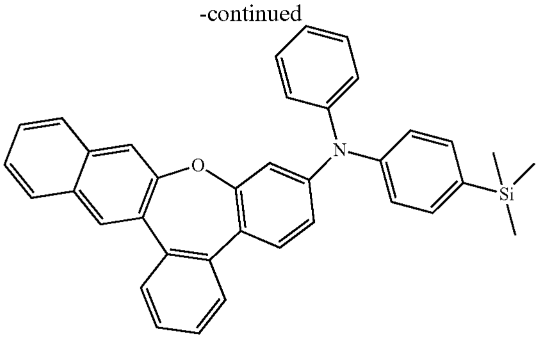

126

2.19 g (yield: 82%) of Compound 126 was synthesized in the same manner as in Synthesis Example 1, except that Compound 1(2)-A was used instead of Compound 1(10)-A, and amine Compound N-3 was used instead of amine compound N-10. The obtained compound was identified by LC-MS and $^{1}$H NMR.

$C_{37}H_{31}NOSi$: M+1 533.22

$^{1}$H NMR (500 MHz, $CDCl_3$) δ=8.10-8.04 (3H, m), 7.96 (2H, d), 7.83 (1H, s), 7.69 (1H, d), 7.61 (1H, t), 7.60 (2H, t), 7.52 (1H, dt), 7.36 (2H, d), 7.24-7.00 (9H, m), 0.88 (9H, s).

Synthesis Example 6: Synthesis of Compound 3239

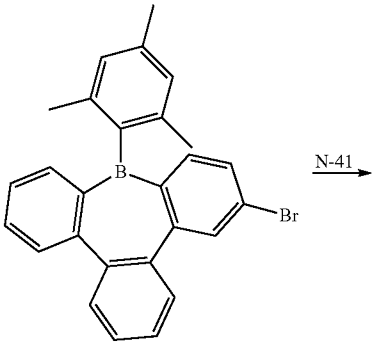

1(16)-A

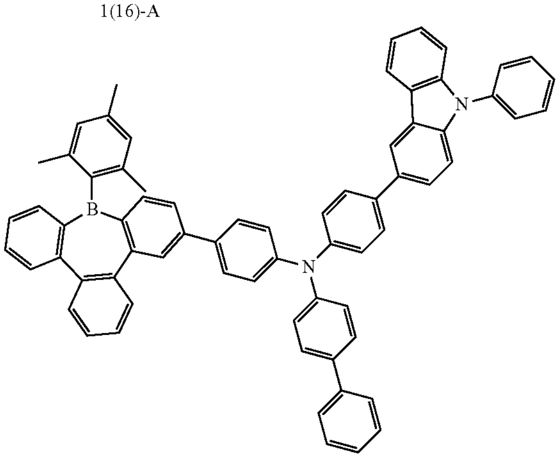

3239

2.95 g (yield: 70%) of Compound 3239 was synthesized in the same manner as in Synthesis Example 3, except that Compound 1(16)-A was used instead of Compound 1(13)-A, a boronic acid of amine Compound N-41 was used instead of the boronic acid of amine Compound N-29. The obtained compound was identified by LC-MS and $^{1}$H NMR.

$C_{63}H_{47}BN_2$: M+1 842.38

$^{1}$H NMR (500 MHz, $CDCl_3$) δ=8.19 (1H, d), 8.13 (1H, d), 8.01-7.87 (7H, m), 7.77-7.75 (3H, m), 7.62-7.37 (22H, m), 7.20 (1H, t), 6.97 (2H, s), 6.48 (1H, d), 2.33 (6H, s), 2.18 (3H, s).

EXAMPLES

Example 1

As a substrate and an ITO anode, a Corning 15 Ω/cm$^2$ (1,200 Å) ITO glass substrate was cut to a size of 50 mm×50 mm×0.7 mm, sonicated with isopropyl alcohol and pure water each for 5 minutes, and then cleaned by exposure to ultraviolet rays and ozone for 30 minutes. Then, the resultant ITO glass substrate was provided to a vacuum deposition apparatus.

2-TNATA was vacuum-deposited on the ITO anode to form a hole injection layer having a thickness of 600 Å, and Compound 126 was vacuum-deposited on the hole injection layer to form a hole transport layer having a thickness of 300 Å.

9,10-di-naphthalene-2-yl-anthracene (ADN) (host) and Compound FD1 (dopant) were co-deposited on the hole transport layer at a weight ratio of 98:2 to form an emission layer having a thickness of 300 Å.

$Alq_3$ was vacuum-deposited on the emission layer to form an electron transport layer having a thickness of 300 Å, LiF was deposited on the electron transport layer to form an electron injection layer having a thickness of 10 Å, and Al was vacuum-deposited on the electron injection layer to form a second electrode (cathode) having a thickness of 3,000 Å, thereby completing the manufacture of an organic light-emitting device.

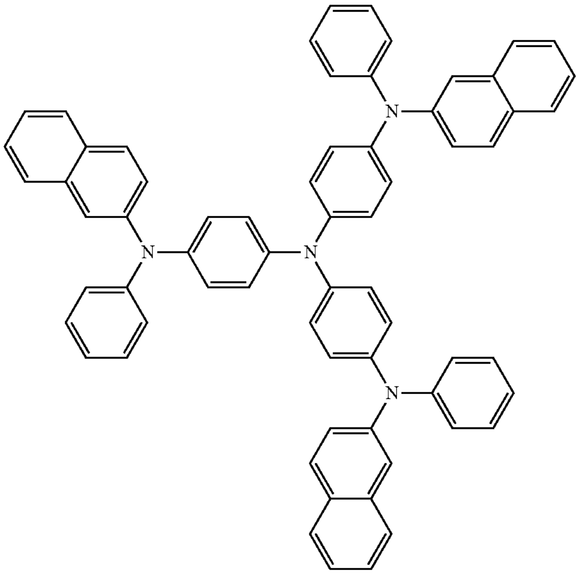

2-TNATA

-continued

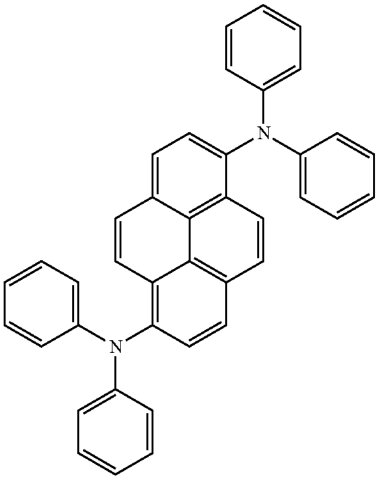

FD1

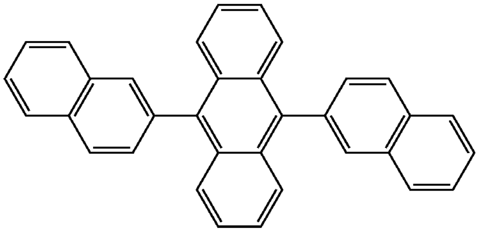

ADN

Examples 2 to 6 and Comparative Examples 1 to 3

Organic light-emitting devices of Examples 2 to 6 and Comparative Examples 1 to 3 were manufactured in the same manner as in Example 1, except that Compounds shown in Table 2 were each used as a material for forming a hole transport layer.

Evaluation Example 1

The driving voltage, current density, luminance, efficiency, and half lifespan of the organic light-emitting devices manufactured according to Examples 1 to 6 and Comparative Examples 1 to 3 were measured by using Keithley SMU 236 and a luminance meter PR650, and results thereof are shown in Table 2. The half lifespan is an amount of time that had lapsed when luminance was 50% of initial luminance.

TABLE 2

| | Hole transport layer | Driving voltage (V) | Current density ($mA/cm^2$) | Luminance ($cd/m^2$) | Efficiency (cd/A) | Emission color | Half lifespan ($hr@100\ uA/cm^2$) |
|---|---|---|---|---|---|---|---|
| Example 1 | Compound 126 | 5.66 | 50 | 3356 | 6.71 | Blue | 329 |
| Example 2 | Compound 1363 | 5.49 | 50 | 3591 | 7.18 | Blue | 340 |
| Example 3 | Compound 1404 | 5.87 | 50 | 3614 | 7.23 | Blue | 337 |
| Example 4 | Compound 2284 | 5.72 | 50 | 3317 | 6.63 | Blue | 341 |
| Example 5 | Compound 2766 | 5.61 | 50 | 3189 | 6.38 | Blue | 325 |
| Example 6 | Compound 3239 | 5.77 | 50 | 3247 | 6.49 | Blue | 330 |
| Comparative Example 1 | NPB | 6.99 | 50 | 2745 | 5.49 | Blue | 266 |
| Comparative Example 2 | Compound A | 6.71 | 50 | 2499 | 5.00 | Blue | 290 |
| Comparative Example 3 | Compound B | 6.35 | 50 | 2910 | 5.82 | Blue | 310 |

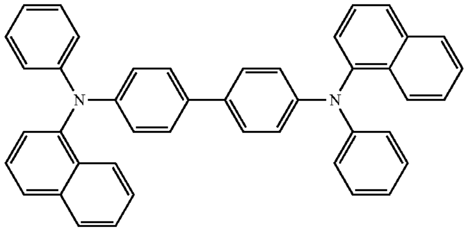

NPB

TABLE 2-continued

| Hole transport layer | Driving voltage (V) | Current density ($mA/cm^2$) | Luminance ($cd/m^2$) | Efficiency (cd/A) | Emission color | Half lifespan ($hr@100\ uA/cm^2$) |
|---|---|---|---|---|---|---|
| 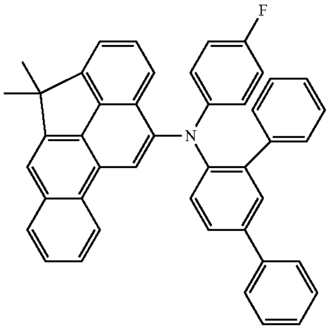 A | | | | | | |
| 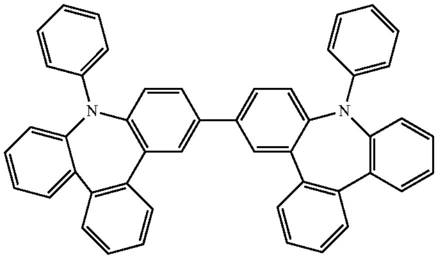 B | | | | | | |

From Table 2, it is confirmed that the organic light-emitting devices of Examples 1 to 6 have a low driving voltage, high luminance, high efficiency, and a long lifespan, as compared with those of the organic light-emitting devices of Comparative Examples 1 to 3.

An organic light-emitting device including the condensed cyclic compound according to an exemplary embodiment of the present disclosure may have a low driving voltage, high efficiency, high luminance, and a long lifespan.

It should be understood that the specific exemplary embodiments of the present disclosure described herein should be considered in a descriptive sense only and not for purposes of limitation. Descriptions of features or aspects within each exemplary embodiment should typically be considered as available for other similar features or aspects in other exemplary embodiments.

While exemplary embodiments have been described with reference to the figures, it will be understood by those of ordinary skill in the art that various changes in form and details may be made therein without departing from the spirit and scope as defined by the following claims.

What is claimed is:

1. A condensed cyclic compound represented by Formula 1:

<Formula 1>

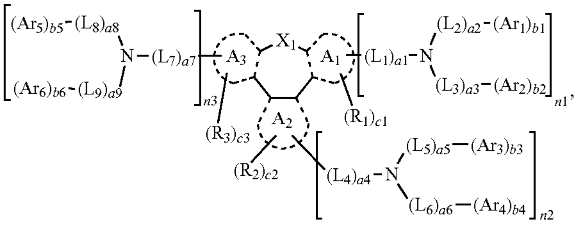

in Formula 1, $X_1$ is selected from O, S, Se, $C(R_4)(R_5)$, $Si(R_4)(R_5)$, and $B(R_4)$, rings $A_1$, $A_2$, and $A_3$ are each independently a $C_5$-$C_{60}$ carbocyclic group or a $C_2$-$C_{30}$ heterocyclic group, when $X_1$ is O, one or more of $A_1$, $A_2$ and $A_3$ are a $C_{10}$-$C_{60}$ carbocyclic group, $L_1$ to $L_9$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a9 are each independently an integer from 0 to 5, $Ar_1$ to $Ar_6$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 to b6 are each independently an integer from 1 to 5, $R_1$ to $R_5$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, c1 to c3 are each independently an integer from 0 to 5, n1 to n3 are each independently 0 or 1, provided that a sum of n1, n2, and n3 is 1, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$, and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group.

2. The condensed cyclic compound of claim 1, wherein rings $A_1$, $A_2$, and $A_3$ in Formula 1 are each independently selected from a benzene group, a naphthalene group, an anthracene group, a phenanthrene group, a pyrene group, a chrysene group, a triphenylene group, an indene group, a fluorene group, a benzofluorene group, a spiro-bifluorene group, a carbazole group, a dibenzofuran group, a dibenzothiophene group, a pyridine group, a pyrazine group, a pyrimidine group, a pyridazine group, a pyrrole group, an imidazole group, a quinoline group, an isoquinoline group, a quinoxaline group, a quinazoline group, a triazine group, an indenopyrazine group, an indenopyridine group, a phenanthroline group, and a phenanthridine group.

3. The condensed cyclic compound of claim 1, wherein rings $A_1$, $A_2$, and $A_3$ in Formula 1 are each independently a benzene group or a naphthalene group.

4. The condensed cyclic compound of claim 1, wherein $L_1$ to $L_9$ in Formula 1 are each independently selected from:

a phenylene group, a pentalenylene group, an indenylene group, a naphthylene group, an azulenylene group, an indacenylene group, an acenaphthylene group, a fluorenylene group, a spiro-bifluorenylene group, a spiro-benzofluorene-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a carbazolylene group, a benzocarbazolylene group, a dibenzocarbazolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azaspiro-bifluorenylene group, an azacarbazolylene group, an azadibenzofuranylene group, an azadibenzothiophenylene group, and an azadibenzosilolylene group; and a phenylene group, a pentalenylene group, an indenylene group, a naphthylene group, an azulenylene group, an indacenylene group, an acenaphthylene group, a fluorenylene group, a spiro-bifluorenylene group, a spiro-benzofluorene-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a carbazolylene group, a benzocarbazolylene group, a dibenzocarbazolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azaspiro-bifluorenylene group, an azacarbazolylene group, an azadibenzofuranylene group, an azadibenzothiophenylene group, and an azadibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, and —Si($Q_{31}$)($Q_{32}$)($Q_{33}$), wherein $Q_{31}$ to $Q_{33}$ are each independently selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

5. The condensed cyclic compound of claim 1, wherein $L_1$ to $L_9$ in Formula 1 are each independently selected from groups represented by Formulae 3-1 to 3-102:

-continued
Formula 3-1
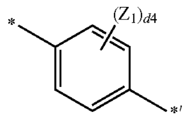
Formula 3-2
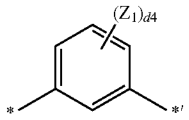
Formula 3-3
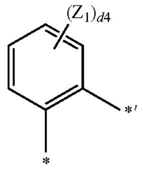
Formula 3-4
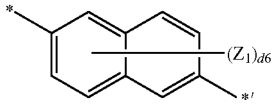
Formula 3-5
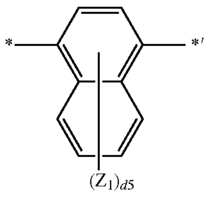
Formula 3-6
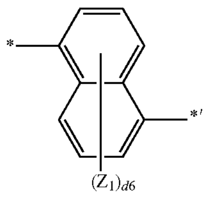
Formula 3-7
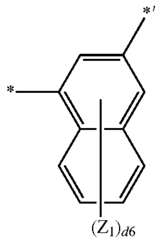
Formula 3-8
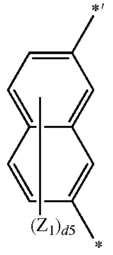
Formula 3-9
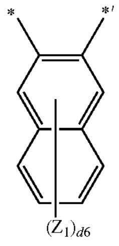
Formula 3-10
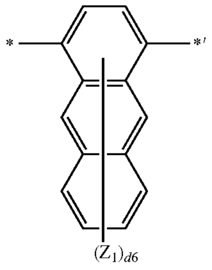
Formula 3-11
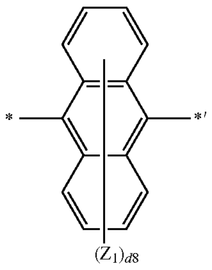
Formula 3-12
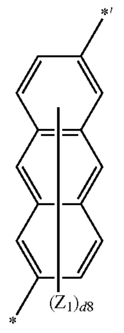
Formula 3-13
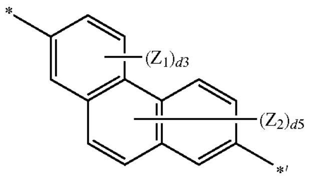
Formula 3-14
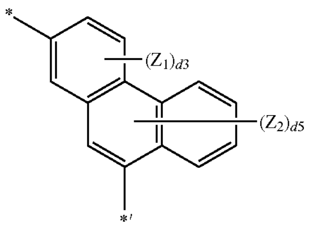

-continued
Formula 3-15
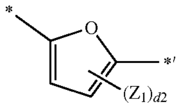
Formula 3-16
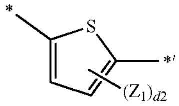
Formula 3-17
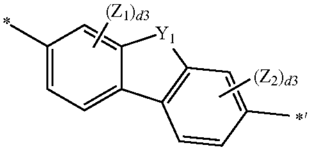
Formula 3-18
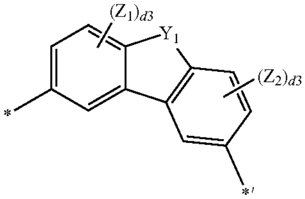
Formula 3-19
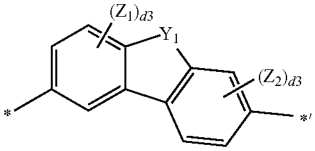
Formula 3-20
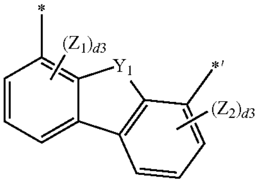
Formula 3-21
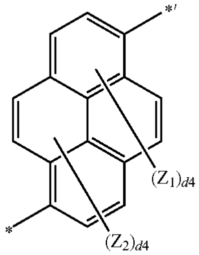
Formula 3-22
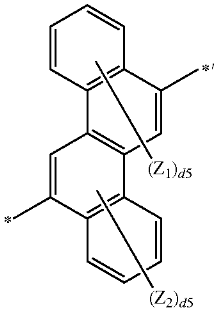
-continued
Formula 3-23
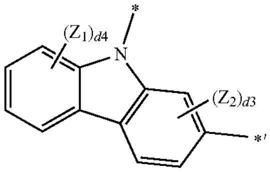
Formula 3-24
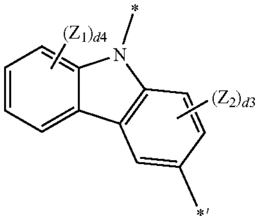
Formula 3-25
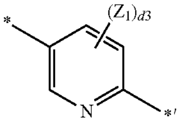
Formula 3-26
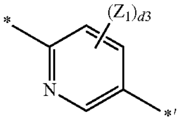
Formula 3-27
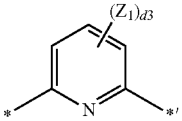
Formula 3-28
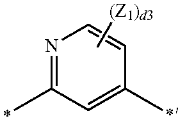
Formula 3-29
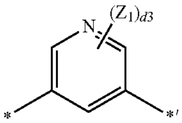
Formula 3-30
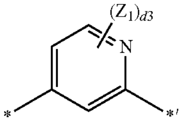
Formula 3-31
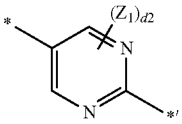
Formula 3-32
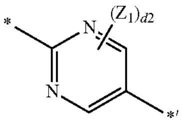

-continued
Formula 3-33
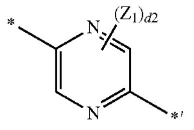
Formula 3-34
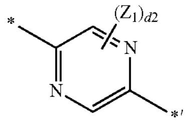
Formula 3-35
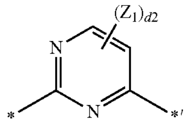
Formula 3-36
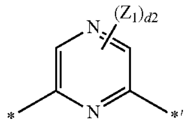
Formula 3-37
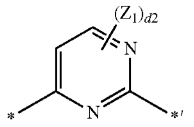
Formula 3-38
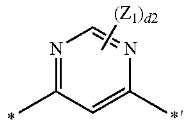
Formula 3-39
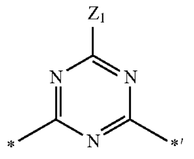
Formula 3-40
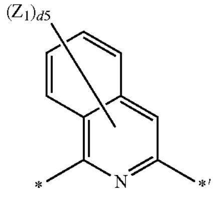
Formula 3-41
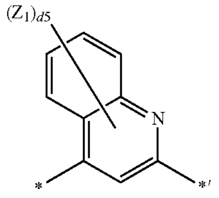
-continued
Formula 3-42
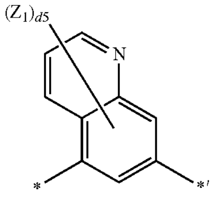
Formula 3-43
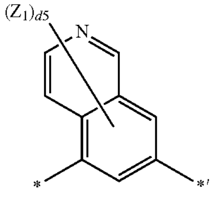
Formula 3-44
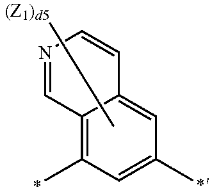
Formula 3-45
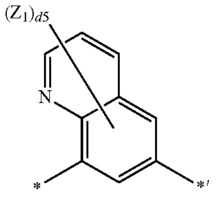
Formula 3-46
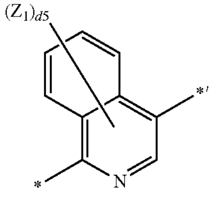
Formula 3-47
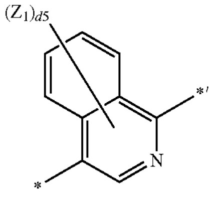
Formula 3-48
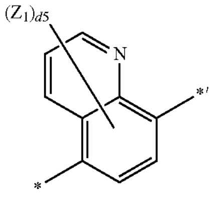

-continued
Formula 3-49
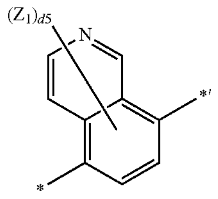
Formula 3-50
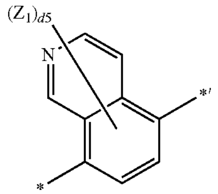
Formula 3-51
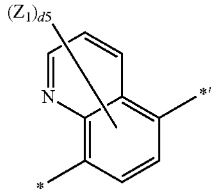
Formula 3-52
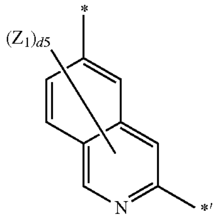
Formula 3-53
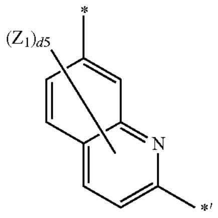
Formula 3-54
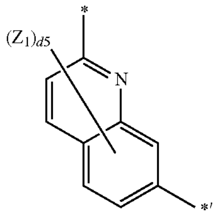
Formula 3-55
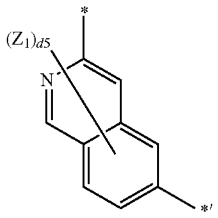
-continued
Formula 3-56
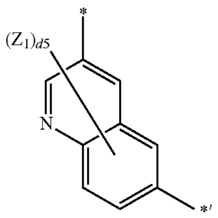
Formula 3-57
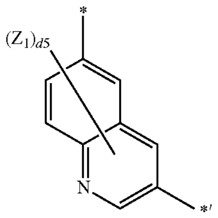
Formula 3-58
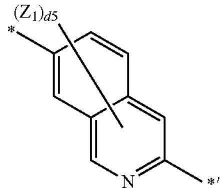
Formula 3-59
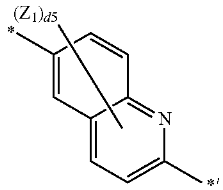
Formula 3-61
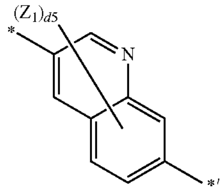
Formula 3-62
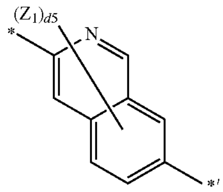
Formula 3-63
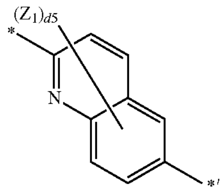

-continued
Formula 3-64
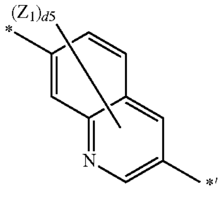
Formula 3-65
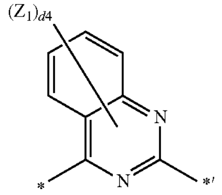
Formula 3-66
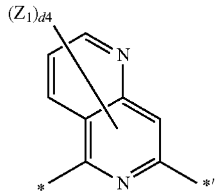
Formula 3-67
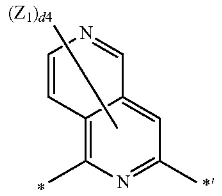
Formula 3-68
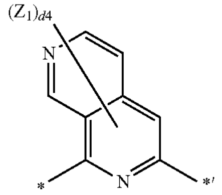
Formula 3-69
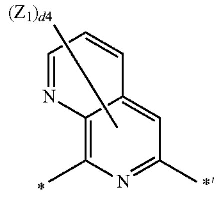
Formula 3-70
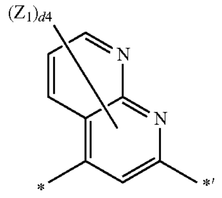
-continued
Formula 3-71
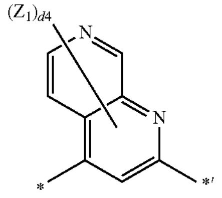
Formula 3-72
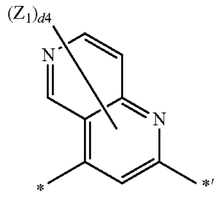
Formula 3-73
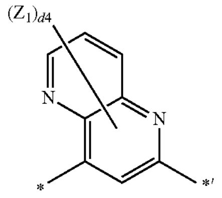
Formula 3-74
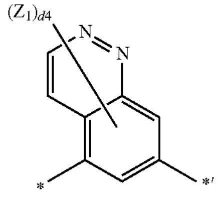
Formula 3-75
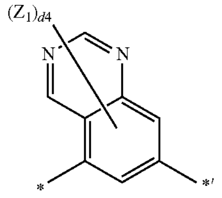
Formula 3-76
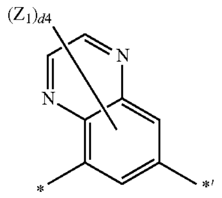
Formula 3-77
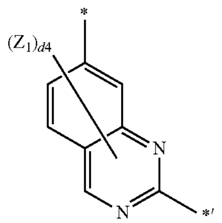

-continued
Formula 3-78
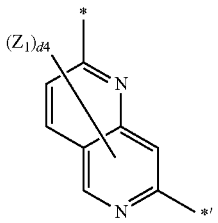
Formula 3-79
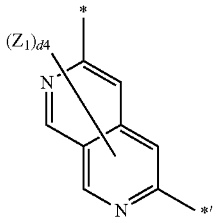
Formula 3-80
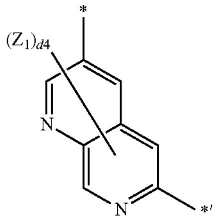
Formula 3-81
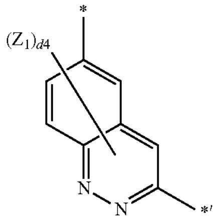
Formula 3-82
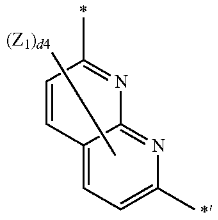
Formula 3-83
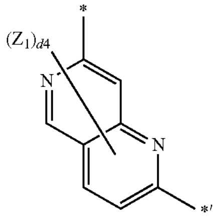
-continued
Formula 3-84
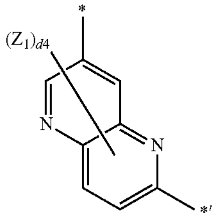
Formula 3-85
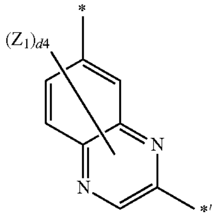
Formula 3-86
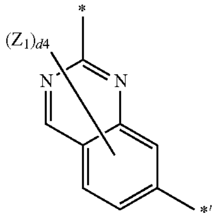
Formula 3-87
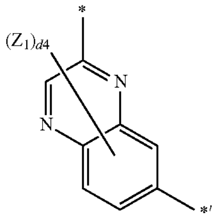
Formula 3-88
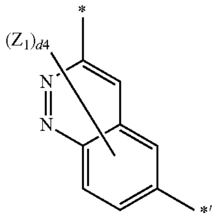
Formula 3-89
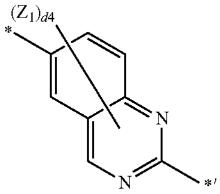
Formula 3-90
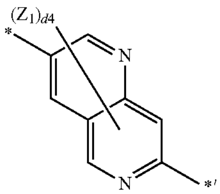

-continued

Formula 3-91

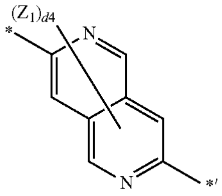

Formula 3-92

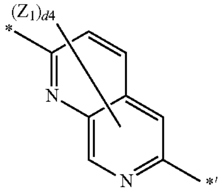

Formula 3-93

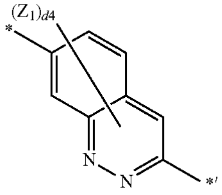

Formula 3-94

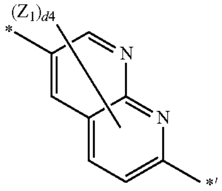

Formula 3-95

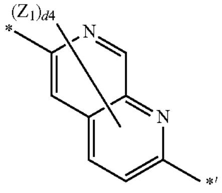

Formula 3-96

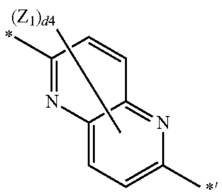

Formula 3-97

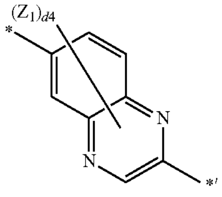

-continued

Formula 3-98

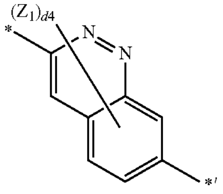

Formula 3-99

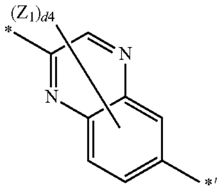

Formula 3-100

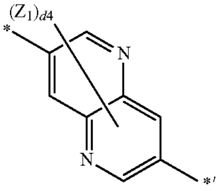

Formula 3-101

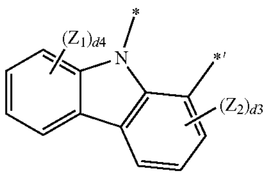

Formula 3-102

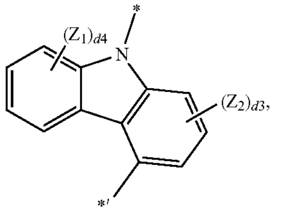

in Formulae 3-1 to 3-102, $Y_1$ is O, S, $C(Z_3)(Z_4)$, $N(Z_5)$, or $Si(Z_6)(Z_7)$, $Z_1$ to $Z_7$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_{31}$ to $Q_{33}$ are each independently selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, d2 is an integer from 0 to 2, d3 is an integer from 0 to 3, d4 is an integer from 0 to 4, d5 is an integer from 0 to 5, d6 is an integer from 0 to 6, d8 is an integer from 0 to 8, and and *' each indicates a binding site to a neighboring atom.

6. The condensed cyclic compound of claim 1, wherein $L_1$ to $L_9$ in Formula 1 are each independently selected from groups represented by Formulae 4-1 to 4-57:

Formula 4-1

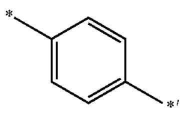

Formula 4-2

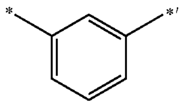

Formula 4-3

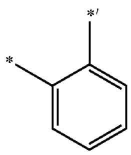

-continued

Formula 4-4

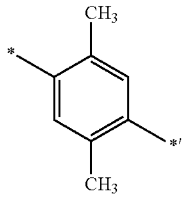

Formula 4-5

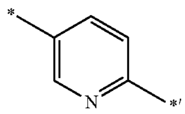

Formula 4-6

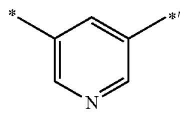

Formula 4-7

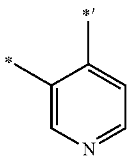

Formula 4-8

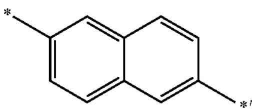

Formula 4-9

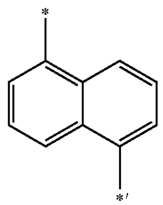

Formula 4-10

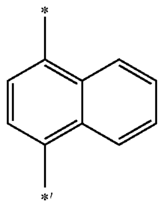

Formula 4-11

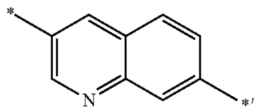

Formula 4-12

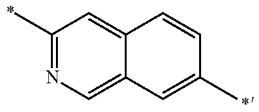

Formula 4-13

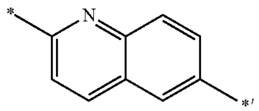

-continued
Formula 4-14
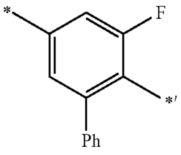
Formula 4-15
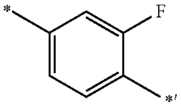
Formula 4-16
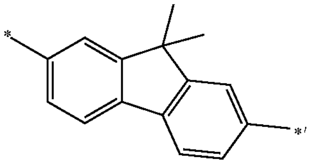
Formula 4-17
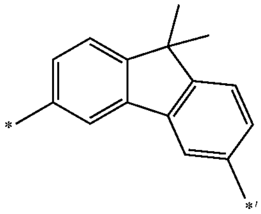
Formula 4-18
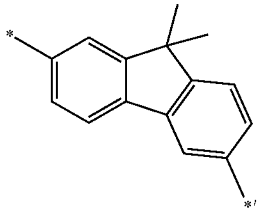
Formula 4-19
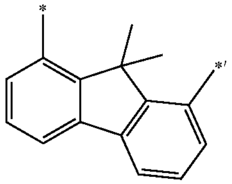
Formula 4-20
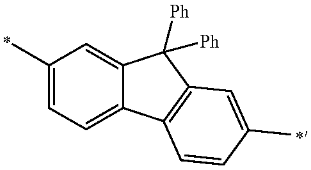
Formula 4-21
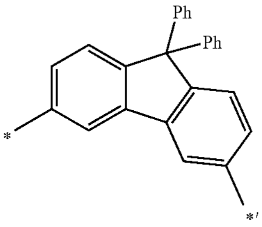
-continued
Formula 4-22
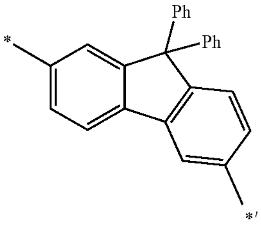
Formula 4-23
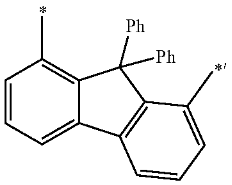
Formula 4-24
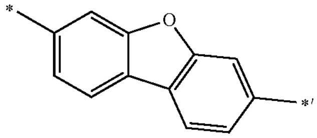
Formula 4-25
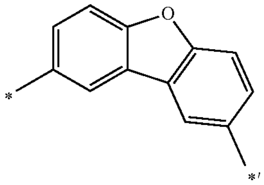
Formula 4-26
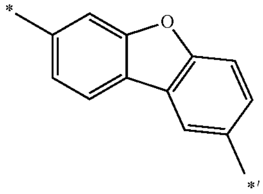
Formula 4-27
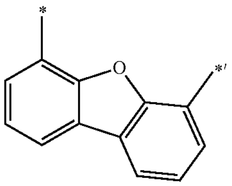
Formula 4-28
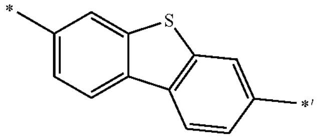
Formula 4-29
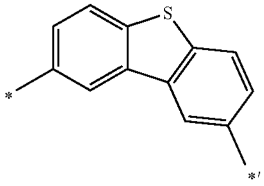

-continued
Formula 4-30
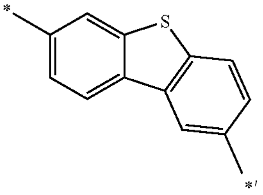
Formula 4-31
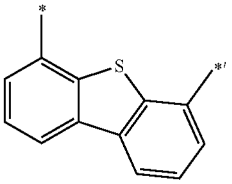
Formula 4-32
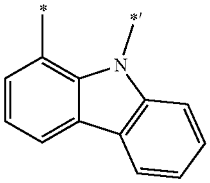
Formula 4-33
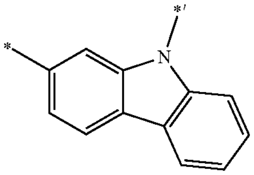
Formula 4-34
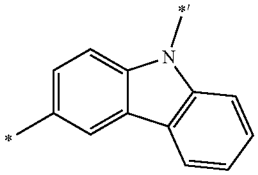
Formula 4-35
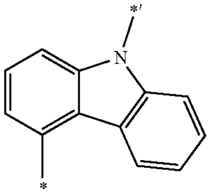
Formula 4-36
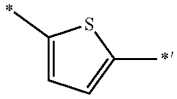
Formula 4-37
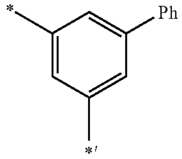
-continued
Formula 4-38
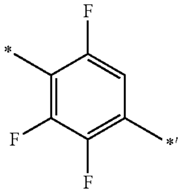
Formula 4-39
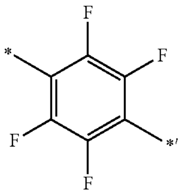
Formula 4-40
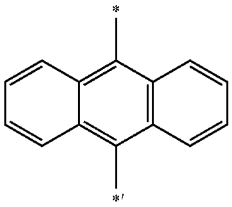
Formula 4-41
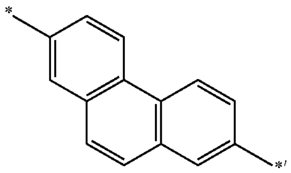
Formula 4-42
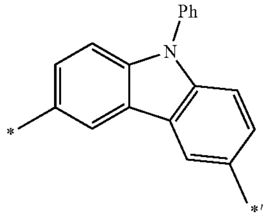
Formula 4-43
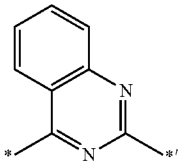
Formula 4-44
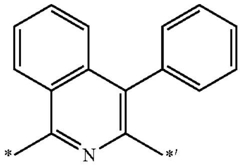
Formula 4-45
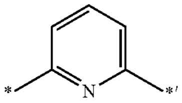

-continued

Formula 4-46

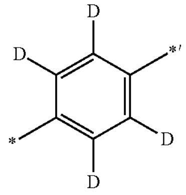

Formula 4-47

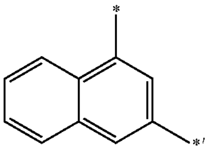

Formula 4-48

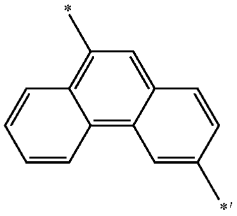

Formula 4-49

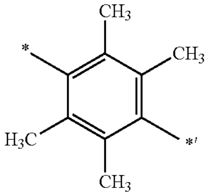

Formula 4-50

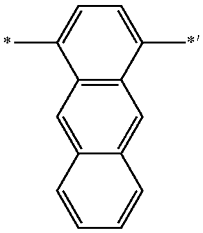

Formula 4-51

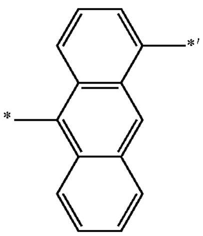

Formula 4-52

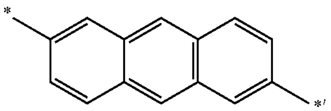

-continued

Formula 4-53

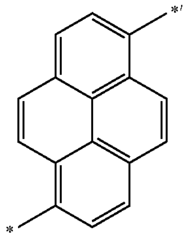

Formula 4-54

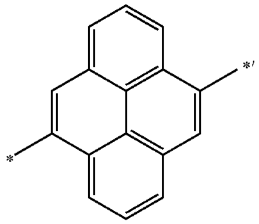

Formula 4-55

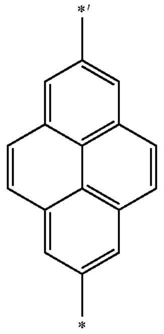

Formula 4-56

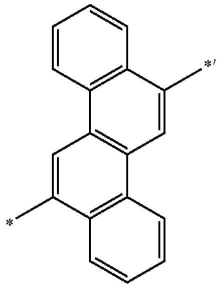

Formula 4-57

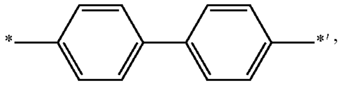

in Formulae 4-1 to 4-57, Ph indicates a phenyl group, and * and *' each indicates a binding site to a neighboring atom.

7. The condensed cyclic compound of claim 1, wherein a1 to a9 in Formula 1 are each independently 0 or 1.

8. The condensed cyclic compound of claim 1, wherein $Ar_1$ to $Ar_6$ in Formula 1 are each independently selected from:

a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group; and a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ are each independently selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

9. The condensed cyclic compound of claim 1, wherein $Ar_1$ to $Ar_6$ in Formula 1 are each independently selected from groups represented by Formulae 5-1 to 5-50 and 6-1 to 6-124:

Formula 5-1

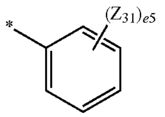

Formula 5-2

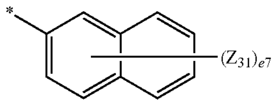

Formula 5-3

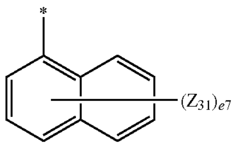

Formula 5-4

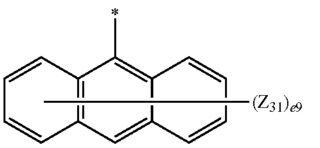

Formula 5-5

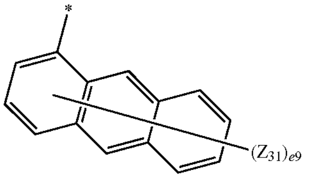

Formula 5-6

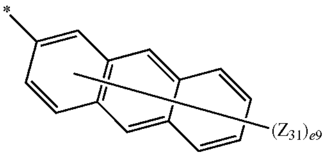

-continued
Formula 5-7
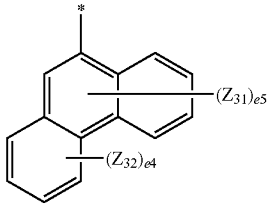
Formula 5-8
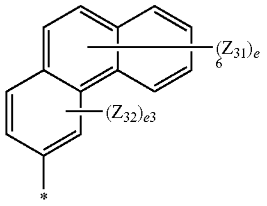
Formula 5-9
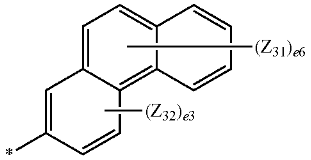
Formula 5-10
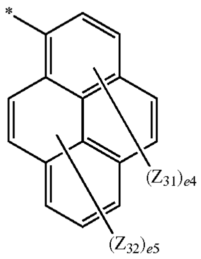
Formula 5-11
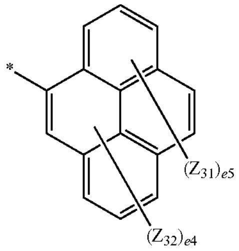
Formula 5-12
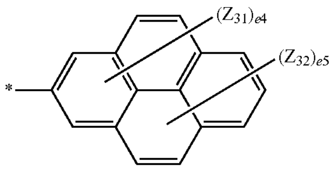
Formula 5-13
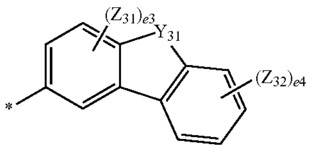
Formula 5-14
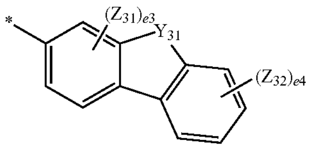
-continued
Formula 5-15
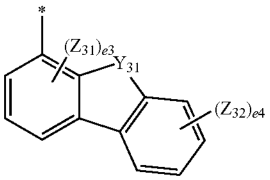
Formula 5-16
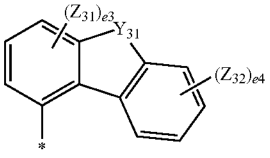
Formula 5-17
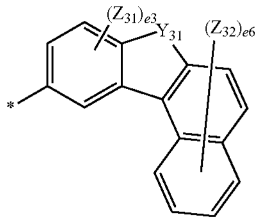
Formula 5-18
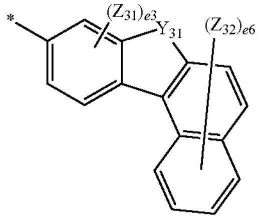
Formula 5-19
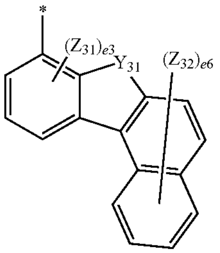
Formula 5-20
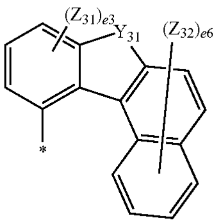
Formula 5-21
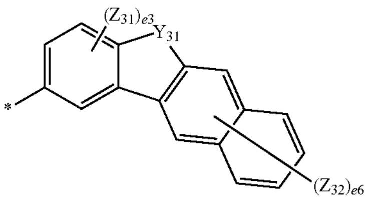

-continued
Formula 5-22
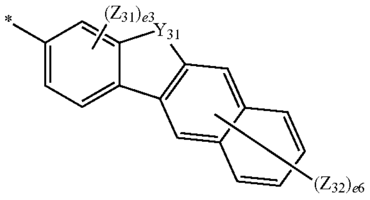
Formula 5-23
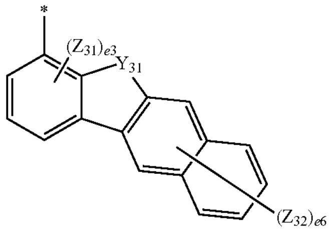
Formula 5-24
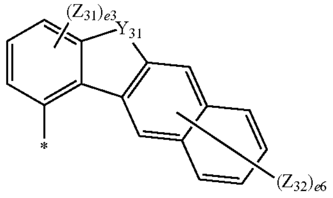
Formula 5-25
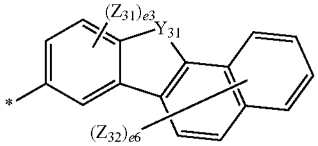
Formula 5-26
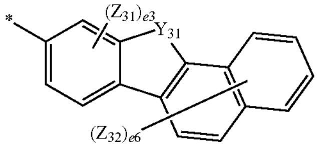
Formula 5-27
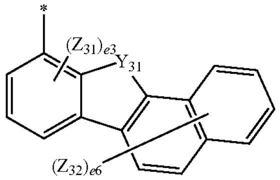
Formula 5-28
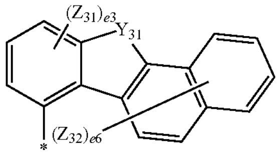
Formula 5-29
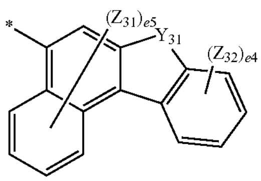
-continued
Formula 5-30
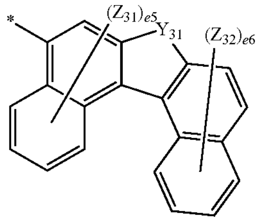
Formula 5-31
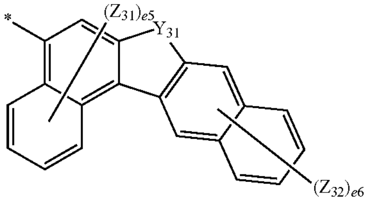
Formula 5-32
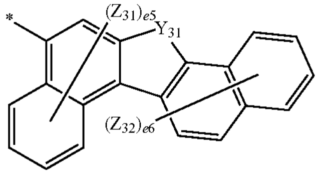
Formula 5-33
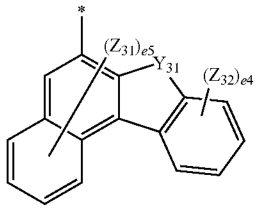
Formula 5-34
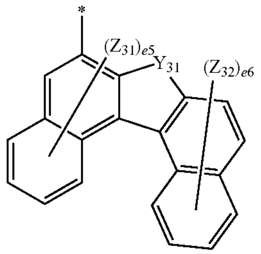
Formula 5-35
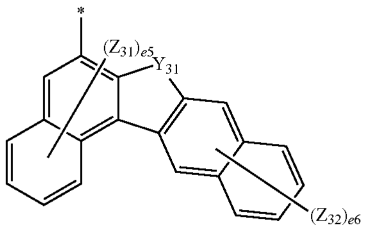
Formula 5-36
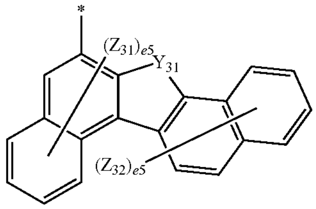

-continued
Formula 5-37
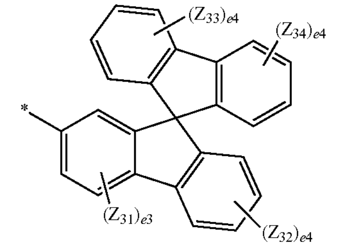
Formula 5-38
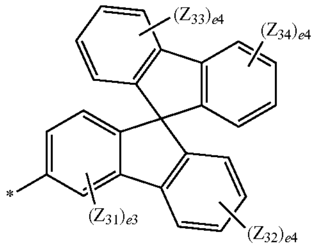
Formula 5-39
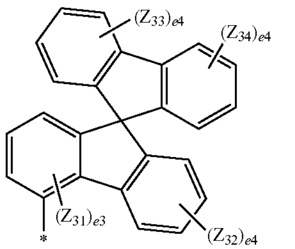
Formula 5-40
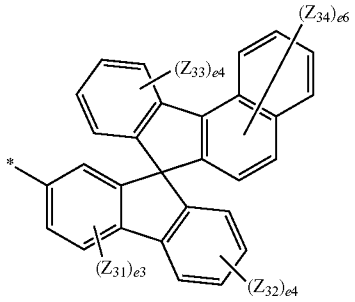
Formula 5-41
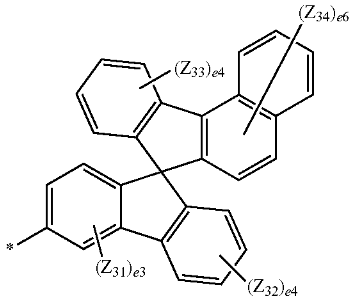
-continued
Formula 5-42
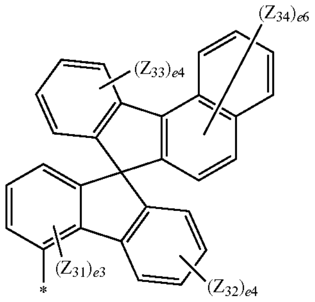
Formula 5-43
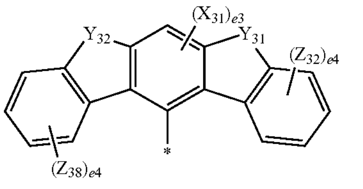
Formula 5-44
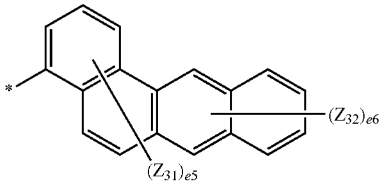
Formula 5-45
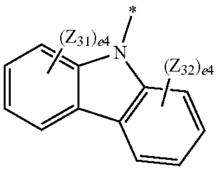
Formula 5-46
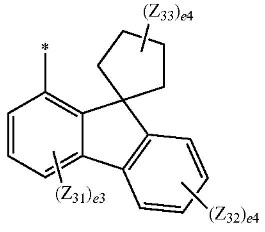
Formula 5-47
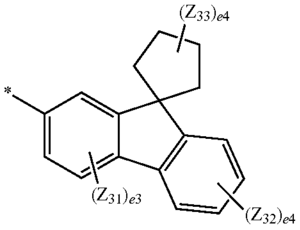
Formula 5-48
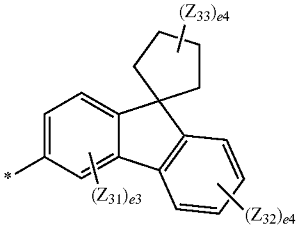

-continued
Formula 5-49
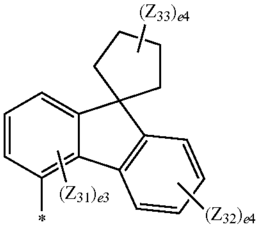
formula 5-50
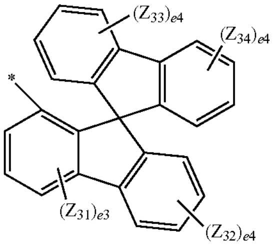
Formula 6-1
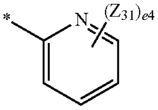
Formula 6-2
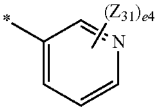
Formula 6-3
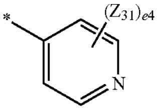
Formula 6-4
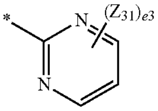
Formula 6-5
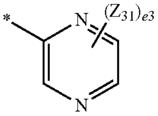
Formula 6-6
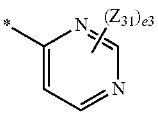
Formula 6-7
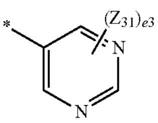
Formula 6-8
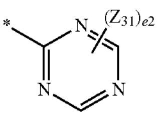
-continued
Formula 6-9
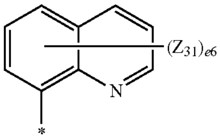
Formula 6-10
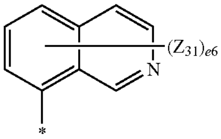
Formula 6-11
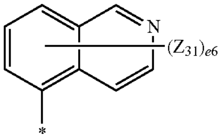
Formula 6-12
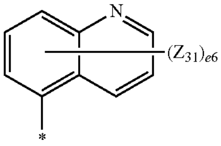
Formula 6-13
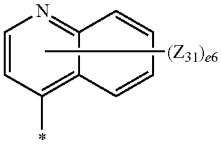
Formula 6-14
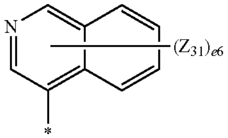
Formula 6-15
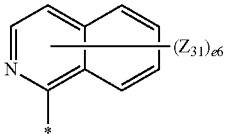
Formula 6-16
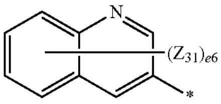
Formula 6-17
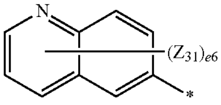
Formula 6-18
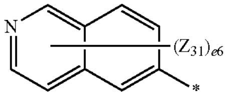
Formula 6-19
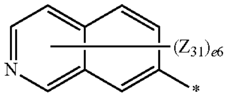

-continued
Formula 6-20
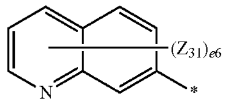
Formula 6-21
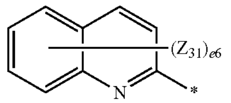
Formula 6-22
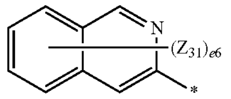
Formula 6-23
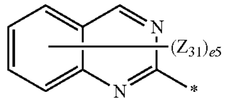
Formula 6-24
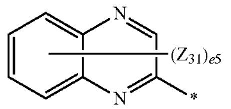
Formula 6-25
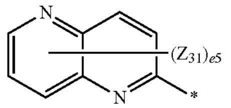
Formula 6-26
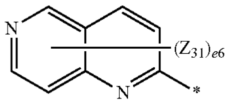
Formula 6-27
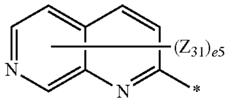
Formula 6-28
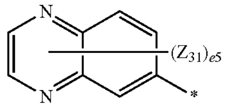
Formula 6-29
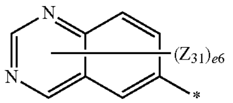
Formula 6-30
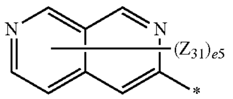
Formula 6-31
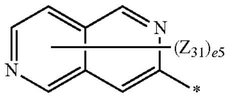
Formula 6-32
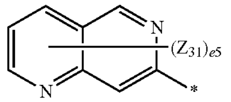
Formula 6-33
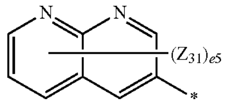
-continued
Formula 6-34
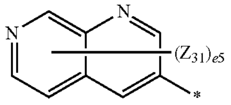
Formula 6-35
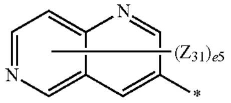
Formula 6-36
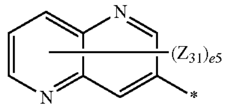
Formula 6-37
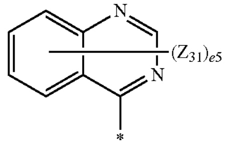
Formula 6-38
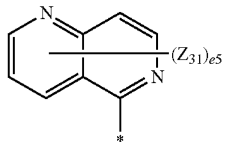
Formula 6-39
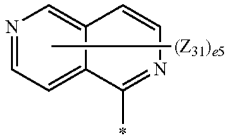
Formula 6-40
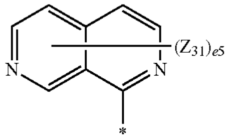
Formula 6-41
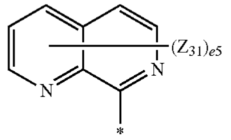
Formula 6-42
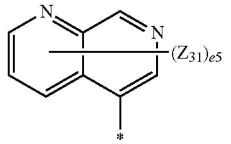
Formula 6-43
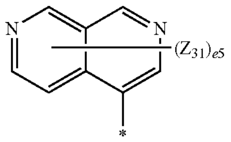
Formula 6-44
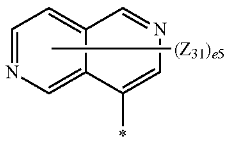

-continued
Formula 6-45
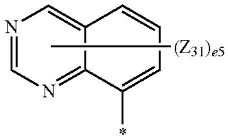
Formula 6-46
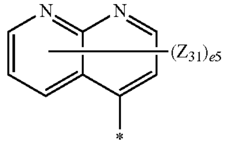
Formula 6-47
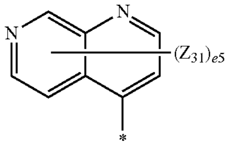
Formula 6-48
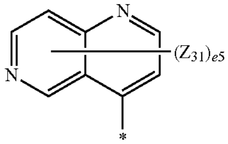
Formula 6-49
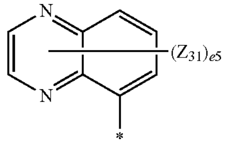
Formula 6-50
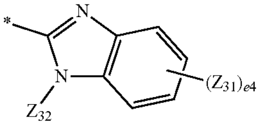
Formula 6-51
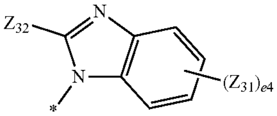
Formula 6-52
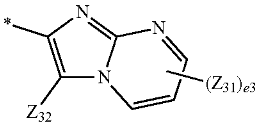
Formula 6-53
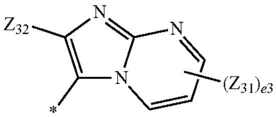
Formula 6-54
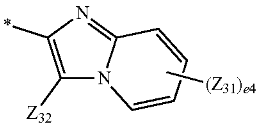
Formula 6-55
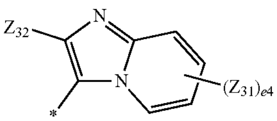
-continued
Formula 6-56
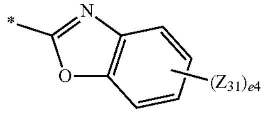
Formula 6-57
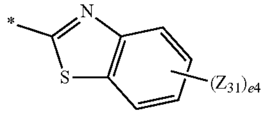
Formula 6-58
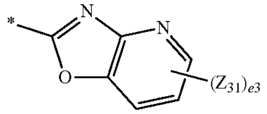
Formula 6-59
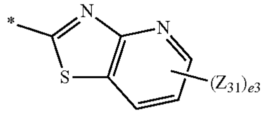
Formula 6-60
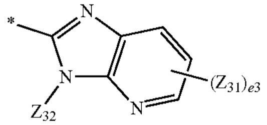
Formula 6-61
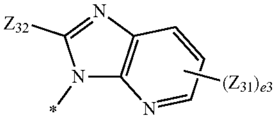
Formula 6-62
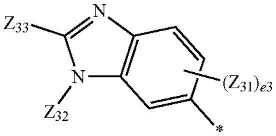
Formula 6-63
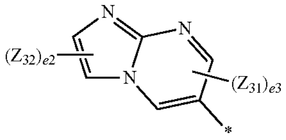
Formula 6-64
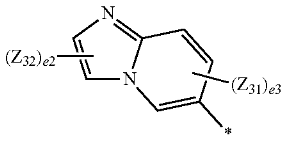
Formula 6-65
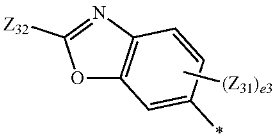
Formula 6-66
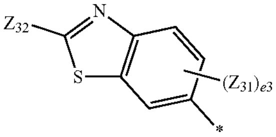

-continued
Formula 6-67
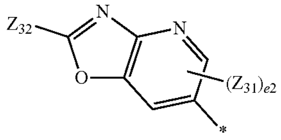
Formula 6-68
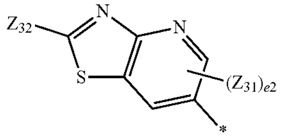
Formula 6-69
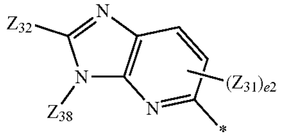
Formula 6-70
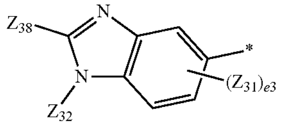
Formula 6-71
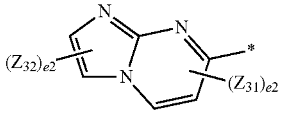
Formula 6-72
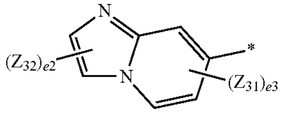
Formula 6-73
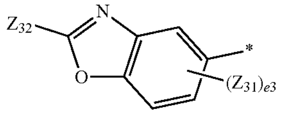
Formula 6-74
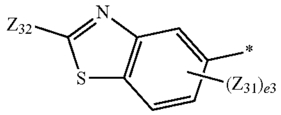
Formula 6-75
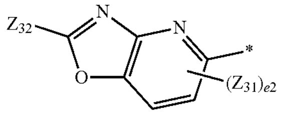
Formula 6-76
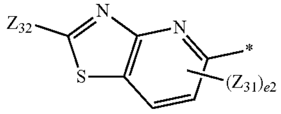
Formula 6-77
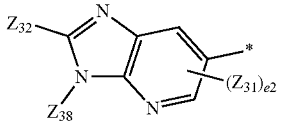
Formula 6-78
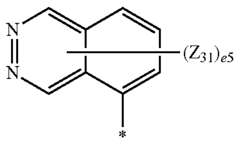
-continued
Formula 6-79
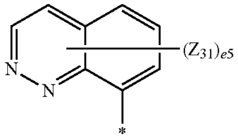
Formula 6-80
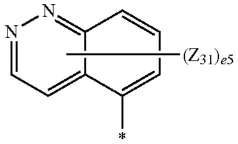
Formula 6-81
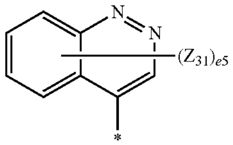
Formula 6-82
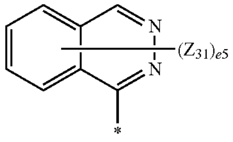
Formula 6-83
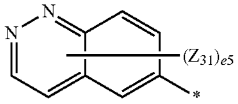
Formula 6-84
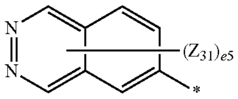
Formula 6-85
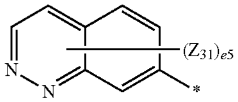
Formula 6-86
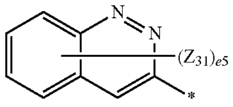
Formula 6-87
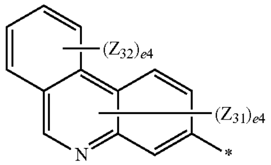
Formula 6-88
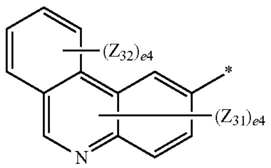
Formula 6-89
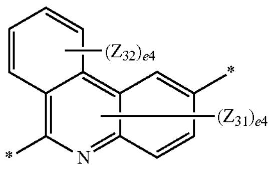

-continued
Formula 6-90
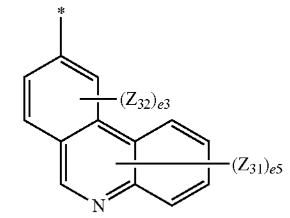
Formula 6-91
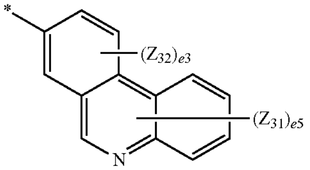
Formula 6-92
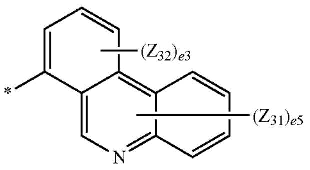
Formula 6-93
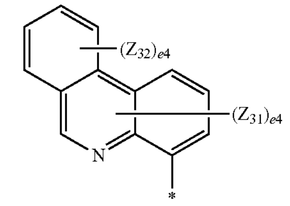
Formula 6-94
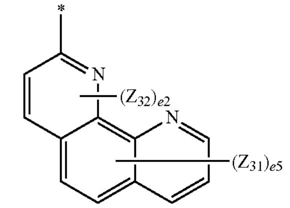
Formula 6-95
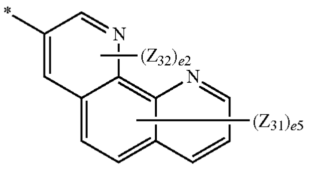
Formula 6-96
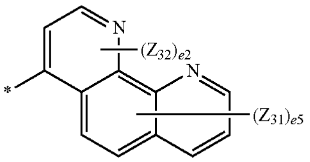
Formula 6-97
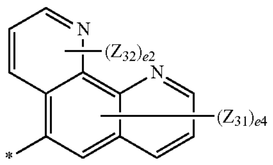
-continued
Formula 6-98
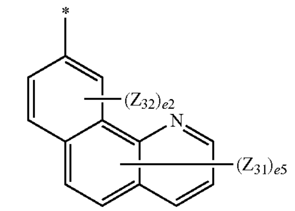
Formula 6-99
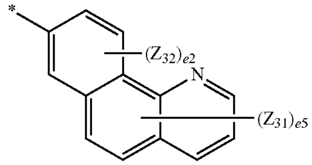
Formula 6-100
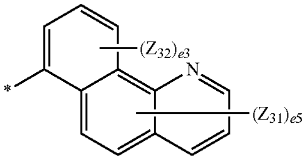
Formula 6-101
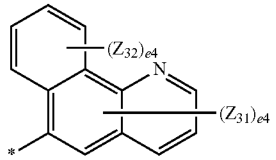
Formula 6-102
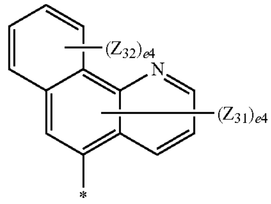
Formula 6-103
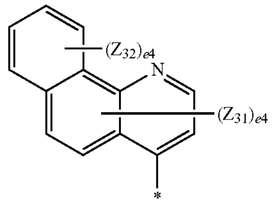
Formula 6-104
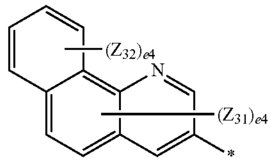
Formula 6-105
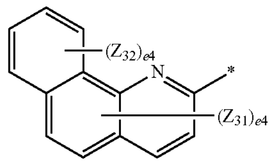

-continued
Formula 6-106
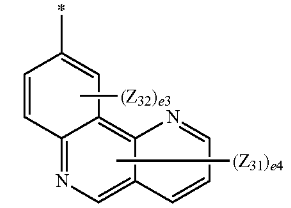
Formula 6-107
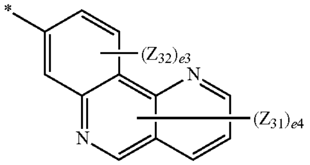
Formula 6-108
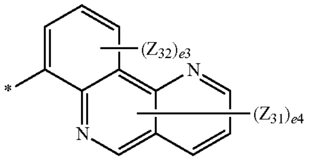
Formula 6-109
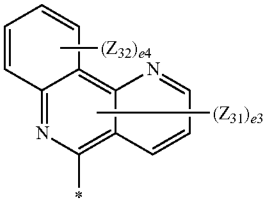
Formula 6-110
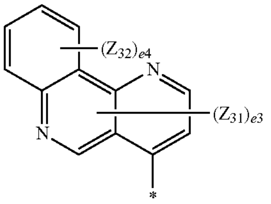
Formula 6-111
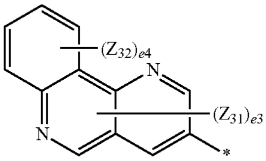
Formula 6-112
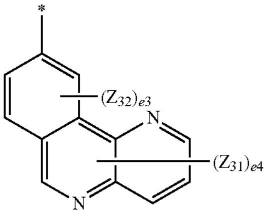
Formula 6-113
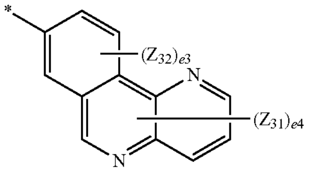
-continued
Formula 6-114
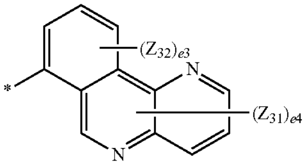
Formula 6-115
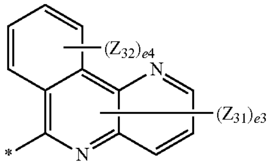
Formula 6-116
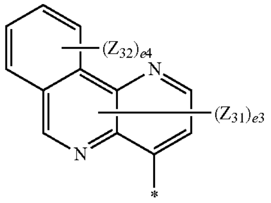
Formula 6-117
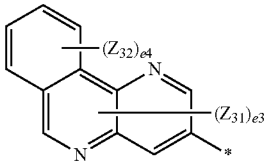
Formula 6-118
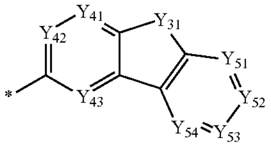
Formula 6-119
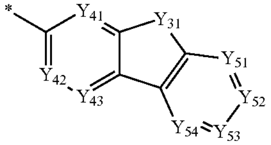
Formula 6-120
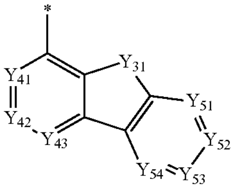
Formula 6-121
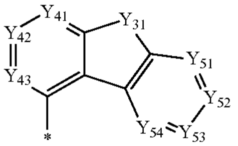
Formula 6-122
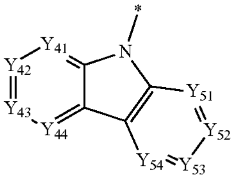

-continued

Formula 6-123

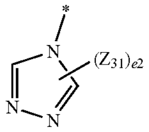

Formula 6-124

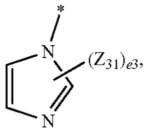

in Formulae 5-1 to 5-50 and 6-1 to 6-124, $Y_{31}$ and $Y_{32}$ are each independently 0, S, $C(Z_{33})(Z_{34})$, $N(Z_{35})$, or $Si(Z_{36})(Z_{37})$, $Y_{41}$ is N or $C(Z_{41})$, $Y_{42}$ is N or $C(Z_{42})$, $Y_{43}$ is N or $C(Z_{43})$, $Y_{44}$ is N or $C(Z_{44})$, $Y_{51}$ is N or $C(Z_{51})$, $Y_{52}$ is N or $C(Z_{52})$, $Y_{53}$ is N or $C(Z_{53})$, $Y_{54}$ is N or $C(Z_{54})$, at least one of $Y_{41}$ to $Y_{43}$ and $Y_{51}$ to $Y_{54}$ in Formulae 6-118 to 6-121 is N, and at least one of $Y_{41}$ to $Y_{44}$ and $Y_{51}$ to $Y_{54}$ in Formula 6-122 is N, $Z_{31}$ to $Z_{37}$, $Z_{41}$ to $Z_{44}$, and $Z_{51}$ to $Z_{54}$ are each independently selected from hydrogen, deuterium, —F, —Cl, —Br, —I, —$CF_3$, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group and —$Si(Q_{31})(Q_{32})(Q_{33})$, $Q_{31}$ to $Q_{33}$ are each independently selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, e2 is an integer from 0 to 2, e3 is an integer from 0 to 3, e4 is an integer from 0 to 4, e5 is an integer from 0 to 5, e6 is an integer from 0 to 6, e7 is an integer from 0 to 7, e9 is an integer from 0 to 9, and indicates a binding site to a neighboring atom.

10. The condensed cyclic compound of claim 1, wherein $Ar_1$ to $Ar_6$ in Formula 1 are each independently selected from groups represented by Formulae 9-1 to 9-116 and 10-1 to 10-121:

Formula 9-1

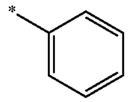

Formula 9-2

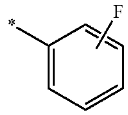

Formula 9-3

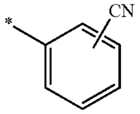

Formula 9-4

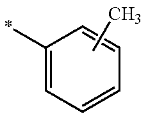

Formula 9-5

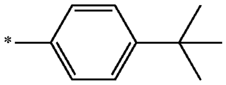

Formula 9-6

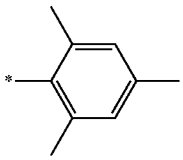

Formula 9-7

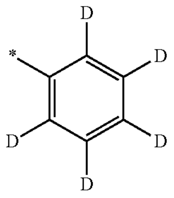

-continued
Formula 9-8
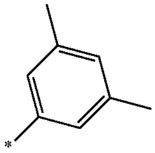
Formula 9-9
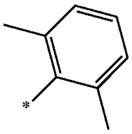
Formula 9-10
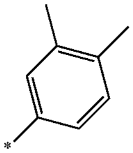
Formula 9-11
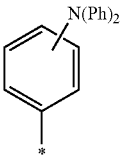
Formula 9-12
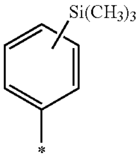
Formula 9-13
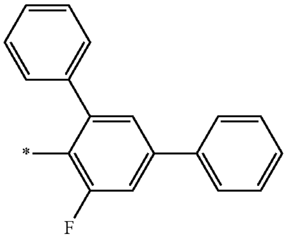
Formula 9-14
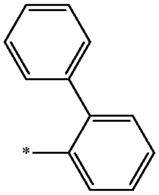
Formula 9-15
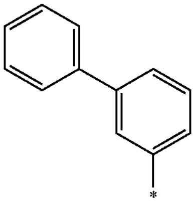
-continued
Formula 9-16
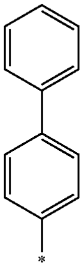
Formula 9-17
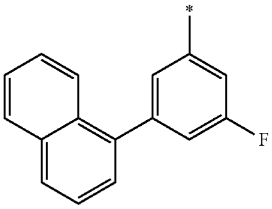
Formula 9-18
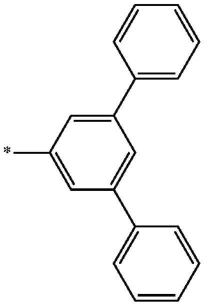
Formula 9-19
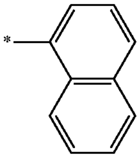
Formula 9-20
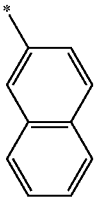
Formula 9-21
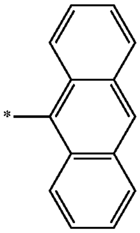

-continued
Formula 9-22
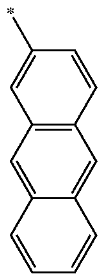
Formula 9-23
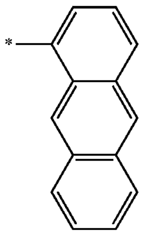
Formula 9-24
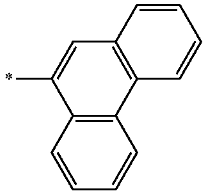
Formula 9-25
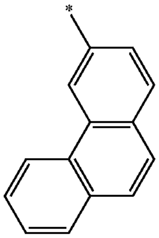
Formula 9-26
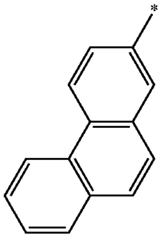
Formula 9-27
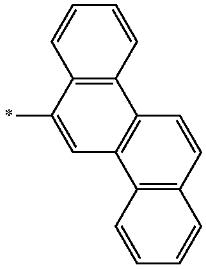
-continued
Formula 9-28
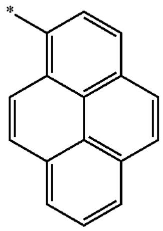
Formula 9-29
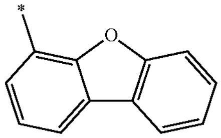
Formula 9-30
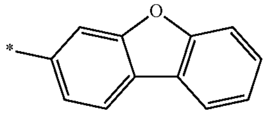
Formula 9-31
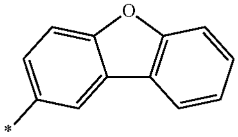
Formula 9-32
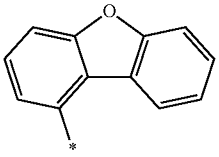
Formula 9-33
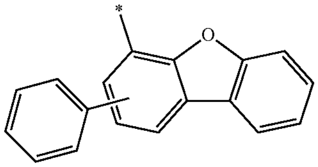
Formula 9-34
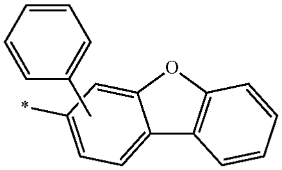
Formula 9-35
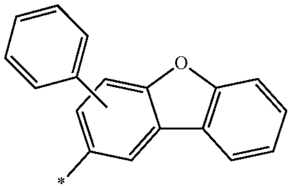
Formula 9-36
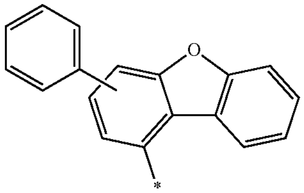

-continued
Formula 9-37
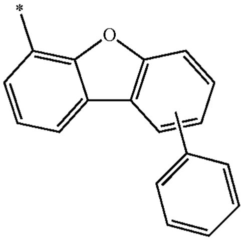
Formula 9-38
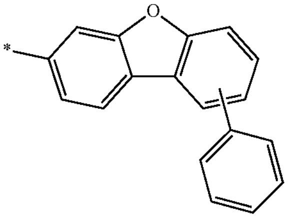
Formula 9-39
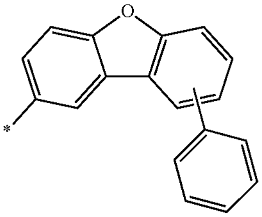
Formula 9-40
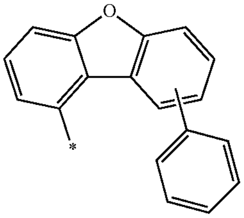
Formula 9-41
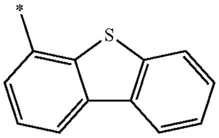
Formula 9-42
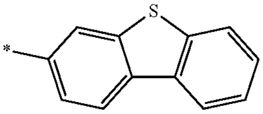
Formula 9-43
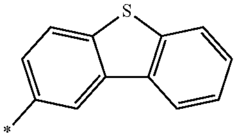
Formula 9-44
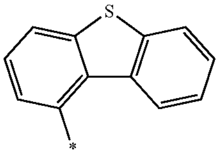
-continued
Formula 9-45
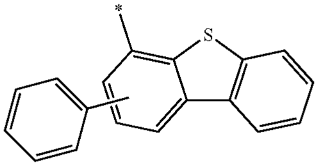
Formula 9-46
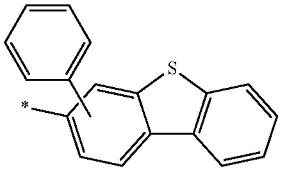
Formula 9-47
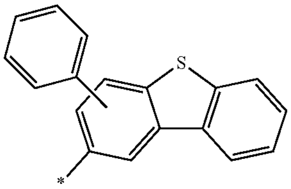
Formula 9-48
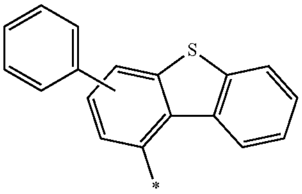
Formula 9-49
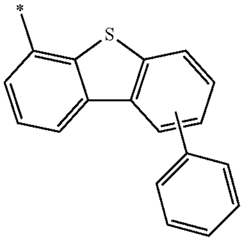
Formula 9-50
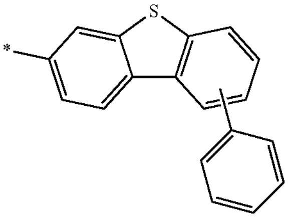
Formula 9-51
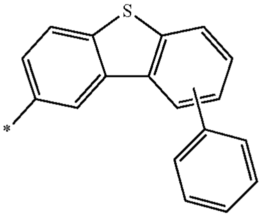

-continued
Formula 9-52
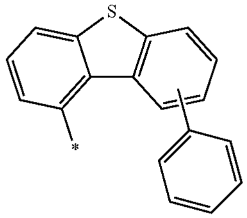
Formula 9-53
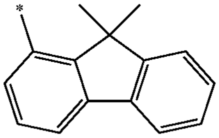
Formula 9-54
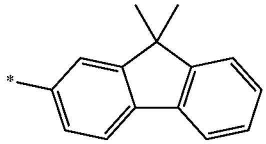
Formula 9-55
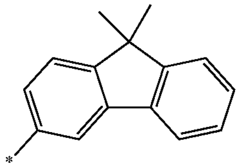
Formula 9-56
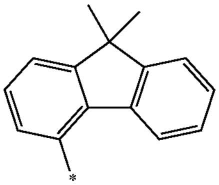
Formula 9-57
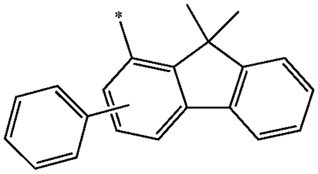
Formula 9-58
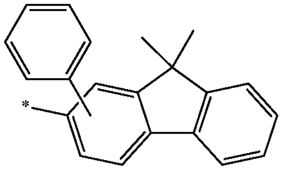
Formula 9-59
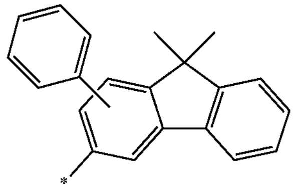
-continued
Formula 9-60
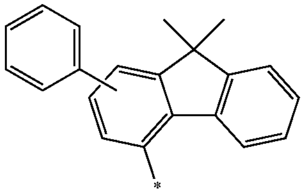
Formula 9-61
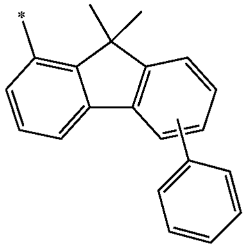
Formula 9-62
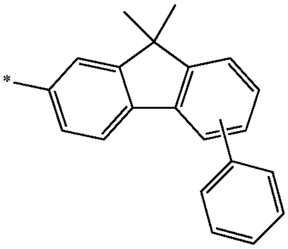
Formula 9-63
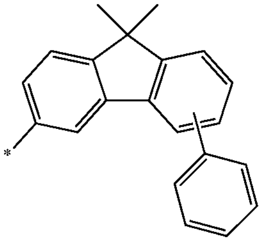
Formula 9-64
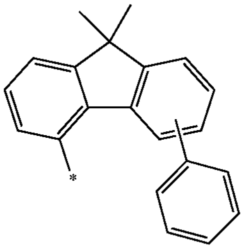
Formula 9-65
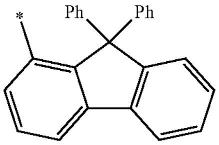
Formula 9-66
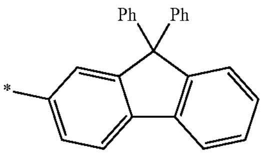

-continued
Formula 9-67
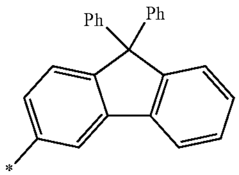
Formula 9-68
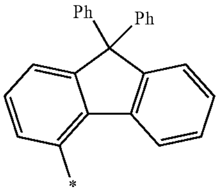
Formula 9-69
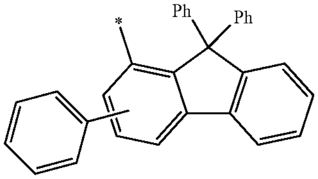
Formula 9-70
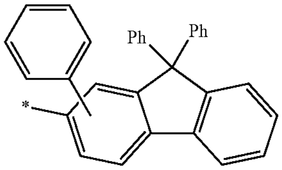
Formula 9-71
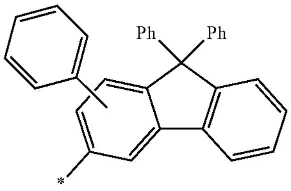
Formula 9-72
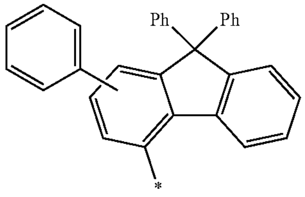
Formula 9-73
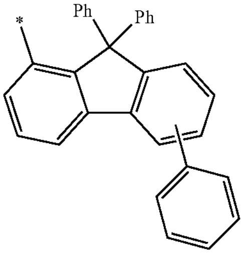
-continued
Formula 9-74
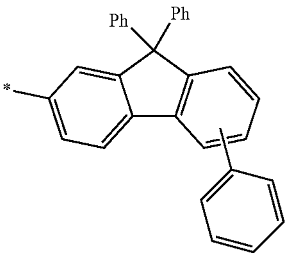
Formula 9-75
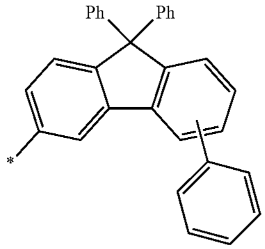
Formula 9-76
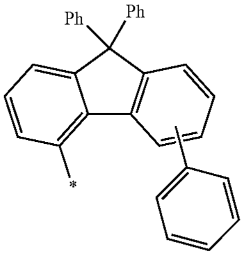
Formula 9-77
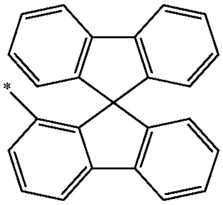
Formula 9-78
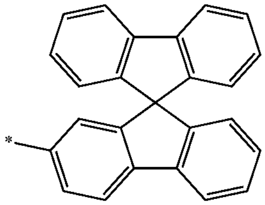
Formula 9-79
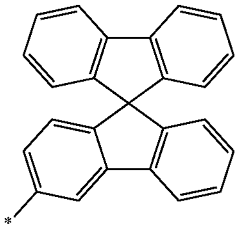

-continued
Formula 9-80
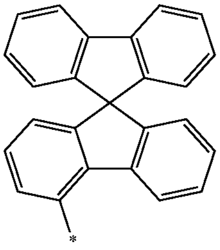
Formula 9-81
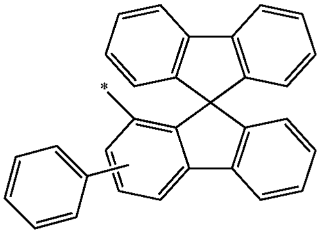
Formula 9-82
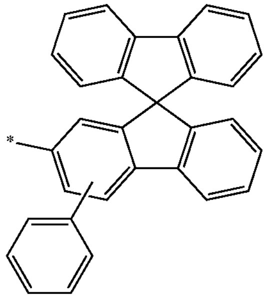
Formula 9-83
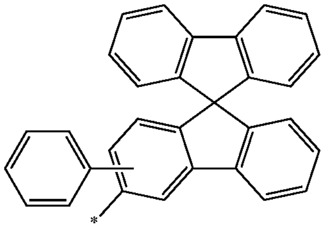
Formula 9-84
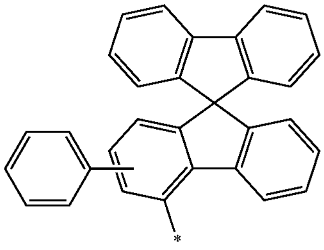
Formula 9-85
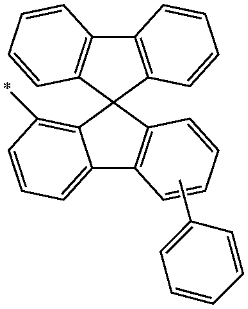
-continued
Formula 9-86
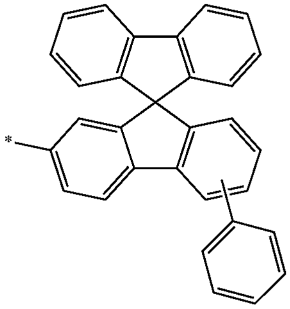
Formula 9-87
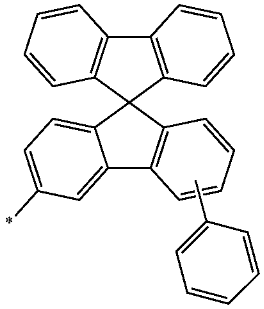
Formula 9-88
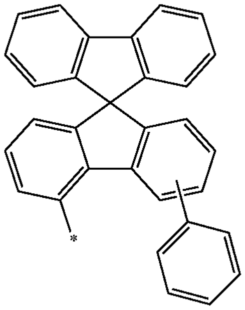
Formula 9-89
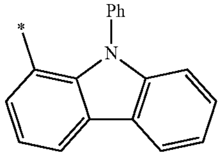
Formula 9-90
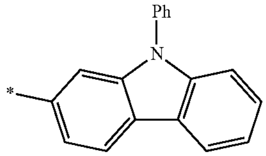
Formula 9-91
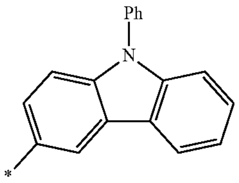

-continued
Formula 9-92
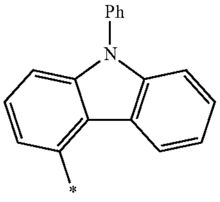
Formula 9-93
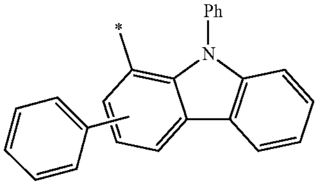
Formula 9-94
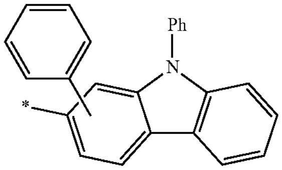
Formula 9-95
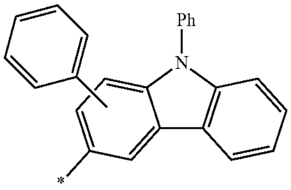
Formula 9-96
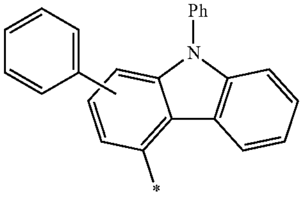
Formula 9-97
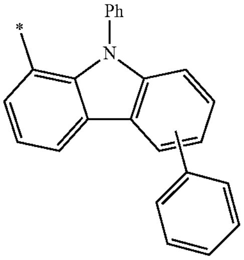
Formula 9-98
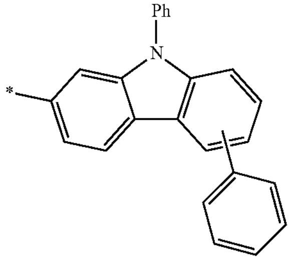
-continued
Formula 9-99
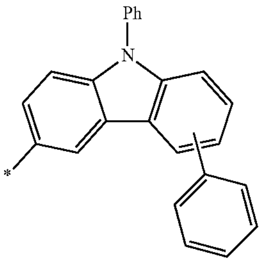
Formula 9-100
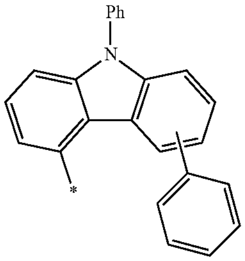
Formula 9-101
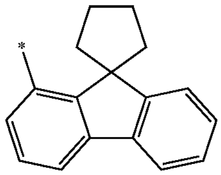
Formula 9-102
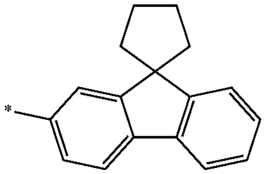
Formula 9-103
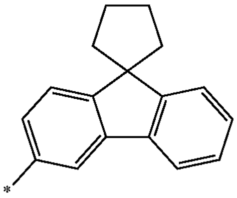
Formula 9-104
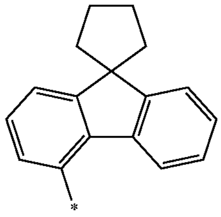
Formula 9-105
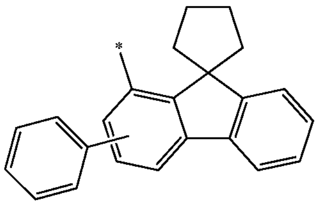

-continued
Formula 9-106
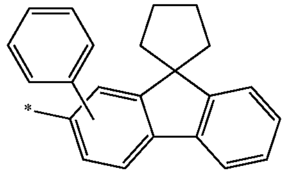
Formula 9-107
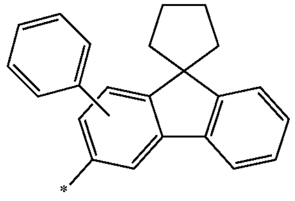
Formula 9-108
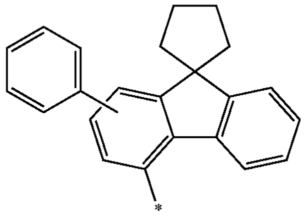
Formula 9-109
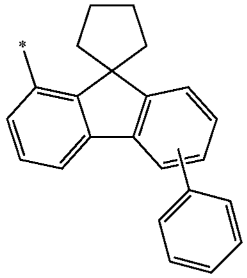
Formula 9-110
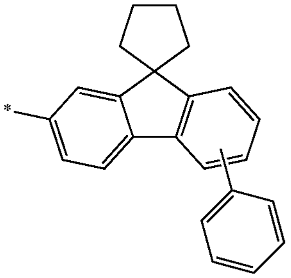
Formula 9-111
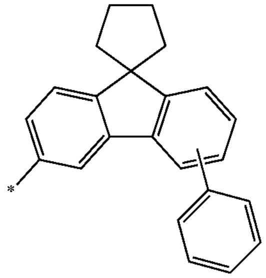
-continued
Formula 9-112
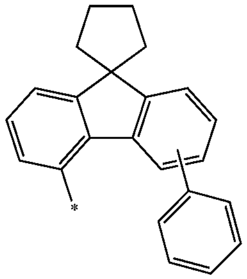
Formula 9-113
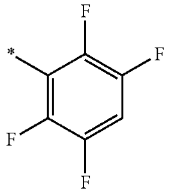
Formula 9-114
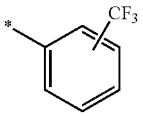
Formula 9-115
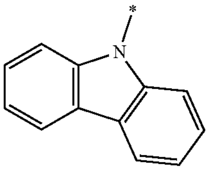
Formula 9-116
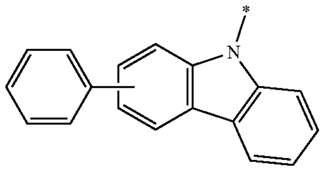
Formula 10-1
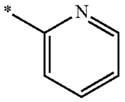
Formula 10-2
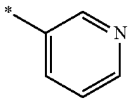
Formula 10-3
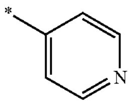
Formula 10-4
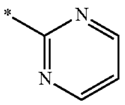
Formula 10-5
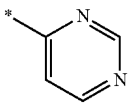

-continued
Formula 10-6
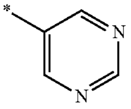
Formula 10-7
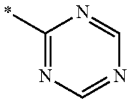
Formula 10-8
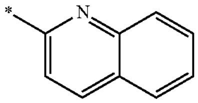
Formula 10-9
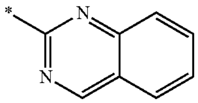
Formula 10-10
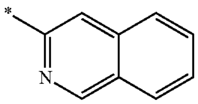
Formula 10-11
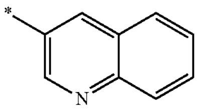
Formula 10-12
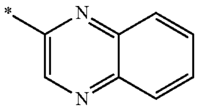
Formula 10-13
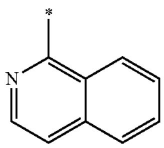
Formula 10-14
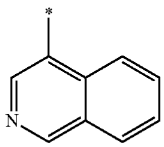
Formula 10-15
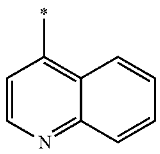
Formula 10-16
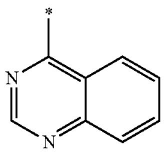
Formula 10-17
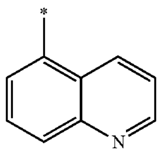
-continued
Formula 10-18
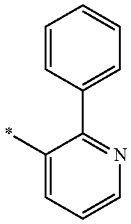
Formula 10-19
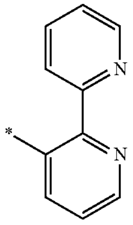
Formula 10-20
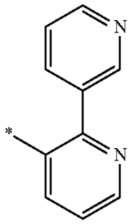
Formula 10-21
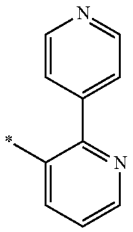
Formula 10-22
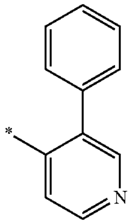
Formula 10-23
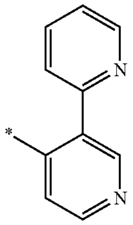
Formula 10-24
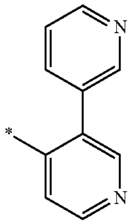

-continued
Formula 10-25
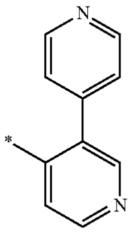
Formula 10-26
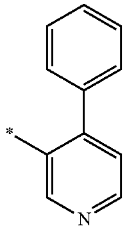
Formula 10-27
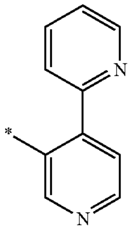
Formula 10-28
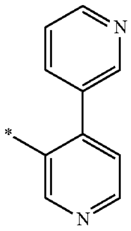
Formula 10-29
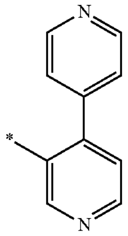
Formula 10-30
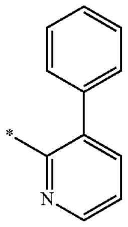
-continued
Formula 10-31
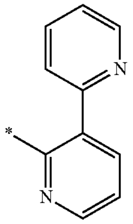
Formula 10-32
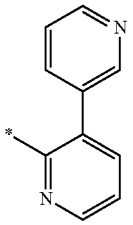
Formula 10-33
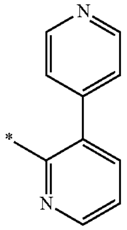
Formula 10-34
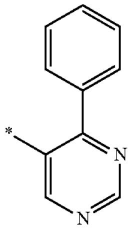
Formula 10-35
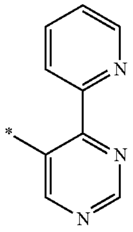
Formula 10-36
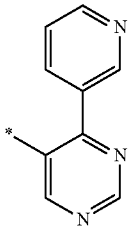

-continued
Formula 10-37
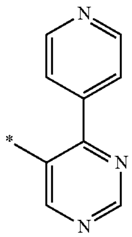
Formula 10-38
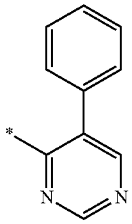
Formula 10-39
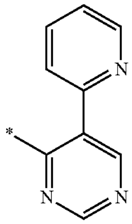
Formula 10-40
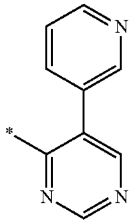
Formula 10-41
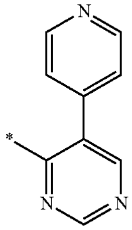
Formula 10-42
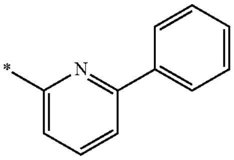
Formula 10-43
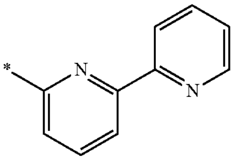
-continued
Formula 10-44
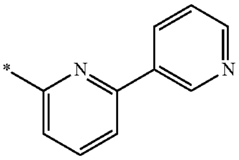
Formula 10-45
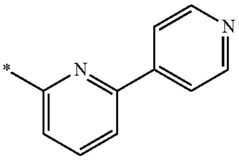
Formula 10-46
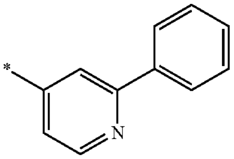
Formula 10-47
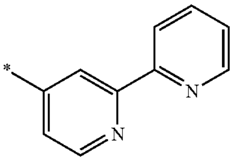
Formula 10-48
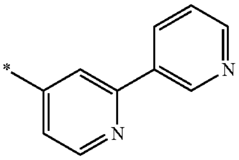
Formula 10-49
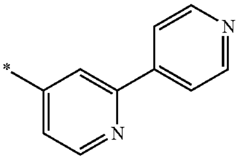
Formula 10-50
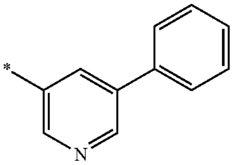
Formula 10-51
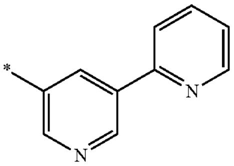
Formula 10-52
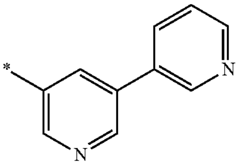

-continued
Formula 10-53
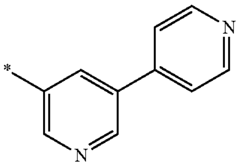
Formula 10-54
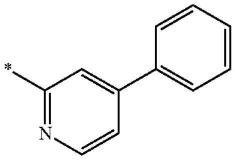
Formula 10-55
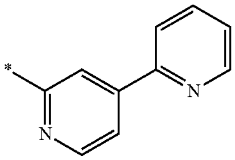
Formula 10-56
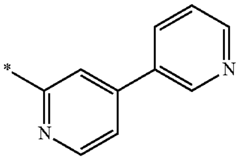
Formula 10-57
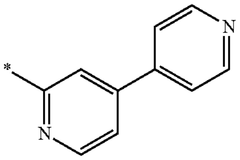
Formula 10-58
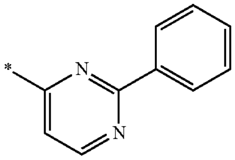
Formula 10-59
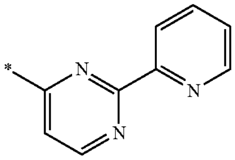
Formula 10-60
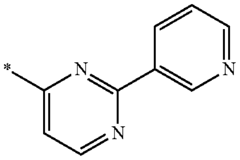
Formula 10-61
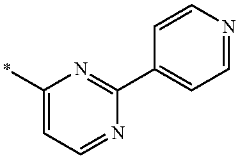
-continued
Formula 10-62
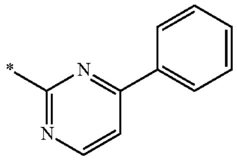
Formula 10-63
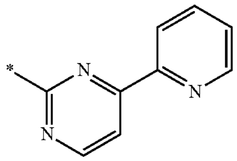
Formula 10-64
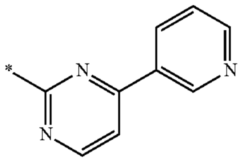
Formula 10-65
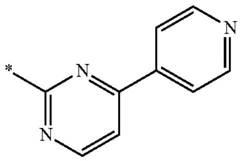
Formula 10-66
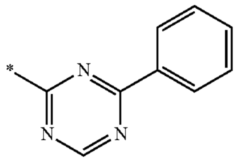
Formula 10-67
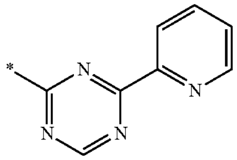
Formula 10-68
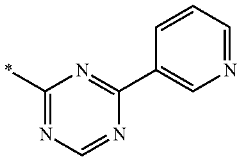
Formula 10-69
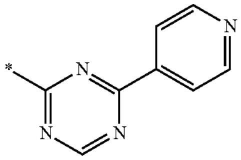
Formula 10-70
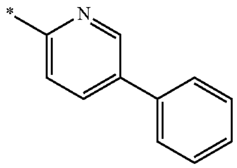

-continued
Formula 10-71
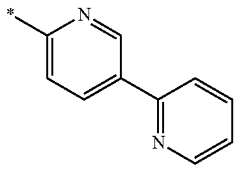
Formula 10-72
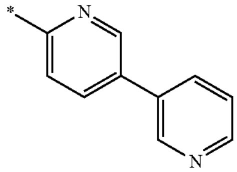
Formula 10-73
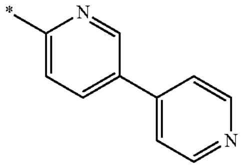
Formula 10-74
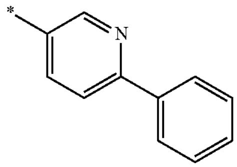
Formula 10-75
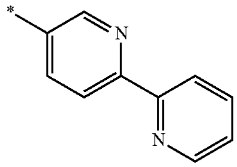
Formula 10-76
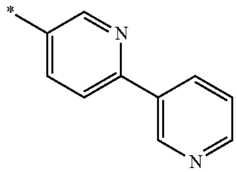
Formula 10-77
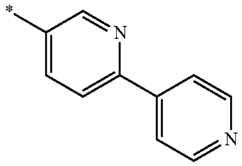
Formula 10-78
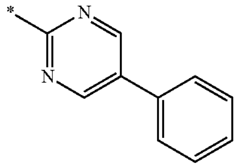
Formula 10-79
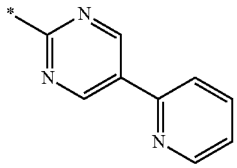
-continued
Formula 10-80
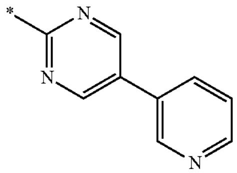
Formula 10-81
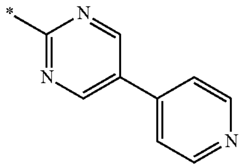
Formula 10-82
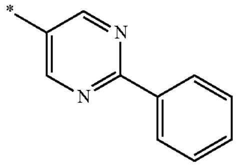
Formula 10-83
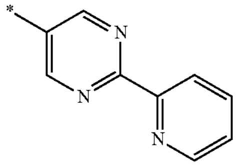
Formula 10-84
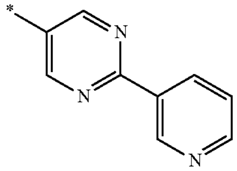
Formula 10-85
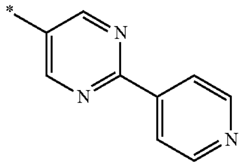
Formula 10-86
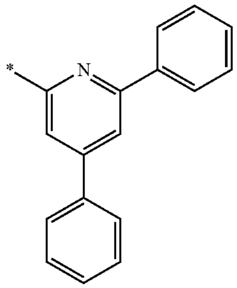

-continued
Formula 10-87
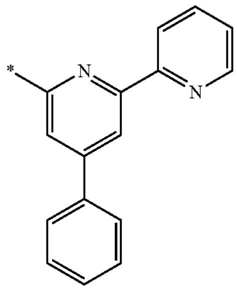
Formula 10-88
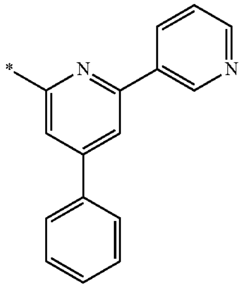
Formula 10-89
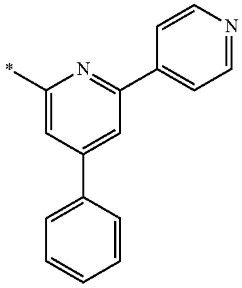
Formula 10-90
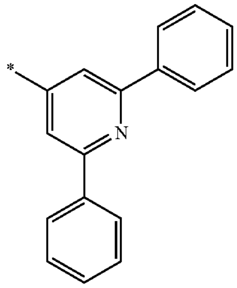
Formula 10-91
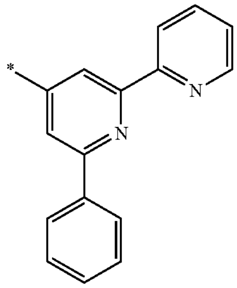
-continued
Fiormula 10-92
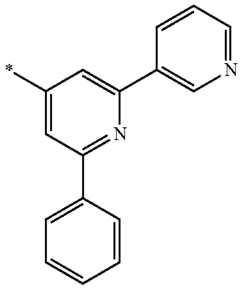
Formula 10-93
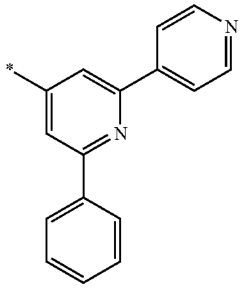
Formula 10-94
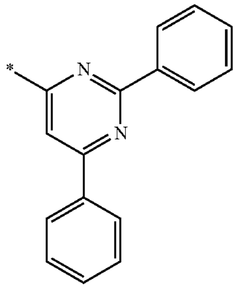
Formula 10-95
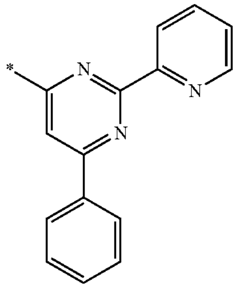
Formula 10-96
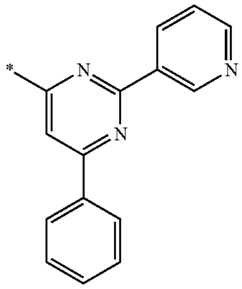

-continued
Formula 10-97
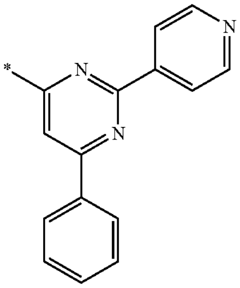
Formula 10-98
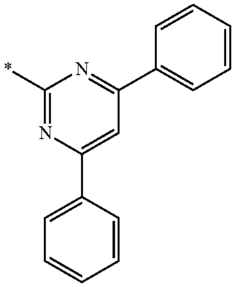
Formula 10-99
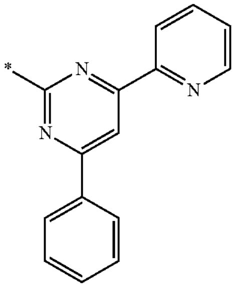
Formula 10-100
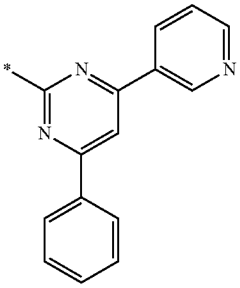
Formula 10-101
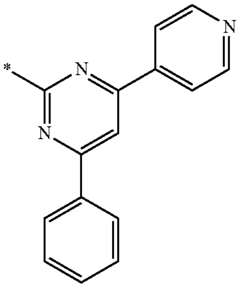
-continued
Formula 10-102
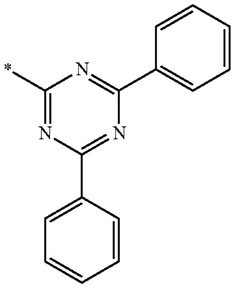
Formula 10-103
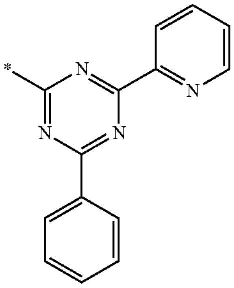
Formula 10-104
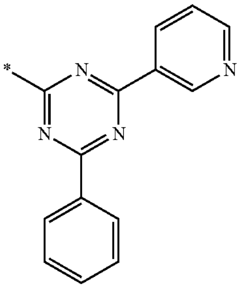
Formula 10-105
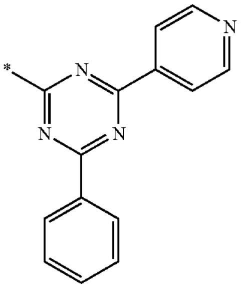
Formula 10-106
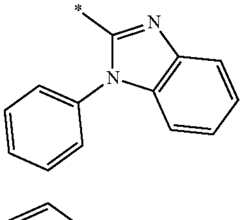
Formula 10-107
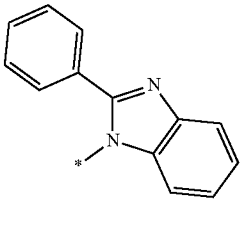

-continued

Formula 10-108

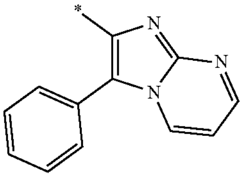

Formula 10-109

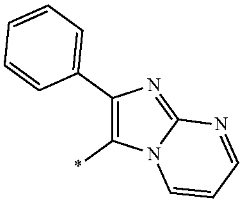

Formula 10-110

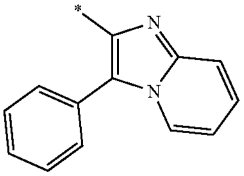

Formula 10-111

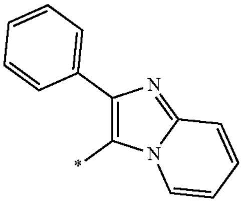

Formula 10-112

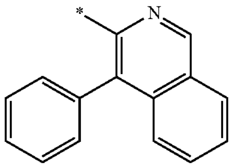

Formula 10-113

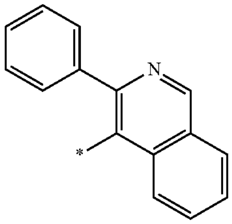

Formula 10-114

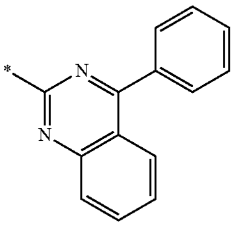

-continued

Formula 10-115

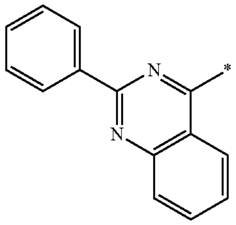

Formula 10-116

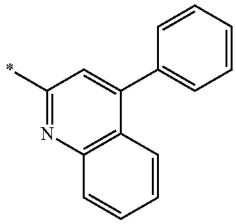

Formula 10-117

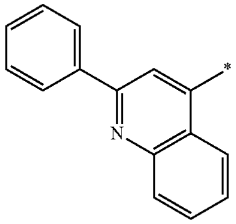

Formula 10-118

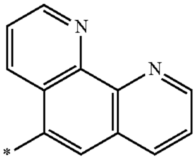

Formula 10-119

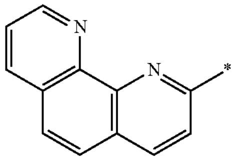

Formula 10-120

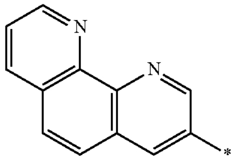

Formula 10-121

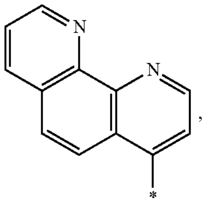

in Formulae 9-1 to 9-116 and 10-1 to 10-121, Ph indicates a phenyl group, and * indicates a binding site to a neighboring atom.

11. The condensed cyclic compound of claim 10, wherein $Ar_1$ to $Ar_6$ in Formula 1 are each independently selected from groups represented by Formulae 9-1 to 9-116 and 10-1 to 10-3.

12. The condensed cyclic compound of claim 1, wherein $R_1$ to $R_5$ in Formula 1 are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a mesityl group, a naphthyl group, and —$Si(Q_1)(Q_2)(Q_3)$, wherein $Q_1$ to $Q_3$ are each independently selected from a $C_1$-$C_{20}$ alkyl group, a $C_1$-$C_{20}$ alkoxy group, a phenyl group, a biphenyl group, a terphenyl group, and a naphthyl group.

13. The condensed cyclic compound of claim 1, wherein the condensed cyclic compound is represented by one of Formulae 1A to 1C:

Formula 1A

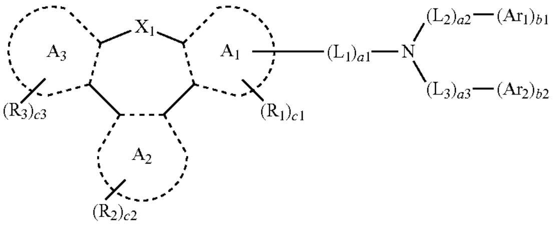

Formula 1B

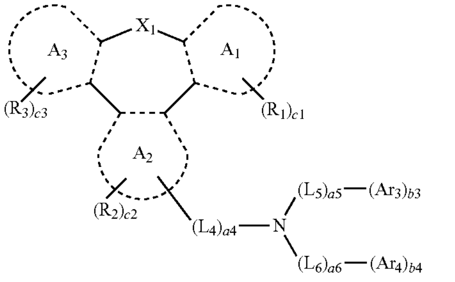

Formula 1C

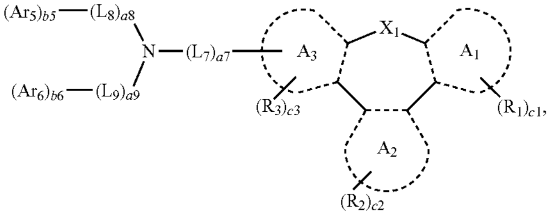

wherein $X_1$, rings $A_1$ to $A_3$, $L_1$ to $L_9$, a1 to a9, $Ar_1$ to $Ar_6$, b1 to b6, $R_1$ to $R_3$, and c1 to c3 in Formulae 1A to 1C are the same as described in claim 1.

14. The condensed cyclic compound of claim 1, wherein the condensed cyclic compound is represented by one of Formulae 1-1 to 1-11:

Formula 1-1

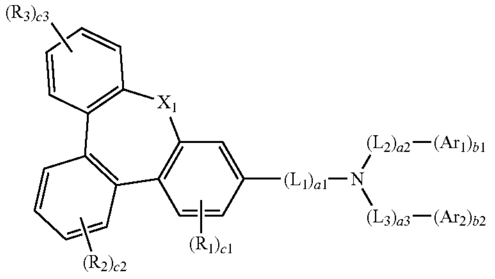

Formula 1-2

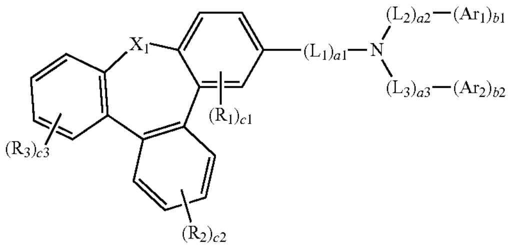

Formula 1-3

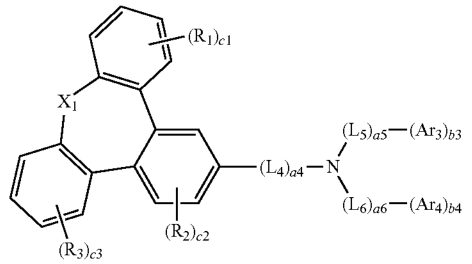

Formula 1-4

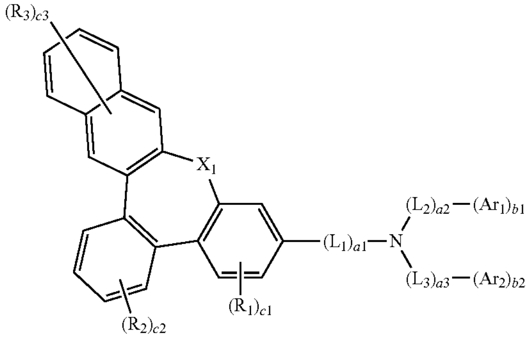

Formula 1-5

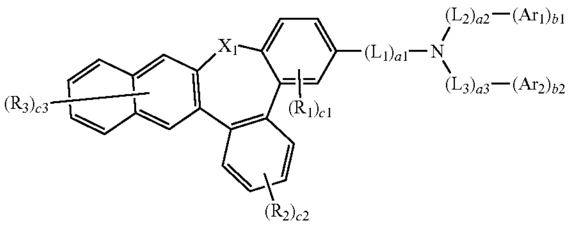

Formula 1-6
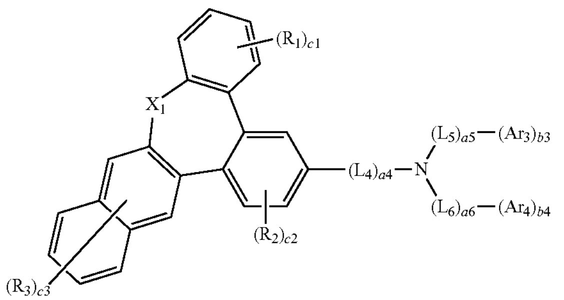
Formula 1-7
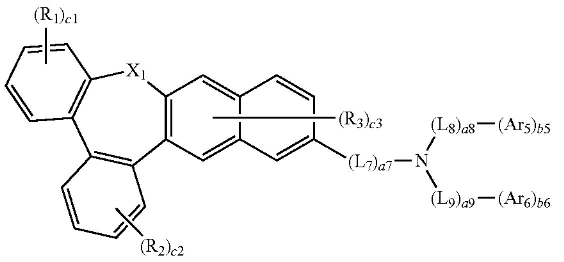
Formula 1-8
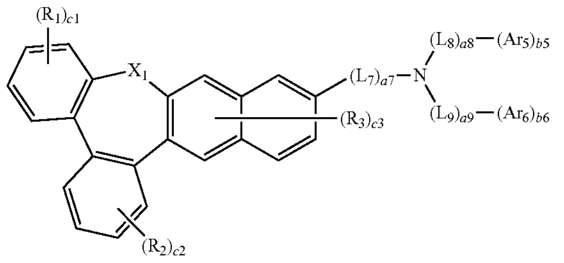
Formula 1-9
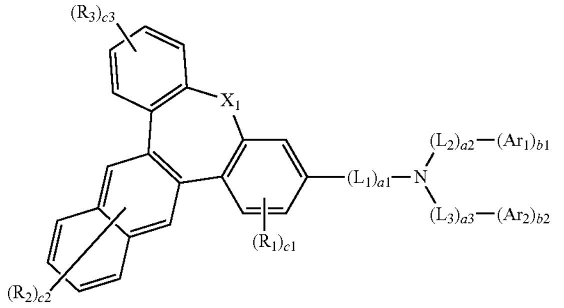
Formula 1-10
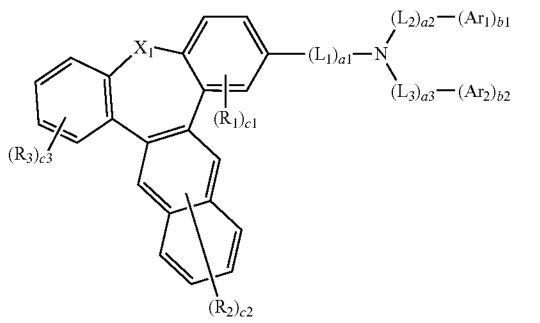
Formula 1-11
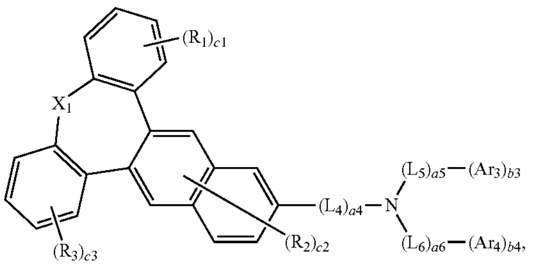
wherein $X_1$, $L_1$ to $L_9$, a1 to a9, $Ar_1$ to $Ar_6$, b1 to b6, $R_1$ to $R_3$, and c1 to c3 in Formulae 1-1 to 1-11 are the same as described in claim 1.
15. The condensed cyclic compound of claim 1, wherein the condensed cyclic compound is represented by one of Formulae 1(2) to 1(18):
Formula 1(2)
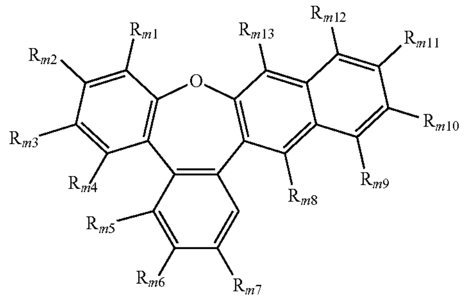
Formula 1(3)
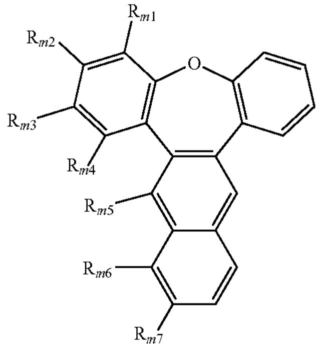
Formula 1(4)
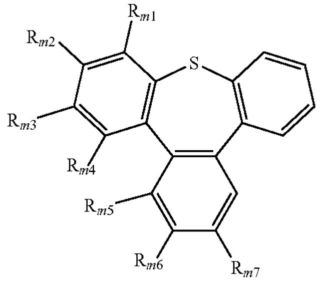

-continued
Formula 1(5)
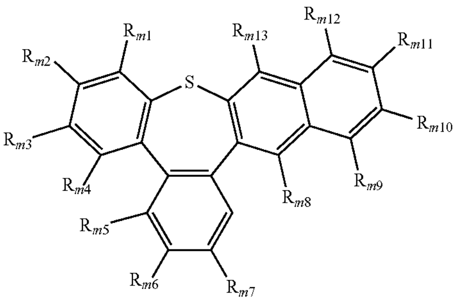
Formula 1(6)
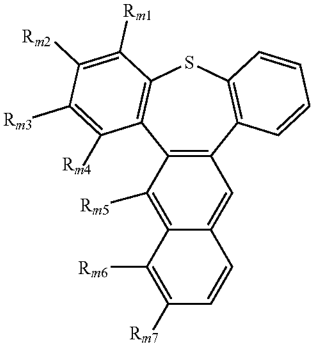
Formula 1(7)
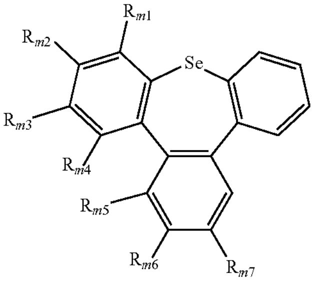
Formula 1(8)
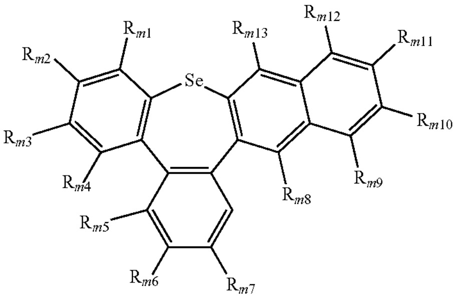
Formula 1(9)
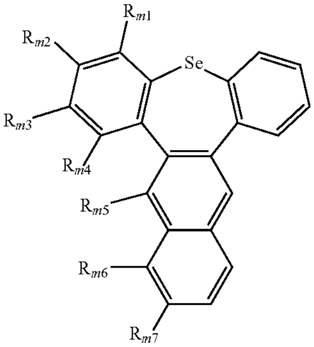
-continued
Formula 1(10)
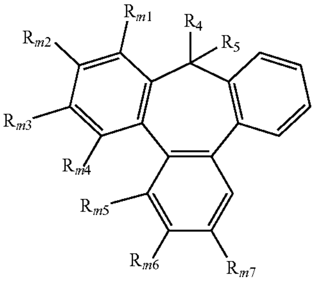
Formula 1(11)
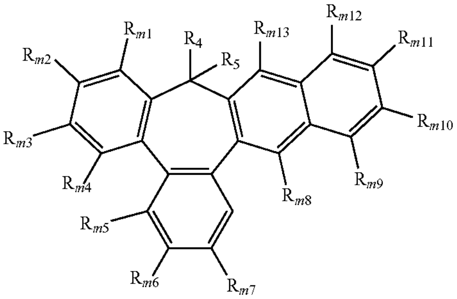
Formula 1(12)
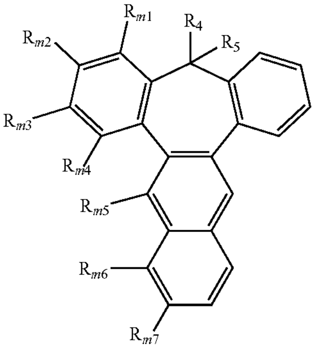
Formula 1(13)
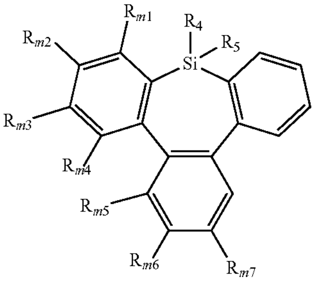
Formula 1(14)
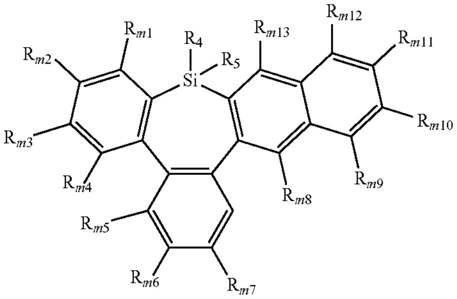

-continued

Formula 1(15)

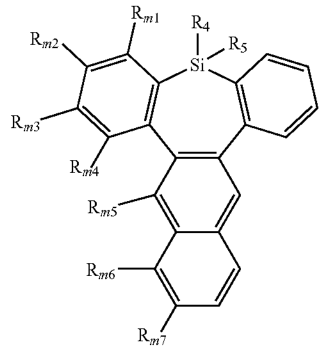

Formula 1(16)

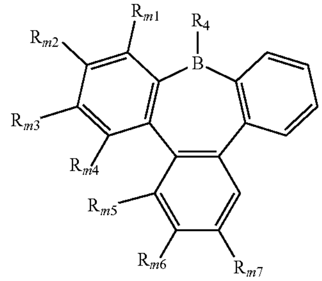

Formula 1(17)

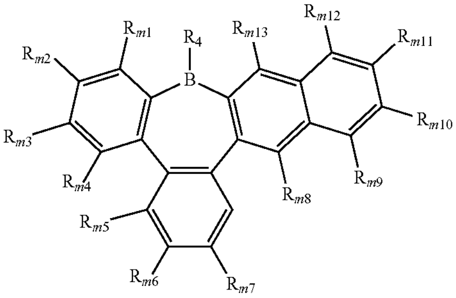

Formula 1(18)

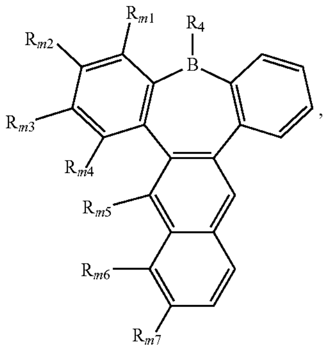

in Formulae 1(1) to 1(18), $R_4$ and $R_5$ are the same as described in claim 1, $R_{m1}$ to $R_{m4}$ are the same as described in connection with $R_1$ in claim 1, $R_{m5}$ to $R_{m7}$ are the same as described in connection with $R_2$ in claim 1, $R_{m8}$ to $R_{m13}$ are the same as described in connection with $R_3$ in claim 1, one of $R_{m1}$ to $R_{m13}$ in Formulae 1(1), 1(3), 1(4), 1(6), 1(7), 1(9), 1(10), 1(12), 1(13), 1(15), 1(16), and 1(18) is selected from groups represented by Formulae N-1 to N-41, and one of $R_{m1}$ to $R_{m13}$ in Formulae 1(2), 1(5), 1(8), 1(11), 1(14), and 1(17) is selected from groups represented by Formulae N-1 to N-41:

Formula N-1

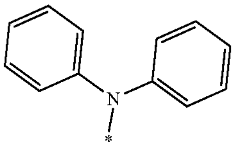

Formula N-2

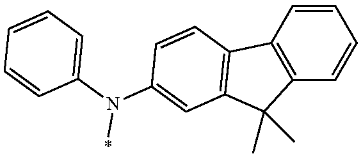

Formula N-3

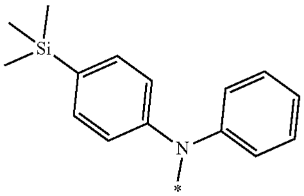

Formula N-4

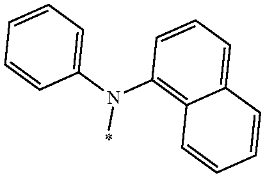

Formula N-5

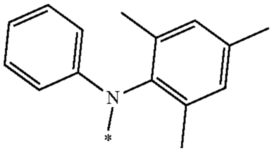

Formula N-6

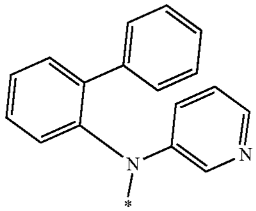

Formula N-7

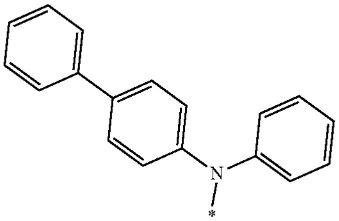

Formula N-8

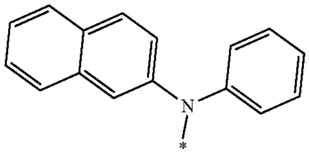

Formula N-9
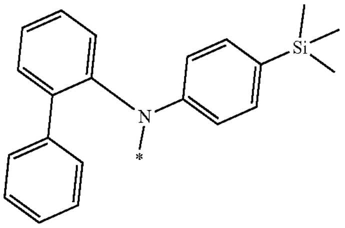
Formula N-10
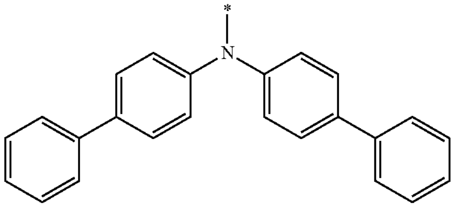
Formula N-11
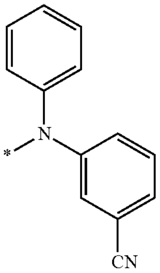
Formula N-12
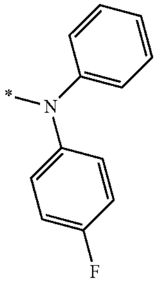
Formula N-13
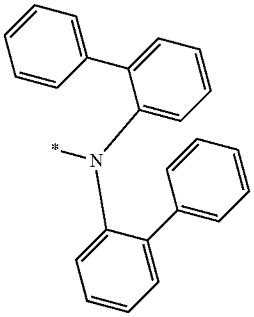
Formula N-14
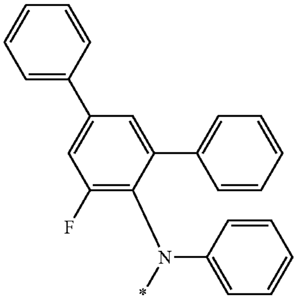
Formula N-15
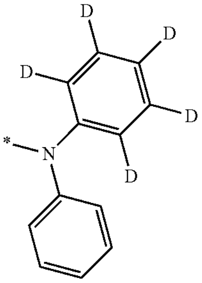
Formula N-16
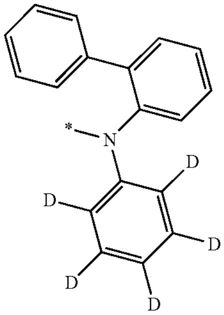
Formula N-17
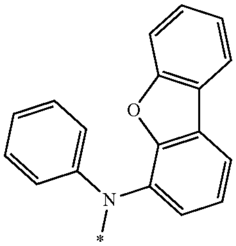
Formula N-18
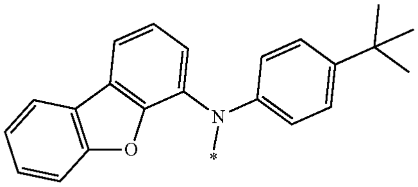

-continued
Formula N-19
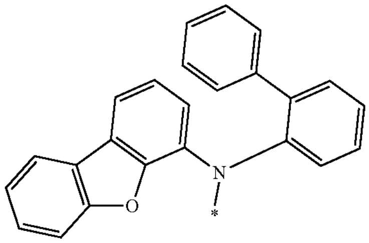
Formula N-20
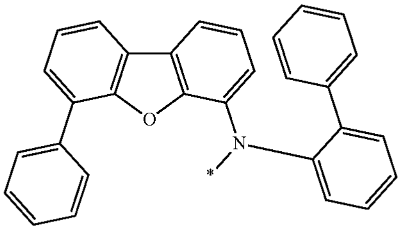
Formula N-21
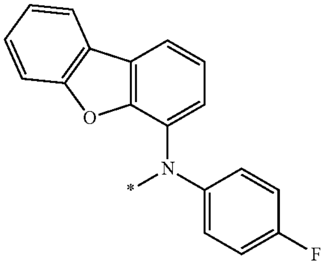
Formula N-22
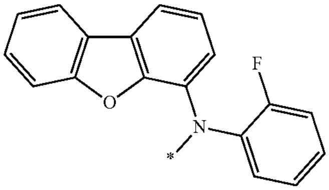
Formula N-23
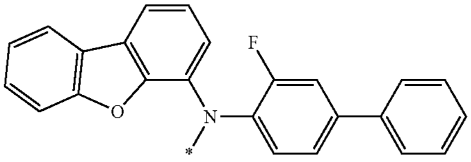
Formula N-24
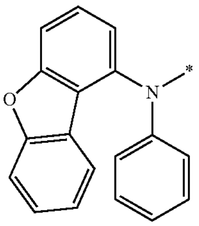
-continued
Formula N-25
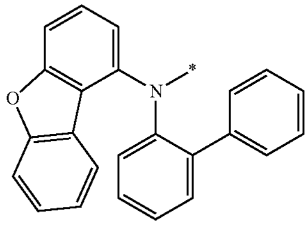
Formula N-26
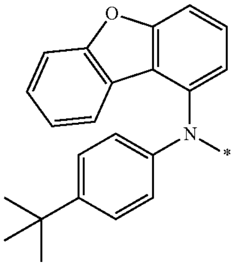
Formula N-27
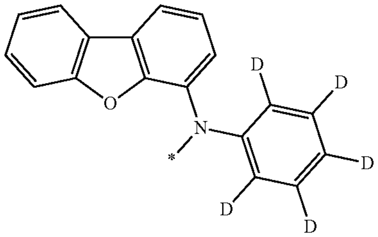
Formula N-28
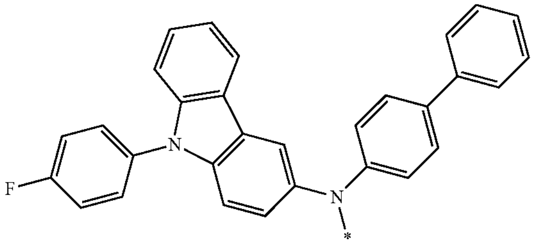
Formula N-29
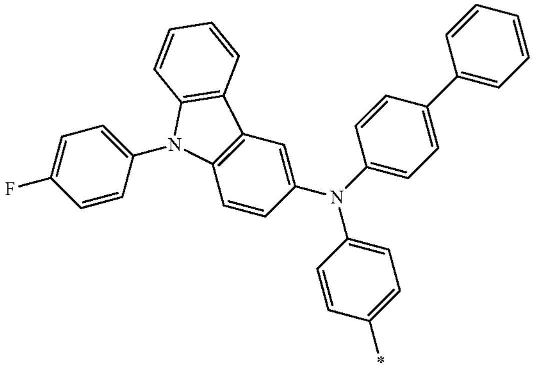

-continued
Formula N-30
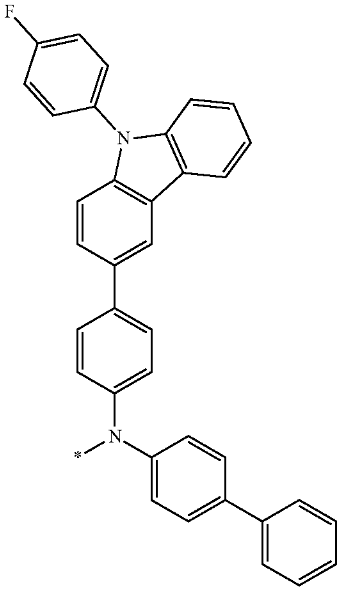
Formula N-31
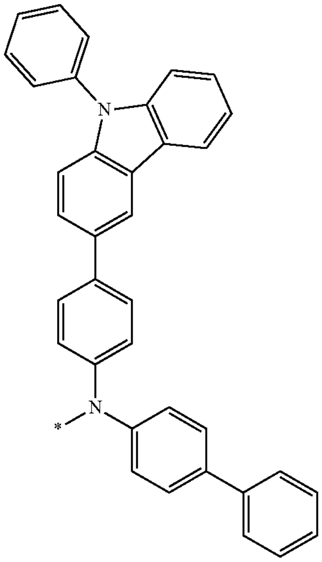
-continued
Formula N-32
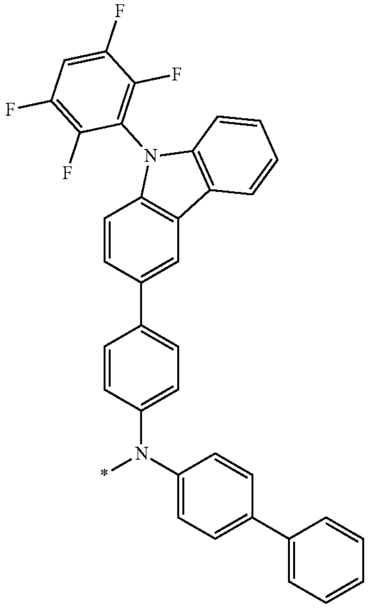
Formula N-33
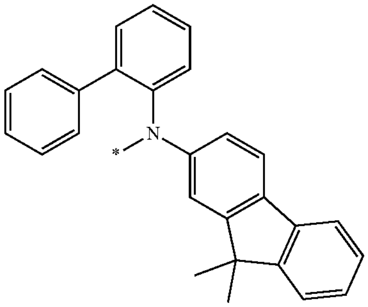
Formula N-34
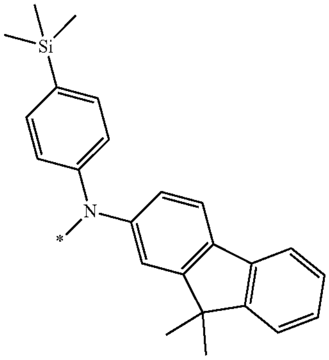
Formula N-35
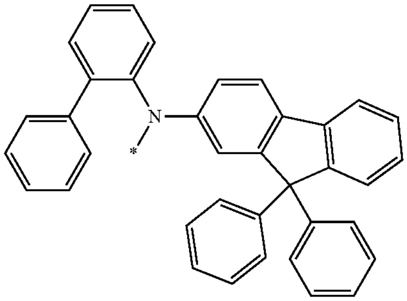

-continued

Formula N-36

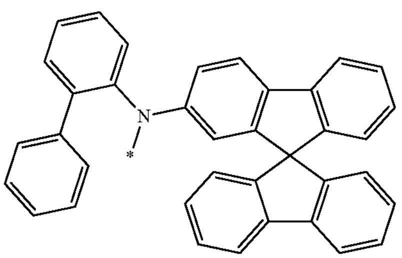

Formula N-37

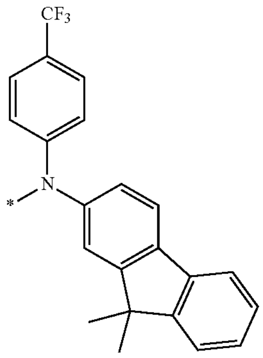

Formula N-38

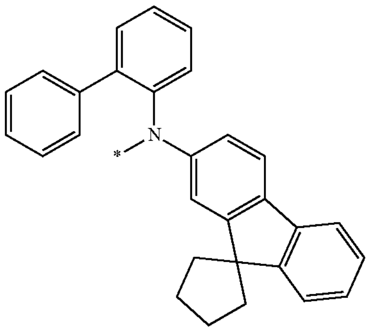

Formula N-39

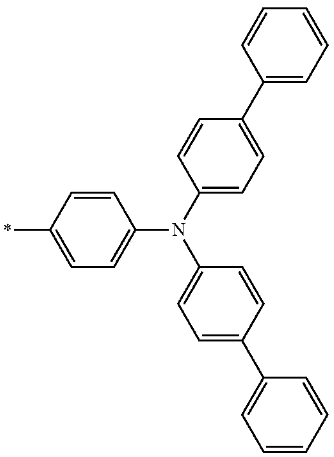

-continued

Formula N-40

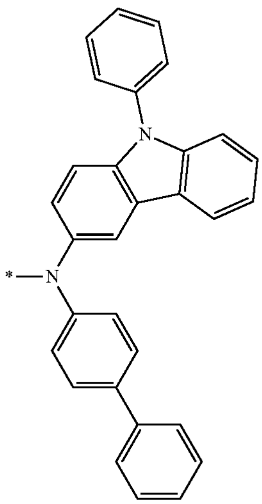

Formula N-41

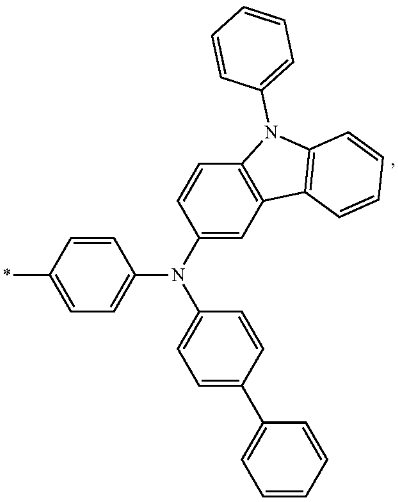

, wherein * in Formulae N-1 to N-41 indicates a binding site to a neighboring atom.

16. An organic light-emitting device comprising:

a first electrode;

a second electrode facing the first electrode; and an organic layer disposed between the first electrode and the second electrode, wherein the organic layer comprises an emission layer and at least one condensed cyclic compound represented by Formula 1:

<Formula 1>

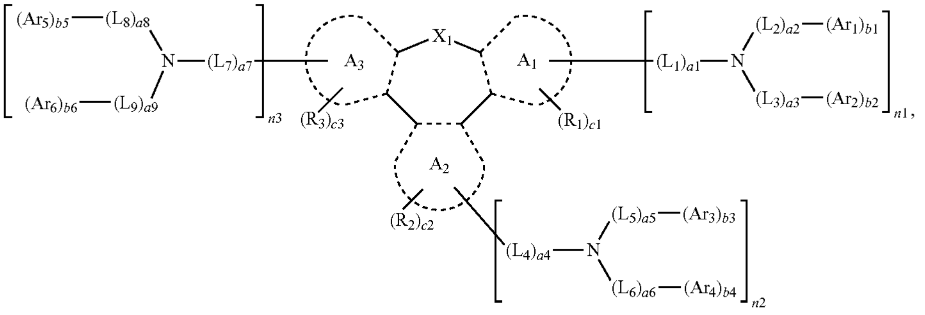

in Formula 1, $X_1$ is selected from O, S, Se, $C(R_4)(R_5)$, $Si(R_4)(R_5)$, and $B(R_4)$, rings $A_1$, $A_2$, and $A_3$ are each independently a $C_5$-$C_{60}$ carbocyclic group or a $C_2$-$C_{30}$ heterocyclic group, when $X_1$ is O, one or more of $A_1$, $A_2$ and $A_3$ are a $C_{10}$-$C_{60}$ carbocyclic group, $L_1$ to $L_9$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a9 are each independently an integer from 0 to 5, $Ar_1$ to $Ar_6$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 to b6 are each independently an integer from 1 to 5, $R_1$ to $R_5$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, c1 to c3 are each independently an integer from 0 to 5, n1 to n3 are each independently 0 or 1, provided that a sum of n1, n2, and n3 is 1, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{60}$ cycloalkyl group, a $C_1$-$C_{10}$ heterocycloalkyl group, a $C_3$-$C_{60}$ cycloalkenyl group, a $C_2$-$C_{60}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group.

17. The organic light-emitting device of claim 16, wherein the first electrode is an anode, the second electrode is a cathode, the organic layer further comprises a hole transport region between the first electrode and the emission layer, and an electron transport region between the emission layer and the second electrode, the hole transport region comprises a hole injection layer, a hole transport layer, an emission auxiliary layer, an electron blocking layer, or any combination thereof, and the electron transport region comprises a hole blocking layer, a buffer layer, an electron transport layer, an electron injection layer, or any combination thereof.

18. The organic light-emitting device of claim 17, wherein at least one of the hole transport region and the emission layer comprises the condensed cyclic compound.

19. The organic light-emitting device of claim 17, wherein the hole transport region comprises a hole transport layer, and the hole transport layer comprises the condensed cyclic compound.

20. The organic light-emitting device of claim 17, wherein the hole transport region comprises a hole injection layer, and the hole injection layer comprises the condensed cyclic compound.

21. An organic light-emitting device comprising:

a first electrode;

a second electrode facing the first electrode;

an emission layer disposed between the first electrode;

a hole transport region disposed between the first electrode and the emission layer; and an electron transport region disposed between the emission layer and the second electrode, wherein at least one of the hole transport region and the emission layer comprises a condensed cyclic compound, wherein the condensed cyclic compound comprises a tetracyclic structure including a 7-membered center ring and three fused side rings, the 7-membered center ring comprises seven carbon atoms, or 6 carbon atoms and one of O, S, Se, Si and B atoms as ring members, each of the three fused side rings shares a two carbon border with the 7-membered center ring, the three fused side rings do not share a border with each other, the three fused side rings are each independently a $C_5$-$C_{60}$ carbocyclic group or a $C_2$-$C_{30}$ heterocyclic group, except when O atom is a ring member of the 7-membered center ring, at least one of the three fused side rings is $C_{10}$-$C_{60}$ carbocyclic group, and one of the three fused side rings is linked to a tertiary amino group.

22. The organic light-emitting device of claim 21, wherein the tertiary amino group is represented by Formula S1:

<Formula S1>

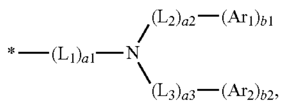

in Formula S1, $L_1$ to $L_3$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a3 are each independently an integer from 0 to 5, $Ar_1$ and $Ar_2$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 and b2 are each independently an integer from 1 to 5, at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group —Si $(Q_{11})(Q_{12})(Q_{13})$, —N$(Q_{11})(Q_{12})$, —B$(Q_{11})(Q_{12})$, —C(=O)$(Q_{11})$, —S(=O)$_2(Q_{11})$, and —P(=O)$(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{21})(Q_{22})(Q_{23})$, —N$(Q_{21})(Q_{22})$, —B$(Q_{21})(Q_{22})$, —C(=O)$(Q_{21})$, —S(=O)$_2(Q_{21})$, and —P(=O)$(Q_{21})(Q_{22})$; and —Si$(Q_{31})(Q_{32})(Q_{33})$, —N$(Q_{31})(Q_{32})$, —B$(Q_{31})(Q_{32})$, —C(=O)$(Q_{31})$, —S(=O)$_2(Q_{31})$, and —P(=O)$(Q_{31})(Q_{32})$, and $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group.

* * * * *